(12) United States Patent
Delgado Oyarzo et al.

(10) Patent No.: US 11,166,942 B2
(45) Date of Patent: Nov. 9, 2021

(54) INHIBITORS OF INTEGRATED STRESS RESPONSE PATHWAY

(71) Applicant: PRAXIS BIOTECH LLC, San Francisco, CA (US)

(72) Inventors: Luz Marina Delgado Oyarzo, Santiago (CL); Gonzalo Andrés Ureta Díaz, Santiago (CL); Brahmam Pujala, Greater Noida (IN); Dayanand Panpatil, Noida (IN); Sebastian Bernales, Piedmont, CA (US); Sarvajit Chakravarty, Edmond, OK (US)

(73) Assignee: PRAXIS BIOTECH LLC, San Francisco, CA (US)

(*) Notice: Subject to any disclaimer, the term of this patent is extended or adjusted under 35 U.S.C. 154(b) by 0 days.

(21) Appl. No.: 16/432,445

(22) Filed: Jun. 5, 2019

(65) Prior Publication Data

US 2020/0101047 A1 Apr. 2, 2020

Related U.S. Application Data

(60) Provisional application No. 62/681,071, filed on Jun. 5, 2018.

(51) Int. Cl.

| | |
|---|---|
| *A61K 31/428* | (2006.01) |
| *A61K 31/4468* | (2006.01) |
| *A61K 31/4525* | (2006.01) |
| *A61K 31/4709* | (2006.01) |
| *A61K 31/495* | (2006.01) |
| *A61K 31/497* | (2006.01) |
| *A61K 31/538* | (2006.01) |
| *A61P 21/00* | (2006.01) |
| *A61P 25/28* | (2006.01) |
| *C07D 221/00* | (2006.01) |
| *C07D 241/04* | (2006.01) |
| *C07D 401/12* | (2006.01) |
| *C07D 403/12* | (2006.01) |
| *C07D 405/12* | (2006.01) |
| *C07D 413/12* | (2006.01) |
| *C07D 417/12* | (2006.01) |
| *C07K 16/00* | (2006.01) |
| *C12N 5/073* | (2010.01) |

(52) U.S. Cl.
CPC ........ *A61K 31/428* (2013.01); *A61K 31/4468* (2013.01); *A61K 31/4525* (2013.01); *A61K 31/4709* (2013.01); *A61K 31/495* (2013.01); *A61K 31/497* (2013.01); *A61K 31/538* (2013.01); *A61P 21/00* (2018.01); *A61P 25/28* (2018.01); *C07D 221/00* (2013.01); *C07D 241/04* (2013.01); *C07D 401/12* (2013.01); *C07D 403/12* (2013.01); *C07D 405/12* (2013.01); *C07D 413/12* (2013.01); *C07D 417/12* (2013.01); *C07K 16/00* (2013.01); *C12N 5/0603* (2013.01); *C12N 2500/30* (2013.01)

(58) Field of Classification Search
CPC ................ C07D 401/12; C07D 401/14; A61K 31/4523; A61P 25/28
USPC ......................................... 546/196; 514/317
See application file for complete search history.

(56) References Cited

U.S. PATENT DOCUMENTS

| | | |
|---|---|---|
| 5,096,901 A | 3/1992 | Ward |
| 2004/0133286 A1 | 7/2004 | Imazaki |
| 2005/0197350 A1 | 9/2005 | Sekiguchi et al. |
| 2010/0035898 A1 | 2/2010 | Beattie |
| 2011/0039860 A1 | 2/2011 | Yang |
| 2011/0300575 A1 | 12/2011 | Imataka |
| 2015/0314018 A1 | 11/2015 | Sahin |
| 2016/0318931 A1 | 11/2016 | Hadida-ruah |
| 2017/0342020 A1 | 11/2017 | Walter et al. |
| 2019/0177310 A1 | 6/2019 | Bernales et al. |
| 2020/0270232 A1 | 8/2020 | Bernales |

FOREIGN PATENT DOCUMENTS

| | | |
|---|---|---|
| WO | 2011095450 A1 | 8/2011 |
| WO | WO-2014/144952 A2 | 9/2014 |
| WO | WO-2014/144952 A3 | 9/2014 |
| WO | WO-2017/193030 A1 | 11/2017 |
| WO | WO-2017/193034 A1 | 11/2017 |
| WO | WO-2017/193041 A1 | 11/2017 |
| WO | WO-2017/193063 A1 | 11/2017 |
| WO | WO-2017/212423 A1 | 12/2017 |
| WO | WO-2017/212425 A1 | 12/2017 |
| WO | 2018225093 A1 | 12/2018 |
| WO | 2019008506 A1 | 1/2019 |
| WO | 2019008507 A1 | 1/2019 |
| WO | WO-2019/032743 A1 | 2/2019 |
| WO | WO-2019/046779 A1 | 3/2019 |
| WO | 2019090069 A1 | 5/2019 |
| WO | 2019090074 A1 | 5/2019 |
| WO | 2019090076 A1 | 5/2019 |
| WO | 2019090078 A1 | 5/2019 |
| WO | 2019090081 A1 | 5/2019 |

(Continued)

OTHER PUBLICATIONS

Layzer, Degenerative Diseases of the Nervous System, Cecil Textbook of Medicine, 20th Edition, vol. 2, pp. 2050-2057 (1996).*
Freshney et al.,Culture of Animal Cells, A Manual of Basic Technique, Alan R. Liss, Inc., 1983, New York, p. 4.*
Dermer et al., Bio/Technology, 1994, 12:320.*
Cecil Textbook of Medicine, edited by Bennet, J.C., and Plum F., 20th edition,vol. 1, 1004-1010, 1996.*
Golub et al., Science, 286, 531 -537, 1999.*
International Search Report dated Oct. 10, 2019, for Patent Application No. PCT/US19/35593, filed Jun. 5, 2019, 5 pages.

(Continued)

*Primary Examiner* — Samantha L Shterengarts
(74) *Attorney, Agent, or Firm* — Morrison & Foerster LLP

(57) ABSTRACT

The present disclosure relates generally to therapeutic agents that may be useful as inhibitors of Integrated Stress Response (ISR) pathway.

42 Claims, 20 Drawing Sheets

(56) References Cited

FOREIGN PATENT DOCUMENTS

| WO | 2019090082 A1 | 5/2019 |
|---|---|---|
| WO | 2019090085 A1 | 5/2019 |
| WO | 2019090088 A1 | 5/2019 |
| WO | 2019090090 A1 | 5/2019 |
| WO | WO-2019/118785 A2 | 6/2019 |
| WO | WO-2019/183589 A1 | 9/2019 |
| WO | 2019193540 A1 | 10/2019 |
| WO | 2019193541 A1 | 10/2019 |
| WO | 2020012339 A1 | 1/2020 |
| WO | 2020031107 A1 | 2/2020 |
| WO | 2020077217 A1 | 4/2020 |
| WO | 2020167994 A1 | 8/2020 |
| WO | 2020168011 A1 | 8/2020 |
| WO | 2020176428 A1 | 9/2020 |
| WO | 2020181247 A1 | 9/2020 |
| WO | 2020216764 A1 | 10/2020 |
| WO | 2020216766 A1 | 10/2020 |
| WO | 2020223536 A1 | 11/2020 |
| WO | 2020223538 A1 | 11/2020 |
| WO | 2020252205 A1 | 12/2020 |
| WO | 2020252207 A1 | 12/2020 |

OTHER PUBLICATIONS

PUBCHEM-CID: 125480315 Create Date: Apr. 10, 2017 pp. 1-5; p. 2 structure.
PUBCHEM-CID: 86000498 Create Date: Nov. 3, 2014 pp. 1-5; p. 2 structure.
Written Opinion of the International Searching Authority dated Oct. 10, 2019, for Patent Application No. PCT/US19/35593, filed Jun. 5, 2019, 7 pages.
Adomavicius, T. et al. (e-pub. Dec. 20, 2018). "The Structural Basis of Translational Control by eIF2 Phosphorylation", Article, 46 pages (including Supplementary Material begins at p. 30 of 46).
Al-Chalabi, A. et al. (2012). "The Genetics And Neuropathology Of Amyotrophic Lateral Sclerosis," *Acta Neuropathol* 124(3):339-352.
Anastassiadis, T. et al. (2011). "Comprehensive Assay Of Kinase Catalytic Activity Reveals Features Of Kinase Inhibitor Selectivity," *Nat Biotechnol.* 29(11):1039-1045.
Ardiles, A.O. et al. (Oct. 15, 2014). "Pannexin 1 Regulates Bidirectional Hippocampal Synaptic Plasticity In Adult Mice," *Front Cell Neurosci.* 8(326):1-11.
ATCC Product Sheet (2018). "CT26.WT (ATCC CRL-2638)", located at www.atc.org, last visited on Jun. 27, 2019, 3 pages.
Axten, J.M. et al. (2012). "Discovery of 7-methyl-5-(1-{[3-(trifluoromethyl)phenyl]acetyl}-2,3-dihydro-1H-indol-5-yl)-7H-pyrrolo[2,3-d]pyrimidin-4-amine (GSK2606414), a potent and selective first-in-class inhibitor of protein kinase R (PKR)-like endoplasmic reticulum kinase (PERK)," *J Med Chem.* 55(16):7193-7207.
Bain, J. et al. (2003). "The Specificities Of Protein Kinase Inhibitors: An Update," *Biochem J.* 371(Pt 1):199-204.
Baird, T.D. et al. (2012). "Eukaryotic Initiation Factor 2 Phosphorylation and Translational Control in Metabolism," *Adv Nutr.* 3(3):307-321.
Bartsch, D. et al. (1995). "Aplysia CREB2 Represses Long-Term Facilitation: Relief of Repression Converts Transient Facilitation Into Long-Term Functional And Structural Change," *Cell* 83(6):979-992.
Beck, D. et al. (2013). "Vemurafenib Potently Induces Endoplasmic Reticulum Stress-Mediated Apoptosis in BRAFV600E Melanoma Cells," *Sci Signal.* 6(260):ra7, 12 pages.
Bi, M. et al. (2005). "ER Stress-Regulated Translation Increases Tolerance to Extreme Hypoxia and Promotes Tumor Growth," *EMBO J.* 24(19):3470-3481.
BioCare Medical, MM620L "Mouse-on-Mouse HRP-Polymer: Mouse Antibodies on Mouse Tissues Polymer Detection Component, Control No. 902-MM620-090617", Biocare Medical, located at <https://biocare.net/wp-content/uploads/MM620.pdf>, lasted visited Feb. 28, 2019, 2 pages.

Bogorad, A.M. et al. (Feb. 9, 2018). "eIF2B Mechanisms of Action and Regulation: A Thermodynamic View", Biochemistry 57:1426-1435.
Borck, G. et al. (2012). "Eif2gamma Mutation That Disrupts Eif2 Complex Integrity Links Intellectual Disability To Impaired Translation Initiation," *Mol Cell* 48(4):641-646.
Brazeau, J.F. (2014). "Triazolo[4,5-d]pyrimidine Derivatives as Inhibitors of GCN2m," *ACS Med Chem Lett.* 5(4):282-283.
Cell Signaling Technology, catalog No. 11815 (Nov. 26, 2018). "ATF-4 (D4B8) Rabbit mAb", located at www.cellsignal.com, last visited on Jun. 27, 2019, 2 pages.
Chang, R.C. et al. (2002). "Involvement of Double-Stranded RNA-Dependent Protein Kinase and Phosphorylation of Eukaryotic Initiation Factor-2alpha in Neuronal Degeneration," *J Neurochem* 83(5):1215-1225.
Chen, A. et al. (2003). "Inducible Enhancement of Memory Storage and Synaptic Plasticity in Transgenic Mice Expressing an Inhibitor of ATF4 (CREB-2) and C/EBP Proteins," *Neuron* 39(4):655-669.
Chen, H.M. et al. (2008). "A Chemical Compound Commonly Used to Inhibit PKR, {8-imidazol-4-ylmethylene)-6H-azolidino[5,4-g]benzothiazol-7-one}, Protects Neurons By Inhibiting Cyclin-Dependent Kinase," *Eur J Neurosci.* 28(10):2003-2016, 26 pages.
Chou, A. et al. (e-pub. Jul. 10, 2017). "Inhibition of the Integrated Stress Response Reverses Cognitive Deficits After Traumatic Brain Injury," *PNAS. USA* 114(31):E6420-E6426.
Clavarino, G. et al. (2016). "Unfolded Protein Response Gene GADD34 is Overexpressed in Rheumatoid Arthritis And Related to the Presence of Circulating Anti-Citrullinated Protein Antibodies," *Autoimmunity* 49(3):172-178.
Cnop, M. et al. (Feb. 9, 2007). "Selective Inhibition Of Eukaryotic Translation Initiation Factor 2 Alpha Dephosphorylation Potentiates Fatty Acid-Induced Endoplasmic Reticulum Stress And Causes Pancreatic Beta-Cell Dysfunction And Apoptosis," *J. Biol. Chem.* 282(6): 3989-3997.
Costa-Mattioli, M. et al. (2007). "eIF2alpha Phosphorylation Bidirectionally Regulates The Switch From Short—To Long-Term Synaptic Plasticity And Memory," *Cell* 129(1):195-206. (and Supplemental Material, 11 pages).
Costa-Mattioli, M. et al. (2005). "Translational Control of Hippocampal Synaptic Plasticity and Memory by the eIF2alpha kinase GCN2," *Nature* 436(7054):1166-1173. (and Supplemental Material, 17 pages).
Costa-Mattioli, M. et al. (2009). "Translational Control of Long-Lasting Synaptic Plasticity And Memory," *Neuron* 61(1):10-26.
Costa-Mattioli, M. et al. (2009). "Translational Regulatory Mechanisms in Synaptic Plasticity and Memory Storage," *Prog. Mol. Biol. Transl. Sci.* 90:293-311.
Couturier, J. et al. (Jan. 8, 2010). "Interaction of Double-Stranded RNA-Dependent Protein Kinase (PKR) with the Death Receptor Signaling Pathway in Amyloid beta (Abeta)-Treated Cells and in APPSLPS1 Knock-in Mice," *J. Biol. Chem.* 285(2):1272-1282.
Couturier, J. et al. (2012). "Pharmacological Inhibition of PKR in Appsweps1de9 Mice Transiently Prevents Inflammation at 12 Months of Age But Increases Abeta42 Levels in the Late Stages of the Alzheimer's Disease," *Curr. Alzheimer Res.* 9(3):344-360.
De Benedetti, A. (2004). "EIF-4E Expression And Its Role In Malignancies And Metastases," *Oncogene* 23(18):3189-3199.
Deng, J. et al. (2004). "Translational Repression Mediates Activation Of Nuclear Factor Kappa B By Phosphorylated Translation Initiation Factor 2," *Mol. Cell Biol.* 24(23):10161-10168.
Dey, S. et al. (2015). "ATF4-Dependent Induction Of Heme Oxygenase 1 Prevents Anoikis And Promotes Metastasis," *J. Clin. Invest.* 125(7):2592-2608.
Dezwaan-McCabe, D. et al. (Dec. 19, 2013). "The Stress-Regulated Transcription Factor CHOP Promotes Hepatic Inflammatory Gene Expression, Fibrosis, And Oncogenesis," *PLoS Genet.* 9(12):e1003937, 14 pages.
Di Prisco, G.V. et al. (Aug. 2014). "Translational Control of MGIuR-Dependent Long-Term Depression and Object-Place Learning by eIF2α," *Nat Neurosci.* 17(8):1073-1082, 29 pages.
Farook, J.M. et al. (2013). "GADD34 Induces Cell Death Through Inactivation Of Akt Following Traumatic Brain Injury," *Cell Death Dis* 4:e754, 9 pages.

(56) References Cited

OTHER PUBLICATIONS

Fels, D.R. et al. (2006). "The PERK/eIF2alpha/ATF4 Module of the UPR in Hypoxia Resistance and Tumor Growth,"*Cancer Biol. Ther.* 5(7):723-728.

Fuster, J.J. et al. (Mar. 19, 2019). "Integrated Stress Response Inhibition in Atherosclerosis", *JACC* 73(10):1170-1172.

Gelman, M.S. et al. (Apr. 5, 2002). "A Principal Role For The Proteasome In Endoplasmic Reticulum-Associated Degradation Of Misfolded Intracellular Cystic Fibrosis Transmembrane Conductance Regulator," *J. Biol. Chem.* 277(14):11709-11714.

Gordiyenko, Y. et al. (e-pub. Dec. 21, 2018). "Structural Basis for the Inhibition of Translation Through eIF2α Phosphorylation," *Article*, 37 pages.

Grolleau, A. et al. (2000). "Impaired Translational Response And Increased Protein Kinase PKR Expression In T Cells From Lupus Patients," *J. Clin. Invest.* 106(12):1561-1568.

Guppy, M. et al. (2005). "Metabolic Depression: A Response Of Cancer Cells To Hypoxia?," *Comp. Biochem. Physiol. B Biochem. Mol. Biol.* 140(2): 233-239.

Halliday, M. et al. (2015, e-pub. Mar. 5, 2015). "Partial Restoration of Protein Synthesis Rates by the Small Molecule ISRIB Prevents Neurodegeneration without Pancreatic Toxicity", *Cell Death Dis.* 6:e1672, 9 pages.

Halliday, M. et al. (2017). "Repurposed Drugs Targeting eIF2a-P-Mediated Translational Repression Prevent Neurodegeneration in Mice," *Brain* 16 pages.

Han, S. et al. (2006). "Macrophage Insulin Receptor Deficiency Increases ER Stress-Induced Apoptosis And Necrotic Core Formation In Advanced Atherosclerotic Lesions," *Cell Metab.* 3(4):257-266.

Harding, H.P. et al. (Mar. 2003). "An Integrated Stress Response Regulates Amino Acid Metabolism And Resistance To Oxidative Stress," *Mol. Cell* 11(3):619-633.

Harding, H.P. et al. (2000). "Perk Is Essential For Translational Regulation And Cell Survival During The Unfolded Protein Response," *Mol. Cell* 5(5):897-904.

Harding, H.P. et al. (2000). "Regulated Translation Initiation Controls Stress-Induced Gene Expression In Mammalian Cells," *Mol. Cell* 6(5):1099-1108.

Hearn, B.R. et al. (2016). "Structure-Activity Studies of Bis-O-Arylglycolamides: Inhibitors of the Integrated A Stress Response," *Chem. Med. Chem* 11:870-880.

Hinnebusch, A.G. (2005). "Translational Regulation of GCN4 and the General Amino Acid Control of Yeast," *Annu. Rev. Microbiol.* 59:407-450.

Hinnebusch, A.G. et al. (May 5, 2015). "Blocking Stress Response for Better Memory?," *Science* 348(6238):967-968.

Hodgson, R.E. (Apr. 1, 2019, e-pub. Feb. 6, 2019). "Cellular eIF2B Subunit Localization: Implications for the Integrated Stress Response and its Control By Small Molecule Drugs," *Mol. Biol. Cell* 30:942-958.

Hosoi, T. et al. (2016, e-pub. Aug. 12, 2016). "Unique Pharmacological Property of ISRIB in Inhibition of AB-Induced Neuronal Cell Death," *J. Pharm. Sci.* 131 (2016):292-295.

International Search Report and Written Opinion of the International Searching Authority dated Apr. 19, 2019, for Patent Application No. PCT/US18/65555, filed Dec. 13, 2018, 16 pages.

Invitation to Pay Additional Fees, dated Feb. 14, 2019, for PCT Application No. PCT/US2018/65555, filed Dec. 13, 2018, 3 pages.

Jackson, R.J. et al. (2010). "The Mechanism Of Eukaryotic Translation Initiation And Principles Of Its Regulation," *Nat. Rev. Mol. Cell Biol.* 11(2):113-127.

Jammi, N.V. et al. (2003). "Small Molecule Inhibitors of the RNA-Dependent Protein Kinase," *Biochem. Biophys. Res. Commun.* 308(1):50-57.

Jiang, H.Y. et al. (2005). "GCN2 Phosphorylation of eIF2alpha Activates NF-kappaB in Response to UV Irradiation," *Biochem. J.* 385(Pt2):371-380.

Kaidanovich-Belinin, O. et al. (2011). "Assessment of Social Interaction Behaviors," *J. Vis. Exp.* 48:e2473, 6 pages.

Kammer, G.M., et al. (May 2002). "Abnormal T Cell Signal Transduction in Systemic Lupus Erythematosus," *Arthritis Rheum.* 46(5):1139-1154.

Kashiwagi, K et al. (2016). "Crystal Structure of Eukaryotic Translation Initiation Factor 2B," *Nature* 000(00):1-17.

Kashiwagi, K et al. (May 3, 2019). "Structural Basis for eIF2B Inhibitionin Integrated Stress Response," *Science* 364(6439):495-499.

Kim, H.J., et al. (2014). "Therapeutic Modulation Of Eif2alpha Phosphorylation Rescues TDP-43 Toxicity In Amyotrophic Lateral Sclerosis Disease Models," *Nat Genet.* 46(2):152-160, 25 pages.

Kim, S.H. et al. (2000). "Human Breast Cancer Cells Contain Elevated Levels And Activity Of The Protein Kinase, PKR," *Oncogene* 19(27):3086-3094.

Kim, S.H., et al. (2002). "Neoplastic Progression In Melanoma And Colon Cancer Is Associated With Increased Expression And Activity Of The Interferon-Inducible Protein Kinase, PKR," *Oncogene* 21(57):8741-8748.

Krishnamoorthy, T. et al. (Aug. 2001). "Tight Binding Of The Phosphorylated Alpha Subunit Of Initiation Factor 2 (eIF2alpha) to the Regulatory Subunits Of Guanine Nucleotide Exchange Factor eIF2B Is Required For Inhibition Of Translation Initiation," *Mol. Cell Biol.* 21(15):5018-5030.

Kusio-Kobialka, M. et al. (Nov. 1, 2012). "The PERK-eIF2alpha Phosphorylation Arm Is A Pro-Survival Pathway Of BCR-ABL Signaling And Confers Resistance To Imatinib Treatment In Chronic Myeloid Leukemia Cells," *Cell Cycle* 11(21):4069-4078.

Lawrence De Koning, A.B., et al. (2003). "Hyperhomocysteinemia and Its Role In The Development Of Atherosclerosis," *Clin. Biochem.* 36(6):431-441.

Lehman, S.L. et al. (Jun. 30, 2015). "Signaling Through Alternative Integrated Stress Response Pathways Compensates for GCN2 Loss in a Mouse Model of Soft Tissue Sarcoma," *Sci. Rep.* 5(11781):1-13.

Li, J. et al. (2018). "Deletion of Tmtc4 Activates the Unfolded ProteinResponse and Causes Postnatal,", *J Clin Invest* 128(11):5150-5162.

Li, K. et al. (2016). "Liver-Specific Gene Inactivation of the Transcription Factor ATF4 Alleviates Alcoholic Liver Steatosis in Mice," *J. Biol Chem.* 291(35):18536-18546.

Lin, Y. et al. (Sep. 3, 2014). "Impaired Eukaryotic Translation Initiation Factor 2B Activity Specifically in Oligodendrocytes Reproduces the Pathology of Vanishing White Matter Disease in Mice", *J Neurosci* 34(36):12182-12191.

Lobo, M.V. et al. (2000). "Levels, Phosphorylation Status And Cellular Localization Of Translational Factor eIF2 In Gastrointestinal Carcinomas," *Histochem. J.* 32(3):139-150.

Lopez, J. et al. (Feb. 11, 2015). "Memory Retrieval Requires Ongoing Protein Synthesis And NMDA Receptor Activity-Mediated AMPA Receptor Trafficking," *J. Neurosci.* 35(6):2465-2475.

Lu, M., et al. (2014). "Opposing Unfolded-Protein-Response Signals Converge On Death Receptor 5 To Control Apoptosis," *Science* 345(6192):98-101.

Lu, P.D. et al. (2004, e-pub. Oct. 11, 2004). "Translation Reinitiation At Alternative Open Reading Frames Regulates Gene Expression In An Integrated Stress Response," *J. Cell Biol.* 167(1):27-33.

Ma, T., et al. (2013). "Suppression of eIF2alpha Kinases Alleviates Alzheimer's Disease-Related Plasticity And Memory Deficits," *Nat. Neurosci.* 16(9):1299-1305.

Ma, X.H., et al. (2014). "Targeting ER Stress-Induced Autophagy Overcomes BRAF Inhibitor Resistance In Melanoma," *J. Clin. Invest.* 124(3):1406-1417.

Marco, S.D. et al. (2012, e-pub. Jun. 12. 2012) "The Translation Inhibitor Pateamine A Prevents Cachexia-Induced Muscle Wasting In Mice," *Nat. Commun.* 12(3):896, 12 pages.

Mihailovich, M., et al. (2007, e-pub. Apr. 16, 2007). "Complex Translational Regulation of BACE1 Involves Upstream Augs And Stimulatory Elements Within the 5' Untranslated Region," *Nucleic Acids Res.* 35(9):2975-2985.

Moller, J.T. et al. (Mar. 21, 1998). "Long-Term Postoperative Cognitive Dysfunction In The Elderly ISPOCD1 Study. ISPOCD

(56) References Cited

OTHER PUBLICATIONS investigators. International Study of Post-Operative Cognitive Dysfunction," *Lancet* 351(9106):857-861.

Moreno, J.A. et al. (2013). "Oral Treatment Targeting The Unfolded Protein Response Prevents Neurodegeneration And Clinical Disease In Prion-Infected Mice," *Sci. Transl. Med.* 5(206):06ra138, 11 pages.

Moreno, J.A. et al. (May 24, 2012). "Sustained Translational Repression By eIF2alpha-P Mediates Prion Neurodegeneration," *Nature* 485(7399):507-511.

Munn, D.H., et al. (May 2005). "GCN2 kinase in T Cells Mediates Proliferative Arrest And Anergy Induction In Response To Indoleamine 2,3-Dioxygenase," *Immunity* 22(5):633-642.

Nagaraju, K. et al. (Jun. 2005). "Activation of the Endoplasmic Reticulum Stress Response In Autoimmune Myositis: Potential Role In Muscle Fiber Damage And Dysfunction," *Arthritis Rheum.* 52(6):1824-1835.

Nagasawa, I. et al. (2017). "BRAF-Mutated Cells Activate GCN2-Mediated Integrated Stress Response As A Cytoprotective Mechanism In Response To Vemurafenib," *Biochem. Biophys. Res. Commun.* 482(4):1491-1497.

Nakamura, T. et al. (Feb. 2014). "Small-Molecule Inhibitors Of PKR Improve Glucose Homeostasis In Obese Diabetic Mice," *Diabetes* 63(2):526-534.

Novoa, I. et al. (2003). "Stress-Induced Gene Expression Requires Programmed Recovery From Translational Repression," *EMBO J.* 22(5):1180-1187.

O'Connor, T. et al. (2008). "Phosphorylation of the Translation Initiation Factor Eif2alpha Increases BACE1 Levels And Promotes Amyloidogenesis," *Neuron* 60(6):988-1009, 42 pages.

Ohno, M. (Apr. 2014). "Roles of eIF2alpha Kinases in the Pathogenesis of Alzheimer's Disease", *Front. Mol. Neurosci.* 7(22):1-8.

Oliveira, M.M. et al. (2019). "The eIF2B Stimulating Drug ISRIB Alleviates Brain Translational Repression and Rescues Long-Term Memory in Alzheimer's Disease Models," *Article*, 44 pages.

Oyadomari, S. et al. (2008). "Dephosphorylation of Translation Initiation Factor 2alpha Enhances Glucose Tolerance And Attenuates Hepatosteatosis In Mice," *Cell Metab.* 7(6):520-532.

Page, G. et al. (2006). "Activated Double-stranded RNA-dependent protein kinase and neuronal death in models of Alzheimer's disease," *Neuroscience* 139(4):1343-1354.

Pakos-Zebrucka, K. et al. (2016, e-pub. Sep. 14, 2016). "The Integrated Stress Response," *EMBO Reports* 17(10):1374-1395.

Palam, L.R. et al. (Apr. 1, 2011). "Phosphorylation of eIF2 Facilitates Ribosomal Bypass of an Inhibitory Upstream ORF to Enhance CHOP Translation," *J. Biol. Chem.* 286(13):10939-10949.

Palam, L.R. et al. (2015, e-pub. Oct. 15, 2015). "Integrated Stress Response is Critical for Gemcitabine Resistance in Pancreatic Ductal Adenocarcinoma," *Cell Death and Disease* 6(e1913):1-13.

Peel, A.L. et al. (2001). "Double-Stranded RNA-Dependent Protein Kinase, PKR, Binds Preferentially To Huntington's Disease (HD) Transcripts And Is Activated In HD Tissue," *Hum. Mol. Genet.* 10(15):1531-1518.

Pike, L.R. et al. (2013). "Transcriptional Up-Regulation Of ULK1 By ATF4 Contributes To Cancer Cell Survival," *Biochem J* 449(2):389-400.

PubChem (Jan. 25, 2012). "AKOS007163870 (N-[2-(4-Chlorophenoxy)ethyl]-1-(3-phenoxypropanoyl)piperidine-4-carboxamide) (PubChemCID:55856026)," located at <https://pubchem.ncbi.nlm.nih.gov/compound/55856026>, last visited Jun. 27, 2019, 10 pages.

PubChem (Jul. 9, 2005). "ISRIB (PubChemCID:1011240)," located at: <https://pubchem.ncbi.nlm.nih.gov/compound/1011240>, lasted visited Jun. 27, 2019, 17 pages.

PubChem (Nov. 29, 2013). "ZINC10313554 MCULE-8385854081 (N-[2-[[2-(2,4-Dichlorophenoxy)acetyl]amino]ethyl]quinoline-2-carboxamide) (PubChemCID:71946601)", 4 pages.

Rabouw, H.H. et al. (Feb. 5, 2019). "Small Molecule ISRIB Suppresses the Integrated Stress Response within a Defined Window of Activation," *PNAS* 116(6):2097-2102.

Radford, H. et al. (2015). "PERK Inhibition Prevents Tau-Mediated Neurodegeneration In A Mouse Model Of Frontotemporal Dementia," *Acta Neuropathol.* 130(5):633-642.

Raught, B. et al. (Oct. 1, 1996). "Expression of a Translationally Regulated, Dominant-Negative CCAAT/Enhancer-Binding Protein Beta Isoform And Up-Regulation Of The Eukaryotic Translation Initiation Factor 2alpha Are Correlated With Neoplastic Transformation Of Mammary Epithelial Cells," *Cancer Res.* 56(19):4382-4386.

Richardson, J.P. et al. (Mar. 2004). "Mutations Causing Childhood Ataxia With Central Nervous System Hypomyelination Reduce Eukaryotic Initiation Factor 2B Complex Formation And Activity," *Mol. Cell Biol.* 24(6):2352-2363.

Robert, F. et al. (2009). "Blocking UV-lnduced Eif2alpha Phosphorylation With Small Molecule Inhibitors Of GCN2," *Chem. Biol. Drug Des* 74(1):57-67.

Rodriguez, P.C. et al. (2010). "L-Arginine Deprivation Regulates Cyclin D3 mRNA Stability In Human T Cells By Controlling HuR Expression," *J. Immunol.* 185(9):5198-5204.

Romero-Ramirez, L. et al. (Apr. 27, 2017). "Integrated Stress Response as a Therapeutic Target for CNS Injuries", HINDAWI 2017(6953156):1-7.

Ron, D. et al. (Jul. 2007). "Signal Integration In The Endoplasmic Reticulum Unfolded Protein Response," *Nat. Rev. Mol. Cell Biol.* 8(7):519-29.

Rosenwald, I.B. et al. (2001). "Expression of Eukaryotic Translation Initiation Factors 4E And 2alpha Is Increased Frequently In Bronchioloalveolar But Not In Squamous Cell Carcinomas Of The Lung," *Cancer* 92(8):2164-2171.

Ryoo, H.D. et al. (2017). "Two Distinct Nodes Of Translational Inhibition In The Integrated Stress Response," *BMP Rep.* 50(11):539-545.

Scaiewicz, V. et al. (2013). "CCAAT/Enhancer-Binding Protein Homologous (CHOP) Protein Promotes Carcinogenesis In The DEN-Induced Hepatocellular Carcinoma Model," *PLoS One* 8(12):e81065.

Scheuner, D., et al. (Jun. 2001). "Translational Control Is Required For The Unfolded Protein Response And In Vivo Glucose Homeostasis," *Mol. Cell* 7(6):1165-1176.

Sekine, Y. et al. (Apr. 9, 2015). "Mutations in a Translation Initiation Factor Identify the Target of a Memory-Enhancing Compound", *Science* aaa6986:1-6.

Sharma, D.K. et al. (2016). "Role of Eukaryotic Initiation Factors during Cellular Stress and Cancer Progression," *J Nucleic Acids* 2016:8235121.

Shrestha, N. et al. (Aug. 17, 2012). "Eukaryotic Initiation Factor 2 (eIF2) Signaling Regulates Proinflammatory Cytokine Expression And Bacterial Invasion," *J. Biol. Chem.* 287(34):28738-28744.

Sidrauski, C. et al. (Apr. 15, 2015). "Pharmacological Dimerization and Activation of the Exchange Factor eIF2B Antagonizes the Integrated Stress Response," *Elife* 4(e07314):1-27.

Sidrauski, C. et al. (Feb. 26, 2015). "The Small Molecule ISRIB Reverses theEffects of eIF2α Phosphorylation on Translation and Stress Granule Assembly," eLIFE 4(e05033):1-16.

Sidrauski, C. et al. (May 28, 2013). "Pharmacological Brake-Release of mRNA Translation Enhances Cognitive Memory", *eLIFE* 2(e00498):1-22.

Southwood, C.M. et al. (Nov. 14, 2002). "The Unfolded Protein Response Modulates Disease Severity In Pelizaeus-Merzbacher Disease," *Neuron* 36(4):585-596.

Stutzbach, L.D. et al. (2013). "The Unfolded Protein Response Is Activated In Disease-Affected Brain Regions In Progressive Supranuclear Palsy And Alzheimer's Disease," *Acta Neuropathol. Commun.* 1(31):1-13.

Tabas, I. et al. (2011). "Integrating The Mechanisms Of Apoptosis Induced By Endoplasmic Reticulum Stress," *Nat. Cell Biol.* 13(3):184-190.

Taylor, S.S. et al. (2005). "PKR and eIF2alpha: Integration Of Kinase Dimerization, Activation, And Substrate Docking," *Cell* 122(6):823-825.

Trinh, M.A. et al. (Oct. 2013). "Translational Control by eIF2α Kinases in Long-lasting Synaptic Plasticity and Long-term Memory," *Neorobiol. Learn Mem.* 105:93-99, 16 pages.

(56) References Cited

OTHER PUBLICATIONS

Trinh, M.A. et al. (Jun. 28, 2012). "Brain-Specific Disruption of the eIF2alpha Kinase PERK Decreases ATF4 Expression and Impairs Behavioral Flexibility," *Cell Rep.* 1(6):676-688.

Tsai, J.C. et al. (Mar. 30, 2018). "Structure of the Nucleotide Exchange Factor eIF2B Reveals Mechanism of Memory-Enhancing Molecule", *Science* 359(6383):1-20.

Van Der Knaap, M.S. et al. (2006). "Vanishing White Matter Disease," *Lancet Neurol.* 5(5):413-423.

Van Der Voorn, J.P. et al. (Sep. 2005). "The Unfolded Protein Response In Vanishing White Matter Disease," *J. Neuropathol. Exp. Neurol.* 64(9):770-775.

Vattem, K.M. et al. (2004). "Reinitiation Involving Upstream ORFS Regulates ATF4 Mrna Translation In Mammalian Cells," *Proc Natl Acad Sci U S A* 101(31):11269-11274.

Vilas-Boas, F. et al. (2016). "Impairment of Stress Granule Assembly Via Inhibition Of The Eif2alpha Phosphorylation Sensitizes Glioma Cells To Chemotherapeutic Agents," *J. Neurooncol.* 127(2):253-60.

Walter, P. et al. (2011). "The Unfolded Protein Response: From Stress Pathway To Homeostatic Regulation," *Science* 334(6059):1081-1086.

Wang, C. et al. (Jul. 19, 2018). "Inhibiting the Integrated Stress ResponsePathway Prevents Aberrant Chondrocyte Differentiation Thereby AlleviatingChondrodysplasia", *eLIFE* 7(e37673):1-35.

Wang, S. et al. (2001). "Expression Of Eukaryotic Translation Initiation Factors 4E And 2alpha Correlates With The Progression Of Thyroid Carcinoma," *Thyroid* 11(12):1101-1107.

Wang, S. et al. (Jul. 1999). "Expression of the Eukaryotic Translation Initiation Factors 4E and 2alpha in Non-Hodgkin's Lymphomas," *Am. J. Pathol.* 155(1):247-255.

Wang, Y. et al. (Aug. 2013). "Amino Acid Deprivation Promotes Tumor Angiogenesis Through The GCN2/ATF4 Pathway," *Neoplasia* 15(8)989-997.

Way, S. et al. (Apr. 2016). "Harnessing the Integrated Stress Response for The Treatment of Multiple Sclerosis," *Lancet Neurol.* 15(4):434-443.

Wek, R.C. et al. (2006). "Coping with Stress: eIF2 Kinases And Translational Control," *Biochem Soc Trans* 34(Pt 1):7-11.

Wek, S.A. et al. (Aug. 1995). "The Histidyl-tRNA Synthetase-Related Sequence In The Eif-2 Alpha Protein Kinase GCN2 Interacts With Trna And Is Required For Activation In Response To Starvation For Different Amino Acids," *Mol. Cell Biol.* 15(8):4497-506.

Wong, Y. L. (Jan. 9, 2019). "eIF2B Activator Prevents Neurological Defects Caused by a Chronic Integrated Stress Response," *eLIFE* 8(e42940):1-31.

Wong, Y. L. et al. (Feb. 28, 2018). "The Small Molecule ISRIB Rescues theStability and Activity of Vanishing White Matter Disease eIF2B Mutant Complexes," *eLIFE* 7(e32733):1-23.

Wortham, N.C. (2015). "eIF2B: Recent Structural and Functional Insightsinto a Key Regulator Of Translation," *Biochemical Society Transactions* 43(6):1234-1240.

Yang, L.B. et al. (Jan. 2003). "Elevated Beta-Secretase Expression And Enzymatic Activity Detected In Sporadic Alzheimer Disease," *Nat. Med.* 9(1):3-4.

Ye, J. et al. (2010). "The GCN2-ATF4 Pathway Is Critical For Tumour Cell Survival And Proliferation In Response To Nutrient Deprivation," *EMBO J.* 29(12):2082-2096. (and Supplemental Material, 9 pages).

Yefidoff-Freedman, R. et al. (e-pub. Jun. 7, 2017). "Development of 1-((1,4-trans)-4-aryloxycyclohexyl)-3-arylurea Activators of the Heme Regulated Inhibitor as Selective Activators of Eucaryotic Translation Initiation Factor 2 Alpha (eIF2#) Phosphorylation Arm of the Integrated Endoplasmic Reticulum Stress Response," *J. Med. Chem.* X(X):1-54.

Zhan, K. et al. (2002). "Phosphorylation of Eukaryotic Initiation Factor 2 By Heme-Regulated Inhibitor Kinase-Related Protein Kinases In Schizosaccharomyces Pombe Is Important For Fesistance To Environmental Stresses," *Mol. Cell Biol.* 22(20):7134-7146.

Zhu, P.J. et al. (Dec. 2011). "Suppression of PKR Promotes Network Excitability And Enhanced Cognition By Interferon-Gamma-Mediated Disinhibition," *Cell* 147(6):1384-1396, 26 pages.

Zyryanova, A.F. (Mar. 30, 2018). "Binding of ISRIB Reveals a Regulatory Site in the Nucleotide Exchange Factor, eIF2B," *Science* 359(6383):1533-1536.

Adams, C.M. et al. (May 2017). "Role of ATF4 in Skeletal Muscle Atrophy," Curr Opin. Clin. Nutr. Metab. Care 20 (3):164-168.

Cao, Y. et al. (2019), "ER Stress-Induced Mediator C/EBP Homologous Protein Thwarts Effector T Cell Activity In Tumors Through T-Bet Repression," Nature Communications 10:1280, 15 pages.

Chen, L. et al. (Aug. 25, 2012). "Tumor Suppression By Small Molecule Inhibitors Of Translation Initiation," Oncotarget 3(8):869-881.

Ebert, S.M. (Oct. 16, 2015, Published, JBC Papers in Press, Sep. 3, 2015). "Identification and Small Molecule Inhibition of an Activating Transcription Factor 4 (ATF4)-dependent Pathway to Age-Related Skeletal Muscle Weakness and Atrophy," 290(42):25497-25511.

Ebert, S.M. et al. (Apr. 2010, e-pub. Mar. 2, 2010). "The Transcription Factor ATF4 Promotes Skeletal Myofiber Atrophy During Fasting," Mol. Endocrinol. 24(4):790-799.

Ebert, S.M. et al. (Aug. 10, 2012). "Stress-induced Skeletal Muscle Gadd45a Expression Reprograms Myonuclei and Causes Muscle Atrophy," Journal of Biology Chemistry 287(33):27290-27301.

Ebert, S.M. et al. (Feb. 28, 2020, e-pub. Jan. 17, 2020). "Activating Transcription Factor 4 (ATF4) Promotes Skeletal Muscle Atrophy By Forming A Heterodimer With The Transcriptional Regulator C/EBPb," JBC (The Journal of Biological Chemistry) 295:2787-2803, 30 pages.

Eley, H.L. (2008, e-pub. Dec. 18, 2007). "Increased Expression Of Phosphorylated Forms Of RNA-Dependent Protein Kinase And Eukaryotic Initiation Factor 2α May Signal Skeletal Muscle Atrophy In Weight-Losing Cancer Patients," British Journal of Cancer 98:443-449.

Hernandez, G. et al. (Jan. 3, 2020). "Pancreatitis Is An FGF21-Deficient State That Is Corrected by Replacement Therapy," Sci. Transl. Med. 12:eaay5186, 12 pages.

Igarashi, T. et al. (2007, e-pub. Feb. 12, 2007). "Clock And ATF4 Transcription System Regulates Drug Resistance In Human Cancer Cell Lines," Oncogene 26:4749-4760.

International Preliminary Report on Patentability dated Jun. 16, 2020, for Patent Application No. PCT/US2018/065555, filed Dec. 13, 2018, 7 pages.

International Search Report and Written Opinion of the International Searching Authority dated Jun. 19, 2020, for Patent Application No. PCT/US2020/019552, filed Feb. 24, 2020, 18 pages.

International Search Report and Written Opinion of the International Searching Authority dated Oct. 30, 2020, for International Patent. Application No. PCT/US20/37309, filed Jun. 11, 2020, 12 pages.

Invitation to Pay Additional Fees, dated Apr. 13, 2020, for PCT Application No. PCT/US2020/019552, filed Feb. 24, 2020, 3 pages.

Jiang, Z. et al. (Feb. 17, 2010). "eIF2α Phosphorylation-Dependent Translation In CA1 Pyramidal Cells Impairs Hippocampal Memory Consolidation Without Affecting General Translation," J. Neurosci. 30(7):2582-2594.

Milani, M. et al. (May 15, 2009). "The Role of ATF4 Stabilization and Autophagy in Resistance of Breast Cancer Cells Treated with Bortezomib," Cancer Res. 69(10):4415-4423.

Namba, T. et al. (2007), "Up-Regulation of 150-kDa Oxygen-Regulated Protein by Celecoxib in Human Gastric Carcinoma Cells," Mol. Pharmacol. 71(3):860-870.

Nguyen, H.G. (May 2, 2018). "Development Of A Stress Response Therapy Targeting Aggressive Prostate Cancer," Sci. Transl. Med. 10(439):1-24, 24 pages.

Onat, U.I. et al. (Mar. 19, 2019). "Intercepting the Lipid-Induced Integrated Stress Response Reduces Atherosclerosis," JACC 73(10):1149-1169.

PubChem (Jul. 30, 2007). "N-(1-Benzylpiperidin-4-yl)-1-cyclopropyl-6,7-difluoro-8-methoxy-4-oxoquinoline-3-carboxamide," PubChem CID 16417729, 13 pages.

(56) References Cited

OTHER PUBLICATIONS

PubChem (Aug. 6, 2016)."N-[[4-[[2-(4-Chlorophenoxy) acetyl]amino]cyclohexyl]methyl]-2-(4-chlorophenyl) acetamide," PubChem-CID: 121258884; 9 pages.

Sacheck, J. M. (2007). "Rapid Disuse And Denervation Atrophy Involve Transcriptional Changes Similar To Those Of Muscle Wasting During Systemic Diseases," *FASEB J.* 21:140-155.

Stone, S. et al. (Jul. 29, 2015). "The Unfolded Protein Response In Multiple Sclerosis," 9(264):1-11, 11 pages.

Thevenot, P.T. et al. (Sep. 18, 2014). "The Stress-Response Sensor Chop Regulates The Function And Accumulation Of Myeloid-Derived Suppressor Cells In Tumors," 41(3):389-401.

U.S. Appl. No. 16/899,520, filed Jun. 11, 2020, for Luz Marina Delgado Oyarzo, et al.

U.S. Appl. No. 16/899,521, filed Jun. 11, 2020, for Sebastian Bernales, et al.

Watanabe, S. et al. (pre-print Feb. 27, 2020). "Resetting Proteostasis With ISRIB Prevents Pulmonary Fibrosis," located at: https://www.biorxiv.org/content/10.1101/2020.02.26.965566v1.article-info, last visted on Jul. 30, 2020, 42 pages.

Youg-Baird, S.K. et al. (Feb. 20, 2020, e-pub. Dec. 10, 2019). "Suppression of MEHMO Syndrome Mutation in eIF2 by Small Molecule ISRIB," Mol. Cell. 77(4):875-886.e7, 66 pages.

Zhu, P. J. et al. (Nov. 15, 2019). "Activation Of The ISR Mediates The Behavioral And Neurophysiological Abnormalities In Down Syndrome," Science 366:843-849, 8 pages.

International Preliminary Report on Patentability dated Dec. 17, 2020, for Patent Application No. PCT/US2019/035593, filed Jun. 5, 2019, 9 pages.

Remission. (obtained on Jan. 13, 2021) Definition of Remission. Medical Dictionary from Harvard located at: https://www.health.harvard.edu/medical-dictionary-of-health-terms/q-through-z#R-terms, last visited on Jan. 13, 2021, 2 pages.

Remission. (obtained on Jan. 13, 2021) Definition of Remission. NIH: Dictionary of Cancer Terms located at: https://www.cancer.gov/publications/dictionaries/cancer-terms/def/remission, last visited on Jan. 13, 2021, 1 page.

\* cited by examiner

US 11,166,942 B2

INHIBITORS OF INTEGRATED STRESS RESPONSE PATHWAY

CROSS REFERENCE TO RELATED APPLICATIONS

This application claims the priority benefit of U.S. Provisional Patent Application No. 62/681,071, filed Jun. 5, 2018, the disclosure of which is hereby incorporated herein by reference in its entirety.

FIELD

The present disclosure relates generally to therapeutic agents that may be useful as inhibitors of Integrated Stress Response (ISR) pathway.

BACKGROUND

Diverse cellular conditions and stresses activate a widely conserved signaling pathway termed the Integrated Stress Response (ISR) pathway. The ISR pathway is activated in response to intrinsic and extrinsic stresses, such as viral infections, hypoxia, glucose and amino acid deprivation, oncogene activation, UV radiation, and endoplasmic reticulum stress. Upon activation of ISR by one or more of these factors, the eukaryotic initiation factor 2 (eIF2, which is comprised of three subunits, α, β and γ) becomes phosphorylated in its α-subunit and rapidly reduces overall protein translation by binding to the eIF2B complex. This phosphorylation inhibits the eIF2B-mediated exchange of GDP for GTP (i.e., a guanine nucleotide exchange factor (GEF) activity), sequestering eIF2B in a complex with eIF2 and reducing general protein translation of most mRNA in the cell. Paradoxically, eIF2a phosphorylation also increases translation of a subset of mRNAs that contain one or more upstream open reading frames (uORFs) in their 5' untranslated region (UTR). These transcripts include the transcriptional modulator activating transcription factor 4 (ATF4), the transcription factor CHOP, the growth arrest and DNA damage-inducible protein GADD34 and the β-secretase BACE-1.

In animals, the ISR modulates a broad translational and transcriptional program involved in diverse processes such as learning memory, immunity, intermediary metabolism, insulin production and resistance to unfolded protein stress in the endoplasmic reticulum, among others. Activation of the ISR pathway has also been associated with numerous pathological conditions including cancer, neurodegenerative diseases (such as amyotrophic lateral sclerosis, Huntington disease, or prior disease), metabolic diseases (metabolic syndrome), autoimmune diseases, inflammatory diseases (such as cystic fibrosis), musculoskeletal diseases (such as myopathy), vascular diseases, and ocular diseases.

BRIEF SUMMARY

Inhibitors of the Integrated Stress Response (ISR) pathway are described, as are methods of making and using the compounds, or salts thereof.

DETAILED DESCRIPTION

Figure 1:
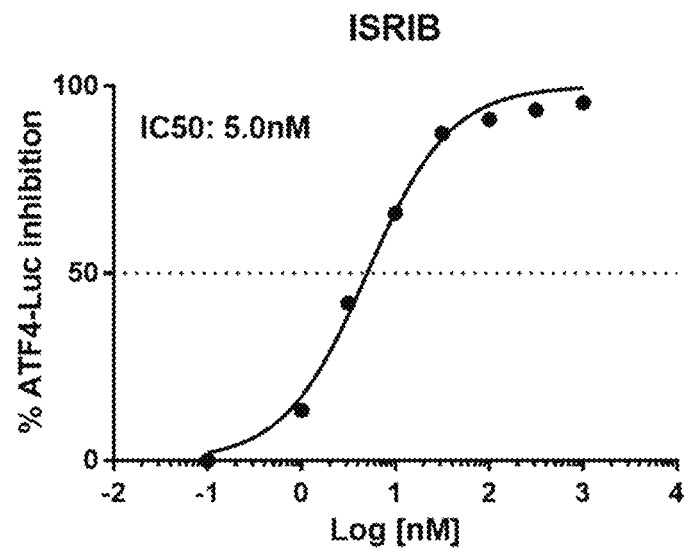
FIG. 1 shows an $IC_{50}$ titration for inhibition of ATF4 in stressed HEK293T cells using a luciferase assay for ISRIB (trans-N,N'-1,4-cyclohexanediylbis[2-(4-chlorophenoxy)-acetamide). ISRIB was found to have an $IC_{50}$ of 5 nM.

Described herein are compounds, including therapeutic agents, that can inhibit the ISR pathway. These compounds could be used in the prevention and/or treatment of certain pathological conditions as described herein, and/or in biotechnology applications that would benefit from increased protein translation.

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Alkylene" as used herein refers to the same residues as alkyl, but having bivalency. Particular alkylene groups are those having 1 to 20 carbon atoms (a "$C_1$-$C_{20}$ alkylene"), having 1 to 10 carbon atoms (a "$C_1$-$C_{10}$ alkylene"), having 6 to 10 carbon atoms (a "$C_6$-$C_{10}$ alkylene"), having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), isopropylene (—$CH_2CH(CH_3)$—), butylene (—$CH_2(CH_2)_2CH_2$—), isobutylene (—$CH_2CH(CH_3)CH_2$—), pentylene (—$CH_2(CH_2)_3CH_2$—), hexylene (—$CH_2(CH_2)_4CH_2$—), heptylene (—$CH_2(CH_2)_5CH_2$—), octylene (—$CH_2(CH_2)_6CH_2$—), and the like.

"Alkenyl" as used herein refers to and includes, unless otherwise stated, an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). An alkenyl group may have "cis" or "trans" configurations, or alternatively have "E" or "Z" configurations. Particular alkenyl groups are those having 2 to 20 carbon atoms (a "$C_2$-$C_{20}$ alkenyl"), having 6 to 10 carbon atoms (a "$C_6$-$C_{10}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, pent-1-enyl, pent-2-enyl, hex-1-enyl, hex-2-enyl, hex-3-enyl, and the like.

"Alkenylene" as used herein refers to the same residues as alkenyl, but having bivalency. Particular alkenylene groups are those having 2 to 20 carbon atoms (a "$C_2$-$C_{20}$ alkenylene"), having 2 to 10 carbon atoms (a "$C_2$-$C_{10}$ alkenylene"), having 6 to 10 carbon atoms (a "$C_6$-$C_{10}$ alkenylene"), having 2 to 6 carbon atoms (a "$C_2$-$C_6$ alkenylene"), 2 to 4 carbon atoms (a "$C_2$-$C_4$ alkenylene") or 2 to 3 carbon atoms (a "$C_2$-$C_3$ alkenylene"). Examples of alkenylene include, but are not limited to, groups such as ethenylene (or vinylene) (—CH=CH—), propenylene (—CH=CHCH_2—), 1,4-but-1-enylene (—CH=CH—$CH_2CH_2$—), 1,4-but-2-enylene (—$CH_2$CH=CH$CH_2$—), 1,6-hex-1-enylene (—CH=CH—$(CH_2)_3CH_2$—), and the like.

"Alkynyl" as used herein refers to and includes, unless otherwise stated, an unsaturated linear (i.e., unbranched) or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 6 to 10 carbon atoms (a "$C_6$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, and the like.

"Alkynylene" as used herein refers to the same residues as alkynyl, but having bivalency. Particular alkynylene groups are those having 2 to 20 carbon atoms (a "$C_2$-$C_{20}$ alkynylene"), having 2 to 10 carbon atoms (a "$C_2$-$C_{10}$ alkynylene"), having 6 to 10 carbon atoms (a "$C_6$-$C_{10}$ alkynylene"), having 2 to 6 carbon atoms (a "$C_2$-$C_6$ alkynylene"), 2 to 4 carbon atoms (a "$C_2$-$C_4$ alkynylene") or 2 to 3 carbon atoms (a "$C_2$-$C_3$ alkynylene"). Examples of alkynylene include, but are not limited to, groups such as ethynylene (or acetylenylene) (—C≡C—), propynylene (—C≡CCH$_2$—), and the like.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Cycloalkylene" as used herein refers to the same residues as cycloalkyl, but having bivalency. Cycloalkylene can consist of one ring or multiple rings which may be fused, spiro or bridged, or combinations thereof. Particular cycloalkylene groups are those having from 3 to 12 annular carbon atoms. A preferred cycloalkylene is a cyclic hydrocarbon having from 3 to 8 annular carbon atoms (a "$C_3$-$C_8$ cycloalkylene"), having 3 to 6 carbon atoms (a "$C_3$-$C_6$ cycloalkylene"), or having from 3 to 4 annular carbon atoms (a "C3-$C_4$ cycloalkylene"). Examples of cycloalkylene include, but are not limited to, cyclopropylene, cyclobutylene, cyclopentylene, cyclohexylene, cycloheptylene, norbornylene, and the like. A cycloalkylene may attach to the remaining structures via the same ring carbon atom or different ring carbon atoms. When a cycloalkylene attaches to the remaining structures via two different ring carbon atoms, the connecting bonds may be cis- or trans- to each other. For example, cyclopropylene may include 1,1-cyclopropylene and 1,2-cyclopropylene (e.g., cis-1,2-cyclopropylene or trans-1,2-cyclopropylene), or a mixture thereof.

"Cycloalkenyl" refers to and includes, unless otherwise stated, an unsaturated cyclic non-aromatic univalent hydrocarbon structure, having at least one site of olefinic unsaturation (i.e., having at least one moiety of the formula C=C) and having the number of carbon atoms designated (i.e., $C_2$-$C_{10}$ means two to ten carbon atoms). Cycloalkenyl can consist of one ring, such as cyclohexenyl, or multiple rings, such as norbornenyl. A preferred cycloalkenyl is an unsaturated cyclic hydrocarbon having from 3 to 8 annular carbon atoms (a "$C_3$-$C_8$ cycloalkenyl"). Examples of cycloalkenyl groups include, but are not limited to, cyclopropenyl, cyclobutenyl, cyclopentenyl, cyclohexenyl, norbornenyl, and the like.

"Cycloalkenylene" as used herein refers to the same residues as cycloalkenyl, but having bivalency.

"Aryl" or "Ar" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Arylene" as used herein refers to the same residues as aryl, but having bivalency. Particular arylene groups are those having from 6 to 14 annular carbon atoms (a "$C_6$-$C_{14}$ arylene").

"Heteroaryl" as used herein refers to an unsaturated aromatic cyclic group having from 1 to 14 annular carbon atoms and at least one annular heteroatom, including but not limited to heteroatoms such as nitrogen, oxygen, and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5 to 14-membered rings having 1 to 12 annular carbon atoms and 1 to 6 annular heteroatoms independently selected from nitrogen, oxygen, and sulfur, 5 to 10-membered rings having 1 to 8 annular carbon atoms and 1 to 4 annular heteroatoms independently selected from nitrogen, oxygen, and sulfur, or 5, 6 or 7-membered rings having 1 to 5 annular carbon atoms and 1 to 4 annular heteroatoms independently selected from nitrogen, oxygen, and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen, and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

"Heteroarylene" as used herein refers to the same residues as heteroaryl, but having bivalency.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. A heterocycle comprising more than one ring may be fused, bridged or spiro, or any combination thereof, but excludes heteroaryl. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

"Heterocyclylene" as used herein refers to the same residues as heterocyclyl, but having bivalency.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoromethyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C=O.

"Thiocarbonyl" refers to the group C=S.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In one embodiment, an optionally substituted group is unsubstituted.

Unless clearly indicated otherwise, "an individual" as used herein intends a mammal, including but not limited to a primate, human, bovine, horse, feline, canine, or rodent. In one variation, the individual is a human.

As used herein, "treatment" or "treating" is an approach for obtaining beneficial or desired results including clinical results. For purposes of this disclosure, beneficial or desired results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. The methods of the present disclosure contemplate any one or more of these aspects of treatment.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents (e.g., a compound, or pharmaceutically acceptable salt thereof), and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

A "therapeutically effective amount" refers to an amount of a compound or salt thereof sufficient to produce a desired therapeutic outcome.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the present disclosure in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound of the present disclosure as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

Compounds

In one aspect, provided is a compound of formula (I):

or a pharmaceutically acceptable salt thereof,
wherein:
$m^1$, $m^2$, $n^1$, $n^2$, $p^1$, $p^2$, $q^1$, and $q^2$, independently of each other, are 0 or 1;
r and s, independently of each other, are 0, 1, or 2;
X is N or $CR^X$;
$R^X$ is selected from the group consisting of hydrogen, $C_1$-$C_6$ alkyl, $C_2$-$C_6$ alkenyl, and $C_2$-$C_6$ alkynyl;
j is 0 or 1;
$R^{j-a}$ and $R^{j-b}$ are taken together to form an oxo (=O) substituent, or $R^{j-a}$ and $R^{j-b}$ are both hydrogen;
k is 0 or 1;
$R^{N-k}$ is H or $C_1$-$C_6$ alkyl;
$R^N$ is H or $C_1$-$C_6$ alkyl;
$A^1$ is selected from the group consisting of:
a substituent of formula ($A^1$-a)

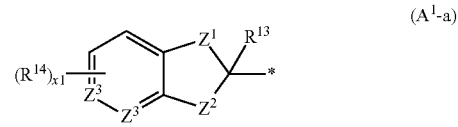

wherein
* represents the attachment point to the remainder of the molecule; $Z^1$ is selected from the group consisting of $CR^{Z1-1}R^{Z1-2}$, $NR^{Z1-2}$, $C(R^{Z1-1}R^{Z1-2})N(R^{Z1-2})$, O, $C(R^{Z1-1}R^{Z1-2})O$, S, $C(R^{Z1-1}R^{Z1-2})S$, and $-CR^{Z1-1}=CR^{Z1-1}-$;
wherein $R^{Z-1}$ is H or $R^{14}$; and $R^{Z1-2}$ is H or $R^{14}$;
$Z^2$ is selected from the group consisting of $CR^{Z2-1}R^{Z2-2}$, $NR^{Z2-2}$, $C(R^{Z2-1}R^{Z2-2})N(R^{Z2-2})$, O, $C(R^{Z2-1}R^{Z2-2})O$, S, $C(R^{Z2-1}R^{Z2-2})S$,
and $-CR^{Z2-1}=CR^{Z2-1}-$;
wherein $R^{Z2-1}$ is H or $R^{14}$; and $R^{Z2-2}$ is H or $R^{14}$;
$Z^3$, independently at each occurrence, is CH, $CR^{14}$, or N;
$R^{13}$ is hydrogen or $R^{14}$, or $R^{13}$ and $R^{Z1-2}$ are taken together to form a double bond between the carbon atom bearing $R^{13}$ and $Z^1$, or $R^{13}$ and $R^{Z2-2}$ are taken together to form a double bond between the carbon atom bearing $R^{13}$ and $Z^2$; and
x1 is 0, 1, 2, 3, or 4;
$C_6$-$C_{14}$ aryl optionally substituted with one or more $R^{14}$ substituents; and
5-14 membered heteroaryl optionally substituted with one or more $R^{14}$ substituents;
$R^{14}$ is selected, independently at each occurrence, from the group consisting of halogen, $NO_2$, $C_1$-$C_6$ alkyl, $C_2$-$C_6$ alkenyl, $C_2$-$C_6$ alkynyl, $C_1$-$C_6$ haloalkyl, —OH, —O($C_1$-$C_6$ alkyl), —O($C_1$-$C_6$ haloalkyl), —SH,

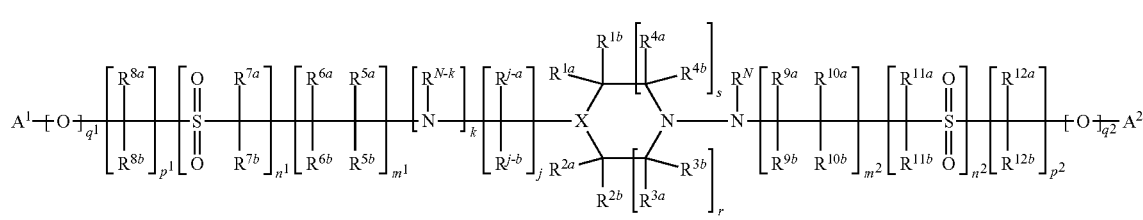

(I)

—S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{14-a}R^{14-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{14-a}R^{14-b}$, S(O)$_2$ OH, —S(O)$_2$O($C_1$-$C_6$ alkyl), —S(O)$_2$O($C_1$-$C_6$ haloalkyl), —S(O)$_2$$NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$$NR^{14-a}R^{14-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{14-a}$ and $R^{14-b}$ are taken together with the nitrogen atom to which they are attached to form a 3-10 membered heterocycle;

$A^2$ is selected from the group consisting of:

a substituent of formula ($A^2$-a)

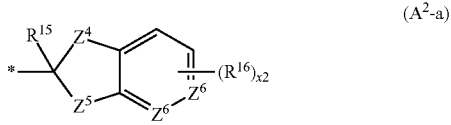

($A^2$-a)

wherein
* represents the attachment point to the remainder of the molecule; $Z^4$ is selected from the group consisting of $CR^{Z4-1}R^{Z4-2}$, $NR^{Z4-2}$, $C(R^{Z4-1}R^{Z4-2})N(R^{Z4-2})$, O, $C(R^{Z4-1}R^{Z4-2})O$, S, $C(R^{Z4-1}R^{Z4-2})S$, and —$CR^{Z4-1}$=$CR^{Z4-1}$—;
wherein $R^{Z4-1}$ is H or $R^{16}$; and $R^{Z4-2}$ is H or $R^{16}$.
$Z^5$ is selected from the group consisting of $CR^{Z5-1}R^{Z5-2}$, $NR^{Z5-2}$,
$C(R^{Z5-1}R^{Z5-2})N(R^{Z5-2})$, O, $C(R^{Z5-1}R^{Z5-2})O$, S, $C(R^{Z5-1}R^{Z5-2})S$,
and —$CR^{Z5-1}$=$CR^{Z5-1}$—.
wherein $R^{Z5-1}$ is H or $R^{16}$; and $R^{Z5-2}$ is H or $R^{16}$.
$Z^6$, independently at each occurrence, is CH, $CR^{16}$, or N;
$R^{15}$ is hydrogen or $R^{16}$, or $R^{15}$ and $R^{Z4-2}$ are taken together to form a double bond between the carbon atom bearing $R^{15}$ and $Z^4$, or $R^{15}$ and $R^{Z5-2}$ are taken together to form a double bond between the carbon atom bearing $R^{15}$ and $Z^5$; and
x2 is 0, 1, 2, 3, or 4;
$C_6$-$C_{14}$ aryl optionally substituted with one or more $R^{16}$ substituents; and
5-14 membered heteroaryl optionally substituted with one or more $R^{16}$ substituents;
$R^{16}$ is selected, independently at each occurrence, from the group consisting of halogen, $NO_2$, $C_1$-$C_6$ alkyl, $C_2$-$C_6$ alkenyl, $C_2$-$C_6$ alkynyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{16-a}R^{16-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{16-a}R^{16-b}$, —S(O)$_2$OH, —S(O)$_2$O($C_1$-$C_6$ alkyl), —S(O)$_2$O($C_1$-$C_6$ haloalkyl), —S(O)$_2$$NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$$NR^{16-a}R^{16-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{16-a}$ and $R^{16-b}$ are taken together with the nitrogen atom to which they are attached to form a 3-10 membered heterocycle;

$R^{1a}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen, or
$R^{1a}$ is taken together with $R^{2a}$ to form a $C_1$-$C_6$ alkylene moiety, or
$R^{1a}$ is taken together with an $R^{3a}$ moiety to form a $C_1$-$C_6$ alkylene moiety;

$R^{1b}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{2a}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{2b}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{3a}$ independently at each occurrence is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen, or $R^{3a}$ is taken together with $R^{4a}$ to form a $C_1$-$C_6$ alkylene moiety;

$R^{3b}$ independently at each occurrence is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{4a}$ independently at each occurrence is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{4b}$ independently at each occurrence is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{5a}$ and $R^{5b}$ are taken together to form an oxo (=O) substituent or an imido (=NH) substituent, or $R^{5a}$ and $R^{5b}$ are both hydrogen;

$R^{6a}$ is selected from the group consisting of hydrogen, —$OR^{6a-a}$, and —$NR^{6a-b}R^{6a-c}$;

$R^{6b}$ is hydrogen;

or $R^{6a}$ and $R^{6b}$ are taken together to form a moiety selected from the group consisting of —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, and —CH$_2$—CH$_2$—CH$_2$—CH$_2$—O—;

$R^{7a}$ and $R^{7b}$ are both hydrogen;

$R^{8a}$ and $R^{8b}$ are taken together to form an oxo (=O) substituent, or $R^{8a}$ and $R^{8b}$ are both hydrogen;

$R^{9a}$ and $R^{9b}$ are taken together to form an oxo (=O) substituent or an imido (=NH) substituent, or $R^{9a}$ and $R^{9b}$ are both hydrogen;

$R^{10a}$ is selected from the group consisting of hydrogen, —OR$^{10a\text{-}a}$, and —NR$^{10a\text{-}b}$R$^{10a\text{-}c}$ and $R^{10b}$ is hydrogen, or $R^{10a}$ and $R^{10b}$ are taken together to form a moiety selected from the group consisting of —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, and —CH$_2$—CH$_2$—CH$_2$—CH$_2$—O—;

$R^{11a}$ and $R^{11b}$ are both hydrogen;

$R^{12a}$ and $R^{12b}$ are taken together to form an oxo (=O) substituent, or $R^{12a}$ and $R^{12b}$ are both hydrogen;

$R^{6a\text{-}a}$ is selected from the group consisting of hydrogen, C$_1$-C$_6$ alkyl, and C$_1$-C$_6$ haloalkyl, or $R^{6a\text{-}a}$ is taken together with $R^{N\text{-}k}$ to form a carbonyl (C=O) moiety;

$R^{10a\text{-}a}$ is selected from the group consisting of hydrogen, C$_1$-C$_6$ alkyl, and C$_1$-C$_6$ haloalkyl, or $R^{10a\text{-}a}$ is taken together with $R^N$ to form a carbonyl (C=O) moiety;

$R^{6a\text{-}b}$ and $R^{6a\text{-}c}$, independently of each other, are selected from the group consisting of hydrogen, C$_1$-C$_6$ alkyl, and C$_1$-C$_6$ haloalkyl; and $R^{10a\text{-}b}$ and $R^{10a\text{-}c}$, independently of each other, are selected from the group consisting of hydrogen, C$_1$-C$_6$ alkyl, and C$_1$-C$_6$ haloalkyl;

provided that:

(i) when j is 1, then k is 1;

(ii) when m$^1$ is 0, n$^1$ is 0, q$^1$ is 0, and p$^1$ is 1, then $R^{8a}$ and $R^{8b}$ are taken together to form an oxo (=O) substituent, and A$^1$ is a substituent of formula (A$^1$-a)

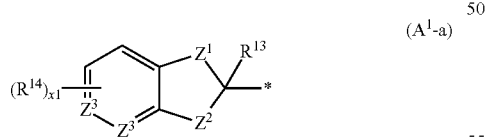

(A$^1$-a)

wherein

* represents the attachment point to the remainder of the molecule; Z$^1$ is selected from the group consisting of CR$^{Z1\text{-}1}$R$^{Z1\text{-}2}$, NR$^{Z1\text{-}2}$, C(R$^{Z1\text{-}1}$R$^{Z1\text{-}2}$)N(R$^{Z1\text{-}2}$), O, C(R$^{Z1\text{-}1}$R$^{Z1\text{-}2}$)O, S, C(R$^{Z1\text{-}1}$R$^{Z1\text{-}2}$)S, and —CR$^{Z1\text{-}1}$=CR$^{Z1\text{-}1}$—;

wherein R$^{Z1\text{-}1}$ is H or R$^{14}$; and R$^{Z1\text{-}2}$ is H or R$^{14}$;

Z$^2$ is selected from the group consisting of CR$^{Z2\text{-}1}$R$^{Z2\text{-}2}$, NR$^{Z2\text{-}2}$, C(R$^{Z2\text{-}1}$R$^{Z2\text{-}2}$)N(R$^{Z2\text{-}2}$), O, C(R$^{Z2\text{-}1}$R$^{Z2\text{-}2}$)O, S, C(RZ$^{2\text{-}1}$R$^{Z2\text{-}2}$)S, and —CR$^{Z2\text{-}1}$=CR$^{Z2\text{-}1}$—;

wherein R$^{Z2\text{-}1}$ is H or R$^{14}$; and RZ$^{2\text{-}2}$ is H or R$^{14}$; Z$^3$, independently at each occurrence, is CH, CR$^{14}$, or N;

$R^{13}$ is hydrogen or R$^{14}$, or $R^{13}$ and $R^{Z1\text{-}2}$ are taken together to form a double bond between the carbon atom bearing $R^{13}$ and Z$^1$, or $R^{13}$ and $R^{Z2\text{-}2}$ are taken together to form a double bond between the carbon atom bearing $R^{13}$ and Z$^2$; and x1 is 0, 1, 2, 3, or 4; and (iii) when m$^2$ is 0, n$^2$ is 0, q$^2$ is 0, and p$^2$ is 1, then $R^{12a}$ and $R^{12b}$ are taken together to form an oxo (=O) substituent, and A$^2$ is a substituent of formula (A$^2$-a)

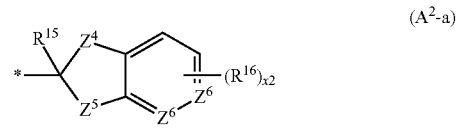

(A$^2$-a)

wherein

* represents the attachment point to the remainder of the molecule;

Z$^4$ is selected from the group consisting of CR$^{Z4\text{-}1}$R$^{Z4\text{-}2}$, NR$^{Z4\text{-}2}$, C(R$^{Z4\text{-}1}$R$^{Z4\text{-}2}$)N(R$^{Z4\text{-}2}$), O, C(R$^{Z4\text{-}1}$R$^{Z4\text{-}2}$)O, S, C(R$^{Z4\text{-}1}$R$^{Z4\text{-}2}$)S, and —CR$^{Z4\text{-}1}$=CR$^{Z4\text{-}1}$—;

wherein R$^{Z4\text{-}1}$ is H or R$^{16}$; and R$^{Z4\text{-}2}$ is H or R$^{16}$.

Z$^5$ is selected from the group consisting of CR$^{Z5\text{-}1}$R$^{Z5\text{-}2}$, NR$^{Z5\text{-}2}$, C(R$^{Z5\text{-}1}$R$^{Z5\text{-}2}$)N(R$^{Z5\text{-}2}$), O, C(R$^{Z5\text{-}1}$R$^{Z5\text{-}2}$)O, S, C(R$^{Z5\text{-}1}$R$^{Z5\text{-}2}$)S, and —CR$^{Z5\text{-}1}$=CR$^{Z5\text{-}1}$—;

wherein R$^{Z5\text{-}1}$ is H or R$^{16}$; and R$^{Z5\text{-}2}$ is H or R$^{16}$.

Z$^6$, independently at each occurrence, is CH, CR$^{16}$, or N;

$R^{15}$ is hydrogen or R$^{16}$, or $R^{15}$ and $R^{Z4\text{-}2}$ are taken together to form a double bond between the carbon atom bearing $R^{15}$ and Z$^4$, or $R^{15}$ and $R^{Z5\text{-}2}$ are taken together to form a double bond between the carbon atom bearing $R^{15}$ and Z$^5$; and x2 is 0, 1, 2, 3, or 4;

(iv) when X is CR$^X$, then k is 1;

(v) when X is N, j is 1, and k is 1, then R$^{j\text{-}a}$ and R$^{j\text{-}b}$ are taken together to form an oxo (=O) substituent;

(vi) when X is N, j is 0 and k is 1; then at least one of (vi-a), (vi-b), (vi-c), or (vi-d) applies:

(vi-a) A$^1$ is C$_6$-C$_{14}$ aryl substituted with one or more R$^{14}$ substituents;

(vi-b) A$^1$ is 5-14 membered heteroaryl optionally substituted with one or more R$^{14}$ substituents;

(vi-c) A$^2$ is C$_6$-C$_{14}$ aryl substituted with one or more R$^{16}$ substituents;

(vi-d) A$^2$ is 5-14 membered heteroaryl optionally substituted with one or more R$^{16}$ substituents; and (vii) when X is N, j is 0, k is 0, m$^1$ is 1, n$^1$ is 0, p$^1$ is 0, and q$^1$ is 0, then A$^1$ is a substituent of formula (A$^1$-a).

In some embodiments of the compound of formula (I), X is CR$^X$ and k is 1, and the compound of formula (I) is a compound of formula (II):

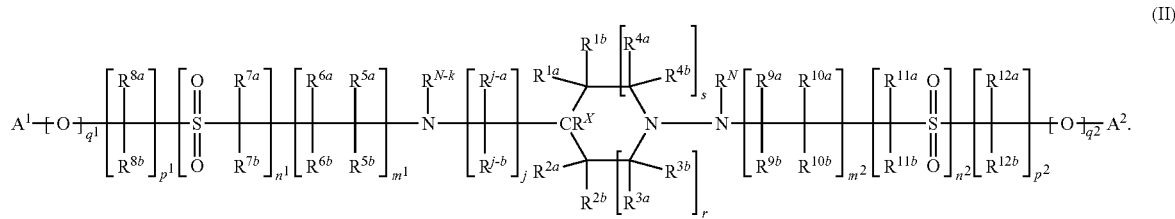

(II)

or a pharmaceutically acceptable salt thereof;

wherein $m^1$, $m^2$, $n^1$, $n^2$, $p^1$, $p^2$, $q^1$, $q^2$, r, s, $R^X$, j, $R^{j-a}$, $R^{j-b}$, $R^{N-k}$, $R^N$, $A^1$, $A^2$, $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{12a}$, and $R^{12b}$ are as defined in compounds of formula (I).

In some embodiments of the compound of formula (I), X is N, and the compound of formula (I) is a compound of formula (III):

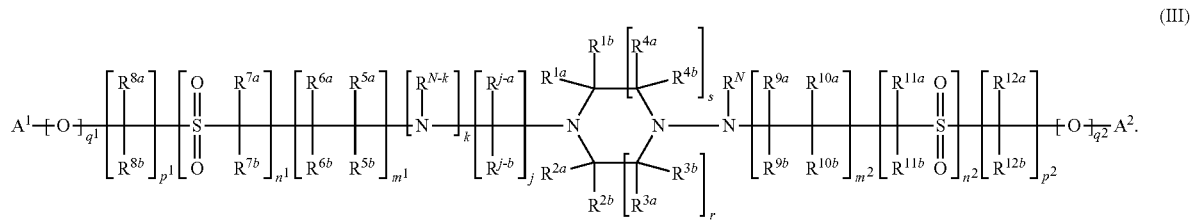

(III)

or a pharmaceutically acceptable salt thereof;

wherein $m^1$, $m^2$, $n^1$, $n^2$, $p^1$, $p^2$, $q^1$, $q^2$, r, s, j, $R^{j-a}$, $R^{j-b}$, k, $R^{N-k}$, $R^N$, $A^1$, $A^2$, $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{12a}$, and $R^{12b}$ are as defined in compounds of formula (I).

In some embodiments of the compounds of formula (I), (II), or (III), r is 0. In some embodiments of the compounds of formula (I), (II), or (III), r is 1. In some embodiments of the compounds of formula (I), (II), or (III), r is 2.

In some embodiments of the compounds of formula (I), (II), or (III), s is 0. In some embodiments of the compounds of formula (I), (II), or (III), s is 1. In some embodiments of the compounds of formula (I), (II), or (III), s is 2.

In some embodiments of the compounds of formula (I), (II), or (III), r is 1 and s is 1. In some embodiments, $R^{1a}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen, or $R^{1a}$ is taken together with $R^{2a}$ to form a $C_1$-$C_6$ alkylene moiety, or $R^{1a}$ is taken together with an $R^{3a}$ moiety to form a $C_1$-$C_6$ alkylene moiety; $R^{1b}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen; $R^{2a}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen; $R^{2b}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen; $R^{3a}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen; or $R^{3a}$ is taken together with $R^{4a}$ to form a $C_1$-$C_6$ alkylene moiety; $R^{3b}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen; $R^{4a}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen; and $R^{41}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen. In some embodiments, $R^{1a}$ is selected from the group consisting of hydrogen, $C_1$-$C_6$ alkyl, —C(O)OH, and halogen. In some embodiments, $R^{1a}$ is hydrogen. In some embodiments, $R^{1a}$ is $C_1$-$C_6$ alkyl. In some embodiments, $R^{1a}$ is methyl. In some embodiments, $R^{1a}$ is —C(O)OH. In some embodiments, $R^{1a}$ is halogen. In some embodiments, $R^{1a}$ is fluoro. In some embodiments, $R^{1b}$ is selected from the group consisting of hydrogen, $C_1$-$C_6$ alkyl, —C(O)OH, and halogen. In some embodiments, $R^{1b}$ is hydrogen. In some embodiments, $R^{1b}$ is $C_1$-$C_6$ alkyl. In some embodiments, $R^{1b}$ is methyl. In some embodiments, $R^{1b}$ is —C(O)OH. In some embodiments, $R^{1b}$ is halogen. In some embodiments, $R^{1b}$ is fluoro. In some embodiments, $R^{2a}$ is selected from the group consisting of hydrogen, $C_1$-$C_6$ alkyl, —C(O)OH, and halogen. In some embodiments, $R^{2a}$ is hydrogen. In some embodiments, $R^{2a}$ is $C_1$-$C_6$ alkyl. In some embodiments, $R^{2a}$ is methyl. In some embodiments, $R^{2a}$ is —C(O)OH. In some embodiments, $R^{2a}$ is halogen. In some embodiments, $R^{2a}$ is fluoro. In some embodiments, $R^{2b}$ is selected from the group consisting of hydrogen, $C_1$-$C_6$ alkyl, —C(O)OH, and halogen. In some embodiments, $R^{2b}$ is hydrogen. In some embodiments, $R^{21}$ is $C_1$-$C_6$ alkyl. In some embodiments, $R^{2b}$ is methyl. In some embodiments, $R^{2b}$ is —C(O)OH. In some embodiments, $R^{2b}$ is halogen. In some embodiments, $R^{2b}$ is fluoro. In some embodiments, $R^{3a}$ is selected from the group consisting of hydrogen, $C_1$-$C_6$ alkyl, —C(O)OH, and halogen. In some embodiments, $R^{3a}$ is hydrogen. In some embodiments, $R^{3a}$ is $C_1$-$C_6$ alkyl. In some embodiments, $R^{3a}$ is methyl. In some embodiments, $R^{3a}$ is —C(O)OH. In some embodiments, $R^{3a}$ is halogen. In some embodiments, $R^{3a}$ is fluoro. In some embodiments, $R^{3b}$ is selected from the group consisting of hydrogen, $C_1$-$C_6$ alkyl, —C(O)OH, and halogen. In some embodiments, $R^{3b}$ is hydrogen. In some embodiments, $R^{3b}$ is $C_1$-$C_6$ alkyl. In some embodiments, $R^{3b}$ is methyl. In some embodiments, $R^{3b}$ is —C(O)OH. In some embodiments, $R^{3b}$ is halogen. In some embodiments, $R^{3b}$ is fluoro. In some embodiments, $R^{4a}$ is selected from the group consisting of hydrogen, $C_1$-$C_6$ alkyl, —C(O)

OH, and halogen. In some embodiments, $R^{4a}$ is hydrogen. In some embodiments, $R^{4a}$ is $C_1$-$C_6$ alkyl. In some embodiments, $R^{4a}$ is methyl. In some embodiments, $R^{4a}$ is —C(O)OH. In some embodiments, $R^{4a}$ is halogen. In some embodiments, $R^{4a}$ is fluoro. In some embodiments, $R^{4b}$ is selected from the group consisting of hydrogen, $C_1$-$C_6$ alkyl, —C(O)OH, and halogen. In some embodiments, $R^{4b}$ is hydrogen. In some embodiments, $R^{4b}$ is $C_1$-$C_6$ alkyl. In some embodiments, $R^{4b}$ is methyl. In some embodiments, $R^{4b}$ is —C(O)OH. In some embodiments, $R^{4b}$ is halogen. In some embodiments, $R^{4b}$ is fluoro. In some embodiment, $R^{1a}$ is taken together with $R^{2a}$ to form a $C_1$-$C_6$ alkylene moiety. In some embodiment, $R^{1a}$ is taken together with $R^{2a}$ to form a methylene (—CH$_2$—) moiety. In some embodiment, $R^{1a}$ is taken together with $R^{2a}$ to form an ethylene (—CH$_2$—CH$_2$—) moiety. In some embodiment, $R^{1a}$ is taken together with $R^{2a}$ to form a propylene (—CH$_2$—CH$_2$—CH$_2$—) moiety. In some embodiment, $R^{1a}$ is taken together with $R^{3a}$ to form a $C_1$-$C_6$ alkylene moiety. In some embodiment, $R^{1a}$ is taken together with $R^{3a}$ to form a methylene (—CH$_2$—) moiety. In some embodiment, $R^{1a}$ is taken together with $R^{3a}$ to form an ethylene (—CH$_2$—CH$_2$—) moiety. In some embodiment, $R^{1a}$ is taken together with $R^{3a}$ to form a propylene (—CH$_2$—CH$_2$—CH$_2$—) moiety. In some embodiment, $R^{3a}$ is taken together with $R^{4a}$ to form a $C_1$-$C_6$ alkylene moiety. In some embodiment, $R^{3a}$ is taken together with $R^{4a}$ to form a methylene (—CH$_2$—) moiety. In some embodiment, $R^{3a}$ is taken together with $R^{4a}$ to form an ethylene (—CH$_2$—CH$_2$—) moiety. In some embodiment, $R^{3a}$ is taken together with $R^{4a}$ to form a propylene (—CH$_2$—CH$_2$—CH$_2$—) moiety. In some embodiments, $R^{1a}$, $R^{1b}$, $R^{2a}$, and $R^{2b}$, are all $C_1$-$C_6$ alkyl, and $R^{3a}$, $R^{3b}$, $R^{4a}$, and $R^{4b}$ are all hydrogen. In some embodiments, $R^{1a}$, $R^{1b}$, $R^{2a}$, and $R^{2b}$, are all methyl, and $R^{3a}$, $R^{3b}$, $R^{4a}$, and $R^{4b}$ are all hydrogen. In some embodiments, $R^{1a}$ and $R^{2a}$ are both $C_1$-$C_6$ alkyl, and $R^{1b}$, $R^{2b}$, $R^{3a}$, $R^{3b}$, $R^{4a}$, and $R^{4b}$ are all hydrogen. In some embodiments, $R^{1a}$ and $R^{2a}$ are both methyl, and $R^{1b}$, $R^{2b}$, $R^{3a}$, $R^{3b}$, $R^{4a}$, and $R^{4b}$ are all hydrogen. In some embodiments, $R^{1a}$ is —C(O)OH and $R^{1b}$, $R^{2a}$, $R^{2b}$, $R^{3a}$, $R^{3b}$, $R^{4a}$, and $R^{4b}$ are all hydrogen. In some embodiments, $R^{3a}$ is fluoro and $R^{1a}$, $R^{1b}$, $R^{2a}$, $R^{2b}$, $R^{3b}$, $R^{4a}$, and $R^{4b}$ are all hydrogen.

In some embodiments of the compounds of formula (I), (II), or (III), $m^1$ is 0, $n^1$ is 0, $p^1$ is 1, $q^1$ is 0, $R^{8a}$ and $R^{8b}$ are taken together to form an oxo (═O) substituent, and $A^1$ is a substituent of formula ($A^1$-a)

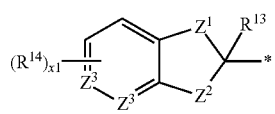

wherein
* represents the attachment point to the remainder of the molecule;
$Z^1$ is selected from the group consisting of $CR^{Z1-1}R^{Z1-2}$, $NR^{Z1-2}$, $C(R^{Z1-1}R^{Z1-2})N(R^{Z1-2})$, O, $C(R^{Z1-1}R^{Z1-2})O$, S, $C(R^{Z1-1}R^{Z1-2})S$,
and —$CR^{Z1-1}$═$CR^{Z1-1}$—;
wherein $R^{Z1-1}$ is H or $R^{14}$; and $R^{Z1-2}$ is H or $R^1$;
$Z^2$ is selected from the group consisting of $CR^{Z2-1}R^{Z2-2}$, $NR^{Z2-2}$, $C(R^{Z2-1}R^{Z2-2})N(R^{Z2-2})$, O, $C(R^{Z2-1}R^{Z2-2})O$, S, $C(R^{Z2-1}R^{Z2-2})S$,
and —$CR^{Z2-1}$═$CR^{Z2-1}$—;
wherein $R^{Z2-1}$ is H or $R^{14}$; and $R^{Z2-2}$ is H or $R^{14}$;
$Z^3$, independently at each occurrence, is CH, $CR^{14}$, or N;

$R^{13}$ is hydrogen or $R^{14}$, or $R^{13}$ and $R^{Z1-2}$ are taken together to form a double bond between the carbon atom bearing $R^{13}$ and $Z^1$, or $R^{13}$ and $R^{Z2-2}$ are taken together to form a double bond between the carbon atom bearing $R^{13}$ and $Z^2$; and x1 is 0, 1, 2, 3, or 4.

In some embodiments of the compounds of formula (I), (II), or (III), $m^1$ is 0, $n^1$ is 0, $p^1$ is 1, $q^1$ is 0, $R^{8a}$ and $R^{8b}$ are taken together to form an oxo (═O) substituent, and $A^1$ is a substituent of formula ($A^1$-a) selected from the group consisting of:

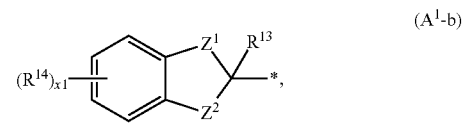

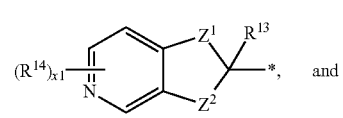

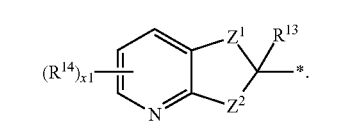

In some embodiments, ($A^1$-a) is ($A^1$-b). In some embodiments, ($A^1$-a) is ($A^1$-c). In some embodiments, ($A^1$-a) is ($A^1$-d). In some embodiments, ($A^1$-a) or ($A^1$-b) is selected from the group consisting of:

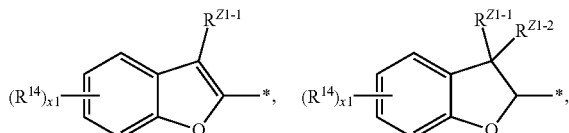

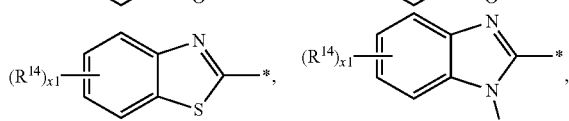

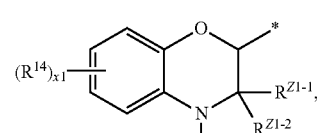

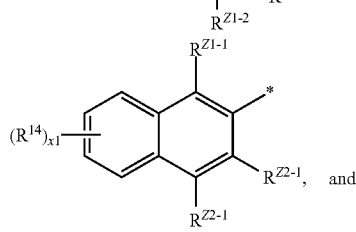

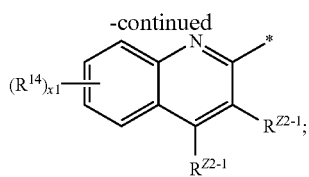

wherein the * represents the attachment point to the remainder of the molecule. In some embodiments, (A¹-a) or (A¹-b) is selected from the group consisting of:

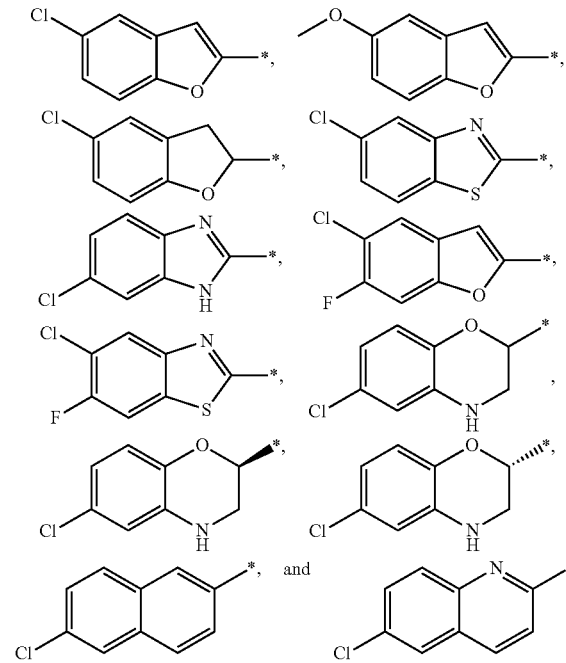

wherein the * represents the attachment point to the remainder of the molecule. In some embodiments, (A¹-a) or (A¹-b) is selected from the group consisting of:

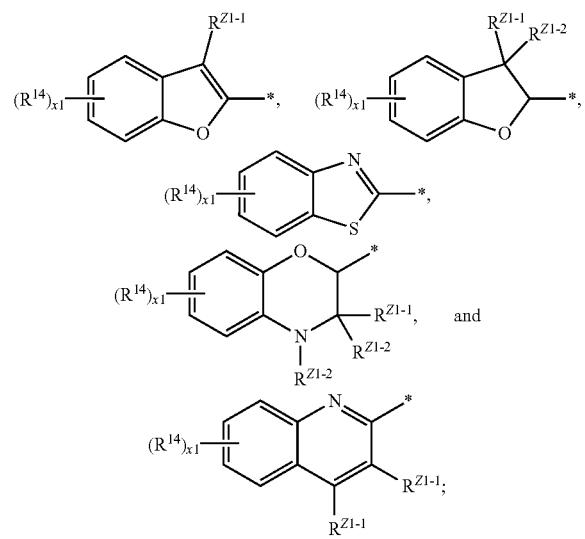

wherein the * represents the attachment point to the remainder of the molecule. In some embodiments, (A¹-a) or (A¹-b) is selected from the group consisting of:

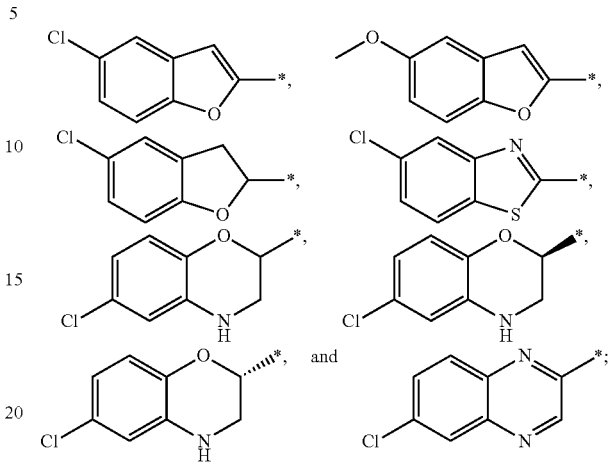

wherein the * represents the attachment point to the remainder of the molecule. In some embodiments, (A¹-a) or (A¹-b) is selected from the group consisting of:

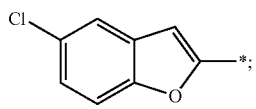

wherein the * represents the attachment point to the remainder of the molecule. In some embodiments, (A¹-a) or (A¹-b) is

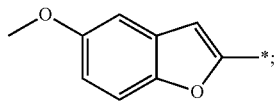

wherein the * represents the attachment point to the remainder of the molecule. In some embodiments, (A¹-a) or (A¹-b) is

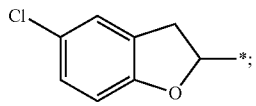

wherein the * represents the attachment point to the remainder of the molecule. In some embodiments, (A¹-a) or (A¹-b) is

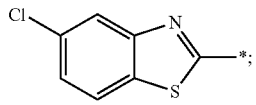

wherein the * represents the attachment point to the remainder of the molecule. In some embodiments, (A¹-a) or (A¹-b) is

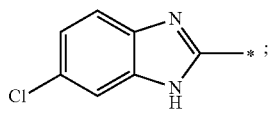

wherein the represents the attachment point to the remainder of the molecule. In some embodiments, (A¹-a) or (A¹-b) is

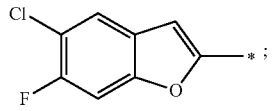

wherein the * represents the attachment point to the remainder of the molecule. In some embodiments, (A¹-a) or (A¹-b) is

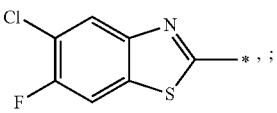

wherein the * represents the attachment point to the remainder of the molecule. In some embodiments, (A¹-a) or (A¹-b) is

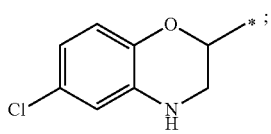

wherein the * represents the attachment point to the remainder of the molecule. In some embodiments, (A¹-a) or (A¹-b) is

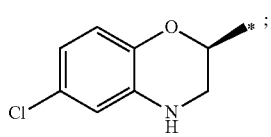

wherein the * represents the attachment point to the remainder of the molecule. In some embodiments, (A¹-a) or (A¹-b) is

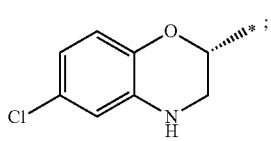

wherein the * represents the attachment point to the remainder of the molecule. In some embodiments, (A¹-a) or (A¹-b) is

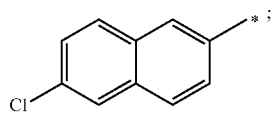

wherein the * represents the attachment point to the remainder of the molecule. In some embodiments, (A¹-a) or (A¹-b) is

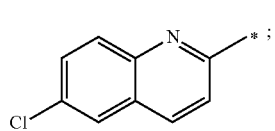

wherein the * represents the attachment point to the remainder of the molecule. In some embodiments, (A¹-a) or (A¹-c) is selected from the group consisting of:

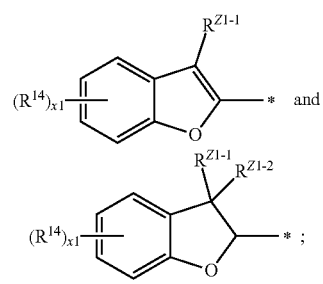

wherein the * represents the attachment point to the remainder of the molecule. In some embodiments, (A¹-a) or (A¹-c) is selected from the group consisting of:

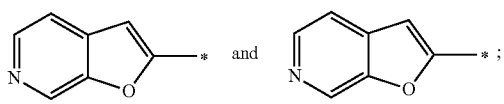

wherein the * represents the attachment point to the remainder of the molecule. In some embodiments, (A¹-a) or (A¹-c) is

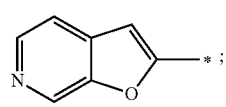

wherein the * represents the attachment point to the remainder of the molecule. In some embodiments, (A¹-a) or (A¹-c) is

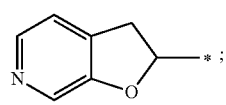

wherein the * represents the attachment point to the remainder of the molecule.

In some embodiments of the compounds of formula (I), (II), or (III), $m^1$ is 0, $n^1$ is 0, $p^1$ is 1, $q^1$ is 1, $R^{8a}$ and $R^{8b}$ are taken together to form an oxo (=O) substituent.

In some embodiments of the compounds of formula (I), (II), or (III), $m^1$ is 1, $n^1$ is 0, $p^1$ is 0, and q is 1. In some embodiments, $R^{5a}$, $R^{5b}$, $R^{6a}$, and $R^{6b}$ are all hydrogen. In some embodiments, $R^{5a}$ and $R^{5b}$ are taken together to form an oxo (=O) substituent or an imido (=NH) substituent, and $R^{6a}$ and $R^{6b}$ are both hydrogen. In some embodiments, $R^{5a}$ and $R^{5b}$ are taken together to form an oxo (=O) substituent, and $R^{6a}$ and $R^{6b}$ are both hydrogen. In some embodiments, $R^{5a}$ and $R^{5b}$ are taken together to form an imido (=NH) substituent, and $R^{6a}$ and $R^{6b}$ are both hydrogen. In some embodiments, $R^{5a}$ and $R^{5b}$ are both hydrogen, and $R^{6a}$ and $R^{6b}$ are taken together to form a moiety selected from the group consisting of —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, and —CH$_2$—CH$_2$—CH$_2$—CH$_2$—O—. In some embodiments, $R^{5a}$ and $R^{5b}$ are both hydrogen, and $R^{6a}$ and $R^{6b}$ are taken together to form a —CH$_2$—O—CH$_2$— moiety.

In some embodiments of the compounds of formula (I), (II), or (III), $m^1$ is 1, $n^1$ is 0, $p^1$ is 0, and $q^1$ is 0, $R^{5a}$, $R^{5b}$, $R^{6a}$, and $R^{6b}$ are all hydrogen, and A1 is a substituent of formula (A$^1$-a)

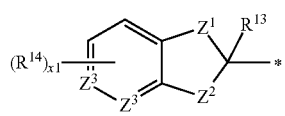

(A$^1$-a)

wherein
* represents the attachment point to the remainder of the molecule; $Z^1$ is selected from the group consisting of CR$^{Z1-1}$R$^{Z1-2}$, NR$^{Z1-2}$, C(R$^{Z1-1}$R$^{Z1-2}$)N(R$^{Z1-2}$), O, C(R$^{Z1-1}$R$^{Z1-2}$)O, S, C(R$^{Z1-1}$R$^{Z1-2}$)S, and —CR$^{Z1-1}$=CR$^{Z1-1}$—;
wherein R$^{Z1-1}$ is H or R$^{14}$; and R$^{Z1-2}$ is H or R$^4$;
$Z^2$ is selected from the group consisting of CR$^{Z2-1}$R$^{Z2-2}$, NR$^{Z2-2}$, C(R$^{Z2-1}$R$^{Z2-2}$)N(R$^{Z2-2}$), O, C(R$^{Z2-1}$R$^{Z2-2}$)O, S, C(R$^{Z2-1}$R$^{Z2-2}$)S, and —CR$^{Z2-1}$=CR$^{Z2-1}$;
wherein R$^{Z2-1}$ is H or R$^{14}$; and R$^{Z2-2}$ is H or R$^{14}$;
$Z^3$, independently at each occurrence, is CH, CR$^{14}$, or N;
$R^{13}$ is hydrogen or $R^{14}$, or $R^{13}$ and R$^{Z1-2}$ are taken together to form a double bond between the carbon atom bearing $R^{13}$ and $Z^1$, or $R^{13}$ and R$^{Z2-2}$ are taken together to form a double bond between the carbon atom bearing $R^{13}$ and $Z^2$; and
x1 is 0, 1, 2, 3, or 4.

In some embodiments of the compounds of formula (I), (II), or (III), $m^1$ is 1, $n^1$ is 0, $p^1$ is 0, and $q^1$ is 0, $R^{5a}$, $R^{5b}$, $R^{6a}$, and $R^{6b}$ are all hydrogen, and $A^1$ is a substituent of formula (A$^1$-a) selected from the group consisting of:

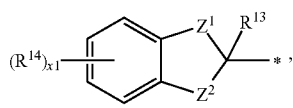

(A$^1$-b)

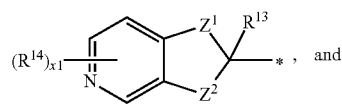

(A$^1$-c)

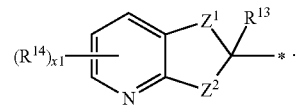

(A$^1$-d)

In some embodiments, (A$^1$-a) is (A$^1$-b). In some embodiments, (A$^1$-a) is (A$^1$-c). In some embodiments, (A$^1$-a) is (A$^1$-d). In some embodiments, (A$^1$-a) or (A$^1$-b) is selected from the group consisting of:

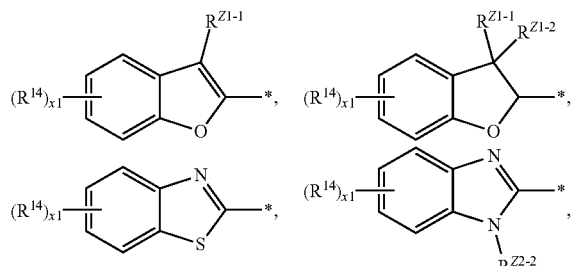

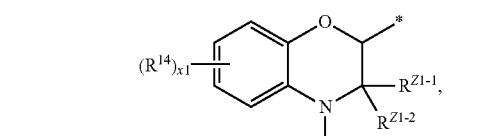

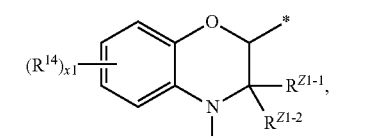

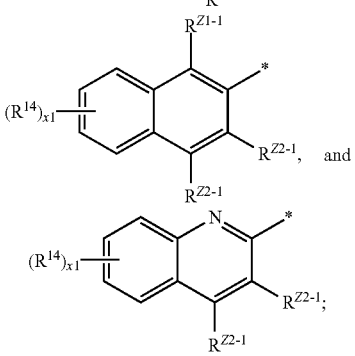

wherein the * represents the attachment point to the remainder of the molecule. In some embodiments, (A$^1$-a) or (A$^1$-b) is selected from the group consisting of:

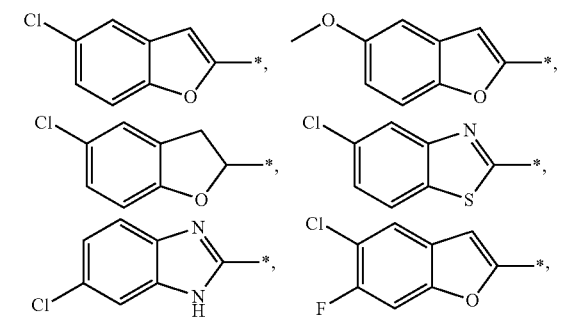

-continued

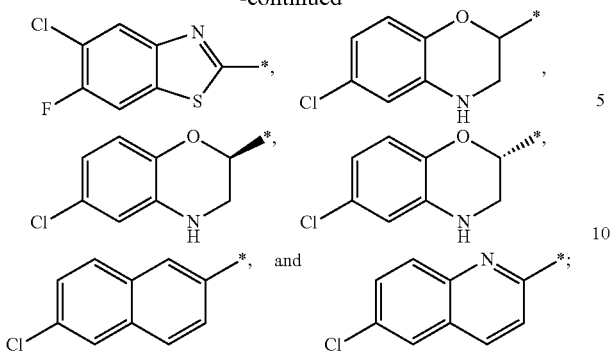

wherein the * represents the attachment point to the remainder of the molecule. In some embodiments, (A¹-a) or (A¹-b) is selected from the group consisting of:

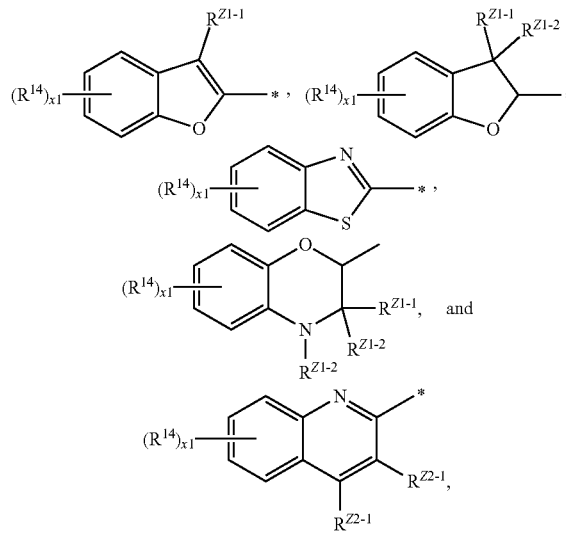

wherein the * represents the attachment point to the remainder of the molecule. In some embodiments, (A¹-a) or (A¹-b) is selected from the group consisting of:

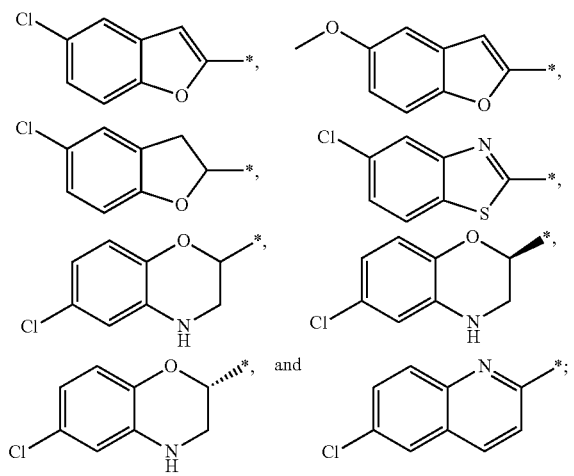

wherein the * represents the attachment point to the remainder of the molecule. In some embodiments, (A¹-a) or (A¹-b) is selected from the group consisting of:

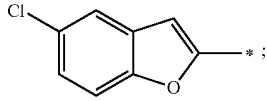

wherein the * represents the attachment point to the remainder of the molecule. In some embodiments, (A¹-a) or (A¹-b) is

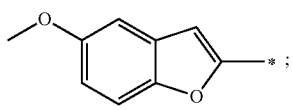

wherein the * represents the attachment point to the remainder of the molecule. In some embodiments, (A¹-a) or (A¹-b) is

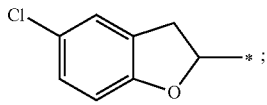

wherein the * represents the attachment point to the remainder of the molecule. In some embodiments, (A¹-a) or (A¹-b) is

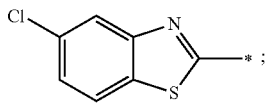

wherein the * represents the attachment point to the remainder of the molecule. In some embodiments, (A¹-a) or (A¹-b) is

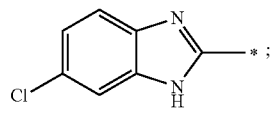

wherein the represents the attachment point to the remainder of the molecule. In some embodiments, (A¹-a) or (A¹-b) is

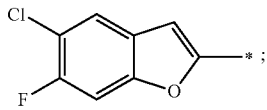

wherein the * represents the attachment point to the remainder of the molecule. In some embodiments, (A¹-a) or (A¹-b) is

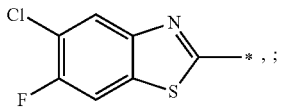

wherein the * represents the attachment point to the remainder of the molecule. In some embodiments, (A¹-a) or (A¹-b) is

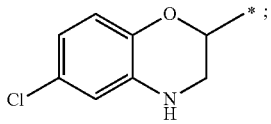

wherein the * represents the attachment point to the remainder of the molecule. In some embodiments, (A¹-a) or (A¹-b) is

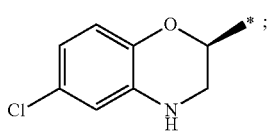

wherein the * represents the attachment point to the remainder of the molecule. In some embodiments, (A¹-a) or (A¹-b) is

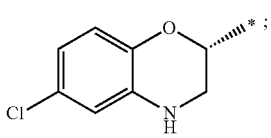

wherein the * represents the attachment point to the remainder of the molecule. In some embodiments, (A¹-a) or (A¹-b) is

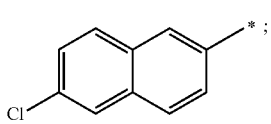

wherein the * represents the attachment point to the remainder of the molecule. In some embodiments, (A¹-a) or (A¹-b) is

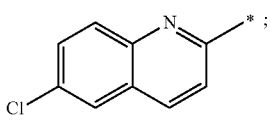

wherein the * represents the attachment point to the remainder of the molecule. In some embodiments, (A¹-a) or (A¹-c) is selected from the group consisting of:

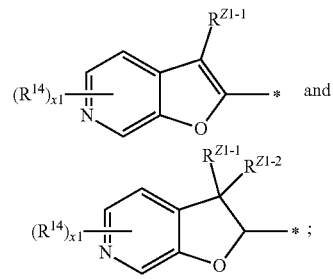

wherein the * represents the attachment point to the remainder of the molecule. In some embodiments, (A¹-a) or (A¹-c) is selected from the group consisting of:

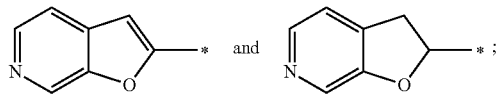

wherein the * represents the attachment point to the remainder of the molecule. In some embodiments, (A¹-a) or (A¹-c) is

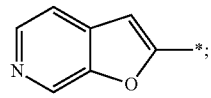

wherein the * represents the attachment point to the remainder of the molecule. In some embodiments, (A¹-a) or (A¹-c) is

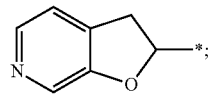

wherein the * represents the attachment point to the remainder of the molecule.

In some embodiments of the compounds of formula (I), (II), or (III), $m^1$ is 1, $n^1$ is 0, $p^1$ is 0, and $q^1$ is 0; $R^{5a}$, $R^{5b}$, and $R^{6b}$ are all hydrogen, and $R^{6a}$ is —$OR^{6a\text{-}a}$ or —$NR^{6a\text{-}b}R^{6a\text{-}c}$. In some embodiments, $R^{6a}$ is —$OR^{6a\text{-}a}$. In some embodiments, $R^{6a}$ is —$OR^{6a\text{-}a}$ and $R^{6a\text{-}a}$ is hydrogen.

In some embodiments of the compounds of formula (I), (II), or (III), $m^1$ is 1, $n^1$ is 0, $p^1$ is 1, and $q^1$ is 1. In some embodiments, $R^{5a}$, $R^{5b}$, $R^{6b}$, $R^{8a}$, and $R^{8b}$ are all hydrogen, and $R^{6a}$ is selected from the group consisting of hydrogen, —$OR^{6a\text{-}a}$, and —$NR^{6a\text{-}b}R^{6a\text{-}c}$. In some embodiments, $R^{5a}$, $R^{5b}$, $R^{6a}$, $R^{6b}$, $R^{8a}$, and $R^{8b}$ are all hydrogen. In some embodiments, $R^{5a}$, $R^{5b}$, $R^{6b}$, $R^{8a}$, and $R^{8b}$ are all hydrogen, and $R^{6a}$ is —$OR^{6a\text{-}a}$. In some embodiments, $R^{5a}$, $R^{5b}$, $R^{6b}$, $R^{8a}$, and $R^{8b}$ are all hydrogen, $R^{6a}$ is —$OR^{6a\text{-}a}$, and $R^{6a\text{-}a}$ is hydrogen. In some embodiments, $R^{5a}$, $R^{5b}$, $R^{6b}$, $R^{8a}$, and $R^{8b}$ are all hydrogen, and $R^{6a}$ is —$NR^{6a\text{-}b}R^{6a\text{-}c}$. In some embodiments, $R^{5a}$, $R^{5b}$, $R^{6b}$, $R^{8a}$, and $R^{8b}$ are all hydrogen, $R^{6a}$ is —$NR^{6a\text{-}b}R^{6a\text{-}c}$, $R^{6a\text{-}b}$ and $R^{6a\text{-}c}$ are both hydrogen. In some embodiments, $R^{5a}$ and $R^{5b}$ are taken together to form an oxo (=O) substituent or an imido (=NH) substituent. In some embodiments, $R^{5a}$ and $R^{5b}$ are taken together to form an oxo (=O) substituent, $R^{6b}$, $R^{8a}$, and $R^{8b}$ are all hydrogen, and $R^{6a}$ is selected from the group consisting of hydrogen, —$OR^{6a-a}$, and —$NR^{6a-b}R^{6a-c}$. In some embodiments, $R^{5a}$ and $R^{5b}$ are taken together to form an oxo (=O) substituent, and $R^{6a}$, $R^{6b}$, $R^{8a}$, and $R^{8b}$ are all hydrogen. In some embodiments, $R^{5a}$ and $R^{5b}$ are taken together to form an oxo (=O) substituent, $R^{6b}$, $R^{8a}$, and $R^{8b}$ are all hydrogen, and $R^{6a}$ is —$OR^{6a-a}$. In some embodiments, $R^{5a}$ and $R^{5b}$ are taken together to form an oxo (=O) substituent, $R^{6b}$, $R^{8a}$, and $R^{8b}$ are all hydrogen, $R^{6a}$ is —$OR^{6a-a}$, and $R^{6a-a}$ is hydrogen. In some embodiments, $R^{5a}$ and $R^{5b}$ are taken together to form an oxo (=O) substituent, $R^{6b}$, $R^{8a}$, and $R^{8b}$ are all hydrogen, and $R^{6a}$ is —$NR^{6a-b}R^{6a-c}$. In some embodiments, $R^{5a}$ and $R^{5b}$ are taken together to form an oxo (=O) substituent, $R^{6b}$, $R^{8a}$, and $R^{8b}$ are all hydrogen, $R^{6a}$ is —$NR^{6a-b}R^{6a-c}$, $R^{6a-b}$ and $R^{6a-c}$ are both hydrogen. In some embodiments, $R^{5a}$ and $R^{5b}$ are taken together to form an imido (=NH) substituent, $R^{6b}$, $R^{8a}$, and $R^{8b}$ are all hydrogen, and $R^{6a}$ is selected from the group consisting of hydrogen, —$OR^{6a-a}$, and —$NR^{6a-b}R^{6a-c}$. In some embodiments, $R^{5a}$ and $R^{5b}$ are taken together to form an imido (=NH) substituent, and $R^{6a}$, $R^{6b}$, $R^{8a}$, and $R^{8b}$ are all hydrogen. In some embodiments, $R^{5a}$ and $R^{5b}$ are taken together to form an imido (=NH) substituent, $R^{6b}$, $R^{8a}$, and $R^{8b}$ are all hydrogen, and $R^{6a}$ is —$OR^{6a-a}$. In some embodiments, $R^{5a}$ and $R^{5b}$ are taken together to form an imido (=NH) substituent, $R^{6b}$, $R^{8a}$, and $R^{8b}$ are all hydrogen, $R^{6a}$ is —$OR^{6a-a}$, and $R^{6a-a}$ is hydrogen. In some embodiments, $R^{5a}$ and $R^{5b}$ are taken together to form an imido (=NH) substituent, $R^{6b}$, $R^{8a}$, and $R^{8b}$ are all hydrogen, and $R^{6a}$ is —$NR^{6a-b}R^{6a-c}$. In some embodiments, $R^{5a}$ and $R^{5b}$ are taken together to form an imido (=NH) substituent, $R^{6b}$, $R^{8a}$, and $R^{8b}$ are all hydrogen, $R^{6a}$ is —$NR^{6a-b}R^{6a-c}$, $R^{6a-b}$ and $R^{6a-c}$ are both hydrogen.

In some embodiments of the compounds of formula (I), (II), or (III), k is 1, $m^1$ is 1, $n^1$ is 0, $p^1$ is 1, $q^1$ is 1, $R^{6a}$ is —$OR^{6a-a}$, and $R^{6a-a}$ is taken together with $R^{N-k}$ to form a carbonyl (C=O) moiety, and $R^{5a}$, $R^{5b}$, $R^{8a}$, and $R^{8b}$ are all hydrogen.

In some embodiments of the compounds of formula (I), (II), or (III), $m^1$ is 0, $n^1$ is 1, $p^1$ is 1, $q^1$ is 1, $R^{1a}$, $R^{7b}$, $R^{8a}$, and $R^{8b}$ are all hydrogen.

In some embodiments of the compounds of formula (I), (II), or (III), $m^2$ is 0, $n^2$ is 0, $p^2$ is 1, $q^2$ is 0, $R^{12a}$ and $R^{12b}$ are taken together to form an oxo (=O) substituent, and $A^2$ is a substituent of formula ($A^2$-a)

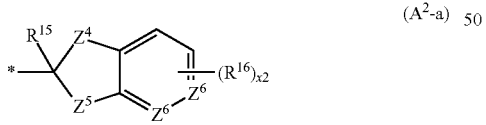

wherein
* represents the attachment point to the remainder of the molecule; $Z^4$ is selected from the group consisting of $CR^{Z4-1}R^{Z4-2}$, $NR^{Z4-2}$, $C(R^{Z4-1}R^{Z4-2})N(R^{Z4-2})$, O, $C(R^{Z4-1}R^{Z4-2})O$, S, $C(R^{Z4-1}R^{Z4-2})$, and —$CR^{Z4-1}$=$CR^{Z4-1}$—;
wherein $R^{Z4-1}$ is H or $R^{16}$; and $R^{Z4-2}$ is H or $R^{16}$. $Z^5$ is selected from the group consisting of $CR^{Z5-1}R^{Z5-2}$, $NR^{Z5-2}$, $C(R^{Z5-1}R^{Z5-2})N(R^{Z5-2})$, O, $C(R^{Z5-1}R^{Z5-2})O$, S, $C(R^{Z5-1}R^{Z5-2})S$, and —$CR^{Z5-1}$=$CR^{Z5-1}$—;
wherein $R^{Z5-1}$ is H or $R^{16}$; and $R^{Z5-2}$ is H or $R^{16}$—

$Z^6$, independently at each occurrence, is CH, $CR^{16}$, or N;

$R^{15}$ is hydrogen or $R^{16}$, or $R^{15}$ and $R^{Z4-2}$ are taken together to form a double bond between the carbon atom bearing $R^{15}$ and $Z^4$, or $R^{15}$ and $R^{Z5-2}$ are taken together to form a double bond between the carbon atom bearing $R^{15}$ and $Z^5$; and x2 is 0, 1, 2, 3, or 4;

In some embodiments of the compounds of formula (I), (II), or (III), $m^2$ is 0, $n^2$ is 0, $p^2$ is 1, $q^2$ is 0, $R^{12a}$ and $R^{12b}$ are taken together to form an oxo (=O) substituent, and $A^2$ is a substituent of formula ($A^2$-a) selected from the group consisting of:

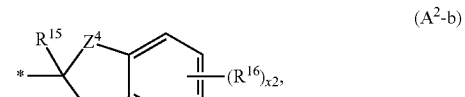

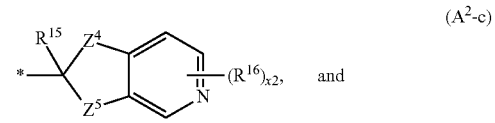

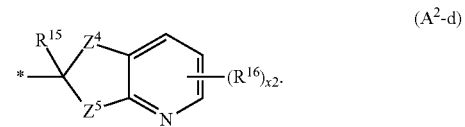

In some embodiments of the compounds of formula (1-1), ($A^2$-a) is ($A^2$-b). In some embodiments of the compounds of formula (1-1), ($A^2$-a) is ($A^2$-c). In some embodiments of the compounds of formula (1-1), ($A^2$-a) is ($A^2$-d). In some embodiments of the compounds of formula (1-1), ($A^2$-a) or ($A^2$-b) is selected from the group consisting of:

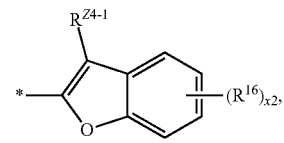

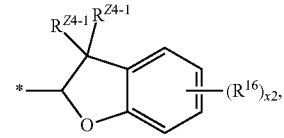

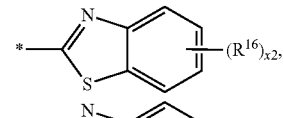

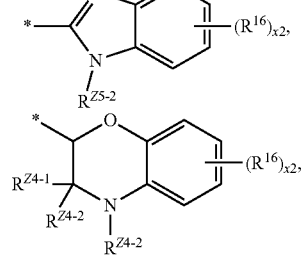

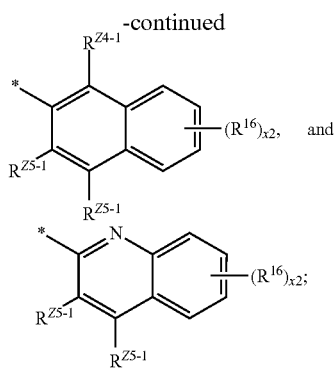

wherein the * represents the attachment point to the remainder of the molecule. In some embodiments, (A²-a) or (A²-b) is selected from the group consisting of:

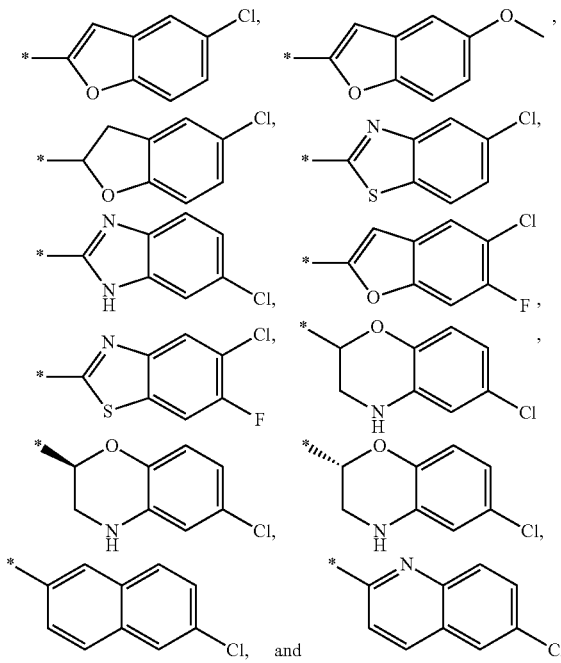

wherein the * represents the attachment point to the remainder of the molecule. In some embodiments, (A²-a) or (A²-b) is selected from the group consisting of:

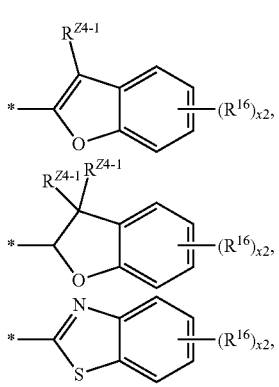

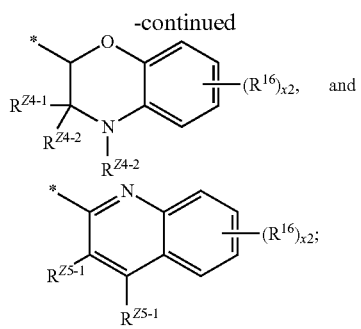

wherein the * represents the attachment point to the remainder of the molecule. In some embodiments, (A²-a) or (A²-b) is selected from the group consisting of:

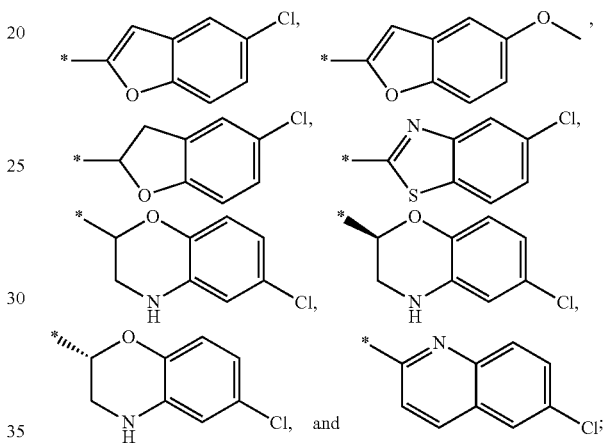

wherein the * represents the attachment point to the remainder of the molecule. In some embodiments, (A²-a) or (A²-b) is

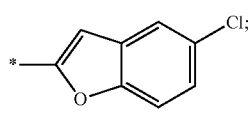

wherein the * represents the attachment point to the remainder of the molecule. In some embodiments, (A²-a) or (A²-b) is

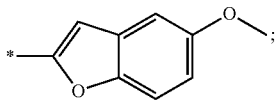 [SMILES: *c1cc2cc(OC)ccc2o1]

wherein the * represents the attachment point to the remainder of the molecule. In some embodiments, (A²-a) or (A²-b) is

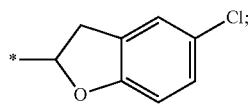 [SMILES: *C1Cc2cc(Cl)ccc2O1]

wherein the * represents the attachment point to the remainder of the molecule. In some embodiments, (A²-a) or (A²-b) is

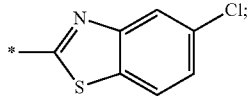 [SMILES: *c1nc2cc(Cl)ccc2s1]

wherein the * represents the attachment point to the remainder of the molecule. In some embodiments, (A²-a) or (A²-b) is

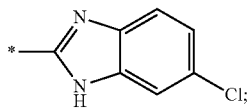 [SMILES: *c1nc2ccc(Cl)cc2[nH]1]

wherein the * represents the attachment point to the remainder of the molecule. In some embodiments, (A²-a) or (A²-b) is

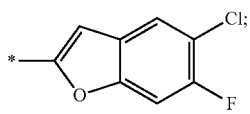

wherein the * represents the attachment point to the remainder of the molecule. In some embodiments, (A²-a) or (A²-b) is

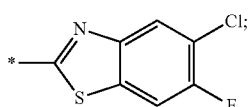

wherein the * represents the attachment point to the remainder of the molecule. In some embodiments, (A²-a) or (A²-b) is

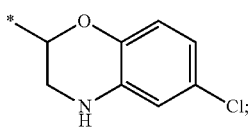 [SMILES: *C1CNc2cc(Cl)ccc2O1]

wherein the * represents the attachment point to the remainder of the molecule. In some embodiments, (A²-a) or (A²-b) is

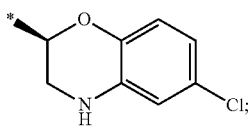 [SMILES: *[C@@H]1CNc2cc(Cl)ccc2O1]

wherein the * represents the attachment point to the remainder of the molecule. In some embodiments, (A²-a) or (A²-b) is

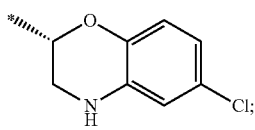

wherein the * represents the attachment point to the remainder of the molecule. In some embodiments, (A²-a) or (A²-b) is

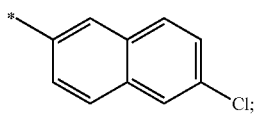

wherein the * represents the attachment point to the remainder of the molecule. In some embodiments, (A²-a) or (A²-b) is

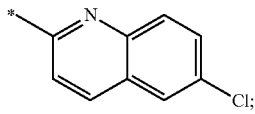

wherein the * represents the attachment point to the remainder of the molecule. In some embodiments of the compounds of formula (1-1), (A²-a) or (A²-c) is selected from the group consisting of:

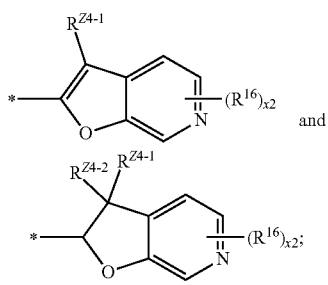

wherein the * represents the attachment point to the remainder of the molecule. In some embodiments, (A²-a) or (A²-c) is selected from the group consisting of:

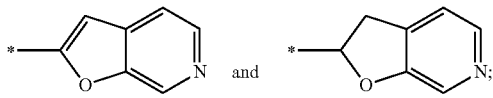

wherein the * represents the attachment point to the remainder of the molecule. In some embodiments, (A²-a) or (A²-c) is

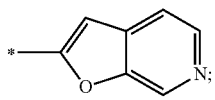

wherein the * represents the attachment point to the remainder of the molecule. In some embodiments, (A²-a) or (A²-c) is

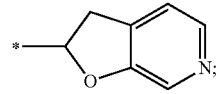

wherein the * represents the attachment point to the remainder of the molecule.

In some embodiments of the compounds of formula (I), (II), or (III), m² is 0, n² is 0, p² is 1, q² is 1, $R^{12a}$ and $R^{12b}$ are taken together to form an oxo (=O) substituent.

In some embodiments of the compounds of formula (I), (II), or (III), m² is 1, n² is 0, p² is 0, and q² is 1. In some embodiments, $R^{9a}$, $R^{9b}$, $R^{10a}$, and $R^{10b}$ are all hydrogen. In some embodiments, $R^{9a}$ and $R^{9b}$ are taken together to form an oxo (=O) substituent or an imido (=NH) substituent, and $R^{10a}$ and $R^{10b}$ are both hydrogen. In some embodiments, $R^{9a}$ and $R^{9b}$ are taken together to form an oxo (=O) substituent, and $R^{10a}$ and $R^{10b}$ are both hydrogen. In some embodiments, $R^{9a}$ and $R^{9b}$ are taken together to form an imido (=NH) substituent, and $R^{10a}$ and $R^{10b}$ are both hydrogen. In some embodiments, $R^{9a}$ and $R^{9b}$ are both hydrogen, and $R^{10a}$ and $R^{10b}$ are taken together to form a moiety selected from the group consisting of —O—CH₂—CH₂—, —CH₂O—CH₂—, —CH₂—CH₂—O—, —O—CH₂—CH₂—CH₂—, —CH₂—O—CH₂—CH₂—, —CH₂—CH₂—O—CH₂—, —CH₂—CH₂—CH₂—O—, —O—CH₂—CH₂—CH₂—CH₂—, —CH₂—O—CH₂—CH₂—CH₂—, —CH₂—CH₂—O—CH₂—CH₂—, —CH₂—CH₂—CH₂—O—CH₂—, and —CH₂—CH₂—CH₂—CH₂—O—. In some embodiments, $R^{9a}$ and $R^{9b}$ are both hydrogen, and $R^{10a}$ and $R^{10b}$ are taken together to form a —CH₂—O—CH₂— moiety.

In some embodiments of the compounds of formula (I), (II), or (III), m² is 1, n² is 0, p² is 0, and q² is 0. In some embodiments, $R^{9a}$, $R^{9b}$, and $R^{10b}$ are all hydrogen, and $R^{10a}$ is selected from the group consisting of hydrogen, —OR$^{10a-a}$, and —NR$^{10a-b}$R$^{10a-c}$. In some embodiments, $R^{10a}$ is hydrogen. In some embodiments, $R^{10a}$ is —OR$^{10a-a}$. In some embodiments, $R^{10a}$ is —OR$^{10a-a}$ and $R^{10a-a}$ is hydrogen.

In some embodiments of the compounds of formula (I), (II), or (III), m² is 1, n² is 0, p² is 1, and q² is 1. In some embodiments, $R^{9a}$, $R^{9b}$, $R^{10b}$, $R^{12a}$, and $R^{12b}$ are all hydrogen, and $R^{10a}$ is selected from the group consisting of hydrogen, —OR$^{10a-a}$, and —NR$^{10a-b}$R$^{10a-c}$. In some embodiments, $R^{9a}$, $R^{9b}$, $R^{10a}$, $R^{10b}$, $R^{12a}$, and $R^{12b}$ are all hydrogen. In some embodiments, $R^{9a}$, $R^{9b}$, $R^{10b}$, $R^{12a}$, and $R^{12b}$ are all hydrogen, and $R^{10a}$ is —OR$^{10a-a}$. In some embodiments, $R^{9a}$, $R^{9b}$, $R^{10b}$, $R^{12a}$, and $R^{12b}$ are all hydrogen, $R^{10a}$ is —OR$^{10a-a}$, and $R^{10a-a}$ is hydrogen. In some embodiments, $R^{9a}$, $R^{9b}$, $R^{10b}$, $R^{12a}$, and $R^{12b}$ are all hydrogen, and $R^{10a}$ is —NR$^{10a-b}$R$^{10a-c}$. In some embodiments, $R^{9a}$, $R^{9b}$, $R^{10b}$, $R^{12a}$, and $R^{12b}$ are all hydrogen, $R^{10a}$ is —NR$^{10a-b}$R$^{10a-c}$, $R^{10a-b}$ and $R^{10a-c}$ are both hydrogen. In some embodiments, $R^{9a}$ and $R^{9b}$ are taken together to form an oxo (=O) substituent or an imido (=NH) substituent. In some embodiments, $R^{9a}$ and $R^{9b}$ are taken together to form an oxo (=O) substituent, $R^{10b}$, $R^{12a}$, and $R^{12b}$ are all hydrogen, and $R^{10a}$ is selected from the group consisting of hydrogen, —OR$^{10a-a}$, and —NR$^{10a-b}$R$^{10a-c}$. In some embodiments, $R^{9a}$ and $R^{9b}$ are taken together to form an oxo (=O) substituent, and $R^{10a}$, $R^{10b}$, $R^{12a}$, and $R^{12b}$ are all hydrogen. In some embodiments, $R^{9a}$ and $R^{9b}$ are taken together to form an oxo (=O) substituent, $R^{10b}$, $R^{12a}$, and $R^{12b}$ are all hydrogen, and $R^{10a}$ is —OR$^{10a-a}$. In some embodiments, $R^{9a}$ and $R^{9b}$ are taken together to form an oxo (=O) substituent, $R^{10b}$, $R^{12a}$, and $R^{12b}$ are all hydrogen, $R^{10a}$ is —OR$^{10a-a}$, and $R^{10a-a}$ is hydrogen. In some embodiments, $R^{9a}$ and $R^{9b}$ are taken together to form an oxo (=O) substituent, $R^{10b}$, $R^{12a}$, and $R^{12b}$ are all hydrogen, and $R^{10a}$ is —NR$^{10a-b}$R$^{10a-c}$. In some embodiments, $R^{9a}$ and $R^{9b}$ are taken together to form an oxo (=O) substituent, $R^{10b}$, $R^{12a}$, and $R^{12b}$ are all hydrogen, $R^{10a}$ is —NR$^{10a-b}$R$^{10a-c}$R$^{10a-b}$ and $R^{10a-c}$ are both hydrogen. In some embodiments, $R^{9a}$ and $R^{9b}$ are taken together to form an imido (=NH) substituent, $R^{10b}$, $R^{12a}$, and $R^{12b}$ are all hydrogen, and $R^{10a}$ is selected from the group consisting of hydrogen, —OR$^{10a-a}$, and —NR$^{10a-b}$R$^{10a-c}$. In some embodiments, $R^{9a}$ and $R^{9b}$ are taken together to form an imido (=NH) substituent, and $R^{10a}$, $R^{10b}$, $R^{12a}$, and $R^{12b}$ are all hydrogen. In some embodiments, $R^{9a}$ and $R^{9b}$ are taken together to form an imido (=NH) substituent, $R^{10b}$, $R^{12a}$, and $R^{12b}$ are all hydrogen, and $R^{10a}$ is —OR$^{10a-a}$. In some embodiments, $R^{9a}$ and $R^{9b}$ are taken together to form an imido (=NH) substituent, $R^{10b}$, $R^{12a}$, and $R^{12b}$ are all hydrogen, $R^{10a}$ is —OR$^{10a-a}$, and $R^{10a-a}$ is hydrogen. In some embodiments, $R^{9a}$ and $R^{9b}$ are taken together to form an imido (=NH) substituent, $R^{10b}$, $R^{12a}$, and $R^{12b}$ are all hydrogen, and $R^{10a}$ is —NR$^{10a-b}$R$^{10a-c}$. In some embodiments, $R^{9a}$ and $R^{9b}$ are taken together to form an imido (=NH) substituent, $R^{10b}$, $R^{12a}$, and $R^{12b}$ are all hydrogen, $R^{10a}$ is —NR$^{10a-b}$R$^{10a-c}$, $R^{10a-b}$ and $R^{10a-c}$ are both hydrogen.

In some embodiments of the compounds of formula (I), (II), or (III), m² is 1, m² is 0, p² is 1, q² is 1, $R^{10a}$ is —OR$^{10a-a}$, and $R^{10a-a}$ is taken together with $R^N$ to form a carbonyl (C=O) moiety, and $R^{9a}$, $R^{9b}$, $R^{12a}$, and $R^{12b}$ are all hydrogen.

In some embodiments of the compounds of formula (I), (II), or (III), m² is 0, n² is 1, p² is 1, q² is 1, $R^{11a}$, $R^{11b}$, $R^{12a}$, and $R^{12b}$ are all hydrogen.

In some embodiments of the compounds of formula (I), (II), or (III), $A^1$ is selected from the group consisting of $C_6$-$C_{14}$ aryl optionally substituted with one or more $R^{14}$ substituents; and 5-14 membered heteroaryl optionally substituted with one or more $R^{14}$ substituents. In some embodiments, $A^1$ is $C_6$-$C_{14}$ aryl optionally substituted with one or more $R^{14}$ substituents. In some embodiments, $A^1$ is $C_6$-$C_{10}$ aryl optionally substituted with one or more $R^{14}$ substituents. In some embodiments, $A^1$ is selected from the group consisting of

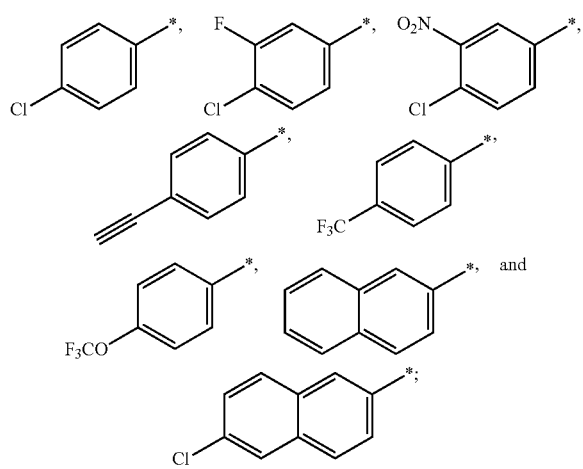

wherein the * represents the attachment point to the remainder of the molecule. In some embodiments, $A^1$ is phenyl optionally substituted with one or more $R^{14}$ substituents. In some embodiments $A^1$ is selected from the group consisting of

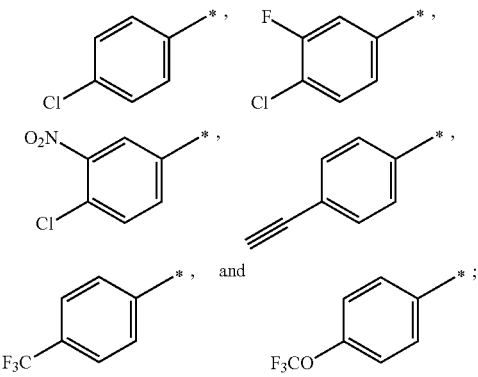

wherein the * represents the attachment point to the remainder of the molecule. In some embodiments, $A^1$ is

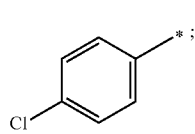

wherein the * represents the attachment point to the remainder of the molecule. In some embodiments, $A^1$ is

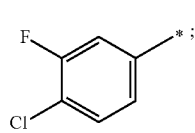

wherein the * represents the attachment point to the remainder of the molecule. In some embodiments, $A^1$ is

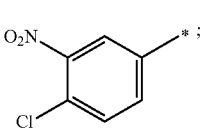

wherein the * represents the attachment point to the remainder of the molecule. In some embodiments, $A^1$ is

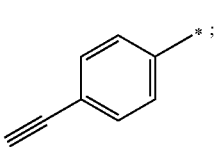

wherein the * represents the attachment point to the remainder of the molecule. In some embodiments, $A^1$ is

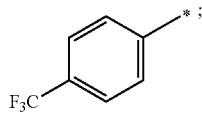

wherein the * represents the attachment point to the remainder of the molecule. In some embodiments, $A^1$ is

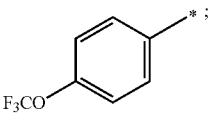

wherein the * represents the attachment point to the remainder of the molecule. In some embodiments, $A^1$ is naphthyl optionally substituted with one or more $R^{14}$ substituents. In some embodiments, $A^1$ is selected from the group consisting of

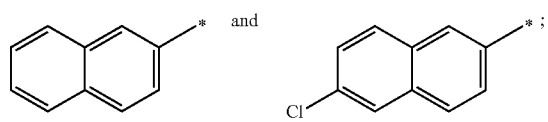

wherein the * represents the attachment point to the remainder of the molecule. In some embodiments, $A^1$ is

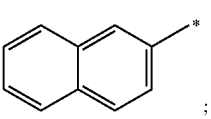

wherein the * represents the attachment point to the remainder of the molecule. In some embodiments, $A^1$ is

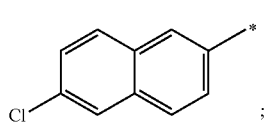

wherein the * represents the attachment point to the remainder of the molecule. In some embodiments, $A^1$ is 5-14 membered heteroaryl optionally substituted with one or more $R^{14}$ substituents. In some embodiments, $A^1$ is 5-10 membered heteroaryl optionally substituted with one or more $R^{14}$ substituents. In some embodiments, $A^1$ is selected from the group consisting of

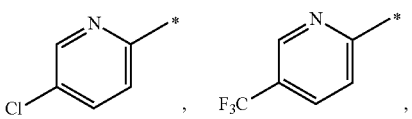

-continued

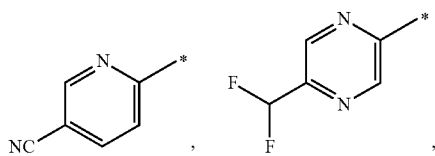

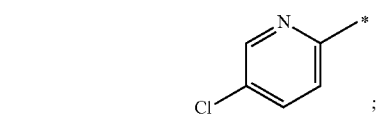

wherein the * represents the attachment point to the remainder of the molecule. In some embodiments, $A^1$ is pyridyl optionally substituted with one or more $R^{14}$ substituents. In some embodiments, $A^1$ is

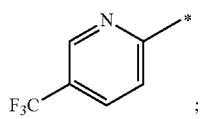

wherein the * represents the attachment point to the remainder of the molecule. In some embodiments, $A^1$ is


wherein the * represents the attachment point to the remainder of the molecule. In some embodiments, $A^1$ is

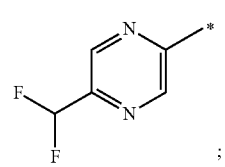

wherein the * represents the attachment point to the remainder of the molecule. In some embodiments, $A^1$ is pyrazinyl optionally substituted with one or more $R^{14}$ substituents. In some embodiments, $A^1$ is wherein the * represents the attachment point to the remainder of the molecule. In some embodiments, $A^1$ is quinolinyl optionally substituted with one or more $R^{14}$ substituents. In some embodiments, $A^1$ is selected from the group consisting of

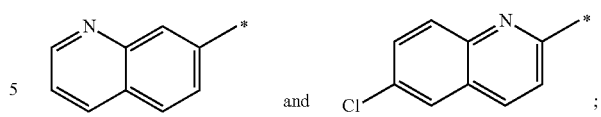

wherein the * represents the attachment point to the remainder of the molecule. In some embodiments, $A^1$ is

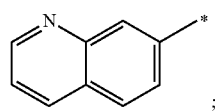

wherein the * represents the attachment point to the remainder of the molecule. In some embodiments, $A^1$ is

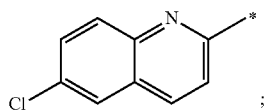

wherein the * represents the attachment point to the remainder of the molecule.

In some embodiments of the compounds of formula (I), (II), or (III), $A^2$ is selected from the group consisting of $C_6$-$C_{14}$ aryl optionally substituted with one or more $R^{16}$ substituents; and 5-14 membered heteroaryl optionally substituted with one or more $R^{16}$ substituents. In some embodiments, $A^2$ is $C_6$-$C_{14}$ aryl optionally substituted with one or more $R^{16}$ substituents. In some embodiments, $A^2$ is $C_6$-$C_{10}$ aryl optionally substituted with one or more $R^{16}$ substituents. In some embodiments, $A^2$ is selected from the group consisting of

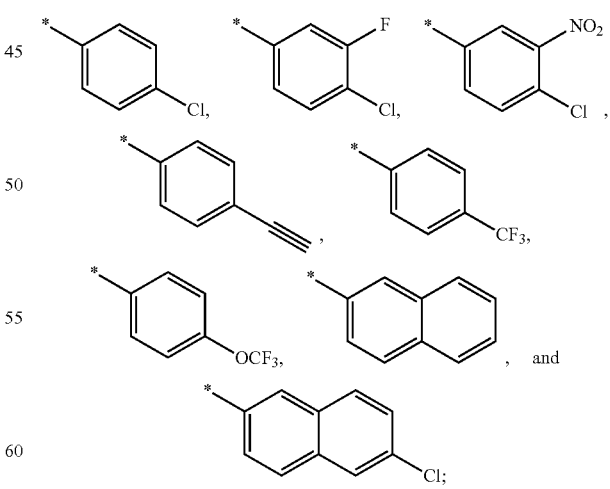

wherein the represents the attachment point to the remainder of the molecule. In some embodiments, $A^2$ is phenyl optionally substituted with one or more $R^{16}$ substituents. In some embodiments, $A^2$ is selected from the group consisting of

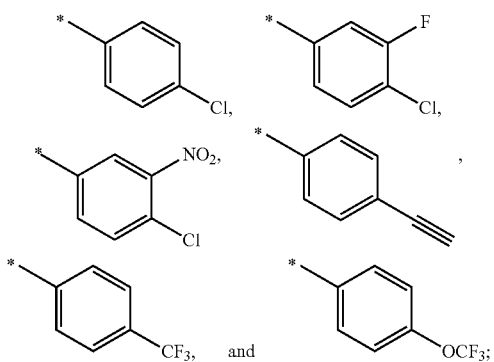

wherein the * represents the attachment point to the remainder of the molecule. In some embodiments, A² is

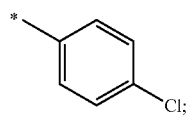

wherein the * represents the attachment point to the remainder of the molecule. In some embodiments, A² is

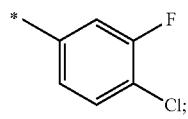

wherein the * represents the attachment point to the remainder of the molecule. In some embodiments, A² is

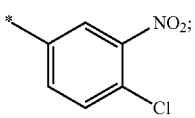

wherein the * represents the attachment point to the remainder of the molecule. In some embodiments, A² is

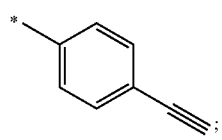

wherein the * represents the attachment point to the remainder of the molecule. In some embodiments, A² is

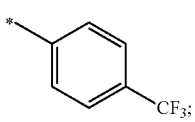

wherein the * represents the attachment point to the remainder of the molecule. In some embodiments, A² is

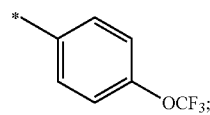

wherein the * represents the attachment point to the remainder of the molecule. In some embodiments, A² is naphthyl optionally substituted with one or more $R^{16}$ substituents. In some embodiments, A² is selected from the group consisting of

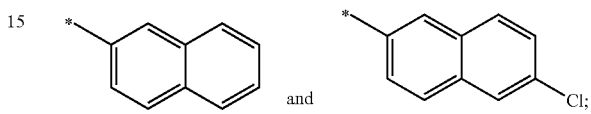

wherein the * represents the attachment point to the remainder of the molecule. In some embodiments, A² is

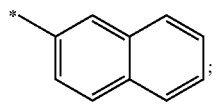

wherein the * represents the attachment point to the remainder of the molecule. In some embodiments, A² is

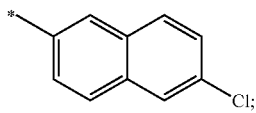

wherein the * represents the attachment point to the remainder of the molecule. In some embodiments, A² is 5-14 membered heteroaryl optionally substituted with one or more $R^{16}$ substituents. In some embodiments, A² is 5-10 membered heteroaryl optionally substituted with one or more $R^{16}$ substituents. In some embodiments, A² is selected from the group consisting of 1,

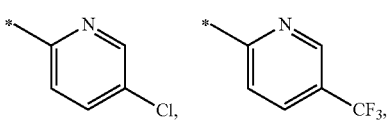

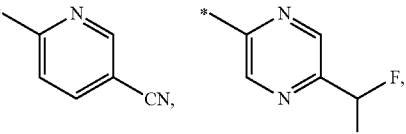

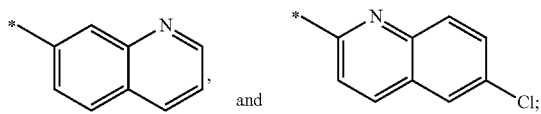

wherein the * represents the attachment point to the remainder of the molecule. In some embodiments, A² is pyridyl optionally substituted with one or more $R^{16}$ substituents. In some embodiments, A² is

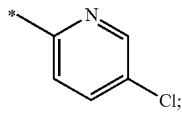

wherein the * represents the attachment point to the remainder of the molecule. In some embodiments, A² is

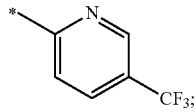

wherein the * represents the attachment point to the remainder of the molecule. In some embodiments, A² is

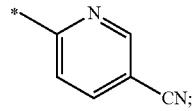

wherein the * represents the attachment point to the remainder of the molecule. In some embodiments, A² is pyrazinyl optionally substituted with one or more $R^{16}$ substituents. In some embodiments, A² is

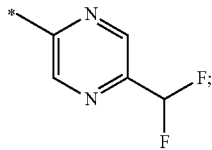

wherein the * represents the attachment point to the remainder of the molecule. In some embodiments, A² is quinolinyl optionally substituted with one or more $R^{16}$ substituents. In some embodiments, A² is selected from the group consisting of

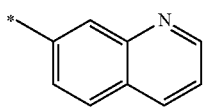 and 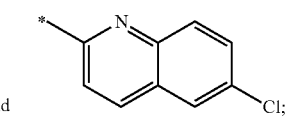

wherein the * represents the attachment point to the remainder of the molecule. In some embodiments, A² is

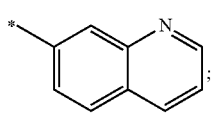

wherein the * represents the attachment point to the remainder of the molecule. In some embodiments, A² is and

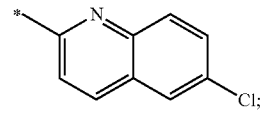

wherein the * represents the attachment point to the remainder of the molecule.

In some embodiments of the compound of formula (I) wherein X is $CR^X$ and k is 1, and in some embodiments of the compound of formula (II), j is 0 or 1. In some embodiments, j is 0. In some embodiments, j is 1. In some embodiments, j is 1, and $R^{j-a}$ and $R^{j-b}$ are taken together to form an oxo (=O) substituent. In some embodiments, j is 1, and $R^{j-a}$ and $R^{j-b}$ are both hydrogen.

In some embodiments of the compound of formula (I) wherein X is $CR^X$ and k is 1, and in some embodiments of the compound of formula (II), $R^X$ is selected from the group consisting of hydrogen, $C_1$-$C_6$ alkyl, $C_2$-$C_6$ alkenyl, and $C_2$-$C_6$ alkynyl. In some embodiments, $R^X$ is hydrogen or $C_2$-$C_6$ alkynyl. In some embodiments, $R^X$ is hydrogen. In some embodiments, $R^X$ is $C_2$-$C_6$ alkynyl. In some embodiments, $R^X$ is ethynyl.

In some embodiments of the compound of formula (I) wherein X is $CR^X$ and k is 1, and in some embodiments of the compound of formula (II), r is 1, s is 1, $R^{1a}$, $R^{1b}$, $R^{2a}$, $R^{2b}$, $R^{3a}$, $R^{3b}$, $R^{4a}$, and $R^{4b}$ are all hydrogen, and $R^X$ is ethynyl.

In some embodiments of the compound of formula (I) wherein X is $CR^X$ and k is 1, and in some embodiments of the compound of formula (II), r is 1, s is 1, $R^{1a}$, $R^{1b}$, $R^{2a}$, $R^{2b}$, $R^{3a}$, $R^{3b}$, $R^{4a}$, and $R^{4b}$ are all hydrogen, and $R^X$ is hydrogen.

In some embodiments of the compound of formula (I) wherein X is $CR^X$ and k is 1, and in some embodiments of the compound of formula (II), r is 1, s is 1, $R^{1a}$, $R^{1b}$, $R^{2a}$, $R^{2b}$, $R^{3b}$, $R^{4a}$, and $R^{4b}$ are all hydrogen, $R^{3a}$ is fluoro, and $R^X$ is hydrogen.

In some embodiments of the compound of formula (I) wherein X is $CR^X$ and k is 1, and in some embodiments of the compound of formula (II), r is 1, s is 1, $R^{1a}$ is —C(O)OH, $R^{1b}$, $R^{2a}$, $R^{2b}$, $R^{3a}$, $R^{3b}$, $R^{4a}$, and $R^{4b}$ are all hydrogen, and $R^X$ is hydrogen.

In some embodiments of the compound of formula (I) wherein X is N, and in some embodiments of the compound of formula (III), j is 0 and k is 0. In some embodiments, j is 0, k is 0, r is 1, s is 1, and $R^{1a}$, $R^{1b}$, $R^{2a}$, $R^{2b}$, $R^{3a}$, $R^{3b}$, $R^{4a}$, and $R^{4b}$ are all hydrogen.

In some embodiments of the compound of formula (I) wherein X is N, and in some embodiments of the compound of formula (III), j is 0 and k is 1. In some embodiments, j is 0, k is 1, r is 1, s is 1, and $R^{1a}$, $R^{1b}$, $R^{2a}$, $R^{2b}$, $R^{3a}$, $R^{3b}$, $R^{4a}$, and $R^{4b}$ are all hydrogen.

In some embodiments of the compound of formula (I) wherein X is N, and in some embodiments of the compound of formula (III), j is 1, $R^{j-a}$ and $R^{j-b}$ are taken together to form an oxo (=O) substituent, and k is 1. In some embodiments, j is 1, $R^{j-a}$ and $R^{j-b}$ are taken together to form an oxo (=O) substituent, k is 1, r is 1, s is 1, and $R^{1a}$, $R^{1b}$, $R^{2a}$, $R^{2b}$, $R^{3a}$, $R^{3b}$, $R^{4a}$, and $R^{4b}$ are all hydrogen.

In some embodiments of the compounds of formula (II) is a compound of formula (II-1-1), (II-1-2), or (II-1-3):
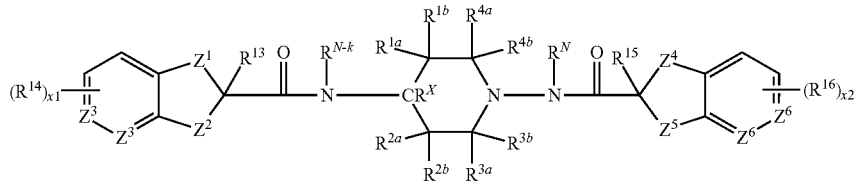
(II-1-1)
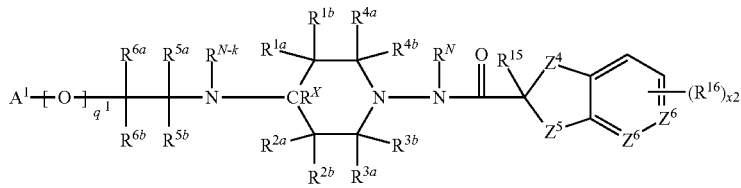
(II-1-2)
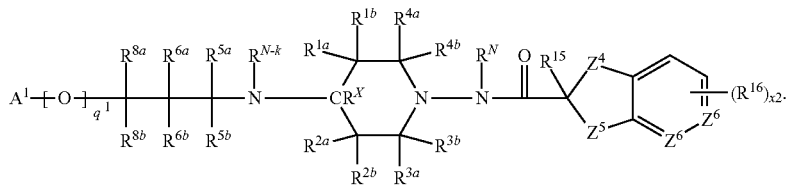
(II-1-3)
In some embodiments of the compounds of formula (II) is a compound of formula (II-2-1), (II-2-2), or (II-2-3):
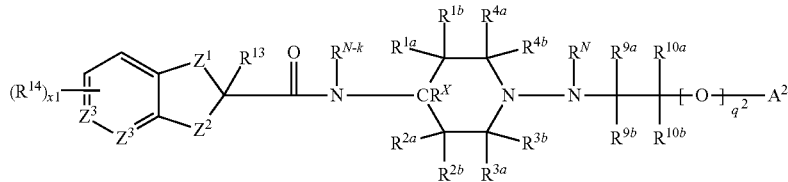
(II-2-1)
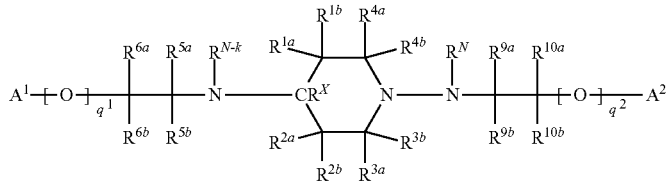
(II-2-2)
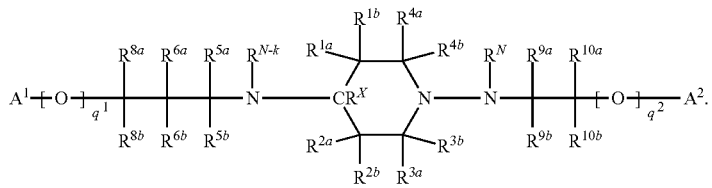
(II-2-3)

In some embodiments of the compounds of formula (II) is a compound of formula (II-3-1), (II-3-2), or (II-3-3):

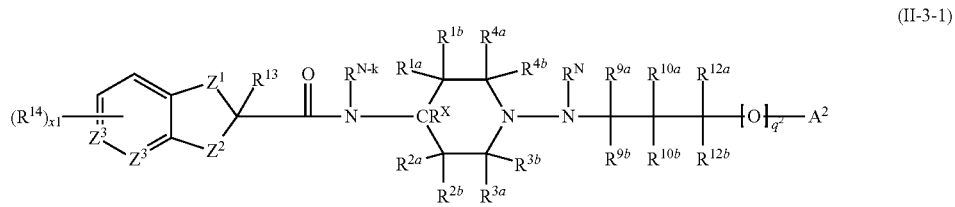
(II-3-1)

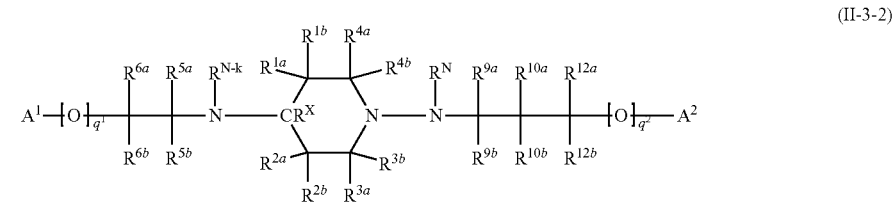
(II-3-2)

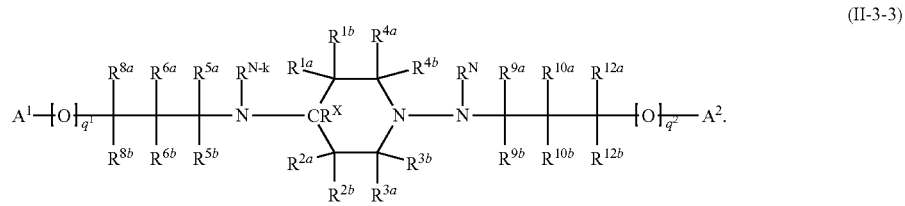
(II-3-3)

In some embodiments of the compounds of formulae (II-1-1), (II-1-2), (II-1-3), (II-2-1), (II-2-2), (II-2-3), (II-3-1), (II-3-2), and (II-3-3), $R^X$ is selected from the group consisting of hydrogen, $C_1$-$C_6$ alkyl, $C_2$-$C_6$ alkenyl, and $C_2$-$C_6$ alkynyl. In some embodiments, $R^X$ is hydrogen or $C_2$-$C_6$ alkynyl. In some embodiments, $R^X$ is hydrogen. In some embodiments, $R^X$ is $C_2$-$C_6$ alkynyl. In some embodiments, $R^X$ is ethynyl.

In some embodiments of the compounds of formula (III) is a compound of formula (III-1-2) or (III-1-3):

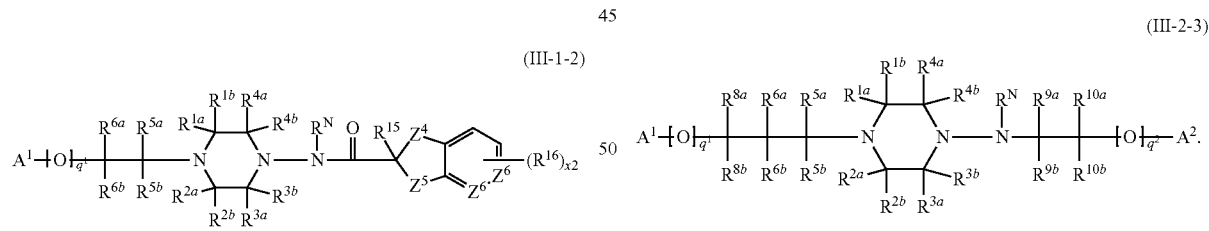
(III-1-2)

(III-1-3)

In some embodiments of the compounds of formula (III) is a compound of formula (III-2-2) or (III-2-3):

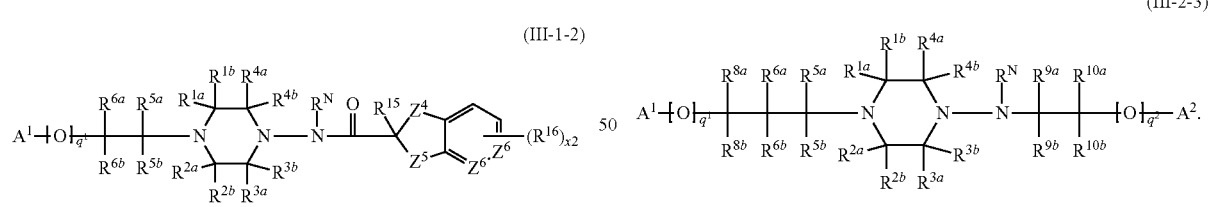
(III-2-2)

(III-2-3)

In some embodiments of the compounds of formula (III) is a compound of formula (III-3-2) or (III-3-3):

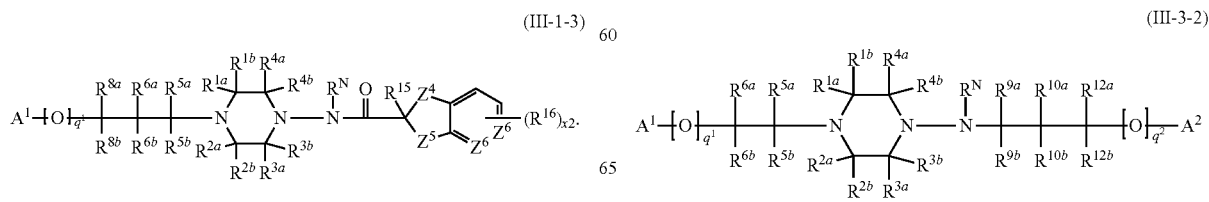
(III-3-2)

-continued (III-3-3)

$$A^1-[O]_{q^1}-\begin{array}{c}R^{8a}\ R^{6a}\ R^{5a}\ R^{1a}\\|\ \ |\ \ |\ \ |\\|\ \ |\ \ |\ \ |\\R^{8b}\ R^{6b}\ R^{5b}\ R^{2a}\end{array}\begin{array}{c}R^{1b}\ R^{4a}\\\diagup\ \diagdown\\N\ \ \ \ \ N\\\diagdown\ \diagup\\R^{2b}\ R^{3a}\end{array}\begin{array}{c}R^{4b}\ R^N\ R^{9a}\ R^{10a}\ R^{12a}\\|\ \ |\ \ |\ \ |\\N-N-|\ \ |\ \ |\ \ |-[O]_{q^2}-A^2\\|\ \ |\ \ |\ \ |\\R^{3b}\ \ \ \ \ R^{9b}\ R^{10b}\ R^{12b}\end{array}$$

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{1a}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen, or $R^{1a}$ is taken together with $R^{2a}$ to form a $C_1$-$C_6$ alkylene moiety, or $R^{1a}$ is taken together with an $R^{3a}$ moiety to form a $C_1$-$C_6$ alkylene moiety; $R^{1b}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen; $R^{2a}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen; $R^{2b}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen; $R^{3a}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen; or $R^{3a}$ is taken together with $R^{4a}$ to form a $C_1$-$C_6$ alkylene moiety; $R^{3b}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen; $R^{4a}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen; and $R^{4b}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen.

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{1a}$ is selected from the group consisting of hydrogen, $C_1$-$C_6$ alkyl, —C(O)OH, and halogen. In some embodiments, $R^{1a}$ is hydrogen. In some embodiments, $R^{1a}$ is $C_1$-$C_6$ alkyl. In some embodiments, $R^{1a}$ is methyl. In some embodiments, $R^{1a}$ is —C(O)OH. In some embodiments, $R^{1a}$ is halogen. In some embodiments, $R^{1a}$ is fluoro.

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{1b}$ is selected from the group consisting of hydrogen, $C_1$-$C_6$ alkyl, —C(O)OH, and halogen. In some embodiments, $R^{1b}$ is hydrogen. In some embodiments, $R^{1b}$ is $C_1$-$C_6$ alkyl. In some embodiments, $R^{1b}$ is methyl. In some embodiments, $R^{1b}$ is —C(O)OH. In some embodiments, $R^{1b}$ is halogen. In some embodiments, $R^{1b}$ is fluoro.

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{2a}$ is selected from the group consisting of hydrogen, $C_1$-$C_6$ alkyl, —C(O)OH, and halogen. In some embodiments, $R^{2a}$ is hydrogen. In some embodiments, $R^{2a}$ is $C_1$-$C_6$ alkyl. In some embodiments, $R^{2a}$ is methyl. In some embodiments, $R^{2a}$ is —C(O)OH. In some embodiments, $R^{2a}$ is halogen. In some embodiments, $R^{2a}$ is fluoro.

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{2b}$ is selected from the group consisting of hydrogen, $C_1$-$C_6$ alkyl, —C(O)OH, and halogen. In some embodiments, $R^{2b}$ is hydrogen. In some embodiments, $R^{2b}$ is $C_1$-$C_6$ alkyl. In some embodiments, $R^{2b}$ is methyl. In some embodiments, $R^{2b}$ is —C(O)OH. In some embodiments, $R^{2b}$ is halogen. In some embodiments, $R^{2b}$ is fluoro. In some embodiments, $R^{3a}$ is selected from the group consisting of hydrogen, $C_1$-$C_6$ alkyl, —C(O)OH, and halogen. In some embodiments, $R^{3a}$ is hydrogen. In some embodiments, $R^{3a}$ is $C_1$-$C_6$ alkyl. In some embodiments, $R^{3a}$ is methyl. In some embodiments, $R^{3a}$ is —C(O)OH. In some embodiments, $R^{3a}$ is halogen.

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{3a}$ is fluoro. In some embodiments, $R^{3b}$ is selected from the group consisting of hydrogen, $C_1$-$C_6$ alkyl, —C(O)OH, and halogen. In some embodiments, $R^{3b}$ is hydrogen. In some embodiments, $R^{3b}$ is $C_1$-$C_6$ alkyl. In some embodiments, $R^{3b}$ is methyl. In some embodiments, $R^{3b}$ is —C(O)OH. In some embodiments, $R^{3b}$ is halogen. In some embodiments, $R^{3b}$ is fluoro.

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{4a}$ is selected from the group consisting of hydrogen, $C_1$-$C_6$ alkyl, —C(O)OH, and halogen. In some embodiments, $R^{4a}$ is hydrogen. In some embodiments, $R^{4a}$ is $C_1$-$C_6$ alkyl. In some embodiments, $R^{4a}$ is methyl. In some embodiments, $R^{4a}$ is —C(O)OH. In some embodiments, $R^{4a}$ is halogen. In some embodiments, $R^{4a}$ is fluoro.

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{4b}$ is selected from the group consisting of hydrogen, $C_1$-$C_6$ alkyl, —C(O)OH, and halogen. In some embodiments, $R^{4b}$ is hydrogen. In some embodiments, $R^{4b}$ is $C_1$-$C_6$ alkyl. In some embodiments, $R^{4b}$ is methyl. In some embodiments, $R^{4b}$ is —C(O)OH. In some embodiments, $R^{4b}$ is halogen. In some embodiments, $R^{4b}$ is fluoro.

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{1a}$ is taken together with $R^{2a}$ to form a $C_1$-$C_6$ alkylene moiety. In some embodiment, $R^{1a}$ is taken together with $R^{2a}$ to form a methylene (—$CH_2$—) moiety. In some embodiment, $R^{1a}$ is taken together with $R^{2a}$ to form an ethylene (—$CH_2$—$CH_2$—) moiety. In some embodiment, $R^{1a}$ is taken together with $R^{2a}$ to form a propylene (—$CH_2$—$CH_2$—$CH_2$—) moiety.

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{1a}$ is taken together with $R^{3a}$ to form a $C_1$-$C_6$ alkylene moiety. In some embodiment, $R^{1a}$ is taken together with $R^{3a}$ to form a methylene (—$CH_2$—) moiety. In some embodiment, $R^{1a}$ is taken together with $R^{3a}$ to form an ethylene (—$CH_2$—$CH_2$—) moiety. In some embodiment, $R^{1a}$ is taken together with $R^{3a}$ to form a propylene (—$CH_2$—$CH_2$—$CH_2$—) moiety.

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{3a}$ is taken together with $R^{4a}$ to form a $C_1$-$C_6$ alkylene moiety. In some embodiment, $R^{3a}$ is taken together with $R^{4a}$ to form a methylene (—$CH_2$—) moiety. In some embodiment, $R^{3a}$ is taken together with $R^{4a}$ to form an ethylene (—$CH_2$—$CH_2$—) moiety. In some embodiment, $R^{3a}$ is taken together with $R^{4a}$ to form a propylene (—$CH_2$—$CH_2$—$CH_2$—) moiety.

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{1a}$, $R^{1b}$, $R^{2a}$, and $R^{2b}$, are all $C_1$-$C_6$ alkyl, and $R^{3a}$, $R^{3b}$, $R^{4a}$, and $R^{4b}$ are all hydrogen. In some embodiments, $R^{1a}$, $R^{1b}$, $R^{2a}$, and $R^{2b}$, are all methyl, and $R^{3a}$, $R^{3b}$, $R^{4a}$, and $R^{4b}$ are all hydrogen.

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{1a}$ and $R^{2a}$ are both $C_1$-$C_6$ alkyl, and $R^{1b}$, $R^{2b}$, $R^{3a}$, $R^{3b}$, $R^{4a}$, and $R^{4b}$ are all hydrogen. In some embodiments, $R^{1a}$ and $R^{2a}$ are both methyl, and $R^{1b}$, $R^{2b}$, $R^{3a}$, $R^{3b}$, $R^{4a}$, and $R^{4b}$ are all hydrogen.

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{1a}$ is —C(O)OH and $R^{1b}$, $R^{2a}$, $R^{2b}$, $R^{3a}$, $R^{3b}$, $R^{4a}$, and $R^{4b}$ are all hydrogen.

In some embodiments of the compounds of formulae (II-1-1), (II-1-2), (II-1-3), (II-2-1), (II-2-2), (II-2-3), (II-3-1), (II-3-2), (II-3-3), (III-1-2), (III-1-3), (III-2-2), (III-2-3), (III-3-2), and (III-3-3), $R^{3a}$ is fluoro and $R^{1a}$, $R^{1b}$, $R^{2a}$, $R^{2b}$, $R^{3b}$, $R^{4a}$, and $R^{4b}$ are all hydrogen.

In some embodiments of the compounds of formulae (II-1-2), (II-2-2), (II-3-2), (III-1-2), (III-2-2), and (III-3-2), $q^1$ is 1. In some embodiments, $R^{5a}$, $R^{5b}$, $R^{6a}$, and $R^{6b}$ are all hydrogen. In some embodiments, $R^{5a}$ and $R^{5b}$ are taken together to form an oxo (=O) substituent or an imido (=NH) substituent, and $R^{6a}$ and $R^{6b}$ are both hydrogen. In some embodiments, $R^{5a}$ and $R^{5b}$ are taken together to form an oxo (=O) substituent, and $R^{6a}$ and $R^{6b}$ are both hydrogen. In some embodiments, $R^{5a}$ and $R^{5b}$ are taken together to form an imido (=NH) substituent, and $R^{6a}$ and $R^{6b}$ are both hydrogen. In some embodiments, $R^{5a}$ and $R^{5b}$ are both hydrogen, and $R^{6a}$ and $R^{6b}$ are taken together to form a moiety selected from the group consisting of —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, and —$CH_2$—$CH_2$—$CH_2$—$CH_2$—O—. In some embodiments, $R^{5a}$ and $R^{5b}$ are both hydrogen, and $R^{6a}$ and $R^{6b}$ are taken together to form a —$CH_2$—O—$CH_2$— moiety.

In some embodiments of the compounds of formulae (II-1-2), (II-2-2), (II-3-2), (III-1-2), (III-2-2), and (III-3-2), $q^1$ is 0; $R^{5a}$, $R^{5b}$, and $R^{6b}$ are all hydrogen, and $R^{6a}$ is —$OR^{6a-a}$ or —$NR^{6a-b}R^{6a-c}$. In some embodiments, $R^{6a}$ is —$OR^{6a-a}$. In some embodiments, $R^{6a}$ is —$OR^{6a-a}$ and $R^{6a-a}$ is hydrogen.

In some embodiments of the compounds of formulae (II-1-3), (II-2-3), (II-3-3), (III-1-3), (III-2-3), and (III-3-3), $q^1$ is 1. In some embodiments, $R^{5a}$, $R^{5b}$, $R^{6b}$, $R^{8a}$, and $R^{8b}$ are all hydrogen, and $R^{6a}$ is selected from the group consisting of hydrogen, —$OR^{6a-a}$, and —$NR^{6a-b}R^{6a-c}$. In some embodiments, $R^{5a}$, $R^{5b}$, $R^{6a}$, $R^{6b}$, $R^{8a}$, and $R^{8b}$ are all hydrogen. In some embodiments, $R^{5a}$, $R^{5b}$, $R^{6b}$, $R^{8a}$, and $R^{8b}$ are all hydrogen, and $R^{6a}$ is —$OR^{6a-a}$. In some embodiments, $R^{5a}R^{5b}$, $R^{6b}$, $R^{8a}$, and $R^{8b}$ are all hydrogen, $R^{6a}$ is —$OR^{6a-a}$, and $R^{6a-a}$ is hydrogen. In some embodiments, $R^{5a}$, $R^{5b}$, $R^{6b}$, $R^{8a}$, and $R^{8b}$ are all hydrogen, and $R^{6a}$ is —$NR^{6a-b}R^{6a-c}$. In some embodiments, $R^{5a}$, $R^{5b}$, $R^{6b}$, $R^{8a}$, and $R^{8b}$ are all hydrogen, $R^{6a}$ is —$NR^{6a-b}R^{6a-c}$, $R^{6a-b}$ and $R^{6a-c}$ are both hydrogen. In some embodiments, $R^{5a}$ and $R^{5b}$ are taken together to form an oxo (=O) substituent or an imido (=NH) substituent. In some embodiments, $R^{5a}$ and $R^{5b}$ are taken together to form an oxo (=O) substituent, $R^{6b}$, $R^{8a}$, and $R^{8b}$ are all hydrogen, and $R^{6a}$ is selected from the group consisting of hydrogen, —$OR^{6a-a}$, and —$NR^{6a-b}R^{6a-c}$. In some embodiments, $R^{5a}$ and $R^{5b}$ are taken together to form an oxo (=O) substituent, and $R^{6a}$, $R^{6b}$, $R^{8a}$, and $R^{8b}$ are all hydrogen. In some embodiments, $R^{5a}$ and $R^{5b}$ are taken together to form an oxo (=O) substituent, $R^{6b}$, $R^{8a}$, and $R^{8b}$ are all hydrogen, and $R^{6a}$ is —$OR^{6a-a}$. In some embodiments, $R^{5a}$ and $R^{5b}$ are taken together to form an oxo (=O) substituent, $R^{6b}$, $R^{8a}$, and $R^{8b}$ are all hydrogen, $R^{6a}$ is —$OR^6a$-a, and $R^{6a-a}$ is hydrogen. In some embodiments, $R^{5a}$ and $R^{5b}$ are taken together to form an oxo (=O) substituent, $R^{6b}$, $R^{8a}$, and $R^{8b}$ are all hydrogen, and $R^{6a}$ is —$NR^{6a-b}R^{6a-c}$. In some embodiments, $R^{5a}$ and $R^{5b}$ are taken together to form an oxo (=O) substituent, $R^{6b}$, $R^{8a}$, and $R^{8b}$ are all hydrogen, $R^{6a}$ is —$NR^{6a-b}R^{6a-c}$, $R^{6a-b}$ and $R^{6a-c}$ are both hydrogen. In some embodiments, $R^{5a}$ and $R^{5b}$ are taken together to form an imido (=NH) substituent, $R^{6b}$, $R^{8a}$, and $R^{8b}$ are all hydrogen, and $R^{6a}$ is selected from the group consisting of hydrogen, —$OR^{6a-a}$, and —$NR^{6a-b}R^{6a-c}$. In some embodiments, $R^{5a}$ and $R^{5b}$ are taken together to form an imido (=NH) substituent, and $R^{6a}$, $R^{6b}$, $R^{8a}$, and $R^{8b}$ are all hydrogen. In some embodiments, $R^{5a}$ and $R^{5b}$ are taken together to form an imido (=NH) substituent, $R^{6b}$, $R^{8a}$, and $R^{8b}$ are all hydrogen, and $R^{6a}$ is —$OR^{6a-a}$. In some embodiments, $R^{5a}$ and $R^{5b}$ are taken together to form an imido (=NH) substituent, $R^{6b}$, $R^{8a}$, and $R^{8b}$ are all hydrogen, $R^{6a}$ is —$OR^{6a-a}$, and $R^{6a-a}$ is hydrogen. In some embodiments, $R^{5a}$ and $R^{5b}$ are taken together to form an imido (=NH) substituent, $R^{6b}$, $R^{8a}$, and $R^{8b}$ are all hydrogen, and $R^{6a}$ is —$NR^{6a-b}R^{6a-c}$. In some embodiments, $R^{5a}$ and $R^{5b}$ are taken together to form an imido (=NH) substituent, $R^{6b}$, $R^{8a}$, and $R^{8b}$ are all hydrogen, $R^{6a}$ is —$NR^{6a-b}R^{6a-c}$, $R^{6a-b}$ and $R^{6a-c}$ are both hydrogen.

In some embodiments of the compounds of formulae (II-1-3), (II-2-3), (II-3-3), (III-1-3), (III-2-3), and (III-3-3), $q^1$ is 1, $R^{6a}$ is —$OR^{6a-a}$, and $R^{6a-a}$ is taken together with $R^{N-k}$ to form a carbonyl (C=O) moiety, and $R^{5a}$, $R^{5b}$, $R^{8a}$, and $R^{8b}$ are all hydrogen.

In some embodiments of the compounds of formulae (II-2-1), (II-2-2), (II-2-3), (III-2-2), and (III-2-3), $q^2$ is 1. In some embodiments, $R^{9a}$, $R^{9b}$, $R^{10a}$, and $R^{10b}$ are all hydrogen. In some embodiments, $R^{9a}$ and $R^{9b}$ are taken together to form an oxo (=O) substituent or an imido (=NH) substituent, and $R^{10a}$ and $R^{10b}$ are both hydrogen. In some embodiments, $R^{9a}$ and $R^{9b}$ are taken together to form an oxo (=O) substituent, and $R^{10a}$ and $R^{10b}$ are both hydrogen. In some embodiments, $R^{9a}$ and $R^{9b}$ are taken together to form an imido (=NH) substituent, and $R^{10a}$ and $R^{10b}$ are both hydrogen. In some embodiments, $R^{9a}$ and $R^{9b}$ are both hydrogen, and $R^{10a}$ and $R^{10b}$ are taken together to form a moiety selected from the group consisting of —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, and —$CH_2$—$CH_2$—$CH_2$—$CH_2$—O—. In some embodiments, $R^{9a}$ and $R^{9b}$ are both hydrogen, and $R^{10a}$ and $R^{10b}$ are taken together to form a —$CH_2$—O—$CH_2$— moiety.

In some embodiments of the compounds of formulae (II-2-1), (II-2-2), (II-2-3), (III-2-2), and (III-2-3), $q^2$ is 0. In some embodiments, $R^{9a}$, $R^{9b}$, and $R^{10b}$ are all hydrogen, and $R^{10a}$ is selected from the group consisting of hydrogen, $-OR^{10a-a}$, and $-NR^{10a-b}R^{10a-c}$. In some embodiments, $R^{10a}$ is hydrogen. In some embodiments, $R^{10a}$ is $-OR^{10a-a}$. In some embodiments, $R^{10a}$ is $-OR^{10a-a}$ and $R^{10a-a}$ is hydrogen.

In some embodiments of the compounds of formulae (II-3-1), (II-3-2), (II-3-3), (III-3-2), and (III-3-3), $q^2$ is 1. In some embodiments, $R^{9a}$, $R^{9b}$, $R^{10b}$, $R^{12a}$, and $R^{12b}$ are all hydrogen, and $R^{10a}$ is selected from the group consisting of hydrogen, $-OR^{10a-a}$, and $-NR^{10a-b}R^{10a-c}$. In some embodiments, $R^{9a}$, $R^{9b}$, $R^{10a}$, $R^{10b}$, $R^{12a}$, and $R^{12b}$ are all hydrogen. In some embodiments, $R^{9a}$, $R^{9b}$, $R^{10b}$, $R^{12a}$, and $R^{12b}$ are all hydrogen, and $R^{10a}$ is $-OR^{10a-a}$. In some embodiments, $R^{9a}$, $R^{9b}$, $R^{10b}$, $R^{12a}$, and $R^{12b}$ are all hydrogen, $R^{10a}$ is $-OR^{10a-a}$, and $R^{10a-a}$ is hydrogen. In some embodiments, $R^{9a}$, $R^{9b}$, $R^{10b}$, $R^{12a}$, and $R^{12b}$ are all hydrogen, and $R^{10a}$ is $-NR^{10a-b}R^{10a-c}$. In some embodiments, $R^{9a}$, $R^{9b}$, $R^{10b}$, $R^{12a}$, and $R^{12b}$ are all hydrogen, $R^{10a}$ is $-NR^{10a-b}R^{10a-c}$, $R^{10a-b}$ and $R^{10a-c}$ are both hydrogen. In some embodiments, $R^{9a}$ and $R^{9b}$ are taken together to form an oxo (=O) substituent or an imido (=NH) substituent. In some embodiments, $R^{9a}$ and $R^{9b}$ are taken together to form an oxo (=O) substituent, $R^{10b}$, $R^{12a}$, and $R^{12b}$ are all hydrogen, and $R^{10a}$ is selected from the group consisting of hydrogen, $-OR^{10a-a}$, and $-NR^{10a-b}R^{10a-c}$. In some embodiments, $R^{9a}$ and $R^{9b}$ are taken together to form an oxo (=O) substituent, and $R^{10a}$, $R^{10b}$, $R^{12a}$, and $R^{12b}$ are all hydrogen. In some embodiments, $R^{9a}$ and $R^{9b}$ are taken together to form an oxo (=O) substituent, $R^{10b}$, $R^{12a}$, and $R^{12b}$ are all hydrogen, and $R^{10a}$ is $-OR^{10a-a}$. In some embodiments, $R^{9a}$ and $R^{9b}$ are taken together to form an oxo (=O) substituent, $R^{10b}$, $R^{12a}$, and $R^{12b}$ are all hydrogen, $R^{10a}$ is $-OR^{10a-a}$, and $R^{10a-a}$ is hydrogen. In some embodiments, $R^{9a}$ and $R^{9b}$ are taken together to form an oxo (=O) substituent, $R^{10b}$, $R^{12a}$, and $R^{12b}$ are all hydrogen, and $R^{10a}$ is $-NR^{10a-b}R^{10a-c}$. In some embodiments, $R^{9a}$ and $R^{9b}$ are taken together to form an oxo (=O) substituent, $R^{10b}$, $R^{12a}$, and $R^{12b}$ are all hydrogen, $R^{10a}$ is $-NR^{10a-b}R^{10a-c}$, $R^{10a-b}$ and $R^{10a-c}$ are both hydrogen. In some embodiments, $R^{9a}$ and $R^{9b}$ are taken together to form an imido (=NH) substituent, $R^{10b}$, $R^{12a}$, and $R^{12b}$ are all hydrogen, and $R^{10a}$ is selected from the group consisting of hydrogen, $-OR^{10a-a}$, and $-NR^{10a-b}R^{10a-c}$. In some embodiments, $R^{9a}$ and $R^{9b}$ are taken together to form an imido (=NH) substituent, and $R^{10a}$, $R^{10b}$, $R^{12a}$, and $R^{12b}$ are all hydrogen. In some embodiments, $R^{9a}$ and $R^{9b}$ are taken together to form an imido (=NH) substituent, $R^{10b}$, $R^{12a}$, and $R^{12b}$ are all hydrogen, and $R^{10a}$ is $-OR^{10a-a}$. In some embodiments, $R^{9a}$ and $R^{9b}$ are taken together to form an imido (=NH) substituent, $R^{10b}$, $R^{12a}$, and $R^{12b}$ are all hydrogen, $R^{10a}$ is $-OR^{10a-a}$, and $R^{10a-a}$ is hydrogen. In some embodiments, $R^{9a}$ and $R^{9b}$ are taken together to form an imido (=NH) substituent, $R^{10b}$, $R^{12a}$, and $R^{12b}$ are all hydrogen, and $R^{10a}$ is $-NR^{10a-b}R^{10a-c}$. In some embodiments, $R^{9a}$ and $R^{9b}$ are taken together to form an imido (=NH) substituent, $R^{10b}$, $R^{12a}$, and $R^{12b}$ are all hydrogen, $R^{10a}$ is $-NR^{10a-b}R^{10a-c}$, $R^{10a-b}$ and $R^{10a-c}$ are both hydrogen.

In some embodiments of the compounds of formulae (II-3-1), (II-3-2), (II-3-3), (III-3-2), and (III-3-3), $q^2$ is 1, $R^{10a}$ is $-OR^{10a-a}$, and $R^{10a-a}$ is taken together with $R^N$ to form a carbonyl (C=O) moiety, and $R^{9a}$, $R^{9b}$, $R^{12a}$, and $R^{12b}$ are all hydrogen.

In some embodiments of the compounds of formulae (II-1-1), (II-2-1), and (II-3-1), $A^1$ is a substituent of formula ($A^1$-a) selected from the group consisting of:

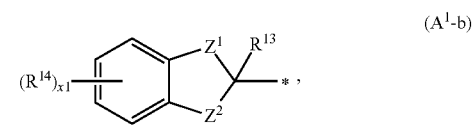

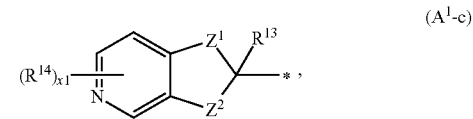

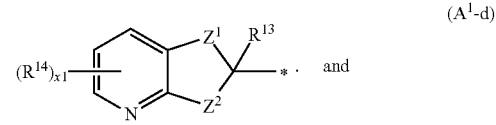

In some embodiments, ($A^1$-a) is ($A^1$-b). In some embodiments, ($A^1$-a) is ($A^1$-c). In some embodiments, ($A^1$-a) is ($A^1$-d). In some embodiments, ($A^1$-a) or ($A^1$-b) is selected from the group consisting of:

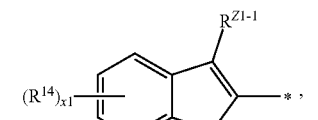

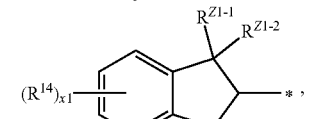

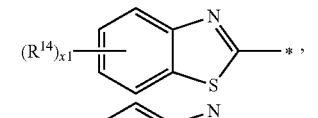

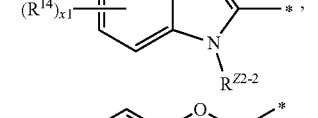

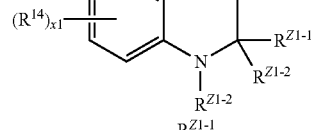

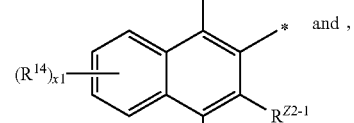

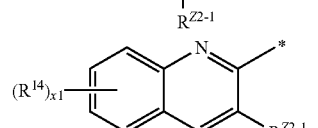

wherein the * represents the attachment point to the remainder of the molecule. In some embodiments, ($A^1$-a) or ($A^1$-b) is selected from the group consisting of:

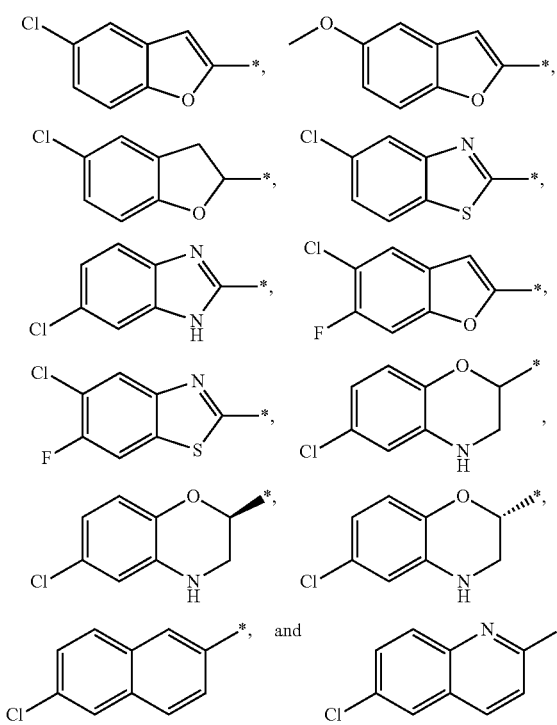

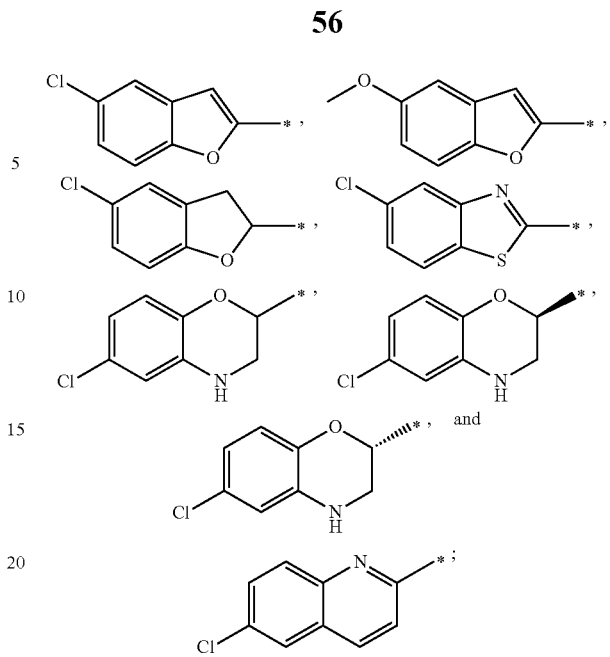

wherein the * represents the attachment point to the remainder of the molecule. In some embodiments, (A¹-a) or (A¹-b) is selected from the group consisting of:

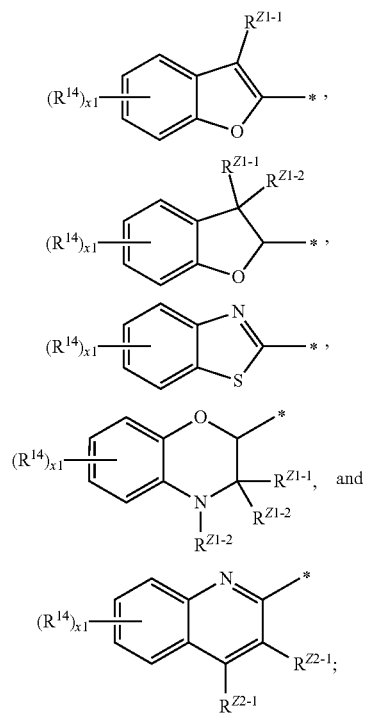

wherein the * represents the attachment point to the remainder of the molecule. In some embodiments, (A¹-a) or (A¹-b) is selected from the group consisting of:

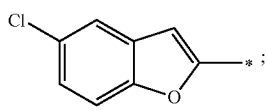

wherein the * represents the attachment point to the remainder of the molecule. In some embodiments, (A¹-a) or (A¹-b) is

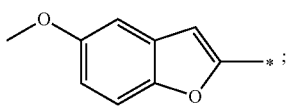

wherein the * represents the attachment point to the remainder of the molecule. In some embodiments, (A¹-a) or (A¹-b) is

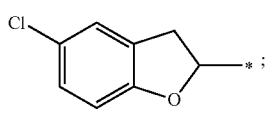

wherein the * represents the attachment point to the remainder of the molecule. In some embodiments, (A¹-a) or (A¹-b) is

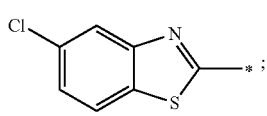

wherein the * represents the attachment point to the remainder of the molecule. In some embodiments, (A¹-a) or (A¹-b) is

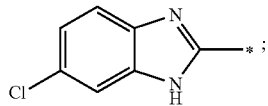

wherein the * represents the attachment point to the remainder of the molecule. In some embodiments, (A¹-a) or (A¹-b) is

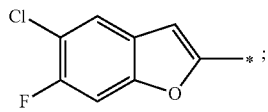

wherein the * represents the attachment point to the remainder of the molecule. In some embodiments, (A¹-a) or (A¹-b) is

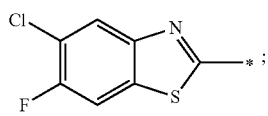

wherein the * represents the attachment point to the remainder of the molecule. In some embodiments, (A¹-a) or (A¹-b) is

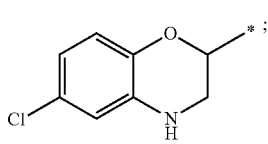

wherein the * represents the attachment point to the remainder of the molecule. In some embodiments, (A¹-a) or (A¹-b) is

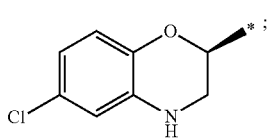

wherein the * represents the attachment point to the remainder of the molecule. In some embodiments, (A¹-a) or (A¹-b) is

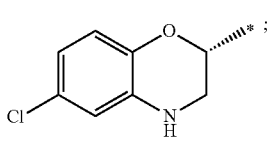

wherein the * represents the attachment point to the remainder of the molecule. In some embodiments, (A¹-a) or (A¹-b) is

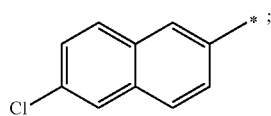

wherein the * represents the attachment point to the remainder of the molecule. In some embodiments, (A¹-a) or (A¹-b) is

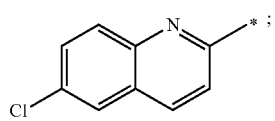

wherein the * represents the attachment point to the remainder of the molecule. In some embodiments, (A¹-a) or (A¹-c) is selected from the group consisting of:

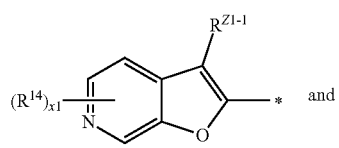

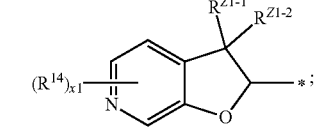

wherein the * represents the attachment point to the remainder of the molecule. In some embodiments, (A¹-a) or (A¹-c) is selected from the group consisting of:

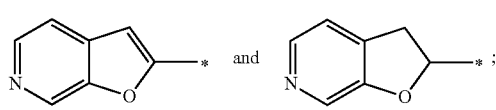

wherein the * represents the attachment point to the remainder of the molecule. In some embodiments, (A¹-a) or (A¹-c) is

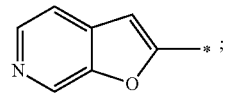

wherein the * represents the attachment point to the remainder of the molecule. In some embodiments, (A¹-a) or (A¹-c) is

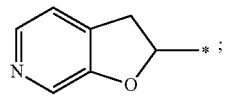

wherein the * represents the attachment point to the remainder of the molecule.

In some embodiments of the compounds of formulae (II-1-2), (II-1-3), (II-2-2), (II-2-3), (II-3-2), (II-3-3), (III-1-2), (III-1-3), (III-2-2), (III-2-3), (III-3-2), and (III-3-3), $A^1$ is selected from the group consisting of $C_6$-$C_{14}$ aryl optionally substituted with one or more $R^{14}$ substituents; and 5-14 membered heteroaryl optionally substituted with one or more $R^{14}$ substituents. In some embodiments, $A^1$ is $C_6$-$C_{14}$ aryl optionally substituted with one or more $R^{14}$ substituents. In some embodiments, $A^1$ is $C_6$-$C_{10}$ aryl optionally substituted with one or more $R^{14}$ substituents. In some embodiments, $A^1$ is selected from the group consisting of

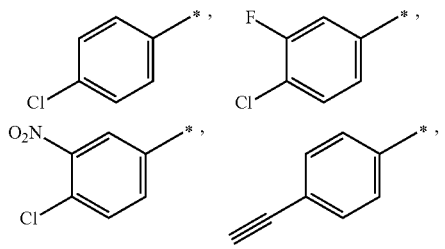

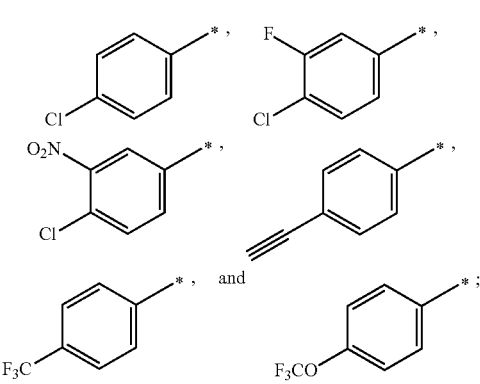

wherein the * represents the attachment point to the remainder of the molecule. In some embodiments, $A^1$ is phenyl optionally substituted with one or more $R^{14}$ substituents. In some embodiments, $A^1$ is selected from the group consisting of

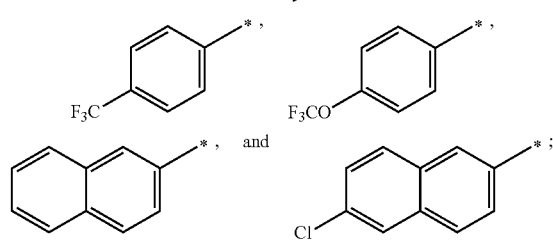

wherein the * represents the attachment point to the remainder of the molecule. In some embodiments, $A^1$ is

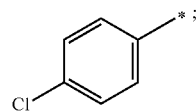

wherein the * represents the attachment point to the remainder of the molecule. In some embodiments, $A^1$ is

wherein the * represents the attachment point to the remainder of the molecule. In some embodiments, $A^1$ is

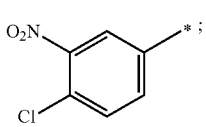

wherein the * represents the attachment point to the remainder of the molecule. In some embodiments, $A^1$ is

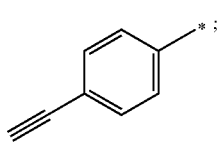

wherein the * represents the attachment point to the remainder of the molecule. In some embodiments, $A^1$ is

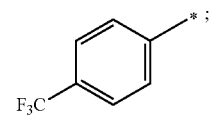

wherein the * represents the attachment point to the remainder of the molecule. In some embodiments, $A^1$ is

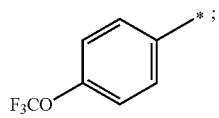

wherein the * represents the attachment point to the remainder of the molecule. In some embodiments, $A^1$ is naphthyl optionally substituted with one or more $R^{14}$ substituents. In some embodiments, $A^1$ is selected from the group consisting of

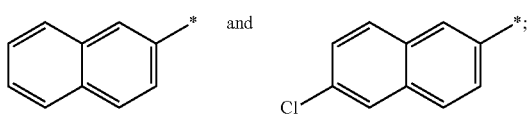 and wherein the * represents the attachment point to the remainder of the molecule. In some embodiments, A¹ is

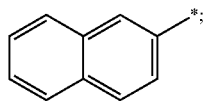

wherein the * represents the attachment point to the remainder of the molecule. In some embodiments, A¹ is

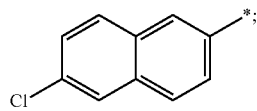

wherein the * represents the attachment point to the remainder of the molecule. In some embodiments, A¹ is 5-14 membered heteroaryl optionally substituted with one or more R¹⁴ substituents. In some embodiments, A¹ is 5-10 membered heteroaryl optionally substituted with one or more R¹⁴ substituents. In some embodiments, A¹ is selected from the group consisting of

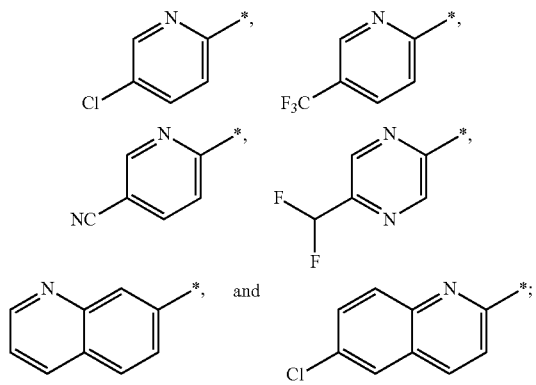

wherein the * represents the attachment point to the remainder of the molecule. In some embodiments, A¹ is pyridyl optionally substituted with one or more R¹⁴ substituents. In some embodiments, A¹ is

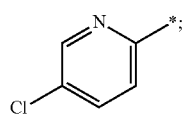

wherein the * represents the attachment point to the remainder of the molecule. In some embodiments, A¹ is

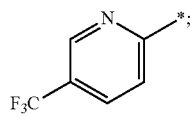

wherein the * represents the attachment point to the remainder of the molecule. In some embodiments, A¹ is

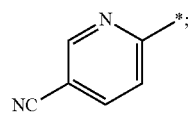

wherein the * represents the attachment point to the remainder of the molecule. In some embodiments, A¹ is pyrazinyl optionally substituted with one or more R¹⁴ substituents. In some embodiments, A¹ is

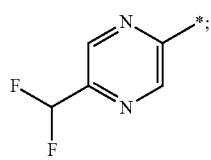

wherein the * represents the attachment point to the remainder of the molecule. In some embodiments, A¹ is quinolinyl optionally substituted with one or more R¹⁴ substituents. In some embodiments, A¹ is selected from the group consisting of

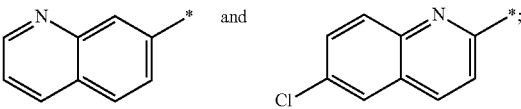

wherein the * represents the attachment point to the remainder of the molecule. In some embodiments, A¹ is

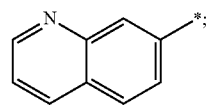

wherein the * represents the attachment point to the remainder of the molecule. In some embodiments, A¹ is and

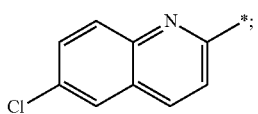

wherein the * represents the attachment point to the remainder of the molecule.

In some embodiments of the compounds of formulae (II-1-1), (II-1-2), (II-1-3), (III-1-3), and (III-2-2), A² is a substituent of formula (A²-a) selected from the group consisting of:

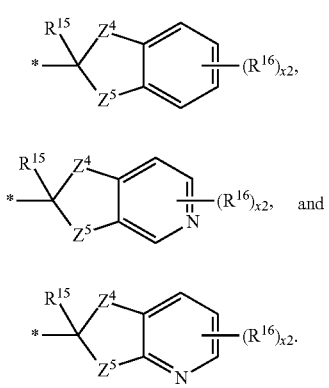

In some embodiments of the compounds of formula (1-1), $(A^2\text{-a})$ is $(A^2\text{-b})$. In some embodiments of the compounds of formula (1-1), $(A^2\text{-a})$ is $(A^2\text{-c})$. In some embodiments of the compounds of formula (1-1), $(A^2\text{-a})$ is $(A^2\text{-d})$. In some embodiments of the compounds of formula (1-1), $(A^2\text{-a})$ or $(A^2\text{-b})$ is selected from the group consisting of:

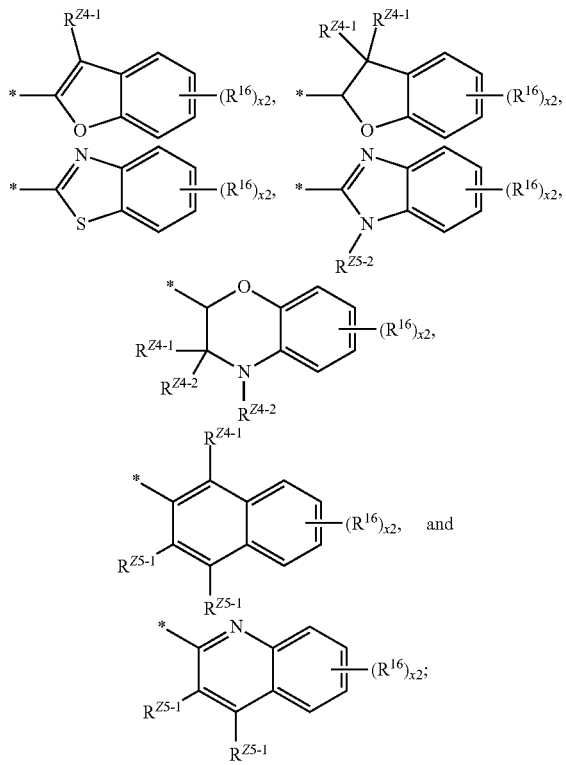

wherein the * represents the attachment point to the remainder of the molecule. In some embodiments, $(A^2\text{-a})$ or $(A^2\text{-b})$ is selected from the group consisting of:

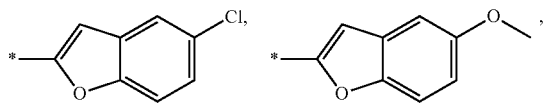

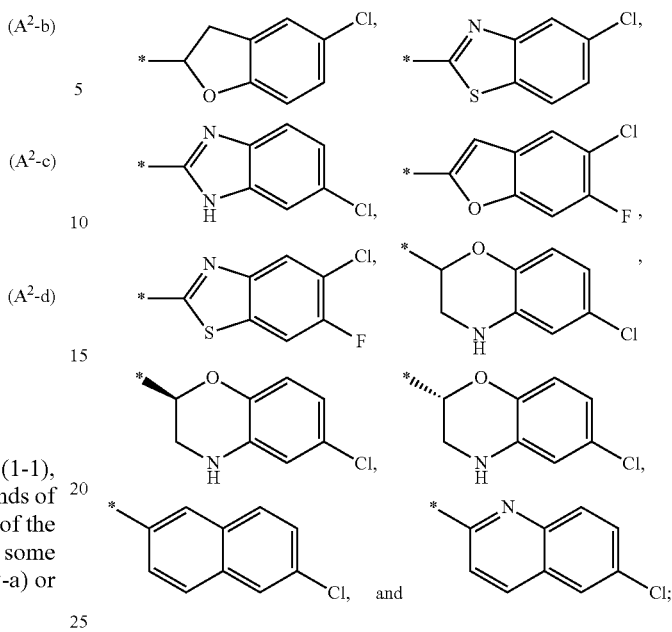

wherein the * represents the attachment point to the remainder of the molecule. In some embodiments, $(A^2\text{-a})$ or $(A^2\text{-b})$ is selected from the group consisting of:

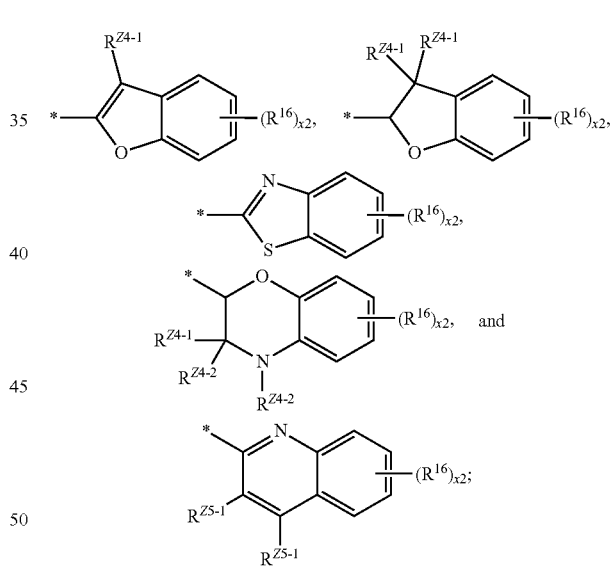

wherein the * represents the attachment point to the remainder of the molecule. In some embodiments, $(A^2\text{-a})$ or $(A^2\text{-b})$ is selected from the group consisting of:

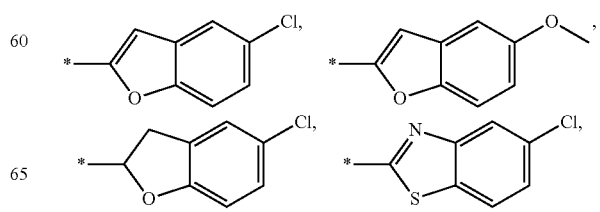

-continued

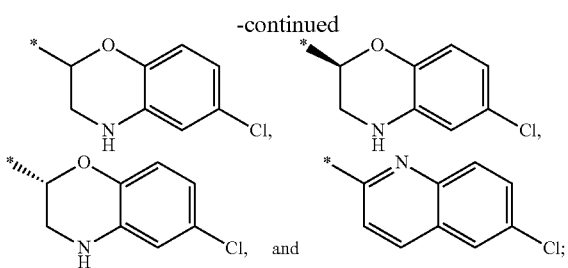
and wherein the * represents the attachment point to the remainder of the molecule. In some embodiments, (A²-a) or (A²-b) is

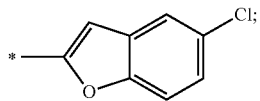

wherein the * represents the attachment point to the remainder of the molecule. In some embodiments, (A²-a) or (A²-b) is

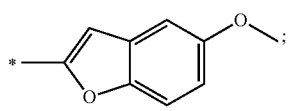

wherein the * represents the attachment point to the remainder of the molecule. In some embodiments, (A²-a) or (A²-b) is

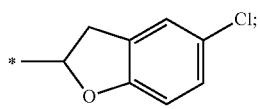

wherein the * represents the attachment point to the remainder of the molecule. In some embodiments, (A²-a) or (A²-b) is

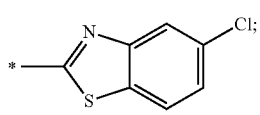

wherein the * represents the attachment point to the remainder of the molecule. In some embodiments, (A²-a) or (A²-b) is

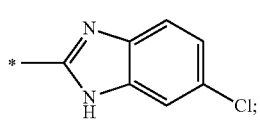

wherein the * represents the attachment point to the remainder of the molecule. In some embodiments, (A²-a) or (A²-b) is

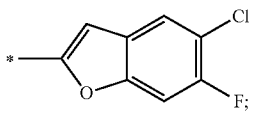

wherein the * represents the attachment point to the remainder of the molecule. In some embodiments, (A²-a) or (A²-b) is

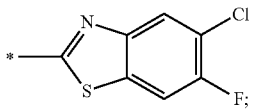

wherein the * represents the attachment point to the remainder of the molecule. In some embodiments, (A²-a) or (A²-b) is

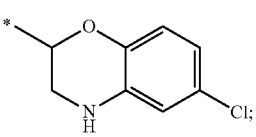

wherein the * represents the attachment point to the remainder of the molecule. In some embodiments, (A²-a) or (A²-b) is

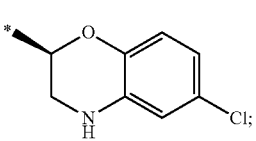

wherein the * represents the attachment point to the remainder of the molecule. In some embodiments, (A²-a) or (A²-b) is

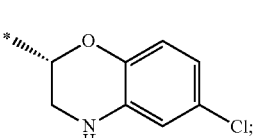

wherein the * represents the attachment point to the remainder of the molecule. In some embodiments, (A²-a) or (A²-b) is

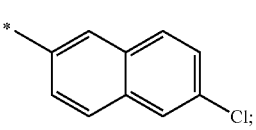

wherein the * represents the attachment point to the remainder of the molecule. In some embodiments, (A²-a) or (A²-b) is

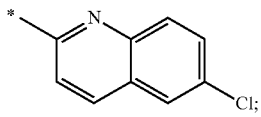

wherein the * represents the attachment point to the remainder of the molecule. In some embodiments of the compounds of formula (1-1), (A²-a) or (A²-c) is selected from the group consisting of:

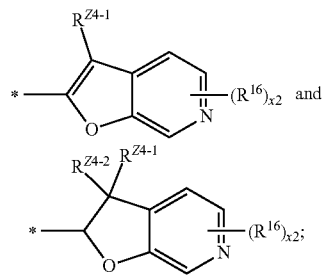

wherein the * represents the attachment point to the remainder of the molecule. In some embodiments, (A²-a) or (A²-c) is selected from the group consisting of:

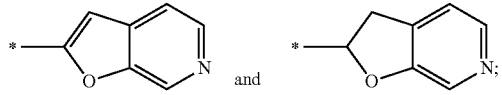

wherein the * represents the attachment point to the remainder of the molecule. In some embodiments, (A²-a) or (A²-c) is

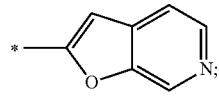

wherein the * represents the attachment point to the remainder of the molecule. In some embodiments, (A²-a) or (A²-c) is

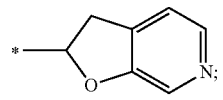

wherein the * represents the attachment point to the remainder of the molecule.

In some embodiments of the compounds of formulae (II-2-1), (II-2-2), (II-2-3), (II-3-1), (II-3-2), (II-3-3), (III-2-2), (III-2-3), (III-3-2), and (III-3-3), $A^2$ is selected from the group consisting of $C_6$-$C_{14}$ aryl optionally substituted with one or more $R^{16}$ substituents; and 5-14 membered heteroaryl optionally substituted with one or more $R^{16}$ substituents. In some embodiments, $A^2$ is $C_6$-$C_{14}$ aryl optionally substituted with one or more $R^{16}$ substituents. In some embodiments, $A^2$ is $C_6$-$C_{10}$ aryl optionally substituted with one or more $R^{16}$ substituents. In some embodiments, $A^2$ is selected from the group consisting of

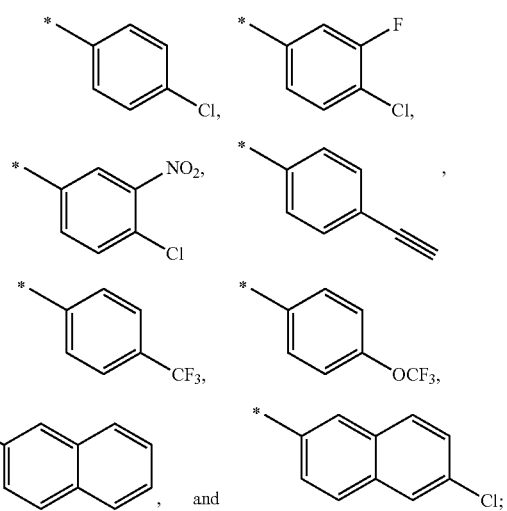

wherein the * represents the attachment point to the remainder of the molecule. In some embodiments, $A^2$ is phenyl optionally substituted with one or more $R^{16}$ substituents. In some embodiments, $A^2$ is selected from the group consisting of

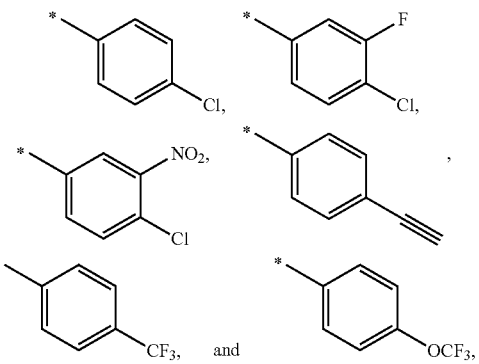

wherein the * represents the attachment point to the remainder of the molecule. In some embodiments, $A^2$ is

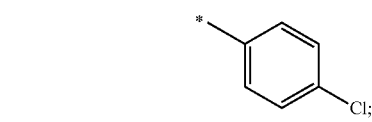

wherein the * represents the attachment point to the remainder of the molecule. In some embodiments, $A^2$ is

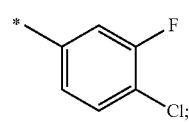

wherein the * represents the attachment point to the remainder of the molecule. In some embodiments, $A^2$ is

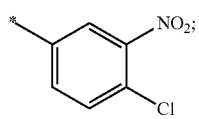

wherein the * represents the attachment point to the remainder of the molecule. In some embodiments, A² is

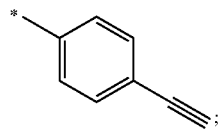

wherein the * represents the attachment point to the remainder of the molecule. In some embodiments, A² is

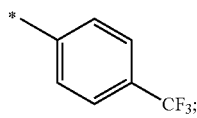

wherein the * represents the attachment point to the remainder of the molecule. In some embodiments, A² is

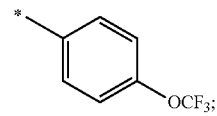

wherein the * represents the attachment point to the remainder of the molecule. In some embodiments, A² is naphthyl optionally substituted with one or more R¹⁶ substituents. In some embodiments A² is selected from the group consisting of

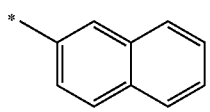 and 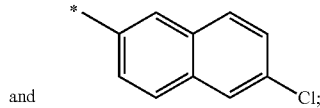

wherein the * represents the attachment point to the remainder of the molecule. In some embodiments, A² is

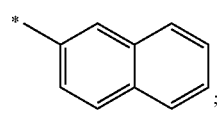

wherein the * represents the attachment point to the remainder of the molecule. In some embodiments, A² is

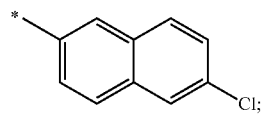

wherein the * represents the attachment point to the remainder of the molecule. In some embodiments, A² is 5-14 membered heteroaryl optionally substituted with one or more R¹⁶ substituents. In some embodiments, A² is 5-10 membered heteroaryl optionally substituted with one or more R¹⁶ substituents. In some embodiments, A² is selected from the group consisting of

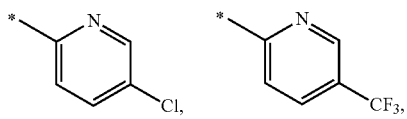

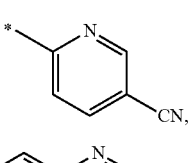 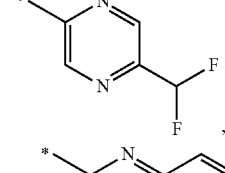

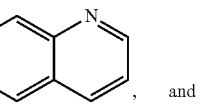, and 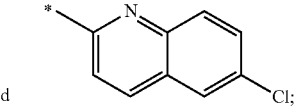

wherein the * represents the attachment point to the remainder of the molecule. In some embodiments, A² is pyridyl optionally substituted with one or more R¹⁶ substituents. In some embodiments, A² is

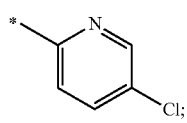

wherein the * represents the attachment point to the remainder of the molecule. In some embodiments, A² is

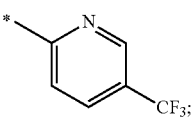

wherein the * represents the attachment point to the remainder of the molecule. In some embodiments, A² is

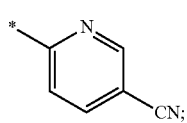 [SMILES: *c1ccc(C#N)cn1]

wherein the * represents the attachment point to the remainder of the molecule. In some embodiments, A² is pyrazinyl optionally substituted with one or more R¹⁶ substituents. In some embodiments, A² is

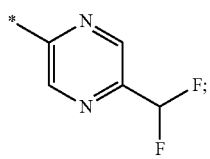 [SMILES: *c1cnc(C(F)F)cn1]

wherein the * represents the attachment point to the remainder of the molecule. In some embodiments, A² is quinolinyl optionally substituted with one or more R¹⁶ substituents. In some embodiments, A² is selected from the group consisting of

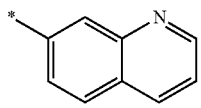 and 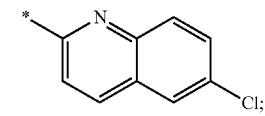

wherein the * represents the attachment point to the remainder of the molecule. In some embodiments, A² is

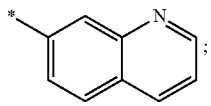 [SMILES: *c1ccc2cccnc2c1]

wherein the * represents the attachment point to the remainder of the molecule. In some embodiments, A² is and

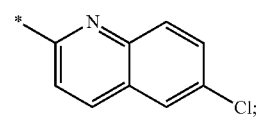 [SMILES: *c1ccc2cc(Cl)ccc2n1]

wherein the * represents the attachment point to the remainder of the molecule.

In one aspect, provided is a compound of formula (IV):

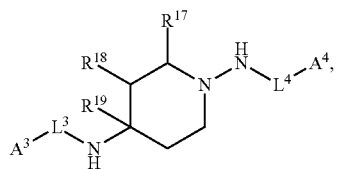

or a pharmaceutically acceptable salt thereof, wherein:
$R^{17}$ is hydrogen or —C(O)OH;
$R^{18}$ is hydrogen or halogen;
$R^{19}$ is hydrogen or $C_2$-$C_6$ alkynyl;
$L^3$ is selected from the group consisting of

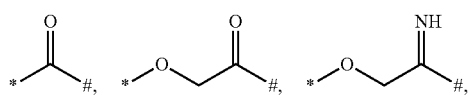

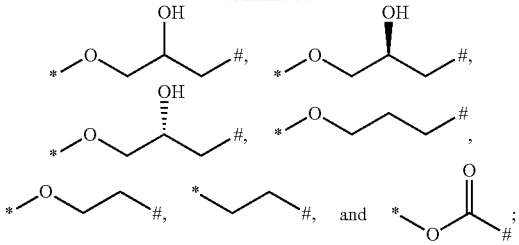

wherein the * represents the attachment point to A³, and the # represents the attachment point to the remainder of the molecule;
$L^4$ is selected from the group consisting of

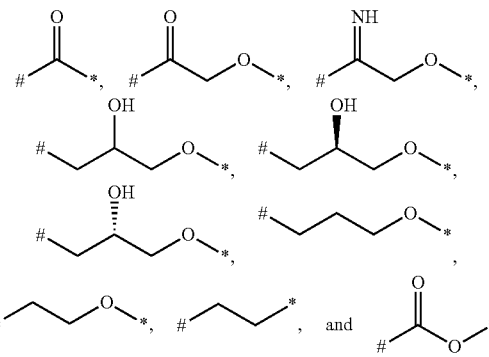

wherein the * represents the attachment point to A⁴, and the # represents the attachment point to the remainder of the molecule;
A³ is selected from the group consisting of phenyl, naphthyl, pyridyl, pyrazinyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, pyridyl, pyrazinyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, CN, —NO₂, $C_1$-$C_6$ alkyl, $C_2$-$C_6$ alkenyl, $C_2$-$C_6$ alkynyl, —O—$C_1$-$C_6$ alkyl, —O—$C_1$-$C_6$ haloalkyl, and $C_1$-$C_6$ haloalkyl;
A⁴ is selected from the group consisting of phenyl, naphthyl, pyridyl, pyrazinyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, pyridyl, pyrazinyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, CN, —NO₂, $C_1$-$C_6$ alkyl, $C_2$-$C_6$ alkenyl, $C_2$-$C_6$ alkynyl, —O—$C_1$-$C_6$ alkyl, —O—$C_1$-$C_6$ haloalkyl, and $C_1$-$C_6$ haloalkyl.

In some embodiments of the compound of Formula (IV), A³ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —NO$_2$, C$_1$-C$_6$ alkyl, C$_2$-C$_6$ alkenyl, C$_2$-C$_6$ alkynyl, and C$_1$-C$_6$ haloalkyl.

In some embodiments of the compound of Formula (IV), A$^4$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —NO$_2$, C$_1$-C$_6$ alkyl, C$_2$-C$_6$ alkenyl, C$_2$-C$_6$ alkynyl, and C$_1$-C$_6$ haloalkyl.

In some embodiments, the compound of formula (IV) is a compound of formula (IV-a):

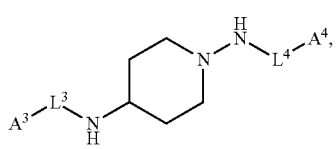

(IV-a)

or a pharmaceutically acceptable salt thereof,
wherein L$^3$, L$^4$, A$^3$, and A$^4$ are as defined for the compound of formula (IV).

In some embodiments, the compound of formula (IV) is a compound of formula (IV-b):

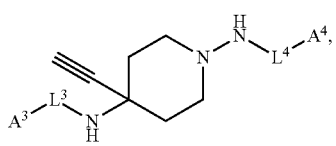

(IV-b)

or a pharmaceutically acceptable salt thereof,
wherein L$^3$, L$^4$, A$^3$, and A$^4$ are as defined for the compound of formula (IV).

In some embodiments, the compound of formula (IV) is a compound of formula (IV-c):

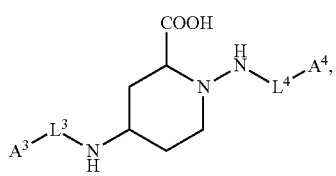

(IV-c)

or a pharmaceutically acceptable salt thereof,
wherein L$^3$, L$^4$, A$^3$, and A$^4$ are as defined for the compound of formula (IV).

In some embodiments, the compound of formula (IV) is a compound of formula (IV-d):

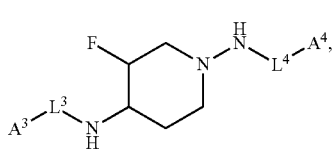

(IV-d)

or a pharmaceutically acceptable salt thereof,
wherein L$^3$, L$^4$, A$^3$, and A$^4$ are as defined for the compound of formula (IV).

In some embodiments of the compounds of formula (IV), (IV-a), (IV-b), (IV-c), and (IV-a), L$^3$ is selected from the group consisting of

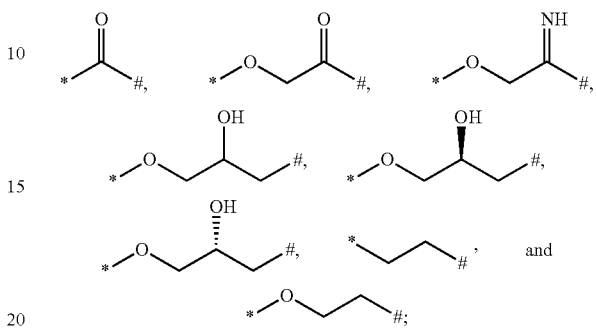

wherein the * represents the attachment point to A$^3$, and the # represents the attachment point to the remainder of the molecule. In some embodiments, L$^3$ is

wherein the * represents the attachment point to A$^3$, and the # represents the attachment point to the remainder of the molecule. In some embodiments, L$^3$ is

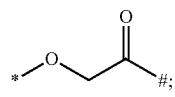

wherein the * represents the attachment point to A$^3$, and the # represents the attachment point to the remainder of the molecule. In some embodiments, L$^3$ is

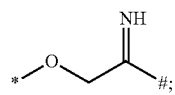

wherein the * represents the attachment point to A$^3$, and the # represents the attachment point to the remainder of the molecule. In some embodiments, L$^3$ is

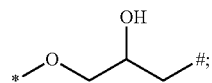

wherein the * represents the attachment point to A$^3$, and the # represents the attachment point to the remainder of the molecule. L3 is

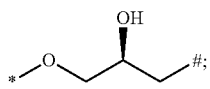

wherein the * represents the attachment point to $A^3$, and the # represents the attachment point to the remainder of the molecule. $L^3$ is

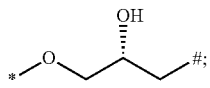

wherein the * represents the attachment point to $A^3$, and the # represents the attachment point to the remainder of the molecule. In some embodiments, $L^3$ is

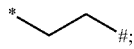

wherein the * represents the attachment point to $A^3$, and the # represents the attachment point to the remainder of the molecule. In some embodiments, $L^3$ is

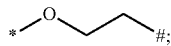

wherein the * represents the attachment point to $A^3$, and the # represents the attachment point to the remainder of the molecule.

In some embodiments of the compounds of formula (IV) (IV-a) (IV-b, (IV-c), and (IV-a), $L^4$ is selected from the group consisting of

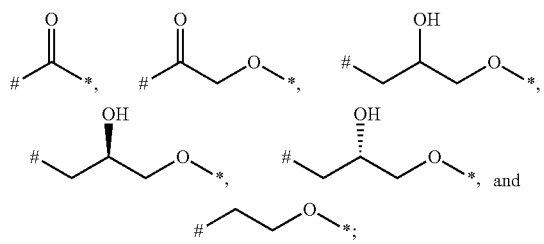

wherein the * represents the attachment point to $A^4$, and the # represents the attachment point to the remainder of the molecule. In some embodiments, $L^4$ is

wherein the * represents the attachment point to $A^4$, and the # represents the attachment point to the remainder of the molecule. In some embodiments, $L^4$ is

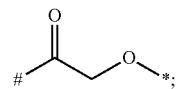

wherein the represents the attachment point to $A^4$, and the # represents the attachment point to the remainder of the molecule. In some embodiments, $L^4$ is

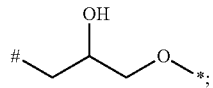

wherein the * represents the attachment point to $A^4$, and the # represents the attachment point to the remainder of the molecule. In some embodiments, $L^4$ is

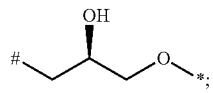

wherein the * represents the attachment point to $A^4$, and the # represents the attachment point to the remainder of the molecule. In some embodiments, $L^4$ is

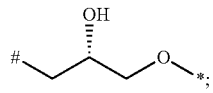

wherein the * represents the attachment point to $A^4$, and the # represents the attachment point to the remainder of the molecule. In some embodiments, $L^4$ is

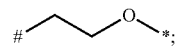

wherein the * represents the attachment point to $A^4$, and the # represents the attachment point to the remainder of the molecule.

In some embodiments of the compounds of formula (IV), (IV-a), (IV-b), (IV-c), and (IV-a), $A^3$ is selected from the group consisting of

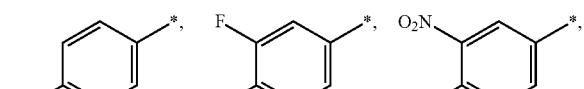

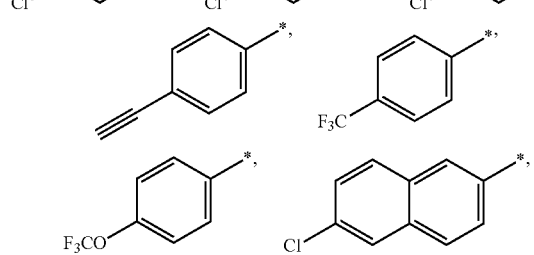

-continued

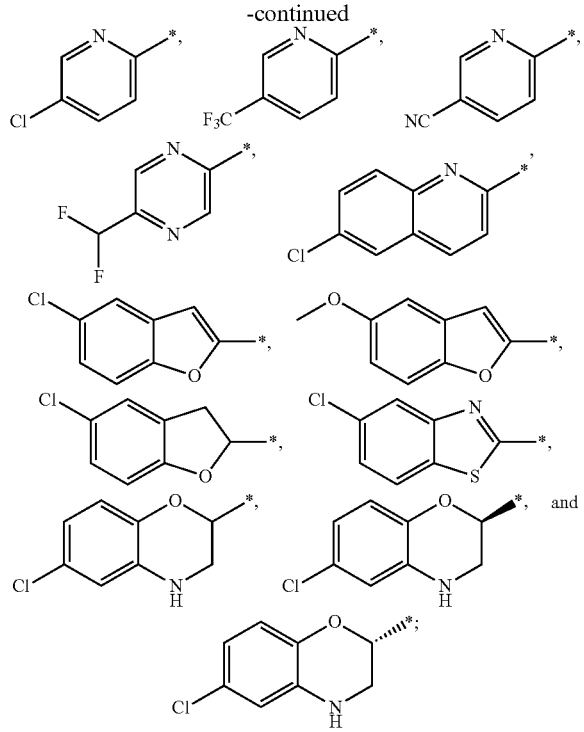

wherein the * represents the attachment point to the remainder of the molecule. In some embodiments, $A^3$ is

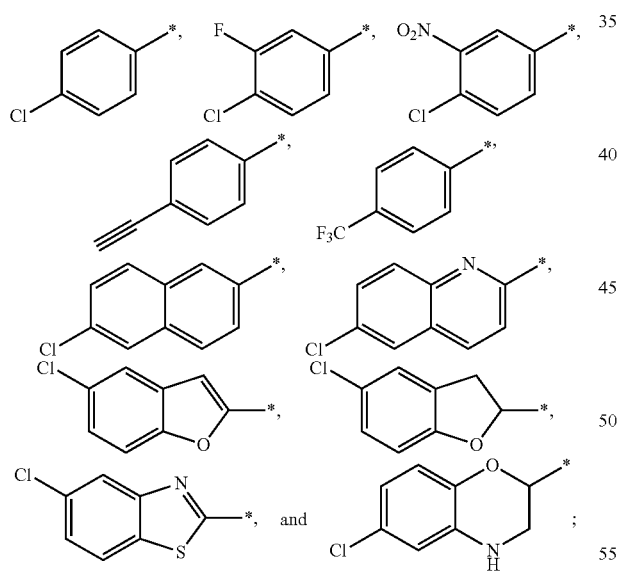

wherein the * represents the attachment point to the remainder of the molecule. In some embodiments, $A^3$ is

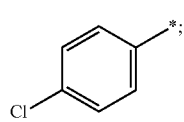

wherein the * represents the attachment point to the remainder of the molecule. In some embodiments, $A^3$ is

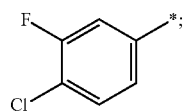

wherein the * represents the attachment point to the remainder of the molecule. In some embodiments, $A^3$ is

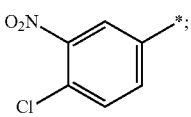

wherein the * represents the attachment point to the remainder of the molecule. In some embodiments, $A^3$ is

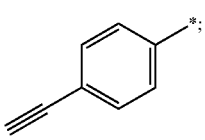

wherein the * represents the attachment point to the remainder of the molecule. In some embodiments, $A^3$ is

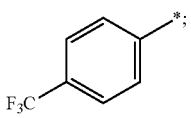

wherein the * represents the attachment point to the remainder of the molecule. In some embodiments, $A^3$ is

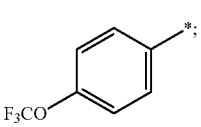

wherein the * represents the attachment point to the remainder of the molecule. In some embodiments, $A^3$ is

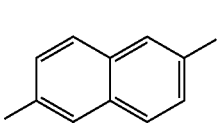

wherein the * represents the attachment point to the remainder of the molecule. In some embodiments, $A^3$ is

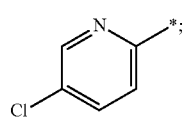

wherein the * represents the attachment point to the remainder of the molecule. In some embodiments, A³ is

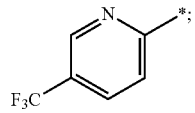

wherein the * represents the attachment point to the remainder of the molecule. In some embodiments, A³ is

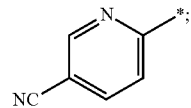

wherein the * represents the attachment point to the remainder of the molecule. In some embodiments, A³ is

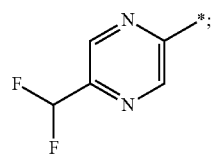

wherein the * represents the attachment point to the remainder of the molecule. In some embodiments, A³ is

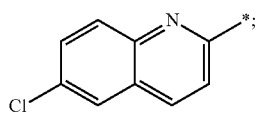

wherein the * represents the attachment point to the remainder of the molecule. In some embodiments, A³ is

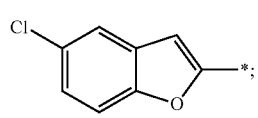

wherein the * represents the attachment point to the remainder of the molecule. In some embodiments, A³ is

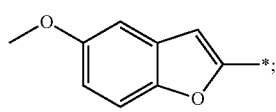

wherein the * represents the attachment point to the remainder of the molecule. In some embodiments, A³ is

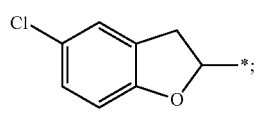

wherein the * represents the attachment point to the remainder of the molecule. In some embodiments, A³ is

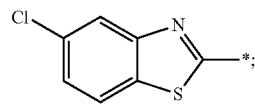

wherein the * represents the attachment point to the remainder of the molecule. In some embodiments, A³ is

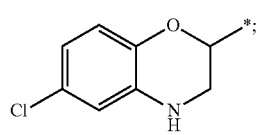

wherein the * represents the attachment point to the remainder of the molecule. In some embodiments, A³ is

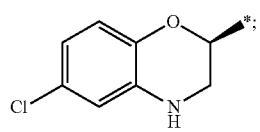

wherein the * represents the attachment point to the remainder of the molecule. In some embodiments, A³ is

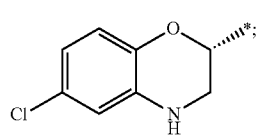

wherein the * represents the attachment point to the remainder of the molecule.

In some embodiments of the compounds of formula (IV), (IV-a), (IV-b), (IV-c), and (IV-a), A⁴ is selected from the group consisting of

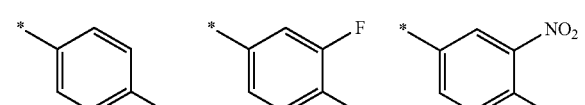
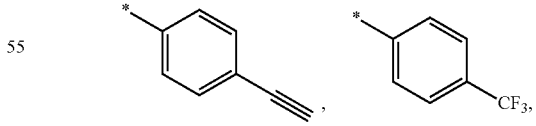
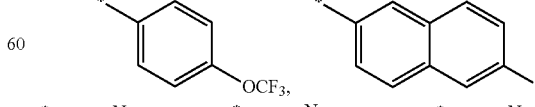
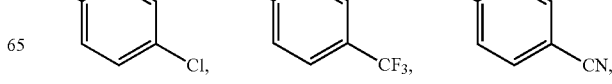

-continued

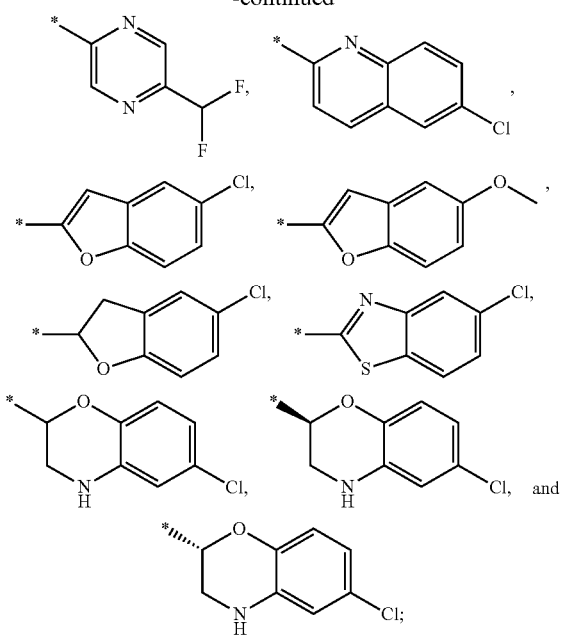

wherein the * represents the attachment point to the remainder of the molecule. In some embodiments, $A^4$ is selected from the group consisting of

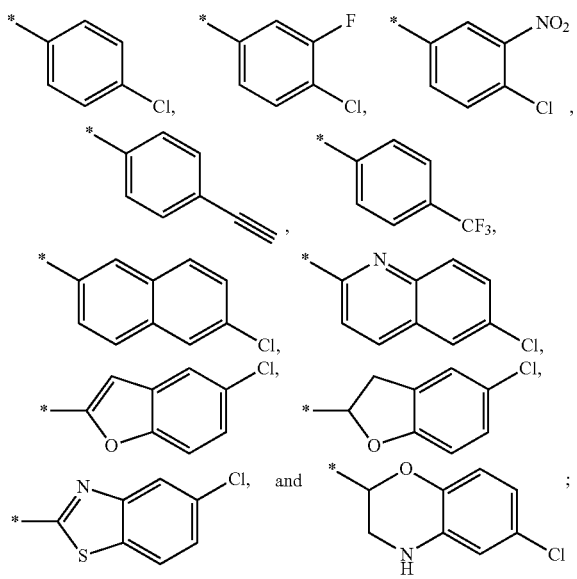

wherein the * represents the attachment point to the remainder of the molecule. In some embodiments, $A^4$ is

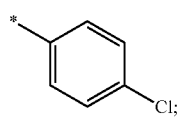

wherein the * represents the attachment point to the remainder of the molecule. In some embodiments, $A^4$ is

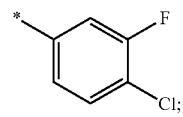 [SMILES: *c1ccc(Cl)c(F)c1]

wherein the * represents the attachment point to the remainder of the molecule. In some embodiments, $A^4$ is

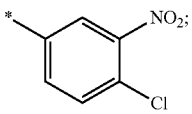 [SMILES: *c1ccc(Cl)c([N+](=O)[O-])c1]

wherein the * represents the attachment point to the remainder of the molecule. In some embodiments, $A^4$ is

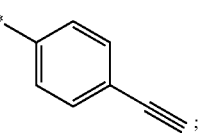

wherein the * represents the attachment point to the remainder of the molecule. In some embodiments, $A^4$ is

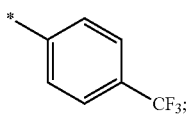

wherein the * represents the attachment point to the remainder of the molecule. In some embodiments, $A^4$ is

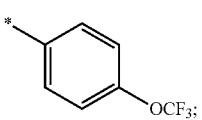

wherein the * represents the attachment point to the remainder of the molecule. In some embodiments, $A^4$ is

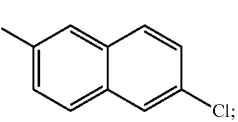

wherein the * represents the attachment point to the remainder of the molecule. In some embodiments, $A^4$ is

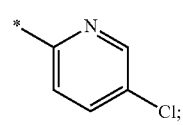

wherein the * represents the attachment point to the remainder of the molecule. In some embodiments, $A^4$ is

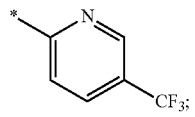

wherein the * represents the attachment point to the remainder of the molecule. In some embodiments, A⁴ is

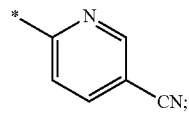

wherein the * represents the attachment point to the remainder of the molecule. In some embodiments, A⁴ is

wherein the * represents the attachment point to the remainder of the molecule. In some embodiments, A⁴ is

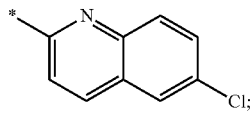 [SMILES: *c1ccc2cc(Cl)ccc2n1]

wherein the * represents the attachment point to the remainder of the molecule. In some embodiments, A⁴ is

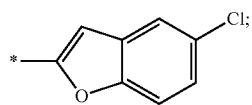 [SMILES: *c1cc2cc(Cl)ccc2o1]

wherein the * represents the attachment point to the remainder of the molecule. In some embodiments, A⁴ is

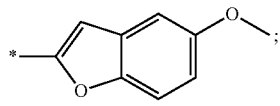 [SMILES: *c1cc2cc(OC)ccc2o1]

wherein the * represents the attachment point to the remainder of the molecule. In some embodiments, A⁴ is

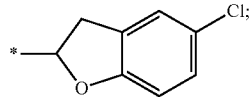

wherein the * represents the attachment point to the remainder of the molecule. In some embodiments, A⁴ is

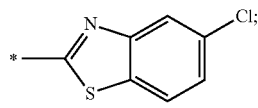

wherein the * represents the attachment point to the remainder of the molecule. In some embodiments, A⁴ is

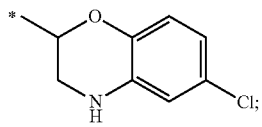

wherein the * represents the attachment point to the remainder of the molecule. In some embodiments, A⁴ is

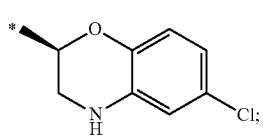

wherein the * represents the attachment point to the remainder of the molecule. In some embodiments, A⁴ is

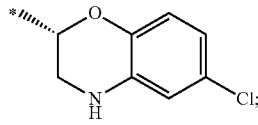

wherein the * represents the attachment point to the remainder of the molecule.

In one aspect, provided is a compound of formula (V):

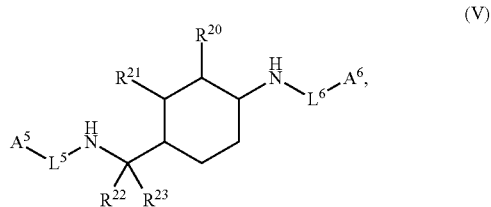

(V)

or a pharmaceutically acceptable salt thereof,
wherein:
  $R^{20}$ is hydrogen or —C(O)OH;
  $R^{21}$ is hydrogen or halogen;
  $R^{22}$ and $R^{23}$ are both hydrogen or $R^{22}$ and $R^{23}$ are taken together to form an oxo (=O) substituent;
  $L^5$ is selected from the group consisting of

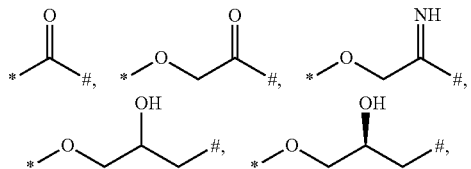

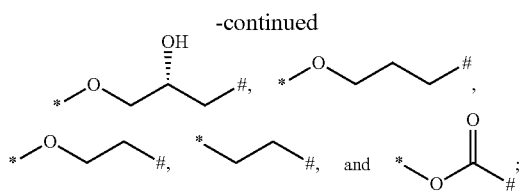

wherein the * represents the attachment point to $A^5$, and the # represents the attachment point to the remainder of the molecule;

$L^6$ is selected from the group consisting of

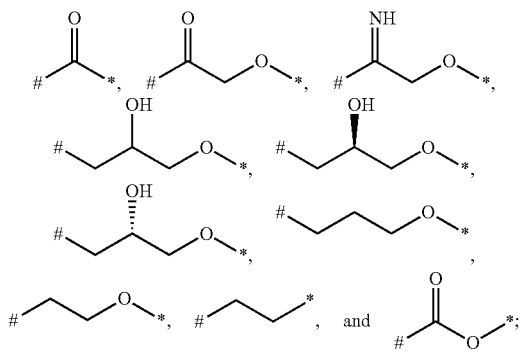

wherein the * represents the attachment point to $A^6$, and the # represents the attachment point to the remainder of the molecule;

$A^5$ is selected from the group consisting of phenyl, naphthyl, pyridyl, pyrazinyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, pyridyl, pyrazinyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, CN, —$NO_2$, $C_1$-$C_6$ alkyl, $C_2$-$C_6$ alkenyl, $C_2$-$C_6$ alkynyl, —O—$C_1$-$C_6$ alkyl, —O—$C_1$-$C_6$ haloalkyl, and $C_1$-$C_6$ haloalkyl;

$A^6$ is selected from the group consisting of phenyl, naphthyl, pyridyl, pyrazinyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, pyridyl, pyrazinyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, CN, —$NO_2$, $C_1$-$C_6$ alkyl, $C_2$-$C_6$ alkenyl, $C_2$-$C_6$ alkynyl, —O—$C_1$-$C_6$ alkyl, —O—$C_1$-$C_6$ haloalkyl, and $C_1$-$C_6$ haloalkyl.

In some embodiments of the compound of Formula (V), $A^5$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —$NO_2$, $C_1$-$C_6$ alkyl, $C_2$-$C_6$ alkenyl, $C_2$-$C_6$ alkynyl, and $C_1$-$C_6$ haloalkyl.

In some embodiments of the compound of Formula (V), $A^6$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —$NO_2$, $C_1$-$C_6$ alkyl, $C_2$-$C_6$ alkenyl, $C_2$-$C_6$ alkynyl, and $C_1$-$C_6$ haloalkyl.

In some embodiments, the compound of formula (V) is a compound of formula (V-a):

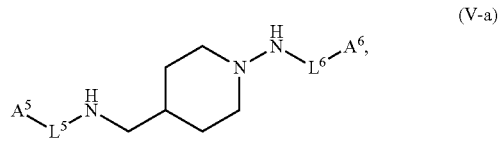

(V-a)

or a pharmaceutically acceptable salt thereof,
wherein $L^5$, $L^6$, $A^5$, and $A^6$ are as defined for the compound of formula (V).

In some embodiments, the compound of formula (V) is a compound of formula (V-b):

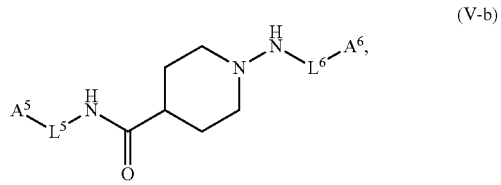

(V-b)

or a pharmaceutically acceptable salt thereof,
wherein $L^5$, $L^6$, $A^5$, and $A^6$ are as defined for the compound of formula (V).

In some embodiments of the compounds of formula (V), (V-a), and (V-b), $L^5$ is selected from the group consisting of

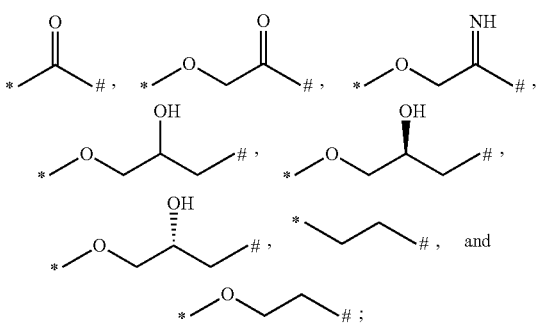

wherein the * represents the attachment point to $A^5$, and the # represents the attachment point to the remainder of the molecule. In some embodiments, $L^5$ is

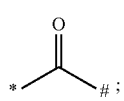

wherein the * represents the attachment point to $A^5$, and the # represents the attachment point to the remainder of the molecule. In some embodiments, $L^5$ is

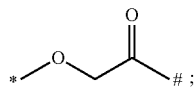

wherein the * represents the attachment point to $A^5$, and the # represents the attachment point to the remainder of the molecule. In some embodiments, $L^5$ is

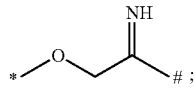

wherein the * represents the attachment point to $A^5$, and the # represents the attachment point to the remainder of the molecule. In some embodiments, $L^5$ is

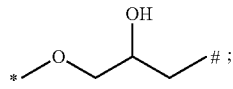

wherein the * represents the attachment point to $A^5$, and the # represents the attachment point to the remainder of the molecule. In some embodiments, $L^5$ is

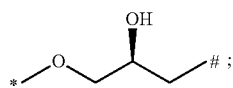

wherein the * represents the attachment point to $A^5$, and the # represents the attachment point to the remainder of the molecule. In some embodiments, $L^5$ is

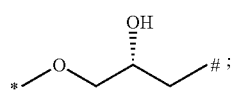

wherein the * represents the attachment point to $A^5$, and the # represents the attachment point to the remainder of the molecule. In some embodiments, $L^5$ is

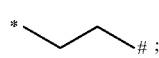

wherein the * represents the attachment point to $A^5$, and the # represents the attachment point to the remainder of the molecule. In some embodiments, $L^5$ is

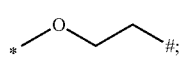

wherein the * represents the attachment point to $A^5$, and the # represents the attachment point to the remainder of the molecule.

In some embodiments of the compounds of formula (V), (V-a), and (V-b), $L^6$ is selected from the group consisting of

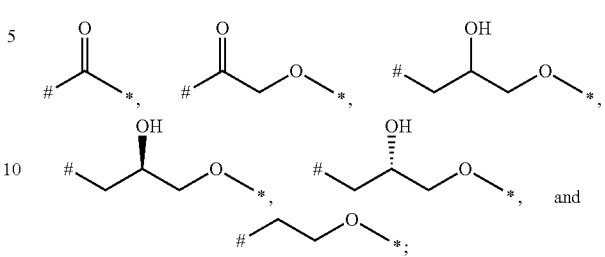

and wherein the * represents the attachment point to $A^6$, and the # represents the attachment point to the remainder of the molecule. In some embodiments, $L^6$ is

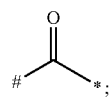

wherein the * represents the attachment point to $A^6$, and the # represents the attachment point to the remainder of the molecule. In some embodiments, $L^6$ is

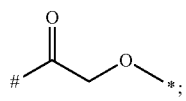

wherein the * represents the attachment point to $A^6$, and the # represents the attachment point to the remainder of the molecule. In some embodiments, $L^6$ is

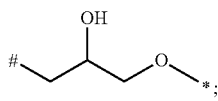

wherein the * represents the attachment point to $A^6$, and the # represents the attachment point to the remainder of the molecule. In some embodiments, $L^6$ is

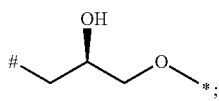

wherein the * represents the attachment point to $A^6$, and the # represents the attachment point to the remainder of the molecule. In some embodiments, $L^6$ is

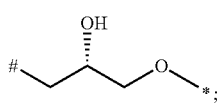

wherein the * represents the attachment point to $A^6$, and the # represents the attachment point to the remainder of the molecule. In some embodiments, $L^6$ is

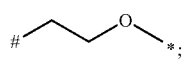

wherein the * represents the attachment point to $A^6$, and the # represents the attachment point to the remainder of the molecule.

In some embodiments of the compounds of formula (V), (V-a), and (V-b), $A^5$ is selected from the group consisting of

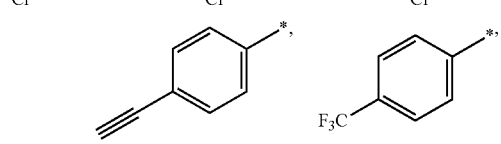

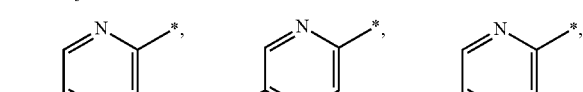

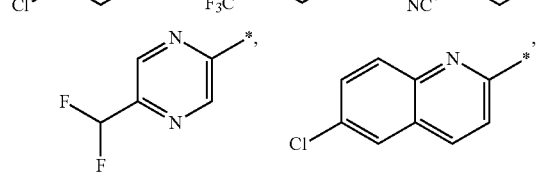

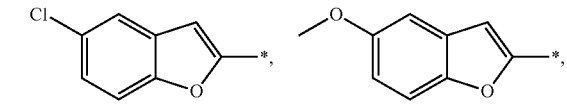

wherein the * represents the attachment point to the remainder of the molecule. In some embodiments, $A^5$ is selected from the group consisting of

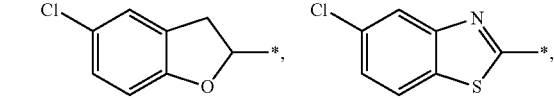

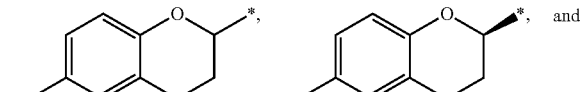

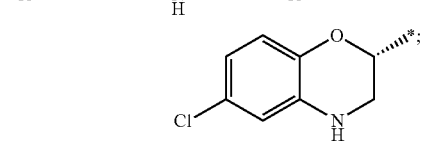

wherein the * represents the attachment point to the remainder of the molecule. In some embodiments, $A^5$ is

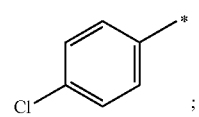

wherein the * represents the attachment point to the remainder of the molecule. In some embodiments, $A^5$ is

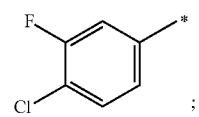

wherein the * represents the attachment point to the remainder of the molecule. In some embodiments, $A^5$ is

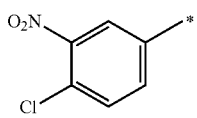

wherein the * represents the attachment point to the remainder of the molecule. In some embodiments, $A^5$ is

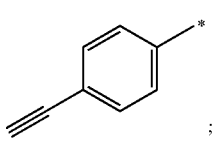

wherein the * represents the attachment point to the remainder of the molecule. In some embodiments, $A^5$ is

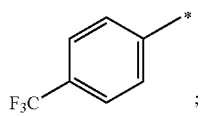

wherein the * represents the attachment point to the remainder of the molecule. In some embodiments, $A^5$ is

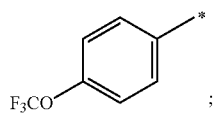

wherein the * represents the attachment point to the remainder of the molecule. In some embodiments, $A^5$ is

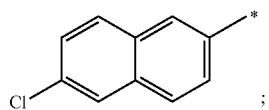

wherein the * represents the attachment point to the remainder of the molecule. In some embodiments, $A^5$ is

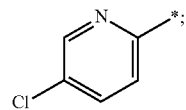

wherein the * represents the attachment point to the remainder of the molecule. In some embodiments, $A^5$ is

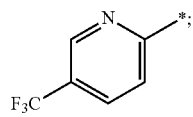

wherein the * represents the attachment point to the remainder of the molecule. In some embodiments, $A^5$ is

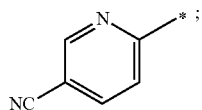

wherein the * represents the attachment point to the remainder of the molecule. In some embodiments, $A^5$ is

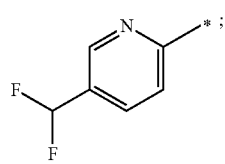

wherein the * represents the attachment point to the remainder of the molecule. In some embodiments, $A^5$ is

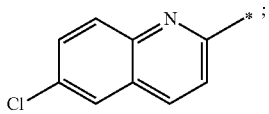

wherein the * represents the attachment point to the remainder of the molecule. In some embodiments, $A^5$ is

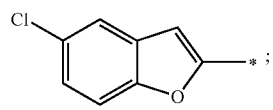

wherein the * represents the attachment point to the remainder of the molecule. In some embodiments, $A^5$ is

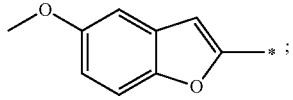

wherein the * represents the attachment point to the remainder of the molecule. In some embodiments, $A^5$ is

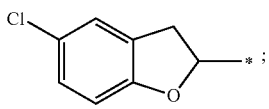

wherein the * represents the attachment point to the remainder of the molecule. In some embodiments, $A^5$ is

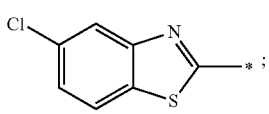

wherein the * represents the attachment point to the remainder of the molecule. In some embodiments, $A^5$ is

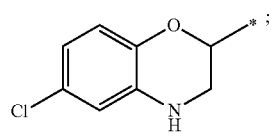

wherein the * represents the attachment point to the remainder of the molecule. In some embodiments, $A^5$ is

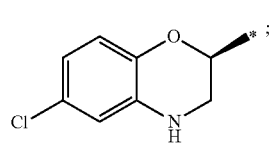

wherein the * represents the attachment point to the remainder of the molecule. In some embodiments, $A^5$ is

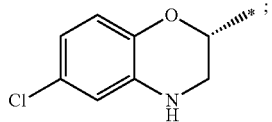

wherein the * represents the attachment point to the remainder of the molecule.

In some embodiments of the compounds of formula (V), (V-a), and (V-b), $A^6$ is selected from the group consisting of

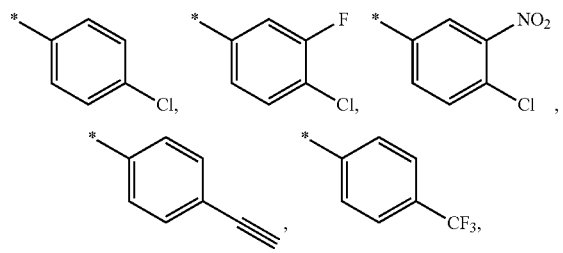

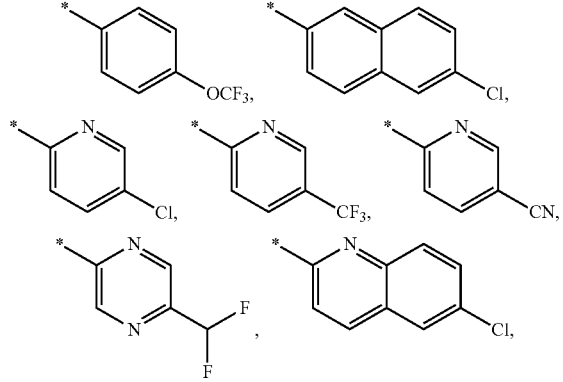

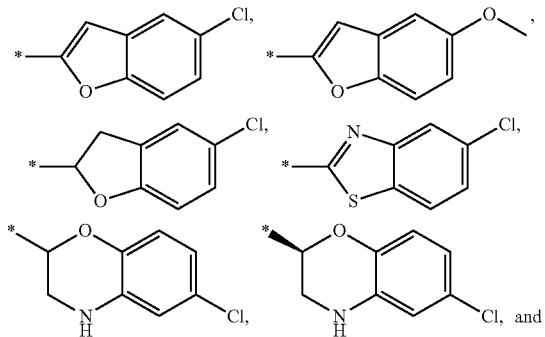

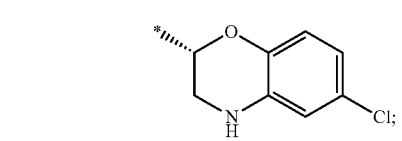

wherein the * represents the attachment point to the remainder of the molecule. In some embodiments, $A^6$ is selected from the group consisting of

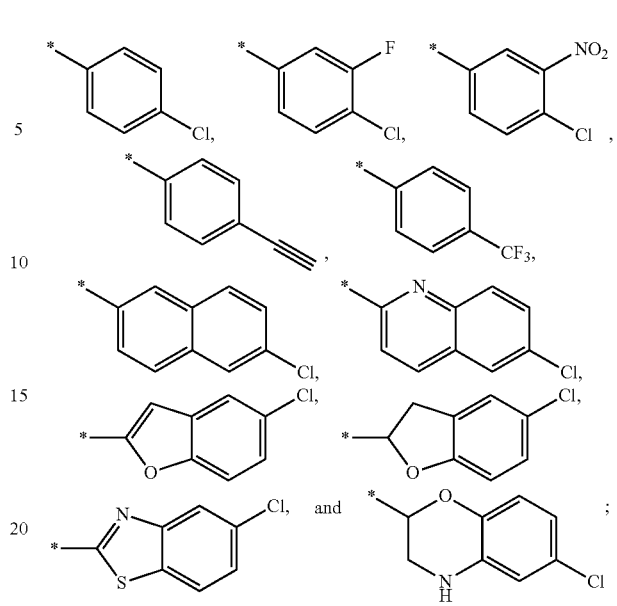

wherein the * represents the attachment point to the remainder of the molecule. In some embodiments, $A^6$ is

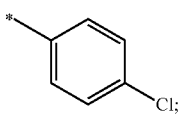

wherein the * represents the attachment point to the remainder of the molecule. In some embodiments, $A^6$ is

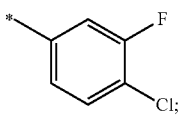

wherein the * represents the attachment point to the remainder of the molecule. In some embodiments, $A^6$ is

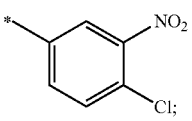

wherein the * represents the attachment point to the remainder of the molecule. In some embodiments, $A^6$ is

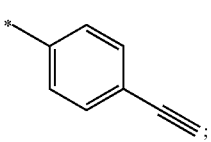

wherein the * represents the attachment point to the remainder of the molecule. In some embodiments, $A^6$ is

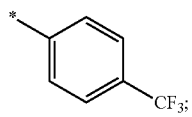 [SMILES: *c1ccc(C(F)(F)F)cc1]

wherein the * represents the attachment point to the remainder of the molecule. In some embodiments, A⁶ is

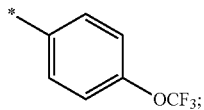

wherein the * represents the attachment point to the remainder of the molecule. In some embodiments, A⁶ is

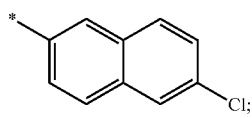 [SMILES: *c1ccc2cc(Cl)ccc2c1]

wherein the * represents the attachment point to the remainder of the molecule. In some embodiments, A⁶ is

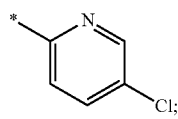

wherein the * represents the attachment point to the remainder of the molecule. In some embodiments, A⁶ is

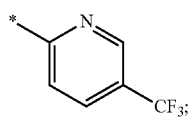

wherein the * represents the attachment point to the remainder of the molecule. In some embodiments, A⁶ is

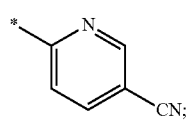

wherein the * represents the attachment point to the remainder of the molecule. In some embodiments, A⁶ is

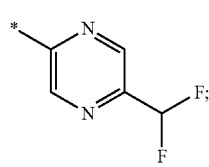

wherein the * represents the attachment point to the remainder of the molecule. In some embodiments, A⁶ is

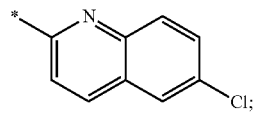 [SMILES: *c1ccc2cc(Cl)ccc2n1]

wherein the * represents the attachment point to the remainder of the molecule. In some embodiments, A⁶ is

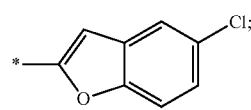 [SMILES: *c1cc2cc(Cl)ccc2o1]

wherein the * represents the attachment point to the remainder of the molecule. In some embodiments, A⁶ is

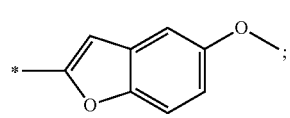

wherein the * represents the attachment point to the remainder of the molecule. In some embodiments, A⁶ is

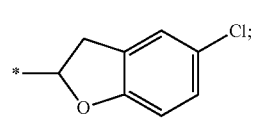 [SMILES: *C1Cc2cc(Cl)ccc2O1]

wherein the * represents the attachment point to the remainder of the molecule. In some embodiments, A⁶ is

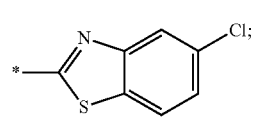 [SMILES: *c1nc2cc(Cl)ccc2s1]

wherein the * represents the attachment point to the remainder of the molecule. In some embodiments, A⁶ is

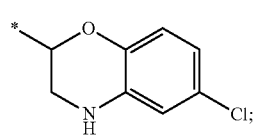

wherein the * represents the attachment point to the remainder of the molecule. In some embodiments, A⁶ is

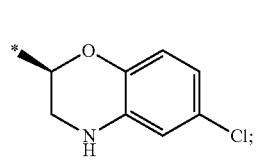 [SMILES: *[C@@H]1CNc2cc(Cl)ccc2O1]

wherein the * represents the attachment point to the remainder of the molecule. In some embodiments, A⁶ is

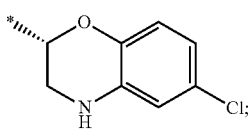 [SMILES: *[C@H]1CNc2cc(Cl)ccc2O1]

wherein the * represents the attachment point to the remainder of the molecule.

In one aspect, provided is a compound of formula (VI):

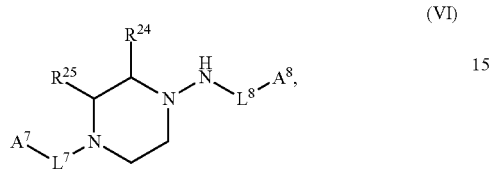

or a pharmaceutically acceptable salt thereof,
wherein:
$R^{24}$ is hydrogen or —C(O)OH;
$R^{25}$ is hydrogen or halogen;
$L^7$ is selected from the group consisting of

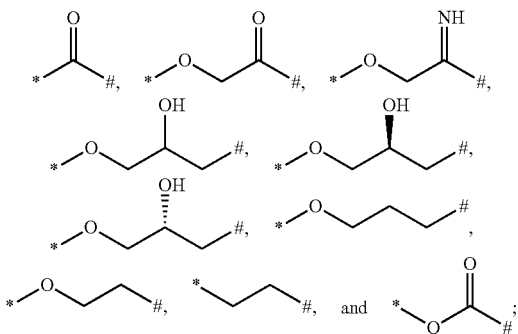

wherein the represents the attachment point to $A^7$, and the # represents the attachment point to the remainder of the molecule;

$L^8$ is selected from the group consisting of

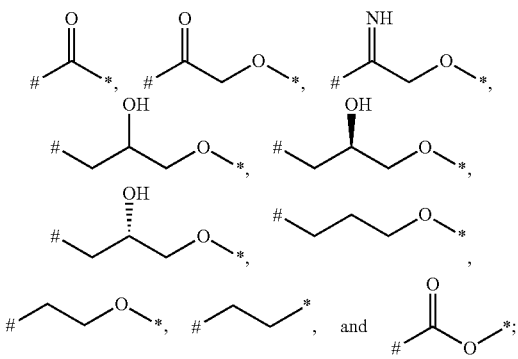

wherein the * represents the attachment point to $A^8$, and the # represents the attachment point to the remainder of the molecule;

$A^7$ is selected from the group consisting of phenyl, naphthyl, pyridyl, pyrazinyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, pyridyl, pyrazinyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, CN, —NO$_2$, $C_1$-$C_6$ alkyl, $C_2$-$C_6$ alkenyl, $C_2$-$C_6$ alkynyl, —O—$C_1$-$C_6$ alkyl, —O—$C_1$-$C_6$ haloalkyl, and $C_1$-$C_6$ haloalkyl;

$A^8$ is selected from the group consisting of phenyl, naphthyl, pyridyl, pyrazinyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, pyridyl, pyrazinyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, CN, —NO$_2$, $C_1$-$C_6$ alkyl, $C_2$-$C_6$ alkenyl, $C_2$-$C_6$ alkynyl, —O—$C_1$-$C_6$ alkyl, —O—$C_1$-$C_6$ haloalkyl, and $C_1$-$C_6$ haloalkyl.

In some embodiments of the compound of Formula (VI), $A^7$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —NO$_2$, $C_1$-$C_6$ alkyl, $C_2$-$C_6$ alkenyl, $C_2$-$C_6$ alkynyl, and $C_1$-$C_6$ haloalkyl.

In some embodiments of the compound of Formula (VI), $A^8$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —NO$_2$, $C_1$-$C_6$ alkyl, $C_2$-$C_6$ alkenyl, $C_2$-$C_6$ alkynyl, and $C_1$-$C_6$ haloalkyl.

In some embodiments, the compound of formula (VI) is a compound of formula (VI-a):

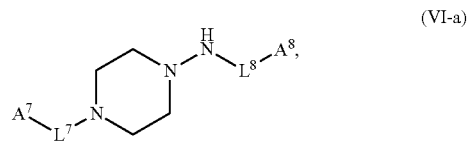

or a pharmaceutically acceptable salt thereof,
wherein $L^7$, $L^8$, $A^7$, and $A^8$ are as defined for the compound of formula (VI).

In some embodiments of the compounds of formula VI) and (VI-a), $L^7$ is selected from the group consisting of

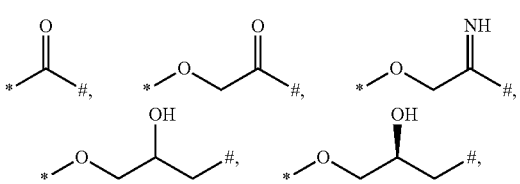

-continued

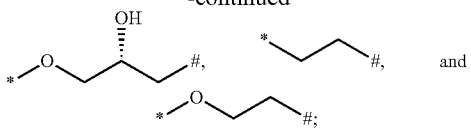

wherein the represents the attachment point to $A^7$, and the # represents the attachment point to the remainder of the molecule. In some embodiments, $L^7$ is

wherein the * represents the attachment point to $A^7$, and the # represents the attachment point to the remainder of the molecule. In some embodiments, $L^7$ is

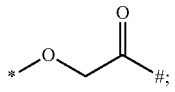

wherein the * represents the attachment point to $A^7$, and the # represents the attachment point to the remainder of the molecule. In some embodiments, $L^7$ is

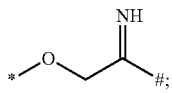

wherein the * represents the attachment point to $A^7$, and the # represents the attachment point to the remainder of the molecule. In some embodiments, $L^7$ is

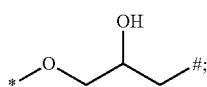

wherein the * represents the attachment point to $A^7$, and the # represents the attachment point to the remainder of the molecule. In some embodiments, $L^7$ is

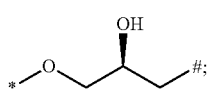

wherein the * represents the attachment point to $A^7$, and the # represents the attachment point to the remainder of the molecule. In some embodiments, $L^7$ is

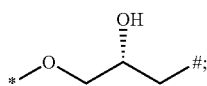

wherein the * represents the attachment point to $A^7$, and the # represents the attachment point to the remainder of the molecule. In some embodiments, $L^7$ is

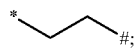

wherein the * represents the attachment point to $A^7$, and the # represents the attachment point to the remainder of the molecule. In some embodiments, $L^7$ is

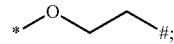

wherein the * represents the attachment point to $A^7$, and the # represents the attachment point to the remainder of the molecule.

In some embodiments of the compounds of formula (VI) and (VI-a), $L^8$ is selected from the group consisting of

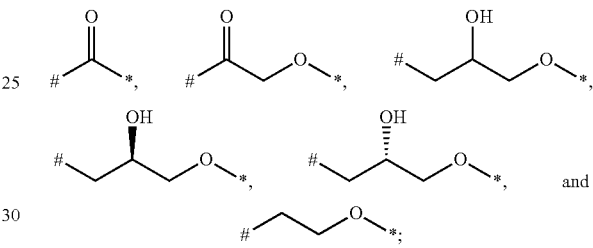

wherein the * represents the attachment point to $A^8$, and the # represents the attachment point to the remainder of the molecule. In some embodiments, $L^8$ is

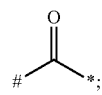

wherein the * represents the attachment point to $A^8$, and the # represents the attachment point to the remainder of the molecule. In some embodiments, $L^8$ is

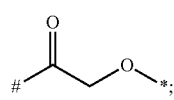

wherein the * represents the attachment point to $A^8$, and the # represents the attachment point to the remainder of the molecule. In some embodiments, $L^8$ is

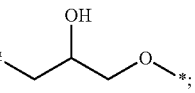

wherein the * represents the attachment point to $A^8$, and the # represents the attachment point to the remainder of the molecule. In some embodiments, $L^8$ is

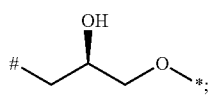

wherein the * represents the attachment point to A⁸, and the # represents the attachment point to the remainder of the molecule. In some embodiments, L⁸ is

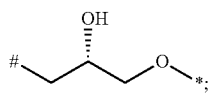

wherein the * represents the attachment point to A⁸, and the # represents the attachment point to the remainder of the molecule. In some embodiments, L⁸ is

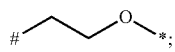

wherein the * represents the attachment point to A⁸, and the # represents the attachment point to the remainder of the molecule.

In some embodiments of the compounds of formula (VI) and (VI-a), A⁷ is selected from the group consisting of

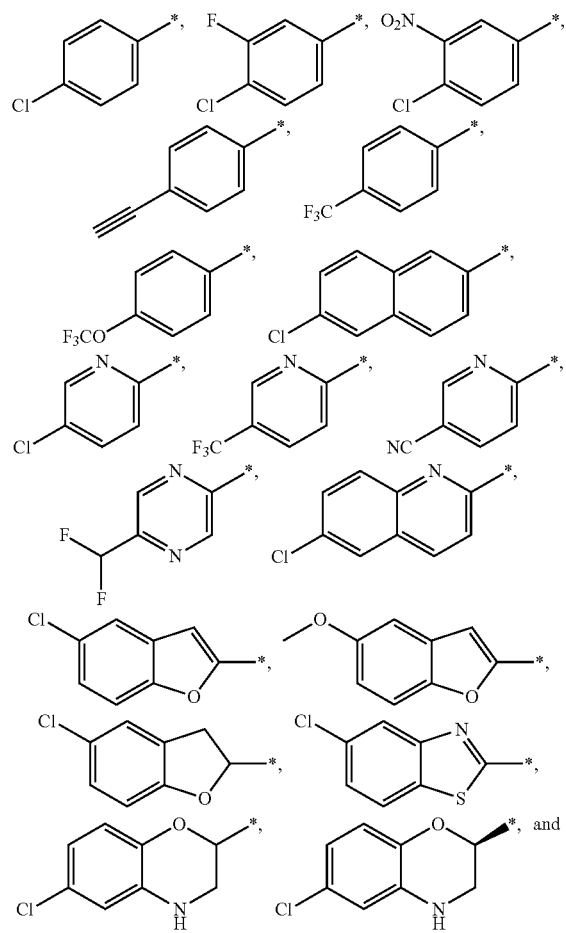

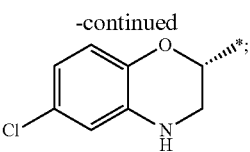

wherein the * represents the attachment point to the remainder of the molecule. In some embodiments, A⁷ is selected from the group consisting of

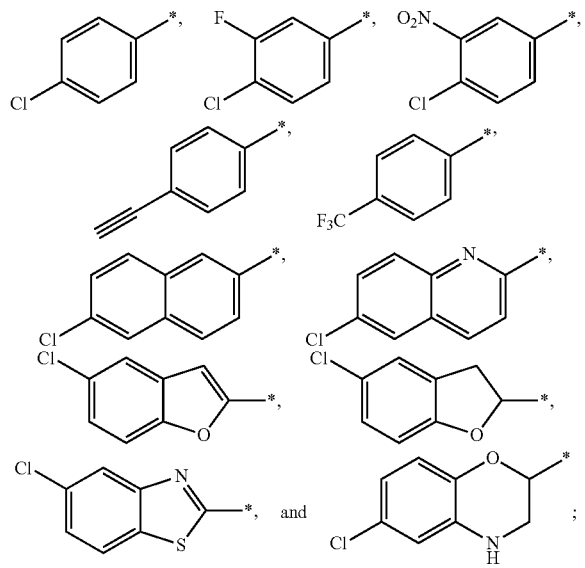

wherein the * represents the attachment point to the remainder of the molecule. In some embodiments, A⁷ is

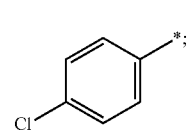

wherein the * represents the attachment point to the remainder of the molecule. In some embodiments, A⁷ is

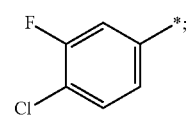

wherein the * represents the attachment point to the remainder of the molecule. In some embodiments, A⁷ is

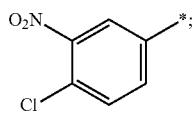

wherein the * represents the attachment point to the remainder of the molecule. In some embodiments, A⁷ is

103

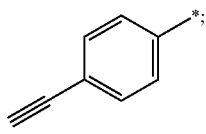

wherein the * represents the attachment point to the remainder of the molecule. In some embodiments, $A^7$ is

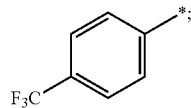

wherein the * represents the attachment point to the remainder of the molecule. In some embodiments, $A^7$ is

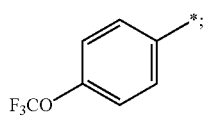

wherein the * represents the attachment point to the remainder of the molecule. In some embodiments, $A^7$ is

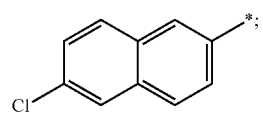

wherein the * represents the attachment point to the remainder of the molecule. In some embodiments, $A^7$ is

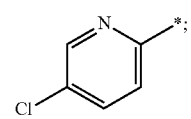

wherein the * represents the attachment point to the remainder of the molecule. In some embodiments, $A^7$ is

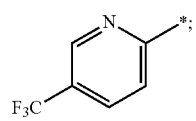

wherein the * represents the attachment point to the remainder of the molecule. In some embodiments, $A^7$ is

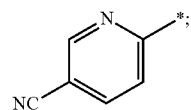

wherein the * represents the attachment point to the remainder of the molecule. In some embodiments, $A^7$ is

104

wherein the * represents the attachment point to the remainder of the molecule. In some embodiments, $A^7$ is

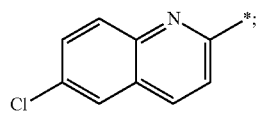

wherein the * represents the attachment point to the remainder of the molecule. In some embodiments, $A^7$ is

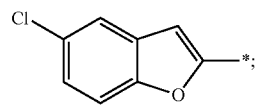

wherein the * represents the attachment point to the remainder of the molecule. In some embodiments, $A^7$ is

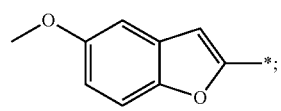

wherein the * represents the attachment point to the remainder of the molecule. In some embodiments, $A^7$ is

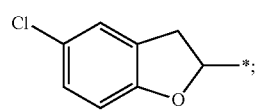

wherein the * re resents the attachment point to the remainder of the molecule. In some embodiments, $A^7$ is

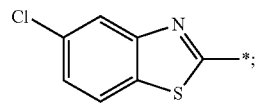

wherein the * represents the attachment point to the remainder of the molecule. In some embodiments, $A^7$ is

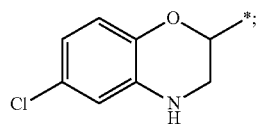

wherein the * represents the attachment point to the remainder of the molecule. In some embodiments, $A^7$ is

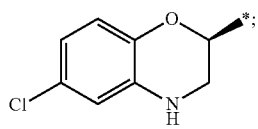

wherein the * represents the attachment point to the remainder of the molecule. In some embodiments, A⁷ is

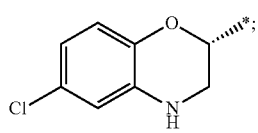

wherein the * represents the attachment point to the remainder of the molecule.

In some embodiments of the compounds of formula (VI) and (VI-a), A⁸ is selected from the group consisting of

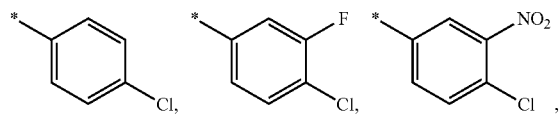

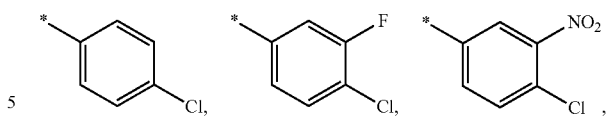

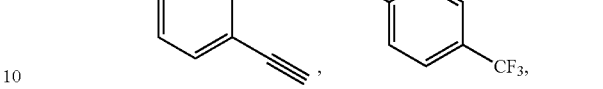

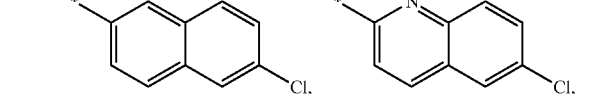

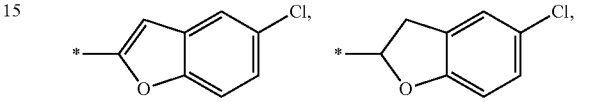

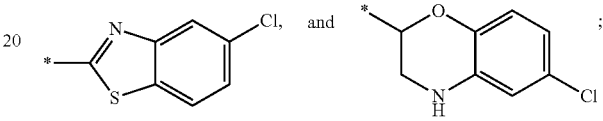

wherein the * represents the attachment point to the remainder of the molecule. In some embodiments, A⁸ is selected from the group consisting of wherein the * represents the attachment point to the remainder of the molecule. In some embodiments, A⁸ is

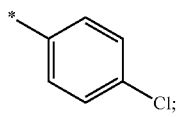 [SMILES: *c1ccc(Cl)cc1]

wherein the * represents the attachment point to the remainder of the molecule. In some embodiments, A⁸ is

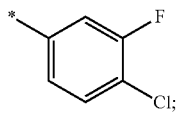 [SMILES: *c1ccc(Cl)c(F)c1]

wherein the * represents the attachment point to the remainder of the molecule. In some embodiments, A⁸ is

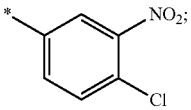 [SMILES: *c1ccc(Cl)c([N+](=O)[O-])c1]

wherein the * represents the attachment point to the remainder of the molecule. In some embodiments, A⁸ is

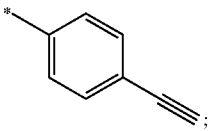

wherein the * represents the attachment point to the remainder of the molecule. In some embodiments, A⁸ is

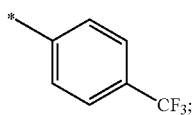

wherein the * represents the attachment point to the remainder of the molecule. In some embodiments, $A^8$ is

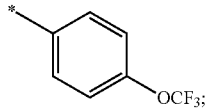

wherein the * represents the attachment point to the remainder of the molecule. In some embodiments, $A^8$ is

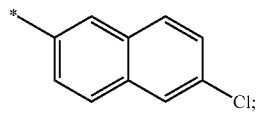

wherein the * represents the attachment point to the remainder of the molecule. In some embodiments, $A^8$ is

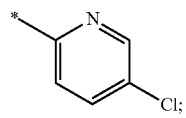

wherein the * represents the attachment point to the remainder of the molecule. In some embodiments, $A^8$ is

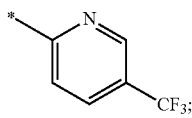

wherein the * represents the attachment point to the remainder of the molecule. In some embodiments, $A^8$ is

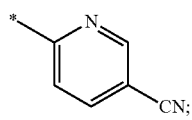

wherein the * represents the attachment point to the remainder of the molecule. In some embodiments, $A^8$ is

wherein the * represents the attachment point to the remainder of the molecule. In some embodiments, $A^8$ is

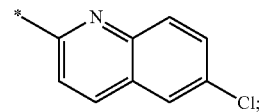

wherein the * represents the attachment point to the remainder of the molecule. In some embodiments, $A^8$ is

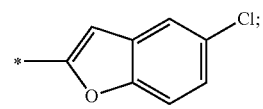

wherein the * represents the attachment point to the remainder of the molecule. In some embodiments, $A^8$ is

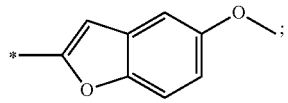

wherein the * represents the attachment point to the remainder of the molecule. In some embodiments, $A^8$ is

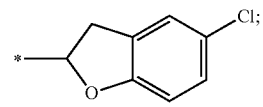

wherein the * represents the attachment point to the remainder of the molecule. In some embodiments, $A^8$ is

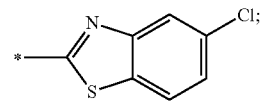

wherein the * represents the attachment point to the remainder of the molecule. In some embodiments, $A^8$ is

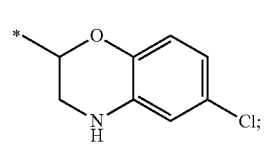

wherein the * represents the attachment point to the remainder of the molecule. In some embodiments, $A^8$ is

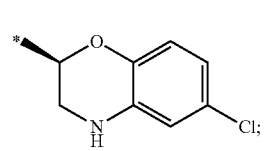

wherein the * represents the attachment point to the remainder of the molecule. In some embodiments, $A^8$ is

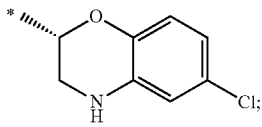

wherein the * represents the attachment point to the remainder of the molecule.

In one aspect, provided is a compound of formula (VII):

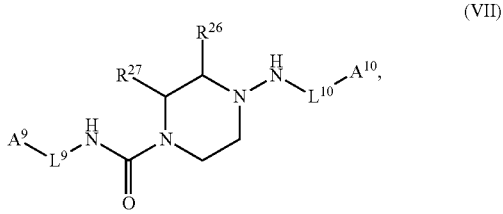

or a pharmaceutically acceptable salt thereof,
wherein:
$R^{26}$ is hydrogen or —C(O)OH;
$R^{27}$ is hydrogen or halogen;
$L^9$ is selected from the group consisting of

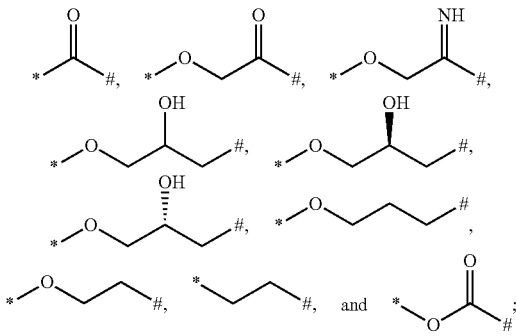

wherein the * represents the attachment point to $A^9$, and the # represents the attachment point to the remainder of the molecule;
$L^{10}$ is selected from the group consisting of

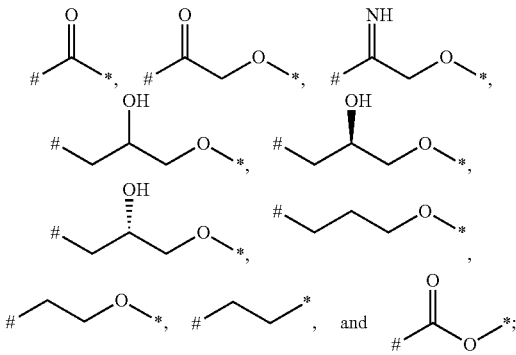

wherein the * represents the attachment point to $A^{10}$, and the # represents the attachment point to the remainder of the molecule;
$A^9$ is selected from the group consisting of phenyl, naphthyl, pyridyl, pyrazinyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, pyridyl, pyrazinyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, CN, —NO₂, $C_1$-$C_6$ alkyl, $C_2$-$C_6$ alkenyl, $C_2$-$C_6$ alkynyl, —O—$C_1$-$C_6$ alkyl, —O—$C_1$-$C_6$ haloalkyl, and $C_1$-$C_6$ haloalkyl;
$A^{10}$ is selected from the group consisting of phenyl, naphthyl, pyridyl, pyrazinyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, pyridyl, pyrazinyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, CN, —NO₂, $C_1$-$C_6$ alkyl, $C_2$-$C_6$ alkenyl, $C_2$-$C_6$ alkynyl, —O—$C_1$-$C_6$ alkyl, —O—$C_1$-$C_6$ haloalkyl, and $C_1$-$C_6$ haloalkyl.

In some embodiments of the compound of Formula (VII), $A^9$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —NO₂, $C_1$-$C_6$ alkyl, $C_2$-$C_6$ alkenyl, $C_2$-$C_6$ alkynyl, and $C_1$-$C_6$ haloalkyl.

In some embodiments of the compound of Formula (VII), $A^{10}$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —NO₂, $C_1$-$C_6$ alkyl, $C_2$-$C_6$ alkenyl, $C_2$-$C_6$ alkynyl, and $C_1$-$C_6$ haloalkyl.

In some embodiments, the compound of formula (VII) is a compound of formula (VII-a):

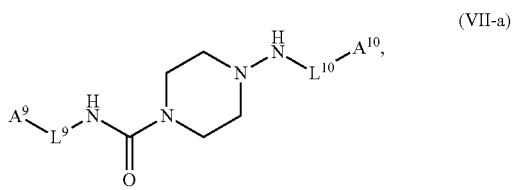

or a pharmaceutically acceptable salt thereof,
wherein $L^9$, $L^{10}$, $A^9$, and $A^{10}$ are as defined for the compound of formula (VII).

In some embodiments of the compounds of formula (VII) and (VII-a), $L^9$ is selected from the group consisting of

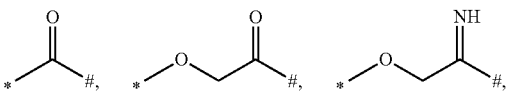

-continued

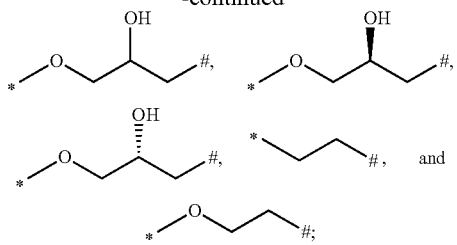
and wherein the * represents the attachment point to A⁹, and the # represents the attachment point to the remainder of the molecule. In some embodiments, L⁹ is

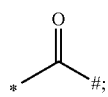

wherein the * represents the attachment point to A⁹, and the # represents the attachment point to the remainder of the molecule. In some embodiments, L⁹ is

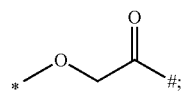

wherein the * represents the attachment point to A⁹, and the # represents the attachment point to the remainder of the molecule. In some embodiments, L⁹ is

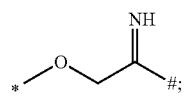

wherein the * represents the attachment point to A⁹, and the # represents the attachment point to the remainder of the molecule. In some embodiments, L⁹ is

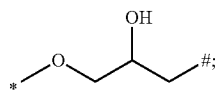

wherein the * represents the attachment point to A⁹, and the # represents the attachment point to the remainder of the molecule. In some embodiments, L⁹ is

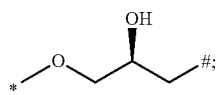

wherein the * represents the attachment point to A⁹, and the # represents the attachment point to the remainder of the molecule. In some embodiments, L⁹ is

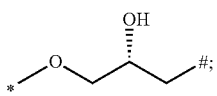

wherein the * represents the attachment point to A⁹, and the # represents the attachment point to the remainder of the molecule. In some embodiments, L⁹ is

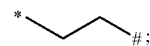

wherein the * represents the attachment point to A⁹, and the # represents the attachment point to the remainder of the molecule. In some embodiments, L⁹ is

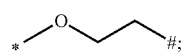

wherein the * represents the attachment point to A⁹, and the # represents the attachment point to the remainder of the molecule.

In some embodiments of the compounds of formula (VII) and (VII-a), L¹⁰ is selected from the group consisting of

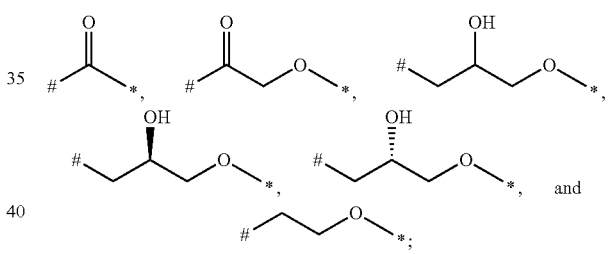

wherein the * represents the attachment point to A¹⁰, and the # represents the attachment point to the remainder of the molecule. In some embodiments, L¹⁰ is

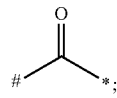

wherein the * represents the attachment point to A¹⁰, and the # represents the attachment point to the remainder of the molecule. In some embodiments, L¹⁰ is

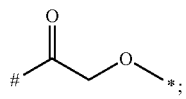

wherein the * represents the attachment point to A¹⁰, and the # represents the attachment point to the remainder of the molecule. In some embodiments, L¹⁰ is

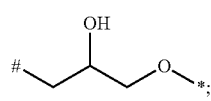

wherein the * represents the attachment point to $A^{10}$, and the # represents the attachment point to the remainder of the molecule. In some embodiments, $L^{10}$ is

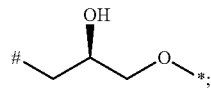

wherein the * represents the attachment point to $A^{10}$, and the # represents the attachment point to the remainder of the molecule. In some embodiments, $L^{10}$ is

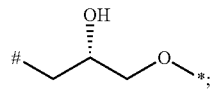

wherein the * represents the attachment point to $A^{10}$, and the # represents the attachment point to the remainder of the molecule. In some embodiments, $L^{10}$ is

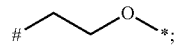

wherein the * represents the attachment point to $A^{10}$, and the # represents the attachment point to the remainder of the molecule.

In some embodiments of the compounds of formula (VII) and (VII-a), $A^9$ is selected from the group consisting of

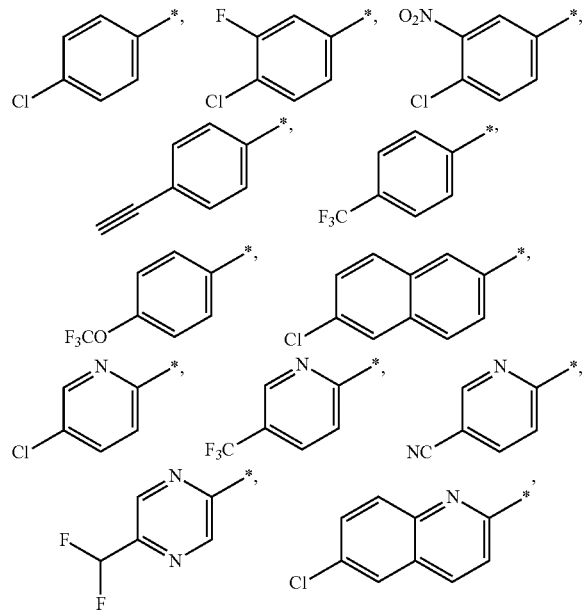

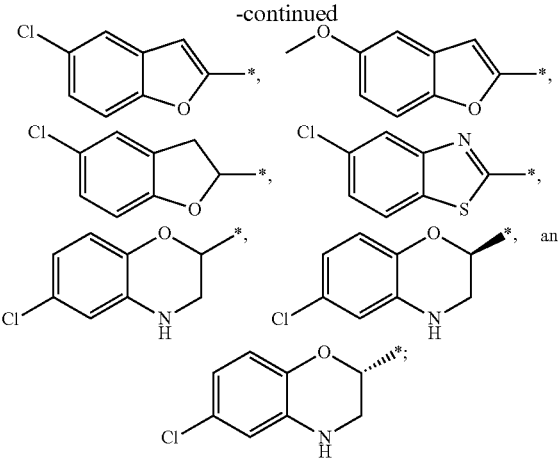

wherein the * represents the attachment point to the remainder of the molecule. In some embodiments, $A^9$ is selected from the group consisting of

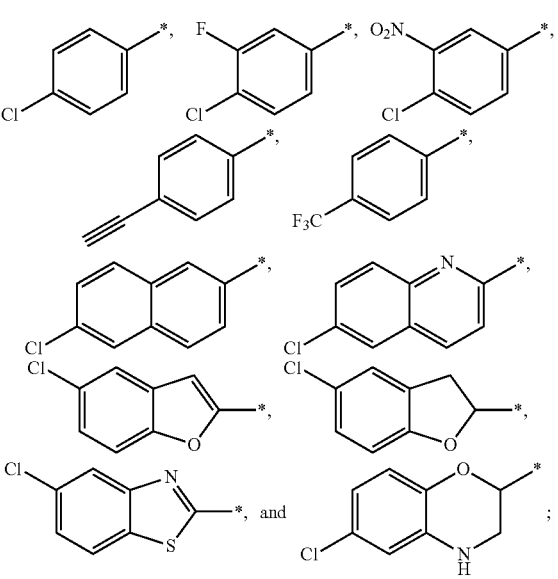

wherein the * represents the attachment point to the remainder of the molecule. In some embodiments, $A^9$ is

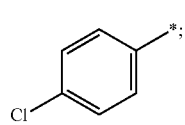

wherein the * represents the attachment point to the remainder of the molecule. In some embodiments, $A^9$ is

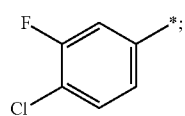

wherein the * represents the attachment point to the remainder of the molecule. In some embodiments, $A^9$ is

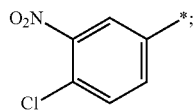

wherein the * represents the attachment point to the remainder of the molecule. In some embodiments, $A^9$ is

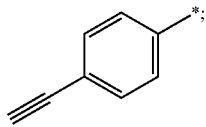

wherein the * represents the attachment point to the remainder of the molecule. In some embodiments, $A^9$ is

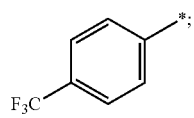

wherein the * represents the attachment point to the remainder of the molecule. In some embodiments, $A^9$ is

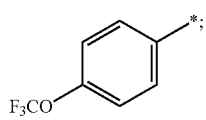

wherein the * represents the attachment point to the remainder of the molecule. In some embodiments, $A^9$ is

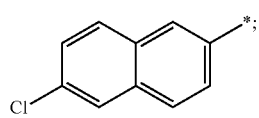

wherein the * represents the attachment point to the remainder of the molecule. In some embodiments, $A^9$ is

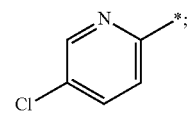

wherein the * represents the attachment point to the remainder of the molecule. In some embodiments, $A^9$ is

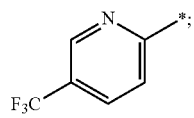

wherein the * represents the attachment point to the remainder of the molecule. In some embodiments, $A^9$ is

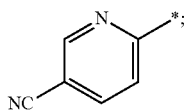

wherein the * represents the attachment point to the remainder of the molecule. In some embodiments, $A^9$ is

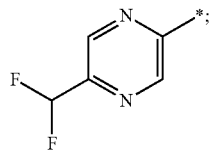

wherein the * represents the attachment point to the remainder of the molecule. In some embodiments, $A^9$ is

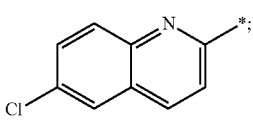

wherein the * represents the attachment point to the remainder of the molecule. In some embodiments, $A^9$ is

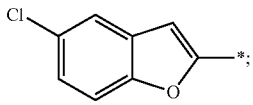

wherein the * represents the attachment point to the remainder of the molecule. In some embodiments, $A^9$ is

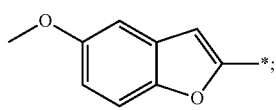

wherein the * represents the attachment point to the remainder of the molecule. In some embodiments, $A^9$ is

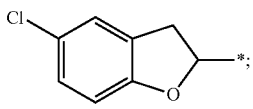

wherein the * represents the attachment point to the remainder of the molecule. In some embodiments, $A^9$ is

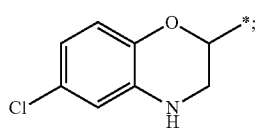

wherein the * represents the attachment point to the remainder of the molecule. In some embodiments, $A^9$ is

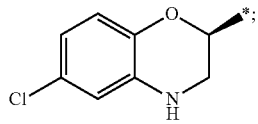

wherein the * represents the attachment point to the remainder of the molecule. In some embodiments, $A^9$ is

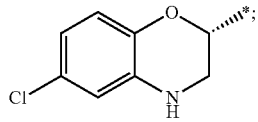

wherein the * represents the attachment point to the remainder of the molecule.

In some embodiments of the compounds of formula (VII) and (VII-a), $A^{10}$ is selected from the group consisting of

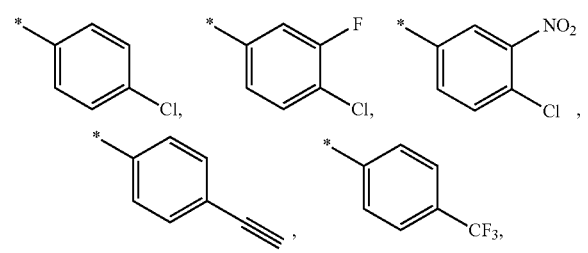

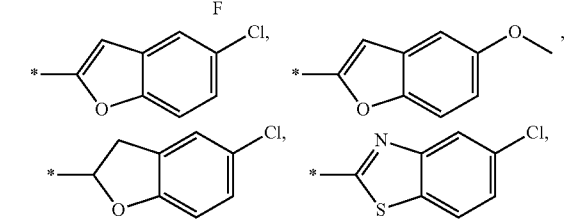

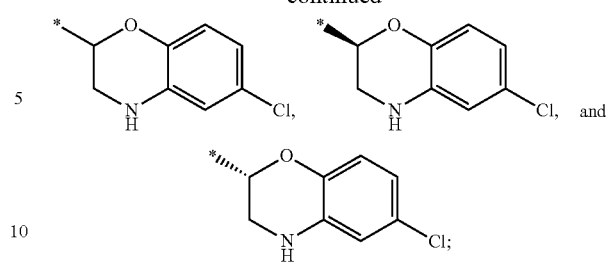

wherein the * represents the attachment point to the remainder of the molecule. In some embodiments $A^{10}$ is selected from the group consisting of

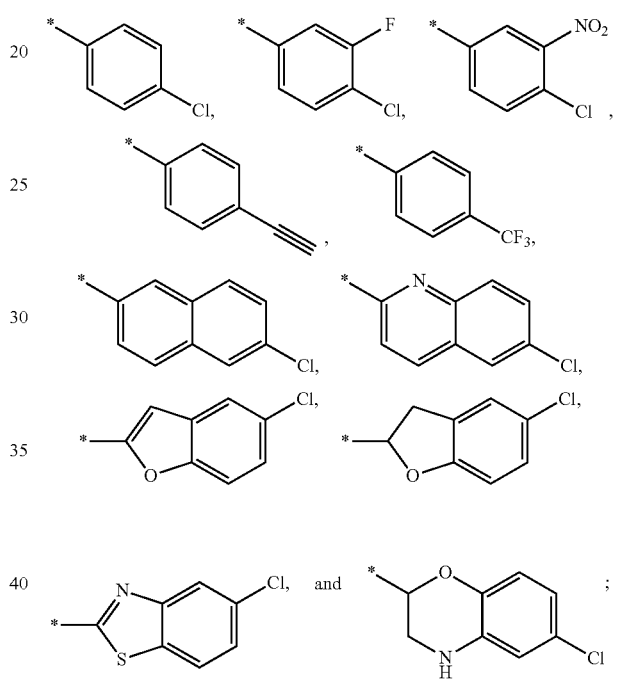

wherein the * represents the attachment point to the remainder of the molecule. In some embodiments, $A^{10}$ is

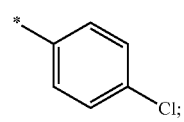 [SMILES: *c1ccc(Cl)cc1]

wherein the * represents the attachment point to the remainder of the molecule. In some embodiments, $A^{10}$ is

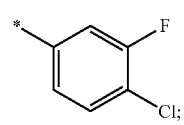 [SMILES: *c1ccc(Cl)c(F)c1]

wherein the * represents the attachment point to the remainder of the molecule. In some embodiments, $A^{10}$ is

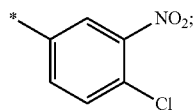 [SMILES: *c1ccc(Cl)c([N+](=O)[O-])c1]

wherein the * represents the attachment point to the remainder of the molecule. In some embodiments, $A^{10}$ is

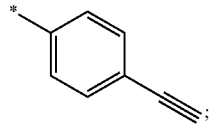 [SMILES: *c1ccc(C#C)cc1]

wherein the * represents the attachment point to the remainder of the molecule. In some embodiments, $A^{10}$ is

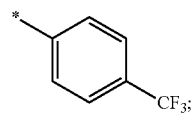 [SMILES: *c1ccc(C(F)(F)F)cc1]

wherein the * represents the attachment point to the remainder of the molecule. In some embodiments, $A^{10}$ is

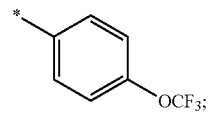 [SMILES: *c1ccc(OC(F)(F)F)cc1]

wherein the * represents the attachment point to the remainder of the molecule. In some embodiments, $A^{10}$ is

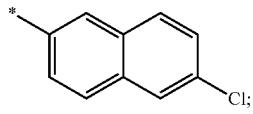 [SMILES: *c1ccc2cc(Cl)ccc2c1]

wherein the * represents the attachment point to the remainder of the molecule. In some embodiments, $A^{10}$ is

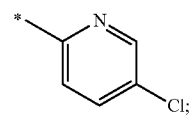

wherein the * represents the attachment point to the remainder of the molecule. In some embodiments, $A^{10}$ is

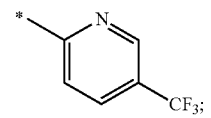

wherein the * represents the attachment point to the remainder of the molecule. In some embodiments, $A^{10}$ is

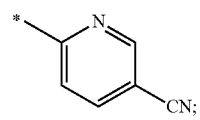

wherein the * represents the attachment point to the remainder of the molecule. In some embodiments, $A^{10}$ is

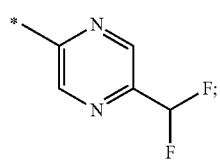

wherein the * represents the attachment point to the remainder of the molecule. In some embodiments, $A^{10}$ is

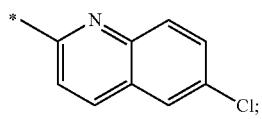

wherein the * represents the attachment point to the remainder of the molecule. In some embodiments, $A^{10}$ is

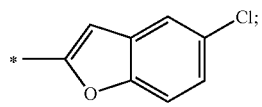

wherein the * represents the attachment point to the remainder of the molecule. In some embodiments, $A^{10}$ is

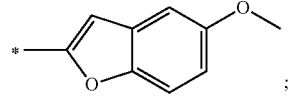

wherein the * represents the attachment point to the remainder of the molecule. In some embodiments, $A^{10}$ is

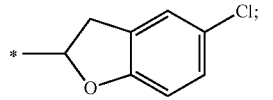

wherein the * represents the attachment point to the remainder of the molecule. In some embodiments, $A^{10}$ is

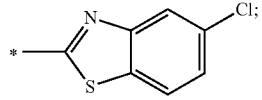

wherein the * represents the attachment point to the remainder of the molecule. In some embodiments, $A^{10}$ is

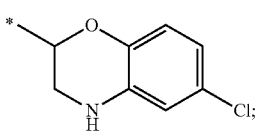

wherein the * represents the attachment point to the remainder of the molecule. In some embodiments, $A^{10}$ is

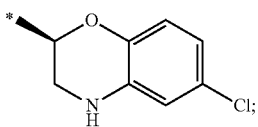

wherein the * represents the attachment point to the remainder of the molecule. In some embodiments, $A^{10}$ is

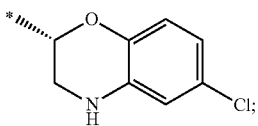

wherein the * represents the attachment point to the remainder of the molecule.

In one aspect, provided is a compound of formula (VIII):

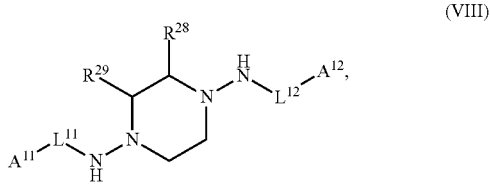

(VIII)

or a pharmaceutically acceptable salt thereof,
wherein:
$R^{28}$ is hydrogen or —C(O)OH;
$R^{29}$ is hydrogen or halogen;
$L^{11}$ is selected from the group consisting of

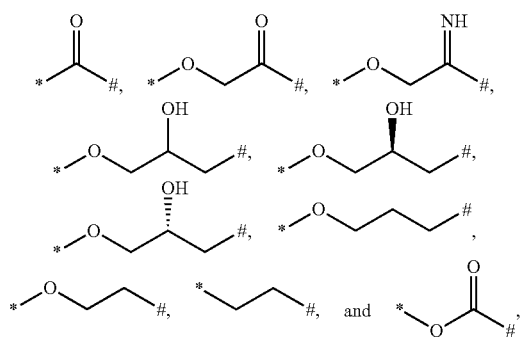

wherein the represents the attachment point to $A^{11}$, and the # represents the attachment point to the remainder of the molecule;

$L^{12}$ is selected from the group consisting of

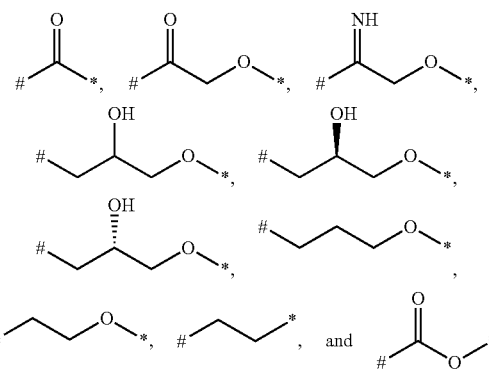

wherein the represents the attachment point to $A^{12}$, and the # represents the attachment point to the remainder of the molecule;

$A^{11}$ is selected from the group consisting of phenyl, naphthyl, pyridyl, pyrazinyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, pyridyl, pyrazinyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, CN, —$NO_2$, $C_1$-$C_6$ alkyl, $C_2$-$C_6$ alkenyl, $C_2$-$C_6$ alkynyl, —O—$C_1$-$C_6$ alkyl, —O—$C_1$-$C_6$ haloalkyl, and $C_1$-$C_6$ haloalkyl;

$A^{12}$ is selected from the group consisting of phenyl, naphthyl, pyridyl, pyrazinyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, pyridyl, pyrazinyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, CN, —$NO_2$, $C_1$-$C_6$ alkyl, $C_2$-$C_6$ alkenyl, $C_2$-$C_6$ alkynyl, —O—$C_1$-$C_6$ alkyl, —O—$C_1$-$C_6$ haloalkyl, and $C_1$-$C_6$ haloalkyl;

provided that the compound of formula (VIII) is not

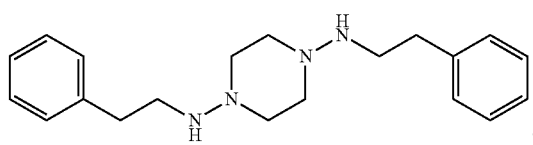

In some embodiments of the compound of Formula (VIII), $A^{11}$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —$NO_2$, $C_1$-$C_6$ alkyl, $C_2$-$C_6$ alkenyl, $C_2$-$C_6$ alkynyl, and $C_1$-$C_6$ haloalkyl; provided that the compound of formula (VIII) is not

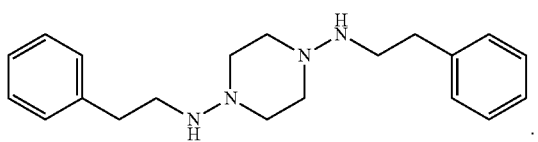 [SMILES: c1ccc(CCNN2CCN(NCCc3ccccc3)CC2)cc1]

In some embodiments of the compound of Formula (VIII), $A^{12}$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —$NO_2$, $C_1$-$C_6$ alkyl, $C_2$-$C_6$ alkenyl, $C_2$-$C_6$ alkynyl, and $C_1$-$C_6$ haloalkyl; provided that the compound of formula (VIII) is not

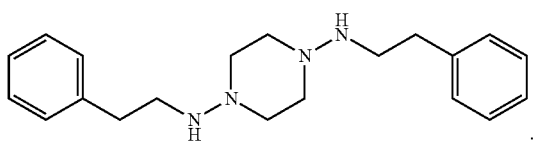 [SMILES: c1ccc(CCNN2CCN(NCCc3ccccc3)CC2)cc1]

In some embodiments, the compound of formula (VIII) is a compound of formula (VIII-a):

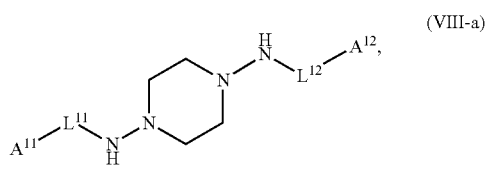

(VIII-a)

or a pharmaceutically acceptable salt thereof,
wherein $L^{11}$, $L^{12}$, $A^{11}$, and $A^{12}$ are as defined for the compound of formula (VIII) provided that the compound of formula (VIII-a) is not

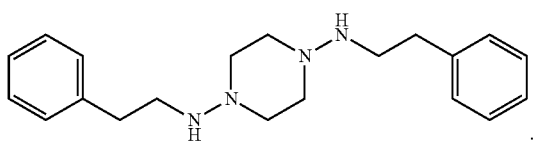

In some embodiments of the compounds of formula (VIII) and (VIII-a), $L^{11}$ is selected from the group consisting of

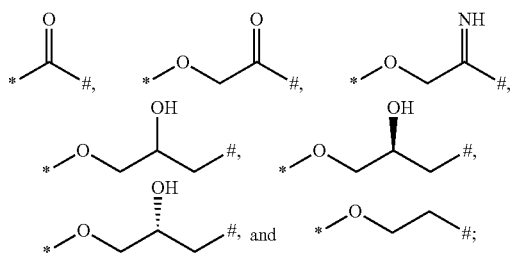

wherein the * represents the attachment point to $A^{11}$, and the # represents the attachment point to the remainder of the molecule. In some embodiments, $L^{11}$ is

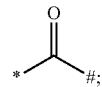

wherein the * represents the attachment point to $A^{11}$, and the # represents the attachment point to the remainder of the molecule. In some embodiments, $L^{11}$ is

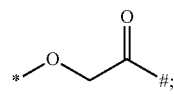

wherein the * represents the attachment point to $A^{11}$, and the # represents the attachment point to the remainder of the molecule. In some embodiments, $L^{11}$ is

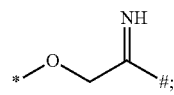

wherein the * represents the attachment point to $A^{11}$, and the # represents the attachment point to the remainder of the molecule. In some embodiments, $L^{11}$ is

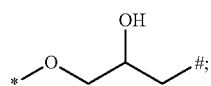

wherein the * represents the attachment point to $A^{11}$, and the # represents the attachment point to the remainder of the molecule. In some embodiments, $L^{11}$ is

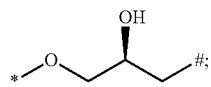

wherein the * represents the attachment point to $A^{11}$, and the # represents the attachment point to the remainder of the molecule. In some embodiments, $L^{11}$ is

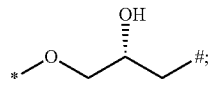

wherein the * represents the attachment point to $A^{11}$, and the # represents the attachment point to the remainder of the molecule. In some embodiments, $L^{11}$

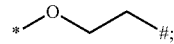

wherein the * represents the attachment point to $A^{11}$, and the # represents the attachment point to the remainder of the molecule.

In some embodiments of the compounds of formula (VIII) and (VIII-a), $L^{12}$ is selected from the group consisting of

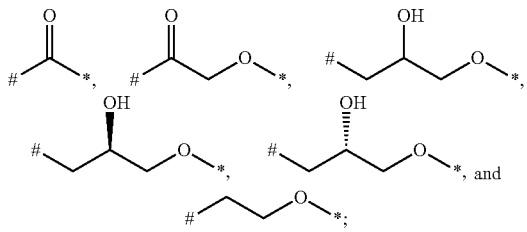

wherein the * represents the attachment point to $A^{12}$, and the # represents the attachment point to the remainder of the molecule. In some embodiments, $L^{12}$ is

wherein the * represents the attachment point to $A^{12}$, and the # represents the attachment point to the remainder of the molecule. In some embodiments, $L^{12}$ is

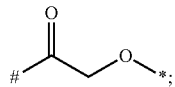

wherein the * represents the attachment point to $A^{12}$, and the # represents the attachment point to the remainder of the molecule. In some embodiments, $L^{12}$ is

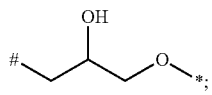

wherein the * represents the attachment point to $A^{12}$, and the # represents the attachment point to the remainder of the molecule. In some embodiments, $L^{12}$ is

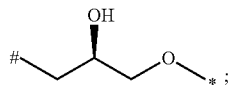

wherein the * represents the attachment point to $A^{12}$, and the # represents the attachment point to the remainder of the molecule. In some embodiments, $L^{12}$ is

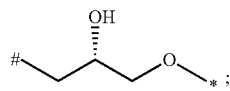

wherein the * represents the attachment point to $A^{12}$, and the # represents the attachment point to the remainder of the molecule. In some embodiments, $L^{12}$ is

wherein the * represents the attachment point to $A^{12}$, and the # represents the attachment point to the remainder of the molecule.

In some embodiments of the compounds of formula (VIII) and (VIII-a), $A^{11}$ is selected from the group consisting of

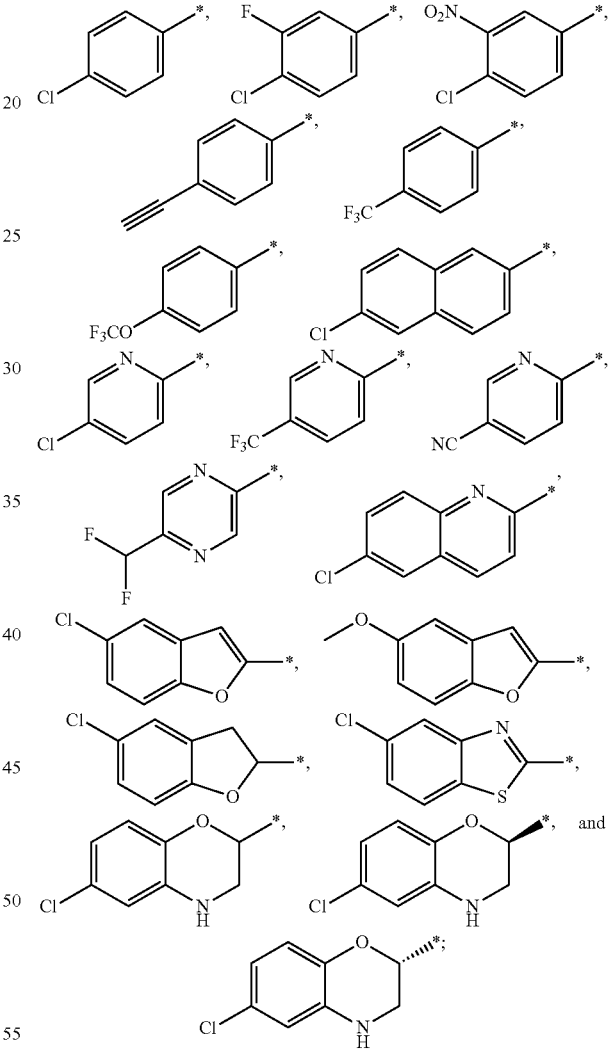

wherein the * represents the attachment point to the remainder of the molecule. In some embodiments, $A^{11}$ is selected from the group consisting of

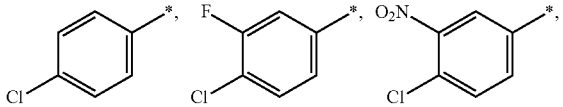

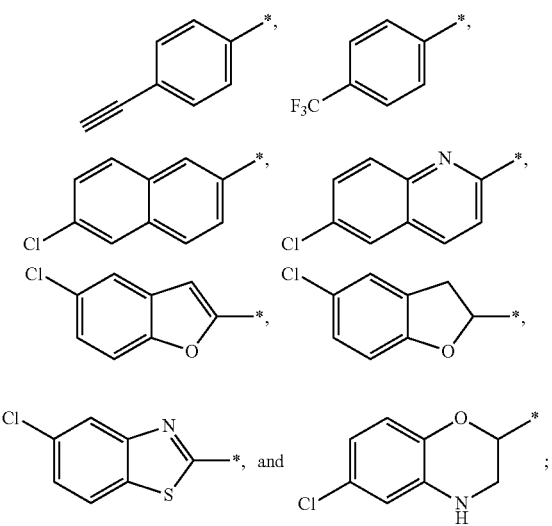

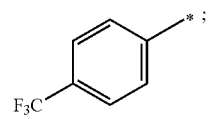

wherein the * represents the attachment point to the remainder of the molecule. In some embodiments, $A^{11}$ is

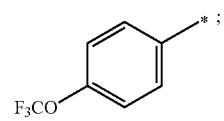

wherein the * represents the attachment point to the remainder of the molecule. In some embodiments, $A^{11}$ is

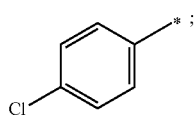

wherein the * represents the attachment point to the remainder of the molecule. In some embodiments, $A^{11}$ is

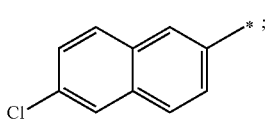

wherein the * represents the attachment point to the remainder of the molecule. In some embodiments, $A^{11}$ is

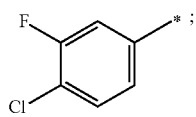

wherein the * represents the attachment point to the remainder of the molecule. In some embodiments, $A^{11}$ is

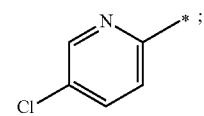

wherein the * represents the attachment point to the remainder of the molecule. In some embodiments, $A^{11}$ is

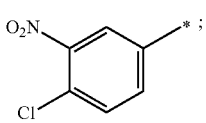

wherein the * represents the attachment point to the remainder of the molecule. In some embodiments, $A^{11}$

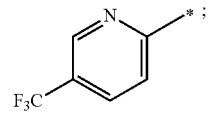

wherein the * represents the attachment point to the remainder of the molecule. In some embodiments, $A^{11}$ is

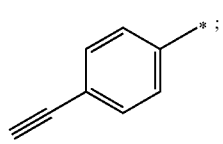

wherein the * represents the attachment point to the remainder of the molecule. In some embodiments, $A^{11}$ is

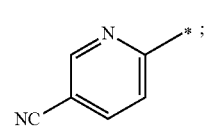

wherein the * represents the attachment point to the remainder of the molecule. In some embodiments, $A^{11}$ is

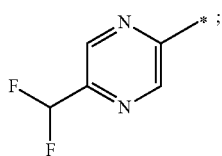

wherein the * represents the attachment point to the remainder of the molecule. In some embodiments, $A^{11}$ is

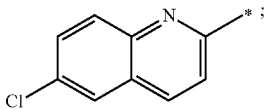

wherein the * represents the attachment point to the remainder of the molecule. In some embodiments, $A^{11}$ is

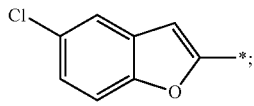

wherein the * represents the attachment point to the remainder of the molecule. In some embodiments, $A^{11}$ is

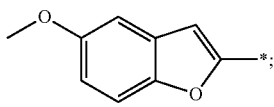

wherein the * represents the attachment point to the remainder of the molecule. In some embodiments, $A^{11}$ is

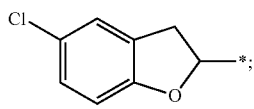

wherein the * represents the attachment point to the remainder of the molecule. In some embodiments, $A^{11}$ is

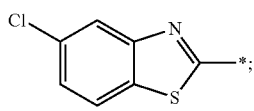

wherein the * represents the attachment point to the remainder of the molecule. In some embodiments, $A^{11}$ is

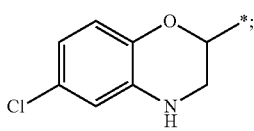

wherein the * represents the attachment point to the remainder of the molecule. In some embodiments, $A^{11}$ is

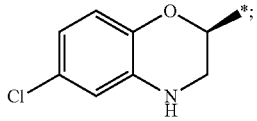

wherein the * represents the attachment point to the remainder of the molecule. In some embodiments, $A^{11}$ is

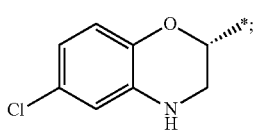

wherein the * represents the attachment point to the remainder of the molecule.

In some embodiments of the compounds of formula (VIII) and (VIII-a), $A^{12}$ is selected from the group consisting of

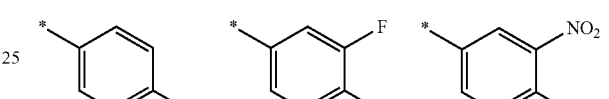
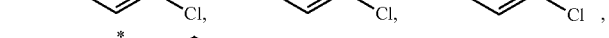
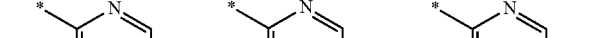
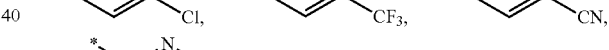
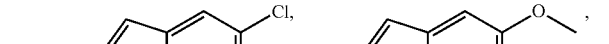
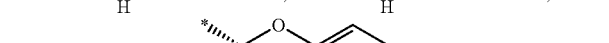
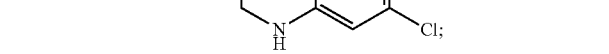

wherein the * represents the attachment point to the remainder of the molecule. In some embodiments, $A^{12}$ is selected from the group consisting of

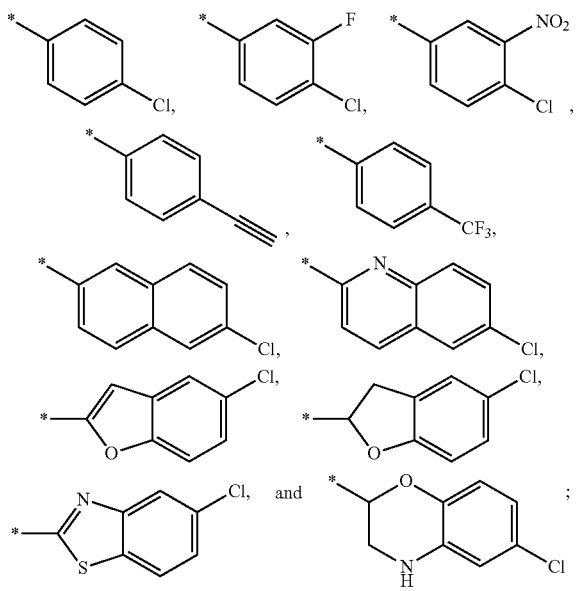

wherein the * represents the attachment point to the remainder of the molecule. In some embodiments, $A^{12}$ is

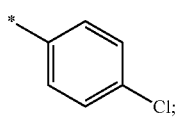

wherein the * represents the attachment point to the remainder of the molecule. In some embodiments, $A^{12}$ is

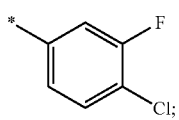

wherein the * represents the attachment point to the remainder of the molecule. In some embodiments, $A^{12}$ is

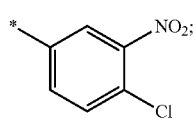

wherein the * represents the attachment point to the remainder of the molecule. In some embodiments, $A^{12}$ is

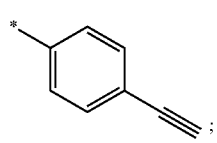 [SMILES: *c1ccc(C#C)cc1]

wherein the * represents the attachment point to the remainder of the molecule. In some embodiments, $A^{12}$ is

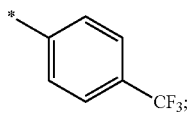 [SMILES: *c1ccc(C(F)(F)F)cc1]

wherein the * represents the attachment point to the remainder of the molecule. In some embodiments, $A^{12}$ is

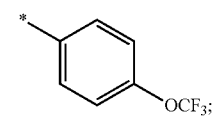

wherein the * represents the attachment point to the remainder of the molecule. In some embodiments, $A^{12}$ is

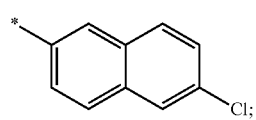

wherein the * represents the attachment point to the remainder of the molecule. In some embodiments, $A^{12}$ is

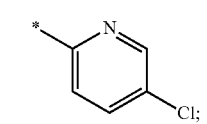 [SMILES: *c1ccc(Cl)cn1]

wherein the * represents the attachment point to the remainder of the molecule. In some embodiments, $A^{12}$ is

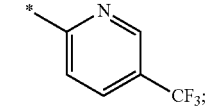 [SMILES: *c1ccc(C(F)(F)F)cn1]

wherein the * represents the attachment point to the remainder of the molecule. In some embodiments, $A^{12}$ is

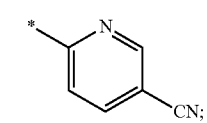 [SMILES: *c1ccc(C#N)cn1]

wherein the * represents the attachment point to the remainder of the molecule. In some embodiments, $A^{12}$ is

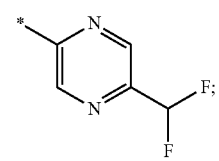 [SMILES: *c1cnc(C(F)F)cn1]

wherein the * represents the attachment point to the remainder of the molecule. In some embodiments, $A^{12}$ is

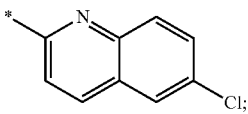 [SMILES: *c1ccc2cc(Cl)ccc2n1]

wherein the * represents the attachment point to the remainder of the molecule. In some embodiments, $A^{12}$ is

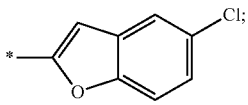

wherein the * represents the attachment point to the remainder of the molecule. In some embodiments, $A^{12}$ is

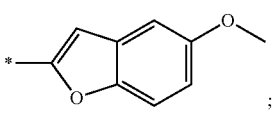 [SMILES: *c1cc2cc(OC)ccc2o1]

wherein the * represents the attachment point to the remainder of the molecule. In some embodiments, $A^{12}$ is

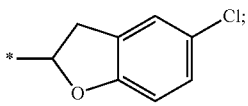 [SMILES: *C1Cc2cc(Cl)ccc2O1]

wherein the * represents the attachment point to the remainder of the molecule. In some embodiments, $A^{12}$ is

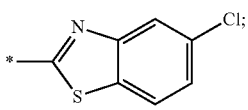 [SMILES: *c1nc2cc(Cl)ccc2s1]

wherein the * represents the attachment point to the remainder of the molecule. In some embodiments, $A^{12}$ is

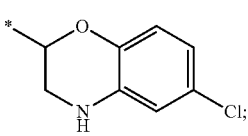

wherein the * represents the attachment point to the remainder of the molecule. In some embodiments, $A^{12}$ is

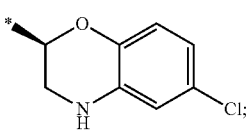 [SMILES: *[C@@H]1CNc2cc(Cl)ccc2O1]

wherein the * represents the attachment point to the remainder of the molecule. In some embodiments, $A^{12}$ is

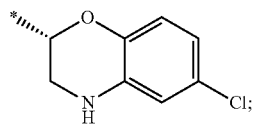

wherein the * represents the attachment point to the remainder of the molecule.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to X of formula (I) may be combined with every description, variation, embodiment or aspect of $m^1$, $m^2$, $n^1$, $n^2$, $p^1$, $p^2$, $q^1$, $q^2$, r, s, j, $R^{j-a}$, $R^{j-b}$, k, $R^{N-k}$, $R^N$, $A^1$, $A^2$, $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{12a}$, and $R^{12b}$ the same as if each and every combination were specifically and individually listed. It is also understood that all descriptions, variations, embodiments or aspects of formula (I), where applicable, apply equally to other formulae detailed herein, and are equally described, the same as if each and every description, variation, embodiment or aspect were separately and individually listed for all formulae. For example, all descriptions, variations, embodiments or aspects of formula (I), where applicable, apply equally to any of formulae (II) and (III) detailed herein, and are equally described, the same as if each and every description, variation, embodiment or aspect were separately and individually listed for all formulae. Similarly, every description, variation, embodiment or aspect provided herein with respect to $A^3$ of formula (IV) may be combined with every description, variation, embodiment or aspect of $R^{17}$, $R^{18}$, $R^{19}$, $L^3$, $L^4$, and $A^4$ the same as if each and every combination were specifically and individually listed. It is also understood that all descriptions, variations, embodiments or aspects of formula (IV), where applicable, apply equally to other formulae detailed herein, and are equally described, the same as if each and every description, variation, embodiment or aspect were separately and individually listed for all formulae. For example, all descriptions, variations, embodiments or aspects of formula (IV) where applicable, apply equally to any of formulae (IV-a), (IV-b), (IV-c), and (IV-d) detailed herein, and are equally described, the same as if each and every description, variation, embodiment or aspect were separately and individually listed for all formulae. Similarly, every description, variation, embodiment or aspect provided herein with respect to $A^5$ of formula (V) may be combined with every description, variation, embodiment or aspect of $R^{20}$, $R^{21}$, $R^{22}$, $R^{23}$, $L^5$, $L^6$, and $A^6$ the same as if each and every combination were specifically and individually listed. It is also understood that all descriptions, variations, embodiments or aspects of formula (V), where applicable, apply equally to other formulae detailed herein, and are equally described, the same as if each and every description, variation, embodiment or aspect were separately and individually listed for all formulae. For example, all descriptions, variations, embodiments or aspects of formula (V) where applicable, apply equally to any of formulae (V-a) and (V-b) detailed herein, and are equally described, the same as if each and every description, variation, embodiment or aspect were separately and individually listed for all formulae. Similarly, every description, variation, embodiment or aspect provided herein with respect to $A^7$ of formula (VI) may be combined with every description, variation, embodiment or aspect of $R^{24}$, $R^{25}$, $L^7$, $L^8$, and $A^8$ the same as if each and every combination were specifically and individually listed. It is also understood that all descriptions, variations, embodiments or aspects of formula (VI), where applicable, apply equally to other formulae detailed herein, and are equally described, the same as if each and every description, variation, embodiment or aspect were separately and individually listed for all formulae. For example, all descriptions, variations, embodiments or aspects of formula (VI) where applicable, apply equally to formula (VI-a) detailed herein, and are equally described, the same as if each and every description, variation, embodiment or aspect were separately and individually listed for all formulae. Similarly, every description, variation, embodiment or aspect provided herein with respect to $A^9$ of formula (VII) may be combined with every description, variation, embodiment or aspect of $R^{26}$, $R^{27}$, $L^9$, $L^{10}$, and $A^{10}$ the same as if each and every combination were specifically and individually listed. It is also understood that all descriptions, variations, embodiments or aspects of formula (VII), where applicable, apply equally to other formulae detailed herein, and are equally described, the same as if each and every description, variation, embodiment or aspect were separately and individually listed for all formulae. For example, all descriptions, variations, embodiments or aspects of formula (VII-a) where applicable, apply equally to formula (VII) detailed herein, and are equally described, the same as if each and every description, variation, embodiment or aspect were separately and individually listed for all formulae. Similarly, every description, variation, embodiment or aspect provided herein with respect to $A^{11}$ of formula (VIII) may be combined with every description, variation, embodiment or aspect of $R^{28}$, $R^{29}$, $L^{11}$, $L^{12}$, and $A^{12}$ the same as if each and every combination were specifically and individually listed. It is also understood that all descriptions, variations, embodiments or aspects of formula (VIII), where applicable, apply equally to other formulae detailed herein, and are equally described, the same as if each and every description, variation, embodiment or aspect were separately and individually listed for all formulae. For example, all descriptions, variations, embodiments or aspects of formula (VIII-a) where applicable, apply equally to formula (VIII) detailed herein, and are equally described, the same as if each and every description, variation, embodiment or aspect were separately and individually listed for all formulae.

Also provided are salts of compounds referred to herein, such as pharmaceutically acceptable salts. The present disclosure also includes any or all of the stereochemical forms, including any enantiomeric or diastereomeric forms, and any tautomers or other forms of the compounds described.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

In some embodiments, provided is compound selected from compounds in Table 1, or a stereoisomer, tautomer, solvate, prodrug or salt thereof. Although certain compounds described in Table 1 are presented as specific stereoisomers and/or in a non-stereochemical form, it is understood that any or all stereochemical forms, including any enantiomeric or diastereomeric forms, and any tautomers or other forms of any of the compounds of Table 1 are herein described.

TABLE 1

| Cpd No. | Structure |
|---|---|
| 1 | 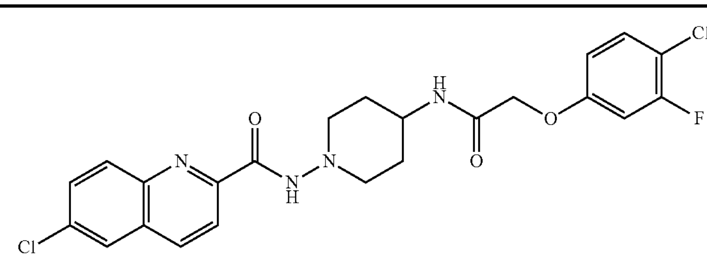 |
| 2 | 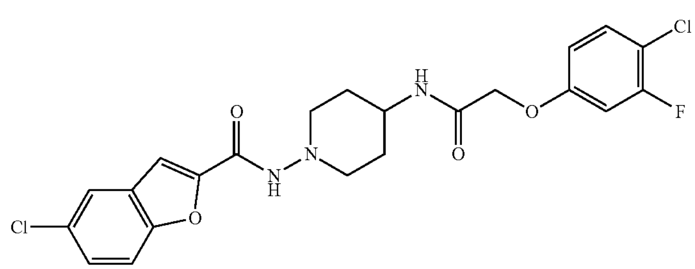 [SMILES: O=C(COc1ccc(Cl)c(F)c1)NC1CCN(NC(=O)c2cc3cc(Cl)ccc3o2)CC1] |

TABLE 1-continued
| Cpd No. | Structure |
|---|---|
| 3 | 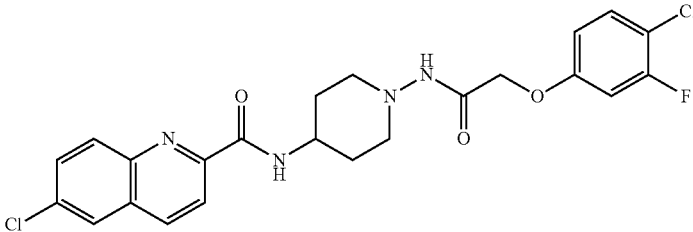 [SMILES: O=C(COc1ccc(Cl)c(F)c1)NN1CCC(NC(=O)c2ccc3cc(Cl)ccc3n2)CC1] |
| 4 | 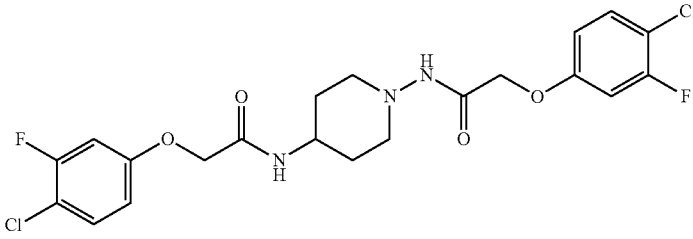 |
| 5 | 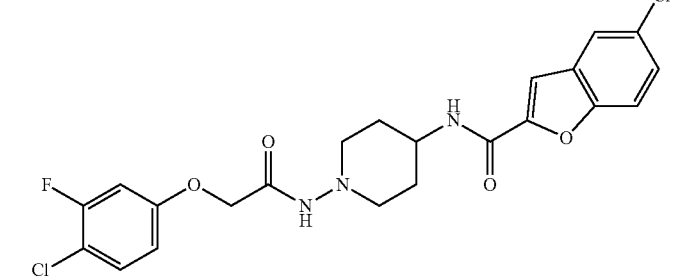 |
| 6 | 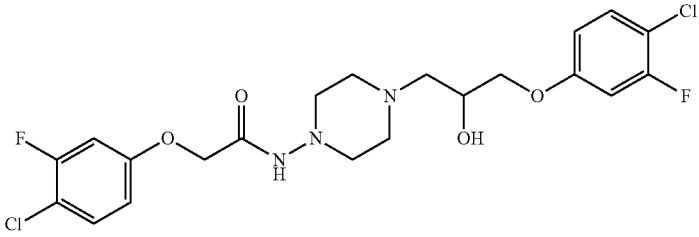 [SMILES: O=C(COc1ccc(Cl)c(F)c1)NN1CCN(CC(O)COc2ccc(Cl)c(F)c2)CC1] |
| 7 | 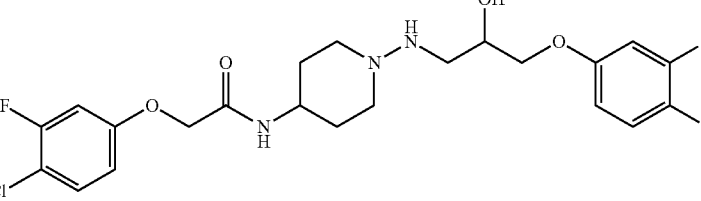 |
| 8 | 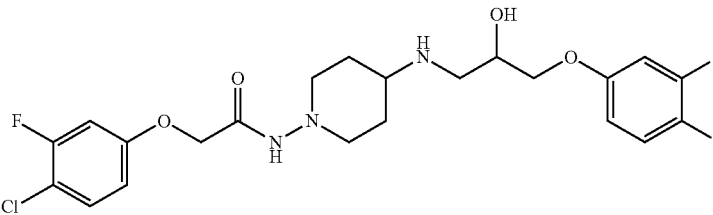 |

TABLE 1-continued

| Cpd No. | Structure |
|---|---|
| 9 | 5-chlorobenzothiazole-2-carbonyl-NH-N(piperidin-4-yl)-NH-C(O)-CH₂-O-(4-chloro-3-fluorophenyl) |
| 10 | 5-chlorobenzothiazole-2-carbonyl-NH-(piperidin-4-yl)-N-NH-C(O)-CH₂-O-(4-chloro-3-fluorophenyl) |
| 11 | 5-chloro-2,3-dihydrobenzofuran-2-carbonyl-NH-N(piperidin-4-yl)-NH-C(O)-CH₂-O-(4-chloro-3-fluorophenyl) |
| 12 | 5-chloro-2,3-dihydrobenzofuran-2-carbonyl-NH-(piperidin-4-yl)-N-NH-C(O)-CH₂-O-(4-chloro-3-fluorophenyl) |
| 13 | 5-chloro-2,3-dihydrobenzofuran-2-carbonyl-NH-N(piperazin-4-yl)-NH-CH(OH)-CH₂-O-(4-chloro-3-fluorophenyl) |

TABLE 1-continued
| Cpd No. | Structure |
|---|---|
| 14 | 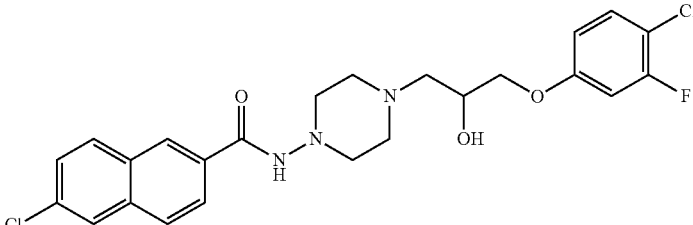 |
| 15 | 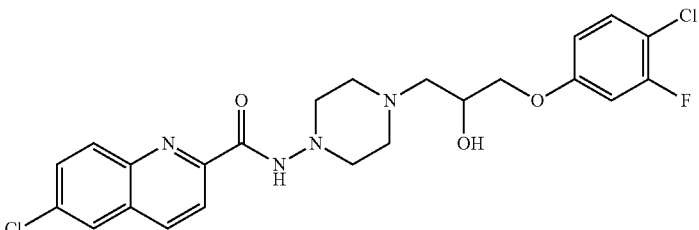 |
| 16 | 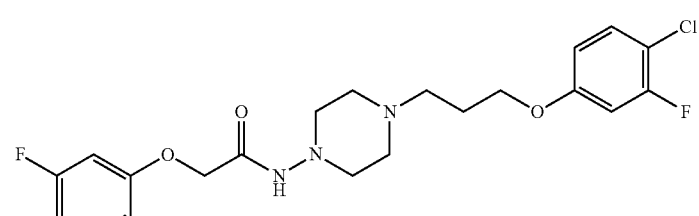 |
| 17 | 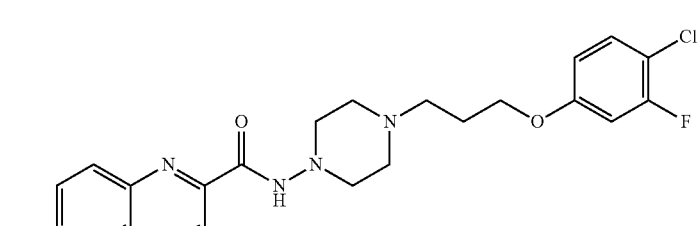 |
| 18 | 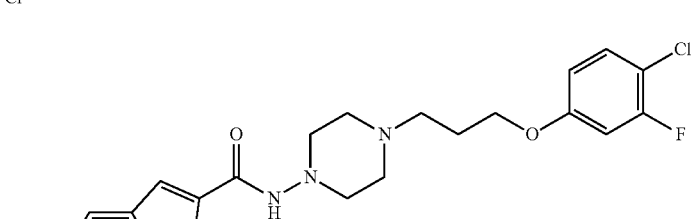 |
| 19 | 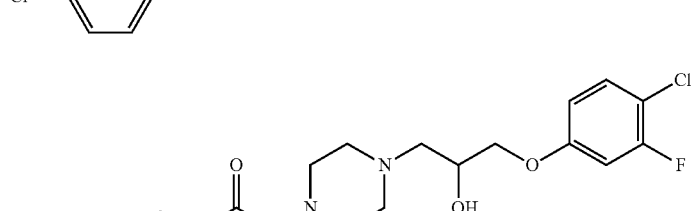 |

TABLE 1-continued

| Cpd No. | Structure |
|---|---|
| 20 | 6-chloroquinoline-2-carboxamide-N-(piperidin-1-yl), piperidine-4-NH-CH₂-CH(OH)-CH₂-O-(4-chloro-3-fluorophenyl) |
| 21 | 5-chloro-2,3-dihydrobenzofuran-2-carboxamide-N-(piperidin-1-yl), piperidine-4-NH-CH₂-CH(OH)-CH₂-O-(4-chloro-3-fluorophenyl) |
| 22 | (4-chloro-3-fluorophenoxy)acetamide-N-(piperidin-1-yl), piperidine-4-NH-CH₂-CH₂-O-(4-chloro-3-fluorophenyl) |
| 23 | 6-chloroquinoline-2-carboxamide-N-(piperidin-1-yl), piperidine-4-NH-CH₂-CH₂-O-(4-chloro-3-fluorophenyl) |
| 24 | 5-chlorobenzofuran-2-carboxamide-N-(piperidin-1-yl), piperidine-4-NH-CH₂-CH₂-O-(4-chloro-3-fluorophenyl) |
| 25 | 6-chloroquinoline-2-carboxamide-N-(piperidin-4-yl), piperidine-1-NH-CH₂-CH(OH)-CH₂-O-(4-chloro-3-fluorophenyl) |

TABLE 1-continued
| Cpd No. | Structure |
|---|---|
| 26 | 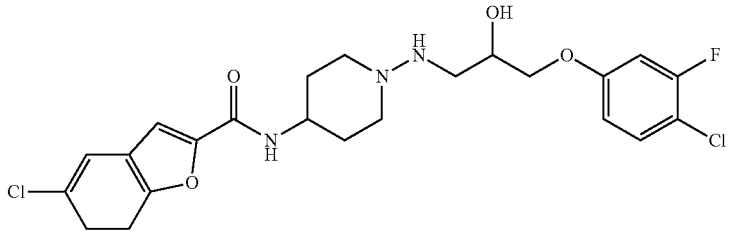 [SMILES: O=C(NC1CCN(NCC(O)COc2ccc(Cl)c(F)c2)CC1)c1cc2c(o1)CCC(Cl)=C2] |
| 27 | 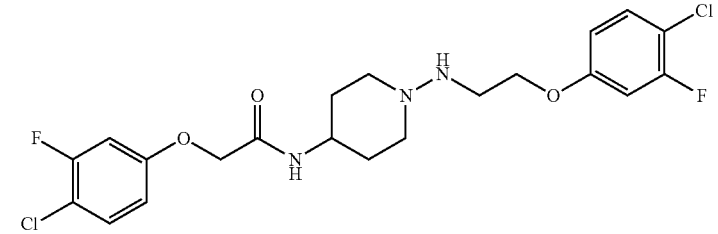 [SMILES: O=C(COc1ccc(Cl)c(F)c1)NC1CCN(NCCOc2ccc(Cl)c(F)c2)CC1] |
| 28 | 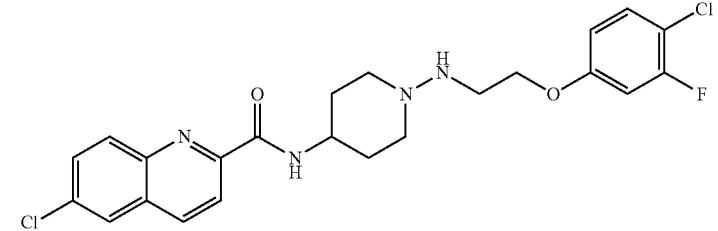 [SMILES: O=C(NC1CCN(NCCOc2ccc(Cl)c(F)c2)CC1)c1ccc2cc(Cl)ccc2n1] |
| 29 | 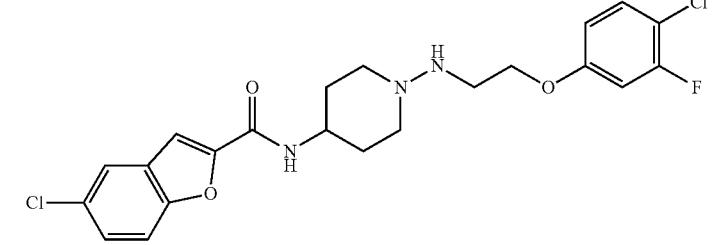 |
| 30 | 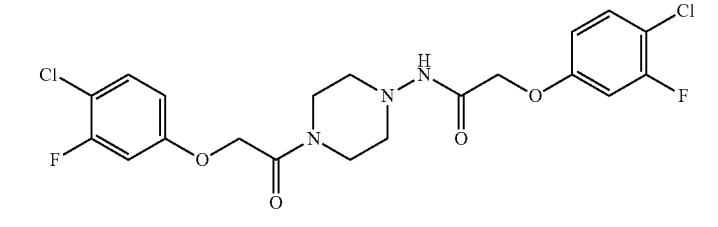 [SMILES: O=C(COc1ccc(Cl)c(F)c1)NN1CCN(C(=O)COc2ccc(Cl)c(F)c2)CC1] |
| 31 | 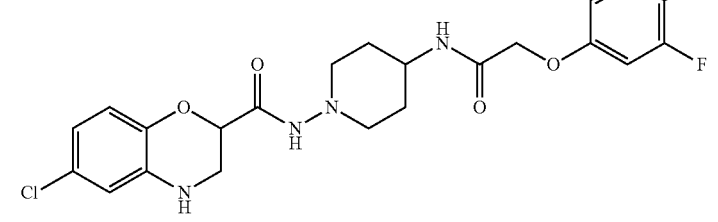 |

TABLE 1-continued
| Cpd No. | Structure |
|---|---|
| 32 | 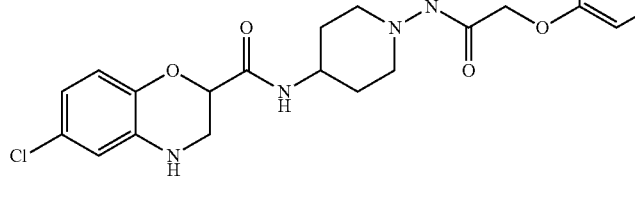 |
| 33 | 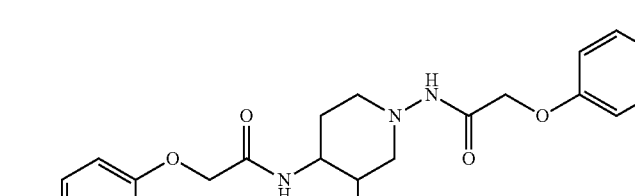 |
| 34 | 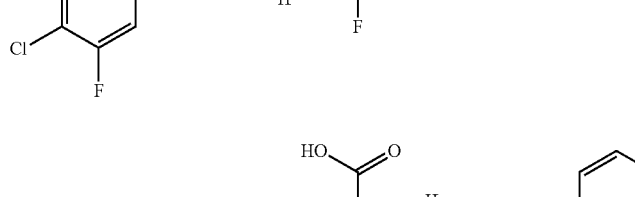 |
| 35 | 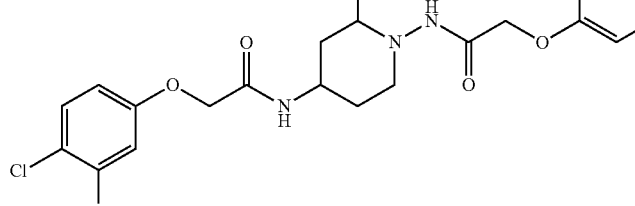 |
| 36 | 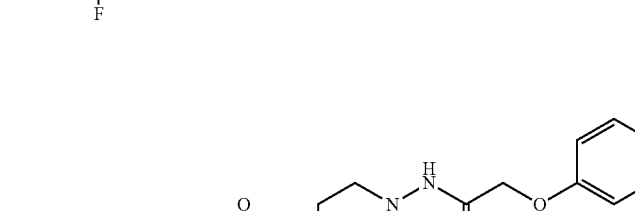 |

TABLE 1-continued

| Cpd No. | Structure |
|---|---|
| 37 | (structure) |
| 38 | (structure) |
| 39 | (structure) |
| 40 | (structure) |
| 41 | (structure) |
| 42 | (structure) |

TABLE 1-continued

| Cpd No. | Structure |
|---|---|
| 43 | *chemical structure* |
| 44 | *chemical structure* |
| 45 | *chemical structure* |
| 46 | *chemical structure* |
| 47 | *chemical structure* |
| 48 | *chemical structure* |

TABLE 1-continued
| Cpd No. | Structure |
|---|---|
| 49 | 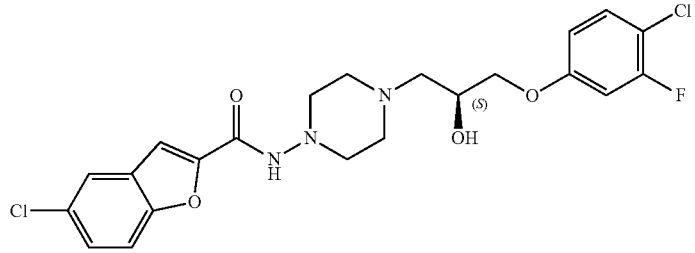 |
| 50 | 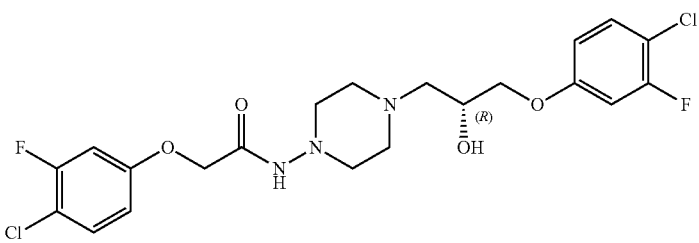 |
| 51 | 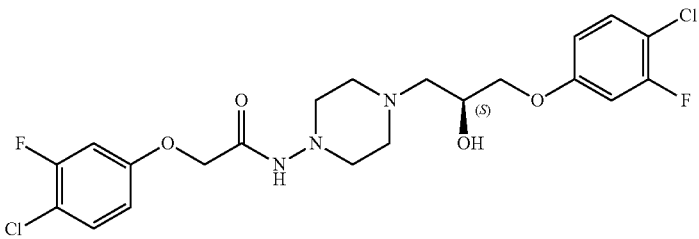 |
| 52 | 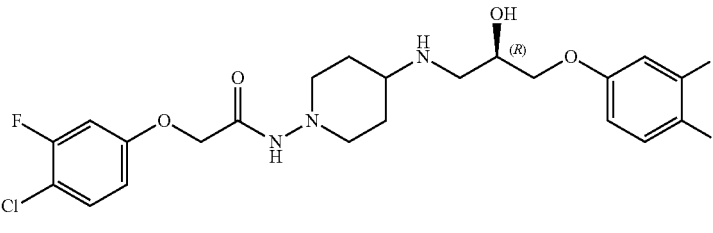 |
| 53 | 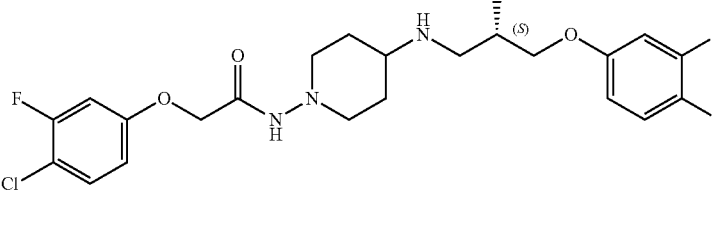 |
| 54 | 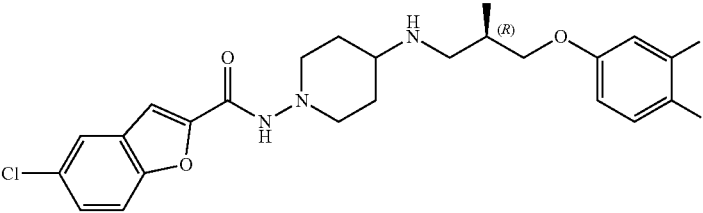 |

TABLE 1-continued

| Cpd No. | Structure |
|---|---|
| 55 | 5-chlorobenzofuran-2-carboxylic acid N'-{1-[(2S)-3-(4-chloro-3-fluorophenoxy)-2-hydroxypropylamino]piperidin-4-yl} hydrazide |
| 56 | 6-chloroquinoline-2-carboxylic acid N'-{1-[(2R)-3-(4-chloro-3-fluorophenoxy)-2-hydroxypropylamino]piperidin-4-yl} hydrazide |
| 57 | 6-chloroquinoline-2-carboxylic acid N'-{1-[(2S)-3-(4-chloro-3-fluorophenoxy)-2-hydroxypropylamino]piperidin-4-yl} hydrazide |
| 58 | 6-chloroquinoline-2-carboxylic acid N'-{4-[(2R)-3-(4-chloro-3-fluorophenoxy)-2-hydroxypropyl]piperazin-1-yl} hydrazide |
| 59 | 6-chloroquinoline-2-carboxylic acid N'-{4-[(2S)-3-(4-chloro-3-fluorophenoxy)-2-hydroxypropyl]piperazin-1-yl} hydrazide |
| 60 | 6-chloronaphthalene-2-carboxylic acid N'-{4-[(2R)-3-(4-chloro-3-fluorophenoxy)-2-hydroxypropyl]piperazin-1-yl} hydrazide |

TABLE 1-continued
| Cpd No. | Structure |
|---|---|
| 61 | 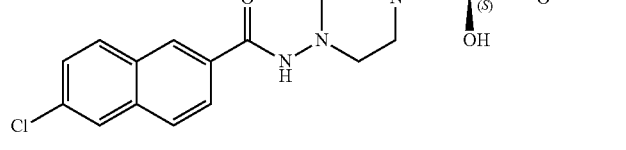 |
| 62 | 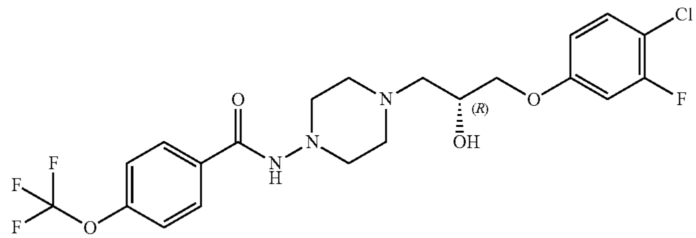 |
| 63 | 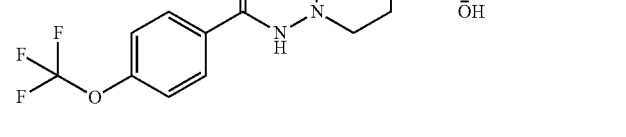 |
| 64 | 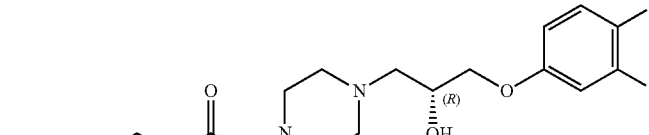 |
| 65 | 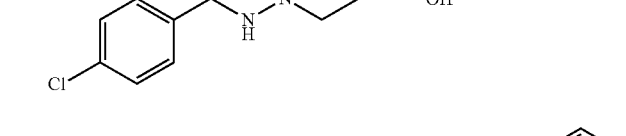 |
| 66 | 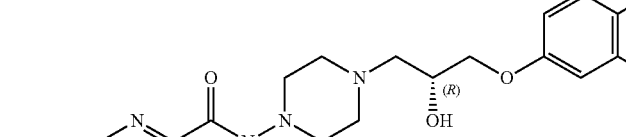 |

TABLE 1-continued
| Cpd No. | Structure |
|---|---|
| 67 | 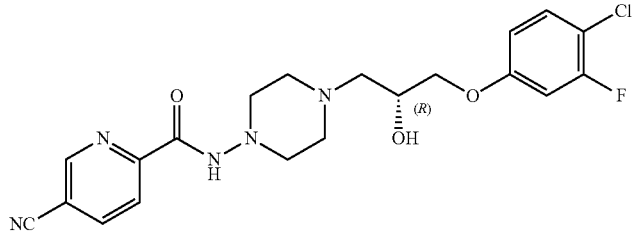 |
| 68 | 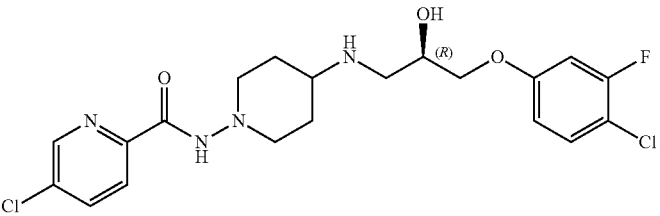 |
| 69 | 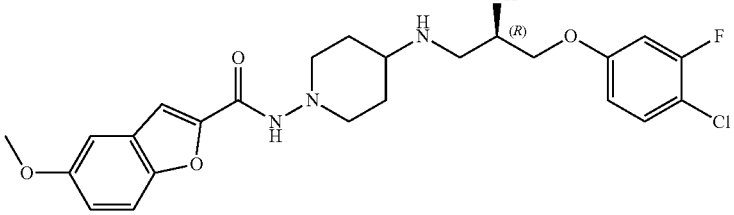 |
| 70 | 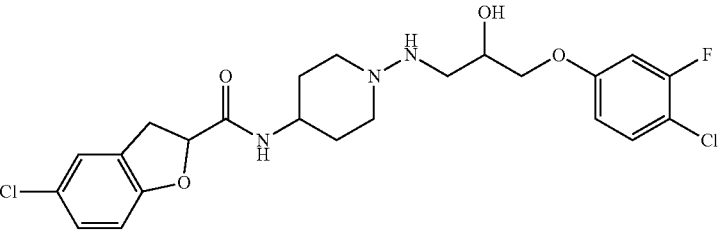 [SMILES: O=C(NC1CCN(NCC(O)COc2ccc(Cl)c(F)c2)CC1)C1Cc2cc(Cl)ccc2O1] |
| 71 | 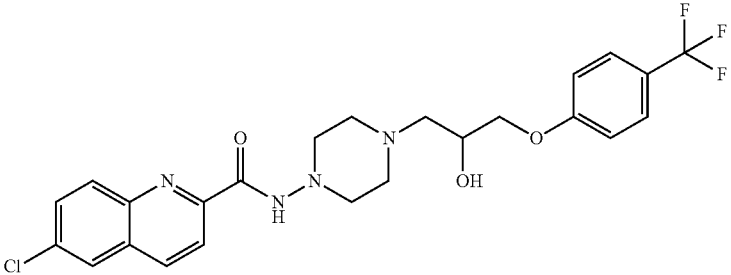 [SMILES: O=C(NN1CCN(CC(O)COc2ccc(C(F)(F)F)cc2)CC1)c1ccc2cc(Cl)ccc2n1] |
| 72 | 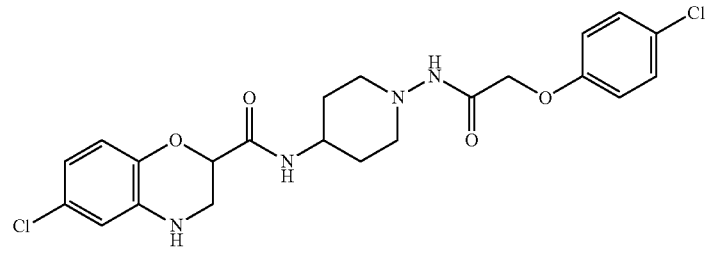 [SMILES: O=C(COc1ccc(Cl)cc1)NN1CCC(NC(=O)C2CNc3cc(Cl)ccc3O2)CC1] |

TABLE 1-continued

| Cpd No. | Structure |
|---|---|
| 73 | (structure) |
| 74 | (structure) |

Pharmaceutical Compositions and Formulations

Pharmaceutical compositions of any of the compounds detailed herein are embraced by this disclosure. Thus, the present disclosure includes pharmaceutical compositions comprising a compound as detailed herein or a salt thereof and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a salt thereof can be formulated as a 10 mg tablet.

Compositions comprising a compound provided herein are also described. In one variation, the composition comprises a compound or salt thereof and a pharmaceutically acceptable carrier or excipient. In another variation, a composition of substantially pure compound is provided. In some embodiments, the composition is for use as a human or veterinary medicament. In some embodiments, the composition is for use in a method described herein. In some embodiments, the composition is for use in the treatment of a disease or disorder described herein.

Methods of Use and Uses

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease or disorder in an individual in need thereof comprising administering a compound describes herein or any embodiment, variation, or aspect thereof, or a pharmaceutically acceptable salt thereof. In some embodiments, the compound, pharmaceutically acceptable salt thereof, or composition is administered to the individual according to a dosage and/or method of administration described herein.

The compounds or salts thereof described herein and compositions described herein are believed to be effective for treating a variety of diseases and disorders. In some embodiments, a compound or salt thereof described herein or a composition described herein may be used in a method of treating a disease or disorder mediated by an integrated stress response (ISR) pathway. In some embodiments, the disease or disorder is mediated by eukaryotic translation initiation factor 2a (eIF2a) or eukaryotic translation initiation factor 2B (eIF2B). In some embodiments, the disease or disorder is mediated by phosphorylation of eIF2a and/or the guanine nucleotide exchange factor (GEF) activity of eIF2B.

In some embodiments, a compound or salt thereof described herein or a composition described herein may be used in a method of treating a disease or disorder, wherein the disease or disorder is a neurodegenerative disease, an inflammatory disease, an autoimmune disease, a metabolic syndrome, a cancer, a vascular disease, a musculoskeletal disease (such as a myopathy), an ocular disease, or a genetic disorder.

In some embodiments, the disease or disorder is a neurodegenerative disease. In some embodiments, the neurodegenerative disease is vanishing white matter disease, childhood ataxia with CNS hypomyelination, intellectual disability syndrome, Alzheimer's disease, prion disease, Creutzfeldt-Jakob disease, Parkinson's disease, amyotrophic lateral sclerosis (ALS) disease, Pelizaeus-Merzbacher disease, a cognitive impairment, a traumatic brain injury, a postoperative cognitive dysfunction (PCD), a neuro-otological syndrome, hearing loss, Huntington's disease, stroke, chronic traumatic encephalopathy, spinal cord injury, dementia, frontotemporal dementia (FTD), depression, or a social behavior impairment. In some embodiments, the cognitive impairment is triggered by ageing, radiation, sepsis, seizure, heart attack, heart surgery, liver failure, hepatic encephalopathy, anesthesia, brain injury, brain surgery, ischemia, chemotherapy, cancer treatment, critical illness, concussion, fibromyalgia, or depression. In some embodiments, the neurodegenerative disease is Alzheimer's disease. In some embodiments, the neurodegenerative disease is ageing-related cognitive impairment. In some embodiments, the neurodegenerative disease is a traumatic brain injury.

In some embodiments, a compound or salt thereof described herein or a composition described herein may be used in a method of treating Alzheimer's disease. In some embodiments, neurodegeneration, cognitive impairment, and/or amyloidogenesis is decreased.

In some embodiments, the disease or disorder is an inflammatory disease. In some embodiments, the inflammatory disease is arthritis, psoriatic arthritis, psoriasis, juvenile idiopathic arthritis, asthma, allergic asthma, bronchial asthma, tuberculosis, chronic airway disorder, cystic fibrosis, glomerulonephritis, membranous nephropathy, sarcoidosis, vasculitis, ichthyosis, transplant rejection, interstitial cystitis, atopic dermatitis, or inflammatory bowel disease. In some embodiments, the inflammatory bowel disease is Crohn' disease, ulcerative colitis, or celiac disease.

In some embodiments, the disease or disorder is an autoimmune disease. In some embodiments, the autoimmune disease is systemic lupus erythematosus, type 1 diabetes, multiple sclerosis, or rheumatoid arthritis.

In some embodiments, the disease or disorder is a metabolic syndrome. In some embodiments, the metabolic syndrome is alcoholic liver steatosis, obesity, glucose intolerance, insulin resistance, hyperglycemia, fatty liver, dyslipidemia, hyperlipidemia, hyperhomocysteinemia, or type 2 diabetes.

In some embodiments, the disease or disorder is a cancer. In some embodiments, the cancer is pancreatic cancer, breast cancer, kidney cancer, bladder cancer, prostate cancer, testicular cancer, urothelial cancer, endometrial cancer, ovarian cancer, cervical cancer, renal cancer, esophageal cancer, gastrointestinal stromal tumor (GIST), multiple myeloma, cancer of secretory cells, thyroid cancer, gastrointestinal carcinoma, chronic myeloid leukemia, hepatocellular carcinoma, colon cancer, melanoma, malignant glioma, glioblastoma, glioblastoma multiforme, astrocytoma, dysplastic gangliocytoma of the cerebellum, Ewing's sarcoma, rhabdomyosarcoma, ependymoma, medulloblastoma, ductal adenocarcinoma, adenosquamous carcinoma, nephroblastoma, acinar cell carcinoma, neuroblastoma, or lung cancer. In some embodiments, the cancer of secretory cells is non-Hodgkin's lymphoma, Burkitt's lymphoma, chronic lymphocytic leukemia, monoclonal gammopathy of undetermined significance (MGUS), plasmacytoma, lymphoplasmacytic lymphoma or acute lymphoblastic leukemia.

In some embodiments, the disease or disorder is a musculoskeletal disease (such as a myopathy). In some embodiments, the musculoskeletal disease is a myopathy, a muscular dystrophy, a muscular atrophy, a muscular wasting, or sarcopenia. In some embodiments, the muscular dystrophy is Duchenne muscular dystrophy (DMD), Becker's disease, myotonic dystrophy, X-linked dilated cardiomyopathy, spinal muscular atrophy (SMA), or metaphyseal chondrodysplasia, Schmid type (MCDS). In some embodiments, the myopathy is a skeletal muscle atrophy. In some embodiments, the musculoskeletal disease (such as the skeletal muscle atrophy) is triggered by ageing, chronic diseases, stroke, malnutrition, bedrest, orthopedic injury, bone fracture, cachexia, starvation, heart failure, obstructive lung disease, renal failure, Acquired Immunodeficiency Syndrome (AIDS), sepsis, an immune disorder, a cancer, ALS, a burn injury, denervation, diabetes, muscle disuse, limb immobilization, mechanical unload, myositis, or a dystrophy.

In some embodiments, the disease or disorder is a genetic disorder, such as Down syndrome or MEHMO syndrome (Mental retardation, Epileptic seizures, Hypogenitalism, Microcephaly, and Obesity).

In some embodiments, a compound or salt thereof described herein or a composition described herein may be used in a method of treating musculoskeletal disease. In some embodiments, skeletal muscle mass, quality and/or strength are increased. In some embodiments, synthesis of muscle proteins is increased. In some embodiments, skeletal muscle fiber atrophy is inhibited.

In some embodiments, the disease or disorder is a vascular disease. In some embodiments, the vascular disease is atherosclerosis, abdominal aortic aneurism, carotid artery disease, deep vein thrombosis, Buerger's disease, chronic venous hypertension, vascular calcification, telangiectasia or lymphoedema.

In some embodiments, the disease or disorder is an ocular disease. In some embodiments, the ocular disease is glaucoma, age-related macular degeneration, inflammatory retinal disease, retinal vascular disease, diabetic retinopathy, uveitis, rosacea, Sjogren's syndrome, or neovascularization in proliferative retinopathy.

In some embodiments, provided herein is a method of inhibiting an ISR pathway. The compounds or salts thereof described herein and compositions described herein are believed to be effective for inhibiting an ISR pathway. In some embodiments, the method of inhibiting an ISR pathway comprises inhibiting the ISR pathway in a cell by administering or delivering to the cell a compound described herein, or a pharmaceutically acceptable salt thereof, or a pharmaceutical composition described herein. In some embodiments, the method of inhibiting an ISR pathway comprises inhibiting the ISR pathway in an individual by administering to the individual a compound described herein, or a pharmaceutically acceptable salt thereof, or a pharmaceutical composition described herein. Inhibition of the ISR pathway can be determined by methods known in the art, such as western blot, immunohistochemistry, or reporter cell line assays.

In some embodiments, the inhibition of the ISR pathway comprises binding eIF2B. In some embodiments, the inhibition of the ISR pathway comprises increasing protein translation, increasing guanine nucleotide exchange factor (GEF) activity of eIF2B, delaying or preventing apoptosis in a cell, and/or inhibiting translation of one or more mRNAs comprising a 5' untranslated region (5'UTR) comprising at least one upstream open reading frame (uORF).

In some embodiments, provided herein are methods of increasing protein production using a compound or salt described herein. The protein production is increased relative to the same condition without the compound or salt. Protein production can be increased either in vivo or in vitro. For example, protein production can be increased in vivo by administering the compound or salt to an individual. In some embodiments, protein production is increased in vitro using the compound or salt with a cell-free protein synthesis system (CFPS) or a cell-based protein expression system. The protein produced can be a heterologous protein (e.g., a recombinant protein) or a native protein. Heterologous protein production can be achieved using a recombinant nucleic acid encoding the protein. In some embodiments, the protein produced is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. The increase in protein production can be determined by methods known in the art, such as western blot or immunohistochemistry.

Cell-free protein synthesis (CFPS) systems are generally known, and include cellular machinery for protein expression in an in vitro environment. In some embodiments, the CFPS system includes a cellular extract (such as a eukaryotic cellular extract), which includes protein expression machinery. In some embodiment, the cellular machinery in the CFPS system comprises eukaryotic cellular machinery, such as eukaryotic initiation factor 2 (eIF2) and/or eukaryotic initiation factor 2B (eIF2B), or one or more subunits thereof.

In some embodiments, there is a cell-free protein synthesis (CFPS) system comprising eukaryotic initiation factor 2 (eIF2) and a nucleic acid encoding a protein with a compound or salt as described herein. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the CFPS system comprises a cell extract comprising the eIF2. In some embodiments, the CFPS system further comprises eIF2B.

In some embodiments, there is a method of producing a protein, comprising contacting a cell-free protein synthesis (CFPS) system comprising eukaryotic initiation factor 2 (eIF2) and a nucleic acid encoding a protein with a compound or salt thereof as described herein. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the CFPS system comprises a cell extract comprising the eIF2. In some embodiments, the CFPS system further comprises eIF2B. In some embodiments, the method comprises purifying the protein.

In some embodiments, there is a method of producing a protein, comprising contacting a eukaryotic cell comprising a nucleic acid encoding the protein with a compound or salt as described herein. In some embodiments, the method comprises culturing the cell in an in vitro culture medium comprising the compound or salt. In some embodiments, the nucleic acid encoding the protein is a recombinant nucleic acid. In some embodiments, the eukaryotic cell is a human embryonic kidney (HEK) cell or a Chinese hamster ovary (CHO) cell. In other embodiments, the eukaryotic cell is a yeast cell (such as *Saccharomyces cerevisiae* or *Pichia pastoris*), a wheat germ cell, an insect cell, a rabbit reticulocyte, a cervical cancer cell (such as a HeLa cell), a baby hamster kidney cell (such as BHK21 cells), a murine myeloma cell (such as NS0 or Sp2/0 cells), an HT-1080 cell, a PER.C6 cell, a plant cell, a hybridoma cell, or a human blood derived leukocyte. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the method comprises purifying the protein.

In some embodiments, there is a method of culturing a eukaryotic cell comprising a nucleic acid encoding a protein, comprising contacting the eukaryotic cell with an in vitro culture medium comprising a compound or salt as described herein. In some embodiments, the nucleic acid encoding the protein is a recombinant nucleic acid. In some embodiments, the eukaryotic cell is a human embryonic kidney (HEK) cell or a Chinese hamster ovary (CHO) cell. In other embodiments, the eukaryotic cell is a yeast cell (such as *Saccharomyces cerevisiae* or *Pichia pastoris*), a wheat germ cell, an insect cell, a rabbit reticulocyte, a cervical cancer cell (such as a HeLa cell), a baby hamster kidney cell (such as BHK21 cells), a murine myeloma cell (such as NSO or Sp2/0 cells), an HT-1080 cell, a PER.C6 cell, a plant cell, a hybridoma cell, or a human blood derived leukocyte. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the method comprises purifying the protein.

In some embodiments, there is an in vitro cell culture medium, comprising the compound or salt described herein, and nutrients for cellular growth. In some embodiments, the culture medium comprises a eukaryotic cell comprising a nucleic acid encoding a protein. In some embodiments, the culture medium further comprises a compound for inducing protein expression. In some embodiments, the nucleic acid encoding the protein is a recombinant nucleic acid. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the eukaryotic cell is a human embryonic kidney (HEK) cell or a Chinese hamster ovary (CHO) cell. In other embodiments, the eukaryotic cell is a yeast cell (such as *Saccharomyces cerevisiae* or *Pichia pastoris*), a wheat germ cell, an insect cell, a rabbit reticulocyte, a cervical cancer cell (such as a HeLa cell), a baby hamster kidney cell (such as BHK21 cells), a murine myeloma cell (such as NSO or Sp2/0 cells), an HT-1080 cell, a PER.C6 cell, a plant cell, a hybridoma cell, or a human blood derived leukocyte.

In some embodiments, provided herein is a method of increasing protein translation in a cell or cell free expression system. In some embodiments, the cell was stressed prior to administration of the compound, salt thereof, or composition. In some embodiments, protein translation is increased by at least about 10%, 20%, 30%, 40%, 50%, 60%, 70%, 80%, 90%, 95%, 98%, 100%, 125%, 150%, 175%, 200%, 250%, or 300% or more. In some embodiments, protein translation is increased by about 10% to about 300% (such as about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 125%, about 125% to about 150%, about 150% to about 175%, about 175% to about 200%, about 200% to about 250%, or about 250% to about 300%) In some embodiments, protein translation is increased as compared to prior to the administration of the compounds, salt thereof, or composition. In some embodiments, protein translation is increased as compared to an unstressed cell, a basal condition where cells are not subjected to a specific stress that activates the ISR. In some embodiments, protein translation is increased as compared to a stressed cell where ISR is active.

Some of the compounds described herein increase protein synthesis in a cell without full inhibition of ATF4 translation, under ISR-stressed or non-ISR stressed conditions. Despite ATF4 participation in various pathologies, the ATF4 protein is an important factor for restoring cellular homeostasis in stressed cells, for example during oxidative stress response, cholesterol metabolism, protein folding amino acid synthesis, and autophagy. Thus, for certain treatments, it may be preferable to limit ATF4 inhibition. In some embodiments, the compound is used to increase protein synthesis by about 10% or more, about 20% or more, about 30% or more, about 40% or more, about 50% or more, about 60% or more, about 70% or more, about 80% or more, about 90% or more, about 100% or more, about 125% or more, about 150% or more, about 175% or more, about 200% or more, about 250% or more, about 300% or more, or about 350% or more, wherein ATF4 protein expression is inhibited by about 75% or less, about 50% or less, about 40% or less, about 30% or less, about 20% or less, about 10% or less, or about 5% or less. In some embodiments the compound is used to increase protein synthesis by about 10% to about 300% (such as about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 125%, about 125% to about 150%, about 150% to about 175%, about 175% to about 200%, about 200% to about 250%, or about 250% to about 300%), wherein ATF4 protein expression is inhibited by about 75% or less (such as about 50% or less, about 40% or less, about 30% or less, about 20% or less, about 10% or less, or about 5% or less).

In some embodiments, provided herein is a method of increasing protein translation in a cell. In some embodiments, the cell was stressed prior to administration of the compound, salt thereof, or composition. In some embodiments, protein translation is increased by at least about 10%, 20%, 30%, 40%, 50%, 60%, 70%, 80%, 90%, 95%, 98%, 100%, 125%, 150%, 175%, 200%, 250%, or 300% or more. In some embodiments, protein translation is increased as compared to prior to the administration of the compounds, salt thereof, or composition. In some embodiments, protein translation is increased as compared to an unstressed cell, a basal condition where cells are not subjected to a specific stress that activates the ISR. In some embodiments, protein translation is increased as compared to a stressed cell where ISR is active.

In some embodiments, provided herein is a method of increasing guanine nucleotide exchange factor (GEF) activity of eIF2B in cells. In some embodiments, provided herein is a method of delaying or preventing apoptosis in a cell. In some embodiments, provided herein is a method of inhibiting translation of one or more mRNAs comprising a 5' untranslated region (5'UTR) that contains at least one upstream open reading frame (uORF), encoding proteins with translational preferences, including but not limited to ATF4, ATF2, ATF5, CHOP, GADD34, BACE-1, C/EBPα, or MAP1LC3B. In some embodiments, the mRNA encodes ATF4, BACE-1, GADD34, or CHOP. In some embodiments, the mRNA encodes ATF4.

In some embodiments, expression of ATF4, BACE-1, GADD34 or CHOP is inhibited. In some embodiments, expression of ATF4 is inhibited. In some embodiments, expression of Aβ is inhibited. ATF4 increases expression of, among others, GADD45A, CDKN1A, and EIF4EBP1, which encode DDIT-1, p21, and 4E-BP1, respectively. These proteins induce musculoskeletal disease and can be modulated by inhibiting expression of ATF4. Accordingly, in some embodiments, expression of one or more of CDKN1A, GADD45A, or EIF4EBP1 is inhibited.

In some embodiments, the compound, salt thereof, or composition inhibits translation of one or more mRNAs comprising a 5' untranslated region (5'UTR) comprising at least one upstream open reading frame (uORF) with an $IC_{50}$ of less than about 1 µM, such as less than about 750 nM, 600 nM, 500 nM, 300 nM, 200 nM, 100 nM, 80 nM, 60 nM, 40 nM, 25 nM, 10 nM, 5 nM, 1 nM, 0.5 nM, 0.1 nM, 0.01 nM, or less. In some embodiments, the compound, salt thereof, or composition inhibits translation of one or more mRNAs comprising a 5' untranslated region (5'UTR) comprising at least one upstream open reading frame (uORF) with an $IC_{50}$ between about 0.01 nM and 1 µM, such as between about 10 nM and 600 nM, about 0.01 nM and 10 nM, 15 nM and 200 nM, or 20 nM and 180 nM.

In some embodiments, the compound, salt thereof, or composition inhibits expression of ATF4 with an $IC_{50}$ of less than about 1 µM, such as less than about 750 nM, 600 nM, 500 nM, 300 nM, 200 nM, 100 nM, 80 nM, 60 nM, 40 nM, 25 nM, 10 nM, 5 nM, 1 nM, 0.5 nM, 0.1 nM, 0.01 nM, or less. In some embodiments, the compound, salt thereof, or composition inhibits expression of ATF4 with an $IC_{50}$ between about 0.01 nM and 1 µM, such as between about 2 nM and 800 nM, 10 nM and 600 nM, about 0.01 nM and 10 nM, 15 nM and 200 nM, or 20 nM and 180 nM.

In some aspects, the half maximal inhibitory concentration ($IC_{50}$) is a measure of the effectiveness of a substance in inhibiting a specific biological or biochemical function. In some aspects, the $IC_{50}$ is a quantitative measure that indicates how much of an inhibitor is needed to inhibit a given biological process or component of a process such as an enzyme, cell, cell receptor or microorganism by half. Methods of determining $IC_{50}$ in vitro and in vivo are known in the art.

In some embodiments, the individual is a mammal. In some embodiments, the individual is a primate, bovine, ovine, porcine, equine, canine, feline, rabbit, or rodent. In some embodiments, the individual is a human. In some embodiments, the individual has any of the diseases or disorders disclosed herein. In some embodiments, the individual is a risk for developing any of the diseases or disorders disclosed herein.

In some embodiments, the individual is human. In some embodiments, the human is at least about or is about any of 21, 25, 30, 35, 40, 45, 50, 55, 60, 65, 70, 75, 80, or 85 years old. In some embodiments, the human is a child. In some embodiments, the human is less than about or about any of 21, 18, 15, 12, 10, 8, 6, 5, 4, 3, 2, or 1 years old.

Also provided herein are uses of a compound described herein or a pharmaceutically acceptable salt thereof, or a pharmaceutical composition described herein, in the manufacture of a medicament. In some embodiments, the manufacture of a medicament is for the treatment of a disorder or disease described herein. In some embodiments, the manufacture of a medicament is for the prevention and/or treatment of a disorder or disease mediated by an ISR pathway. In some embodiments, the manufacture of a medicament is for the prevention and/or treatment of a disorder or disease mediated by eIF2a or eIF2B. In some embodiments, the manufacture of a medicament is for the prevention and/or treatment of a disorder or disease mediated by phosphorylation of eIF2a and/or the GEF activity of eIF2B.

Combinations

In certain aspects, a compound described herein is administered to an individual for treatment of a disease in combination with one or more additional pharmaceutical agents that can treat the disease. For example, in some embodiments, an effective amount of the compound is administered to an individual for the treatment of cancer in combination with one or more additional anticancer agents.

In some embodiments, activity of the additional pharmaceutical agent (such as additional anticancer agent) is inhibited by an activated ISR pathway. An ISR inhibitor, such as one of the compounds described herein, can inhibit the ISR pathway to enhance functionality of the additional pharmaceutical agent. By way of example, certain BRAF inhibitors (e.g., vemurafenib or dabrafenib) activate the ISR pathway in BRAF-mutated melanoma cells (e.g., BRAF with a V600F mutation) through the expression of ATF4. In some embodiments, there is a method of treating cancer comprising administering to an individual with cancer an effective amount of a compound described herein in combination with an effective amount of a BRAF inhibitor. In some embodiments, there is a method of treating a BRAF-mutated melanoma comprising administering to an individual with a BRAF-mutated melanoma an effective amount of a compound described herein in combination with an effective amount of a BRAF inhibitor. In some embodiments, there is a method of treating a BRAF-mutated melanoma comprising administering to an individual with a BRAF-mutated melanoma an effective amount of a compound described herein in combination with an effective amount of vemurafenib or dabrafenib.

As another example, certain anticancer agents (such as ubiquitin-proteasome pathway inhibitors (such as bortezomib), Cox-2 inhibitors (e.g., celecoxib), platinum-based antineoplastic drugs (e.g., cisplatin), anthracyclines (e.g. doxorubicin), or topoisomerase inhibitors (e.g., etoposide)) are used to treat cancer, but may have limited functionality against solid tumors. Resistance in certain solid tumors (e.g., breast cancers) has been associated with ATF4 stabilization and induction of autophagy. In some embodiments, an effective amount of an ISR inhibitor compound as described herein is administered to an individual with cancer to increase sensitivity to one or more anticancer agents. In some embodiments, there is a method of treating a refractory cancer (such as a solid tumor) in an individual, comprising administering to the individual an effective amount of a compound described herein in combination with an effective amount of an anticancer agent. In some embodiments, there is a method of treating a refractory cancer (such as a solid tumor) in an individual, comprising administering to the individual an effective amount of a compound described herein in combination with an effective amount of an ubiquitin-proteasome pathway inhibitor (e.g., bortezomib), a Cox-2 inhibitor (e.g., celecoxib), a platinum-based antineoplastic drug (e.g., cisplatin), an anthracycline (e.g. doxorubicin), or a topoisomerase inhibitor (e.g., etoposide). In some embodiments, the refractory cancer is breast cancer. In some embodiments, the refractory cancer is melanoma.

In some embodiments, a compound described herein is used to treat cancer in combination with one or more anti-cancer agents, such as an anti-neoplastic agent, an immune checkpoint inhibitor, or any other suitable anti-cancer agent. Exemplary immune checkpoint inhibitors include anti-PD-1, anti-PD-L1, anti GITR, anti-OX-40, anti-LAG3, anti-TIM-3, anti-41BB, anti-CTLA-4 antibodies. Exemplary anti-neoplastic agents can include, for example, anti-microtubule agents, platinum coordination complexes, alkylating agents, topoisomerase II inhibitors, topoisomerase I inhibitors, antimetabolites, antibiotic agents, hormones and hormonal analogs, signal transduction pathway inhibitors, non-receptor tyrosine kinase angiogenesis inhibitors, proteasome inhibitors, and inhibitors of cancer metabolism. Other anti-cancer agents can include one or more of an immuno-stimulant, an antibody or fragment thereof (e.g., an anti-CD20, anti-HER2, anti-CD52, or anti-VEGF antibody or fragment thereof), or an immunotoxin (e.g., an anti-CD33 antibody or fragment thereof, an anti-CD22 antibody or fragment thereof, a calicheamicin conjugate, or a pseudomonas exotoxin conjugate).

ATF4-mediated expression of CHOP has also been shown to regulate the function and accumulation of myeloid-derived suppressor cells (MDSCs) in tumors. MDSCs in tumors reduce the ability to prime T cell function and reduce antitumoral or anticancer responses. Certain immunotherapeutic agents (such as anti-PD-1, anti PD-Li, anti-GITR, anti-OX-40, anti-LAG3, anti-TIM-3, anti-41BB, or anti-CTLA-4 antibodies) have been used to boost the immune response against cancer. ATF4-mediated expression of AXL has been associated with poor response to anti-PD1 therapy in melanoma. In some embodiments, an effective amount of an ISR inhibitor compound as described herein is administered to an individual with cancer to increase sensitivity to one or more immunotherapeutic agents. In some embodiments, there is a method of treating a refractory cancer (such as a melanoma) in an individual, comprising administering to the individual an effective amount of a compound described herein in combination with an effective amount of an immunotherapeutic agent (e.g. anti-PD-1, anti PD-L1, anti-GITR, anti-OX-40, anti-LAG3, anti-TIM-3, anti-41BB, or anti-CTLA-4 antibodies). In some embodiments, the refractory cancer is melanoma.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the present disclosure may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition provided herein may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

Articles of Manufacture and Kits

The present disclosure further provides articles of manufacture comprising a compound described herein or a salt thereof, a composition described herein, or one or more unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the present disclosure, which comprises one or more compounds described herein or a composition comprising a compound described herein. The kits may employ any of the compounds disclosed herein. In one variation, the kit employs a compound described herein or a salt thereof. The kits may be used for any one or more of the uses described herein, and, accordingly, may contain instructions for the treatment of any disease or described herein, for example for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to an individual.

General Synthetic Methods

The compounds of the present disclosure may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High-Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

Chromatography, recrystallization and other conventional separation procedures may also be used with intermediates or final products where it is desired to obtain a particular isomer of a compound or to otherwise purify a product of a reaction.

General methods of preparing compounds according to the present disclosure are depicted in the schemes below.

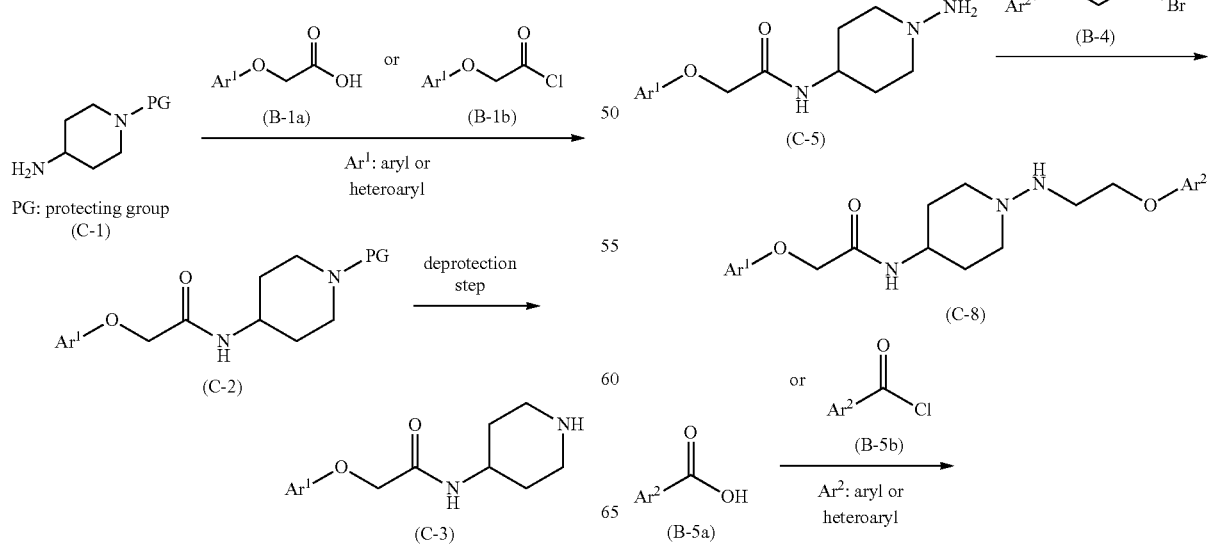

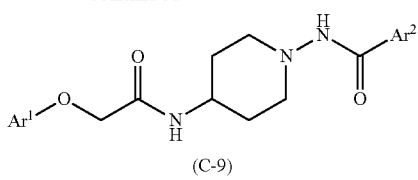
(C-9)

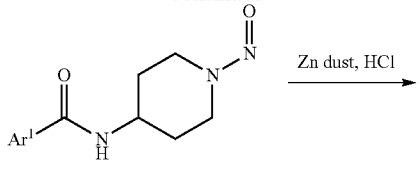
(D-3)

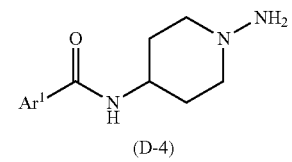
(D-4)

Compounds disclosed herein, such as compounds of formula (C-6), (C-7), (C-8), and (C-9), for example, can be synthesized according to the general method described in the scheme above. A compound of formula (C-1) is reacted with a carboxylic acid (B-1a), or a carboxylic acid derivative (e.g. an acyl chloride of formula (B-1b)), under suitable conditions to give a compound of formula (C-2). The compound of formula (C-2) is deprotected to give a compound of formula (C-3). The compound of formula (C-3) is subjected to nitrosation conditions (e.g. reacted with sodium nitrite) under suitable conditions to give a compound of formula (C-4). The compound of formula (C-4) is reduced (e.g. with Zn dust) under suitable conditions to give a compound of formula (C-5). The compound of formula (C-5) is reacted with a carboxylic acid (B-2a), or a carboxylic acid derivative (e.g. an acyl chloride of formula (B-2b), to give a compound of formula (C-6). The compound of formula (C-5) is reacted with an oxirane derivative of formula (B-3) to give a compound of formula (C-7). The compound of formula (C-5) is reacted with a haloalkyl derivative, such as a bromoalkyl compound of formula (B-4), to give a compound of formula (C-8). The compound of formula (C-5) is reacted with a carboxylic acid (B-5a), or a carboxylic acid derivative (e.g. an acyl chloride of formula (B-5b)), to give a compound of formula (C-9).

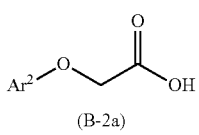
(B-2a)

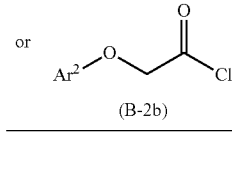
(B-2b)

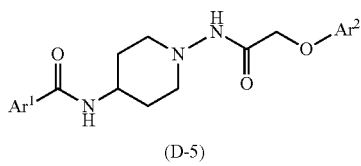
(D-5)

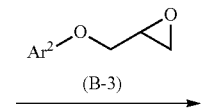
(B-3)

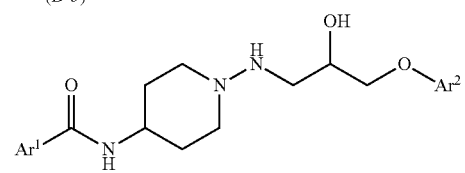
(D-6)

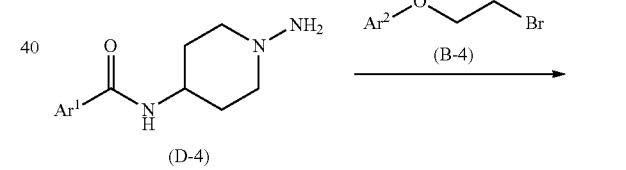
(D-4)    (B-4)

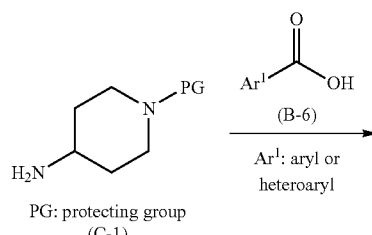
PG: protecting group
(C-1)

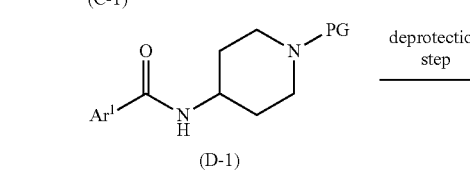
(D-1)

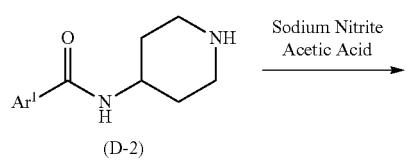
(D-2)

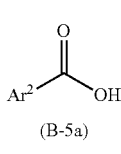
(D-2)

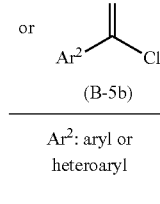
(B-5a)

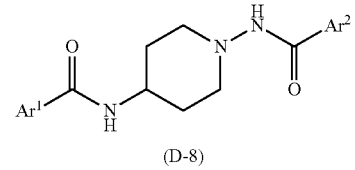
(D-8)

Compounds disclosed herein, such as compounds of formula (D-5), (D-6), (D-7), and (D-8), for example, can be synthesized according to the general method described in the scheme above. A compound of formula (C-1) is reacted with a carboxylic acid (B-6) under suitable conditions to give a compound of formula (D-1). The compound of formula (D-1) is deprotected to give a compound of formula (D-2). The compound of formula (D-2) is subjected to nitrosation conditions (e.g. reacted with sodium nitrite) under suitable conditions to give a compound of formula (D-3). The compound of formula (D-3) is reduced (e.g. with Zn dust) under suitable conditions to give a compound of formula (D-4). The compound of formula (D-4) is reacted with a carboxylic acid (B-2a), or a carboxylic acid derivative (e.g. an acyl chloride of formula (B-2b), to give a compound of formula (D-5). The compound of formula (D-4) is reacted with an oxirane derivative of formula (B-3) to give a compound of formula (D-6). The compound of formula (D-4) is reacted with a haloalkyl derivative, such as a bromoalkyl compound of formula (B-4), to give a compound of formula (D-7). The compound of formula (D-4) is reacted with a carboxylic acid (B-5a), or a carboxylic acid derivative (e.g. an acyl chloride of formula (B-5b), to give a compound of formula (D-8).

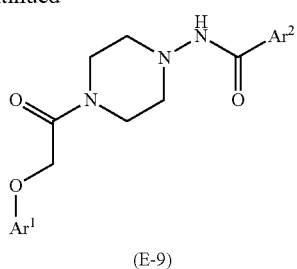

(E-9)

Compounds disclosed herein, such as compounds of formula (E-6), (E-7), (E-8), and (E-9), for example, can be synthesized according to the general method described in the scheme above. A compound of formula (E-1) is reacted with a carboxylic acid (B-1a), or a carboxylic acid derivative (e.g. an acyl chloride of formula (B-1b), under suitable conditions to give a compound of formula (E-2). The compound of formula (E-2) is deprotected to give a compound of formula (E-3). The compound of formula (E-3) is subjected to nitrosation conditions (e.g. reacted with sodium nitrite) under suitable conditions to give a compound of formula (E-4). The compound of formula (E-4) is reduced (e.g. with Zn dust) under suitable conditions to give a compound of formula (E-5). The compound of formula (E-5) is reacted with a carboxylic acid (B-2a), or a carboxylic acid derivative (e.g. an acyl chloride of formula (B-2b), to give a compound of formula (E-6). The compound of formula (E-5) is reacted with an oxirane derivative of formula (B-3) to give a compound of formula (E-7). The compound of formula (E-5) is reacted with a haloalkyl derivative, such as a bromoalkyl compound of formula (B-4), to give a compound of formula (E-8). The compound of formula (E-5) is reacted with a carboxylic acid (B-5a), or a carboxylic acid derivative (e.g. an acyl chloride of formula (B-5b), to give a compound of formula (E-9).

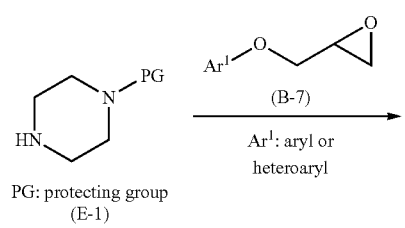

PG: protecting group
(E-1)

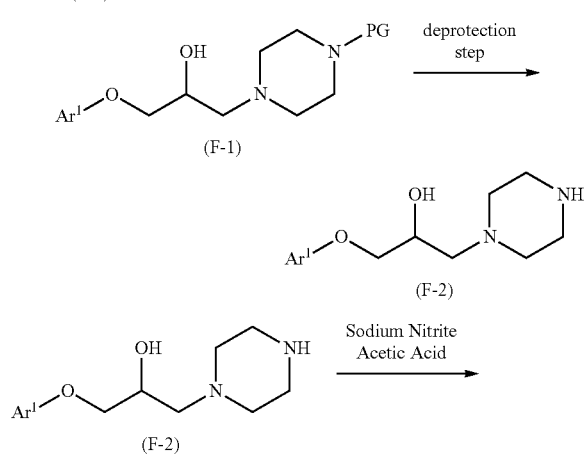

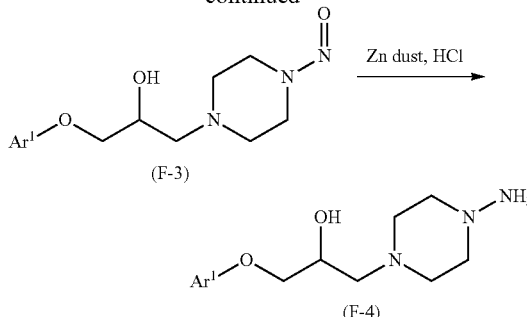

(F-3)

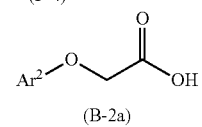

(F-4)

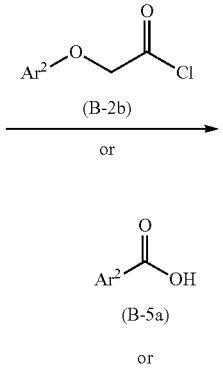

(F-4)

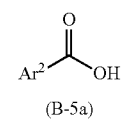

(B-5a)

or

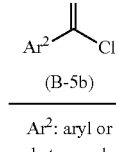

(B-5b)

Ar$^2$: aryl or heteroaryl

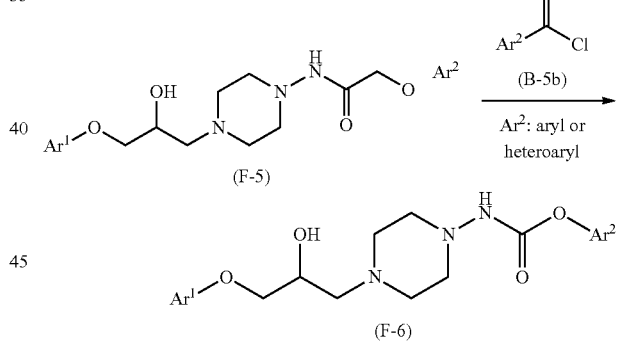

Compounds disclosed herein, such as compounds of formula (F-5) and (F-6), for example, can be synthesized according to the general method described in the scheme above. A compound of formula (E-1) is reacted with an oxirane derivative of formula (B-7) under suitable conditions to give a compound of formula (F-1). The compound of formula (F-1) is deprotected to give a compound of formula (F-2). The compound of formula (F-2) is subjected to nitrosation conditions (e.g. reacted with sodium nitrite) under suitable conditions to give a compound of formula (F-3). The compound of formula (F-3) is reduced (e.g. with Zn dust) under suitable conditions to give a compound of formula (F-4). The compound of formula (F-4) is reacted with a carboxylic acid (B-2a), or a carboxylic acid derivative (e.g. an acyl chloride of formula (B-2b), to give a compound of formula (F-5). The compound of formula (F-4) is reacted with a carboxylic acid (B-5a), or a carboxylic acid derivative (e.g. an acyl chloride of formula (B-5b), to give a compound of formula (F-6).

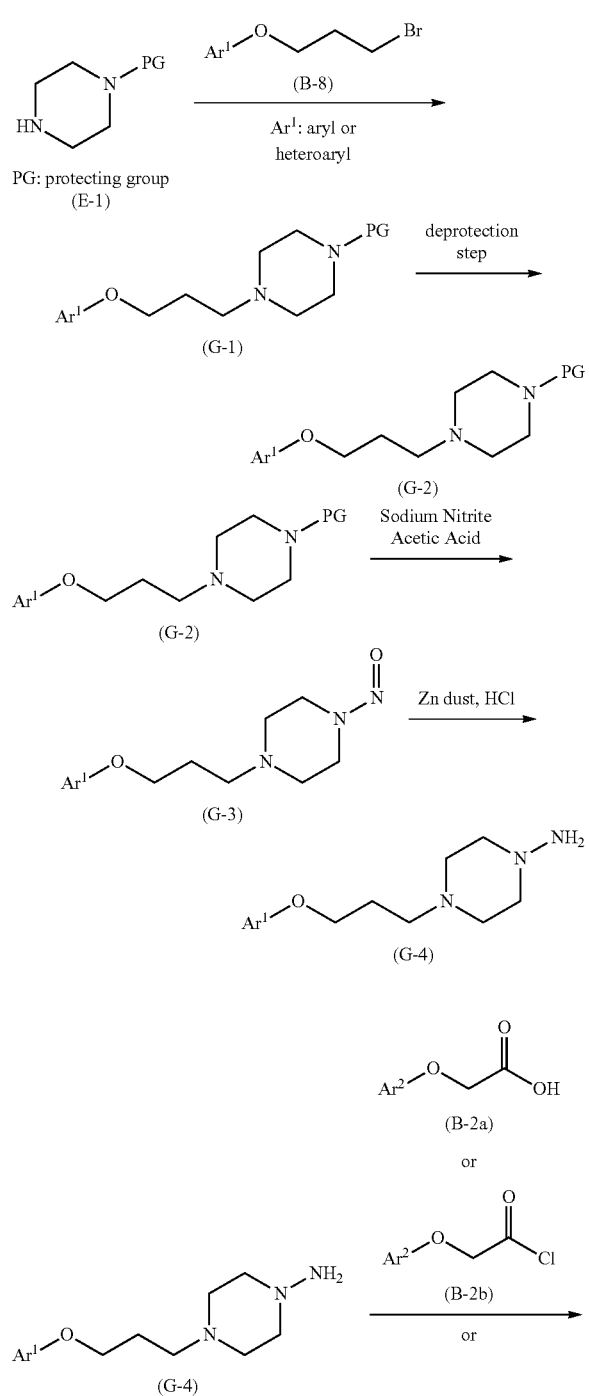
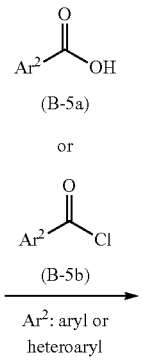
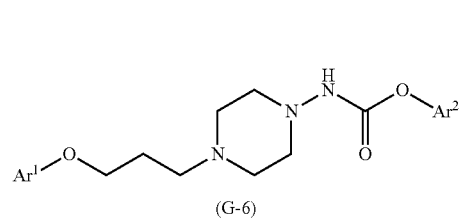

Compounds disclosed herein, such as compounds of formula (G-5) and (G-6), for example, can be synthesized according to the general method described in the scheme above. A compound of formula (E-1) is reacted with a haloalkyl derivative, such as a bromoalkyl compound of formula (B-8), to give a compound of formula (G-1). The compound of formula (G-1) is deprotected to give a compound of formula (G-2). The compound of formula (G-2) is subjected to nitrosation conditions (e.g. reacted with sodium nitrite) under suitable conditions to give a compound of formula (G-3). The compound of formula (G-3) is reduced (e.g. with Zn dust) under suitable conditions to give a compound of formula (G-4). The compound of formula (G-4) is reacted with a carboxylic acid (B-2a), or a carboxylic acid derivative (e.g. an acyl chloride of formula (B-2b), to give a compound of formula (G-5). The compound of formula (G-4) is reacted with a carboxylic acid (B-5a), or a carboxylic acid derivative (e.g. an acyl chloride of formula (B-5b), to give a compound of formula (G-6).

ENUMERATED EMBODIMENTS

The following enumerated embodiments are representative of some aspects of the invention.

Embodiment 1. A compound of formula (I):

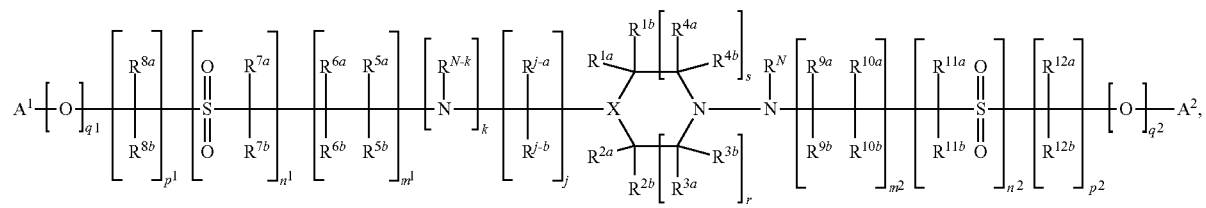

(I)

or a pharmaceutically acceptable salt thereof, wherein:

$m^1$, $m^2$, $n^1$, $n^2$, $p^1$, $p^2$, $q^1$, and $q^2$, independently of each other, are 0 or 1;

r and s, independently of each other, are 0, 1, or 2;

X is N or $CR^X$;

$R^X$ is selected from the group consisting of hydrogen, $C_1$-$C_6$ alkyl, $C_2$-$C_6$ alkenyl, and $C_2$-C6 alkynyl;

j is 0 or 1;

$R^{j\text{-}a}$ and $R^{j\text{-}b}$ are taken together to form an oxo (=O) substituent, or $R^{j\text{-}a}$ and $R^{j\text{-}b}$ are both hydrogen;

k is 0 or 1;

$R^{N\text{-}k}$ is H or $C_1$-$C_6$ alkyl;

$R^N$ is H or $C_1$-$C_6$ alkyl;

$A^1$ is selected from the group consisting of:

$C_6$-$C_{14}$ aryl optionally substituted with one or more $R^{14}$ substituents; and 5-14 membered heteroaryl optionally substituted with one or more $R^{14}$ substituents;

$R^{14}$ is selected, independently at each occurrence, from the group consisting of halogen, $NO_2$, $C_1$-$C_6$ alkyl, $C_2$-$C_6$ alkenyl, $C_2$-$C_6$ alkynyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{14\text{-}a}R^{14\text{-}b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{14\text{-}a}R^{14\text{-}b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{14\text{-}a}R^{14\text{-}b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{14\text{-}a}$ and $R^{14\text{-}b}$ are taken together with the nitrogen atom to which they are attached to form a 3-10 membered heterocycle;

$A^2$ is selected from the group consisting of:

C6-$C_{14}$ aryl optionally substituted with one or more $R^{16}$ substituents; and 5-14 membered heteroaryl optionally substituted with one or more $R^{16}$ substituents;

$R^{16}$ is selected, independently at each occurrence, from the group consisting of halogen, $NO_2$, $C_1$-$C_6$ alkyl, $C_2$-$C_6$ alkenyl, $C_2$-$C_6$ alkynyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{16\text{-}a}R^{16\text{-}b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^6$—$R^{16\text{-}b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{16\text{-}a}R^{16\text{-}b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{16\text{-}a}$ and $R^{16\text{-}b}$ are taken together with the nitrogen atom to which they are attached to form a 3-10 membered heterocycle;

$R^{1a}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen, or $R^{1a}$ is taken together with $R^{2a}$ to form a $C_1$-$C_6$ alkylene moiety, or $R^{1a}$ is taken together with an $R^{3a}$ moiety to form a $C_1$-$C_6$ alkylene moiety;

$R^{1b}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{2a}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{2b}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{3a}$ independently at each occurrence is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen, or $R^{3a}$ is taken together with $R^{4a}$ to form a $C_1$-$C_6$ alkylene moiety;

$R^{3b}$ independently at each occurrence is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{4a}$ independently at each occurrence is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{4b}$ independently at each occurrence is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{5a}$ and $R^{5b}$ are taken together to form an oxo (=O) substituent or an imido (=NH) substituent, or $R^{5a}$ and $R^{5b}$ are both hydrogen;

$R^{6a}$ is selected from the group consisting of hydrogen, —$OR^{6a\text{-}a}$, and —$NR^{6a\text{-}b}R^{6a\text{-}c}$; $R^{6b}$ is hydrogen;

or $R^{6a}$ and $R^{6b}$ are taken together to form a moiety selected from the group consisting of —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, and —$CH_2$—$CH_2$—$CH_2$—$CH_2$—O—;

$R^{7a}$ and $R^{7b}$ are both hydrogen;

$R^{8a}$ and $R^{8b}$ are taken together to form an oxo (=O) substituent, or $R^{8a}$ and $R^{8b}$ are both hydrogen;

$R^{9a}$ and $R^{9b}$ are taken together to form an oxo (=O) substituent or an imido (=NH) substituent, or $R^{9a}$ and $R^{9b}$ are both hydrogen;

$R^{10a}$ is selected from the group consisting of hydrogen, —$OR^{10a\text{-}a}$, and —$NR^{10a\text{-}b}R^{10a\text{-}c}$ and $R^{10b}$ is hydrogen, or $R^{10a}$ and $R^{10b}$ are taken together to form a moiety selected from the group consisting of —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, and —CH$_2$—CH$_2$—CH$_2$—CH$_2$—O—;

$R^{11a}$ and $R^{11b}$ are both hydrogen;

$R^{12a}$ and $R^{12b}$ are taken together to form an oxo (═O) substituent, or $R^{12a}$ and $R^{12b}$ are both hydrogen;

$R^{6a-a}$ is selected from the group consisting of hydrogen, $C_1$-$C_6$ alkyl, and $C_1$-$C_6$ haloalkyl, or $R^{6a-a}$ is taken together with $R^{N-k}$ to form a carbonyl (C═O) moiety;

$R^{10a-a}$ is selected from the group consisting of hydrogen, $C_1$-$C_6$ alkyl, and $C_1$-$C_6$ haloalkyl, or $R^{10a-a}$ is taken together with $R^N$ to form a carbonyl (C═O) moiety;

$R^{6a-b}$ and $R^{6a-c}$, independently of each other, are selected from the group consisting of hydrogen, $C_1$-$C_6$ alkyl, and $C_1$-$C_6$ haloalkyl; and $R^{10a-b}$ and $R^{10a-c}$, independently of each other, are selected from the group consisting of hydrogen, $C_1$-$C_6$ alkyl, and $C_1$-$C_6$ haloalkyl;

provided that:
(i) when j is 1, then k is 1;
(ii) when $m^1$ is 0, $n^1$ is 0, $q^1$ is 0, and $p^1$ is 1, then $R^{8a}$ and $R^{8b}$ are taken together to form an oxo (═O) substituent, and $A^1$ is a substituent of formula ($A^1$-a)

wherein
* represents the attachment point to the remainder of the molecule;

$Z^1$ is selected from the group consisting of $CR^{Z1-1}R^{Z1-2}$, $NR^{Z1-2}$, $C(R^{Z1-1}R^{Z1-2})N(R^{Z1-2})$, O, $C(R^{Z1-1}R^{Z1-2})O$, S, $C(R^{Z1-1}R^{Z1-2})S$, and —$CR^{Z1-1}$═$CR^{Z1-1}$—;

wherein $R^{Z1-1}$ is H or $R^{14}$; and $R^{Z1-2}$ is H or $R^{14}$;

$Z^2$ is selected from the group consisting of $CR^{Z2-2}R^{Z2-2}$, $NR^{Z2-2}$, $C(R^{Z2-1}R^{Z2-2})N(R^{Z2-2})$, O, $C(R^{Z2-1}R^{Z2-2})O$, S, $C(R^{Z2-1}R^{Z2-2})S$, and —$CR^{Z2-1}$═$CR^{Z2-1}$—.

wherein $R^{Z2-1}$ is H or $R^{14}$; and $R^{Z2-2}$ is H or $R^{14}$;

$Z^3$, independently at each occurrence, is CH, $CR^{14}$, or N;

$R^{13}$ is hydrogen or $R^{14}$, or $R^{13}$ and $R^{Z1-2}$ are taken together to form a double bond between the carbon atom bearing $R^{13}$ and $Z^1$, or $R^{13}$ and $R^{Z2-2}$ are taken together to form a double bond between the carbon atom bearing $R^{13}$ and $Z^2$; and x1 is 0, 1, 2, 3, or 4; and (iii) when $m^2$ is 0, $n^2$ is 0, $q^2$ is 0, and $p^2$ is 1, then $R^{12a}$ and $R^{12b}$ are taken together to form an oxo (═O) substituent, and $A^2$ is a substituent of formula ($A^2$-a)

wherein
* represents the attachment point to the remainder of the molecule; $Z^4$ is selected from the group consisting of $CR^{Z4-1}R^{Z4-2}$, $NR^{Z4-2}$, $C(R^{Z4-1}R^{Z4-2})N(R^{Z4-2})$, O, $C(R^{Z4-1}R^{Z4-2})O$, S, $C(R^{Z4-1}R^{Z4-2})S$, and —$CR^{Z4-1}$═$CR^{Z4-1}$—;

wherein $R^{Z4-1}$ is H or $R^{16}$; and $R^{Z4-2}$ is H or $R^{16}$;

$Z^5$ is selected from the group consisting of $CR^{Z5-1}R^{Z5-2}$, $NR^{Z5-2}$, $C(R^{Z5-1}R^{Z5-2})N(R^{Z5-2})$, O, $C(R^{Z5-1}R^{Z5-2})O$, S, $C(R^{Z5-1}R^{Z5-2})S$, and —$CR^{Z5-1}$═$CR^{Z5-1}$—;

wherein $R^{Z5-1}$ is H or $R^{16}$; and $R^{Z5-2}$ is H or $R^{16}$;

$Z^6$, independently at each occurrence, is CH, $CR^{16}$, or N;

$R^{15}$ is hydrogen or $R^{16}$, or $R^{15}$ and $R^{Z4-2}$ are taken together to form a double bond between the carbon atom bearing $R^{15}$ and $Z^4$, or $R^{15}$ and $R^{Z5-2}$ are taken together to form a double bond between the carbon atom bearing $R^{15}$ and $Z^5$; and x2 is 0, 1, 2, 3, or 4;

(iv) when X is $CR^X$, then k is 1;
(v) when X is N, j is 1, and k is 1, then $R^{j-a}$ and $R^{j-b}$ are taken together to form an oxo (═O) substituent;
(vi) when X is N, j is 0 and k is 1; then at least one of (vi-a), (vi-b), (vi-c), or (vi-d) applies:
(vi-a) $A^1$ is $C_6$-$C_{14}$ aryl substituted with one or more $R^{14}$ substituents;
(vi-b) $A^1$ is 5-14 membered heteroaryl optionally substituted with one or more $R^{14}$ substituents;
(vi-c) $A^2$ is $C_6$-$C_{14}$ aryl substituted with one or more $R^{16}$ substituents;
(vi-d) $A^2$ is 5-14 membered heteroaryl optionally substituted with one or more $R^{16}$ substituents; and
(vii) when X is N, j is 0, k is 0, $m^1$ is 1, $n^1$ is 0, $p^1$ is 0, and $q^1$ is 0, then A1 is a substituent of formula ($A^1$-a).

Embodiment 2. The compound of embodiment 1, or a pharmaceutically acceptable salt thereof, wherein k is 1, X is $CR^X$ and the compound of formula (I) is a compound of formula (II):

Embodiment 3. The compound of embodiment 1, or a pharmaceutically acceptable salt thereof, wherein X is N and the compound of formula (I) is a compound of formula (III):

(III)

Embodiment 4. A compound of formula (IV):

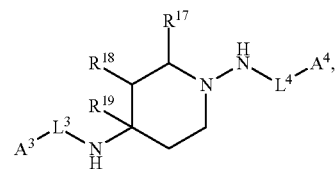

(IV)

or a pharmaceutically acceptable salt thereof,
wherein:
$R^{17}$ is hydrogen or —C(O)OH;
$R^{18}$ is hydrogen or halogen;
$R^{19}$ is hydrogen or $C_2$-$C_6$ alkynyl;
$L^3$ is selected from the group consisting of #

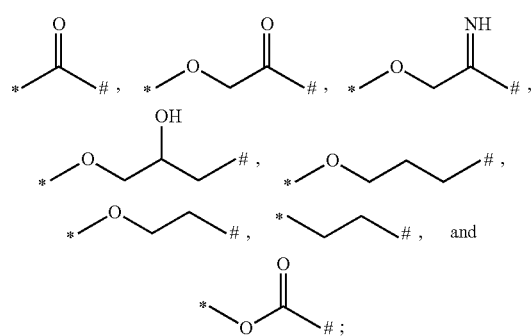

wherein the * represents the attachment point to $A^3$, and the # represents the attachment point to the remainder of the molecule; $L^4$ is selected from the group consisting of

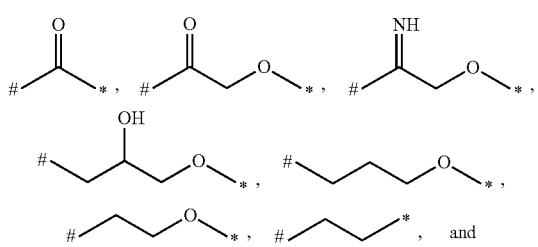

-continued

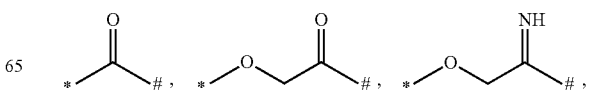

wherein the * represents the attachment point to $A^4$, and the # represents the attachment point to the remainder of the molecule;
$A^3$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —$NO_2$, $C_1$-$C_6$ alkyl, $C_2$-$C_6$ alkenyl, $C_2$-$C_6$ alkynyl, and $C_1$-$C_6$ haloalkyl;
$A^4$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —$NO_2$, $C_1$-$C_6$ alkyl, $C_2$-$C_6$ alkenyl, $C_2$-$C_6$ alkynyl, and $C_1$-$C_6$ haloalkyl.

Embodiment 5. A compound of formula (V):

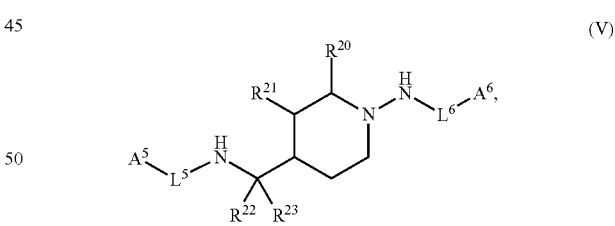

(V)

or a pharmaceutically acceptable salt thereof,
wherein:
$R^{20}$ is hydrogen or —C(O)OH;
$R^{21}$ is hydrogen or halogen;
$R^{22}$ and $R^{23}$ are both hydrogen or $R^{22}$ and $R^{23}$ are taken together to form an oxo (=O) substituent;
$L^5$ is selected from the group consisting of

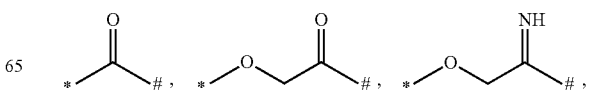

-continued

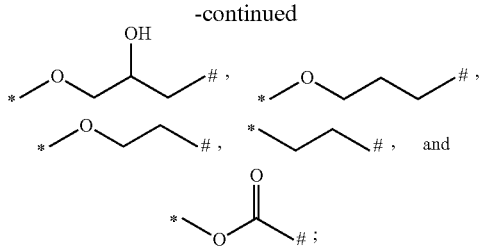

wherein the * represents the attachment point to $A^5$, and the # represents the attachment point to the remainder of the molecule;

$L^6$ is selected from the group consisting of

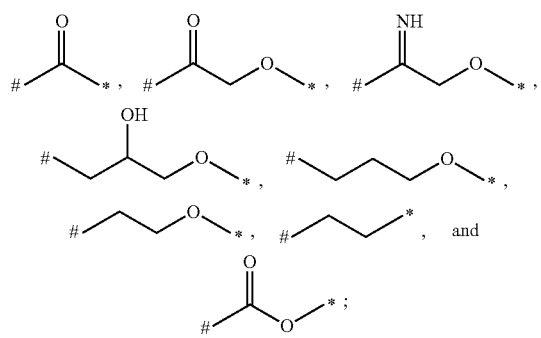

wherein the * represents the attachment point to $A^6$, and the # represents the attachment point to the remainder of the molecule;

$A^5$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —$NO_2$, $C_1$-$C_6$ alkyl, $C_2$-$C_6$ alkenyl, $C_2$-$C_6$ alkynyl, and $C_1$-$C_6$ haloalkyl;

$A^6$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —$NO_2$, $C_1$-$C_6$ alkyl, $C_2$-$C_6$ alkenyl, $C_2$-$C_6$ alkynyl, and $C_1$-$C_6$ haloalkyl.

Embodiment 6. A compound of formula (VI):

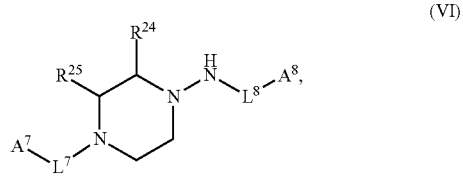

or a pharmaceutically acceptable salt thereof, wherein:

$R^{24}$ is hydrogen or —C(O)OH;

$R^{25}$ is hydrogen or halogen;

$L^7$ is selected from the group consisting of

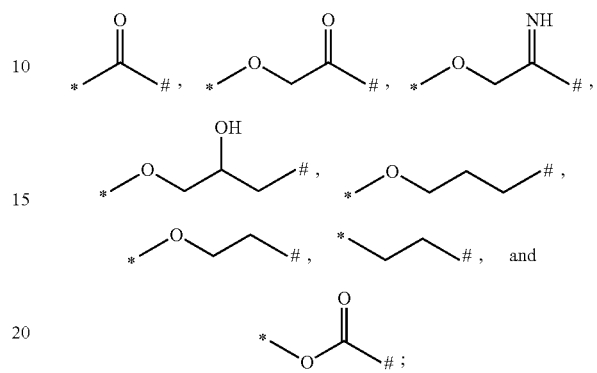

wherein the * represents the attachment point to $A^7$, and the # represents the attachment point to the remainder of the molecule;

$L^8$ is selected from the group consisting of

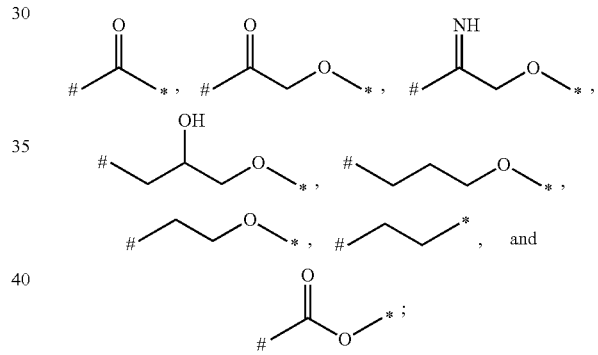

wherein the * represents the attachment point to $A^8$, and the # represents the attachment point to the remainder of the molecule;

$A^7$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —$NO_2$, $C_1$-$C_6$ alkyl, $C_2$-$C_6$ alkenyl, $C_2$-$C_6$ alkynyl, and $C_1$-$C_6$ haloalkyl;

$A^8$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —$NO_2$, $C_1$-$C_6$ alkyl, $C_2$-$C_6$ alkenyl, $C_2$-$C_6$ alkynyl, and $C_1$-$C_6$ haloalkyl.

Embodiment 7. A compound of formula (VII):

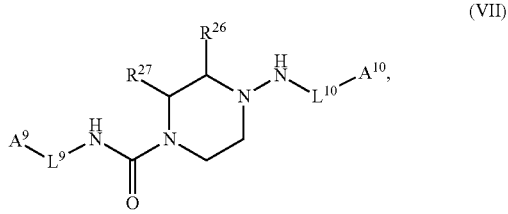

(VII)

or a pharmaceutically acceptable salt thereof,
wherein:
$R^{26}$ is hydrogen or —C(O)OH;
$R^{27}$ is hydrogen or halogen;
$L^9$ is selected from the group consisting of

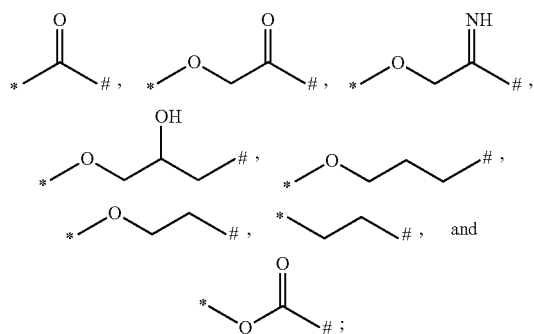

wherein the * represents the attachment point to $A^9$, and the # represents the attachment point to the remainder of the molecule;
$L^{10}$ is selected from the group consisting of

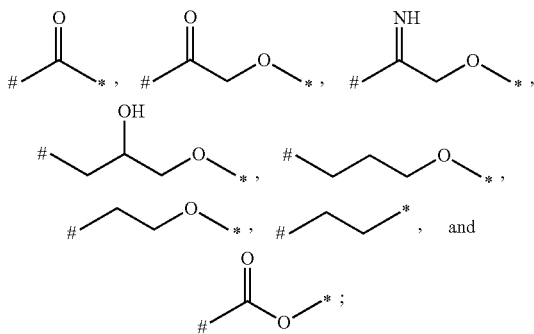

wherein the * represents the attachment point to $A^{10}$, and the # represents the attachment point to the remainder of the molecule;
$A^9$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —$NO_2$, $C_1$-$C_6$ alkyl, $C_2$-$C_6$ alkenyl, $C_2$-$C_6$ alkynyl, and $C_1$-$C_6$ haloalkyl;
$A^{10}$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —$NO_2$, $C_1$-$C_6$ alkyl, $C_2$-$C_6$ alkenyl, $C_2$-$C_6$ alkynyl, and $C_1$-$C_6$ haloalkyl.

Embodiment 8. A compound of formula (VIII):

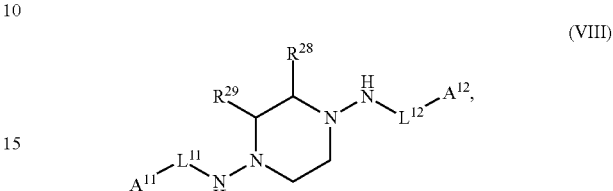

(VIII)

or a pharmaceutically acceptable salt thereof,
wherein:
$R^{28}$ is hydrogen or —C(O)OH;
$R^{29}$ is hydrogen or halogen;
$L^{11}$ is selected from the group consisting of

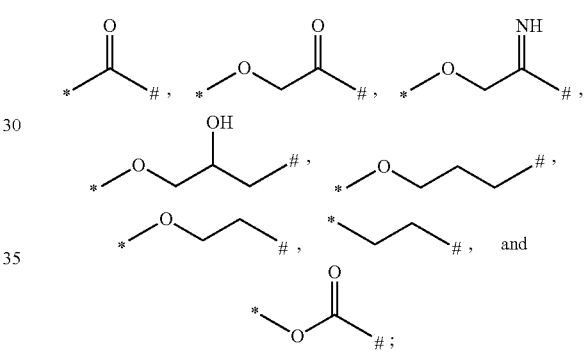

wherein the * represents the attachment point to $A^{11}$, and the # represents the attachment point to the remainder of the molecule;
$L^{12}$ is selected from the group consisting of

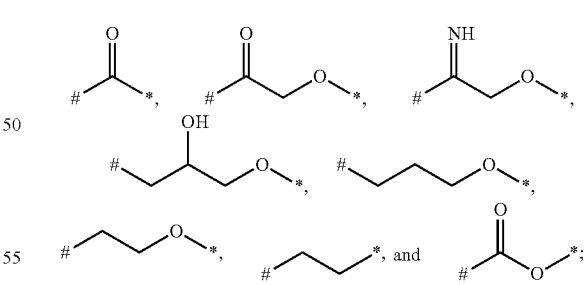

wherein the * represents the attachment point to $A^{12}$, and the # represents the attachment point to the remainder of the molecule;
$A^{11}$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —NO$_2$, C$_1$-C$_6$ alkyl, C$_2$-C$_6$ alkenyl, C$_2$-C$_6$ alkynyl, and C$_1$-C$_6$ haloalkyl;

A$^{12}$ is selected from the group consisting of phenyl, naphthyl, quinolinyl, benzofuranyl, 2,3-dihydrobenzofuranyl, benzothiazolyl, and 3,4-dihydro-2H-benzo[b][1,4]oxazinyl, wherein each of the phenyl, naphthyl, quinolinyl, benzofuranyl, 2,3-dihydrobenzofuranyl, benzothiazolyl, or 3,4-dihydro-2H-benzo[b][1,4]oxazinyl is optionally substituted with 1, 2, 3, or 4 substituents selected from the group consisting of halogen, —NO$_2$, C$_1$-C$_6$ alkyl, C$_2$-C$_6$ alkenyl, C$_2$-C$_6$ alkynyl, and C$_1$-C$_6$ haloalkyl;

provided that the compound of formula (VIII) is not

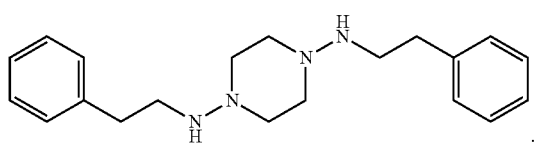 [SMILES: c1ccc(CCNN2CCN(NCCc3ccccc3)CC2)cc1]

Embodiment 9. A compound selected from the group consisting of a compound of Table 1, or a pharmaceutically acceptable salt thereof.

Embodiment 10. A pharmaceutical composition comprising a compound of any one of the preceeding embodiments, or a pharmaceutically acceptable salt thereof, and a pharmaceutically acceptable carrier.

Embodiment 11. A method of treating a disease or disorder mediated by an integrated stress response (ISR) pathway in an individual in need thereof comprising administering to the individual a therapeutically effective amount of a compound of any one of embodiments 1 to 9, or a pharmaceutically acceptable salt thereof, or a therapeutically effective amount of a pharmaceutical composition of embodiment 10.

Embodiment 12. The method of embodiment 11, wherein the compound, the pharmaceutically acceptable salt, or the pharmaceutical composition is administered in combination with a therapeutically effective amount of one or more additional anti-cancer agents.

Embodiment 13. The method of embodiment 11, wherein the disease or disorder is mediated by phosphorylation of eIF2a and/or the guanine nucleotide exchange factor (GEF) activity of eIF2B.

Embodiment 14. The method of any one of embodiments 11-13, wherein the disease or disorder is mediated by a decrease in protein synthesis.

Embodiment 15. The method of any one of embodiments 11-14, wherein the disease or disorder is mediated by the expression of ATF4, CHOP or BACE-1.

Embodiment 16. The method of any of embodiments 11-15, wherein the disease or disorder is a neurodegenerative disease, an inflammatory disease, an autoimmune disease, a metabolic syndrome, a cancer, a vascular disease, an ocular disease, or a musculoskeletal disease.

Embodiment 17. The method of embodiment 20, wherein the disease is vanishing white matter disease, childhood ataxia with CNS hypomyelination, intellectual disability syndrome, Alzheimer's disease, prion disease, Creutzfeldt-Jakob disease, Parkinson's disease, amyotrophic lateral sclerosis (ALS) disease, cognitive impairment, frontotemporal dementia (FTD), traumatic brain injury, postoperative cognitive dysfunction (PCD), neuro-otological syndromes, hearing loss, Huntington's disease, stroke, chronic traumatic encephalopathy, spinal cord injury, dementias or cognitive impairment, arthritis, psoriatic arthritis, psoriasis, juvenile idiopathic arthritis, asthma, allergic asthma, bronchial asthma, tuberculosis, chronic airway disorder, cystic fibrosis, glomerulonephritis, membranous nephropathy, sarcoidosis, vasculitis, ichthyosis, transplant rejection, interstitial cystitis, atopic dermatitis or inflammatory bowel disease, Crohn's disease, ulcerative colitis, celiac disease, systemic lupus erythematosus, type 1 diabetes, multiple sclerosis, rheumatoid arthritis, alcoholic liver steatosis, obesity, glucose intolerance, insulin resistance, hyperglycemia, fatty liver, dyslipidemia, hyperlipidemia, type 2 diabetes, pancreatic cancer, breast cancer, kidney cancer, bladder cancer, prostate cancer, testicular cancer, urothelial cancer, endometrial cancer, ovarian cancer, cervical cancer, renal cancer, esophageal cancer, gastrointestinal stromal tumor (GIST), multiple myeloma, cancer of secretory cells, thyroid cancer, gastrointestinal carcinoma, chronic myeloid leukemia, hepatocellular carcinoma, colon cancer, melanoma, malignant glioma, glioblastoma, glioblastoma multiforme, astrocytoma, dysplastic gangliocytoma of the cerebellum, Ewing's sarcoma, rhabdomyosarcoma, ependymoma, medulloblastoma, ductal adenocarcinoma, adenosquamous carcinoma, nephroblastoma, acinar cell carcinoma, lung cancer, non-Hodgkin's lymphoma, Burkitt's lymphoma, chronic lymphocytic leukemia, monoclonal gammopathy of undetermined significance (MGUS), plasmocytoma, lymphoplasmacytic lymphoma, acute lymphoblastic leukemia, Pelizaeus-Merzbacher disease, atherosclerosis, abdominal aortic aneurism, carotid artery disease, deep vein thrombosis, Buerger's disease, chronic venous hypertension, vascular calcification, telangiectasia or lymphoedema, glaucoma, age-related macular degeneration, inflammatory retinal disease, retinal vascular disease, diabetic retinopathy, uveitis, rosacea, Sjogren's syndrome or neovascularization in proliferative retinopathy, hyperhomocysteinemia, skeletal muscle atrophy, myopathy, muscular dystrophy, muscular wasting, sarcopenia, Duchenne muscular dystrophy (DMD), Becker's disease, myotonic dystrophy, X-linked dilated cardiomyopathy, or spinal muscular atrophy (SMA).

Embodiment 18. A method of producing a protein, comprising contacting a eukaryotic cell comprising a nucleic acid encoding the protein with the compound or salt of any one of embodiments 1-9.

Embodiment 19. The method of embodiment 18, comprising culturing the cell in an in vitro culture medium comprising the compound or salt.

Embodiment 20. A method of culturing a eukaryotic cell comprising a nucleic acid encoding a protein, comprising contacting the eukaryotic cell with an in vitro culture medium comprising a compound or salt of any one of embodiments 1-9.

Embodiment 21. The method of any one of embodiments 18-20, wherein the nucleic acid encoding the protein is a recombinant nucleic acid.

Embodiment 22. The method of any one of embodiments 18-21, wherein the cell is a human embryonic kidney (HEK) cell or a Chinese hamster ovary (CHO) cell.

Embodiment 23. A method of producing a protein, comprising contacting a cell-free protein synthesis (CFPS) system comprising eukaryotic initiation factor 2 (eIF2) and a nucleic acid encoding a protein with the compound or salt of any one of embodiments 1-9.

Embodiment 24. The method of any one of embodiments 18-23, wherein the protein is an antibody or a fragment thereof.

Embodiment 25. The method of any one of embodiments 18-24, comprising purifying the protein.

Embodiment 26. An in vitro cell culture medium, comprising the compound or salt of any one of embodiments 1-9 and nutrients for cellular growth.

Embodiment 27. The cell culture medium of embodiment 26, comprising a eukaryotic cell comprising a nucleic acid encoding a protein.

Embodiment 28. The cell culture medium of embodiment 26 or 27, further comprising a compound for inducing protein expression.

Embodiment 29. The cell culture medium of any one of embodiments 26-28, wherein the nucleic acid encoding the protein is a recombinant nucleic acid.

Embodiment 30. The cell culture medium of any one of embodiments 26-29, wherein the protein is an antibody or a fragment thereof.

Embodiment 31. The cell culture medium of any one of embodiments 26-30, wherein the eukaryotic cell is a human embryonic kidney (HEK) cell or a Chinese hamster ovary (CHO) cell.

Embodiment 32. A cell-free protein synthesis (CFPS) system comprising eukaryotic initiation factor 2 (eIF2) and a nucleic acid encoding a protein with the compound or salt of any one of embodiments 1-9.

Embodiment 33. The CFPS system of embodiment 32, comprising a eukaryotic cell extract comprising eIF2.

Embodiment 34. The CFPS system of embodiments 32 and 33, further comprising eIF2B.

Embodiment 35. The CFPS system of any one of embodiments 32-34, wherein the protein is an antibody or a fragment thereof.

EXAMPLES

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

The chemical reactions in the Examples described can be readily adapted to prepare a number of other compounds disclosed herein, and alternative methods for preparing the compounds of this disclosure are deemed to be within the scope of this disclosure. For example, the synthesis of non-exemplified compounds according to the present disclosure can be successfully performed by modifications apparent to those skilled in the art, e.g., by appropriately protecting interfering groups, by utilizing other suitable reagents known in the art other than those described, or by making routine modifications of reaction conditions, reagents, and starting materials. Alternatively, other reactions disclosed herein or known in the art will be recognized as having applicability for preparing other compounds of the present disclosure.

In some cases, stereoisomers are separated to give single enantiomers or diastereomers as single, unknown stereoisomers, and are arbitrarily drawn as single isomers. Where appropriate, information is given on separation method and elution time and order. In the biological examples, compounds tested were prepared in accordance to the synthetic procedures described therein. For any given compound of unknown absolute stereochemistry for which specific rotation is available, biological data for that compound was obtained using the enantiomer or diastereoisomer associated with said specific rotation.

In some cases, optical rotation was determined on Jasco DIP-360 digital polarimeter at a wavelength of 589 nm (sodium D line) and are reported as $[\alpha]_D^T$ for a given temperature T (expressed in ° C.). Where appropriate, information is given on solvent and concentration (expressed as g/100 mL).

Abbreviations br. s. Broad singlet
chloroform-d Deuterated chloroform
methanol-$d_4$ Deuterated methanol
DIAD Diisopropyl azodicarboxylate
DCM Dichloromethane
DEA Diethylamine
DIPEA Diisopropylethylamine
DMF N,N-Dimethylformamide
DMSO-$d_6$ Deuterated dimethylsulfoxide
d Doublet
EDC.HCl 1-Ethyl-3-(3-dimethylaminopropyl)carbodiimide hydrochloric acid
EtOAc Ethyl acetate
EtOH Ethanol
g Gram
HATU (O-(7-azabenzotriazol-1-yl)-N,N,N',N'-tetramethyluronium hexafluorophosphate)
HOBT Hydroxybenzotriazole
HPLC High Performance Liquid Chromatography
L Litre
LCMS Liquid Chromatography Mass Spectrometry
MeCN Acetonitrile
MeOH Methanol
mg Milligram
mL Millilitre
mmol Millimoles
m multiplet
NMR Nuclear Magnetic Resonance
q quartet
RT Room temperature
s singlet
SFC Supercritical Fluid Chromatography
TFA trifluoroacetic acid
THF Tetrahydrofuran
TLC Thin layer chromatography
t triplet

EXAMPLES

Example 1

Synthesis of 6-chloro-N-(4-(2-(4-chloro-3-fluorophenoxy)acetamido)piperidin-1-yl)quinoline-2-carboxamide

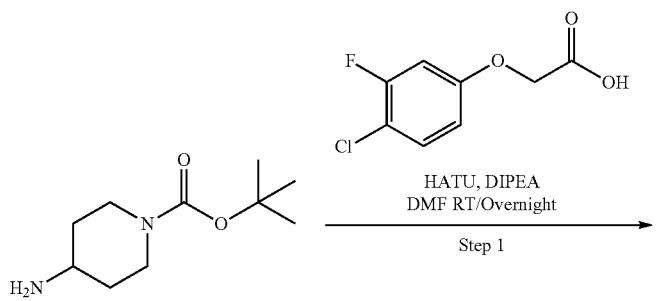

-continued
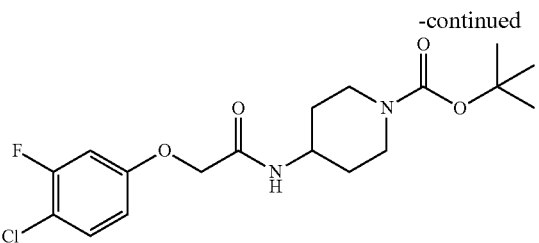
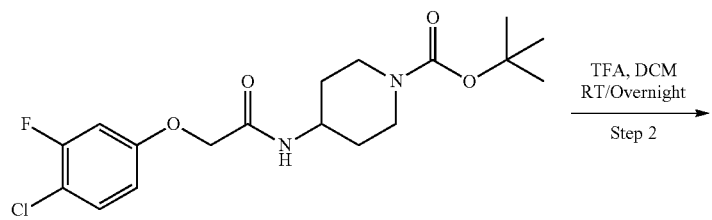
TFA, DCM
RT/Overnight
Step 2
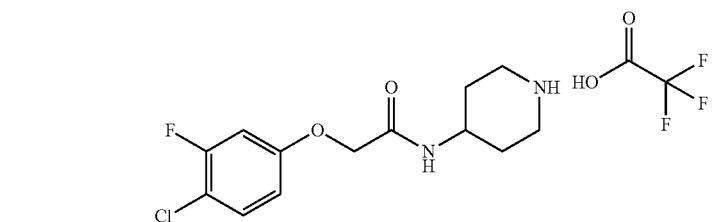
Acetic Acid,
Sodium Nitrite
H₂O RT/Overnight
Step 3
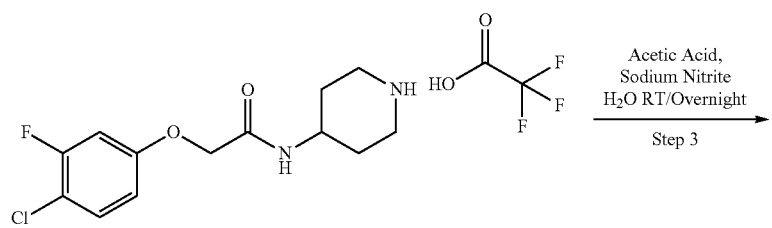
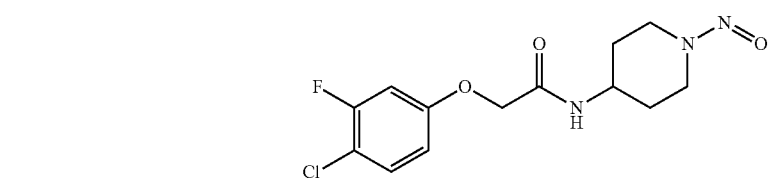
Zn dust, HCl
H₂O RT/Overnight
Step 4
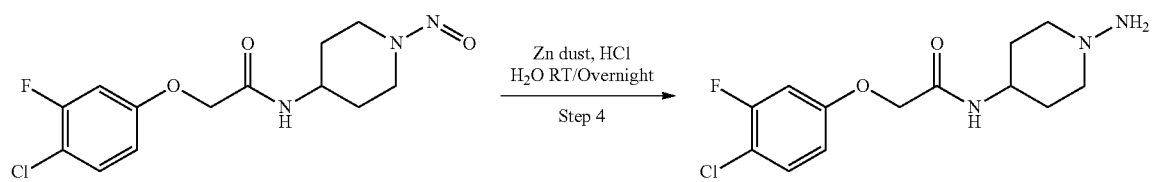
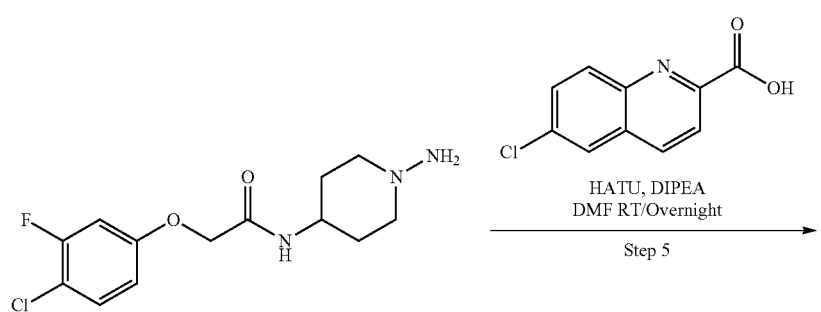
HATU, DIPEA
DMF RT/Overnight
Step 5

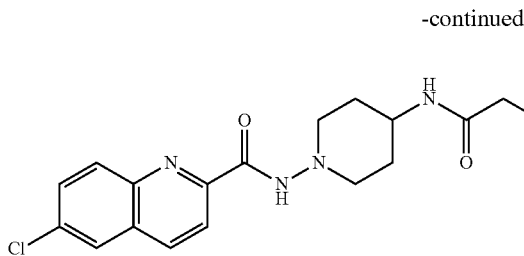

Step 1—Synthesis of tert-butyl 4-(2-(4-chloro-3-fluorophenoxy)acetamido)piperidine-1-carboxylate To a stirred solution of tert-butyl 4-aminopiperidine-1-carboxylate (0.500 g, 2.50 mmol, 1.0 equiv) in DMF (10 mL) was added 2-(4-chloro-3-fluorophenoxy)acetic acid (0.510 g, 2.50 mmol, 1.0 equiv) and HATU (1.90 g, 5.00 mmol, 2.0 equiv) at RT. The resulting reaction mixture was stirred for 10 minutes and DIPEA (1.4 mL, 7.5 mmol, 3.00 equiv) was added. The reaction mixture was allowed to stir at RT for overnight. Product formation was confirmed by LCMS. The reaction mixture was diluted with water (50 mL) and extracted with ethyl acetate (100 mL×2). Combined organic extracts were washed with water (20 mL×4), dried over anhydrous $Na_2SO_4$ and concentrated to obtain tert-butyl 4-(2-(4-chloro-3-fluorophenoxy)acetamido)piperidine-1-carboxylate (1.00 g, quantitative yield) as a brown semisolid. LCMS: 387.2 $[M+H]^+$.

Step 2—Synthesis of 2-(4-chloro-3-fluorophenoxy)-N-(piperidin-4-yl)acetamide 2,2,2-trifluoroacetate To a stirred solution of tert-butyl 4-(2-(4-chloro-3-fluorophenoxy)acetamido)piperidine-1-carboxylate (1.00 g, 2.5 mmol) in DCM (15 mL) was added TFA (1 mL). The resultant reaction mixture was stirred at RT for overnight. Progress of the reaction was monitored by NMR spectroscopy. After completion of the reaction, the reaction mixture was concentrated under reduced pressure to obtain 2-(4-chloro-3-fluorophenoxy)-N-(piperidin-4-yl)acetamide 2,2,2-trifluoroacetate (1.00 g, quantitative yield) as a brown semisolid. LCMS: 287 $[M+H]^+$; $^1$H NMR (400 MHz, DMSO-$d_6$) δ 8.55 (br. s., 1H), 8.31-8.18 (m, 2H), 7.49 (t, J=9.0 Hz, 1H), 7.06 (dd, J=2.6, 11.4 Hz, 1H), 6.84 (dd, J=2.0, 9.0 Hz, 1H), 4.54 (s, 2H), 3.90 (d, J=7.0 Hz, 1H), 3.27 (d, J=12.7 Hz, 2H), 3.09-2.93 (m, 2H), 1.88 (d, J=11.4 Hz, 2H), 1.69-1.54 (m, 2H).

Step 3—Synthesis of 2-(4-chloro-3-fluorophenoxy)-N-(1-nitrosopiperidin-4-yl)acetamide To a stirred solution of 2-(4-chloro-3-fluorophenoxy)-N-(piperidin-4-yl)acetamide 2,2,2-trifluoroacetate (6.0 g, 15.66 mmol, 1.0 equiv) in water (30 mL) was added acetic acid (10 mL) and sodium nitrite (4.3 g, 62.66 mmol, 4.0 equiv) at RT. The reaction mixture was allowed to stir at RT overnight. Product formation was confirmed by LCMS. The reaction mixture was diluted with water (50 mL). The resulting solid was filtered off, washed with water (20 mL×4) and dried under vacuum to obtain to 2-(4-chloro-3-fluorophenoxy)-N-(1-nitrosopiperidin-4-yl)acetamide (2.8 g, 60% yield as an off white solid). LCMS: 316 $[M+H]^+$; $^1$H NMR (400 MHz, DMSO-$d_6$) δ 8.13 (d, J=7.0 Hz, 1H), 7.50 (t, J=8.8 Hz, 1H), 7.07 (dd, J=2.6, 11.4 Hz, 1H), 6.94-6.75 (m, 1H), 4.68-4.58 (m, 1H), 4.58-4.47 (m, 2H), 4.18-4.01 (m, 1H), 3.99-3.82 (m, 1H), 3.03-2.82 (m, 1H), 1.98 (d, J=12.3 Hz, 1H), 1.78 (d, J=12.7 Hz, 1H), 1.70-1.53 (m, 1H), 1.35-1.23 (m, 1H).

Step 4—Synthesis of N-(1-aminopiperidin-4-yl)-2-(4-chloro-3-fluorophenoxy)acetamide To a solution of 2-(4-chloro-3-fluorophenoxy)-N-(1-nitrosopiperidin-4-yl)acetamide (0.100 g, 0.31 mmol, 1.0 equiv) in water (5 mL) was added acetic acid (1 mL) and Zn dust (0.208 g, 3.1 mmol, 10.0 equiv) at RT. The reaction mixture was allowed to stir at RT overnight. Product formation was confirmed by LCMS. The reaction mixture was filtered through Celite®. The resulting filtrate was basified by liquid ammonia and extracted with ethyl acetate (50 mL×2). Combined organic layer was washed with water (20 mL×4), dried over anhydrous $Na_2SO_4$ and concentrated to obtain N-(1-aminopiperidin-4-yl)-2-(4-chloro-3-fluorophenoxy)acetamide (0.100 g, quantitative yield) as an off white solid. LCMS: 302 $[M+H]^+$.

Step 5—Synthesis of 6-chloro-N-(4-(2-(4-chloro-3-fluorophenoxy)acetamido)piperidin-1-yl)quinoline-2-carboxamide To a solution of N-(1-aminopiperidin-4-yl)-2-(4-chloro-3-fluorophenoxy) acetamide (0.100 g, 0.33 mmol, 1.0 equiv) in DMF (5 mL) was added 6-chloroquinoline-2-carboxylic acid (0.070 g, 0.33 mmol, 1.0 equiv) and HATU (0.208 g, 0.66 mmol, 2.0 equiv) at RT. The resulting reaction mixture was stirred for 10 minutes and DIPEA (0.28 mL, 0.99 mmol, 3.0 equiv) was added. The reaction mixture was allowed to stir at RT overnight. Product formation was confirmed by LCMS. The reaction mixture was diluted with water (20 mL) and extracted with ethyl acetate (50 mL×2). Combined organic layer was washed with water (20 mL×4), dried over anhydrous $Na_2SO_4$ and concentrated. The crude product was purified by reverse phase HPLC to obtain 6-chloro-N-(4-(2-(4-chloro-3-fluorophenoxy)acetamido)piperidin-1-yl)quinoline-2-carboxamide (Compound 1-10 mg, 6% yield) as an off white solid. LCMS: 491 $[M+H]^+$; $^1$H NMR (400 MHz, DMSO-$d_6$) δ 9.77 (s, 1H), 8.53 (d, J=8.3 Hz, 1H), 8.24 (d, J=1.8 Hz, 1H), 8.18-8.03 (m, 3H), 7.88 (dd, J=2.4, 9.0 Hz, 1H), 7.51 (t, J=8.8 Hz, 1H), 7.09 (dd, J=2.9, 11.6 Hz, 1H), 6.87 (d, J=7.5 Hz, 1H), 4.54 (s, 2H), 3.68 (br. s., 1H), 3.03 (d, J=10.5 Hz, 2H), 2.87 (t, J=10.7 Hz, 2H), 1.79 (d, J=10.5 Hz, 2H), 1.75-1.58 (m, 2H).

Example 2

Synthesis of 5-chloro-N-(4-(2-(4-chloro-3-fluoro-phenoxy)acetamido)piperidin-1-yl)benzofuran-2-carboxamide

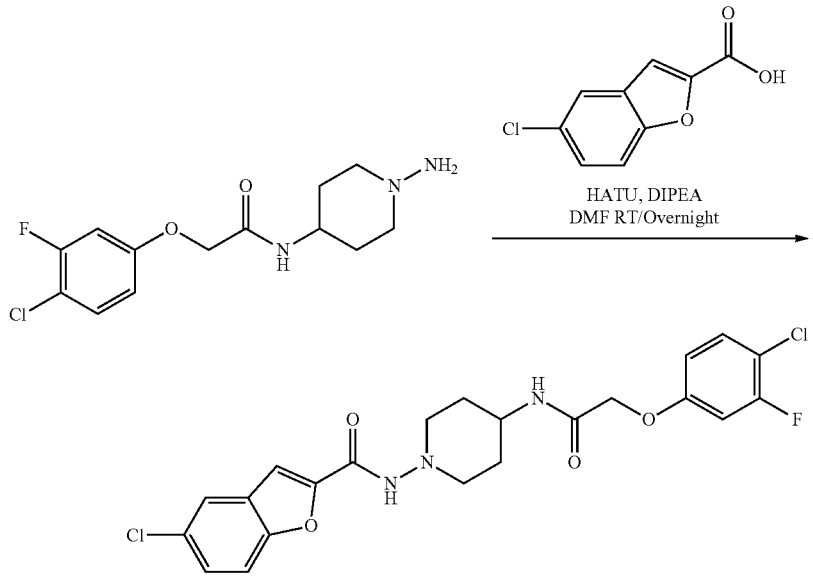

To a solution of N-(1-aminopiperidin-4-yl)-2-(4-chloro-3-fluorophenoxy)acetamide (0.100 g, 0.33 mmol, 1.0 equiv) in DMF (5 mL) was added 5-chlorobenzofuran-2-carboxylic acid (0.065 g, 0.33 mmol, 1.0 equiv) and HATU (0.250 g, 0.66 mmol, 2.0 equiv) at RT. The resulting reaction mixture was stirred for 10 minutes. DIPEA (0.28 mL, 0.99 mmol, 3.0 equiv) was added. The reaction mixture was allowed to stir at RT overnight. Product formation was confirmed by LCMS. The reaction mixture was diluted with water (25 mL) and extracted with ethyl acetate (50 mL×2). Combined organic layer was washed with water (20 mL×4), dried over anhydrous $Na_2SO_4$ and concentrated. The crude product was purified by reverse phase HPLC to obtain 5-chloro-N-(4-(2-(4-chloro-3-fluorophenoxy)acetamido)piperidin-1-yl)benzofuran-2-carboxamide (Compound 2-20 mg, 12% yield) as an off white solid. LCMS 480 [M+H]$^+$; $^1$H NMR (400 MHz, DMSO-$d_6$) δ 9.79 (s, 1H), 8.08 (d, J=7.5 Hz, 1H), 7.86 (s, 1H), 7.70 (d, J=9.2 Hz, 1H), 7.54-7.38 (m, 3H), 7.08 (d, J=8.8 Hz, 1H), 6.86 (d, J=11.8 Hz, 1H), 4.53 (s, 2H), 3.66 (br. s., 1H), 2.99 (br. s., 2H), 2.78 (br. s., 2H), 1.75 (br. s., 2H), 1.66 (br. s., 2H).

Example 3

Synthesis of 6-chloro-N-(1-(2-(4-chloro-3-fluoro-phenoxy)acetamido)piperidin-4-yl)quinoline-2-carboxamide

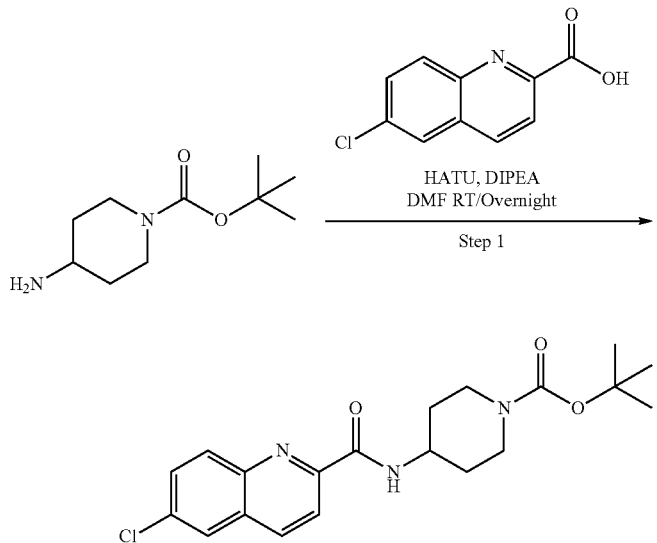

-continued
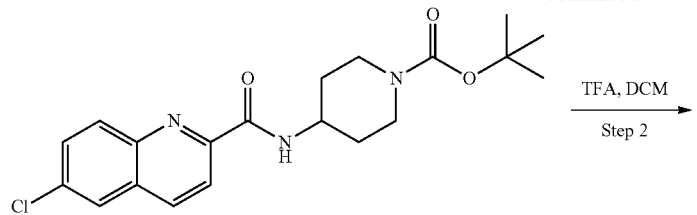
TFA, DCM
Step 2
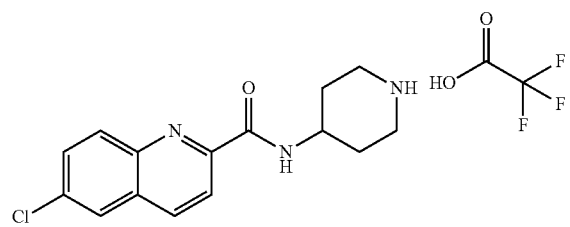
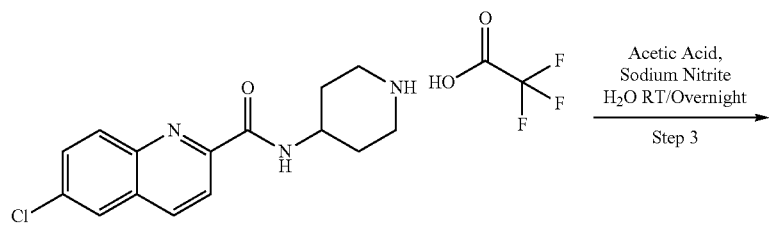
Acetic Acid, Sodium Nitrite
H₂O RT/Overnight
Step 3
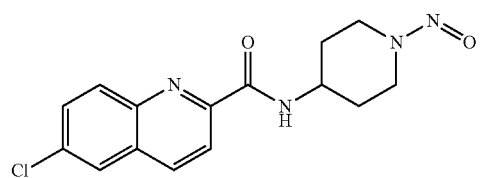
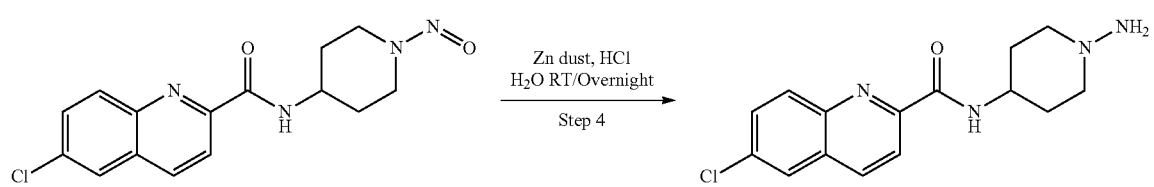
Zn dust, HCl
H₂O RT/Overnight
Step 4
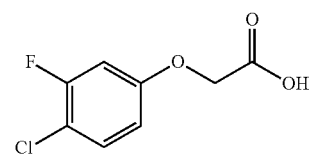
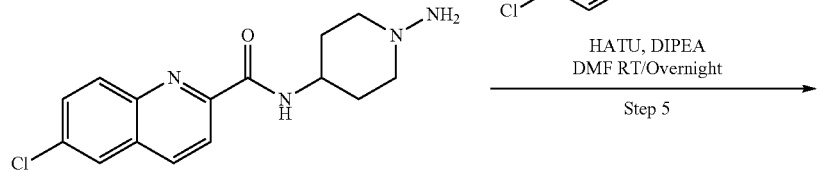
HATU, DIPEA
DMF RT/Overnight
Step 5
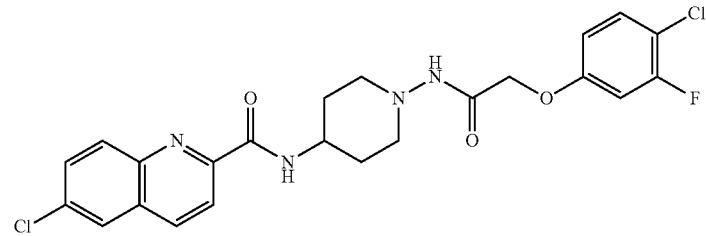

Step 1—Synthesis of tert-butyl 4-(6-chloroquinoline-2-carboxamido)piperidine-1-carboxylate To a stirred solution of tert-butyl 4-aminopiperidine-1-carboxylate (1.00 g, 5.00 mmol, 1.0 equiv) in DMF (10 mL) was added 6-chloroquinoline-2-carboxylic acid (1.040 g, 5.00 mmol, 1.0 equiv) and HATU (3.800 g, 10.00 mmol, 2.0 equiv) at RT. The resulting reaction mixture was stirred for 10 minutes and DIPEA (2.6 mL, 15.00 mmol, 3.00 equiv) was added. The reaction mixture was allowed to stir at RT for overnight. Product formation was confirmed by LCMS. The reaction mixture was diluted with water (50 mL) and extracted with ethyl acetate (100 mL×2). Combined organic extracts were washed with water (20 mL×4), dried over anhydrous $Na_2SO_4$ and concentrated to obtain tert-butyl 4-(6-chloroquinoline-2-carboxamido)piperidine-1-carboxylate (1.50 g, quantitative yield) as a brown semisolid. LCMS: 390.2 $[M+H]^+$.

Step 2—Synthesis of 6-chloro-N-(piperidin-4-yl)quinoline-2-carboxamide 2,2,2-trifluoroacetate To a stirred solution of tert-butyl 4-(6-chloroquinoline-2-carboxamido)piperidine-1-carboxylate (1.50 g, 3.80 mmol) in DCM (15 mL) was added TFA (5 mL). The resultant reaction mixture was stirred at RT for overnight. Progress of the reaction was monitored by NMR spectroscopy. After completion of the reaction, the reaction mixture was concentrated under reduced pressure to obtain 6-chloro-N-(piperidin-4-yl)quinoline-2-carboxamide 2,2,2-trifluoroacetate (1.00 g, 65% yield) as a brown solid. LCMS: 290 $[M+H]^+$; $^1H$ NMR (400 MHz, DMSO-$d_6$) δ 8.98 (d, J=7.9 Hz, 1H), 8.64 (br. s., 1H), 8.55 (d, J=8.3 Hz, 1H), 8.38 (br. s., 1H), 8.25 (d, J=2.2 Hz, 1H), 8.18 (d, J=8.8 Hz, 2H), 7.89 (dd, J=2.2, 9.2 Hz, 1 H), 4.21-4.08 (m, 1H), 3.36 (d, J=12.7 Hz, 2H), 3.16-3.01 (m, 2H), 2.05-1.96 (m, 2H), 1.96-1.82 (m, 2H).

Step 3—Synthesis of 6-chloro-N-(1-nitrosopiperidin-4-yl)quinoline-2-carboxamide To a stirred solution of 6-chloro-N-(piperidin-4-yl)quinoline-2-carboxamide 2,2,2-trifluoroacetate (1.0 g, 2.50 mmol, 1.0 equiv) in water (15 mL) was added acetic acid (5 mL) and sodium nitrite (0.730 g, 10.03 mmol, 4.0 equiv) at RT. The reaction mixture was allowed to stir at RT overnight. Product formation was confirmed by LCMS. The reaction mixture was diluted with water (50 mL). The resulting solid was filtered off, washed with water (20 mL×4) and dried under vacuum to obtain to 6-chloro-N-(1-nitrosopiperidin-4-yl) quinoline-2-carboxamide (1.40 g, quantitative yield) as a white solid. LCMS: 319 $[M+H]^+$. Step 4—Synthesis of N-(1-aminopiperidin-4-yl)-6-chloroquinoline-2-carboxamide:

To a solution of 6-chloro-N-(1-nitrosopiperidin-4-yl) quinoline-2-carboxamide (0.100 g, 0.31 mmol, 1.0 equiv) in water (5 mL) was added acetic acid (5 mL) and Zn dust (0.045 g, 0.62 mmol, 2.00 equiv). The reaction mixture was allowed to stir at RT overnight. Product formation was confirmed by LCMS. The reaction mixture was filtered through Celite®. The resulting filtrate was basified by liquid ammonia and extracted with ethyl acetate (50 mL×2). Combined organic layer was washed with water (20 mL×4), dried over anhydrous $Na_2SO_4$ and concentrated to obtain N-(1-aminopiperidin-4-yl)-6-chloroquinoline-2-carboxamide (0.100 g, 96% yield) as a brown semisolid. LCMS: 305 $[M+H]^+$.

Step 5—Synthesis of 6-chloro-N-(1-(2-(4-chloro-3-fluorophenoxy)acetamido)piperidin-4-yl)quinoline-2-carboxamide To a solution of N-(1-aminopiperidin-4-yl)-6-chloroquinoline-2-carboxamide (0.100 g, 0.32 mmol, 1.0 equiv) in DMF (5 mL) was added 2-(4-chloro-3-fluorophenoxy)acetic acid (0.068 g, 0.32 mmol, 1.0 equiv) and HATU (0.244 g, 0.64 mmol, 2.0 equiv) at RT. The resulting reaction mixture was stirred for 10 minutes and DIPEA (0.25 mL, 0.96 mmol, 3.0 equiv) was added. The reaction mixture was allowed to stir at RT overnight. Product formation was confirmed by LCMS. The reaction mixture was diluted with water (20 mL) and extracted with ethyl acetate (50 mL×2). Combined organic layer was washed with water (20 mL×4), dried over anhydrous $Na_2SO_4$ and concentrated. The crude product was purified by reverse phase HPLC to obtain 6-chloro-N-(1-(2-(4-chloro-3-fluorophenoxy)acetamido)piperidin-4-yl)quinoline-2-carboxamide (Compound 3-7 mg, 5% yield) as a white solid. LCMS: 491 $[M+H]^+$; $^1H$ NMR (400 MHz, DMSO-$d_6$) δ 9.18 (s, 1H), 8.79 (d, J=8.8 Hz, 1H), 8.54 (d, J=8.8 Hz, 1H), 8.25 (br. s., 1H), 8.23-8.11 (m, 2H), 7.89 (d, J=8.3 Hz, 1H), 7.58-7.41 (m, 1 H), 7.03 (br. s., 1H), 6.78 (br. s., 1H), 4.94 (s, 1H), 4.50 (s, 1H), 3.11 (br. s., 1H), 2.95 (br. s., 2H), 2.73 (br. s., 2H), 1.85 (br. s., 4H).

Example 4

Synthesis of N,N'-(piperidine-1,4-diyl)bis(2-(4-chloro-3-fluorophenoxy)acetamide)

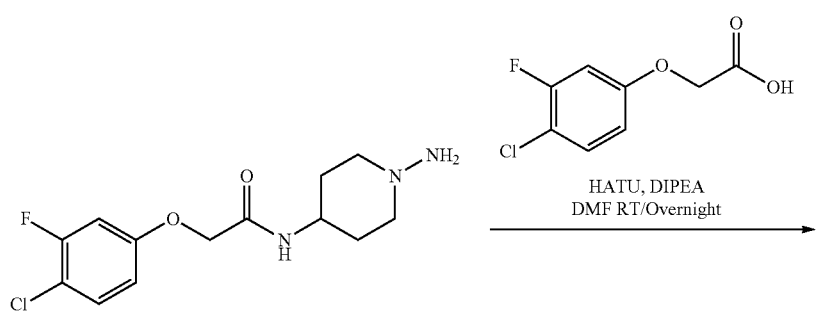

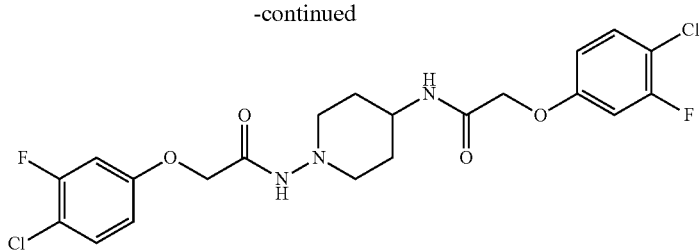

To a solution of N-(1-aminopiperidin-4-yl)-2-(4-chloro-3-fluorophenoxy) acetamide (0.100 g, 0.33 mmol, 1.0 equiv) in DMF (5 mL) was added 2-(4-chloro-3-fluorophenoxy) acetic acid (0.068 g, 0.33 mmol, 1.0 equiv) and HATU (0.250 g, 0.66 mmol, 2.0 equiv) at RT. The resulting reaction mixture was stirred for 10 minutes and DIPEA (0.28 mL, 0.99 mmol, 3.0 equiv) was added. The reaction mixture was allowed to stir at RT overnight. Product formation was confirmed by LCMS. The reaction mixture was diluted with water (20 mL) and extracted with ethyl acetate (50 mL×2). Combined organic layer was washed with water (20 mL×4), dried over anhydrous $Na_2SO_4$ and concentrated. The crude product was purified by reverse phase HPLC to obtain N,N'-(piperidine-1,4-diyl)bis(2-(4-chloro-3-fluorophenoxy) acetamide) (Compound 4-20 mg, 13% yield) as a white solid. LCMS: 488 [M+H]$^+$; $^1$H NMR (400 MHz, DMSO-d$_6$) δ 9.15 (s, 1H), 8.79 (br. s., 1H), 8.05 (d, J=7.5 Hz, 1H), 7.54-7.42 (m, 2H), 7.05 (s, 1H), 7.08 (s, 1H), 6.85 (d, J=6.6 Hz, 1H), 4.90 (s, 1H), 4.58-4.40 (m, 3H), 3.59 (br. s., 2 H), 3.05 (br. s., 1H), 2.88 (br. s., 1H), 2.66 (d, J=11.0 Hz, 1H), 1.73 (br. s., 2H), 1.58 (d, J=9.2 Hz, 2H).

Example 5

Synthesis of 5-chloro-N-(1-(2-(4-chloro-3-fluorophenoxy)acetamido)piperidin-4-yl)benzofuran-2-carboxamide

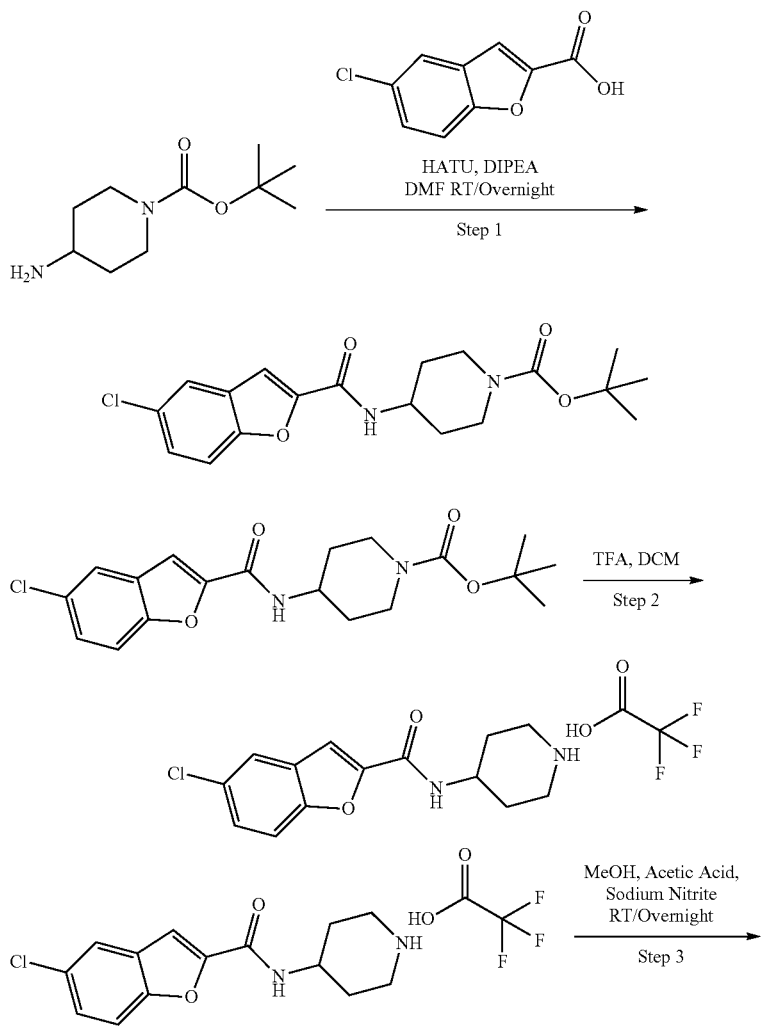

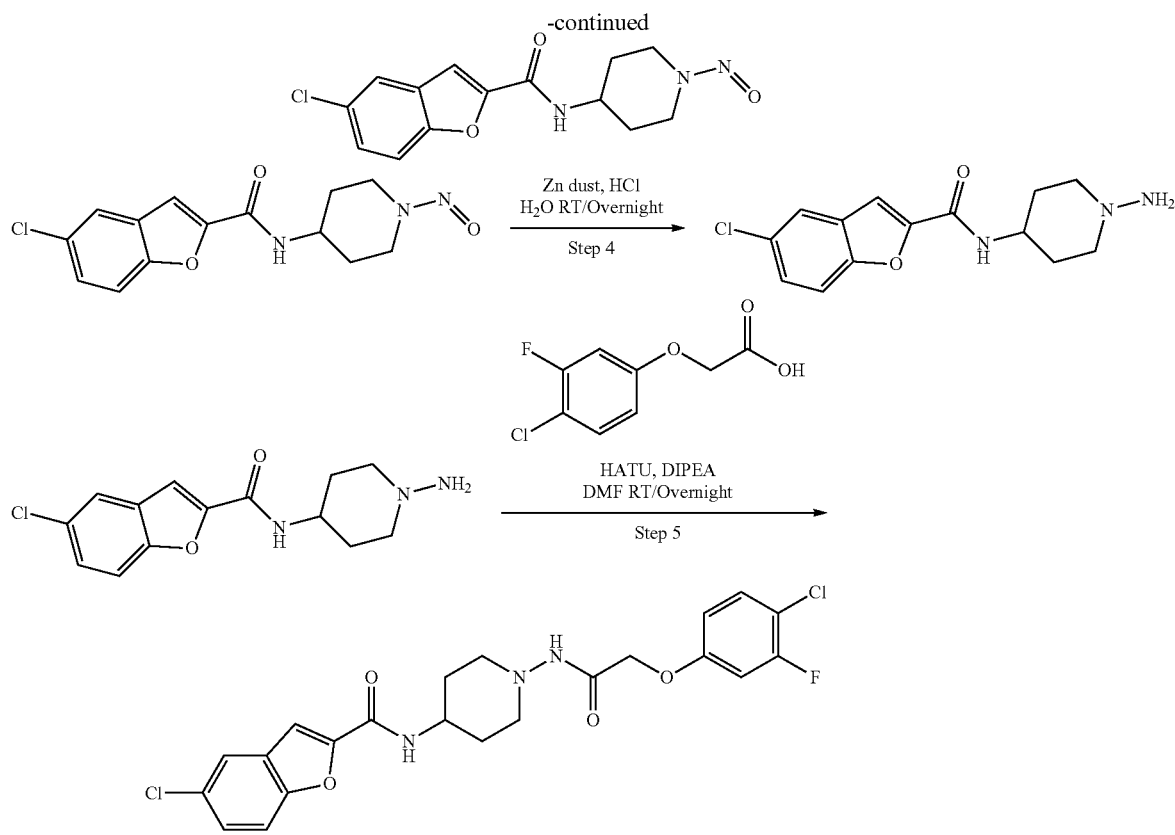

Step 1—Synthesis of tert-butyl 4-(5-chlorobenzo-furan-2-carboxamido)cyclohexane-1-carboxylate To a stirred solution of tert-butyl 4-aminopiperidine-1-carboxylate (1.02 g, 5.10 mmiol, 1.0 equiv) in DMF (10 mL) was added 5-chlorobenzofuran-2-carboxylic acid (1.0 g, 5.1 mmol, 1.0 equiv) and HATU (3.800 g, 10.02 mmol, 2.0 equiv) at RT. The resulting reaction mixture was stirred for 10 minutes and DIPEA (2.5 mL, 15.00 mmol, 3.00 equiv) was added. The reaction mixture was allowed to stir at RT for overnight. Product formation was confirmed by LCMS. The reaction mixture was diluted with water (50 mL) and extracted with ethyl acetate (100 mL×2). Combined organic extracts were washed with water (20 mL×4), dried over anhydrous $Na_2SO_4$ and concentrated. The crude product obtained was treated with ether-hexane (50:50) to obtain tert-butyl 4-(5-chlorobenzofuran-2-carboxamido)piperidine-1-carboxylate (0.800 g, 43% yield) as an off-white solid. LCMS: 379.2 [M+H]$^+$.

Step 2—Synthesis of 5-chloro-N-(piperidin-4-yl)benzofuran-2-carboxamide 2,2,2-trifluoroacetate To a stirred solution of tert-butyl 4-(5-chlorobenzofuran-2-carboxamido)piperidine-1-carboxylate (0.800 g, 2.32 mmol) in DCM (10 mL) was added TFA (3 mL). The resultant reaction mixture was stirred at RT for overnight. Progress of the reaction was monitored by NMR spectroscopy. After completion of the reaction, the reaction mixture was concentrated under reduced pressure. The crude product obtained was treated with diethyl ether to obtain 5-chloro-N-(piperidin-4-yl)benzofuran-2-carboxamide 2,2,2-trifluoroacetate (0.960 g, quantitative yield) as an off-white solid. LCMS: 279.3 [M+H]$^+$.

Step 3—Synthesis of 5-chloro-N-(1-nitrosopiperidin-4-yl)benzofuran-2-carboxamide To a stirred solution of 5-chloro-N-(piperidin-4-yl)benzofuran-2-carboxamide 2,2,2-trifluoroacetate (0.500 g, 1.25 mmol, 1.0 equiv) in water (20 mL) was added acetic acid (5 mL) and sodium nitrite (0.345 g, 5.00 mmol, 4.0 equiv). The reaction mixture was allowed to stir at RT overnight. Product formation was confirmed by LCMS. The reaction mixture was diluted with water (50 mL). The resulting solid was filtered off, washed with water (20 mL×4) and dried under vacuum to obtain to 5-chloro-N-(1-nitrosopiperidin-4-yl)benzofuran-2-carboxamide (0.320 g, 81% yield) as an off-white solid). LCMS: 308.1 [M+H]$^+$.

Step 4—Synthesis of N-(1-aminopiperidin-4-yl)-5-chlorobenzofuran-2-carboxamide

To a solution of 5-chloro-N-(1-nitrosopiperidin-4-yl)benzofuran-2-carboxamide (0.300 g, 0.97 mmol, 1.0 equiv) in MeOH (10 mL) was added concentrated HCl (0.5 mL) and Zn dust (0.123 g, 1.89 mmol, 2.0 equiv). The reaction mixture was allowed to stir at RT overnight. Product formation was confirmed by LCMS. The reaction mixture was filtered through Celite®. The resulting filtrate was basified by liquid ammonia and extracted with ethyl acetate (50 mL×2). Combined organic layer was washed with water (20 mL×4), dried over anhydrous $Na_2SO_4$ and concentrated to obtain N-(1-aminopiperidin-4-yl)-5-chlorobenzofuran-2-carboxamide (0.340 g, quantitative yield) as a brown semi-solid. LCMS: 294.1 [M+H]⁺.

Step 5—Synthesis of 5-chloro-N-(1-(2-(4-chloro-3-fluorophenoxy)acetamido)piperidin-4-yl)benzofuran-2-carboxamide To a solution of N-(1-aminopiperidin-4-yl)-5-chlorobenzofuran-2-carboxamide (0.200 g, 0.68 mmol, 1.0 equiv) in DMF (5 mL) was added 2-(4-chloro-3-fluorophenoxy)acetic acid (0.139 g, 0.68 mmol, 1.0 equiv) and HATU (0.512 g, 1.365 mmol, 2.0 equiv) at RT. The resulting reaction mixture was stirred for 10 minutes and DIPEA (0.3 mL, 2.04 mmol, 3.0 equiv) was added. The reaction mixture was allowed to stir at RT overnight. Product formation was confirmed by LCMS. The reaction mixture was diluted with water (20 mL) and extracted with ethyl acetate (50 mL×2). Combined organic layer was washed with water (20 mL×4), dried over anhydrous $Na_2SO_4$ and concentrated. The crude product was purified by reverse phase HPLC to obtain 5-chloro-N-(1-(2-(4-chloro-3-fluorophenoxy)acetamido)piperidin-4-yl)benzofuran-2-carboxamide (Compound 5-20 mg, 5% yield) as a white solid. LCMS: 480.2 [M+H]⁺; ¹H NMR (400 MHz, DMSO-$d_6$) δ 9.18 (s, 1H), 8.70 (d, J=7.5 Hz, 1H), 7.87 (br. s., 1 H), 7.70 (d, J=8.8 Hz, 1H), 7.57-7.42 (m, 1H), 7.09-6.98 (m, 1H), 6.87-6.78 (m, 1H), 4.93-4.49 (s, 2H), 4.49 3.76 (br. s., 1H), 3.09 (br. s., 1H), 2.93 (d, J=10.5 Hz, 2H), 2.74-2.63 (m, 2H), 1.85-1.69 (m, 4H).

Example 6

Synthesis of 2-(4-chloro-3-fluorophenoxy)-N-(4-(3-(4-chloro-3-fluorophenoxy)-2-hydroxypropyl)piperazin-1-yl)acetamide

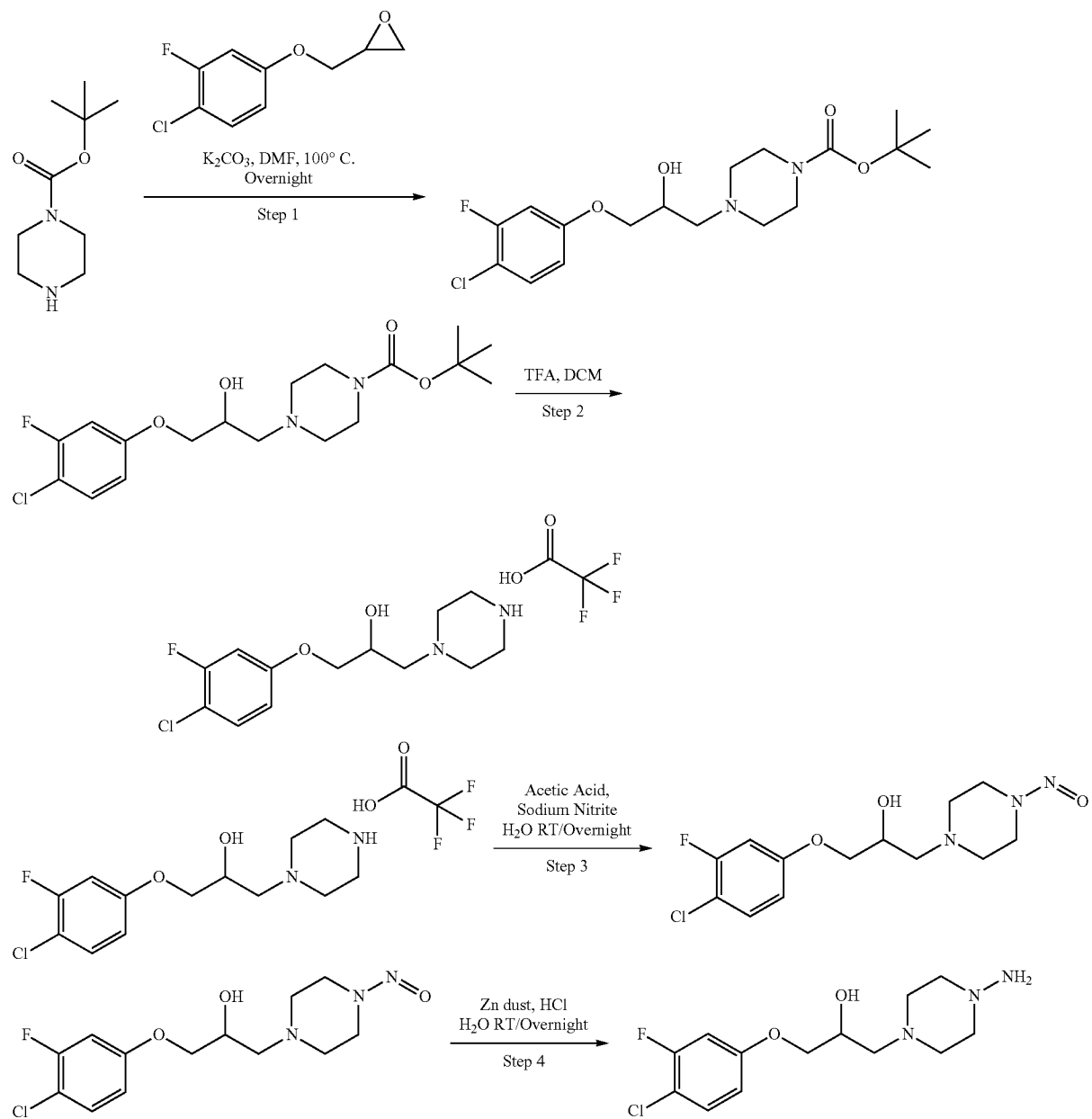

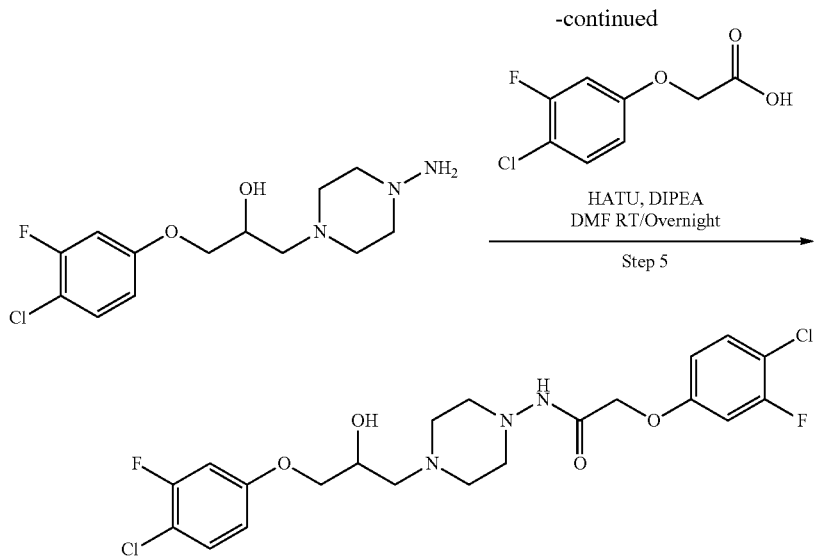

Step 1—Synthesis of tert-butyl 4-(3-(4-chloro-3-fluorophenoxy)-2-hydroxypropyl)piperazine-1-carboxylate To a stirred solution of tert-butyl piperazine-1-carboxylate (2.00 g, 10.05 mmol, 1 equiv) in DMF (10 mL) was added 2-((4-chloro-3-fluorophenoxy)methyl)oxirane (2.2 g, 11.0 mmol, 1.1 equiv) and K2CO3 (4.1 g, 30.0 mmol, 3 equiv) at RT. The resultant reaction mixture was heated at 100° C. for overnight. Progress of the reaction was monitored by LCMS. After completion of the reaction, the reaction mixture was diluted with water (100 mL) and extracted with ethyl acetate (150 mL×2). Combined organic layer was washed with water (50 mL×4), dried over anhydrous $Na_2SO_4$ and concentrated under reduced pressure. The crude product obtained was purified by flash chromatography (0-5% MeOH in DCM as an eluent) to obtain tert-butyl 4-(3-(4-chloro-3-fluorophenoxy)-2-hydroxypropyl)piperazine-1-carboxylate (2.3 g, 55% yield) as an off white solid. LCMS: 389.3 [M+H]$^+$; $^1$H NMR (400 MHz, DMSO-d$_6$) δ7.46 (t, J=9.0 Hz, 1H), 7.06 (dd, J=2.6, 11.8 Hz, 1H), 6.83 (dd, J=2.2, 8.8 Hz, 1H), 4.93 (d, J=4.8 Hz, 1H), 4.10-3.81 (m, 5H), 2.47-2.21 (m, 8H), 1.39 (s, 9H).

Step 2—Synthesis of 1-(4-chloro-3-fluorophenoxy)-3-(piperazin-1-yl)propan-2-ol 2,2,2-trifluoroacetate To a stirred solution of tert-butyl 4-(3-(4-chloro-3-fluorophenoxy)-2-hydroxypropyl)piperazine-1-carboxylate (1.500 g, 5.92 mmol) in DCM (30 mL) was added TFA (5 mL). The resultant reaction mixture was stirred at RT for overnight. Progress of the reaction was monitored by NMR spectroscopy. After completion of the reaction, the reaction mixture was concentrated under reduced pressure. The crude product obtained was treated with diethyl ether to obtain 1-(4-chloro-3-fluorophenoxy)-3-(piperazin-1-yl)propan-2-ol 2,2,2-trifluoroacetate (2.30 g, quantitative yield) as an brown semisolid. LCMS: 289.2 [M+H]$^+$.

Step 3—Synthesis of 1-(4-chloro-3-fluorophenoxy)-3-(4-nitrosopiperazin-1-yl)propan-2-ol To a stirred solution of 1-(4-chloro-3-fluorophenoxy)-3-(piperazin-1-yl)propan-2-ol 2,2,2-trifluoroacetate (1.0 g, 2.48 mmol, 1.0 equiv) in water (50 mL) was added acetic acid (10 mL) and sodium nitrite (0.68 g, 9.90 mmol, 4.0 equiv). The reaction mixture was allowed to stir at RT overnight. Product formation was confirmed by LCMS. The reaction mixture was diluted with water (50 mL). The resulting solid was filtered off, washed with water (20 mL×4) and dried under vacuum to obtain to 1-(4-chloro-3-fluorophenoxy)-3-(4-nitrosopiperazin-1-yl)propan-2-ol (0.690 g, 87% yield) as an off-white solid). LCMS: 318.08 [M+H]$^+$.

Step 4—Synthesis of 1-(4-aminopiperazin-1-yl)-3-(4-chloro-3-fluorophenoxy)propan-2-ol To a solution of 1-(4-chloro-3-fluorophenoxy)-3-(4-nitrosopiperazin-1-yl)propan-2-ol (0.600 g, 1.89 mmol, 1.0 equiv) in MeOH (10 mL) was added concentrated HCl (0.5 mL) and Zn dust (00.369 g, 5.67 mmol, 3.0 equiv). The reaction mixture was allowed to stir at RT overnight. Product formation was confirmed by LCMS. The reaction mixture was filtered through Celite®. The resulting filtrate was basified by liquid ammonia and extracted with ethyl acetate (50 mL×2). Combined organic layer was washed with water (20 mL×4), dried over anhydrous $Na_2SO_4$ and concentrated to obtain 1-(4-aminopiperazin-1-yl)-3-(4-chloro-3-fluorophenoxy)propan-2-ol (0.690 g, quantitative yield) as an off-white solid. LCMS: 304 [M+H]$^+$.

Step 5—Synthesis of 2-(4-chloro-3-fluorophenoxy)-N-(4-(3-(4-chloro-3-fluorophenoxy)-2-hydroxypropyl)piperazin-1-yl)acetamide To a solution of 1-(4-aminopiperazin-1-yl)-3-(4-chloro-3-fluorophenoxy)propan-2-ol (0.200 g, 0.66 mmol, 1.0 equiv) in DMF (05 mL) was added 2-(4-chloro-3-fluorophenoxy)acetic acid_(0.134 g, 0.66 mmol, 1.0 equiv) and HATU (0.503 g, 1.32 mmol, 2.0 equiv) at RT. The resulting reaction mixture was stirred for 10 minutes and DIPEA (0.3 mL, 1.98 mmol, 3.0 equiv) was added. The reaction mixture was allowed to stir at RT overnight. Product formation was confirmed by LCMS. The reaction mixture was diluted with water (20 mL) and extracted with ethyl acetate (50 mL×2). Combined organic layer was washed with water (20 mL×4), dried over anhydrous $Na_2SO_4$ and concentrated. The crude product was purified by reverse phase HPLC to obtain 2-(4-chloro-3-fluorophenoxy)-N-(4-(3-(4-chloro-3-fluorophenoxy)-2-hydroxypropyl)piperazin-1-yl)acetamide (Compound 6-0.040 g, 12% yield) as an off-white solid. LCMS: 490.2 [M+H]$^+$; $^1$H NMR (400 MHz, DMSO-d$_6$) δ

9.15 (br. s., 1H), 8.81 (br. s., 1 H), 7.52-7.39 (m, 3H), 7.04 (s, 1H), 7.07 (s, 1H), 6.84 (d, J=7.9 Hz, 2H), 4.88 (s, 2H), 4.47 (s, 1H), 4.00 (d, J=7.5 Hz, 1H), 3.92-3.83 (m, 2H), 2.90 (br. s., 1H), 2.76 (br. s., 3H), 2.35 (d, J=18.0 Hz, 4H).

Example 7

Synthesis of 6-chloro-N-(4-(2-(4-chloro-3-fluorophenoxy)acetamido)piperidin-1-yl)-3,4-dihydro-2H-benzo[b][1,4]oxazine-2-carboxamide

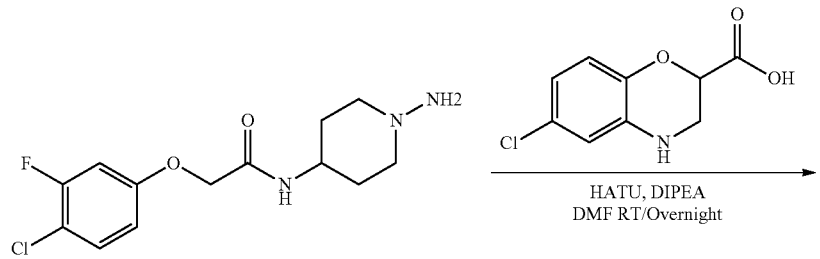

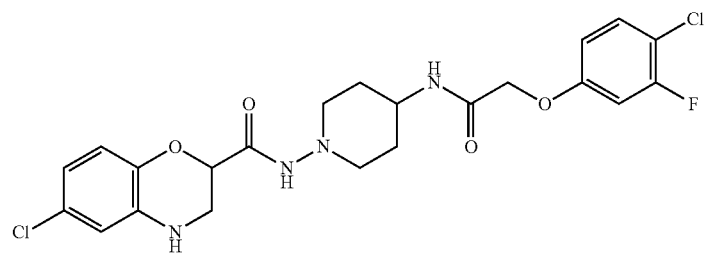

To a solution of N-(1-aminopiperidin-4-yl)-2-(4-chloro-3-fluorophenoxy) acetamide (0.100 g, 0.33 mmol, 1.0 equiv) in DMF (05 mL) was added 6-chloro-3,4-dihydro-2H-benzo[b][1,4]oxazine-2-carboxylic acid (0.071 g, 0.33 mmol, 1.0 equiv) and HATU (0.251 g, 0.66 mmol, 2.0 equiv) at RT. The resulting reaction mixture was stir for 10 minutes. DIPEA (0.28 mL, 0.99 mmol, 3.0 equiv) was added. The reaction mixture was allowed to stir at RT overnight. Product formation was confirmed by LCMS. The reaction mixture was diluted with water (50 mL) and extracted with ethyl acetate (100 mL×2). Combined organic extracts were washed with water (50 mL×4), dried over anhydrous Na$_2$SO$_4$ and concentrated. The crude product was purified by reversed phase HPLC to obtain 6-chloro-N-(4-(2-(4-chloro-3-fluorophenoxy)acetamido)piperidin-1-yl)-3,4-dihydro-2H-benzo[b][1,4]oxazine-2-carboxamide (Compound 31-05 mg, 3% Yield) as an off white solid. LCMS: 497 [M+H]$^+$; $^1$H NMR (400 MHz, DMSO-d$_6$) δ 9.01 (s, 1H), 8.03 (d, J=7.9 Hz, 1H), 7.49 (t, J=8.8 Hz, 1H), 7.06 (d, J=11.4 Hz, 1H), 6.85 (d, J=8.8 Hz, 1H), 6.76 (d, J=8.3 Hz, 1H), 6.67 (d, J=8.3 Hz, 1 H), 6.57 (br. s., 1H), 6.54-6.40 (m, 1H), 6.17 (br. s., 1H), 4.51 (s, 2H), 3.60 (br. s., 1H), 3.40 (d, J=12.3 Hz, 1H), 3.20 (dd, J=7.9, 11.8 Hz, 2H), 2.88 (br. s., 1H), 2.72-2.59 (m, 2H), 1.70 (br. s., 2H), 1.58 (d, J=14.5 Hz, 2H).

Example 8

Synthesis of 5-chloro-N-(4-(3-(4-chloro-3-fluorophenoxy)-2-hydroxypropyl)piperazin-1-yl)benzofuran-2-carboxamide

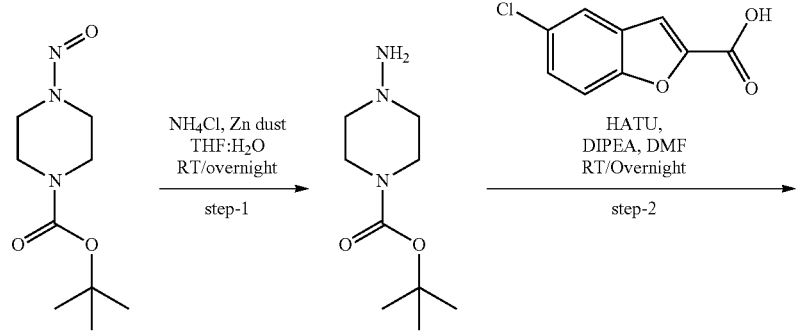

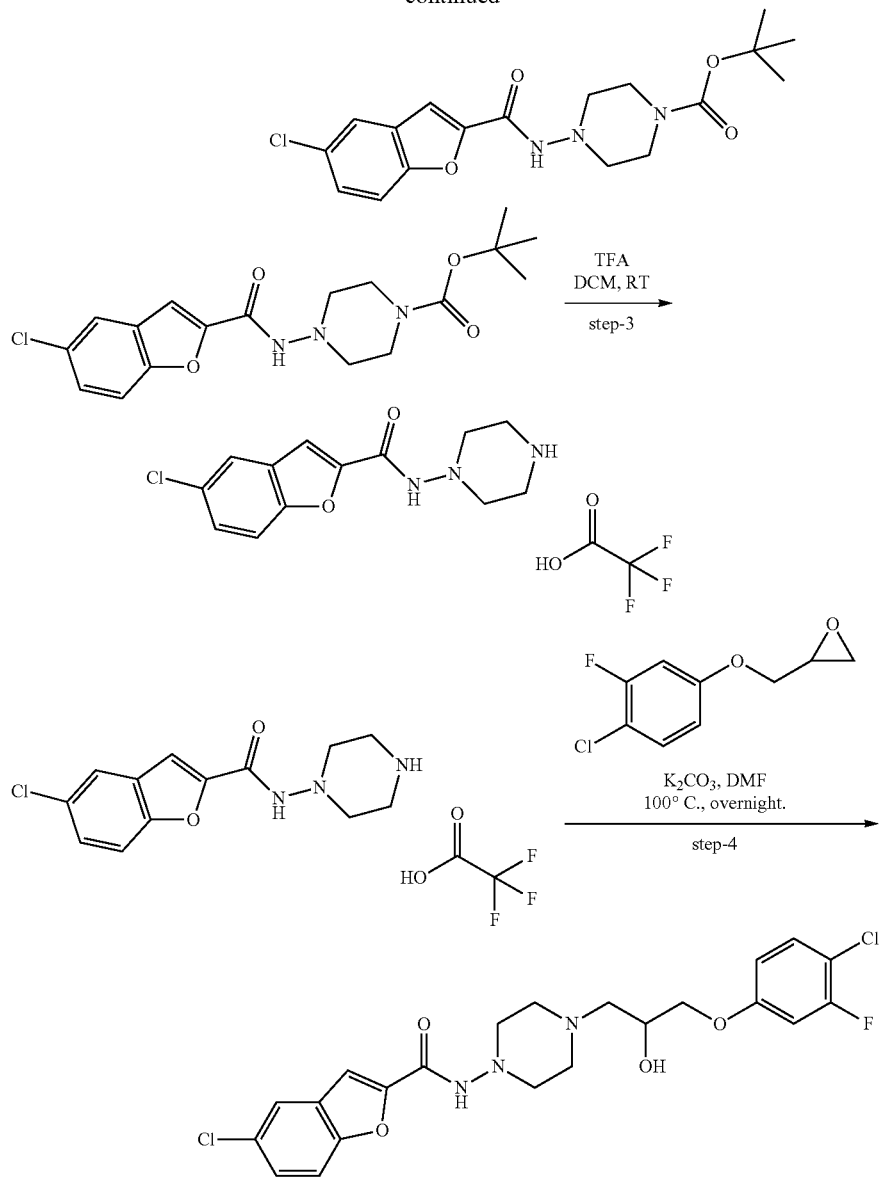

Step 1—Synthesis of tert-butyl 4-aminopiperazine-1-carboxylate

To a stirred solution of tert-butyl 4-nitrosopiperazine-1-carboxylate (0.500 g, 2.32 mmol, 1 equiv) in THF:H2O (10:10 mL) was added NH$_4$Cl (1.98 g, 37.17 mmol, 16.0 equiv) and then Zn dust (1.21 g, 18.58 mmol, 8.0 equiv) was added portion wise. After completion of addition the reaction mixture was stirred at RT for overnight. Progress of the reaction was monitored by LCMS. Reaction mixture was diluted with water (100 mL) and filtered off over Celite® bed and filtrate was extracted with DCM (100 mL×2). Organic layer was separated and dried over anhydrous Na$_2$SO$_4$ and concentrated under reduced pressure to obtain tert-butyl 4-aminopiperazine-1-carboxylate (0.420 g, 96% Yield) as a yellow semi solid. LCMS 202.3 [M+H]$^+$; $^1$H NMR (400 MHz, Chloroform-d) δ 3.47 (br. s., 4H), 3.14 (br. s., 2H), 2.56 (br. s., 4 H), 1.45 (s, 9H).

Step 2—Synthesis of tert-butyl 4-(5-chlorobenzofuran-2-carboxamido)piperazine-1-carboxylate To a stirred solution of 5-chlorobenzofuran-2-carboxylic acid (0.100 g, 0.50 mmol, 1.0 equiv) in DMF (05 mL) was added HATU (0.380 g, 1.01 mmol, 2.0 equiv) at RT and stirred for 10 minutes. Then tert-butyl 4-aminopiperazine-1-carboxylate (0.112 g, 0.55 mmol, 1.1 equiv) was added followed by the addition of DIPEA (0.2 mL, 1.52 mmol, 3.0 equiv). The resulting reaction mixture was allowed to stir at RT for overnight. Product formation was confirmed by LCMS. The reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure, to obtain tert-butyl 4-(5-chlorobenzofuran-2-carboxamido)piperazine-1-carboxylate (0.140 g, 66% Yield) as an off-white solid. LCMS 380.3 [M+H]$^+$; $^1$H NMR (400 MHz, DMSO-d$_6$) δ 9.90 (s, 1H), 7.87 (s, 1H), 7.70 (d, J=8.8 Hz, 1H), 7.57-7.44 (m, 2H), 3.42 (br. s., 4H), 2.83 (br. s., 4H), 1.50-1.29 (m, 9H).

Step 3—Synthesis of 5-chloro-N-(piperazin-1-yl) benzofuran-2-carboxamide 2,2,2-trifluoroacetate To a stirred solution of tert-butyl 4-(5-chlorobenzofuran-2-carboxamido)piperazine-1-carboxylate (0.140 g, 0.0.36 mmol, 1.0 equiv) in DCM (5 mL). was added TFA (1 mL) and the resultant reaction mixture was stirred at RT for 1 h under nitrogen atmosphere. Reaction was monitored by TLC and LCMS. After completion of reaction, the reaction mixture was concentrated under reduced pressure to obtain crude product which was crystallized in diethyl ether to obtain 5-chloro-N-(piperazin-1-yl)benzofuran-2-carboxamide 2,2,2-trifluoroacetate (0.130 g, 90% Yield) as an off-white solid. LCMS 280.3 [M+H]$^+$; $^1$H NMR (400 MHz, DMSO-d$_6$) δ 10.20 (s, 1H), 8.73 (br. s., 2H), 7.88 (d, J=1.8 Hz, 1H), 7.71 (d, J=8.8 Hz, 1H), 7.58-7.42 (m, 2H), 3.08-3.12 (m, 4H), 3.17-2.97 (m, 4H).

Step 4—Synthesis of 5-chloro-N-(4-(3-(4-chloro-3-fluorophenoxy)-2-hydroxypropyl)piperazin-1-yl) benzofuran-2-carboxamide To a stirred solution of 5-chloro-N-(piperazin-1-yl)benzofuran-2-carboxamide 2,2,2-trifluoroacetate (0.130 g, 0.33 mmol, 1.0 equiv) and 2-((4-chloro-3-fluorophenoxy) methyl)oxirane (0.066 g, 0.33 mmol, 1.0 equiv) in DMF (05 mL), was added K$_2$CO$_3$ (0.091 g, 0.66 mmol, 2.0 equiv) and the resultant reaction mixture was heated at 100° C. for overnight. Progress of the reaction was monitored by LCMS. After completion of reaction, the reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure to obtain crude product which was purified by reversed-phase HPLC to obtain 5-chloro-N-(4-(3-(4-chloro-3-fluorophenoxy)-2-hydroxypropyl)piperazin-1-yl) benzofuran-2-carboxamide (Compound 19-0.015 g, 09% Yield) as a white solid. LCMS 482.3 [M+H]$^+$; $^1$H NMR (400 MHz, DMSO-d$_6$) δ 10.21 (br. s., 1H), 9.64 (br. s., 1H), 7.89 (s, 1H), 7.71 (d, J=9.2 Hz, 1H), 7.61-7.44 (m, 2H), 7.11 (dd, J=2.6, 11.4 Hz, 1H), 6.87 (d, J=8.3 Hz, 1H), 6.01 (br. s., 1H), 4.31 (br. s., 1H), 4.01 (d, J=4.4 Hz, 2H), 3.60 (br. s., 2H), 3.21 (br. s., 8H).

Example 9

Synthesis of 6-chloro-N-(4-(3-(4-chloro-3-fluorophenoxy)-2-hydroxypropyl)piperazin-1-yl)-2-naphthamide

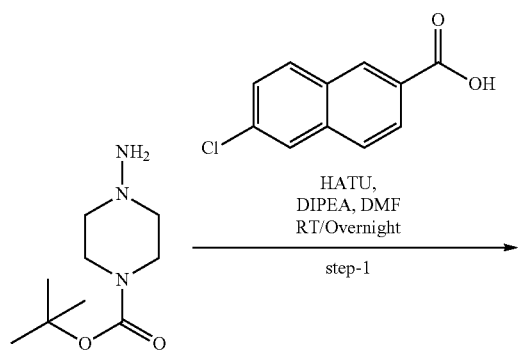

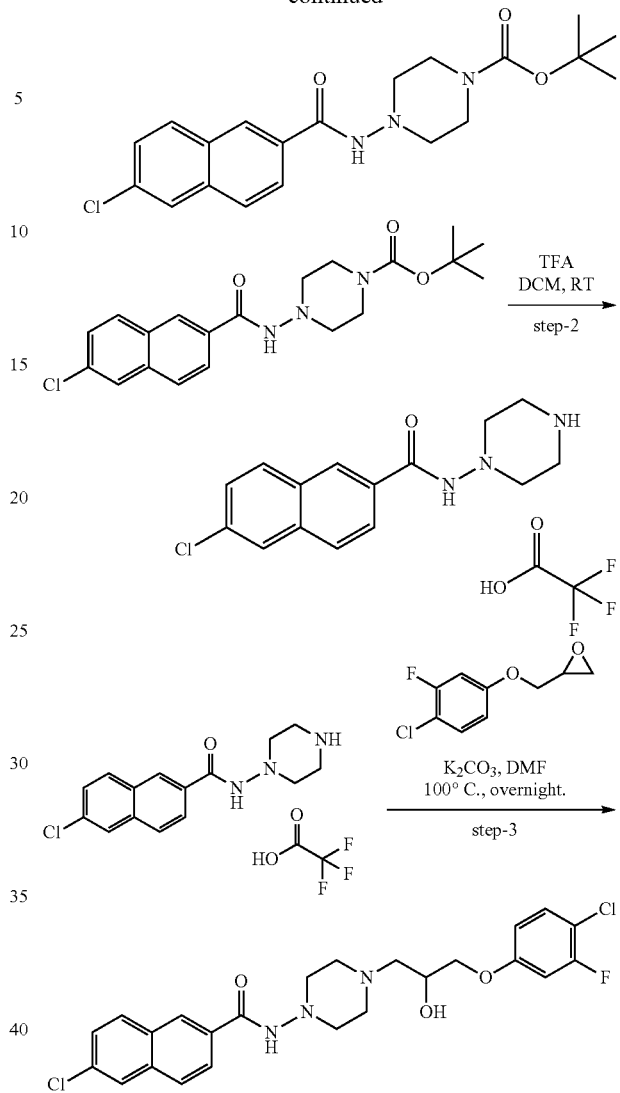

Step 1—Synthesis of tert-butyl 4-(6-chloro-2-naphthamido)piperazine-1-carboxylate To a stirred solution of 6-chloro-2-naphthoic acid (0.100 g, 0.48 mmol, 1.0 equiv) in DMF (05 mL) was added HATU (0.368 g, 0.97 mmol, 2.0 equiv) at RT and stirred for 10 minutes. Then tert-butyl 4-aminopiperazine-1-carboxylate (0.097 g, 0.48 mmol, 1.0 equiv) was added followed by the addition of DIPEA (0.2 mL, 1.45 mmol, 3.0 equiv). The resulting reaction mixture was allowed to stir at RT for overnight. Product formation was confirmed by LCMS. the reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure, to obtain tert-butyl 4-(6-chloro-2-naphthamido)piperazine-1-carboxylate (0.160 g, 85% Yield) as an off-white solid. LCMS 390.2 [M+H]$^+$; $^1$H NMR (400 MHz, DMSO-d$_6$) δ 9.69 (s, 1H), 8.39 (s, 1H), 8.18-8.03 (m, 2H), 7.97 (t, J=9.0 Hz, 1H), 7.90 (d, J=8.8 Hz, 1H), 7.60 (d, J=7.0 Hz, 2H), 3.44 (br. s., 3H), 2.94-2.84 (m, 4H), 1.53-1.32 (m, 9H).

Step 2—Synthesis of 6-chloro-N-(piperazin-1-yl)-2-naphthamide 2,2,2-trifluoroacetate To a stirred solution of tert-butyl 4-(6-chloro-2-naphthamido)piperazine-1-carboxylate (0.160 g, 0.41 mmol, 1.0 equiv) in DCM (05 mL) was added TFA (1 mL) and the resultant reaction mixture was stirred at RT for 1 h under nitrogen atmosphere. Reaction was monitored by TLC and LCMS. After completion of reaction, the reaction mixture was concentrated under reduced pressure to obtain sticky crude product which was crystallized in diethyl ether to obtain 6-chloro-N-(piperazin-1-yl)-2-naphthamide 2,2,2-trifluoroacetate (0.140 g, 84% Yield) as an off-white solid. LCMS 290.2 [M+H]$^+$; $^1$H NMR (400 MHz, DMSO-d$_6$) δ 9.98 (s, 1H), 8.65 (br. s., 2H), 8.41 (s, 1H), 8.19-8.05 (m, 2H), 8.00 (d, J=8.3 Hz, 1H), 7.91 (d, J=7.0 Hz, 1H), 7.62 (dd, J=1.8, 8.8 Hz, 1H), 3.25 (br. s., 4H), 3.16 (br. s., 4H).

Step 3—Synthesis of 6-chloro-N-(4-(3-(4-chloro-3-fluorophenoxy)-2-hydroxypropyl)piperazin-1-yl)-2-naphthamide To a stirred solution of 6-chloro-N-(piperazin-1-yl)-2-naphthamide trifluoroacetate (0.140 g, 0.34 mmol, 1.0 equiv) and 2-((4-chloro-3-fluorophenoxy)methyl)oxirane (0.070 g, 0.34 mmol, 1.0 equiv) in DMF (05 mL), was added K$_2$CO$_3$ (0.095 g, 0.69 mmol, 2.0 equiv) and the resultant reaction mixture was heated at 100° C. for overnight. Progress of the reaction was monitored by LCMS. After completion of reaction, the reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure to obtain crude which was purified by reversed-phase HPLC to obtain 6-chloro-N-(4-(3-(4-chloro-3-fluorophenoxy)-2-hydroxypropyl)piperazin-1-yl)-2-naphthamide (Compound 14-0.005 g, 04% Yield) as white solid. LCMS 492.2 [M+H]$^+$; $^1$H NMR (400 MHz, DMSO-d$_6$) δ 9.99 (br. s., 1H), 9.62 (br. s., 1H), 8.42 (s, 1H), 8.21-8.05 (m, 2 H), 8.00 (d, J=8.3 Hz, 1H), 7.91 (d, J=9.2 Hz, 1H), 7.62 (d, J=10.5 Hz, 1H), 7.55-7.42 (m, 1H), 7.11 (d, J=11.0 Hz, 1H), 6.88 (d, J=7.5 Hz, 1H), 6.01 (br. s., 1H), 4.32 (br. s., 2H), 4.01 (d, J=4.4 Hz, 2H), 3.62 (br. s., 2H), 3.26 (br. s., 6H).

Example 10

Synthesis of 2-(4-chloro-3-fluorophenoxy)-N-(4-((2-(4-chloro-3-fluorophenoxy)ethyl)amino)piperidin-1-yl)acetamide

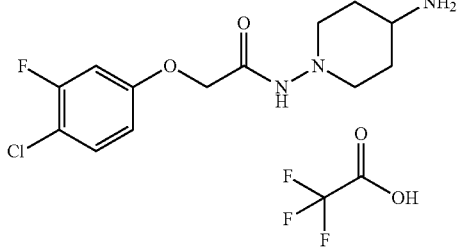
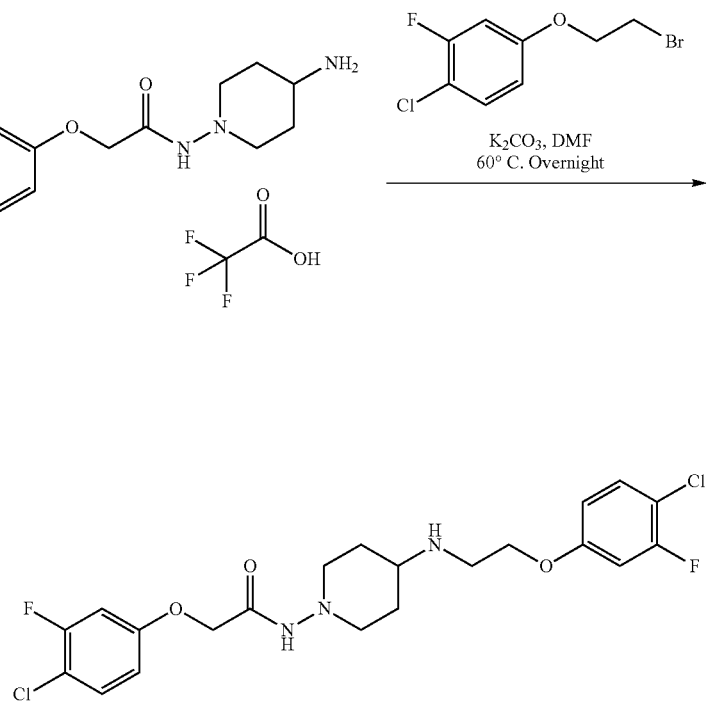

To a stirred solution of N-(4-aminopiperidin-1-yl)-2-(4-chloro-3-fluorophenoxy)acetamide 2,2,2-trifluoroacetate (0.100 g, 0.24 mmol, 1.0 equiv) and 4-(2-bromoethoxy)-1-chloro-2-fluorobenzene (0.062 g, 0.24 mmol, 1.0 equiv) in DMF (05 mL), was added K$_2$CO$_3$ (0.068 g, 0.49 mmol, 2.0 equiv) and the resultant reaction mixture was heated at 60° C. for overnight. Progress of the reaction was monitored by LCMS. The reaction mixture was diluted with water (20 mL) and extracted with ethyl acetate (50 mL×2). Combined organic layer was washed with water (20 mL×4), dried over anhydrous Na$_2$SO$_4$ and concentrated. The crude product was purified by reverse phase HPLC to obtain 2-(4-chloro-3-fluorophenoxy)-N-(4-((2-(4-chloro-3-fluorophenoxy)ethyl)amino)piperidin-1-yl)acetamide (Compound 22-0.018 g, 16% Yield) as a white solid. LCMS 474.3 [M+H]$^+$; $^1$H NMR (400 MHz, DMSO-d$_6$) δ 9.12 (br. s., 1H), 8.78 (br. s., 1 H), 7.45-7.54 (m, 2H), 7.04-7.13 (m, 2H), 6.84 (d, J=8.77 Hz, 2 H), 4.88 (s, 2H), 4.46 (s, 2H), 4.05 (br. s., 2H), 2.65 (d, J=12.28 Hz, 2H), 1.87 (br. s., 2H), 1.39 (br. s., 3H), 1.23 (br. s., 2H).

Example 11
Synthesis of 6-chloro-N-(4-((2-(4-chloro-3-fluorophenoxy)ethyl)amino)piperidin-1-yl)quinoline-2-carboxamide
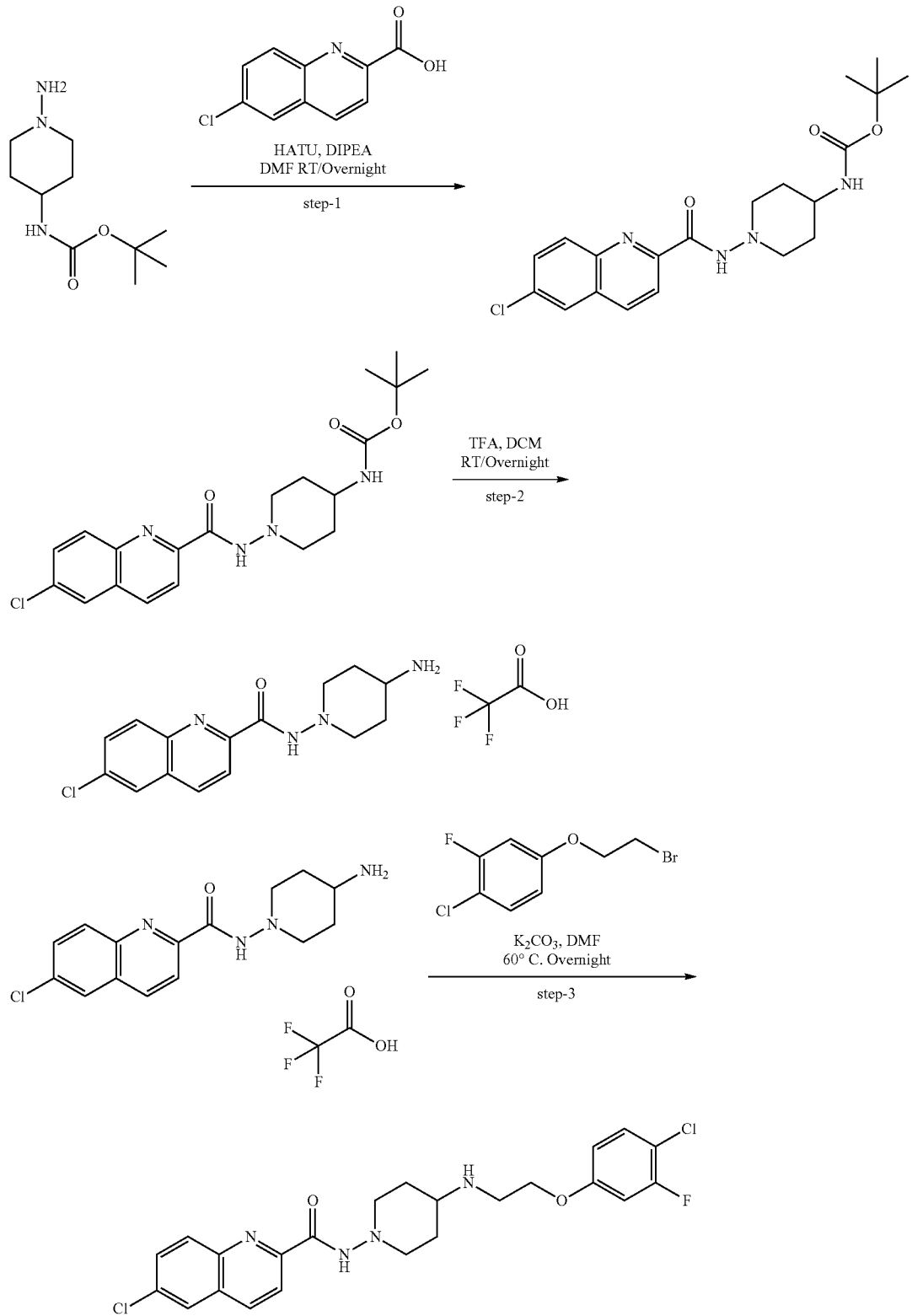

Step 1—Synthesis of tert-butyl (1-(6-chloroquinoline-2-carboxamido)piperidin-4-yl)carbamate To a stirred solution of tert-butyl (1-aminopiperidin-4-yl)carbamate (0.170 g, 0.79 mmol, 1.0 equiv) in DMF (5 mL) was added HATU (0.450 g, 1.18 mmol, 1.5 equiv) at RT and stirred for 10 minutes. Then 6-chloroquinoline-2-carboxylic acid (0.241 g, 1.18 mmol, 1.5 equiv) was added followed by the addition of DIPEA (0.6 mL, 3.16 mmol, 4.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to obtain tert-butyl (1-(6-chloroquinoline-2-carboxamido)piperidin-4-yl)carbamate (0.100 g, 32% Yield) as an off-white solid. LCMS 405.2 [M+H]$^+$; $^1$H NMR (400 MHz, DMSO-d$_6$) δ 9.72 (s, 1H), 8.53 (d, J=8.3 Hz, 1H), 8.24 (d, J=1.8 Hz, 1H), 8.14 (t, J=7.7 Hz, 1H), 7.96-7.81 (m, 1H), 6.85 (br. s., 1 H), 2.97 (br. s., 2H), 2.91-2.74 (m, 2H), 1.75 (br. s., 2H), 1.56 (d, J=10.1 Hz, 2H), 1.47-1.28 (m, 9H).

Step 2—Synthesis of N-(4-aminopiperidin-1-yl)-6-chloroquinoline-2-carboxamide 2,2,2-trifluoroacetate To a stirred solution of tert-butyl (1-(6-chloroquinoline-2-carboxamido)piperidin-4-yl)carbamate (0.100 g, 0.24 mmol, 1.0 equiv) in DCM (10 mL), was added trifluoroacetic acid (0.2 mL) and the resultant reaction mixture was stirred at RT for 1 h under nitrogen atmosphere. Reaction was monitored by TLC and LCMS. After completion of reaction, the reaction mixture was concentrated under reduced pressure to obtain sticky crude compound which was triturated with hexane (10 mL) and diethyl ether and dried under vacuum to obtain N-(4-aminopiperidin-1-yl)-6-chloroquinoline-2-carboxamide 2,2,2-trifluoroacetate (0.100 g, 97% Yield) as an yellow solid. LCMS 305.2 [M+H]$^+$; $^1$H NMR (400 MHz, DMSO-d$_6$) δ 9.85 (s, 1H), 8.54 (d, J=8.3 Hz, 1H), 8.25 (s, 1H), 8.14 (dd, J=3.9, 8.8 Hz, 2H), 8.01-7.73 (m, 3H), 3.04 (br. s., 2H), 2.89 (d, J=12.3 Hz, 2H), 1.94 (br. s., 2H), 1.69 (d, J=12.3 Hz, 2H).

Step 3—Synthesis of 6-chloro-N-(4-((2-(4-chloro-3-fluorophenoxy)ethyl)amino)piperidin-1-yl)quinoline-2-carboxamide To a stirred solution of N-(4-aminopiperidin-1-yl)-6-chloroquinoline-2-carboxamide trifluoroacetate (0.100 g, 0.23 mmol, 1.0 equiv) and 4-(2-bromoethoxy)-1-chloro-2-fluorobenzene (0.060 g, 0.23 mmol, 1.0 equiv) in DMF (05 mL), was added K$_2$CO$_3$ (0.066 g, 0.47 mmol, 2.0 equiv) and the resultant reaction mixture was heated at 60° C. for overnight. Progress of the reaction was monitored by LCMS. Product formation was confirmed by LCMS. The reaction mixture was diluted with water (50 mL). The resulting solid was filtered off, washed with water (20 mL×4) and dried under vacuum. The crude product was purified by reverse phase HPLC to obtain 6-chloro-N-(4-((2-(4-chloro-3-fluorophenoxy)ethyl)amino)piperidin-1-yl)quinoline-2-carboxamide (Compound 23-0.006 g, 04% Yield) as a white solid. LCMS 477.2 [M+H]$^+$; $^1$H NMR $^1$H NMR (400 MHz, DMSO-d$_6$) δ ppm 9.92 (br. s., 1H), 8.72 (s, 1H), 8.54 (d, J=8.33 Hz, 1H), 8.26 (s, 1H), 8.14 (dd, J=8.99, 5.04 Hz, 2H), 7.89 (d, J=7.02 Hz, 1H), 7.54 (d, J=8.77 Hz, 1H), 7.17 (d, J=9.21 Hz, 1H), 6.93 (d, J=7.89 Hz, 1H), 4.28 (br. s., 2H), 3.11 (d, J=9.65 Hz, 3H), 2.90 (d, J=12.28 Hz, 3H), 2.67 (br. s., 1H), 2.03-2.19 (m, 2H), 1.75 (s, 2H).

Example 12

Synthesis of 5-chloro-N-(4-((2-(4-chloro-3-fluorophenoxy)ethyl)amino)piperidin-1-yl)benzofuran-2-carboxamide

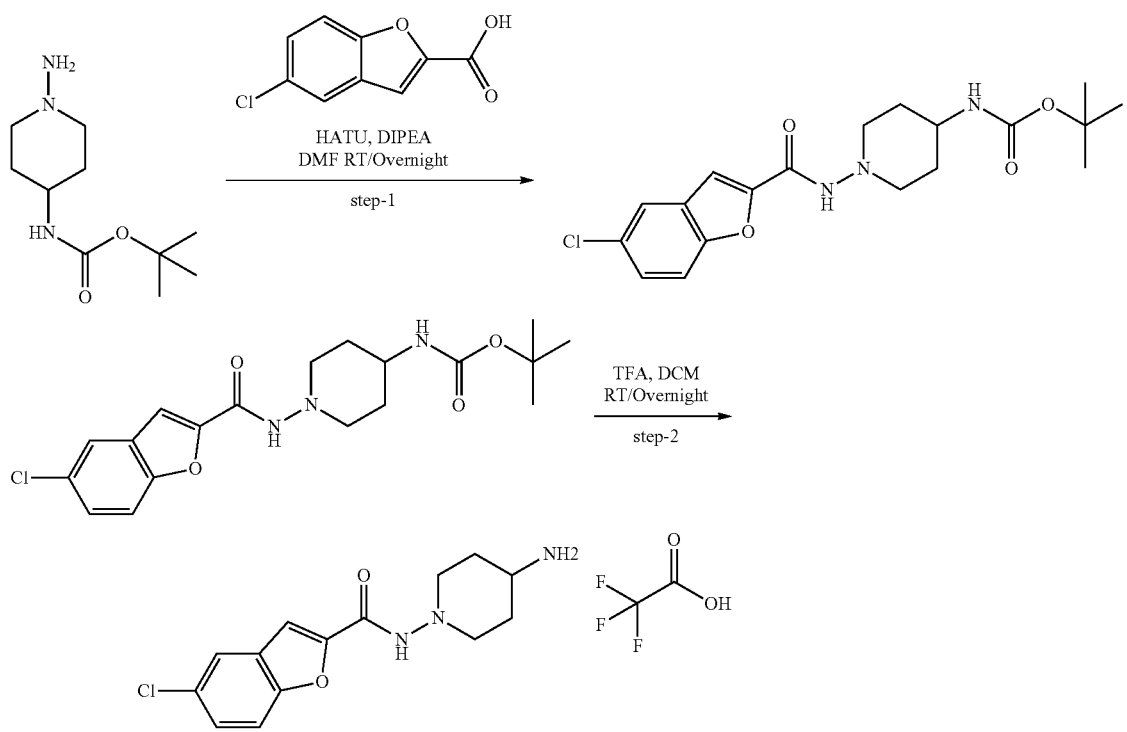

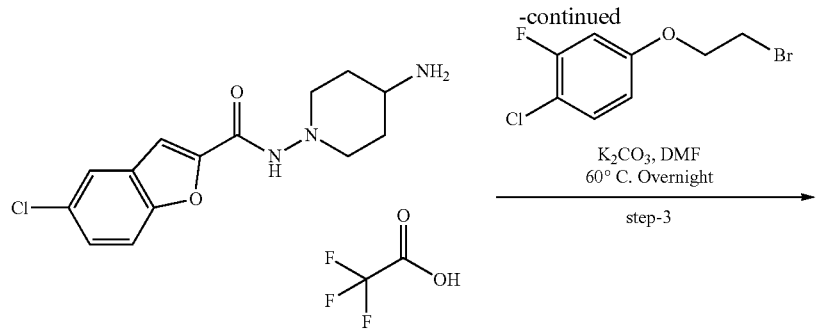

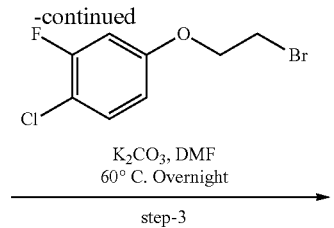

Step 1—Synthesis of tert-butyl (1-(5-chlorobenzofuran-2-carboxamido)piperidin-4-yl)carbamate To a stirred solution of tert-butyl (1-aminopiperidin-4-yl) carbamate (0.100 g, 0.46 mmol, 1.0 equiv) in DMF (05 mL) was added HATU (0.265 g, 0.69 mmol, 1.5 equiv) at RT and stirred for 10 minutes. Then 5-chlorobenzofuran-2-carboxylic acid (0.137 g, 0.69 mmol, 1.5 equiv) was added followed by the addition of DIPEA (0.35 mL, 1.86 mmol, 4.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to obtain tert-butyl (1-(5-chlorobenzofuran-2-carboxamido)piperidin-4-yl)carbamate (0.150 g, 82% Yield) as an yellow solid. LCMS 394.2 [M+H]$^+$; $^1$H NMR (400 MHz, DMSO-$d_6$) δ 9.75 (s, 1H), 7.86 (s, 1 H), 7.69 (d, J=8.8 Hz, 1H), 7.58-7.33 (m, 2H), 6.85 (d, J=7.5 Hz, 1H), 3.25 (br. s., 1H), 2.96 (d, J=11.0 Hz, 2H), 2.82-2.63 (m, 2H), 1.74 (d, J=11.8 Hz, 2H), 1.66-1.45 (m, 2H), 1.45-1.28 (m, 9H).

Step 2—Synthesis of N-(4-aminopiperidin-1-yl)-5-chlorobenzofuran-2-carboxamide 2,2,2-trifluoroacetate To a stirred solution of tert-butyl (1-(5-chlorobenzofuran-2-carboxamido)piperidin-4-yl)carbamate (0.150 g, 0.38 mmol, 1.0 equiv) in DCM (15 mL), was added trifluoroacetic acid (0.3 mL) and the resultant reaction mixture was stirred at RT for 1 h under nitrogen atmosphere. Reaction was monitored by TLC and LCMS. After completion of reaction, the reaction mixture was concentrated under reduced pressure to obtain crude product which was crystallized in diethyl ether and dried under vacuum to obtain N-(4-aminopiperidin-1-yl)-5-chlorobenzofuran-2-carboxamide 2,2,2-trifluoroacetate (0.160 g, Quant. Yield) as an yellow solid. LCMS 294.1 [M+H]$^+$; $^1$H NMR (400 MHz, DMSO-$d_6$) δ 9.89 (s, 1H), 7.98 (br. s., 2H), 7.90-7.80 (m, 1H), 7.69 (d, J=8.8 Hz, 1H), 7.60-7.42 (m, 2H), 3.03 (d, J=10.5 Hz, 3H), 2.78 (t, J=11.0 Hz, 2 H), 1.94 (d, J=11.4 Hz, 2H), 1.66 (d, J=9.6 Hz, 2H).

Step 3—Synthesis of 5-chloro-N-(4-((2-(4-chloro-3-fluorophenoxy)ethyl)amino)piperidin-1-yl)benzofuran-2-carboxamide To a stirred solution of N-(4-aminopiperidin-1-yl)-5-chlorobenzofuran-2-carboxamide trifluoroacetate (0.160 g, 0.39 mmol, 1.0 equiv) and 4-(2-bromoethoxy)-1-chloro-2-fluorobenzene (0.100 g, 0.39 mmol, 1.0 equiv) in DMF (05 mL), was added K$_2$CO3(0.108 g, 0.78 mmol, 2.0 equiv) and the resultant reaction mixture was heated at 60° C. for overnight. Progress of the reaction was monitored by LCMS. Product formation was confirmed by LCMS. The reaction mixture was diluted with water (50 mL). The resulting solid was filtered off, washed with water (20 mL×4) and dried under vacuum. The crude product was purified by reversed phase HPLC to obtain 5-chloro-N-(4-((2-(4-chloro-3-fluorophenoxy)ethyl)amino)piperidin-1-yl)benzofuran-2-carboxamide (Compound 24-0.020 g, 10% Yield) as an off white solid. LCMS 466.2 [M+H]$^+$; $^1$H NMR (400 MHz, DMSO-$d_6$) δ 9.73 (s, 1H), 7.86 (s, 1H), 7.69 (d, J=8.77 Hz, 1H), 7.38-7.58 (m, 4H), 7.08 (dd, J=11.40, 2.63 Hz, 1H), 6.84 (d, J=7.02 Hz, 1H), 4.03 (t, J=5.48 Hz, 2H), 2.99 (d, J=10.09 Hz, 2H), 2.89 (t, J=5.26 Hz, 2H), 2.73 (t, J=9.87 Hz, 2H), 1.86 (d, J=16.66 Hz, 3H), 1.34-1.45 (m, 2H).

Example 13
Synthesis of 2-(4-chloro-3-fluorophenoxy)-N-(4-((3-(4-chloro-3-fluorophenoxy)-2-hydroxypropyl)amino)piperidin-1-yl)acetamide
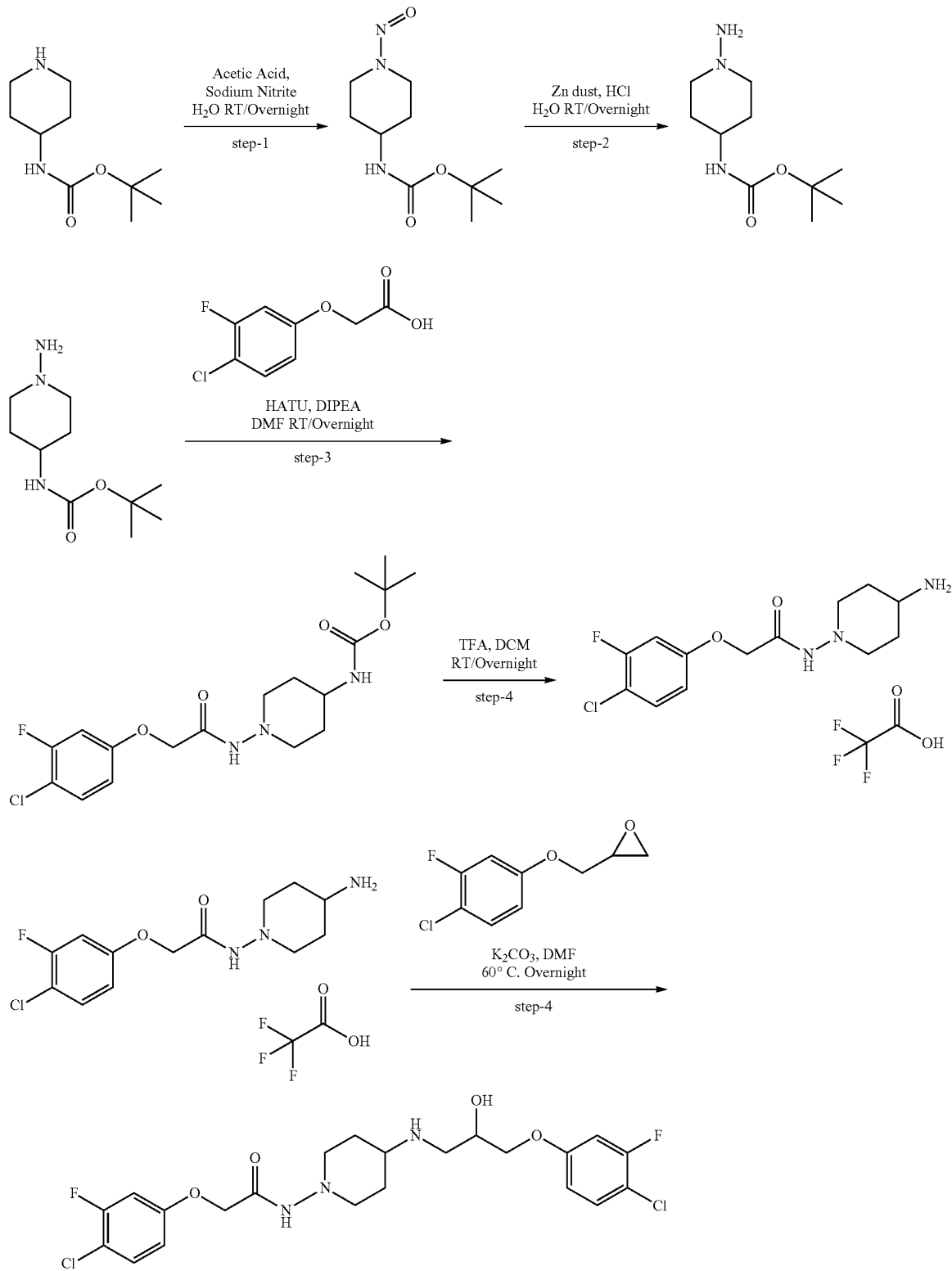

Step 1—Synthesis of tert-butyl (1-nitrosopiperidin-4-yl)carbamate

To a stirred solution of tert-butyl piperidin-4-ylcarbamate (5.0 gm, 25 mmol, 1.0 equiv) in water (120 mL) was added acetic acid (40 mL) and sodium nitrite (6.9 gm, 100 mmol, 4.0 equiv) at RT. The reaction mixture was allowed to stir at RT overnight. Product formation was confirmed by LCMS. The reaction mixture was diluted with water (50 mL). The resulting solid was filtered off, washed with water (20 mL×4) and dried under vacuum to obtain to tert-butyl (1-nitrosopiperidin-4-yl)carbamate (5.6 gm, 97% Yield) a white solid. LCMS 230.2 [M+H]$^+$; $^1$H NMR (400 MHz, DMSO-d$_6$) δ 6.96 (d, J=6.1 Hz, 1H), 4.52 (d, J=13.2 Hz, 2H), 3.95-3.80 (m, 1H), 3.67 (br. s., 1H), 3.03-2.85 (m, 1H), 1.97 (d, J=11.0 Hz, 1H), 1.76 (d, J=10.5 Hz, 1H), 1.60-1.44 (m, 1H), 1.39 (s, 8H), 1.25-1.10 (m, 1H).

Step 2—Synthesis of tert-butyl (1-aminopiperidin-4-yl)carbamate

To a stirred solution of tert-butyl (1-nitrosopiperidin-4-yl)carbamate (0.500 g, 2.18 mmol, 1 equiv) in THF:H2O (20:20 mL) was added NH$_4$Cl (1.88 g, 39.9 mmol, 16.0 equiv) and then Zn dust (1.21 g, 17.4 mmol, 8.0 equiv) was added portion wise. After addition, the reaction mixture was stirred at RT for overnight. Progress of the reaction was monitored by LCMS. The reaction mixture was diluted with water (100 mL), filtered over celite bed and filtrate was extracted with DCM (100 mL×2). Combined organic layer was dried over anhydrous Na$_2$SO$_4$ and concentrated under reduced pressure, to obtain tert-butyl (1-aminopiperidin-4-yl)carbamate (0.400 g, 85% Yield) as an off white solid. LCMS 216.2 [M+H]$^+$; $^1$H NMR (400 MHz, DMSO-d$_6$) δ 6.70 (d, J=6.1 Hz, 1H), 3.37 (br. s., 2H), 3.14 (br. s., 1H), 2.84 (d, J=10.1 Hz, 2H), 2.04 (t, J=10.7 Hz, 2H), 1.64 (d, J=11.4 Hz, 2H), 1.51-1.26 (m, 10H).

Step 3—Synthesis of tert-butyl (1-(2-(4-chloro-3-fluorophenoxy)acetamido)piperidin-4-yl)carbamate To a stirred solution of tert-butyl (1-aminopiperidin-4-yl) carbamate (0.200 g, 0.93 mmol, 1.0 equiv) in DMF (10 mL) was added HATU (0.530 g, 1.39 mmol, 1.5 equiv) at RT and stirred for 10 minutes. Then 2-(4-chloro-3-fluorophenoxy) acetic acid (0.188 g, 0.93 mmol, 1.0 equiv) was added followed by the addition of DIPEA (0.7 mL, 3.72 mmol, 4.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to obtain tert-butyl (1-(2-(4-chloro-3-fluorophenoxy)acetamido)piperidin-4-yl) carbamate (0.250 g, 67% Yield) as an off-white solid. LCMS 402.2 [M+H]$^+$; $^1$H NMR (400 MHz, DMSO-d$_6$) δ 9.71 (s, 1H), 8.53 (d, J=8.8 Hz, 1H), 8.24 (s, 1H), 8.14 (t, J=7.7 Hz, 2H), 7.93-7.86 (m, 1H), 6.85 (d, J=7.5 Hz, 1H), 2.99 (d, J=10.1 Hz, 2H), 2.87-2.74 (m, 2H), 1.75 (br. s., 2H), 1.56 (d, J=9.6 Hz, 2H), 1.39 (s, 9H).

Step 4—Synthesis of N-(4-aminopiperidin-1-yl)-2-(4-chloro-3-fluorophenoxy)acetamide 2,2,2-trifluoroacetate To a stirred solution of tert-butyl (1-(2-(4-chloro-3-fluorophenoxy)acetamido)piperidin-4-yl)carbamate (0.250 g, 0.623 mmol, 1.0 equiv) in DCM (10 mL), was added trifluoroacetic acid (0.1 mL) and the resultant reaction mixture was stirred at RT for 1 h under nitrogen atmosphere. Reaction was monitored by TLC and LCMS. After completion of reaction, the reaction mixture was concentrated under reduced pressure to obtain crude product which was crystallized in diethyl ether and dried under vacuum to obtain N-(4-aminopiperidin-1-yl)-2-(4-chloro-3-fluorophenoxy) acetamide 2,2,2-trifluoroacetate (0.130 g, 50% Yield) as an off white solid. LCMS 302.2 [M+H]$^+$; $^1$H NMR (400 MHz, DMSO-d$_6$) δ 9.26 (s, 1H), 8.00 (br. s., 2H), 7.55-7.39 (m, 1H), 7.14-6.92 (m, 1H), 6.88-6.72 (m, 1H), 4.90 (s, 1 H), 4.48 (s, 1H), 3.07 (br. s., 1H), 2.99 (br. s., 1H), 2.91 (d, J=10.5 Hz, 1H), 2.75-2.53 (m, 2 H), 1.89 (br. s., 2H), 1.76-1.51 (m, 2H).

Step 5—Synthesis of 2-(4-chloro-3-fluorophenoxy)-N-(4-((3-(4-chloro-3-fluorophenoxy)-2-hydroxypropyl)amino)piperidin-1-yl)acetamide To a stirred solution of N-(4-aminopiperidin-1-yl)-2-(4-chloro-3-fluorophenoxy)acetamide trifluoroacetate (0.100 g, 0.24 mmol, 1.0 equiv) and 2-((4-chloro-3-fluorophenoxy) methyl)oxirane (0.048 g, 0.24 mmol, 1.0 equiv) in DMF (05 mL), was added K$_2$CO$_3$(0.066 g, 0.48 mmol, 2.0 equiv) and the resultant reaction mixture was heated at 60° C. for overnight. Progress of the reaction was monitored by LCMS. Product formation was confirmed by LCMS. The reaction mixture was diluted with water (50 mL). The resulting solid was filtered off, washed with water (20 mL×4) and dried under vacuum. The crude product was purified by reverse phase HPLC to obtain 2-(4-chloro-3-fluorophenoxy)-N-(4-((3-(4-chloro-3-fluorophenoxy)-2-hydroxypropyl)amino)piperidin-1-yl)acetamide (Compound 8-0.034 g, 28% Yield) as a white solid. LCMS 504.2 [M+H]$^+$; $^1$H NMR (400 MHz, DMSO-d$_6$) δ 9.08 (br. s., 1 H), 8.76 (br. s., 1H), 7.39-7.50 (m, 2H), 7.00-7.11 (m, 2H), 6.83 (d, J=7.02 Hz, 2H), 5.00 (d, J=4.82 Hz, 2H), 4.87 (s, 2H), 4.46 (s, 2H), 3.99 (d, J=9.21 Hz, 1H), 3.71 (d, J=9.21 Hz, 1 H), 3.00 (br. s., 1H), 2.88 (d, J=9.65 Hz, 1H), 1.80 (br. s., 2H), 1.61 (br. s., 2H), 1.32 (d, J=9.21 Hz, 2H).

Example 14

Synthesis of 5-chloro-N-(4-((3-(4-chloro-3-fluorophenoxy)-2-hydroxypropyl)amino) piperidin-1-yl) benzofuran-2-carboxamide

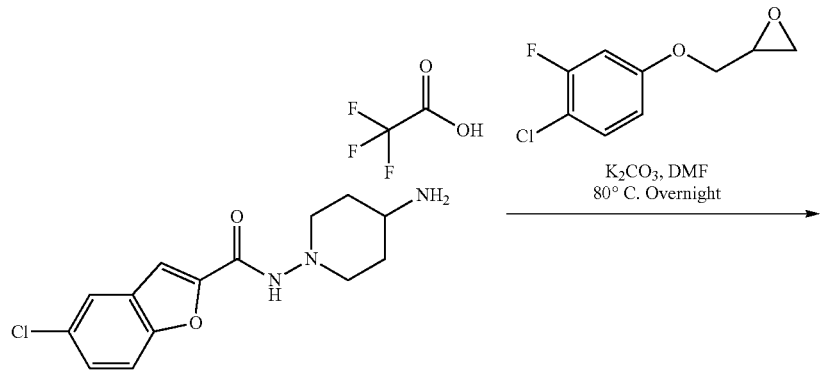

Step 1—Synthesis of 5-chloro-N-(4-((3-(4-chloro-3-fluorophenoxy)-2-hydroxypropyl) amino)piperidin-1-yl)benzofuran-2-carboxamide To a stirred solution of N-(4-aminopiperidin-1-yl)-5-chlorobenzofuran-2-carboxamide 2,2,2-trifluoroacetate (0.200 g, 0.49 mmol, 1.0 equiv) and 2-((4-chloro-3-fluorophenoxy) methyl)oxirane (0.99 g, 0.49 mmol, 1.0 equiv) in DMF (05 mL), was added K2C03 (0.135 g, 0.98 mmol, 2.0 equiv) and the resultant reaction mixture was heated at 80° C. for overnight. Progress of the reaction was monitored by LCMS. Product formation was confirmed by LCMS. The reaction mixture was diluted with water (20 mL) and extracted with ethyl acetate (50 mL×2). Combined organic layer was washed with water (20 mL×4), dried over anhydrous Na2SO4 and concentrated. The crude product was

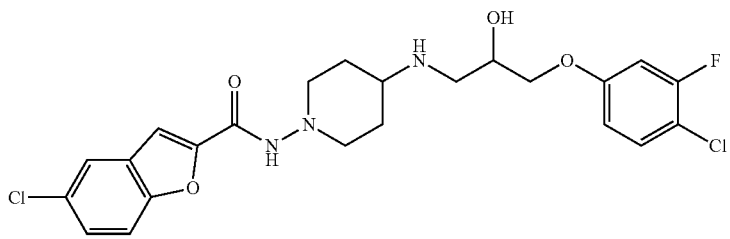

purified by reverse phase HPLC to obtain 5-chloro-N-(4-((3-(4-chloro-3-fluorophenoxy)-2-hydroxypropyl)amino) piperidin-1-yl)benzofuran-2-carboxamide (Compound 21-0.006 g, 04% Yield) a white solid. LCMS 496.2 [M+H]$^+$; $^1$H NMR (400 MHz, DMSO-$d_6$) δ 9.77 (s, 1H), 8.20 (br. s., 1H), 7.86 (d, J=1.75 Hz, 1H), 7.69 (d, J=8.77 Hz, 1H), 7.39-7.57 (m, 3H), 7.08 (dd, J=11.62, 2.85 Hz, 1 H), 6.84 (d, J=8.33 Hz, 1H), 4.01 (d, J=5.26 Hz, 1H), 3.93 (d, J=6.14 Hz, 2H), 3.01 (d, J=10.52 Hz, 2H), 2.62-2.87 (m, 4H), 1.89 (br. s., 2H), 1.46 (br. s., 2H).

Example 15

Synthesis of 6-chloro-N-(4-((3-(4-chloro-3-fluorophenoxy)-2-hydroxypropyl)amino)piperidin-1-yl) quinoline-2-carboxamide

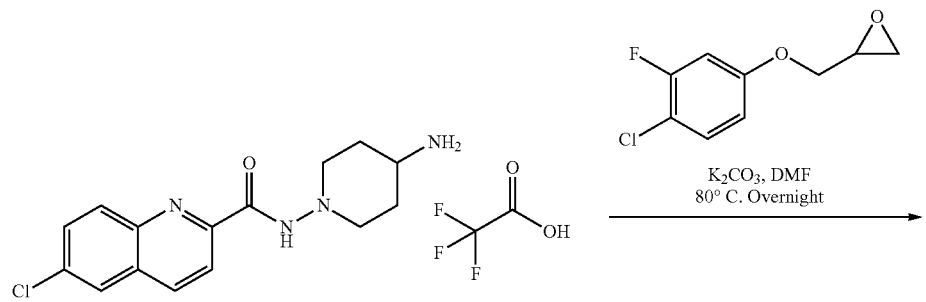

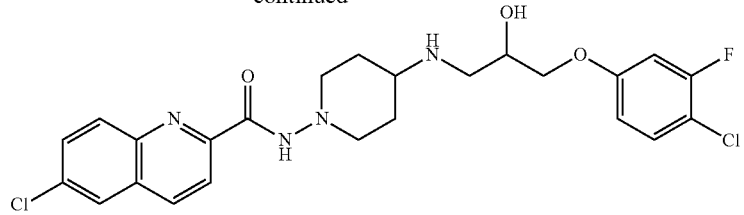

To a stirred solution of N-(4-aminopiperidin-1-yl)-6-chloroquinoline-2-carboxamide 2,2,2-trifluoroacetate (0.230 g, 0.55 mmol, 1.0 equiv) and 2-((4-chloro-3-fluorophenoxy)methyl)oxirane (0.111 g, 0.55 mmol, 1.0 equiv) in DMF (05 mL), was added $K_2CO_3$ (0.150 g, 1.1 mmol, 2.0 equiv) and the resultant reaction mixture was heated at 80° C. for overnight. Progress of the reaction was monitored by LCMS. Product formation was confirmed by LCMS. The reaction mixture was diluted with water (20 mL) and extracted with ethyl acetate (50 mL×2). Combined organic layer was washed with water (20 mL×4), dried over anhydrous Na2SO4 and concentrated. The crude product was purified by reverse phase HPLC to obtain 6-chloro-N-(4-((3-(4-chloro-3-fluorophenoxy)-2-hydroxypropyl)amino)piperidin-1-yl)quinoline-2-carboxamide (Compound 20-0.044 g, 14% Yield) a white solid. LCMS 507.3 [M+H]$^+$; $^1$H NMR (400 MHz, DMSO-d$_6$) δ 9.75 (s, 1H), 8.53 (d, J=8.33 Hz, 1H), 8.24 (s, 1H), 8.08-8.21 (m, 3H), 7.88 (dd, J=8.77, 2.19 Hz, 1H), 7.48 (t, J=8.99 Hz, 1H), 7.09 (dd, J=11.62, 2.85 Hz, 1 H), 6.86 (d, J=7.02 Hz, 1H), 3.99-4.05 (m, 1H), 3.95 (d, J=6.14 Hz, 2H), 3.05 (d, J=10.09 Hz, 2H) 2.72-2.91 (m, 4H) 1.94 (br. s., 2H) 1.53 (br. s., 2H).

Example 16

Synthesis of 2-(4-chloro-3-fluorophenoxy)-N-(4-(3-(4-chloro-3-fluorophenoxy)propyl)piperazin-1-yl)acetamide

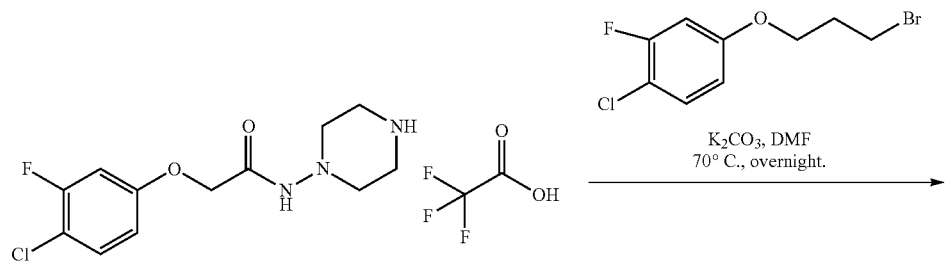

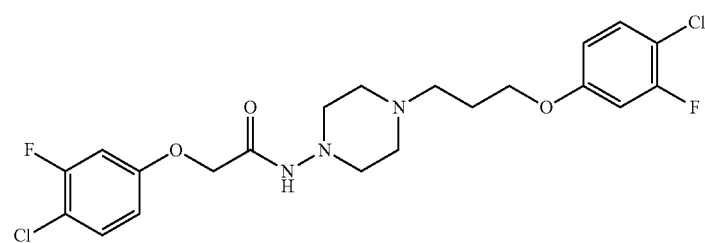

To a stirred solution of 2-(4-chloro-3-fluorophenoxy)-N-(piperazin-1-yl)acetamide 2,2,2-trifluoroacetate (0.320 g, 0.98 mmol, 1.0 equiv) in DMF (5 mL) was added K2CO3 (0.220 g, 1.96 mmol, 2.0 equiv) and 4-(3-bromopropoxy)-1-chloro-2-fluorobenzene (0.213 g, 0.98 mmol, 1.0 equiv). The resultant reaction mixture was heated at 70° C. for overnight. Product formation was confirmed by LCMS. The reaction mixture was diluted with water (50 mL). The resulting solid was filtered off, washed with water (20 mL×4) and dried under vacuum. The crude product was purified by reversed phase HPLC to obtain 2-(4-chloro-3-fluorophenoxy)-N-(4-(3-(4-chloro-3-fluorophenoxy)propyl) piperazin-1-yl)acetamide as a formate salt (Compound 16-0.03 g, 8% Yield) as a white solid. LCMS 474.2 [M+H]$^+$; $^1$H NMR (400 MHz, DMSO-d$_6$) δ 8.81 (br. s., 1H), 7.48-7.38 (m, 2H), 7.10-6.97 (m, 2H), 6.84-6.75 (m, 2H), 4.88 (s, 2H), 4.47 (s, 2H), 4.01 (t, J=5.9 Hz, 4H), 2.77 (br. s., 3H), 2.67 (br. s., 1H), 1.91-1.73 (m, 4H).

Example 17

Synthesis of 5-chloro-N-(4-(3-(4-chloro-3-fluorophenoxy) propyl)piperazin-1-yl) benzofuran-2-carboxamide

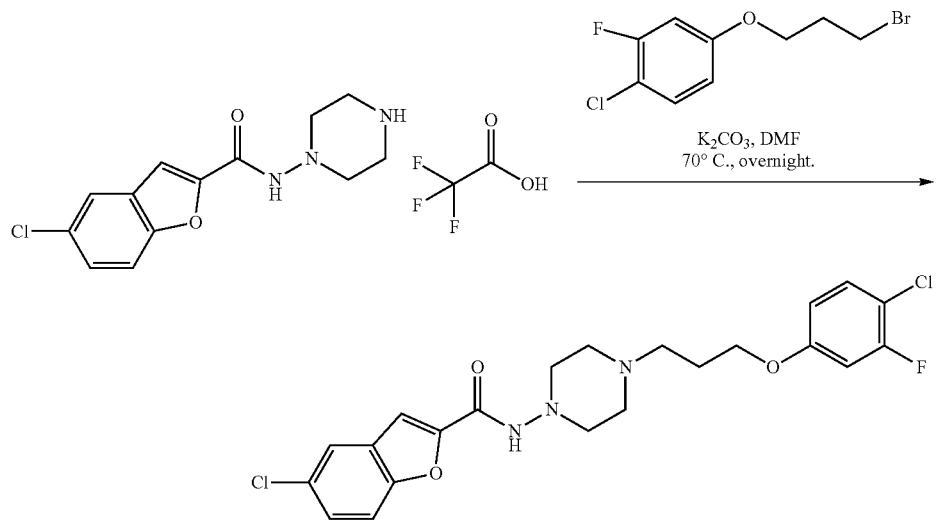

To a stirred solution of 5-chloro-N-(piperazin-1-yl)benzofuran-2-carboxamide 2,2,2-trifluoroacetate (0.200 g, 0.50 mmol, 1.0 equiv) and 4-(3-bromopropoxy)-1-chloro-2-fluorobenzene (0.135 g, 0.50 mmol, 1.0 equiv) in DMF (07 mL), was added K$_2$CO$_3$ (0.140 g, 1.01 mmol, 2.0 equiv) and the resultant reaction mixture was heated at 70° C. for overnight. Product formation was confirmed by LCMS. The reaction mixture was diluted with water (50 mL). The resulting solid was filtered off, washed with water (20 mL×4) and dried under vacuum. The crude product was purified by reversed phase HPLC to obtain 5-chloro-N-(4-(3-(4-chloro-3-fluorophenoxy) propyl)piperazin-1-yl) benzofuran-2-carboxamide (Compound 18-0.054 g, 20% Yield) as a white solid. LCMS 466.2 [M+H]$^+$; $^1$H NMR (400 MHz, DMSO-d$_6$) δ 9.81 (s, 1H), 7.86 (br. s., 1H), 7.70 (d, J=8.77 Hz, 1H), 7.36-7.58 (m, 3H), 7.07 (d, J=12.28 Hz, 1H), 6.83 (d, J=7.89 Hz, 1H), 3.96-4.11 (m, 2H), 2.89 (br. s., 4H), 2.43 (br. s., 3H), 2.33 (br. s., 6H), 1.86 (br. s., 2H).

Example 18

Synthesis of 6-chloro-N-(4-(3-(4-chloro-3-fluorophenoxy)propyl)piperazin-1-yl)quinoline-2-carboxamide

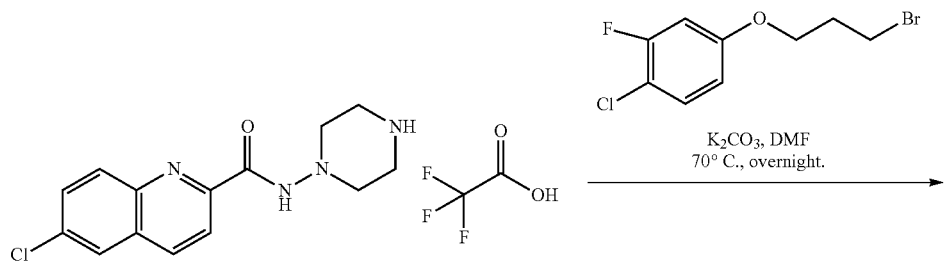

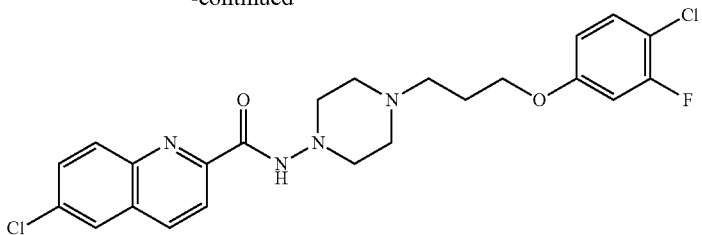

To a stirred solution of 6-chloro-N-(piperazin-1-yl)quinoline-2-carboxamide 2,2,2-trifluoroacetate (0.220 g, 0.54 mmol, 1.0 equiv) and 4-(3-bromopropoxy)-1-chloro-2-fluorobenzene (0.145 g, 0.54 mmol, 1.0 equiv) in DMF (07 mL), was added K$_2$CO$_3$ (0.150 g, 1.08 mmol, 2.0 equiv) and the resultant reaction mixture was heated at 70° C. for overnight. Product formation was confirmed by LCMS. The reaction mixture was diluted with water (50 mL). The resulting solid was filtered off, washed with water (20 mL×4) and dried under vacuum. The crude product was purified by reversed phase HPLC to obtain 6-chloro-N-(4-(3-(4-chloro-3-fluorophenoxy)propyl)piperazin-1-yl)quinoline-2-carboxamide (Compound 17-0.070 g, 28% Yield) a white solid. LCMS 477.2 [M+H]$^+$; $^1$H NMR (400 MHz, DMSO-d$_6$) δ 10.31 (s, 1H), 9.34 (br. s., 1H), 8.55 (d, J=8.3 Hz, 1H), 8.27 (d, J=2.2 Hz, 1H), 8.16 (t, J=8.3 Hz, 1 H), 7.90 (dd, J=2.2, 9.2 Hz, 1H), 7.58-7.50 (m, 1H), 7.10 (dd, J=2.6, 11.4 Hz, 1H), 6.88-6.81 (m, 1H), 4.10 (t, J=5.7 Hz, 2H), 3.62 (d, J=6.6 Hz, 2H), 3.27-3.17 (m, 8H), 2.14 (br. s., 2H).

Example 19

Synthesis of 6-chloro-N-(4-(3-(4-chloro-3-fluorophenoxy)-2-hydroxypropyl)piperazin-1-yl)quinoline-2-carboxamide

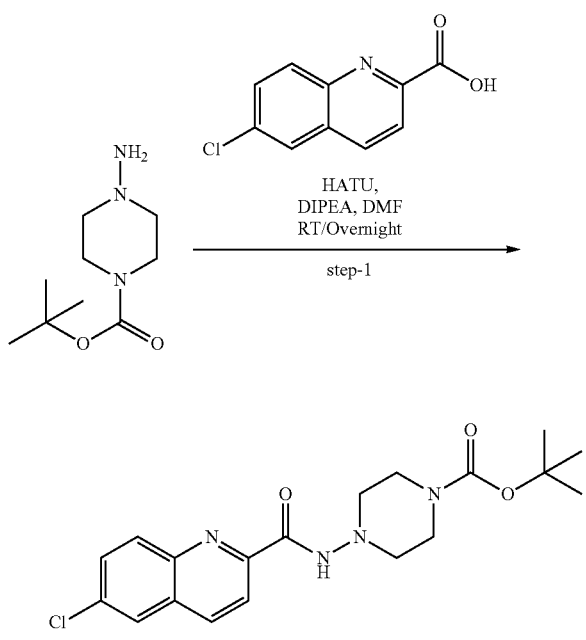

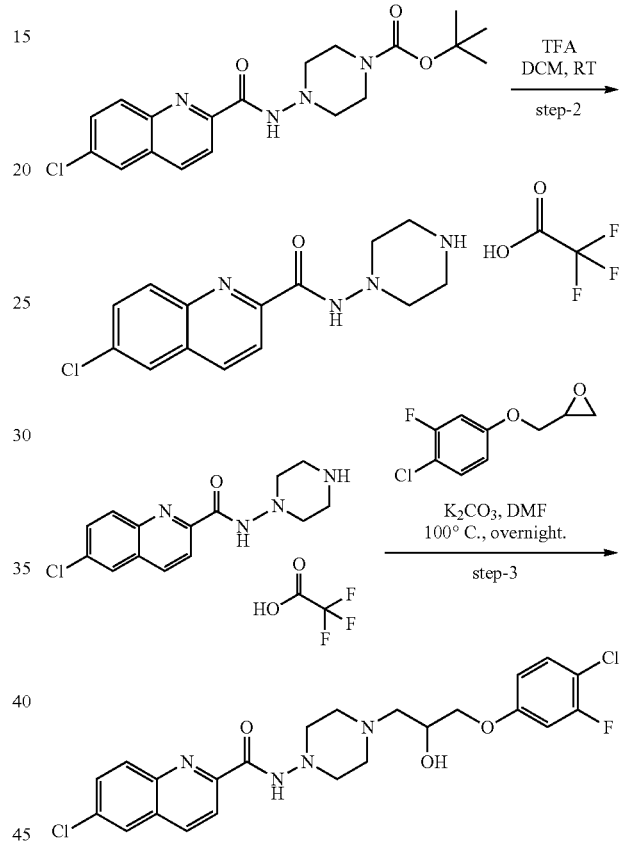

Step 1—Synthesis of tert-butyl 4-(6-chloroquinoline-2-carboxamido)piperazine-1-carboxylate To a stirred solution of tert-butyl 4-aminopiperazine-1-carboxylate (0.200 g, 0.99 mmol, 1.0 equiv) in DMF (05 mL) was added HATU (0.753 g, 1.98 mmol, 2.0 equiv) at RT and stirred for 10 minutes. Then 6-chloroquinoline-2-carboxylic acid (0.206 g, 0.99 mmol, 1.0 equiv) was added followed by the addition of DIPEA (0.6 mL, 2.97 mmol, 3.0 equiv). The resulting reaction mixture was allowed to stir at RT for overnight. Product formation was confirmed by LCMS. The reaction mixture was diluted with water (50 mL) and extracted with EtOAc (50 mL×2). The combined organic layer was washed with water (30 mL×3), brine solution (30 mL×2), dried over anhydrous sodium sulfate and concentrated under reduced pressure, to obtain tert-butyl 4-(6-chloroquinoline-2-carboxamido)piperazine-1-carboxylate (0.140 g, 36% Yield) as a brown solid. LCMS 390 [M+H]$^+$; $^1$H NMR (400 MHz, DMSO-d$_6$) δ 9.95 (br. s., 1H), 8.53 (d, J=8.3 Hz, 1H), 8.24 (br. s., 1H), 8.15 (d, J=5.3 Hz, 2H), 7.88 (d, J=7.5 Hz, 1H), 3.45 (br. s., 4H), 2.90 (d, J=11.0 Hz, 4H), 1.42 (s, 9H).

Step 2—Synthesis of 6-chloro-N-(piperazin-1-yl)quinoline-2-carboxamide 2,2,2-trifluoroacetate To a stirred solution of tert-butyl 4-(6-chloroquinoline-2-carboxamido)piperazine-1-carboxylate (0.140 g, 0.35 mmol, 1.0 equiv) in DCM (10 mL), was added trifluoroacetic acid (02 mL) and the resultant reaction mixture was stirred at RT for 1 h under nitrogen atmosphere. Reaction was monitored by TLC and LCMS. After completion of reaction, the reaction mixture was concentrated under reduced pressure to obtain crude product which was crystallized in diethyl ether and dried under vacuum to obtain 6-chloro-N-(piperazin-1-yl)quinoline-2-carboxamide 2,2,2-trifluoroacetate (0.100 g, 68% Yield) as a brown solid. LCMS 291.2 [M+H]$^+$; $^1$H NMR (400 MHz, DMSO-d$_6$) δ 10.28 (br. s., 2H), 8.64 (br. s., 2H), 8.55 (d, J=8.3 Hz, 1H), 8.26 (br. s., 1H), 8.15 (t, J=8.1 Hz, 2H), 7.90 (d, J=9.2 Hz, 1H), 3.25 (br. s., 4H), 3.17 (br. s., 4H)

Step 3—Synthesis of 6-chloro-N-(4-(3-(4-chloro-3-fluorophenoxy)-2-hydroxypropyl)piperazin-1-yl) quinoline-2-carboxamide To a stirred solution of 6-chloro-N-(piperazin-1-yl)quinoline-2-carboxamide trifluoroacetate (0.100 g, 0.25 mmol, 1.0 equiv) 2-((4-chloro-3-fluorophenoxy)methyl)oxirane (0.063 g, 0.31 mmol, 1.2 equiv) in DMF (05 mL), was added K$_2$CO$_3$ (0.070 g, 0.50 mmol, 2.0 equiv) and the resultant reaction mixture was heated at 100° C. for overnight. Progress of the reaction was monitored by LCMS. After completion of reaction, the reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure to obtain crude which was purified by reversed-phase HPLC to obtain 6-chloro-N-(4-(3-(4-chloro-3-fluorophenoxy)-2-hydroxypropyl)piperazin-1-yl)quinoline-2-carboxamide (Compound 15-0.015 g, 12% Yield) as an off white solid. LCMS 493.3 [M+H]$^+$; $^1$H NMR $^1$H NMR (400 MHz, DMSO-d$_6$) δ 9.79 (s, 1H), 8.53 (d, J=8.8 Hz, 2 H), 8.24 (s, 1H), 8.14 (t, J=8.8 Hz, 2H), 7.88 (d, J=8.8 Hz, 1H), 7.47 (t, J=8.8 Hz, 1H), 7.08 (d, J=14.0 Hz, 1H), 6.86 (d, J=6.6 Hz, 1H), 4.95 (br. s., 1H), 4.03 (d, J=7.0 Hz, 2H), 3.92 (d, J=9.6 Hz, 2H), 2.94 (br. s., 4H), 2.67 (br. s., 2H), 2.33 (br. s., 2H).

Example 20

Synthesis of 2-(4-chloro-3-fluorophenoxy)-N-(4-(2-(4-chloro-3-fluorophenoxy)acetyl)piperazin-1-yl) acetamide

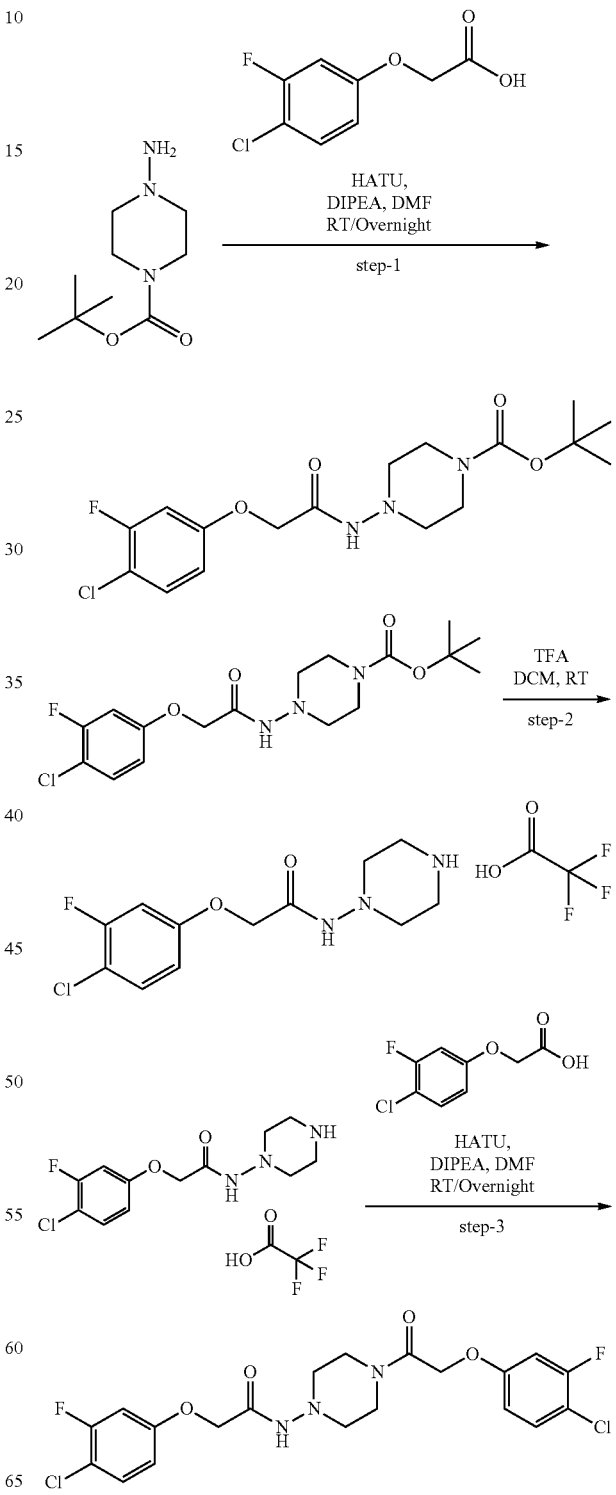

Step 1—Synthesis of tert-butyl 4-(2-(4-chloro-3-fluorophenoxy)acetamido)piperazine-1-carboxylate To a stirred solution of tert-butyl 4-aminopiperazine-1-carboxylate (0.200 g, 0.99 mmol, 1.0 equiv) in DMF (05 mL) was added HATU (0.753 g, 1.98 mmol, 2.0 equiv) at RT and stirred for 10 minutes. Then 2-(4-chloro-3-fluorophenoxy)acetic acid (0.201 g, 0.99 mmol, 1.0 equiv) was added followed by the addition of DIPEA (0.6 mL, 2.97 mmol, 3.0 equiv). The resulting reaction mixture was allowed to stir at RT for overnight. Product formation was confirmed by LCMS. The reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure, to obtain tert-butyl 4-(2-(4-chloro-3-fluorophenoxy)acetamido)piperazine-1-carboxylate (0.150 g, 38% Yield) as a semi solid. LCMS 388.2 [M+H]$^+$; $^1$H NMR (400 MHz, DMSO-d$_6$) δ 7.57-7.36 (m, 1H), 7.11-6.94 (m, 1H), 6.92-6.69 (m, 1H), 5.76 (s, 1H), 5.04-4.79 (m, 1H), 4.48 (s, 1H), 3.85 (br. s., 1H), 2.92 (br. s., 2H), 2.70 (d, J=11.8 Hz, 2H), 1.40 (s, 9H).

Step 2—2-(4-chloro-3-fluorophenoxy)-N-(piperazin-1-yl)acetamide 2,2,2-trifluoroacetate To a stirred solution of tert-butyl 4-(2-(4-chloro-3-fluorophenoxy)acetamido)piperazine-1-carboxylate (0.150 g, 0.38 mmol, 1.0 equiv) in DCM (10 mL), was added trifluoroacetic acid (02 mL) and the resultant reaction mixture was stirred at RT for 1 h under nitrogen atmosphere. Reaction was monitored by TLC and LCMS. After completion of reaction, the reaction mixture was concentrated under reduced pressure to obtain crude product which was crystallized in diethyl ether and dried under vacuum to obtain 2-(4-chloro-3-fluorophenoxy)-N-(piperazin-1-yl)acetamide 2,2,2-trifluoroacetate (0.140 g, 90% Yield) as an off-white solid. LCMS 288.1 [M+H]$^+$; $^1$H NMR (400 MHz, DMSO-d$_6$) δ 9.58 (br. s., 1H), 9.12 (br. s., 1H), 8.62 (br. s., 1H), 7.60-7.35 (m, 1H), 7.17-6.95 (m, 1H), 6.82 (dd, J=8.8, 16.2 Hz, 1H), 4.94 (s, 1H), 4.51 (s, 2H), 3.63 (br. s., 2H), 3.31 (br. s., 2H), 3.00 (br. s., 2H).

Step 3 Synthesis of 2-(4-chloro-3-fluorophenoxy)-N-(4-(2-(4-chloro-3-fluorophenoxy)acetyl)piperazin-1-yl)acetamide To a stirred solution of 2-(4-chloro-3-fluorophenoxy)-N-(piperazin-1-yl)acetamide trifluoroacetate (0.140 g, 0.36 mmol, 1.0 equiv) in DMF (05 mL) was added HATU (0.274 g, 0.72 mmol, 2.0 equiv) at RT and stirred for 10 minutes. Then 2-(4-chloro-3-fluorophenoxy)acetic acid (0.075 g, 0.36 mmol, 1.0 equiv) was added followed by the addition of DIPEA (0.18 mL, 1.08 mmol, 3.0 equiv). The resulting reaction mixture was allowed to stir at RT for overnight. Product formation was confirmed by LCMS. the reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure to obtain crude which was purified by reversed-phase HPLC to obtain 2-(4-chloro-3-fluorophenoxy)-N-(4-(2-(4-chloro-3-fluorophenoxy)acetyl)piperazin-1-yl)acetamide (Compound 30-0.050 g, 30% Yield) as white solid. LCMS 474.2 [M+H]$^+$; $^1$H NMR (400 MHz, DMSO-d$_6$) δ 7.55-7.36 (m, 2H), 7.14-6.97 (m, 2H), 6.91-6.75 (m, 2H), 4.94 (d, J=17.5 Hz, 3H), 4.50 (s, 1H), 4.25 (br. s., 1H), 3.50 (br. s., 2H), 3.17 (br. s., 1H), 3.06 (br. s., 1H), 2.81 (br. s., 1H), 2.75 (br. s., 1H), 2.33 (br. s., 2 H).

Example 21

Synthesis of 6-chloro-N-(4-(3-(4-chloro-3-fluorophenoxy)propyl)piperazin-1-yl)-3,4-dihydro-2H-benzo[b][1,4]oxazine-2-carboxamide

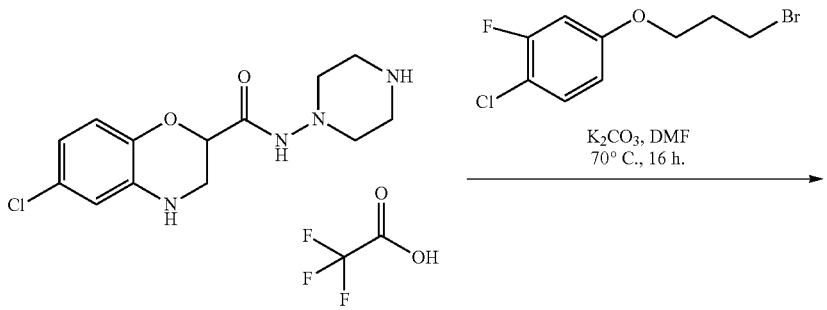

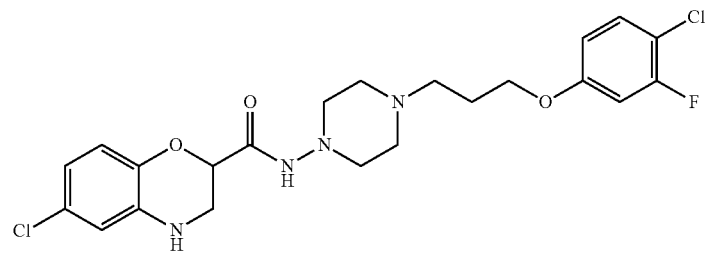

To a stirred solution of 6-chloro-N-(piperazin-1-yl)-3,4-dihydro-2H-benzo[b][1,4]oxazine-2-carboxamide 2,2,2-trifluoroacetate (0.300 g, 0.73 mmol, 1.0 equiv) and 4-(3-bromopropoxy)-1-chloro-2-fluorobenzene (0.195 g, 0.73 mmol, 1.0 equiv) in DMF (06 mL), was added K₂CO₃ (0.202 g, 1.46 mmol, 2.0 equiv) and the resultant reaction mixture was heated at 70° C. for overnight. Product formation was confirmed by LCMS. The reaction mixture was diluted with water (20 mL) and extracted with ethyl acetate (50 mL×2). Combined organic layer was washed with water (20 mL×4), dried over anhydrous Na2SO4 and concentrated. The crude product was purified by reverse phase HPLC to obtain 6-chloro-N-(4-(3-(4-chloro-3-fluorophenoxy)propyl)piperazin-1-yl)-3,4-dihydro-2H-benzo[b][1,4]oxazine-2-carboxamide (Compound 44-0.012 g, 09% Yield) as a white solid. LCMS 482.1 [M+H]⁺; ¹H NMR (400 MHz, DMSO-d₆) δ 9.03 (s, 1H), 8.79 (s, 1H), 7.45 (t, J=8.77 Hz, 1H), 7.04 (d, J=2.63 Hz, 1 H), 7.07 (d, J=2.63 Hz, 1H), 6.74-6.85 (m, 2H), 6.66 (s, 1H), 6.46-6.53 (m, 1H), 6.18 (br. s., 1H), 4.40 (dd, J=7.24, 2.85 Hz, 1H), 4.01 (t, J=6.36 Hz, 2H), 3.41 (d, J=11.84 Hz, 1H), 3.18-3.23 (m, 1H), 2.72-2.83 (m, 4H), 2.33-2.43 (m, 4H), 1.76-1.88 (m, 3H).

Example 22

Synthesis of 7-chloro-N-(1-(2-(3-chloro-4-fluorophenoxy)acetamido)piperidin-4-yl)-6-fluoro-3,4-dihydro-2H-benzo[b][1,4]oxazine-3-carboxamide

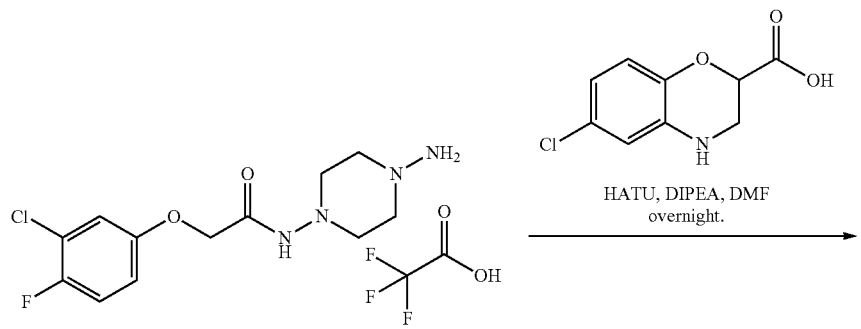

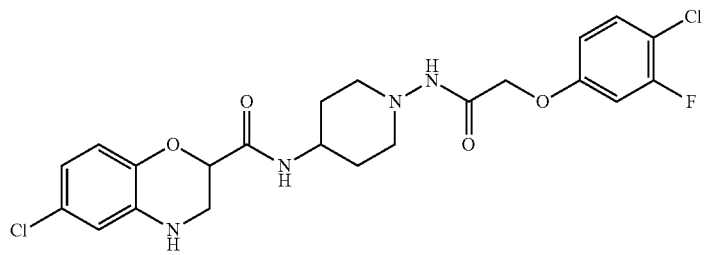

To a stirred solution of N-(4-aminopiperidne-1-yl)-2-(3-chloro-4-fluorophenoxy)acetamide trifluoroacetate (0.340 g, 0.819 mmol, 1.0 equiv) and 6-chloro-3,4-dihyro-2H-benzo-1,4-oxazine-2-carboxylic acid (0.172 g, 0.819 mmol, 1.0 equiv), HATU (0.172 g, 0.819 mmol, 1.0 equiv) in DMF (07 mL), was added DIPEA (0.422 g, 3.27 mmol, 4.0 equiv) and the resultant reaction mixture was stir overnight at RT. Product formation was confirmed by LCMS. The reaction mixture was diluted with water (50 mL). The resulting solid was filtered off, washed with methanol and dried under vacuum to obtain of 7-chloro-N-(1-(2-(3-chloro-4-fluorophenoxy)acetamido)piperidin-4-yl)-6-fluoro-3,4-dihydro-2H-benzo[b][1,4]oxazine-3-carboxamide (Compound 32-0.026 g, 7.3% Yield) as a white solid. LCMS 497.2 [M+H]⁺; ¹H NMR (400 MHz, DMSO-d₆) δ 9.13 (br. s., 1H), 7.92 (d, J=7.45 Hz, 1H), 7.42-7.49 (m, 1H), 6.99 (d, J=11.40 Hz, 1H), 6.77 (br. s., 1H), 6.59 (br. s., 1H), 6.49 (br. s., 1H), 6.19 (br. s., 1 H), 4.89 (s, 2H), 3.57 (br. s., 1H), 3.44 (d, J=9.21 Hz, 1H), 3.15-3.23 (m, 2H), 3.05 (br. s., 1 H), 2.88 (br. s., 2H), 2.65 (d, J=13.59 Hz, 2H), 1.65 (br. s., 3H).

Example 23

Synthesis of N,N'-(piperidine-1,4-diyl)bis(2-(4-chlorophenoxy)acetamide)

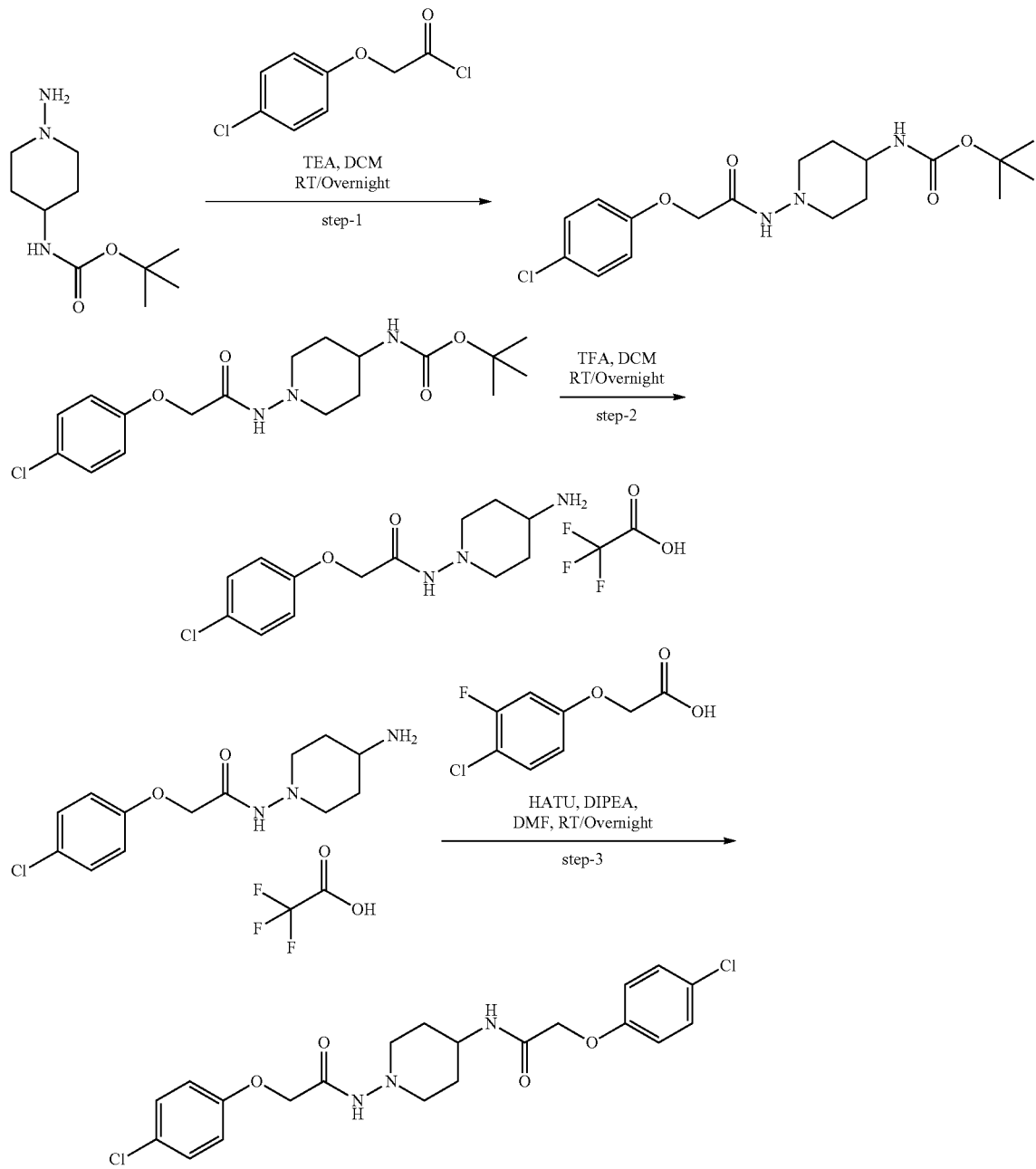

Step 1—Synthesis of tert-butyl (1-(2-(4-chlorophenoxy)acetamido)piperidin-4-yl)carbamate To a stirred solution of tert-butyl (1-aminopiperidin-4-yl)carbamate (0.100 g, 0.46 mmol, 1.0 equiv) in DCM (05 mL) was added 2-(4-chlorophenoxy)acetyl chloride (0.095 g, 0.46 mmol, 1.0 equiv) and followed by the addition of TEA (0.2 mL, 1.39 mmol, 3.0 equiv). The resulting reaction mixture was allowed to stir at RT for overnight. Product formation was confirmed by LCMS. The reaction mixture was diluted with water (20 mL) and extracted with ethyl acetate (50 mL×2). Combined organic layer was washed with water (20 mL×4), dried over anhydrous Na2SO4 and concentrated under reduced pressure to obtain tert-butyl (1-(2-(4-chlorophenoxy)acetamido)piperidin-4-yl)carbamate (0.170 g, 95% Yield) as a white solid. LCMS 384.1 [M+H]$^+$; $^1$H NMR (400 MHz, DMSO-d$_6$) δ 9.07 (s, 1H), 8.72 (br. s., 1H), 7.39-7.23 (m, 2H), 7.00-6.87 (m, 2H), 6.87-6.72 (m, 1H), 4.85-4.74 (m, 1H), 4.41 (s, 1H), 3.33 (br. s., 4H), 2.84 (d, J=10.5 Hz, 2H), 1.71 (br. s., 2H), 1.47 (d, J=10.1 Hz, 1H), 1.44-1.28 (m, 9H).

Step 2—Synthesis of N-(4-aminopiperidin-1-yl)-2-(4-chlorophenoxy)acetamide 2,2,2-trifluoroacetate To a stirred solution of tert-butyl (1-(2-(4-chlorophenoxy)acetamido)piperidin-4-yl)carbamate (0.170 g, 0.44 mmol, 1.0 equiv) in DCM (05 mL), was added trifluoroacetic acid (0.3 mL) and the resultant reaction mixture was stirred at RT for 1 h under nitrogen atmosphere. Reaction was monitored by TLC and LCMS. After completion of reaction, the reaction mixture was concentrated under reduced pressure to obtain crude product which was crystallized in diethyl ether and dried under vacuum to obtain N-(4-aminopiperidin-1-yl)-2-(4-chlorophenoxy)acetamide 2,2,2-trifluoroacetate (0.290 g, Quant. Yield) as a brown semi solid. LCMS 284.1 [M+H]$^+$;

Step 3—Synthesis of N,N'-(piperidine-1,4-diyl)bis(2-(4-chlorophenoxy)acetamide)

To a stirred solution of N-(4-aminopiperidin-1-yl)-2-(4-chlorophenoxy)acetamide. trifluoroacetate (0.290 g, 0.73 mmol, 1.0 equiv) in DMF (05 mL) was added HATU (0.416 g, 1.09 mmol, 1.5 equiv) at RT and stirred for 10 minutes. Then 2-(4-chloro-3-fluorophenoxy) acetic acid (0.136 g, 0.73 mmol, 1.0 equiv) was added followed by the addition of DIPEA (0.5 mL, 2.92 mmol, 4.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum. The crude product was purified by reverse phase HPLC to obtain N,N'-(piperidine-1,4-diyl)bis(2-(4-chlorophenoxy)acetamide) (Compound 45-0.100 g, 30% Yield) as an off white solid. LCMS 452.2 [M+H]$^+$; $^1$H NMR (400 MHz, DMSO-d$_6$) δ 9.12 (s, 1H), 8.03 (d, J=7.89 Hz, 1H), 7.28-7.39 (m, 4H), 6.92-7.03 (m, 4H), 4.84 (s, 1H), 4.40-4.50 (m, 3H), 3.61 (br. s., 1H), 3.04 (br. s., 1H), 2.88 (d, J=7.02 Hz, 1H), 2.65 (d, J=12.28 Hz, 2H), 1.73 (br. s., 2H), 1.59 (d, J=9.21 Hz, 2H).

Example 24

Chiral resolution of 6-chloro-N-(4-(2-(4-chloro-3-fluorophenoxy)acetamido)piperidin-1-yl)-3,4-dihydro-2H-benzo[b][1,4]oxazine-2-carboxamide

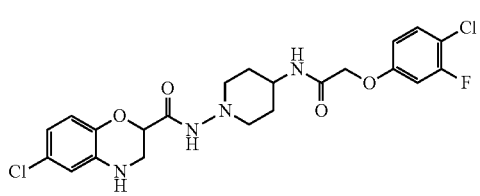
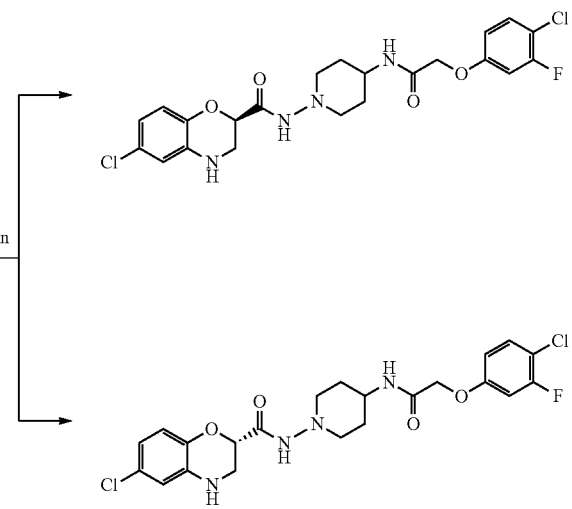

The enantiomers, (R)-6-chloro-N-(4-(2-(4-chloro-3-fluorophenoxy)acetamido)piperidin-1-yl)-3,4-dihydro-2H-benzo[b][1,4]oxazine-2-carboxamide (Compound 46-[α]$_D^{20}$= −14.92° (c=0.05, MeOH); elution time: 6.89 min) and (S)-6-chloro-N-(4-(2-(4-chloro-3-fluorophenoxy)acetamido)piperidin-1-yl)-3,4-dihydro-2H-benzo[b][1,4]oxazine-2-carboxamide (Compound 47-[α]$_D^{20}$=1.28° (c=0.05, MeOH); elution time: 12.75 min), were separated by chiral SFC (Chiralcel© OD-H, 250×20 mm, 5µ). Isocratic program with analytical grade liquid carbon dioxide and HPLC grade MeOH. LCMS: 497.3 [M+H]$^+$; $^1$H NMR (400 MHz, DMSO-d$_6$) δ 9.02 (s, 1H), 8.04 (d, J=7.5 Hz, 1H), 7.50 (t, J=8.8 Hz, 2H), 7.06 (d, J=11.0 Hz, 1H), 6.85 (d, J=8.8 Hz, 1H), 6.76 (d, J=8.3 Hz, 1H), 6.65-6.55 (m, 1H), 6.49 (d, J=6.1 Hz, 1H), 4.51 (s, 2H), 3.60 (br. s., 2H), 3.52-3.42 (m, 2H), 3.42-3.36 (m, 1H), 3.21 (d, J=5.7 Hz, 2H), 2.97-2.78 (m, 3H), 2.65 (d, J=14.0 Hz, 3H), 1.71 (d, J=5.7 Hz, 2H), 1.57 (d, J=12.7 Hz, 2H).

Example 25

Chiral resolution of 5-chloro-N-(4-(3-(4-chloro-3-fluorophenoxy)-2-hydroxypropyl)piperazin-1-yl)benzofuran-2-carboxamide

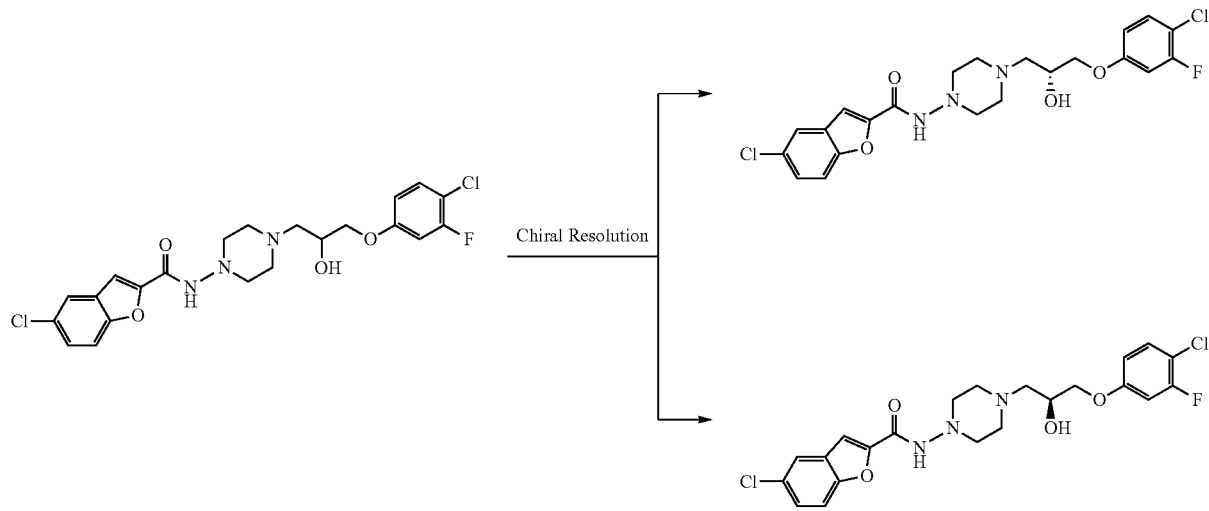 [SMILES: O=C(NN1CCN(C[C@@H](O)COc2ccc(Cl)c(F)c2)CC1)c1cc2cc(Cl)ccc2o1 ; O=C(NN1CCN(CC(O)COc2ccc(Cl)c(F)c2)CC1)c1cc2cc(Cl)ccc2o1 ; O=C(NN1CCN(C[C@H](O)COc2ccc(Cl)c(F)c2)CC1)c1cc2cc(Cl)ccc2o1]

The enantiomers, (R)-5-chloro-N-(4-(3-(4-chloro-3-fluorophenoxy)-2-hydroxypropyl)piperazin-1-yl)benzofuran-2-carboxamide (Compound 48-$[\alpha]_D^{20}$=−39.80° (c=0.05, MeOH); elution time: 29.6 min) and (S)-5-chloro-N-(4-(3-(4-chloro-3-fluorophenoxy)-2-hydroxypropyl)piperazin-1-yl)benzofuran-2-carboxamide (Compound 49-$[\alpha]_D^{20}$=3.24° (c=0.05, MeOH); elution time: 34.8 min), were separated by chiral SFC (Chiralpak® IA, 250×20 mm, 5μ). Isocratic program with analytical grade liquid carbon dioxide and HPLC grade MeOH (0.2% DEA). LCMS: 482.3 [M+H]$^+$; $^1$H NMR (400 MHz, DMSO-d$_6$) δ 9.79 (br. s., 1H), 7.86 (s, 1H), 7.70 (d, J=8.8 Hz, 1H), 7.52-7.41 (m, 2H), 7.16-7.06 (m, 1H), 6.86 (d, J=10.5 Hz, 1H), 4.94 (br. s., 1H), 4.01 (d, J=6.6 Hz, 1H), 3.92 (br. s., 2H), 2.89 (br. s., 4H), 2.67 (br. s., 4H).

Example 26

Chiral resolution of 2-(4-chloro-3-fluorophenoxy)-N-(4-(3-(4-chloro-3-fluorophenoxy)-2-hydroxypropyl)piperazin-1-yl)acetamide

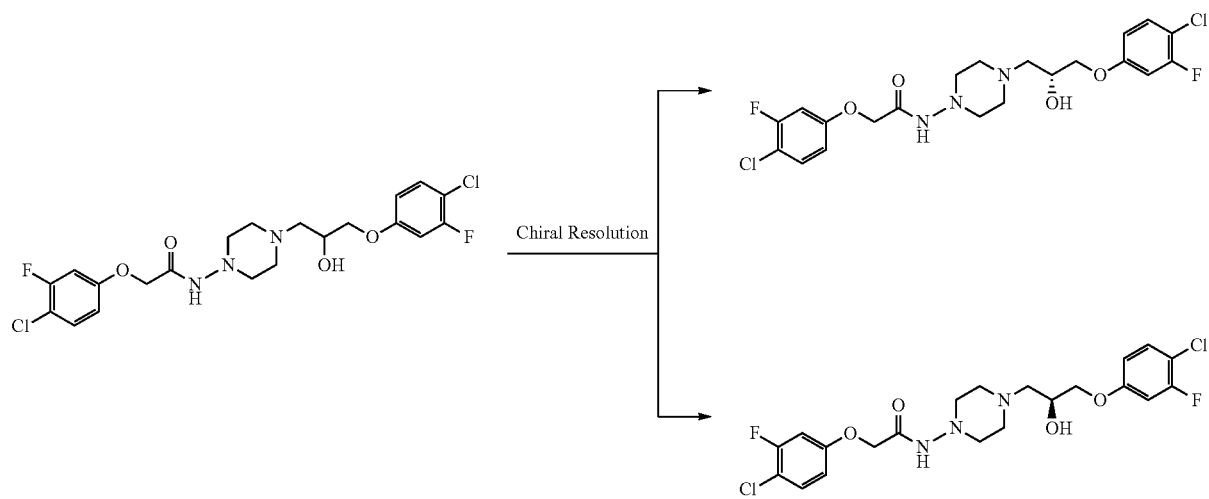 [SMILES: O=C(COc1ccc(Cl)c(F)c1)NN1CCN(C[C@@H](O)COc2ccc(Cl)c(F)c2)CC1 ; O=C(COc1ccc(Cl)c(F)c1)NN1CCN(CC(O)COc2ccc(Cl)c(F)c2)CC1 ; O=C(COc1ccc(Cl)c(F)c1)NN1CCN(C[C@H](O)COc2ccc(Cl)c(F)c2)CC1]

The enantiomers, (R)-2-(4-chloro-3-fluorophenoxy)-N-(4-(3-(4-chloro-3-fluorophenoxy)-2-hydroxypropyl)piperazin-1-yl)acetamide (Compound 50-$[\alpha]_D^{20}$=−1.00° (c=0.05, MeOH); elution time: 15.99 min) and (S)-2-(4-chloro-3-fluorophenoxy)-N-(4-(3-(4-chloro-3-fluorophenoxy)-2-hydroxypropyl)piperazin-1-yl)acetamide (Compound 51-$[\alpha]_D^{20}$=1.920 (c=0.05, MeOH); elution time: 25.3 min), were separated by chiral SFC (Chiralpak® ADH, 250×20 mm, 5μ). Isocratic program with analytical grade liquid carbon dioxide and HPLC grade EtOH (0.2% DEA in Hexane). LCMS: 490.3 [M+H]+; 1H NMR (400 MHz, DMSO-$d_6$) δ 9.08 (br. s., 1 H), 8.76 (br. s., 1H), 7.39-7.50 (m, 2H), 7.00-7.11 (m, 2H), 6.83 (d, J=7.02 Hz, 2H), 5.00 (d, J=4.82 Hz, 2H), 4.87 (s, 2H), 4.46 (s, 2H), 3.99 (d, J=9.21 Hz, 1H), 3.71 (d, J=9.21 Hz, 1 H), 3.00 (br. s., 1H), 2.88 (d, J=9.65 Hz, 1H), 1.80 (br. s., 2H), 1.61 (br. s., 2H), 1.32 (d, J=9.21 Hz, 2H).

Example 27

Chiral Resolution of 2-(4-chloro-3-fluorophenoxy)-N-(4-((3-(4-chloro-3-fluorophenoxy)-2-hydroxypropyl)amino)piperidin-1-yl)acetamide

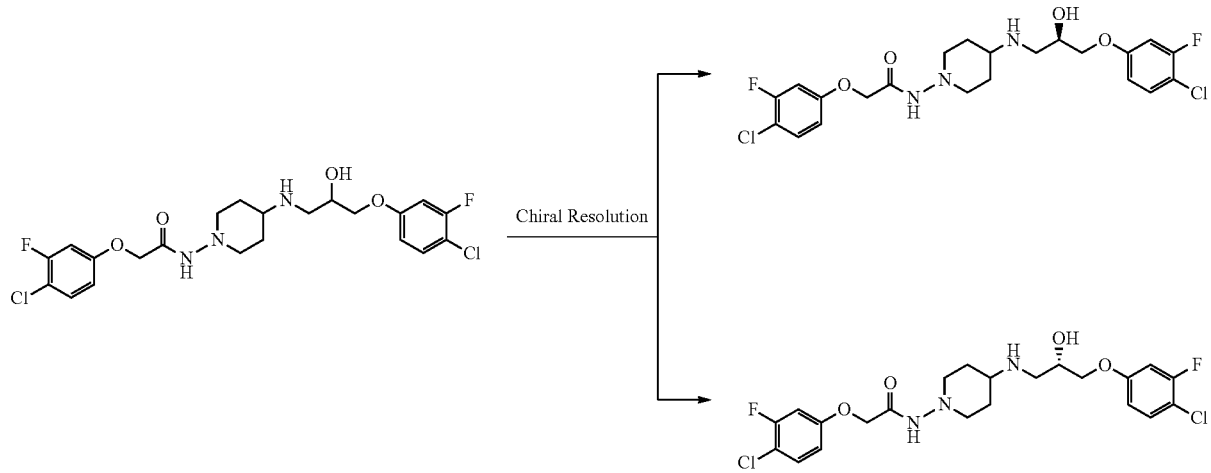 [SMILES: O=C(COc1ccc(Cl)c(F)c1)NN1CCC(NC[C@@H](O)COc2ccc(Cl)c(F)c2)CC1 ; O=C(COc1ccc(Cl)c(F)c1)NN1CCC(NCC(O)COc2ccc(Cl)c(F)c2)CC1 ; O=C(COc1ccc(Cl)c(F)c1)NN1CCC(NC[C@H](O)COc2ccc(Cl)c(F)c2)CC1]

The enantiomers, (R)-2-(4-chloro-3-fluorophenoxy)-N-(4-((3-(4-chloro-3-fluorophenoxy)-2-hydroxypropyl)amino)piperidin-1-yl)acetamide (Compound 52-$[\alpha]_D^{20}$=−27.04° (c=0.05, MeOH); elution time: 20.4 min) and (S)-2-(4-chloro-3-fluorophenoxy)-N-(4-((3-(4-chloro-3-fluorophenoxy)-2-hydroxypropyl)amino)piperidin-1-yl)acetamide (Compound 53-$[\alpha]_D^{20}$=1.520 (c=0.05, MeOH); elution time: 25.4 min), were separated by chiral SFC (Chiralpak® IC, 250×20 mm, 5μ). Isocratic program with analytical grade liquid carbon dioxide and HPLC grade EtOH (0.2% DEA in Hexane). LCMS: 504.3 [M+H]+; 1H NMR (400 MHz, DMSO-$d_6$) δ 9.08 (br. s., 1H), 8.76 (br. s., 1H), 7.39-7.50 (m, 2H), 7.00-7.11 (m, 2H), 6.83 (d, J=7.02 Hz, 2H), 5.00 (d, J=4.82 Hz, 2H), 4.87 (s, 2H), 4.46 (s, 2H), 3.99 (d, J=9.21 Hz, 1H), 3.71 (d, J=9.21 Hz, 1H), 3.00 (br. s., 1H), 2.88 (d, J=9.65 Hz, 1 H), 1.80 (br. s., 2 H), 1.61 (br. s., 2H), 1.32 (d, J=9.21 Hz, 2H).

Example 28

Synthesis of (R)-5-chloro-N-(4-(3-(4-chloro-3-fluorophenoxy)-2-hydroxypropyl)amino)piperazin-1-yl)benzofuran-2-carboxamide

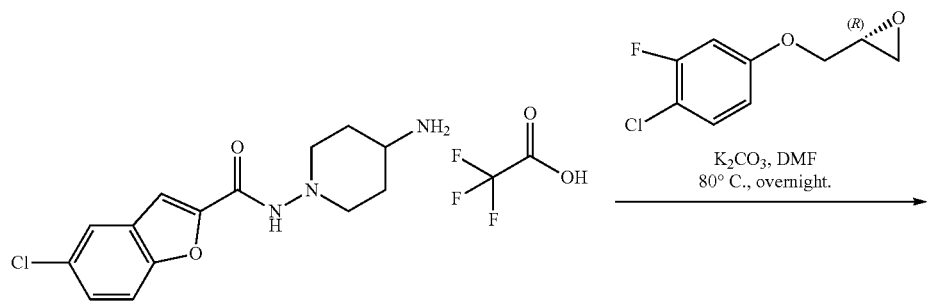

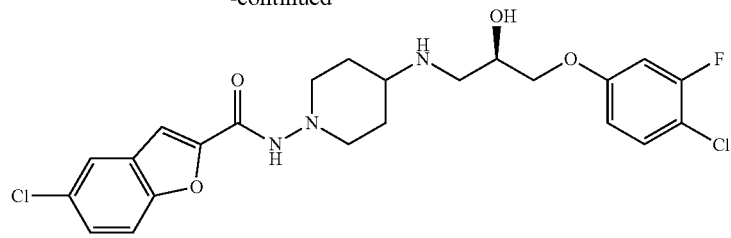

To a stirred solution of N-(4-aminopiperidin-1-yl)-5-chlorobenzofuran-2-carboxamide 2,2,2-trifluoroacetate (0.200 g, 0.491 mmol, 1.0 equiv) in DMF (5 mL) was added $K_2CO_3$ (0.135 g, 0.98 mmol, 2.0 equiv) and (R)-2-(4-chloro-3-fluorophenoxy) methyl)oxirane (0.09 g, 0.491 mmol, 1.0 equiv). The resultant reaction mixture was heated at 80° C. for overnight. Product formation was confirmed by LCMS. The reaction mixture was diluted with water (10 mL) and extracted by ethyl acetate (50 mL×2). The organic layer washed with $NaHCO_3$, brine, dried over $NaSO_4$ filter conc. under reduced pressure to obtain (R)-5-chloro-N-(4-(3-(4-chloro-3-fluorophenoxy)-2-hyroxypropyl)amino)piperazin-1-yl)benzofuran-2-carboxamide (Compound 54-0.040 g, 16% Yield) as a white solid. LCMS 496.4 $[M+H]^+$; $^1H$ NMR (400 MHz, DMSO-$d_6$) δ 9.72 (s, 1H), 7.86 (s, 1H), 7.68 (s, 1H), 7.55-7.38 (m, 3H), 7.06 (d, J=2.9 Hz, 1H), 7.09 (d, J=2.4 Hz, 1H), 6.84 (d, J=7.8 Hz, 1H), 5.02 (br. s., 1H), 4.01 (dd, J=3.7, 10.0 Hz, 1H), 3.96-3.81 (m, 3H), 2.99 (d, J=9.8 Hz, 2H), 2.77-2.62 (m, 3 H), 1.82 (br. s., 2H), 1.38 (d, J=10.3 Hz, 2H).

Example 29

Synthesis of (S)-5-chloro-N-(4-((3-(4-chloro-3-fluorophenoxy)-2-hydroxypropyl)amino)piperidin-1-yl)benzofuran-2-carboxamide

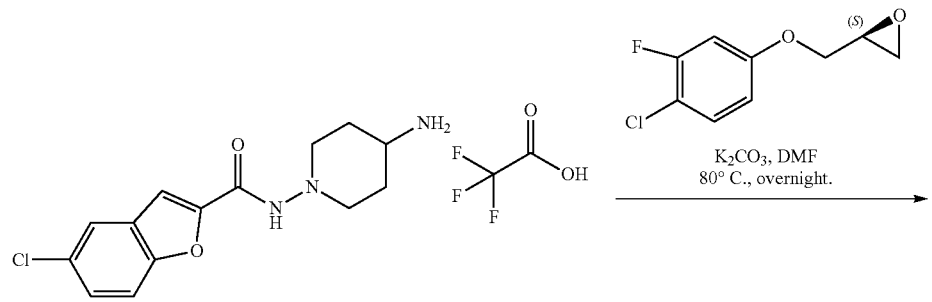

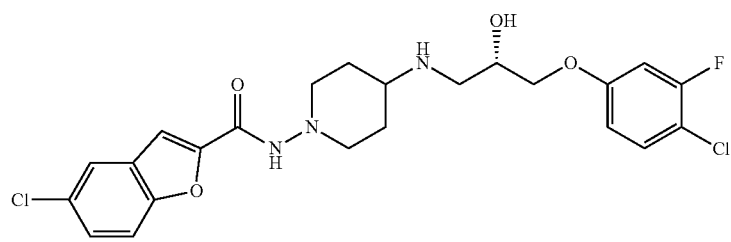

To a stirred solution of N-(4-aminopiperidin-1-yl)-5-chlorobenzofuran-2-carboxamide 2,2,2-trifluoroacetate (0.200 g, 0.491 mmol, 1.0 equiv) in DMF (5 mL) was added $K_2CO_3$ (0.135 g, 0.98 mmol, 2.0 equiv) and (S)-2-(4-chloro-3-fluorophenoxy) methyl)oxirane (0.09 g, 0.491 mmol, 1.0 equiv). The resultant reaction mixture was heated at 80° C. for overnight. Product formation was confirmed by LCMS. The reaction mixture was diluted with water (10 mL) and extracted by ethyl acetate (50 mL×2). The organic layer washed with $NaHCO_3$, brine, dried over $NaSO_4$ filter conc. under reduced pressure to obtain (S)-5-chloro-N-(4-((3-(4-chloro-3-fluorophenoxy)-2-hydroxypropyl)amino)piperidin-1-yl)benzofuran-2-carboxamide (Compound 55-0.010 g, 10% Yield) as a white solid. LCMS 496.4 [M+H]$^+$; $^1$H NMR (400 MHz, DMSO-$d_6$) δ 9.72 (s, 1H), 7.86 (s, 1H), 7.68 (s, 1H), 7.55-7.38 (m, 3H), 7.06 (d, J=2.9 Hz, 1H), 7.09 (d, J=2.4 Hz, 1H), 6.84 (d, J=7.8 Hz, 1H), 5.02 (br. s., 1H), 4.01 (dd, J=3.7, 10.0 Hz, 1H), 3.96-3.81 (m, 3H), 2.99 (d, J=9.8 Hz, 2H), 2.77-2.62 (m, 3 H), 1.82 (br. s., 2H), 1.38 (d, J=10.3 Hz, 2H).

Example 30

Chiral Resolution of 6-chloro-N-(4-((3-(4-chloro-3-fluorophenoxy)-2-hydroxypropyl)amino)piperidin-1-yl)quinoline-2-carboxamide

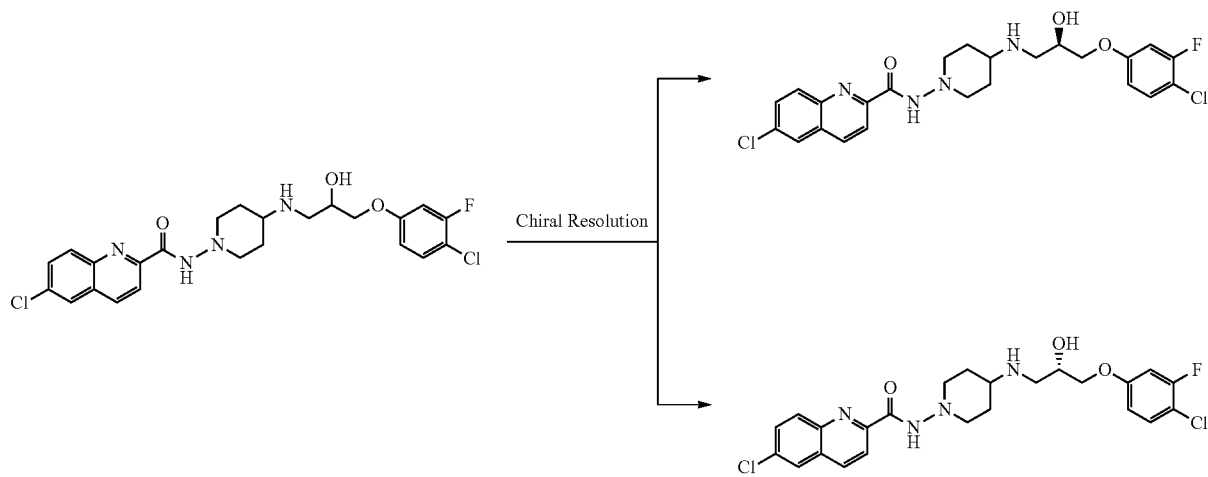 [SMILES: O=C(NN1CCC(NC[C@@H](O)COc2ccc(Cl)c(F)c2)CC1)c1ccc2cc(Cl)ccc2n1 ; O=C(NN1CCC(NCC(O)COc2ccc(Cl)c(F)c2)CC1)c1ccc2cc(Cl)ccc2n1 ; O=C(NN1CCC(NC[C@H](O)COc2ccc(Cl)c(F)c2)CC1)c1ccc2cc(Cl)ccc2n1]

The enantiomers, (R)-6-chloro-N-(4-((3-(4-chloro-3-fluorophenoxy)-2-hydroxypropyl)amino)piperidin-1-yl)quinoline-2-carboxamide (Compound 56-[α]$_D^{20}$=–1.60° (c=0.05, MeOH); elution time: 32.8 min) and (S)-6-chloro-N-(4-((3-(4-chloro-3-fluorophenoxy)-2-hydroxypropyl) amino)piperidin-1-yl)quinoline-2-carboxamide (Compound 57-[α]$_D^{20}$=6.76° (c=0.05, MeOH); elution time: 40.42 min), were separated by chiral SFC (Chiralpak® ADH, 250×20 mm, 5μ). Isocratic program with analytical grade liquid carbon dioxide and HPLC grade EtOH (0.2% DEA in Hexane). LCMS: 507.4 [M+H]$^+$; $^1$H NMR (400 MHz, DMSO-$d_6$) δ 9.67 (s, 1H), 8.53 (d, J=8.8 Hz, 1H), 8.24 (d, J=2.0 Hz, 1H), 8.14 (dd, J=5.9, 8.8 Hz, 1H), 7.88 (d, J=9.3 Hz, 1H), 7.46 (t, J=8.8 Hz, 1H), 7.08 (d, J=11.7 Hz, 1H), 6.85 (d, J=9.8 Hz, 1H), 5.02 (br. s., 1H), 4.02 (d, J=9.8 Hz, 1H), 3.97-3.71 (m, 2H), 3.01 (br. s., 2H), 2.91-2.71 (m, 2H), 2.67 (br. s., 2H), 2.61 (br. s., 2H), 1.85 (br. s., 2H), 1.43 (br. s., 2H).

Example 31

Chiral resolution of 6-chloro-N-(4-(3-(4-chloro-3-fluorophenoxy)-2-hydroxypropyl)piperazin-1-yl)quinoline-2-carboxamide

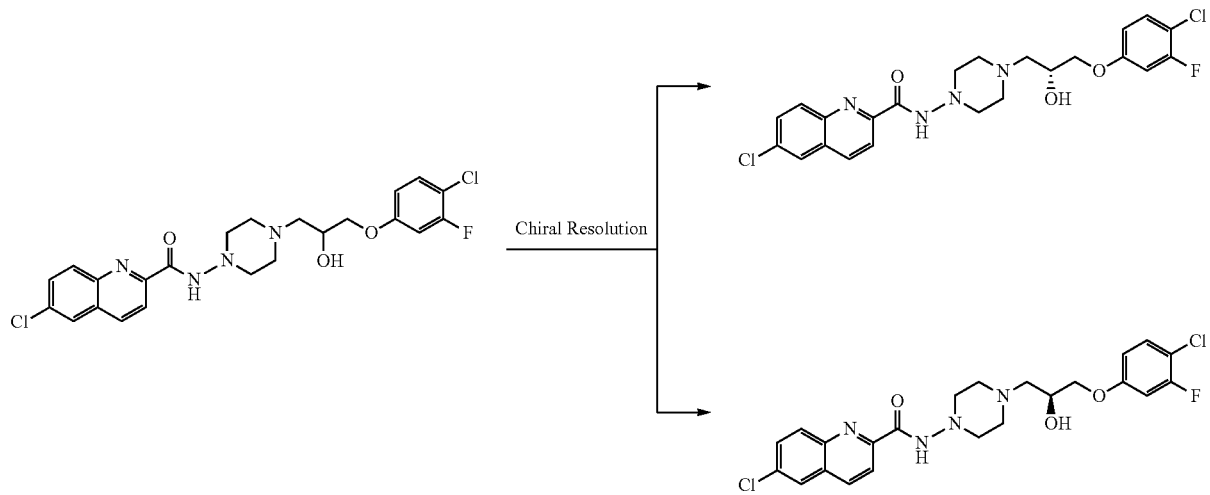 [SMILES: O=C(NN1CCN(C[C@@H](O)COc2ccc(Cl)c(F)c2)CC1)c1ccc2cc(Cl)ccc2n1 ; O=C(NN1CCN(CC(O)COc2ccc(Cl)c(F)c2)CC1)c1ccc2cc(Cl)ccc2n1 ; O=C(NN1CCN(C[C@H](O)COc2ccc(Cl)c(F)c2)CC1)c1ccc2cc(Cl)ccc2n1]

The enantiomers, (R)-6-chloro-N-(4-(3-(4-chloro-3-fluorophenoxy)-2-hydroxypropyl)piperazin-1-yl)quinoline-2-carboxamide (Compound 58-$[\alpha]_D^{20}$=−14.80° (c=0.05, MeOH); elution time: 29.17 min) and (S)-6-chloro-N-(4-(3-(4-chloro-3-fluorophenoxy)-2-hydroxypropyl)piperazin-1-yl)quinoline-2-carboxamide (Compound 59-$[\alpha]_D^{20}$=43.12° (c=0.05, MeOH); elution time: 39.19 min), were separated by chiral SFC (Chiralpak© IA, 250×20 mm, 5μ). Isocratic program with analytical grade liquid carbon dioxide and HPLC grade MeOH. LCMS: 493.4 [M+H]$^+$; $^1$H NMR (400 MHz, DMSO-$d_6$) δ 9.79 (s, 1H), 8.53 (d, J=8.8 Hz, 1H), 8.24 (d, J=2.2 Hz, 1H), 8.14 (t, J=8.8 Hz, 2H), 7.88 (dd, J=2.4, 9.0 Hz, 1H), 7.47 (t, J=8.8 Hz, 1H), 7.08 (dd, J=2.6, 11.4 Hz, 1H), 6.86 (dd, J=1.8, 9.2 Hz, 1H), 4.95 (d, J=4.4 Hz, 1H), 4.08-3.98 (m, 1H), 3.98-3.83 (m, 2H), 2.94 (t, J=4.6 Hz, 4H), 2.59 (br. s., 4 H).

Example 32

Chiral resolution of 6-chloro-N-(4-(3-(4-chloro-3-fluorophenoxy)-2-hydroxypropyl)piperazin-1-yl)-2-naphthamide

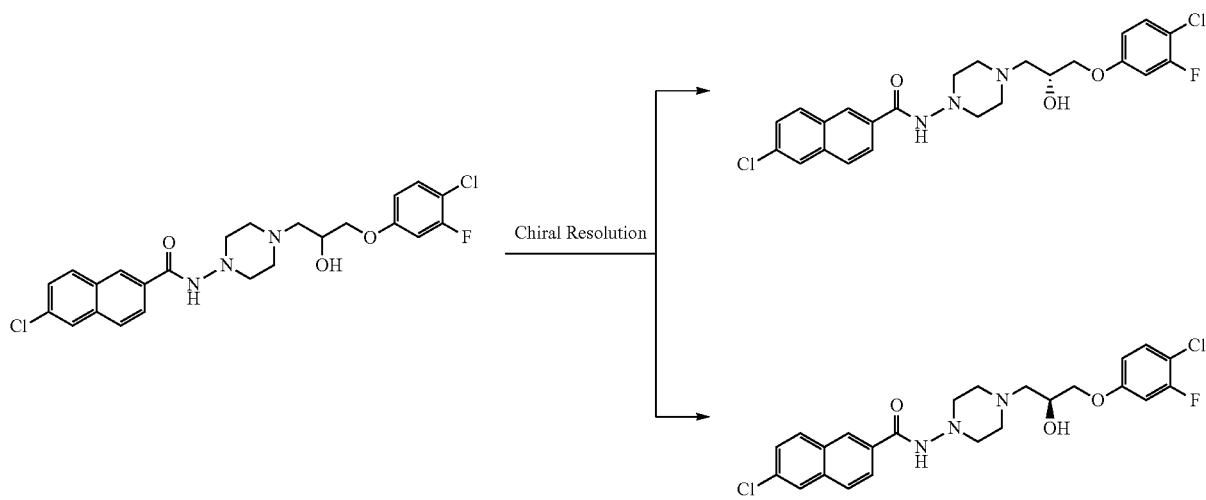 [SMILES: O=C(NN1CCN(C[C@@H](O)COc2ccc(Cl)c(F)c2)CC1)c1ccc2cc(Cl)ccc2c1 ; O=C(NN1CCN(CC(O)COc2ccc(Cl)c(F)c2)CC1)c1ccc2cc(Cl)ccc2c1 ; O=C(NN1CCN(C[C@H](O)COc2ccc(Cl)c(F)c2)CC1)c1ccc2cc(Cl)ccc2c1]

The enantiomers, (R)-6-chloro-N-(4-(3-(4-chloro-3-fluorophenoxy)-2-hydroxypropyl)piperazin-1-yl)-2-naphthamide (Compound 60-$[\alpha]_D^{20}$=−15.88° (c=0.05, MeOH); elution time: 29.55 min) and (S)-6-chloro-N-(4-(3-(4-chloro-3-fluorophenoxy)-2-hydroxypropyl)piperazin-1-yl)-2-naphthamide (Compound 61-$[\alpha]_D^{20}$=7.72° (c=0.05, MeOH); elution time: 35.21 min), were separated by chiral SFC (Chiralpak® IA, 250×20 mm, 5μ). Isocratic program with analytical grade liquid carbon dioxide and HPLC grade MeOH.). LCMS: 492.2 [M+H]$^+$; $^1$H NMR (400 MHz, DMSO-$d_6$) δ 9.59 (s, 1H), 8.38 (s, 1H), 8.16-8.06 (m, 2H), 7.98 (d, J=8.3 Hz, 1H), 7.89 (d, J=8.8 Hz, 1H), 7.60 (dd, J=1.8, 8.8 Hz, 1H), 7.47 (t, J=8.8 Hz, 1H), 7.08 (dd, J=2.6, 11.4 Hz, 1H), 6.86 (d, J=7.5 Hz, 1H), 4.96 (d, J=4.4 Hz, 1H), 4.09-3.97 (m, 1H), 3.97-3.76 (m, 2H), 2.92 (br. s., 4H), 2.57 (br. s., 4H).

Example 33

Synthesis of (R)-N-(4-(3-(4-chloro-3-fluorophenoxy)-2-hydroxypropyl)piperazin-1-yl)-4-(trifluoromethoxy)benzamide

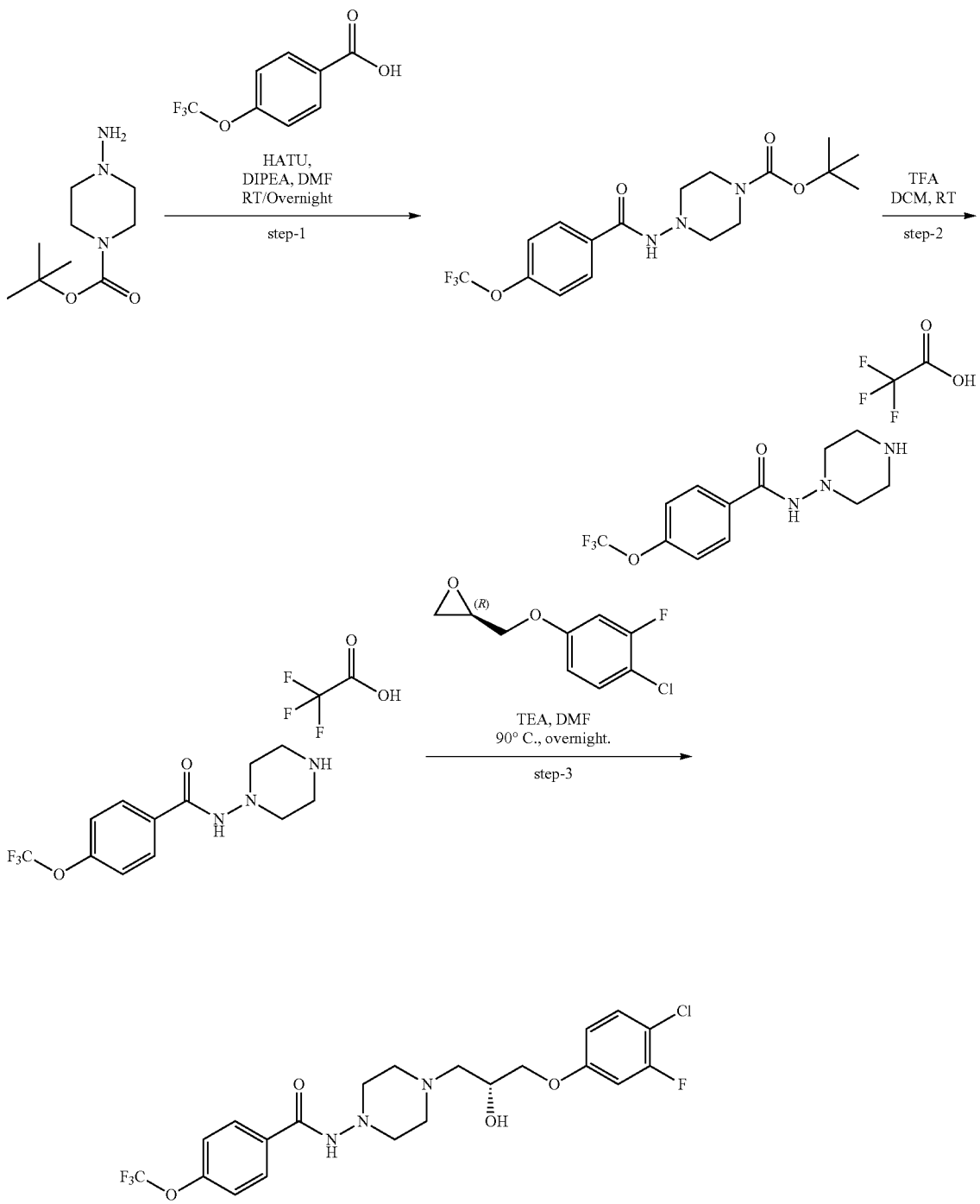

Step 1—Synthesis of tert-butyl 4-(4-(trifluoromethoxy)benzamido)piperazine-1-carboxylate To a stirred solution of tert-butyl 4-aminopiperazine-1-carboxylate (487 mg, 2.4 mmol, 1.0 equiv) in DMF (5 mL) was added HATU (1824 mg, 4.8 mmol, 2.0 equiv) at RT and stirred for 10 minutes. Then 4-(trifluoromethoxy)benzoic acid (500 mg, 2.4 mmol, 1.0 equiv) was added followed by the addition of DIPEA (1.3 mL, 7.2 mmol, 3.0 equiv). The resulting reaction mixture was allowed to stir at RT for overnight. Product formation was confirmed by LCMS. The reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure, to obtain tert-butyl 4-(4-(trifluoromethoxy)benzamido)piperazine-1-carboxylate (300 mg, 32% Yield) as an off white solid. LCMS 390.1 [M+H]$^+$; $^1$H NMR (400 MHz, DMSO-$d_6$) δ 9.62 (s, 1H), 7.89 (m, J=8.77 Hz, 2H), 7.46 (m, J=8.33 Hz, 2H), 3.42 (br. s., 4H), 2.83 (t, J=4.82 Hz, 4H), 1.41 (s, 9 H).

Step 2—Synthesis of N-(piperazin-1-yl)-4-(trifluoromethoxy)benzamide 2,2,2-trifluoroacetate To a stirred solution of tert-butyl 4-(4-(trifluoromethoxy) benzamido)piperazine-1-carboxylate (300 mg, 0.77 mmol, 1.0 equiv) in DCM (10 mL), was added trifluoroacetic acid (01 mL) and the resultant reaction mixture was stirred at RT for overnight under nitrogen atmosphere. Reaction was monitored by LCMS. After completion of reaction, the reaction mixture was concentrated under reduced pressure. The crude product crystallized in diethyl ether and dried under vacuum to obtain N-(piperazin-1-yl)-4-(trifluoromethoxy)benzamide 2,2,2-trifluoroacetate (200 mg, 64% Yield) as an off white solid. LCMS 290.1 [M+H]$^+$; $^1$H NMR (400 MHz, DMSO-$d_6$) δ 9.91 (s, 1H), 8.73 (br. s., 2H), 7.91 (m, J=8.33 Hz, 2H), 7.47 (m, J=7.89 Hz, 2H), 3.20 (br. s., 4H), 3.12 (br. s., 4H).

Step 3—Synthesis of (R)-N-(4-(3-(4-chloro-3-fluorophenoxy)-2-hydroxypropyl)piperazin-1-yl)-4-(trifluoromethoxy)benzamide To a stirred solution of N-(piperazin-1-yl)-4-(trifluoromethoxy)benzamide 2,2,2-trifluoroacetate (200 mg, 0.49 mmol, 1.0 equiv) (R)-2-((4-chloro-3-fluorophenoxy) methyl)oxirane (100 mg, 0.49 mmol, 1.0 equiv) in DMF (05 mL), was added TEA (0.3 mL, 1.96 mmol, 4.0 equiv) and the resultant reaction mixture was heated at 90° C. for overnight. Progress of the reaction was monitored by LCMS. After completion of reaction, the reaction mixture was diluted with water (50 mL) and extracted with EtOAc (50 mL×2). The combined organic layer was washed with water (50 mL×4), dried over anhydrous sodium sulfate and concentrated under reduced pressure to obtain crude which was purified by reversed phase HPLC to obtain (R)-N-(4-(3-(4-chloro-3-fluorophenoxy)-2-hydroxypropyl)piperazin-1-yl)-4-(trifluoromethoxy)benzamide (Compound 62-70 mg, 30% Yield) as a white solid. LCMS 492.4 [M+H]$^+$; $^1$H NMR (400 MHz, DMSO-$d_6$) δ 9.91 (br. s., 1H), 9.51 (br. s., 1H), 7.90 (d, J=7.89 Hz, 3H), 7.46 (d, J=7.45 Hz, 3H), 7.09 (d, J=10.52 Hz, 1H), 6.86 (d, J=7.45 Hz, 1H), 5.99 (br. s., 1H), 4.95 (br. s., 1H), 4.34 (br. s., 1H), 3.98-4.03 (m, 2H), 3.94 (br. s., 1H), 3.59 (br. s., 2H), 2.89 (br. s., 2H).

Example 34

Synthesis of (R)-4-chloro-N-(4-(3-(4-chloro-3-fluorophenoxy)-2-hydroxypropyl)piperazin-1-yl)benzamide

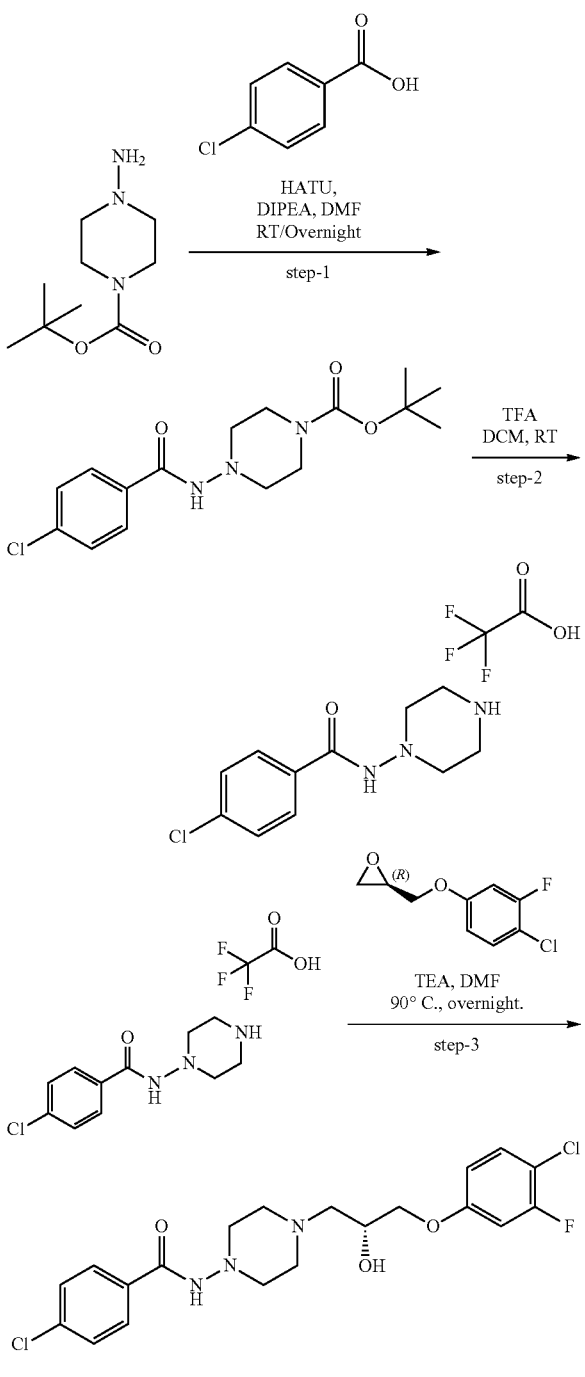

Step 1—Synthesis of tert-butyl 4-(4-chlorobenzamido)piperazine-1-carboxylate To a stirred solution of tert-butyl 4-aminopiperazine-1-carboxylate (644 mg, 3.2 mmol, 1.0 equiv) in DMF (5 mL) was added HATU (2432 mg, 6.4 mmol, 2.0 equiv) at RT and stirred for 10 minutes. Then 4-chlorobenzoic acid (500 mg, 3.2 mmol, 1.0 equiv) was added followed by the addition of DIPEA (1.7 mL, 9.6 mmol, 3.0 equiv). The resulting reaction mixture was allowed to stir at RT for overnight. Product formation was confirmed by LCMS. The reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure, to obtain tert-butyl 4-(4-chlorobenzamido)piperazine-1-carboxylate (300 mg, 28% Yield) as an off white solid. LCMS 340.1 [M+H]$^+$; $^1$H NMR (400 MHz, DMSO-d$_6$) δ 9.59 (s, 1H), 7.79 (m, J=8.33 Hz, 2 H), 7.53 (m, J=8.77 Hz, 2H), 3.41 (br. s., 4H), 2.82 (t, J=4.60 Hz, 4H), 1.41 (s, 9H).

Step 2—Synthesis of 4-chloro-N-(piperazin-1-yl)benzamide 2,2,2-trifluoroacetate

To a stirred solution of tert-butyl 4-(4-chlorobenzamido)piperazine-1-carboxylate (300 mg, 0.88 mmol, 1.0 equiv) in DCM (10 mL), was added trifluoroacetic acid (01 mL) and the resultant reaction mixture was stirred at RT for overnight under nitrogen atmosphere. Reaction was monitored by LCMS. After completion of reaction, the reaction mixture was concentrated under reduced pressure. The crude product crystallized in diethyl ether and dried under vacuum to obtain 4-chloro-N-(piperazin-1-yl)benzamide 2,2,2-trifluoroacetate (200 mg, 65% Yield) as an off white solid. LCMS 240.1 [M+H]$^+$; $^1$H NMR (400 MHz, DMSO-d$_6$) δ 9.87 (s, 2H), 8.62 (br. s., 2H), 7.80 (m, J=8.33 Hz, 2H), 7.55 (m, J=8.33 Hz, 2H), 3.22 (br. s., 4H), 3.11 (br. s., 4 H).

Step 3—Synthesis of (R)-4-chloro-N-(4-(3-(4-chloro-3-fluorophenoxy)-2-hydroxypropyl)piperazin-1-yl)benzamide To a stirred solution of 4-chloro-N-(piperazin-1-yl)benzamide 2,2,2-trifluoroacetate (200 mg, 0.56 mmol, 1.0 equiv) (R)-2-((4-chloro-3-fluorophenoxy)methyl)oxirane (114 mg, 0.56 mmol, 1.0 equiv) in DMF (05 mL), was added TEA (0.3 mL, 2.24 mmol, 4.0 equiv) and the resultant reaction mixture was heated at 90° C. for overnight. Progress of the reaction was monitored by LCMS. After completion of reaction, the reaction mixture was diluted with water (50 mL) and extracted with EtOAc (50 mL×2). The combined organic layer was washed with water (50 mL×4), dried over anhydrous sodium sulfate and concentrated under reduced pressure to obtain crude which was purified by reversed phase HPLC to obtain (R)-4-chloro-N-(4-(3-(4-chloro-3-fluorophenoxy)-2-hydroxypropyl)piperazin-1-yl)benzamide (Compound 63-40 mg, 17% Yield) as a white solid. LCMS 442.3 [M+H]$^+$; $^1$H NMR (400 MHz, DMSO-d$_6$) 59.48 (s, 1H), 7.78 (d, J=8.77 Hz, 2H), 7.36-7.61 (m, 3H), 7.07 (dd, J=11.84, 2.63 Hz, 1H), 6.76-6.92 (m, 1H), 4.94 (d, J=4.38 Hz, 1H), 4.01 (d, J=6.14 Hz, 1H), 3.79-3.96 (m, 2H), 2.87 (d, J=4.82 Hz, 4H), 2.44 (d, J=5.26 Hz, 4H).

Example 35

Synthesis of (R)-5-chloro-N-(4-(3-(4-chloro-3-fluorophenoxy)-2-hydroxypropyl)piperazin-1-yl)picolinamide

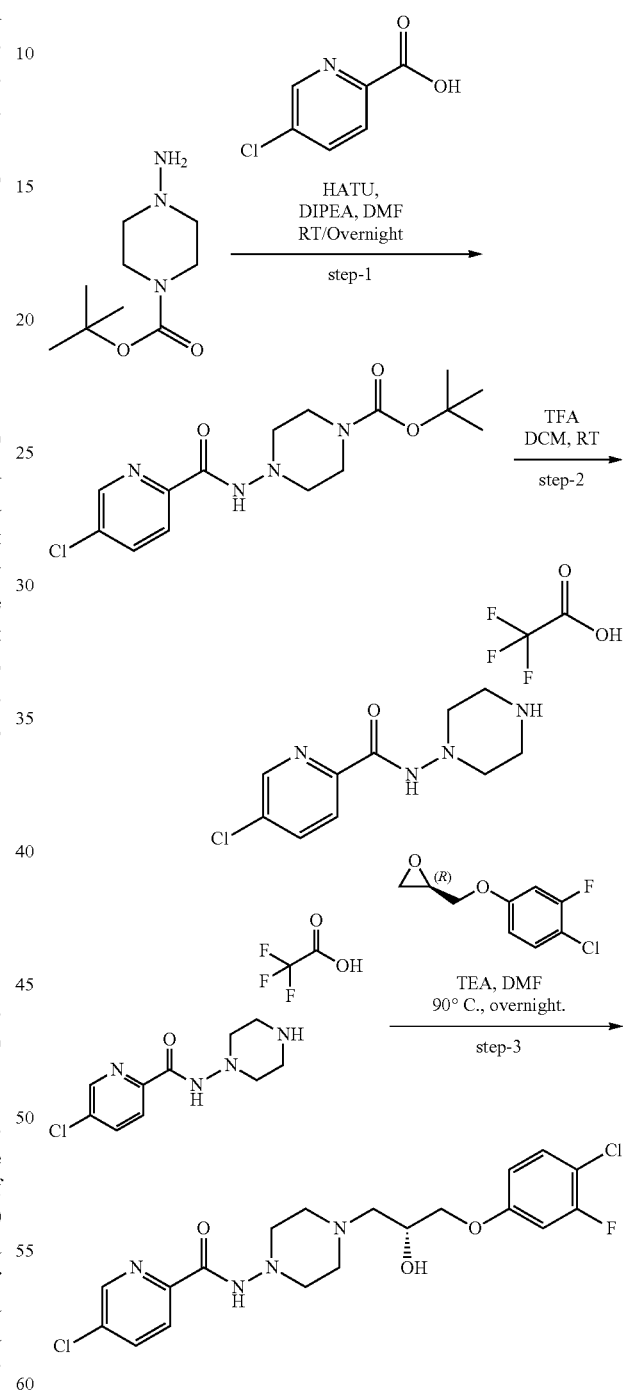

Step 1—Synthesis of tert-butyl 4-(5-chloropicolinamido)piperazine-1-carboxylate

To a stirred solution of tert-butyl 4-aminopiperazine-1-carboxylate (384 mg, 1.9 mmol, 1.0 equiv) in DMF (05 mL) was added HATU (1451 mg, 3.8 mmol, 2.0 equiv) at RT and stirred for 10 minutes. Then 5-chloropicolinic acid (300 mg, 1.9 mmol, 1.0 equiv) was added followed by the addition of DIPEA (1.0 mL, 5.7 mmol, 3.0 equiv). The resulting reaction mixture was allowed to stir at RT for overnight. Product formation was confirmed by LCMS. the reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure, to obtain tert-butyl 4-(5-chloropicolinamido)piperazine-1-carboxylate (100 mg, 15% Yield) as an off white solid. LCMS 341.1 [M+H]$^+$; $^1$H NMR (400 MHz, DMSO-d$_6$) δ 9.86 (s, 1H), 8.67 (d, J=1.75 Hz, 1H), 8.12 (dd, J=8.55, 2.41 Hz, 1H), 8.01 (d, J=8.77 Hz, 1H), 3.40 (t, J=4.82 Hz, 4H), 2.81 (t, J=4.82 Hz, 4H), 1.34-1.47 (m, 9H).

Step 2—Synthesis of 5-chloro-N-(piperazin-1-yl)picolinamide 2,2,2-trifluoroacetate To a stirred solution of tert-butyl 4-(5-chloropicolinamido)piperazine-1-carboxylate (100 mg, 0.29 mmol, 1.0 equiv) in DCM (05 mL), was added trifluoroacetic acid (01 mL) and the resultant reaction mixture was stirred at RT for overnight under nitrogen atmosphere. Reaction was monitored by TLC and LCMS. After completion of reaction, the reaction mixture was concentrated under reduced pressure. The crude product crystallized in diethyl ether and dried under vacuum to obtain 5-chloro-N-(piperazin-1-yl)picolinamide 2,2,2-trifluoroacetate (100 mg, 96% Yield) as an off white solid. LCMS 240.9 [M+H]$^+$; $^1$H NMR (400 MHz, DMSO-d$_6$) δ 10.22 (br. s., 1H), 8.69 (br. s., 1H), 8.62 (br. s., 2H), 8.13 (d, J=6.58 Hz, 1H), 8.01 (d, J=7.89 Hz, 1H), 3.22 (br. s., 4H), 3.09 (br. s., 4H).

Step 3—Synthesis of (R)-5-chloro-N-(4-(3-(4-chloro-3-fluorophenoxy)-2-hydroxypropyl)piperazin-1-yl)picolinamide To a stirred solution of 5-chloro-N-(piperazin-1-yl)picolinamide 2,2,2-trifluoroacetate (100 mg, 0.28 mmol, 1.0 equiv) (R)-2-((4-chloro-3-fluorophenoxy)methyl)oxirane (58 mg, 0.28 mmol, 1.0 equiv) in DMF (05 mL), was added TEA (0.2 mL, 1.12 mmol, 4.0 equiv) and the resultant reaction mixture was heated at 90° C. for overnight. Progress of the reaction was monitored by LCMS. After completion of reaction, the reaction mixture was diluted with water (100 mL) and extracted with EtOAc (50 mL×2). The combined organic layer was washed with water (50 mL×4), dried over anhydrous sodium sulfate and concentrated under reduced pressure to obtain crude which was purified by reversed-phase HPLC to obtain (R)-5-chloro-N-(4-(3-(4-chloro-3-fluorophenoxy)-2-hydroxypropyl)piperazin-1-yl) picolinamide (Compound 64-80 mg, 65% Yield) as an off white solid. LCMS 443.3 [M+H]$^+$; $^1$H NMR (400 MHz, DMSO-d$_6$) δ 9.74 (br. s., 1H), 8.67 (d, J=2.63 Hz, 1H), 8.11 (dd, J=8.55, 2.41 Hz, 1H), 8.00 (d, J=8.77 Hz, 1H), 7.47 (t, J=8.99 Hz, 1H), 7.09 (d, J=2.63 Hz, 1H), 6.86 (dd, J=8.99, 1.97 Hz, 1H), 4.96 (br. s., 1H), 3.97-4.05 (m, 1H), 3.84-3.94 (m, 2H), 2.88 (br. s., 4H), 2.56 (br. s., 2H), 2.33 (br. s., 2H), 1.91 (s, 1 H).

Example 36

Synthesis of (R)-N-(4-(3-(4-chloro-3-fluorophenoxy)-2-hydroxypropyl)piperazin-1-yl)-5-(trifluoromethyl)picolinamide

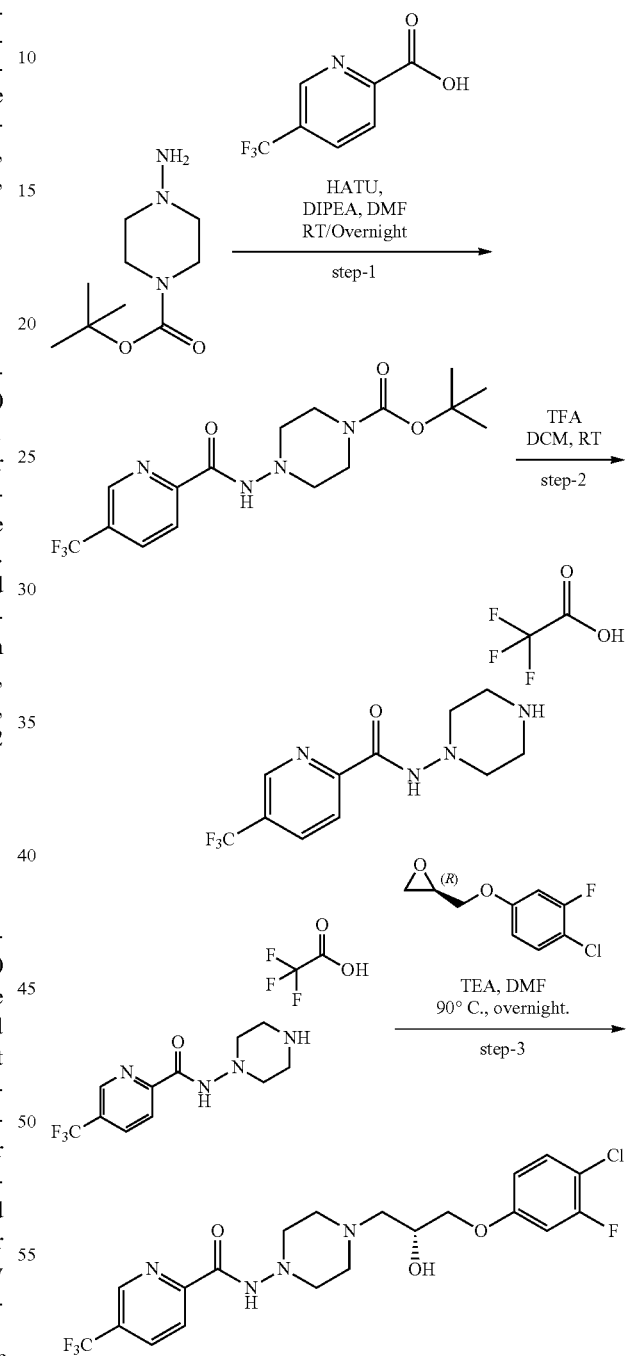

Step 1—Synthesis of tert-butyl 4-(5-(trifluoromethyl)picolinamido)piperazine-1-carboxylate To a stirred solution of tert-butyl 4-aminopiperazine-1-carboxylate (315 mg, 1.5 mmol, 1.0 equiv) in DMF (05 mL) was added HATU (1140 mg, 3.0 mmol, 2.0 equiv) at RT and stirred for 10 minutes. Then 5-(trifluoromethyl)picolinic acid (300 mg, 1.5 mmol, 1.0 equiv) was added followed by the addition of DIPEA (0.8 mL, 4.5 mmol, 3.0 equiv). The resulting reaction mixture was allowed to stir at RT for overnight. Product formation was confirmed by LCMS. the reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure, to obtain tert-butyl 4-(5-(trifluoromethyl)picolinamido)piperazine-1-carboxylate (100 mg, 17% Yield) as a brown solid. LCMS 375.1 [M+H]$^+$; $^1$H NMR (400 MHz, DMSO-d$_6$) δ 10.04 (s, 1H), 9.00 (br. s., 1H), 8.93 (s, 1H), 8.41 (d, J=7.89 Hz, 1H), 8.19 (d, J=8.33 Hz, 1H), 3.42 (br. s., 4H), 2.87-2.94 (m, 4 H), 1.41 (d, J=3.51 Hz, 9H).

Step 2—Synthesis of N-(piperazin-1-yl)-5-(trifluoromethyl)picolinamide 2,2,2-trifluoroacetate To a stirred solution of tert-butyl 4-(5-(trifluoromethyl) picolinamido)piperazine-1-carboxylate (100 mg, 0.26 mmol, 1.0 equiv) in DCM (05 mL), was added trifluoroacetic acid (01 mL) and the resultant reaction mixture was stirred at RT for overnight under nitrogen atmosphere. Reaction was monitored by TLC and LCMS. After completion of reaction, the reaction mixture was concentrated under reduced pressure. The crude product crystallized in diethyl ether and dried under vacuum to obtain N-(piperazin-1-yl)-5-(trifluoromethyl)picolinamide 2,2,2-trifluoroacetate (100 mg) as an off white solid. LCMS 275 [M+H]$^+$;

Step 3—Synthesis of (R)-N-(4-(3-(4-chloro-3-fluorophenoxy)-2-hydroxypropyl)piperazin-1-yl)-5-(trifluoromethyl)picolinamide To a stirred solution of N-(piperazin-1-yl)-5-(trifluoromethyl)picolinamide 2,2,2-trifluoroacetate (100 mg, 0.25 mmol, 1.0 equiv) (R)-2-((4-chloro-3-fluorophenoxy) methyl)oxirane (52 mg, 0.25 mmol, 1.0 equiv) in DMF (05 mL), was added TEA (0.14 mL, 1.0 mmol, 4.0 equiv) and the resultant reaction mixture was heated at 90° C. for overnight. Progress of the reaction was monitored by LCMS. After completion of reaction, the reaction mixture was diluted with water (100 mL) and extracted with EtOAc (50 mL×2). The combined organic layer was washed with water (50 mL×4), dried over anhydrous sodium sulfate and concentrated under reduced pressure to obtain crude which was purified by reversed-phase HPLC to obtain (R)-N-(4-(3-(4-chloro-3-fluorophenoxy)-2-hydroxypropyl)piperazin-1-yl)-5-(trifluoromethyl)picolinamide (Compound 65-50 mg, 42% Yield) as an off white solid. LCMS 477.4 [M+H]$^+$; $^1$H NMR (400 MHz, DMSO-d$_6$) δ 9.87 (br. s., 1H), 9.02 (br. s., 1H), 8.43 (d, J=8.77 Hz, 1H), 8.19 (d, J=7.89 Hz, 1H), 7.49 (t, J=8.77 Hz, 2H), 7.09 (d, J=11.84 Hz, 1H), 6.87 (d, J=6.58 Hz, 1H), 5.94 (br. s., 1H), 4.00 (br. s., 4H), 3.58 (br. s., 2H), 2.67 (br. s., 3H), 2.33 (br. s., 3H).

Example 37

Synthesis of (R)-N-(4-(3-(4-chloro-3-fluorophenoxy)-2-hydroxypropyl)piperazin-1-yl)-5-(difluoromethyl)pyrazine-2-carboxamide

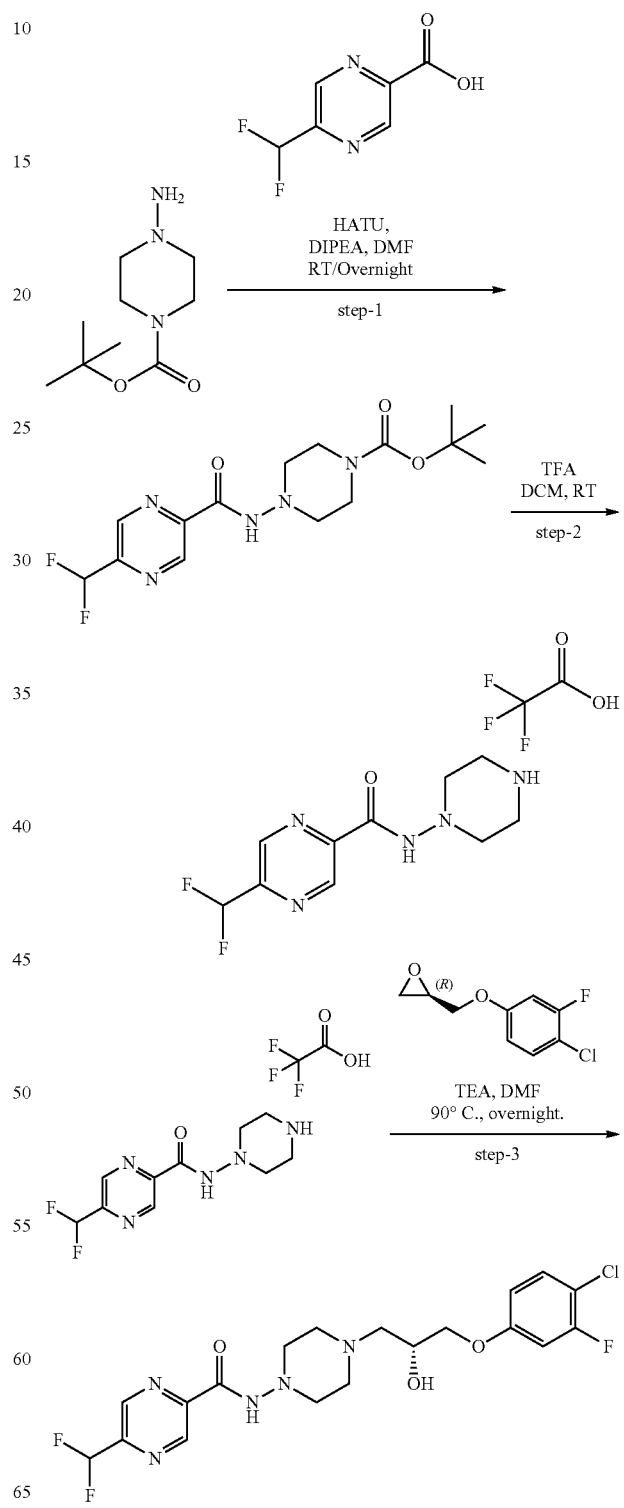

Step 1—Synthesis of tert-butyl 4-(5-(difluoromethyl)pyrazine-2-carboxamido)piperazine-1-carboxylate To a stirred solution of tert-butyl 4-aminopiperazine-1-carboxylate (578 mg, 2.8 mmol, 1.0 equiv) in DMF (05 mL) was added HATU (2128 mg, 5.6 mmol, 2.0 equiv) at RT and stirred for 10 minutes. Then 5-(difluoromethyl)pyrazine-2-carboxylic acid (500 mg, 2.8 mmol, 1.0 equiv) was added followed by the addition of DIPEA (1.5 mL, 8.4 mmol, 3.0 equiv). The resulting reaction mixture was allowed to stir at RT for overnight. Product formation was confirmed by LCMS. the reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure, to obtain tert-butyl 4-(5-(difluoromethyl)pyrazine-2-carboxamido)piperazine-1-carboxylate (400 mg, 39% Yield) as a brown solid. LCMS 358.2 [M+H]$^+$; $^1$H NMR (400 MHz, DMSO-d$_6$) δ 10.13 (s, 1H), 9.24 (s, 1H), 8.99 (s, 1H), 3.34-3.49 (m, 4H), 2.84 (t, J=5.04 Hz, 4H), 1.41 (s, 9H).

Step 2—Synthesis of 5-(difluoromethyl)-N-(piperazin-1-yl)pyrazine-2-carboxamide 2,2,2-trifluoroacetate To a stirred solution of tert-butyl 4-(5-(difluoromethyl) pyrazine-2-carboxamido)piperazine-1-carboxylate (400 mg, 1.12 mmol, 1.0 equiv) in DCM (10 mL), was added trifluoroacetic acid (3 mL) and the resultant reaction mixture was stirred at RT for overnight under nitrogen atmosphere. Reaction was monitored by TLC and LCMS. After completion of reaction, the reaction mixture was concentrated under reduced pressure. The crude product crystallized in diethyl ether and dried under vacuum to obtain 5-(difluoromethyl)-N-(piperazin-1-yl)pyrazine-2-carboxamide 2,2,2-trifluoroacetate (200 mg, 48% Yield) as an off white solid. LCMS 258.2 [M+H]$^+$; $^1$H NMR (400 MHz, DMSO-d$_6$) δ 10.46 (br. s., 1H), 9.25 (br. s., 1H), 9.01 (br. s., 1H), 8.73 (br. s., 2H), 3.17 (br. s., 4H), 3.11 (br. s., 4H).

Step 3—Synthesis of (R)-N-(4-(3-(4-chloro-3-fluorophenoxy)-2-hydroxypropyl)piperazin-1-yl)-5-(difluoromethyl)pyrazine-2-carboxamide To a stirred solution of 5-(difluoromethyl)-N-(piperazin-1-yl)pyrazine-2-carboxamide 2,2,2-trifluoroacetate (200 mg, 0.53 mmol, 1.0 equiv) (R)-2-((4-chloro-3-fluorophenoxy)methyl)oxirane (108 mg, 0.53 mmol, 1.0 equiv) in DMF (05 mL), was added TEA (0.3 mL, 2.12 mmol, 4.0 equiv) and the resultant reaction mixture was heated at 90° C. for overnight. Progress of the reaction was monitored by LCMS. After completion of reaction, the reaction mixture was diluted with water (100 mL) and extracted with EtOAc (50 mL×2). The combined organic layer was washed with water (50 mL×4), dried over anhydrous sodium sulfate and concentrated under reduced pressure to obtain crude which was purified by reversed-phase HPLC to obtain (R)-N-(4-(3-(4-chloro-3-fluorophenoxy)-2-hydroxypropyl)piperazin-1-yl)-5-(difluoromethyl)pyrazine-2-carboxamide (Compound 66-100 mg, 42% Yield) as a white solid. LCMS 460.3 [M+H]$^+$; $^1$H NMR (400 MHz, DMSO-d$_6$) δ10.02 (s, 1H), 9.23 (s, 1H), 8.99 (s, 1H), 7.47 (t, J=8.99 Hz, 1H), 7.21 (s, 1H), 7.04-7.11 (m, 1H), 6.86 (dt, J=9.10, 1.37 Hz, 1H), 4.96 (d, J=4.38 Hz, 1H), 3.97-4.08 (m, 1H), 3.82-3.95 (m, 2H), 2.89 (t, J=4.82 Hz, 4H), 2.67 (br. s., 3H), 2.30-2.44 (m, 2H).

Example 38

Synthesis of (R)-N-(4-(3-(4-chloro-3-fluorophenoxy)-2-hydroxypropyl)piperazin-1-yl)-5-cyanopicolinamide

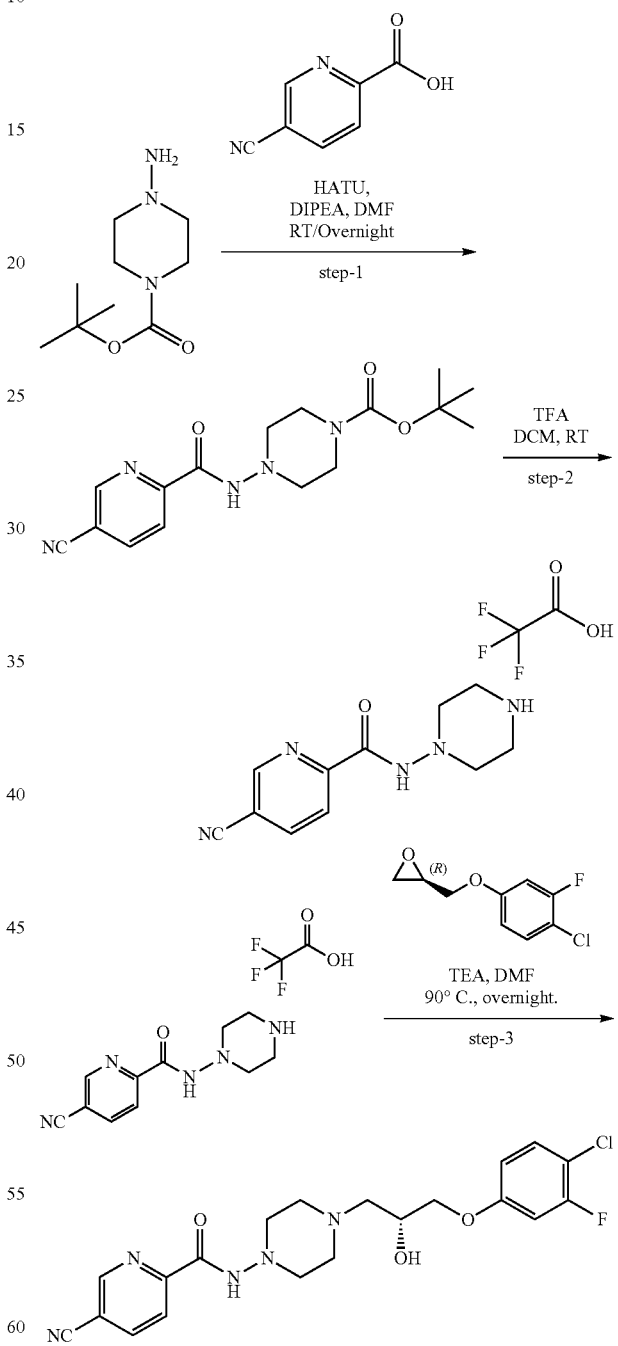

Step 1—Synthesis of tert-butyl 4-(5-cyanopicolinamido)piperazine-1-carboxylate To a stirred solution of tert-butyl 4-aminopiperazine-1-carboxylate (679 mg, 3.37 mmol, 1.0 equiv) in DMF (05 mL) was added HATU (2561 mg, 6.74 mmol, 2.0 equiv) at RT and stirred for 10 minutes. Then 5-cyanopicolinic acid (500 mg, 3.37 mmol, 1.0 equiv) was added followed by the addition of DIPEA (1.8 mL, 10.1 mmol, 3.0 equiv). The resulting reaction mixture was allowed to stir at RT for overnight. Product formation was confirmed by LCMS. the reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure, to obtain tert-butyl 4-(5-cyanopicolinamido)piperazine-1-carboxylate (400 mg, 35% Yield) as an yellow solid. LCMS 332.2 [M+H]$^+$; $^1$H NMR (400 MHz, DMSO-d$_6$) δ 10.06 (s, 1H), 9.09 (s, 1H), 8.50 (dd, J=8.33, 1.75 Hz, 1H), 8.14 (d, J=7.89 Hz, 1H), 3.42 (br. s., 4H), 2.82 (t, J=4.82 Hz, 4H), 1.41 (s, 9H).

Step 2—Synthesis of 5-cyano-N-(piperazin-1-yl)picolinamide 2,2,2-trifluoroacetate To a stirred solution of tert-butyl 4-(5-cyanopicolinamido)piperazine-1-carboxylate (400 mg, 1.20 mmol, 1.0 equiv) in DCM (10 mL), was added trifluoroacetic acid (03 mL) and the resultant reaction mixture was stirred at RT for overnight under nitrogen atmosphere. Reaction was monitored by TLC and LCMS. After completion of reaction, the reaction mixture was concentrated under reduced pressure. The crude product crystallized in diethyl ether and dried under vacuum to obtain 5-cyano-N-(piperazin-1-yl)picolinamide 2,2,2-trifluoroacetate (200 mg, 48% Yield) as an off white solid. LCMS 232.2 [M+H]$^+$; $^1$H NMR (400 MHz, DMSO-d$_6$) δ 10.40 (s, 1H), 9.11 (s, 1H), 8.60 (br. s., 2H), 8.52 (dd, J=8.11, 1.97 Hz, 1H), 8.15 (d, J=8.33 Hz, 1H), 3.23 (br. s., 4H), 3.10 (d, J=4.82 Hz, 4H)

Step 3—Synthesis of (R)-N-(4-(3-(4-chloro-3-fluorophenoxy)-2-hydroxypropyl)piperazin-1-yl)-5-cyanopicolinamide To a stirred solution of 5-cyano-N-(piperazin-1-yl)picolinamide 2,2,2-trifluoroacetate (200 mg, 0.57 mmol, 1.0 equiv) (R)-2-((4-chloro-3-fluorophenoxy)methyl)oxirane (117 mg, 0.57 mmol, 1.0 equiv) in DMF (05 mL), was added TEA (0.32 mL, 2.28 mmol, 4.0 equiv) and the resultant reaction mixture was heated at 90° C. for overnight. Progress of the reaction was monitored by LCMS. After completion of reaction, the reaction mixture was diluted with water (100 mL) and extracted with EtOAc (50 mL×2). The combined organic layer was washed with water (50 mL×4), dried over anhydrous sodium sulfate and concentrated under reduced pressure to obtain crude which was purified by reversed-phase HPLC to obtain (R)-N-(4-(3-(4-chloro-3-fluorophenoxy)-2-hydroxypropyl)piperazin-1-yl)-5-cyanopicolinamide (Compound 67-90 mg, 37% Yield) as a white solid. LCMS 434.3 [M+H]$^+$; $^1$H NMR (400 MHz, DMSO-d$_6$) δ 9.94 (s, 1H), 9.09 (s, 1H), 8.50 (dd, J=8.11, 1.97 Hz, 1H), 8.11-8.20 (m, 1H), 7.47 (t, J=8.99 Hz, 1H), 7.07 (dd, J=11.40, 2.63 Hz, 1H), 6.82-6.90 (m, 1H), 4.97 (br. s., 1H), 4.00 (d, J=6.58 Hz, 1H), 3.84-3.96 (m, 2H), 2.87 (t, J=4.60 Hz, 4H), 2.29-2.44 (m, 2H), 2.12 (m, 3 H).

Example 39

Synthesis of (R)-5-chloro-N-(4-((3-(4-chloro-3-fluorophenoxy)-2-hydroxypropyl)amino)piperidin-1-yl)picolinamide

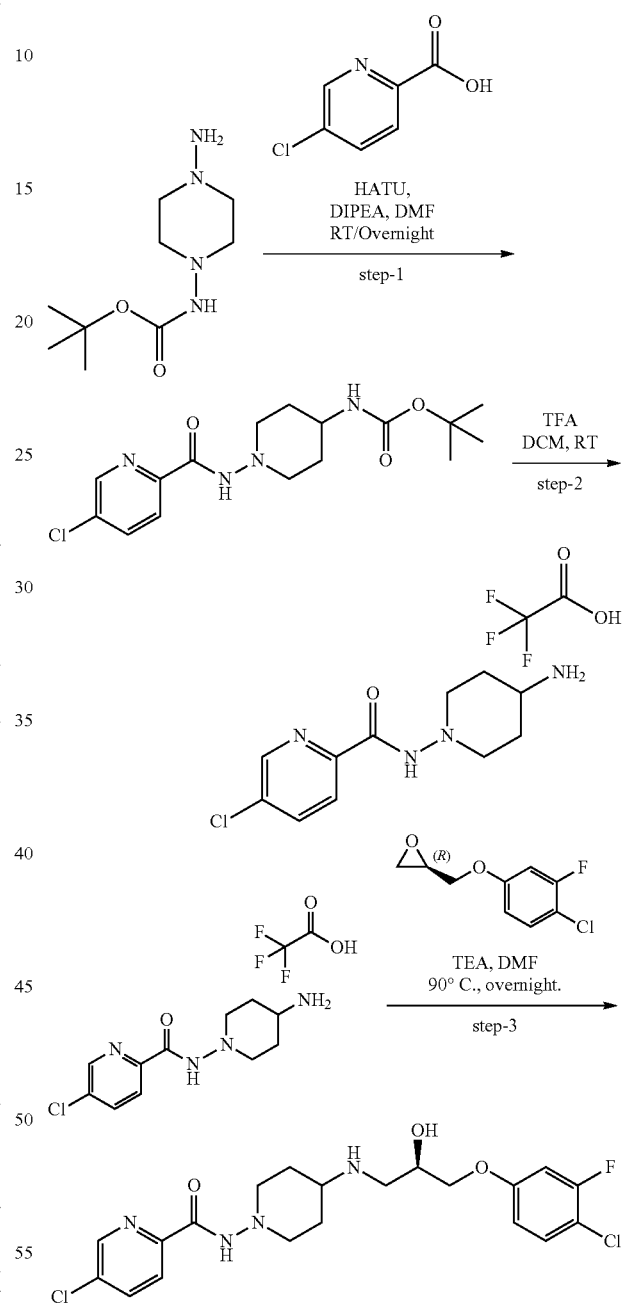

Step 1—Synthesis of tert-butyl (1-(5-chloropicolinamido)piperidin-4-yl)carbamate To a stirred solution of tert-butyl (1-aminopiperidin-4-yl) carbamate (500 mg, 2.32 mmol, 1.0 equiv) in DMF (05 mL) was added HATU (1763 mg, 4.64 mmol, 2.0 equiv) at RT and stirred for 10 minutes. Then 5-chloropicolinic acid (365 mg, 2.32 mmol, 1.0 equiv) was added followed by the addition of DIPEA (1.2 mL, 6.96 mmol, 3.0 equiv). The resulting reaction mixture was allowed to stir at RT for overnight. Product formation was confirmed by LCMS. the reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure, to obtain tert-butyl (1-(5-chloropicolinamido)piperidin-4-yl)carbamate (500 mg, 60% Yield) as an off white solid. LCMS 355.1 [M+H]$^+$; $^1$H NMR (400 MHz, DMSO-d$_6$) δ 9.61 (s, 1 H), 8.66 (d, J=2.19 Hz, 1H), 8.11 (dd, J=8.33, 2.19 Hz, 1H), 7.99 (d, J=8.33 Hz, 1H), 6.83 (d, J=7.02 Hz, 1H), 3.23 (br. s., 1H), 2.84-3.00 (m, 3H), 2.62-2.84 (m, 2H), 1.73 (d, J=11.40 Hz, 2H), 1.47-1.66 (m, 2H), 1.38 (s, 9H).

Step 2—Synthesis of N-(4-aminopiperidin-1-yl)-5-chloropicolinamide 2,2,2-trifluoroacetate To a stirred solution of tert-butyl (1-(5-chloropicolinamido)piperidin-4-yl)carbamate (500 mg, 1.41 mmol, 1.0 equiv) in DCM (10 mL), was added trifluoroacetic acid (02 mL) and the resultant reaction mixture was stirred at RT for overnight under nitrogen atmosphere. Reaction was monitored by TLC and LCMS. After completion of reaction, the reaction mixture was concentrated under reduced pressure. The crude product crystallized in diethyl ether and dried under vacuum to obtain N-(4-aminopiperidin-1-yl)-5-chloropicolinamide 2,2,2-trifluoroacetate (400 mg, 77% Yield) as an off white solid. LCMS 255.2 [M+H]$^+$; $^1$H NMR (400 MHz, DMSO-d$_6$) δ 9.79 (s, 1H), 8.67 (br. s., 1H), 8.12 (d, J=6.14 Hz, 1H), 8.00 (d, J=8.77 Hz, 1H), 7.85 (br. s., 3H), 2.98 (d, J=10.96 Hz, 3H), 2.79 (t, J=11.62 Hz, 2H), 1.91 (d, J=10.96 Hz, 3 H), 1.65 (d, J=8.77 Hz, 3H).

Step 3—Synthesis of (R)-S-chloro-N-(4-((3-(4-chloro-3-fluorophenoxy)-2-hydroxypropyl) amino) piperidin-1-yl)picolinamide To a stirred solution of N-(4-aminopiperidin-1-yl)-5-chloropicolinamide 2,2,2-trifluoroacetate (200 mg, 0.54 mmol, 1.0 equiv) (R)-2-((4-chloro-3-fluorophenoxy)methyl)oxirane (109 mg, 0.54 mmol, 1.0 equiv) in DMF (05 mL), was added TEA (0.3 mL, 2.16 mmol, 4.0 equiv) and the resultant reaction mixture was heated at 90° C. for overnight. Progress of the reaction was monitored by LCMS. After completion of reaction, the reaction mixture was diluted with water (100 mL) and extracted with EtOAc (50 mL×2). The combined organic layer was washed with water (50 mL×4), dried over anhydrous sodium sulfate and concentrated under reduced pressure to obtain crude which was purified by reversed-phase HPLC to obtain (R)-5-chloro-N-(4-((3-(4-chloro-3-fluorophenoxy)-2-hydroxypropyl)amino)piperidin-1-yl)picolinamide (Compound 68-60 mg, 25% Yield) as an off white solid. LCMS 457.3 [M+H]$^+$; $^1$H NMR $^1$H NMR (400 MHz, DMSO-d$_6$) δ 9.60 (s, 1H), 8.66 (d, J=2.19 Hz, 1H), 8.22 (br. s., 1H), 8.11 (dd, J=8.33, 2.63 Hz, 1H), 7.99 (d, J=8.33 Hz, 1H), 7.46 (t, J=8.77 Hz, 1H), 7.09 (d, J=2.63 Hz, 1H), 6.85 (d, J=9.21 Hz, 1H), 4.01 (dd, J=9.87, 3.73 Hz, 1H), 3.83-3.93 (m, 2H), 2.96 (d, J=10.09 Hz, 2H), 2.62-2.78 (m, 4H), 1.85 (br. s., 2H), 1.42 (d, J=10.09 Hz, 3H).

Example 40

Synthesis of (R)-N-(4-((3-(4-chloro-3-fluorophenoxy)-2-hydroxypropyl)amino)piperidin-1-yl)-5-methoxybenzofuran-2-carboxamide

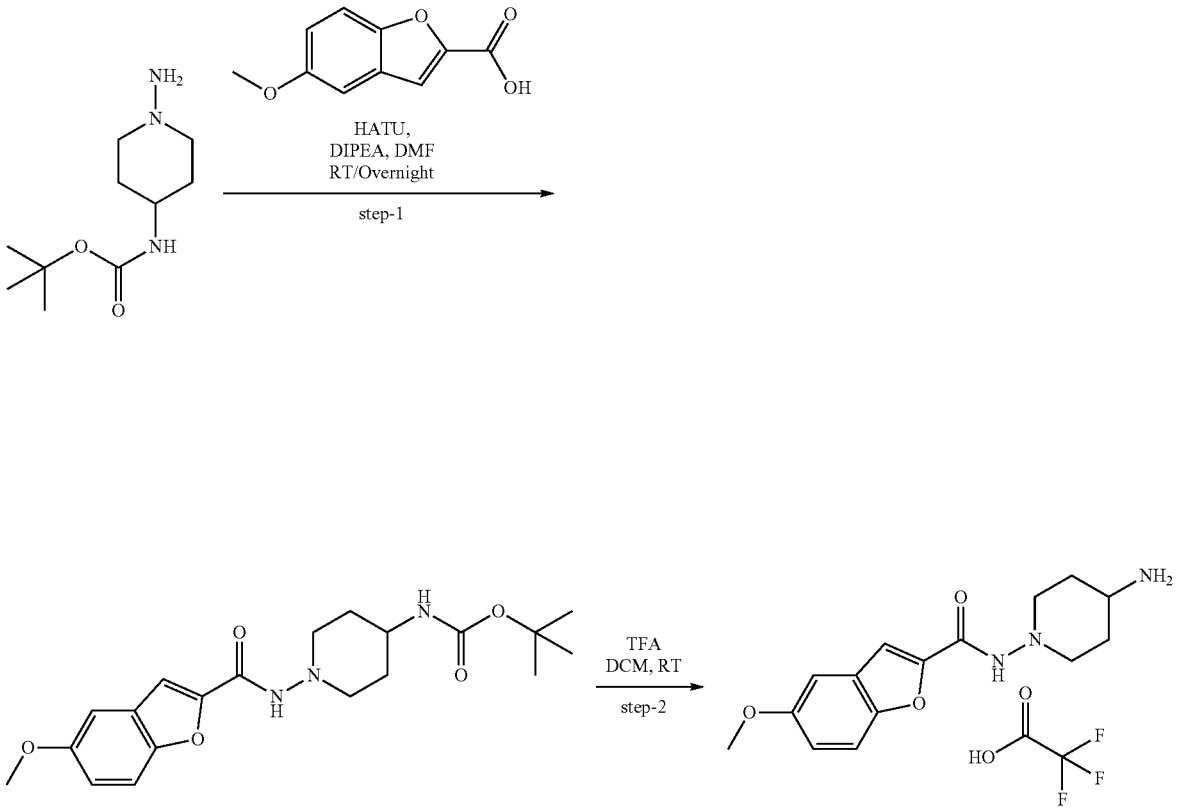

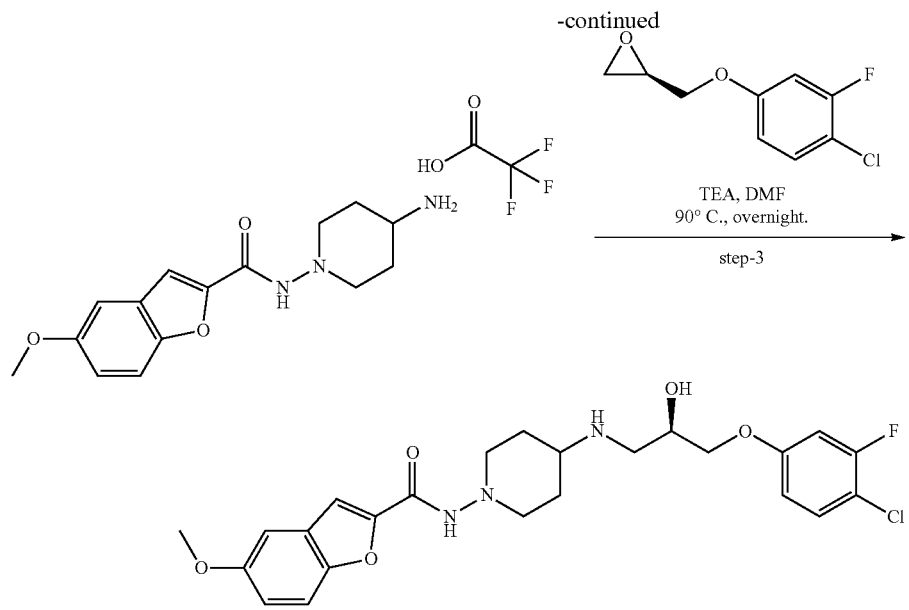

Step 1—Synthesis of tert-butyl (1-(5-methoxyben-zofuran-2-carboxamido)piperidin-4-yl)carbamate To a stirred solution of tert-butyl (1-aminopiperidin-4-yl) carbamate (224 mg, 1.04 mmol, 1.0 equiv) in DMF (5 mL) was added HATU (790 mg, 2.08 mmol, 2.0 equiv) at RT and stirred for 10 minutes. Then 5-methoxybenzofuran-2-carboxylic acid (200 mg, 1.04 mmol, 1.0 equiv) was added followed by the addition of DIPEA (0.6 mL, 3.12 mmol, 3.0 equiv). The resulting reaction mixture was allowed to stir at RT for overnight. Product formation was confirmed by LCMS. the reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure, to obtain tert-butyl (1-(5-methoxybenzofuran-2-carboxamido)piperidin-4-yl)carbamate (300 mg, 74% Yield) as an off white solid. LCMS 390.2 [M+H]$^+$; $^1$H NMR (400 MHz, DMSO-d$_6$) δ 9.62 (s, 1H), 7.53 (d, J=8.77 Hz, 1H), 7.44 (s, 1H), 7.24 (br. s., 1H), 6.97-7.08 (m, 1H), 6.84 (d, J=6.58 Hz, 1H), 3.79 (s, 3H), 3.23 (br. s., 1H), 2.95 (d, J=10.09 Hz, 2H), 2.62-2.81 (m, 2 H), 1.74 (d, J=9.65 Hz, 2H), 1.53 (d, J=10.52 Hz, 2H), 1.38 (s, 9H).

Step 2—Synthesis of N-(4-aminopiperidin-1-yl)-5-methoxybenzofuran-2-carboxamide 2,2,2-trifluoroacetate To a stirred solution of tert-butyl (1-(5-methoxybenzofuran-2-carboxamido)piperidin-4-yl)carbamate (300 mg, 0.77 mmol, 1.0 equiv) in DCM (05 mL), was added trifluoroacetic acid (02 mL) and the resultant reaction mixture was stirred at RT for overnight under nitrogen atmosphere. Reaction was monitored by TLC and LCMS. After completion of reaction, the reaction mixture was concentrated under reduced pressure. The crude product crystallized in diethyl ether and dried under vacuum to obtain N-(4-aminopiperidin-1-yl)-5-methoxybenzofuran-2-carboxamide 2,2,2-trifluoroacetate (300 mg) as an off white solid. LCMS 290.2 [M+H]$^+$; $^1$H NMR (400 MHz, DMSO-d$_6$) δ 9.76 (br. s., 1H), 7.88 (br. s., 2H), 7.54 (d, J=8.77 Hz, 1H), 7.45 (br. s., 1H), 7.25 (br. s., 1H), 7.05 (d, J=7.45 Hz, 1H), 3.80 (s, 3 H), 3.02 (d, J=8.77 Hz, 2H), 2.79 (t, J=10.74 Hz, 2H), 1.92 (d, J=11.40 Hz, 2H), 1.65 (d, J=10.52 Hz, 2H).

Step 3 Synthesis of (R)-N-(4-((3-(4-chloro-3-fluorophenoxy)-2-hydroxypropyl)amino)piperidin-1-yl)-5-methoxybenzofuran-2-carboxamide To a stirred solution of N-(4-aminopiperidin-1-yl)-5-methoxybenzofuran-2-carboxamide trifluoroacetate (200 mg, 0.51 mmol, 1.0 equiv) (R)-2-((4-chloro-3-fluorophenoxy)methyl)oxirane (104 mg, 0.51 mmol, 1.0 equiv) in DMF (05 mL), was added TEA (0.3 mL, 2.04 mmol, 4.0 equiv) and the resultant reaction mixture was heated at 90° C. for overnight. Progress of the reaction was monitored by LCMS. After completion of reaction, the reaction mixture was diluted with water (100 mL) and extracted with EtOAc (50 mL×2). The combined organic layer was washed with water (50 mL×4), dried over anhydrous sodium sulfate and concentrated under reduced pressure to obtain crude which was purified by reversed-phase HPLC to obtain (R)-N-(4-((3-(4-chloro-3-fluorophenoxy)-2-hydroxypropyl)amino)piperidin-1-yl)-5-methoxybenzofuran-2-carboxamide (Compound 69-60 mg, 24% Yield) as a white solid. LCMS 491.16 [M+H]$^+$; $^1$H NMR (400 MHz, DMSO-d$_6$) δ 9.65 (s, 1H), 8.24 (s, 1H), 7.41-7.59 (m, 3H), 7.24 (br. s., 1H), 6.98-7.09 (m, 2H), 6.85 (d, J=8.77 Hz, 1H), 4.01 (d, J=5.26 Hz, 1H), 3.86-3.96 (m, 2H), 3.79 (s, 3H), 3.00 (d, J=9.65 Hz, 3H), 2.61-2.83 (m, 4H), 1.88 (br. s., 2H), 1.46 (br. s., 2H).

Example 41

Synthesis of 5-chloro-N-(4-(2-(4-chloro-3-fluoro-phenoxy) acetamido) piperidin-1-yl)-2,3-dihydrobenzofuran-2-carboxamide

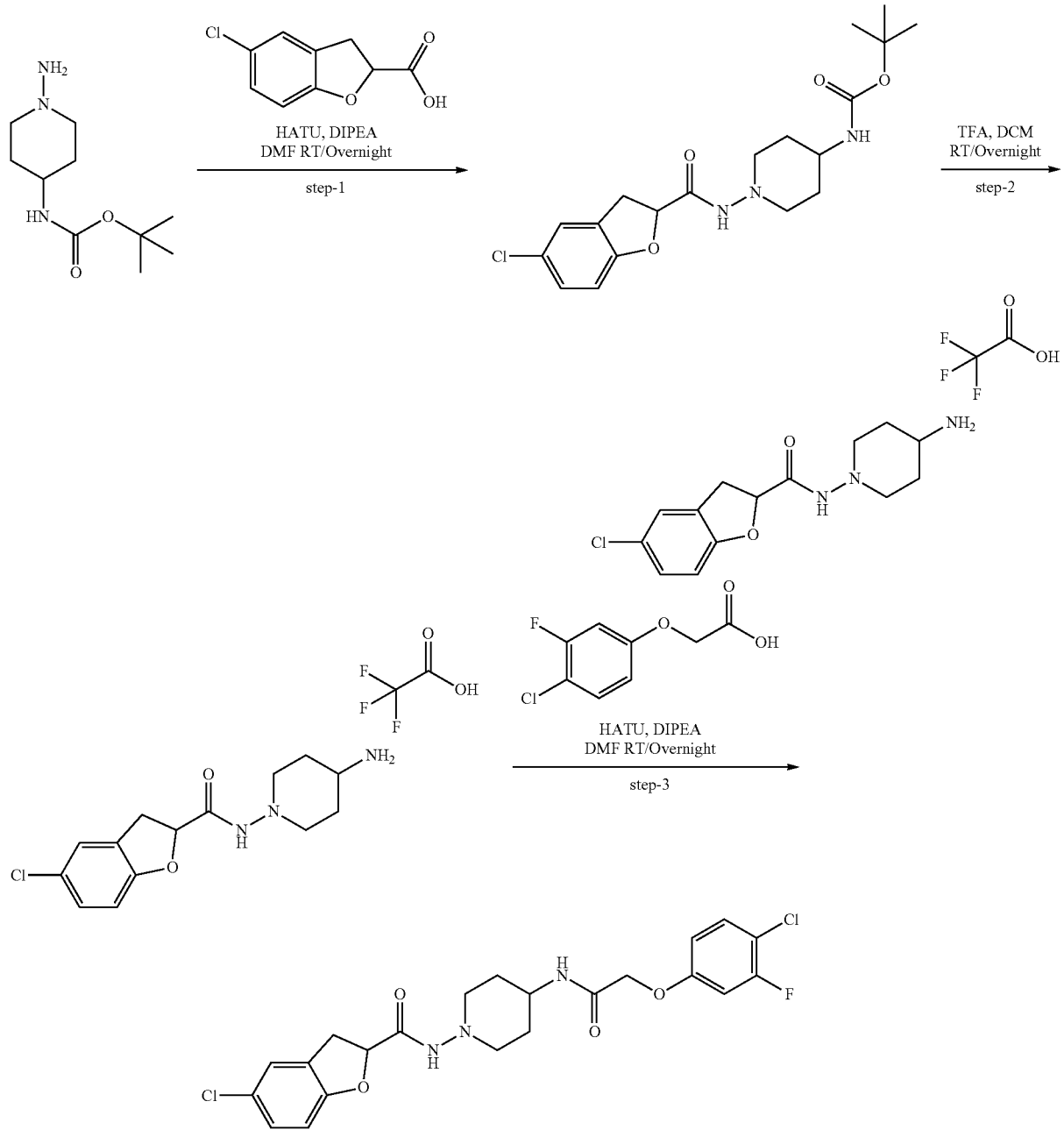

Step 1—Synthesis of tert-butyl (1-(5-chloro-2,3-dihydrobenzofuran-2-carboxamido)piperidin-4-yl) carbamate To a stirred solution of tert-butyl (1-aminopiperidin-4-yl) carbamate (0.200 g, 0.93 mmol, 1.0 equiv) in DMF (05 mL) was added HATU (0.706 g, 1.86 mmol, 2.0 equiv) at RT and stirred for 10 minutes. 5-chloro-2,3-dihydrobenzofuran-2-carboxylic acid (0.184 g, 0.93 mmol, 1.0 equiv) was added followed by the addition of DIPEA (0.5 mL, 2.79 mmol, 3.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to obtain tert-butyl (1-(5-chloro-2,3-dihydrobenzofuran-2-carboxamido)piperidin-4-yl)carbamate (0.300 g, 81% yield) as an off white solid. LCMS 396.2 [M+H]$^+$; $^1$H NMR (400 MHz, DMSO-d$_6$) δ 9.16 (s, 1H), 7.23-7.29 (m, 1H), 7.10-7.17 (m, 1H), 6.78-6.84 (m, 2H), 5.06 (dd, J=10.09, 7.02 Hz, 1H), 3.44 (d, J=10.52 Hz, 1H), 3.13-3.22 (m, 2H), 2.82-2.91 (m, 2H), 2.57-2.64 (m, 2H), 1.69 (br. s., 2H), 1.46 (d, J=11.84 Hz, 2H), 1.37 (s, 9H).

Step 2—Synthesis of N-(4-aminopiperidin-1-yl)-5-chloro-2,3-dihydrobenzofuran-2-carboxamide 2,2,2-trifluoroacetate To a stirred solution of tert-butyl (1-(5-chloro-2,3-dihydrobenzofuran-2-carboxamido)piperidin-4-yl)carbamate (0.300 g, 0.75 mmol, 1.0 equiv) in DCM (10 mL), was added trifluoroacetic acid (0.3 mL) and the resultant reaction mixture was stirred at RT for 1 h under nitrogen atmosphere. Reaction was monitored by TLC and LCMS. After completion of reaction, the reaction mixture was concentrated under reduced pressure to obtain sticky crude compound which was triturated with hexane (10 mL) and diethyl ether and dried under vacuum to obtain N-(4-aminopiperidin-1-yl)-5-chloro-2,3-dihydrobenzofuran-2-carboxamide 2,2,2-trifluoroacetate (0.200 g, 90% yield) as an off white solid. LCMS 296.2 [M+H]$^+$; $^1$H NMR (400 MHz, DMSO-d$_6$) δ 9.32 (br. s., 1H), 7.24-7.32 (m, 1H), 7.15 (d, J=7.89 Hz, 1H), 6.82 (d, J=7.89 Hz, 2H), 5.09 (d, J=7.45 Hz, 1H), 3.42-3.52 (m, 1H), 3.21 (dd, J=16.22, 6.58 Hz, 2 H), 2.99 (br. s., 2H), 2.59-2.68 (m, 2H), 1.89 (br. s., 2H), 1.59 (d, J=10.96 Hz, 2H).

Step 3—Synthesis of 5-chloro-N-(4-(2-(4-chloro-3-fluorophenoxy) acetamido) piperidin-1-yl)-2,3-dihydrobenzofuran-2-carboxamide To a stirred solution of N-(4-aminopiperidin-1-yl)-5-chloro-2,3-dihydrobenzofuran-2-carboxamide 2,2,2-trifluoroacetate salt (0.200 g, 0.48 mmol, 1.0 equiv) in DMF (05 mL) was added HATU (0.364 g, 0.96 mmol, 2.0 equiv) at RT and stirred for 10 minutes. 2-(4-chloro-3-fluorophenoxy) acetic acid (0.099 g, 0.48 mmol, 1.0 equiv) was added followed by the addition of DIPEA (0.3 mL, 1.44 mmol, 3.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to obtain 5-chloro-N-(4-(2-(4-chloro-3-fluorophenoxy) acetamido) piperidin-1-yl)-2,3-dihydrobenzofuran-2-carboxamide (Compound 11-0.200 g, 86% Yield) as an off white solid. LCMS 482.3 [M+H]$^+$; $^1$H NMR (400 MHz, DMSO-d$_6$) δ 9.23 (s, 1H), 8.04 (d, J=7.89 Hz, 1H), 7.48-7.54 (m, 1H), 7.24-7.33 (m, 1H), 7.05-7.20 (m, 2H), 6.76-6.88 (m, 2H), 5.07 (dd, J=10.09, 7.02 Hz, 1H), 4.51 (s, 2H), 3.60 (br. s., 1H), 3.43 (dd, J=16.22, 10.09 Hz, 1H), 3.19 (d, J=6.58 Hz, 1H), 2.87 (d, J=14.03 Hz, 3H), 2.65 (d, J=12.72 Hz, 1H), 1.70 (br. s., 2H), 1.57 (d, J=8.77 Hz, 2H).

Example 42

Synthesis of 5-chloro-N-(1-(2-(4-chloro-3-fluorophenoxy)acetamido)piperidin-4-yl)-2,3-dihydrobenzofuran-2-carboxamide

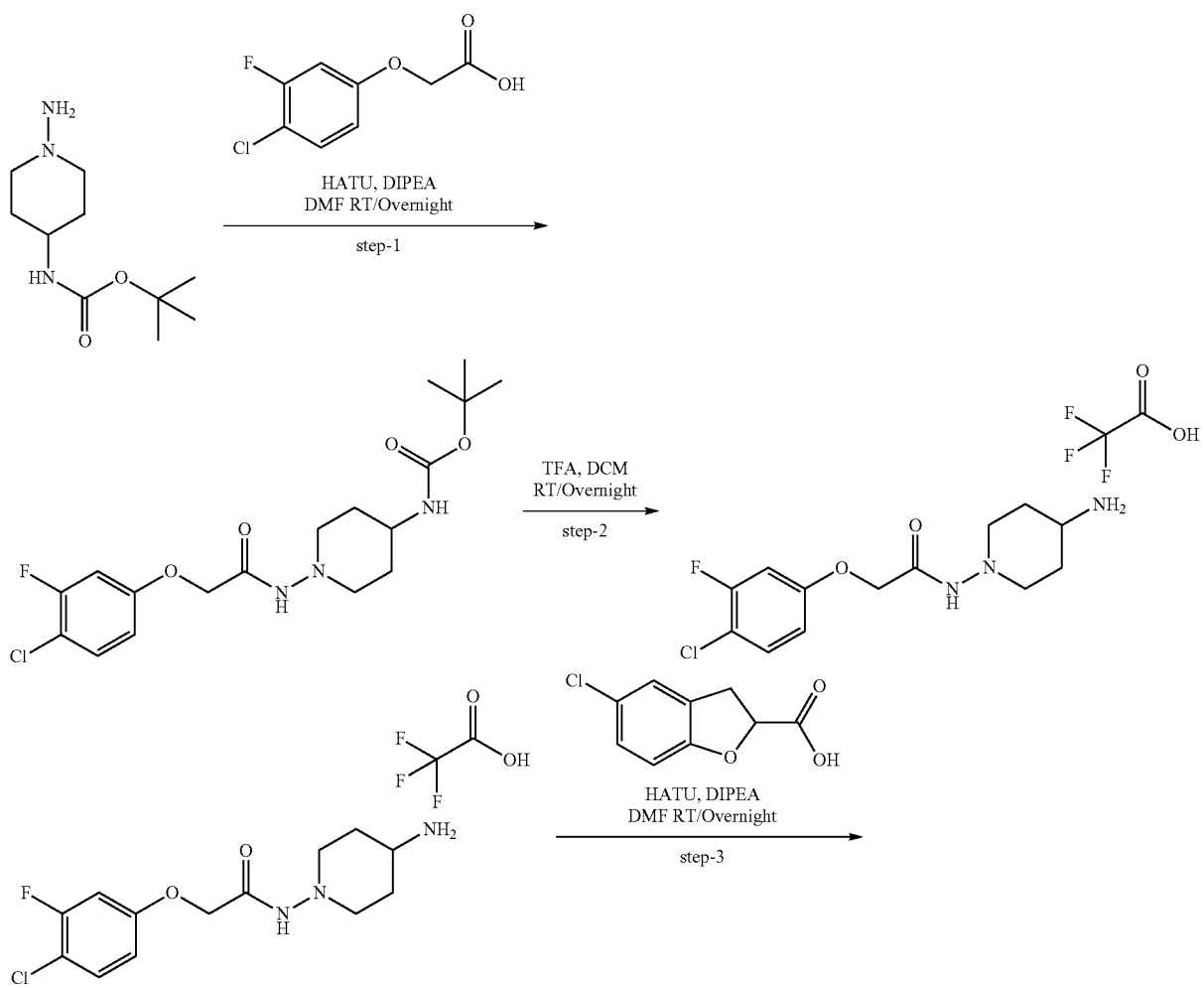

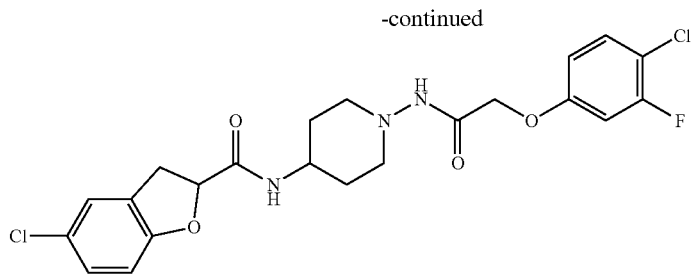

Step 1—Synthesis of tert-butyl (1-(2-(4-chloro-3-fluorophenoxy)acetamido)piperidin-4-yl)carbamate To a stirred solution of tert-butyl (1-aminopiperidin-4-yl)carbamate (0.200 g, 0.93 mmol, 1.0 equiv) in DMF (05 mL) was added HATU (0.706 g, 1.86 mmol, 2.0 equiv) at RT and stirred for 10 minutes. 2-(4-chloro-3-fluorophenoxy)acetic acid (0.190 g, 0.93 mmol, 1.0 equiv) was added followed by the addition of DIPEA (0.5 mL, 2.79 mmol, 3.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to obtain tert-butyl (1-(2-(4-chloro-3-fluorophenoxy)acetamido)piperidin-4-yl)carbamate (0.300 g, 80% yield) as an off white solid. LCMS 402.2 [M+H]$^+$; $^1$H NMR (400 MHz, DMSO-d$_6$) δ 9.08 (s, 1H), 8.74 (s, 1 H), 7.44-7.51 (m, 1H), 7.05 (dd, J=11.40, 2.63 Hz, 1H), 6.83 (dd, J=9.43, 2.41 Hz, 1H), 4.88 (s, 2H), 4.46 (s, 1H), 3.20 (br. s., 1H), 2.83-2.91 (m, 2H), 2.57-2.64 (m, 1H), 1.72 (br. s., 2 H), 1.44-1.53 (m, 2H), 1.38 (s, 9H).

Step 2—Synthesis of N-(4-aminopiperidin-1-yl)-2-(4-chloro-3-fluorophenoxy)acetamide 2,2,2-trifluoroacetate To a stirred solution of tert-butyl (1-(2-(4-chloro-3-fluorophenoxy)acetamido)piperidin-4-yl)carbamate (0.300 g, 0.74 mmol, 1.0 equiv) in DCM (10 mL). was added trifluoroacetic acid (0.3 mL) and the resultant reaction mixture was stirred at RT for 1 h under nitrogen atmosphere. Reaction was monitored by TLC and LCMS. After completion of reaction, the reaction mixture was concentrated under reduced pressure to obtain sticky crude compound which was triturated with hexane (10 mL) and diethyl ether and dried under vacuum to obtain N-(4-aminopiperidin-1-yl)-2-(4-chloro-3-fluorophenoxy)acetamide 2,2,2-trifluoroacetate (0.200 g, 90% yield) as an off white solid. LCMS 302.1 [M+H]$^+$; $^1$H NMR (400 MHz, DMSO-d$_6$) δ 9.08 (s, 1H), 8.74 (s, 1H), 7.44-7.51 (m, 1H), 7.05 (dd, J=11.40, 2.63 Hz, 1H), 6.83 (dd, J=9.43, 2.41 Hz, 1H), 4.88 (s, 2H), 4.46 (s, 1H), 3.20 (br. s., 1H), 2.83-2.91 (m, 2H), 2.57-2.64 (m, 1H), 1.72 (br. s., 2H), 1.44-1.53 (m, 2H). Step 3—Synthesis of 5-chloro-N-(1-(2-(4-chloro-3-fluorophenoxy)acetamido)piperidin-4-yl)-2,3-dihydrobenzofuran-2-carboxamide:

To a stirred solution of N-(4-aminopiperidin-1-yl)-2-(4-chloro-3-fluorophenoxy)acetamide 2,2,2-trifluoroacetate (0.200 g, 0.48 mmol, 1.0 equiv) in DMF (05 mL) was added HATU (0.364 g, 0.96 mmol, 2.0 equiv) at RT and stirred for 10 minutes. 5-chloro-2,3-dihydrobenzofuran-2-carboxylic acid (0.095 g, 0.48 mmol, 1.0 equiv) was added followed by the addition of DIPEA (0.3 mL, 1.44 mmol, 3.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to obtain 5-chloro-N-(1-(2-(4-chloro-3-fluorophenoxy)acetamido)piperidin-4-yl)-2,3-dihydrobenzofuran-2-carboxamide (Compound 12-0.200 g, 86% Yield) as an off white solid. LCMS 482.3 [M+H]$^+$; $^1$H NMR (400 MHz, DMSO-d$_6$) δ 9.13 (s, 1H), 8.79 (br. s., 1H), 8.14 (br. s., 1H), 7.46-7.54 (m, 1H), 7.27 (s, 1H), 7.16 (d, J=8.33 Hz, 1H), 6.99 (dd, J=11.40, 2.63 Hz, 1H), 6.83 (d, J=2.63 Hz, 1H), 4.47 (s, 2 H), 3.57 (br. s., 1H), 3.41-3.48 (m, 1H), 3.21 (dd, J=16.01, 6.80 Hz, 2H), 3.04 (br. s., 1H), 2.88 (br. s., 1H), 2.59-2.71 (m, 2H), 1.64-1.77 (m, 4H).

Example 43

Synthesis of 2-(4-chloro-3-fluorophenoxy)-N-(1-((3-(4-chloro-3-fluorophenoxy)-2-hydroxypropyl)amino)piperidin-4-yl)acetamide

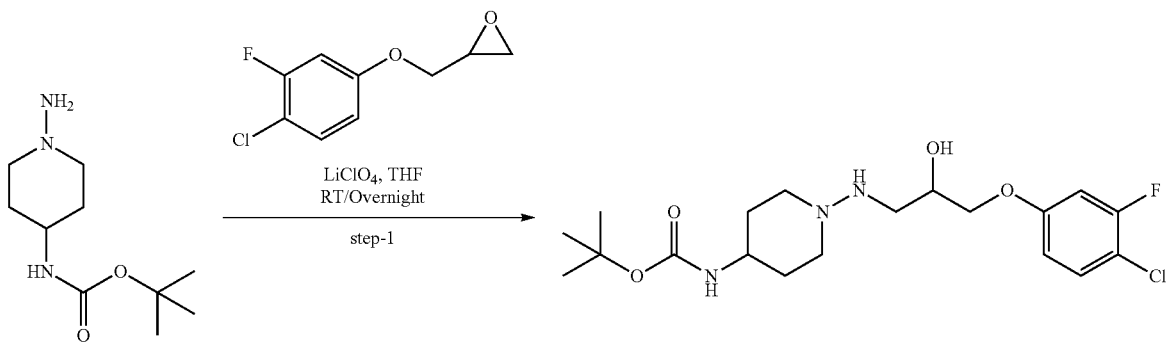

-continued
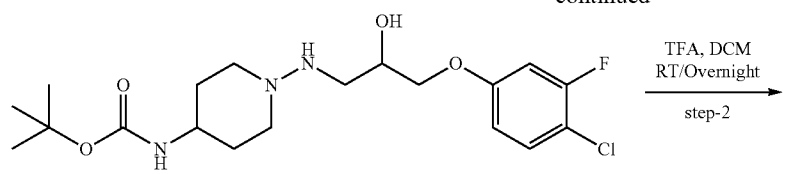
TFA, DCM
RT/Overnight
step-2
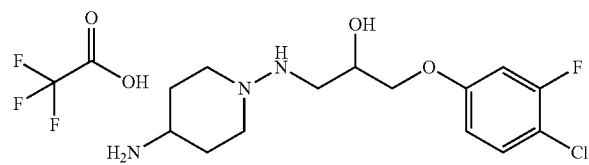
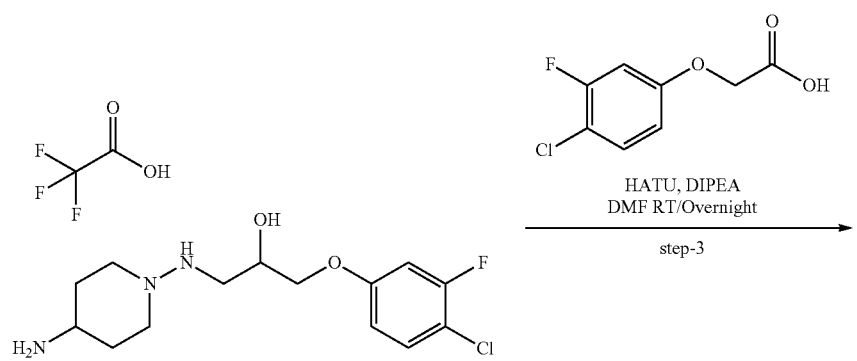
HATU, DIPEA
DMF RT/Overnight
step-3
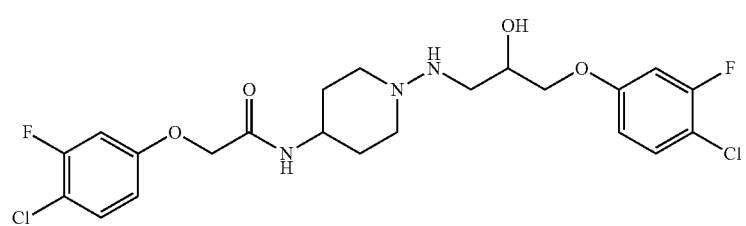

Step 1—Synthesis of tert-butyl (1-((3-(4-chloro-3-fluorophenoxy)-2-hydroxypropyl)amino)piperidin-4-yl)carbamate:

To a stirred solution of tert-butyl (1-aminopiperidin-4-yl)carbamate (0.500 g, 2.3 mmol, 1.0 equiv) in THF (05 mL) was added LiClO$_4$ (0.487 g, 4.6 mmol, 2.0 equiv) at RT and stirred for 10 minutes. Then 2-((4-chloro-3-fluorophenoxy)methyl)oxirane (0.469 g, 2.3 mmol, 1.0 equiv). The resulting reaction mixture was allowed to stir at RT for overnight. Product formation was confirmed by LCMS. The reaction mixture was diluted with water (50 mL) and extracted with EtOAc (100 mL×2). The combined organic layer was washed with water (50 mL), brine solution (50 mL×2), dried over anhydrous sodium sulfate and concentrated under reduced pressure to obtain tert-butyl (1-((3-(4-chloro-3-fluorophenoxy)-2-hydroxypropyl)amino)piperidin-4-yl)carbamate (0.400 g, 41% Yield) as a white solid. LCMS 418.1 [M+H]$^+$; $^1$H NMR (400 MHz, DMSO-d$_6$) δ 8.08 (br. s., 1H), 7.52 (t, J=8.99 Hz, 1H), 7.11 (dd, J=11.40, 3.07 Hz, 1H), 6.88 (d, J=8.77 Hz, 1H), 6.09 (br. s., 1H), 5.78 (br. s., 1H), 4.60 (br. s., 1H), 4.01 (d, J=4.82 Hz, 1H), 3.86 (d, J=12.28 Hz, 2H), 3.71-3.81 (m, 1H), 3.66 (br. s., 1H), 3.58 (br. s., 1H), 3.50 (d, J=13.15 Hz, 1H), 3.34 (br. s., 1H), 2.15 (d, J=14.03 Hz, 2H), 2.08 (s, 2H), 1.37 (s, 9H).

Step 2—Synthesis of 1-((4-aminopiperidin-1-yl)amino)-3-(4-chloro-3-fluorophenoxy)propan-2-ol 2,2,2-trifluoroacetate To a stirred solution of tert-butyl (1-((3-(4-chloro-3-fluorophenoxy)-2-hydroxypropyl) amino) piperidin-4-yl)carbamate (0.400 g, 0.95 mmol, 1.0 equiv) in DCM (10 mL), was added trifluoroacetic acid (4 mL) and the resultant reaction mixture was stirred at RT for 1 h under nitrogen atmosphere. Reaction was monitored by TLC and LCMS. After completion of reaction, the reaction mixture was concentrated under reduced pressure to obtain sticky crude compound which was triturated with hexane (10 mL) and diethyl ether and dried under vacuum to obtain 1-((4-aminopiperidin-1-yl)amino)-3-(4-chloro-3-fluorophenoxy)propan-2-ol 2,2,2-trifluoroacetate (0.400 g, Quantitative yield) as an off white solid. LCMS 318.2 [M+H]$^+$; $^1$H NMR (400 MHz, DMSO-d$_6$) δ 8.08 (br. s., 1H), 7.52 (t, J=8.99 Hz, 1H), 7.11 (dd, J=11.40, 3.07 Hz, 1H), 6.88 (d, J=8.77 Hz, 1H), 6.09 (br. s., 1H), 5.78 (br. s., 1H), 4.60 (br. s., 1H), 4.01 (d, J=4.82 Hz, 1H), 3.86 (d, J=12.28 Hz, 2H), 3.71-3.81 (m, 1H), 3.66 (br. s., 1H), 3.58 (br. s., 1H), 3.50 (d, J=13.15 Hz, 1H), 3.34 (br. s., 1H), 2.15 (d, J=14.03 Hz, 2H), 2.08 (s, 2H).

Step 3—Synthesis of 2-(4-chloro-3-fluorophenoxy)-N-(1-((3-(4-chloro-3-fluorophenoxy)-2-hydroxypropyl)amino)piperidin-4-yl)acetamide To a stirred solution of 1-((4-aminopiperidin-1-yl)amino)-3-(4-chloro-3-fluorophenoxy)propan-2-ol 2,2,2-trifluoroacetate (0.100 g, 0.23 mmol, 1.0 equiv) in DMF (05 mL) was added HATU (0.175 g, 0.46 mmol, 2.0 equiv) at RT and stirred for 10 minutes. 2-(4-chloro-3-fluorophenoxy)acetic acid (0.048 g, 0.23 mmol, 1.0 equiv) was added followed by the addition of DIPEA (0.2 mL, 0.69 mmol, 3.0 equiv). Product formation was confirmed by LCMS. the reaction mixture was diluted with water (50 mL) and extracted with EtOAc (50 mL×2). The combined organic layer was washed with water (50 mL), brine solution (50 mL×2), dried over anhydrous sodium sulfate and concentrated under reduced pressure to obtain crude which was purified by reverse phase of HPLC to obtain 2-(4-chloro-3-fluorophenoxy)-N-(1-((3-(4-chloro-3-fluorophenoxy)-2-hydroxypropyl)amino)piperidin-4-yl)acetamide (Compound 7-0.015 g, 13% Yield) as an off white solid. LCMS 504.3 [M+H]$^+$; $^1$H NMR (400 MHz, DMSO-d$_6$) δ 8.50 (br. s., 1H), 8.41 (br. s., 1H), 7.50 (td, J=8.77, 3.07 Hz, 2H), 7.04-7.16 (m, 2H), 6.87 (t, J=7.45 Hz, 2H), 6.07 (br. s., 1H), 4.58 (s, 2H), 4.01 (d, J=6.14 Hz, 3H), 3.84 (br. s., 2H), 3.75 (br. s., 1H), 3.53 (d, J=13.59 Hz, 3H), 2.02 (br. s., 3H), 1.94 (br. s., 1H).

Example 44

Synthesis of 6-chloro-N-(1-((3-(4-chloro-3-fluorophenoxy)-2-hydroxypropyl)amino)piperidin-4-yl)quinoline-2-carboxamide

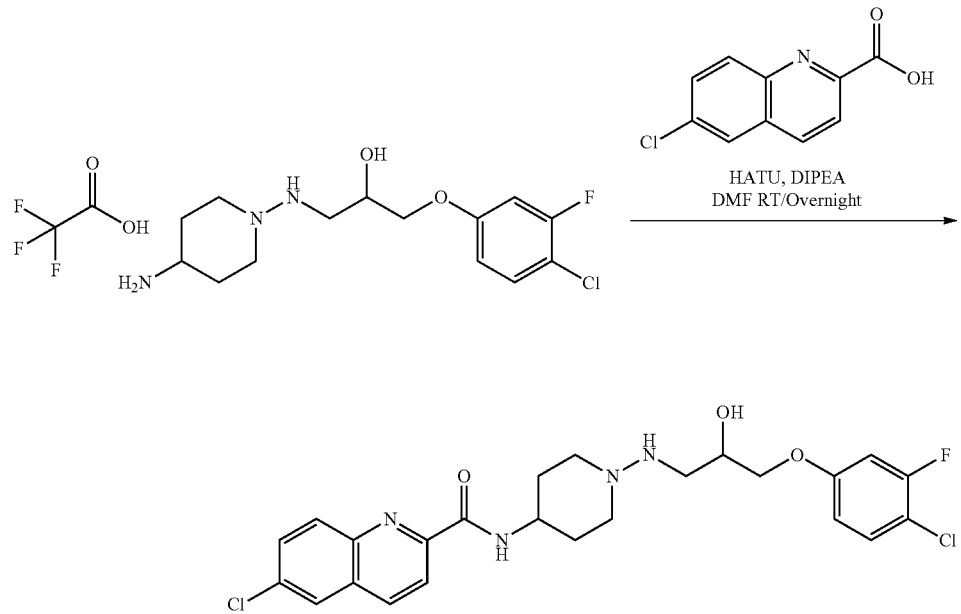

To a stirred solution of 1-((4-aminopiperidin-1-yl)amino)-3-(4-chloro-3-fluorophenoxy)propan-2-ol 2,2,2-trifluoroacetatesalt (0.100 g, 0.23 mmol, 1.0 equiv) in DMF (05 mL) was added HATU (0.175 g, 0.46 mmol, 2.0 equiv) at RT and stirred for 10 minutes. 6-chloroquinoline-2-carboxylic acid (0.048 g, 0.23 mmol, 1.0 equiv) was added followed by the addition of DIPEA (0.2 mL, 0.69 mmol, 3.0 equiv). Product formation was confirmed by LCMS. The reaction mixture was diluted with water (50 mL) and extracted with EtOAc (50 mL×2). The combined organic layer was washed with water (50 mL), brine solution (50 mL×2), dried over anhydrous sodium sulfate and concentrated under reduced pressure to obtain crude which was purified by reverse phase of HPLC to obtain 6-chloro-N-(1-((3-(4-chloro-3-fluorophenoxy)-2-hydroxypropyl)amino)piperidin-4-yl)quinoline-2-carboxamide (Compound 25-0.020 g, 17% Yield) as an off white solid. LCMS 507.4 [M+H]+; 1H NMR (400 MHz, DMSO-d6) δ 8.96 (d, J=8.77 Hz, 1H), 8.57 (d, J=8.77 Hz, 1H), 8.28 (d, J=2.63 Hz, 1H), 8.16 (d, J=9.21 Hz, 1H), 8.21 (d, J=8.33 Hz, 1H), 7.91 (dd, J=9.21, 2.19 Hz, 1H), 7.52 (t, J=8.99 Hz, 1H), 7.14 (dd, J=11.18, 2.85 Hz, 1H), 6.84-6.97 (m, 2H), 6.16 (br. s., 1H), 4.67 (br. s., 1H), 4.26 (br. s., 1 H), 3.92-4.08 (m, 3H), 3.81 (d, J=13.15 Hz, 1H), 3.54-3.71 (m, 3H), 2.24-2.37 (m, 2H), 2.08 (br. s., 2H).

Example 45

Synthesis of 5-chloro-N-(1-((3-(4-chloro-3-fluorophenoxy)-2-hydroxypropyl)amino)piperidin-4-yl)-2,3-dihydrobenzofuran-2-carboxamide

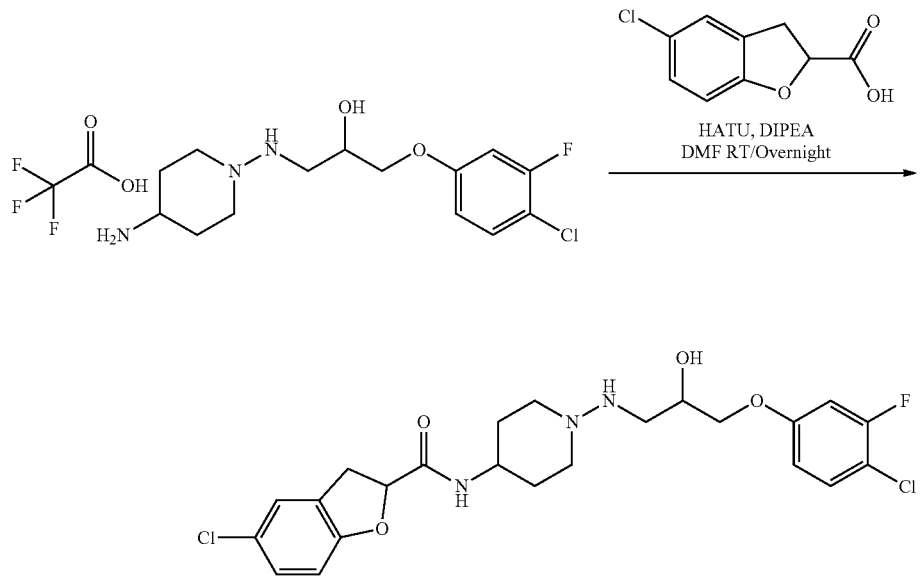

To a stirred solution of 1-((4-aminopiperidin-1-yl)amino)-3-(4-chloro-3-fluorophenoxy)propan-2-ol 2,2,2-trifluoroacetatesalt (0.100 g, 0.23 mmol, 1.0 equiv) in DMF (05 mL) was added HATU (0.175 g, 0.46 mmol, 2.0 equiv) at RT and stirred for 10 minutes. 5-chloro-2,3-dihydrobenzofuran-2-carboxylic acid (0.046 g, 0.23 mmol, 1.0 equiv) was added followed by the addition of DIPEA (0.2 mL, 0.69 mmol, 3.0 equiv). Product formation was confirmed by LCMS. The reaction mixture was diluted with water (50 mL) and extracted with EtOAc (50 mL×2). The combined organic layer was washed with water (50 mL), brine solution (50 mL×2), dried over anhydrous sodium sulfate and concentrated under reduced pressure to obtain crude which was purified by reverse phase of HPLC to obtain 5-chloro-N-(1-((3-(4-chloro-3-fluorophenoxy)-2-hydroxypropyl)amino)piperidin-4-yl)-2,3-dihydrobenzofuran-2-carboxamide (Compound 70-0.020 g, 17% Yield) as an off white solid. LCMS 498.3 [M+H]+; 1H NMR (400 MHz, DMSO-d6) δ 8.48 (br. s., 1H), 8.38 (br. s., 1H), 7.46-7.54 (m, 1H), 7.28 (s, 1H), 7.08-7.24 (m, 2H), 6.83-6.95 (m, 2H), 6.06 (br. s., 1H), 5.21 (dd, J=9.87, 6.80 Hz, 1 H), 4.01 (dd, J=9.65, 4.38 Hz, 2H), 3.86 (d, J=12.28 Hz, 2H), 3.74 (br. s., 1H), 3.44-3.58 (m, 4H), 3.14-3.26 (m, 2H), 1.99 (br. s., 4H).

Example 46

Synthesis of 5-chloro-N-(1-((3-(4-chloro-3-fluoro-phenoxy)-2-hydroxypropyl)amino)piperidin-4-yl)benzofuran-2-carboxamide

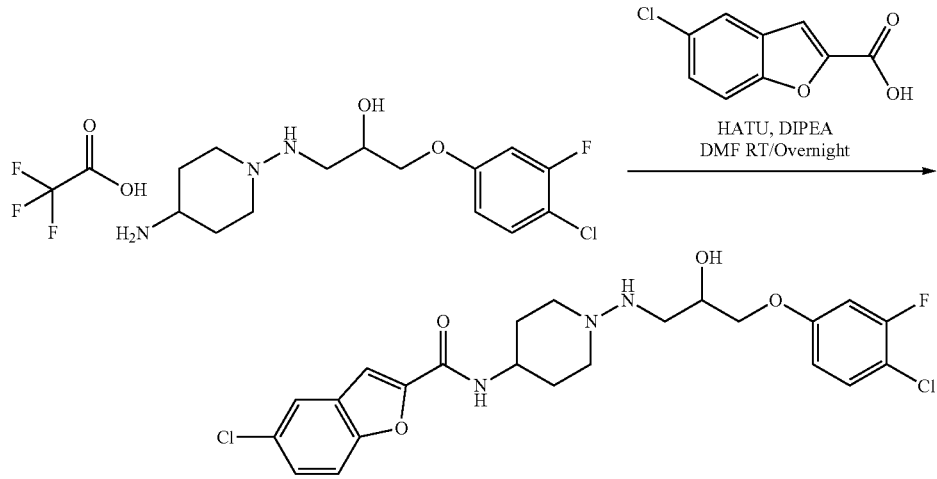

To a stirred solution of 1-((4-aminopiperidin-1-yl)amino)-3-(4-chloro-3-fluorophenoxy)propan-2-ol trifluoroacetate (0.100 g, 0.23 mmol, 1.0 equiv) in DMF (05 mL) was added HATU (0.175 g, 0.46 mmol, 2.0 equiv) at RT and stirred for 10 minutes. 5-chlorobenzofuran-2-carboxylic acid (0.045 g, 0.23 mmol, 1.0 equiv) was added followed by the addition of DIPEA (0.2 mL, 0.69 mmol, 3.0 equiv). Product formation was confirmed by LCMS. The reaction mixture was diluted with water (50 mL) and extracted with EtOAc (50 mL×2). The combined organic layer was washed with water (50 mL), brine solution (50 mL×2), dried over anhydrous sodium sulfate and concentrated under reduced pressure to obtain crude which was purified by reverse phase of HPLC to obtain 5-chloro-N-(1-((3-(4-chloro-3-fluorophenoxy)-2-hydroxypropyl)amino)piperidin-4-yl)benzofuran-2-carboxamide (Compound 26-0.020 g, 17% Yield) as an off white solid. LCMS 496.3 [M+H]$^+$; $^1$H NMR (400 MHz, DMSO-$d_6$) δ 8.93 (d, J=7.45 Hz, 1H), 7.89 (d, J=2.19 Hz, 1H), 7.71 (d, J=8.77 Hz, 1H), 7.62 (s, 1H), 7.43-7.55 (m, 2H), 7.13 (dd, J=11.40, 2.63 Hz, 1H), 6.89 (d, J=9.21 Hz, 1H), 6.15 (br. s., 1H), 4.69 (br. s., 1H), 4.21 (br. s., 1H), 3.92-4.05 (m, 3H), 3.88 (d, J=10.52 Hz, 1H), 3.58 (d, J=13.15 Hz, 3 H), 2.14 (br. s., 4H).

Example 47

Synthesis of 5-chloro-N-(4-(3-(4-chloro-3-fluoro-phenoxy)-2-hydroxypropyl) piperazin-1-yl)-2,3-dihydrobenzofuran-2-carboxamide

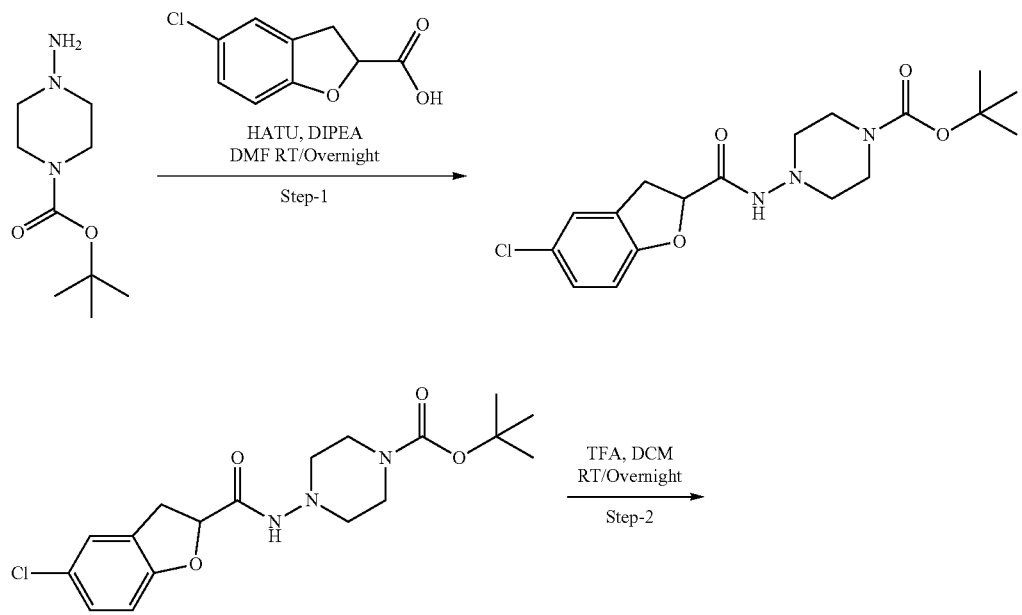

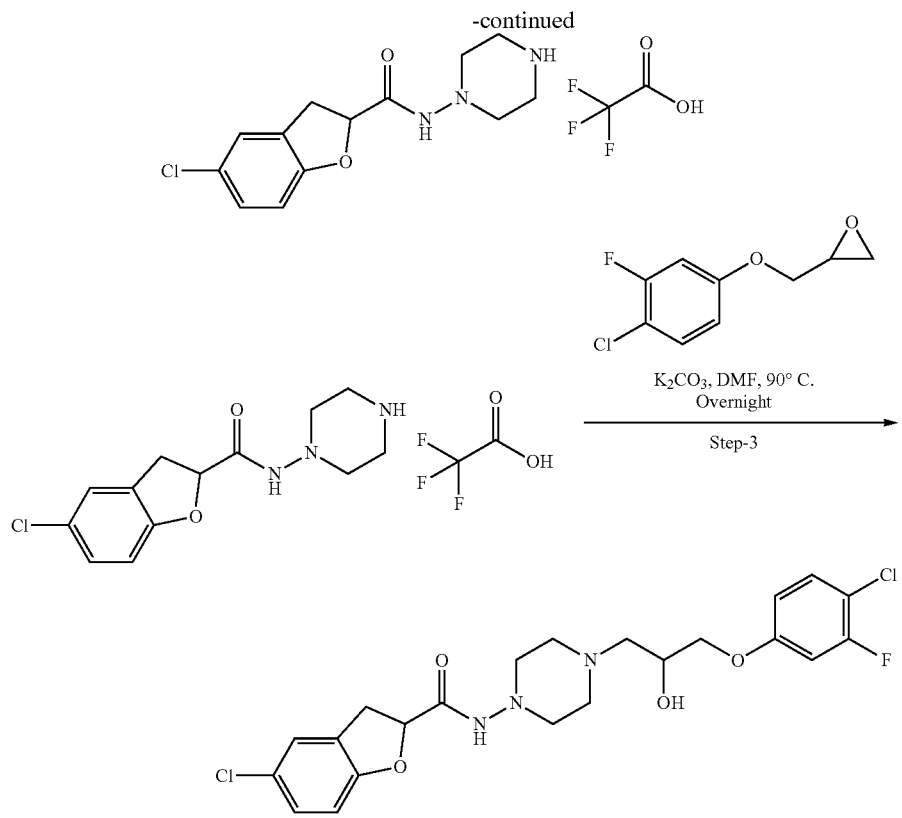

Step 1—Synthesis of tert-butyl 4-(S-chloro-2,3-dihydrobenzofuran-2-carboxamido)piperazine-1-carboxylate To a stirred solution of tert-butyl 4-aminopiperazine-1-carboxylate (0.200 g, 0.99 mmol, 1.0 equiv) in DMF (05 mL) was added HATU (0.752 g, 1.98 mmol, 2.0 equiv) at RT and stirred for 10 minutes. Then 5-chloro-2,3-dihydrobenzofuran-2-carboxylic acid (0.197 g, 0.99 mmol, 1.0 equiv) was added followed by the addition of DIPEA (0.5 mL, 2.97 mmol, 3.0 equiv). The resulting reaction mixture was allowed to stir at RT for overnight. Product formation was confirmed by LCMS. After completion of the reaction the reaction mixture was diluted with water (100 mL) and extracted with ethyl acetate (150 mL×2). Combined organic layer was washed with water (50 mL×4), dried over anhydrous sodium sulfate and concentrated under reduced pressure to obtain tert-butyl 4-(5-chloro-2,3-dihydrobenzofuran-2-carboxamido)piperazine-1-carboxylate (0.200 g, 52% yield) as an off white solid. LCMS 382.2 [M+H]$^+$; $^1$H NMR (400 MHz, DMSO-d$_6$) δ 9.67 (s, 1H), 7.28 (br. s., 1H), 7.16 (d, J=8.33 Hz, 1H), 6.84 (s, 1H), 5.10 (dd, J=10.09, 7.02 Hz, 1H), 3.23 (dd, J=16.01, 7.24 Hz, 4H), 2.92-3.07 (m, 4H), 2.03-2.14 (m, 2H), 1.37 (s, 9H).

Step 2—Synthesis of 5-chloro-N-(piperazin-1-yl)-2,3-dihydrobenzofuran-2-carboxamide 2,2,2-trifluoroacetate To a stirred solution of tert-butyl 4-(5-chloro-2,3-dihydrobenzofuran-2-carboxamido)piperazine-1-carboxylate (0.200 g, 0.52 mmol, 1.0 equiv) in DCM (10 mL), was added trifluoroacetic acid (02 mL) and the resultant reaction mixture was stirred at RT for 1 h under nitrogen atmosphere. Reaction was monitored by TLC and LCMS. After completion of reaction, the reaction mixture was concentrated under reduced pressure to obtain sticky crude compound which was triturated with hexane (10 mL) and diethyl ether and dried under vacuum to obtain 5-chloro-N-(piperazin-1-yl)-2,3-dihydrobenzofuran-2-carboxamide 2,2,2-trifluoroacetate (0.200 g, Quantitative yield) as a semisolid. LCMS 282.2 [M+H]$^+$; $^1$H NMR (400 MHz, DMSO-d$_6$) δ 9.67 (s, 1H), 8.64 (br. s., 1H), 7.28 (br. s., 1H), 7.16 (d, J=8.33 Hz, 1 H), 6.84 (s, 1H), 5.10 (dd, J=10.09, 7.02 Hz, 1H), 3.23 (dd, J=16.01, 7.24 Hz, 4H), 2.92-3.07 (m, 4H), 2.03-2.14 (m, 2H).

Step 3—Synthesis of 5-chloro-N-(4-(3-(4-chloro-3-fluorophenoxy)-2-hydroxypropyl)piperazin-1-yl)-2,3-dihydrobenzofuran-2-carboxamide To a stirred solution of 5-chloro-N-(piperazin-1-yl)-2,3-dihydrobenzofuran-2-carboxamide 2,2,2-trifluoroacetate (0.200 g, 0.50 mmol, 1 equiv) in DMF (05 mL) was added 2-((4-chloro-3-fluorophenoxy)methyl)oxirane (0.102 g, 0.50 mmol, 1.0 equiv) and K2CO$_3$ (0.276 g, 1.0 mmol, 2.0 equiv) at RT. The resultant reaction mixture was heated at 90° C. for overnight. Progress of the reaction was monitored by LCMS. After completion of the reaction the reaction mixture was diluted with water (100 mL) and extracted with ethyl acetate (100 mL×2). Combined organic layer was washed with water (50 mL×4), dried over anhydrous sodium sulfate and concentrated under reduced pressure. The crude product which was purified by reverse phase of HPLC to obtain 5-chloro-N-(4-(3-(4-chloro-3-fluorophenoxy)-2-hydroxypropyl) piperazin-1-yl)-2,3-dihydrobenzofuran-2-carboxamide (Compound 13-0.040 g, 17% Yield) a white solid. LCMS 484.4 [M+H]$^+$; $^1$H NMR (400 MHz, DMSO-d$_6$) δ 9.75 (br. s., 1H), 7.47 (br. s., 2H), 7.05-7.17 (m, 2H), 6.84 (t, J=7.89 Hz, 2H), 5.58 (s, 1H), 5.09 (br. s., 2H), 4.93 (br. s., 2H), 4.30 (s, 1H), 3.99 (br. s., 2H), 3.90 (br. s., 2H), 3.54 (br. s., 1H), 3.47 (br. s., 1H), 2.76 (br. s., 2H), 2.18 (br. s., 2H).

Example 48

Synthesis of 6-chloro-N-(4-(2-hydroxy-3-(4-(trifluoromethyl)phenoxy) propyl)piperazin-1-yl)quinoline-2-carboxamide

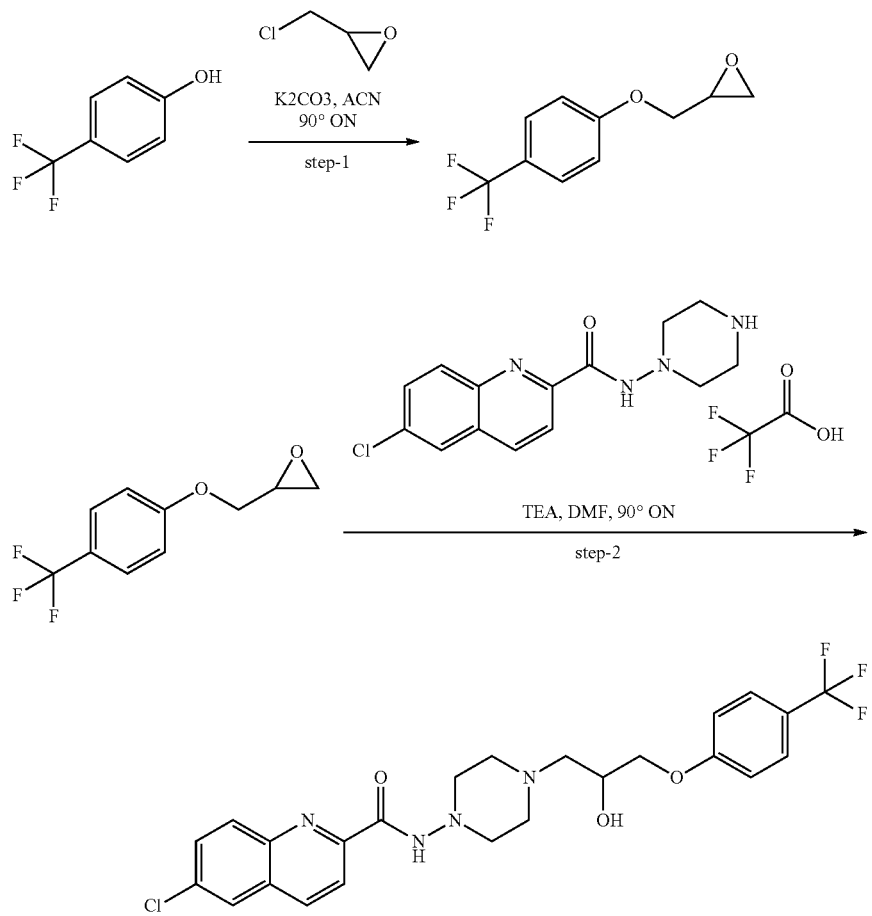

Step 1—Synthesis of 2-((4-(trifluoromethyl)phenoxy)methyl)oxirane

To a stirred solution of 4-(trifluoromethyl)phenol (1.0 g, 6.1 mmol, 1.0 equiv) 2-(chloromethyl)oxirane (0.681 g, 7.4 mmol, 1.2 equiv) in ACN (20 mL), was added K2CO3 (1.68 g, 12.2 mmol, 2.0 equiv) and the resultant reaction mixture was heated at 90° C. for overnight. Progress of the reaction was monitored by $^1$H NMR. After completion of reaction, the reaction mixture was diluted with water (100 mL) and extracted with EtOAc (100 mL×2). The combined organic layer was washed with water (50 mL), brine solution (50 mL×2), dried over anhydrous sodium sulfate and concentrated under reduced pressure to obtain 2-((4-(trifluoromethyl)phenoxy)methyl)oxirane (0.400 g, 30% Yield) as a yellow oil. $^1$H NMR (400 MHz, DMSO-d$_6$) δ 7.66 (m, J=8.33 Hz, 2H), 7.15 (m, J=8.77 Hz, 2H), 4.44 (dd, J=11.40, 2.63 Hz, 1H), 3.92 (dd, J=11.84, 6.58 Hz, 1H), 3.34-3.41 (m, 1H), 2.84-2.92 (m, 1H), 2.73 (dd, J=4.82, 2.63 Hz, 1H).

Step 2—Synthesis of 6-chloro-N-(4-(2-hydroxy-3-(4-(trifluoromethyl)phenoxy)propyl)piperazin-1-yl)quinoline-2-carboxamide To a stirred solution of 6-chloro-N-(piperazin-1-yl)quinoline-2-carboxamide 2,2,2-trifluoroacetate (0.200 g, 0.49 mmol, 1.0 equiv) 2-((4-(trifluoromethyl)phenoxy)methyl)oxirane (0.108 g, 0.49 mmol, 1.0 equiv) in DMF (05 mL), was added TEA (0.3 mL, 1.96 mmol, 2.0 equiv) and the resultant reaction mixture was heated at 90° C. for overnight. Progress of the reaction was monitored by LCMS. After completion of reaction, the reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure to obtain crude which was purified by reversed-phase HPLC to obtain 6-chloro-N-(4-(2-hydroxy-3-(4-(trifluoromethyl) phenoxy) propyl)piperazin-1-yl)quinoline-2-carboxamide (Compound 71-0.010 g, 05% Yield) as an off white solid. LCMS 509.4 [M+H]$^+$; $^1$H NMR (400 MHz, DMSO-d$_6$) δ 9.79 (s, 1H), 8.53 (d, J=8.77 Hz, 1H), 8.24 (d, J=2.19 Hz, 1H), 8.14 (t, J=8.99 Hz, 2H), 7.88 (dd, J=9.21, 2.19 Hz, 1H), 7.66 (m, J=8.77 Hz, 2H), 7.15 (m, J=8.33 Hz, 2H), 4.11 (br. s., 1H), 3.92-4.03 (m, 2H), 2.94 (br. s., 4H), 2.66 (br. s., 1H), 2.60 (br. s., 3H), 2.38-2.47 (m, 2H).

Example 49

Synthesis of 2-(4-chloro-3-fluorophenoxy)-N-(4-(2-(4-chloro-3-nitrophenoxy)acetamido)piperidin-1-yl)acetamide

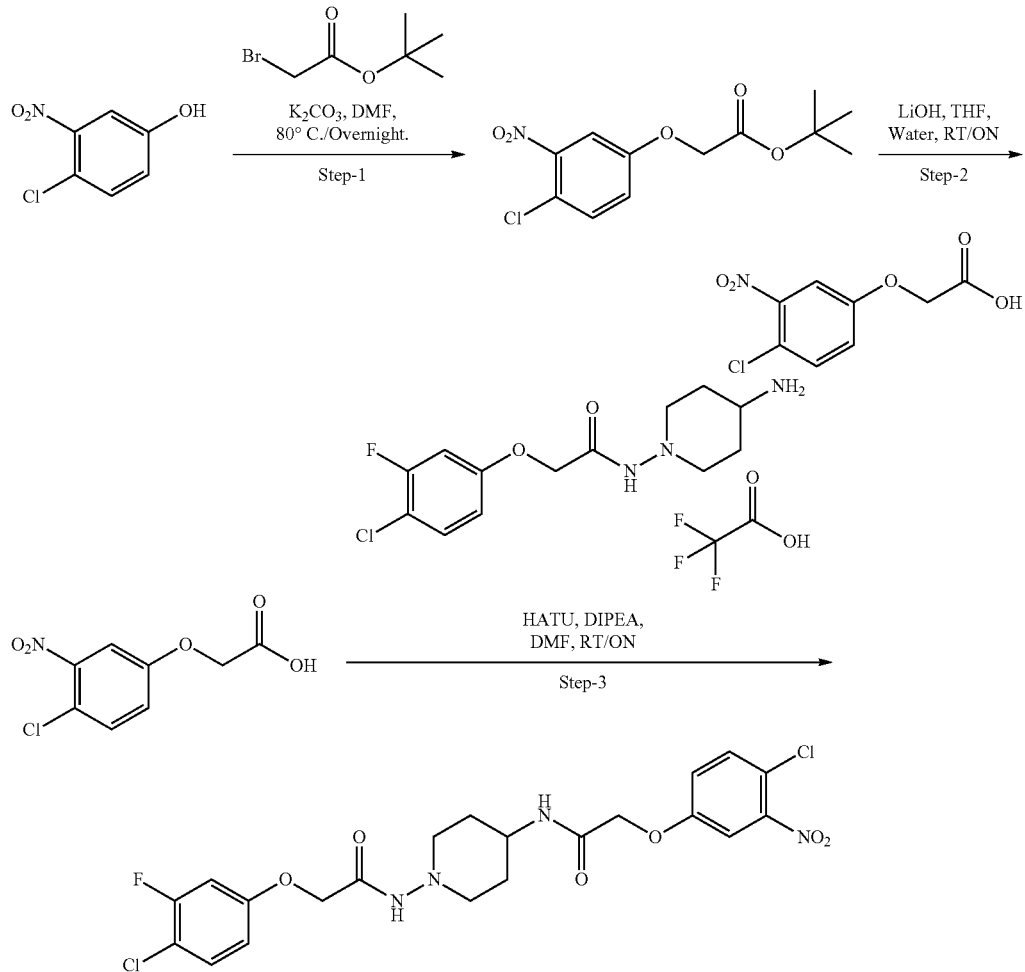

Step 1—Synthesis of tert-butyl 2-(4-chloro-3-nitrophenoxy)acetate

To a solution of 4-chloro-3-nitrophenol (1.0 g, 5.7 mmol, 1.0 equiv) in DMF (10 mL) was added tert-butyl 2-bromoacetate (1.33 g, 5.7 mmol, 1.2 equiv), $K_2CO_3$ (1.57 g, 11.4 mmol, 2.0 equiv). The resulting reaction mixture was heated at 80° C. for overnight. Product formation was confirmed by $^1$H NMR. After completion of reaction, the mixture was diluted with water (50 mL) and extracted with ethyl acetate (100 mL×2). Combined organic extracts were washed with water (50 mL×4), dried over anhydrous $Na_2SO_4$ and concentrated to obtain tert-butyl 2-(4-chloro-3-nitrophenoxy)acetate (1.0 g, 61%) as colorless oil. $^1$H NMR (400 MHz, DMSO-$d_6$) δ 7.62-7.75 (m, 2H), 7.29 (dd, J=8.77, 3.07 Hz, 1H), 4.82 (s, 2H), 1.42 (s, 9H).

Step 2—Synthesis of 2-(4-chloro-3-nitrophenoxy)acetic acid

To a stirred solution of tert-butyl 2-(4-chloro-3-nitrophenoxy)acetate (1.0 g, 3.4 mmol, 1.0 equiv) in THF (10 mL) and water (5 mL), was added LiOH (0.168 g, 6.9 mmol, 2.0 equiv). The mixture was allowed to stir at RT for overnight. Product formation was confirmed by $^1$H NMR Spectroscopy. After the completion of reaction, the reaction mixture was concentrated and diluted with water (50 mL). Aqueous layer was acidify with 3N HCl (pH ~ 3.0), extracted with EtOAc (50 mL×3). Combined organic extracts were washed with water (50 mL), dried over anhydrous $Na_2SO_4$ and concentrated to obtain 2-(4-chloro-3-nitrophenoxy)acetic acid (Quantitative Yield) as a brown solid. $^1$H NMR (400 MHz, DMSO-$d_6$) δ13.20 (br. s., 1H), 7.64-7.71 (m, 2H), 7.30 (dd, J=8.77, 3.07 Hz, 1H), 4.84 (s, 2H).

Step 3—Synthesis of 2-(4-chloro-3-fluorophenoxy)-N-(4-(2-(4-chloro-3-nitrophenoxy) acetamido)piperidin-1-yl)acetamide To a stirred solution of N-(4-aminopiperidin-1-yl)-2-(4-chloro-3-fluorophenoxy)acetamide 2,2,2-trifluoroacetate (0.200 g, 0.48 mmol, 1.0 equiv) in DMF (05 mL) was added HATU (0.364 g, 0.96 mmol, 2.0 equiv) at RT and stirred for 10 minutes. 2-(4-chloro-3-nitrophenoxy)acetic acid (0.111 g, 0.48 mmol, 1.0 equiv) was added followed by the addition of DIPEA (0.3 mL, 1.44 mmol, 3.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to obtain 2-(4-chloro-3-fluorophenoxy)-N-(4-(2-(4-chloro-3-nitrophenoxy)acetamido)piperidin-1-yl)acetamide (Compound 39-0.100 g, 40% Yield) a white solid. LCMS 515.3 [M+H]$^+$; $^1$H NMR (400 MHz, DMSO-d$_6$) δ 9.15 (s, 1H), 8.80 (br. s., 1H), 8.11 (d, J=8.33 Hz, 1H), 7.68-7.74 (m, 1H), 7.46-7.52 (m, 1H), 7.31 (dd, J=8.77, 3.07 Hz, 1 H), 7.06 (dd, J=11.18, 2.85 Hz, 1H), 6.84 (d, J=9.21 Hz, 1H), 4.90 (s, 2H), 4.47 (s, 2H), 3.61 (br. s., 1H), 3.07 (br. s., 1H), 2.90 (d, J=10.52 Hz, 1H), 2.57-2.71 (m, 2H), 1.73 (br. s., 2H), 1.48-1.67 (m, 2H).

Example 50

Synthesis of 2-(4-chloro-3-fluorophenoxy)-N-(1-(2-(4-chloro-3-nitrophenoxy)acetamido)piperidin-4-yl)acetamide

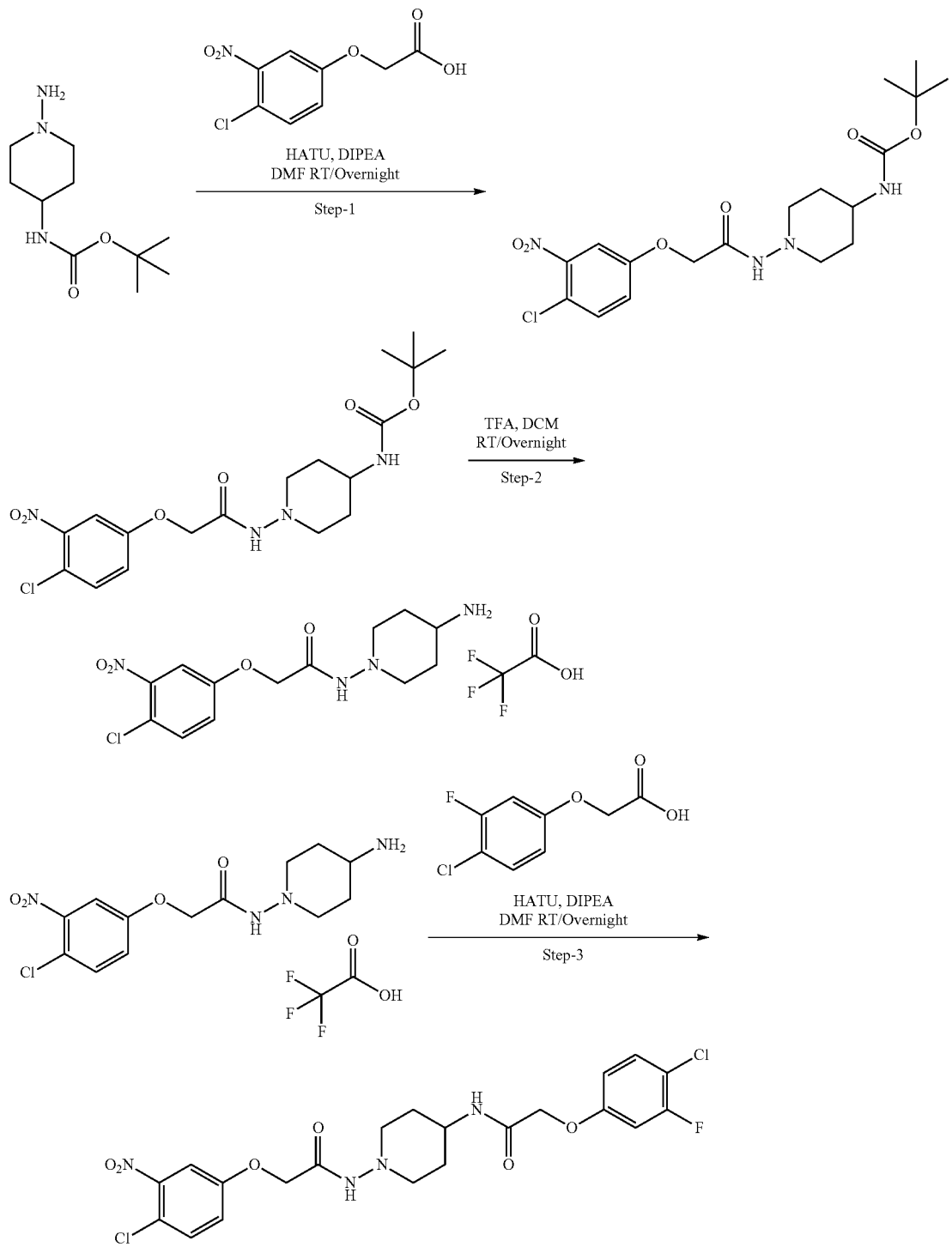

Step 1—Synthesis of tert-butyl (1-(2-(4-chloro-3-nitrophenoxy)acetamido)piperidin-4-yl)carbamate To a stirred solution of tert-butyl (1-aminopiperidin-4-yl)carbamate (0.200 g, 0.93 mmol, 1.0 equiv) in DMF (05 mL) was added HATU (0.706 g, 1.86 mmol, 2.0 equiv) at RT and stirred for 10 minutes. Then 2-(4-chloro-3-nitrophenoxy)acetic acid (0.213 g, 0.93 mmol, 1.0 equiv) was added followed by the addition of DIPEA (0.5 mL, 2.79 mmol, 3.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to obtain tert-butyl (1-(2-(4-chloro-3-nitrophenoxy)acetamido)piperidin-4-yl)carbamate (0.200 g, 50% yield) as a white solid. LCMS 429.3 [M+H]$^+$; $^1$H NMR (400 MHz, DMSO-d$_6$) δ 9.14 (s, 1H), 8.80 (s, 1 H), 7.67-7.75 (m, 1H), 7.26-7.30 (m, 1H), 6.83 (br. s., 1H), 4.98 (s, 2H), 4.56 (s, 1H), 3.17 (br. s., 1H), 3.03 (br. s., 1H), 2.84-2.90 (m, 1H), 2.56-2.63 (m, 1H), 1.71 (br. s., 2H), 1.47 (d, J=10.09 Hz, 2H), 1.38 (s, 9H).

Step 2—Synthesis of N-(4-aminopiperidin-1-yl)-2-(4-chloro-3-nitrophenoxy)acetamide trifluoroacetate To a stirred solution of tert-butyl (1-(2-(4-chloro-3-nitrophenoxy)acetamido)piperidin-4-yl)carbamate (0.200 g, 0.46 mmol, 1.0 equiv) in DCM (10 mL), was added trifluoroacetic acid (2 mL) and the resultant reaction mixture was stirred at RT for 1 h under nitrogen atmosphere. Reaction was monitored by TLC and LCMS. After completion of reaction, the reaction mixture was concentrated under reduced pressure to obtain sticky crude compound which was triturated with hexane (10 mL) and diethyl ether and dried under vacuum to obtain N-(4-aminopiperidin-1-yl)-2-(4-chloro-3-nitrophenoxy)acetamide trifluoroacetate (0.200 g, Quantitative yield) as a white solid. LCMS 329.1 [M+H]$^+$; $^1$H NMR (400 MHz, DMSO-d$_6$) δ 9.14 (s, 1H), 8.80 (s, 1H), 7.67-7.75 (m, 1H), 7.26-7.30 (m, 1H), 6.83 (br. s., 1H), 4.98 (s, 2H), 4.56 (s, 1H), 3.17 (br. s., 1H), 3.03 (br. s., 1H), 2.84-2.90 (m, 1H), 2.56-2.63 (m, 1H), 1.71 (br. s., 2H), 1.47 (d, J=10.09 Hz, 2H).

Step 3—Synthesis of 2-(4-chloro-3-fluorophenoxy)-N-(1-(2-(4-chloro-3-nitrophenoxy) acetamido) piperidin-4-yl)acetamide To a stirred solution of N-(4-aminopiperidin-1-yl)-2-(4-chloro-3-nitrophenoxy)acetamide 2,2,2-trifluoroacetate (0.200 g, 0.45 mmol, 1.0 equiv) in DMF (05 mL) was added HATU (0.342 g, 0.90 mmol, 2.0 equiv) at RT and stirred for 10 minutes. 2-(4-chloro-3-fluorophenoxy)acetic acid (0.093 g, 0.45 mmol, 1.0 equiv) was added followed by the addition of DIPEA (0.3 mL, 1.35 mmol, 3.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to gives crude which was purified by reverse phase of HPLC to obtain 2-(4-chloro-3-fluorophenoxy)-N-(1-(2-(4-chloro-3-nitrophenoxy)acetamido)piperidin-4-yl)acetamide (Compound 75-0.100 g, 43% Yield) as a white solid. LCMS 515.4 [M+H]$^+$; $^1$H NMR (400 MHz, DMSO-d$_6$) δ 9.20 (s, 1H), 8.85 (br. s., 1H), 8.05 (d, J=7.45 Hz, 1H), 7.65-7.73 (m, 1H), 7.50 (t, J=8.77 Hz, 1H), 7.23 (dd, J=8.99, 2.85 Hz, 1H), 7.05-7.10 (m, 1H), 6.86 (d, J=2.19 Hz, 1H), 5.00 (s, 2H), 4.51 (s, 2H), 3.61 (br. s., 2H), 3.06 (br. s., 1H), 2.90 (d, J=10.52 Hz, 1H), 2.67 (br. s., 1H), 1.74 (br. s., 2H), 1.61 (d, J=11.84 Hz, 2H).

Example 51

Synthesis of 5-chloro-N-(1-(2-(4-chloro-3-fluorophenoxy)acetamido)piperidin-4-yl)benzo[d]thiazole-2-carboxamide

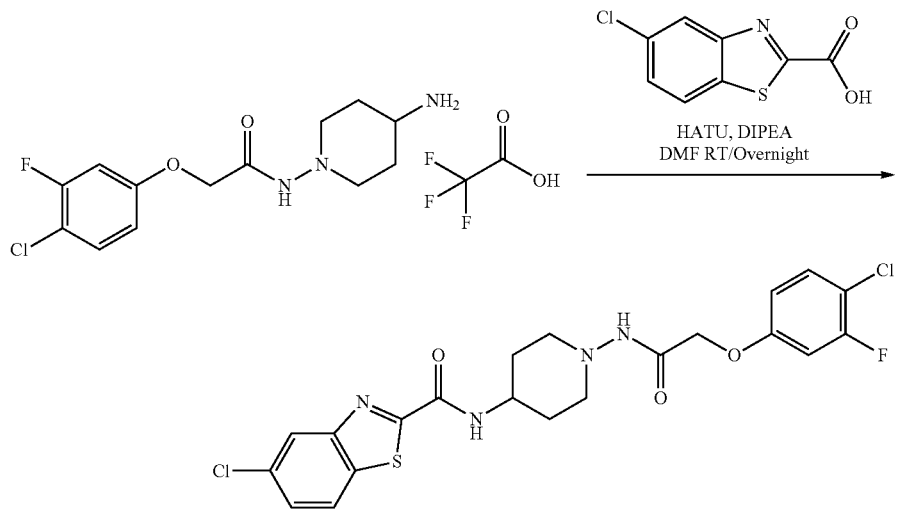

To a stirred solution of N-(4-aminopiperidin-1-yl)-2-(4-chloro-3-fluorophenoxy)acetamide 2,2,2-trifluoroacetate (0.200 g, 0.48 mmol, 1.0 equiv) in DMF (05 mL) was added HATU (0.364 g, 0.96 mmol, 2.0 equiv) at RT and stirred for 10 minutes. 5-chlorobenzo[d]thiazole-2-carboxylic acid (0.102 g, 0.48 mmol, 1.0 equiv) was added followed by the addition of DIPEA (0.3 mL, 1.44 mmol, 3.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to obtain 5-chloro-N-(1-(2-(4-chloro-3-fluorophenoxy)acetamido)piperidin-4-yl)benzo[d]thiazole-2-carboxamide (Compound 10-0.100 g, 42% Yield) as a white solid. LCMS 497.3 [M+H]⁺; $^1$H NMR (400 MHz, DMSO-d$_6$) δ 9.26 (d, J=8.33 Hz, 1H), 8.82 (s, 1H), 8.28 (d, J=8.77 Hz, 1H), 8.17 (s, 1H), 7.65 (dd, J=8.55, 1.97 Hz, 1H), 7.45-7.54 (m, 1H), 7.07 (d, J=14.03 Hz, 1H), 6.85 (d, J=10.96 Hz, 1H), 4.49 (s, 2H), 3.80 (br. s., 1H), 3.07-3.18 (m, 2H), 2.93 (d, J=10.96 Hz, 1H), 2.71 (br. s., 1H), 1.82 (d, J=11.84 Hz, 4H).

Example 52

Synthesis of 5-chloro-N-(4-(2-(4-chloro-3-fluorophenoxy)acetamido)piperidin-1-yl)benzo[d]thiazole-2-carboxamide

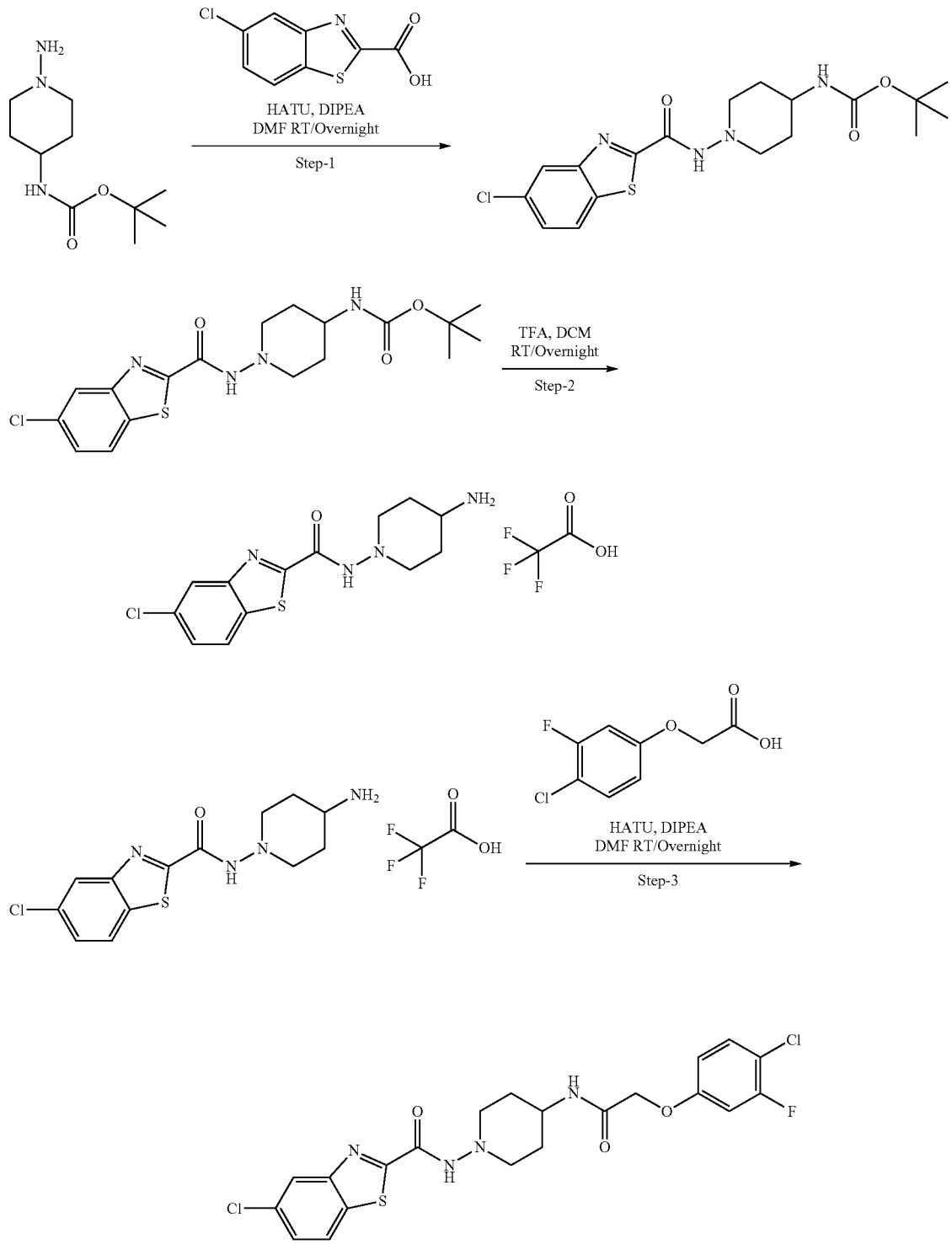

Step 1—Synthesis of tert-butyl (1-(5-chlorobenzo[d]thiazole-2-carboxamido)piperidin-4-yl)carbamate To a stirred solution of tert-butyl (1-aminopiperidin-4-yl)carbamate (0.200 g, 0.93 mmol, 1.0 equiv) in DMF (05 mL) was added HATU (0.706 g, 1.86 mmol, 2.0 equiv) at RT and stirred for 10 minutes. 5-chlorobenzo[d]thiazole-2-carboxylic acid (0.198 g, 0.93 mmol, 1.0 equiv) was added followed by the addition of DIPEA (0.5 mL, 2.79 mmol, 3.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to obtain tert-butyl (1-(5-chlorobenzo[d]thiazole-2-carboxamido)piperidin-4-yl)carbamate (0.200 g, 52% yield) as an off white solid. LCMS 411.1 [M+H]$^+$; $^1$H NMR (400 MHz, DMSO-d$_6$) δ 10.23 (s, 1H), 8.27 (d, J=8.77 Hz, 1H), 8.15 (d, J=2.19 Hz, 1H), 7.64 (dd, J=8.55, 1.97 Hz, 1H), 6.85 (d, J=8.33 Hz, 1H), 3.23 (br. s., 1H), 2.96 (d, J=11.84 Hz, 2H), 2.79 (t, J=10.30 Hz, 2H), 1.74 (d, J=10.52 Hz, 2H), 1.53 (d, J=10.52 Hz, 2H), 1.39 (s, 9H).

Step 2—Synthesis of N-(4-aminopiperidin-1-yl)-5-chlorobenzo[d]thiazole-2-carboxamide 2,2,2-trifluoroacetate To a stirred solution of tert-butyl (1-(5-chlorobenzo[d]thiazole-2-carboxamido)piperidin-4-yl)carbamate (0.200 g, 0.48 mmol, 1.0 equiv) in DCM (10 mL), was added trifluoroacetic acid (0.2 mL) and the resultant reaction mixture was stirred at RT for 1 h under nitrogen atmosphere. Reaction was monitored by TLC and LCMS. After completion of reaction, the reaction mixture was concentrated under reduced pressure to obtain sticky crude compound which was triturated with hexane (10 mL) and diethyl ether and dried under vacuum to obtain N-(4-aminopiperidin-1-yl)-5-chlorobenzo[d]thiazole-2-carboxamide 2,2,2-trifluoroacetate (0.200 g, Quantitative yield) as an off white solid. LCMS 310.9 [M+H]$^+$; $^1$H NMR (400 MHz, DMSO-d$_6$) δ 10.38 (br. s., 1H), 8.28 (d, J=8.77 Hz, 1H), 8.16 (d, J=1.75 Hz, 2 H), 7.64-7.71 (m, 1H), 3.03 (br. s., 2H), 2.82-2.88 (m, 1H), 1.93 (d, J=12.72 Hz, 2H), 1.64-1.73 (m, 2H), 1.53 (s, 2H).

Step 3—Synthesis of 5-chloro-N-(4-(2-(4-chloro-3-fluorophenoxy)acetamido) piperidin-1-yl)benzo[d]thiazole-2-carboxamide To a stirred solution of N-(4-aminopiperidin-1-yl)-5-chlorobenzo[d]thiazole-2-carboxamide 2,2,2-trifluoroacetate (0.200 g, 0.47 mmol, 1.0 equiv) in DMF (05 mL) was added HATU (0.350 g, 0.92 mmol, 2.0 equiv) at RT and stirred for 10 minutes. 2-(4-chloro-3-fluorophenoxy)acetic acid (0.096 g, 0.47 mmol, 1.0 equiv) was added followed by the addition of DIPEA (0.3 mL, 1.41 mmol, 3.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to gives crude. The crude which was purified by reverse phase of HPLC to obtain 5-chloro-N-(4-(2-(4-chloro-3-fluorophenoxy)acetamido)piperidin-1-yl)benzo[d]thiazole-2-carboxamide (Compound 9-0.100 g, 42% Yield) as an off white solid. LCMS 497.3 [M+H]$^+$; $^1$H NMR (400 MHz, DMSO-d$_6$) δ 10.27 (s, 1H), 8.28 (d, J=8.77 Hz, 1H), 8.16 (d, J=1.75 Hz, 1H), 8.09 (d, J=7.89 Hz, 1H), 7.64 (dd, J=8.77, 1.75 Hz, 1H), 7.43-7.52 (m, 1H), 7.08 (dd, J=11.18, 2.85 Hz, 1H), 6.87 (d, J=9.21 Hz, 1H), 4.53 (s, 2H), 3.66 (br. s., 1H), 2.95-3.07 (m, 2H), 2.79-2.91 (m, 2H), 1.76 (d, J=10.09 Hz, 2H), 1.57-1.68 (m, 2H).

Example 53

Synthesis of (S)-6-chloro-N-(1-(2-(4-chlorophenoxy)acetamido)piperidin-4-yl)-3,4-dihydro-2H-benzo[b][1,4]oxazine-2-carboxamide

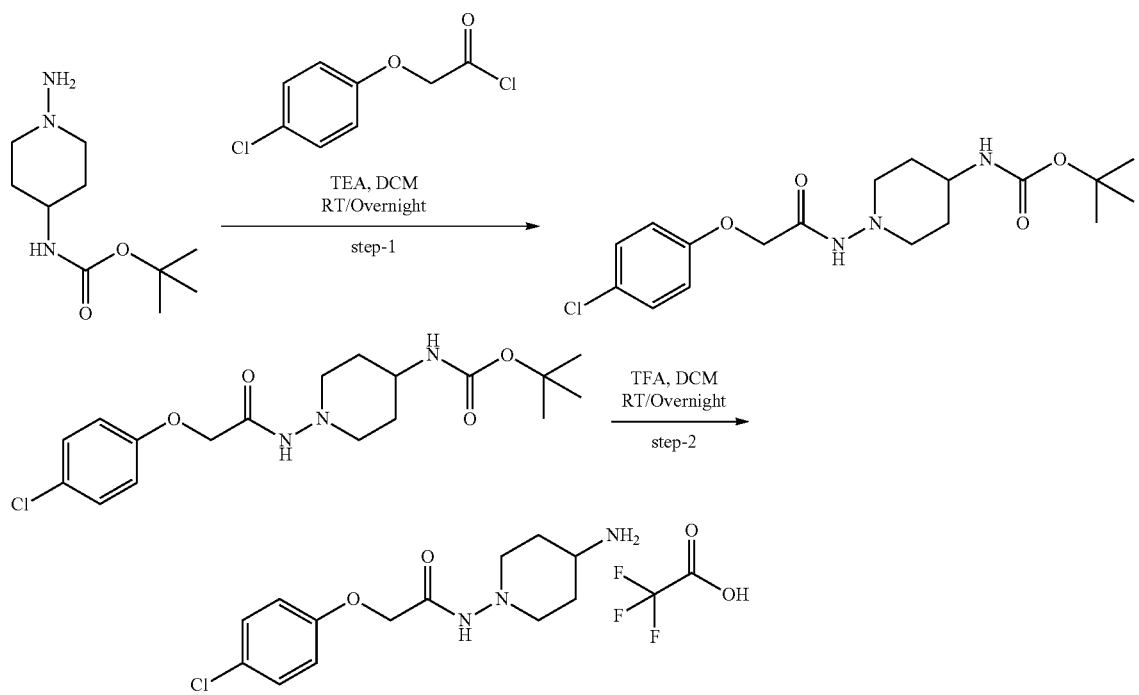

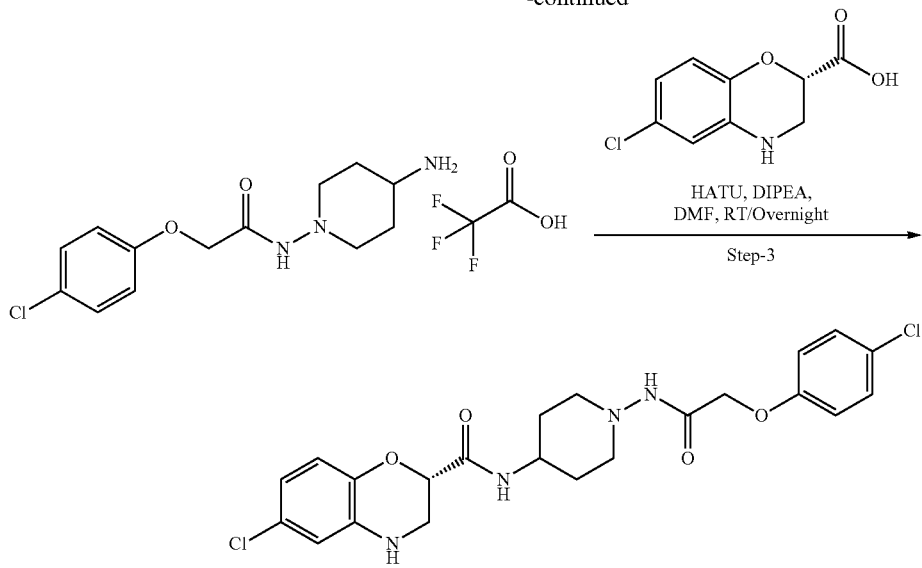

Step 1—Synthesis of tert-butyl (1-(2-(4-chlorophenoxy)acetamido)piperidin-4-yl)carbamate To a stirred solution of tert-butyl (1-aminopiperidin-4-yl) carbamate (0.100 g, 0.46 mmol, 1.0 equiv) in DCM (10 mL) was added 2-(4-chlorophenoxy)acetyl chloride (0.095 g, 0.46 mmol, 1.0 equiv) and followed by the addition of TEA (0.2 mL, 1.39 mmol, 3.0 equiv). The resulting reaction mixture was allowed to stir at RT for overnight. Product formation was confirmed by LCMS. The reaction mixture was diluted with water (20 mL) and extracted with ethyl acetate (50 mL×2). Combined organic layer was washed with water (20 mL×4), dried over anhydrous Na2SO4 and concentrated under reduced pressure to obtain tert-butyl (1-(2-(4-chlorophenoxy)acetamido)piperidin-4-yl)carbamate (0.100 g, 56% Yield) as a white solid. LCMS 384.1 [M+H]$^+$; $^1$H NMR (400 MHz, DMSO-d$_6$) δ 9.07 (s, 1H), 8.72 (br. s., 1H), 7.39-7.23 (m, 2H), 7.00-6.87 (m, 2H), 6.87-6.72 (m, 1H), 4.85-4.74 (m, 1H), 4.41 (s, 1H), 3.33 (br. s., 4H), 2.84 (d, J=10.5 Hz, 2H), 1.71 (br. s., 2H), 1.47 (d, J=10.1 Hz, 1H), 1.44-1.28 (m, 9H).

Step 2—Synthesis of N-(4-aminopiperidin-1-yl)-2-(4-chlorophenoxy)acetamide 2,2,2-trifluoroacetate To a stirred solution of tert-butyl (1-(2-(4-chlorophenoxy) acetamido)piperidin-4-yl)carbamate (0.100 g, 0.26 mmol, 1.0 equiv) in DCM (10 mL), was added trifluoroacetic acid (02 mL) and the resultant reaction mixture was stirred at RT for 1 h under nitrogen atmosphere. Reaction was monitored by TLC and LCMS. After completion of reaction, the reaction mixture was concentrated under reduced pressure to obtain crude product which was crystallized in diethyl ether and dried under vacuum to obtain N-(4-aminopiperidin-1-yl)-2-(4-chlorophenoxy)acetamide 2,2,2-trifluoroacetate (0.100 g, Quant. Yield) as a brown semi solid. LCMS 284.1 [M+H]$^+$; $^1$H NMR (400 MHz, DMSO-d$_6$) δ 9.07 (s, 1H), 8.72 (br. s., 1H), 7.39-7.23 (m, 2H), 7.00-6.87 (m, 2H), 6.87-6.72 (m, 1H), 4.85-4.74 (m, 1H), 4.41 (s, 1H), 3.33 (br. s., 4H), 2.84 (d, J=10.5 Hz, 2H), 1.71 (br. s., 2H), 1.47 (d, J=10.1 Hz, 1H).

Step 3—Synthesis of (S)-6-chloro-N-(1-(2-(4-chlorophenoxy)acetamido)piperidin-4-yl)-3,4-dihydro-2H-benzo[b][1,4]oxazine-2-carboxamide To a stirred solution of N-(4-aminopiperidin-1-yl)-2-(4-chlorophenoxy)acetamide 2,2,2-trifluoroacetate (0.100 g, 0.25 mmol, 1.0 equiv) in DMF (05 mL) was added HATU (0.190 g, 0.50 mmol, 2.0 equiv) at RT and stirred for 10 minutes. (S)-6-chloro-3,4-dihydro-2H-benzo[b][1,4] oxazine-2-carboxylic acid (0.054 g, 0.25 mmol, 1.0 equiv) was added followed by the addition of DIPEA (0.12 mL, 0.75 mmol, 3.0 equiv). The resulting reaction mixture was allowed to stir at RT for overnight. Product formation was confirmed by LCMS. After completion of reaction, the mixture was diluted with water (50 mL) and extracted with ethyl acetate (100 mL×2). Combined organic extracts were washed with water (50 mL×4), dried over anhydrous Na2SO4 and concentrated to gives crude which was purified by reverse phase of HPLC to obtain (S)-6-chloro-N-(1-(2-(4-chlorophenoxy)acetamido)piperidin-4-yl)-3,4-dihydro-2H-benzo[b][1,4]oxazine-2-carboxamide (Compound 72-0.025 g, 21% Yield) as an off white solid. LCMS 479.3 [M+H]$^+$; $^1$H NMR (400 MHz, DMSO-d$_6$) δ 9.11 (s, 1H), 8.76 (br. s., 1H), 7.92 (d, J=7.89 Hz, 1H), 7.30-7.39 (m, 2H), 6.96 (d, J=9.21 Hz, 1H), 6.88 (d, J=9.21 Hz, 1 H), 6.78 (dd, J=8.33, 3.95 Hz, 1H), 6.60 (d, J=2.19 Hz, 1H), 6.50 (d, J=8.77 Hz, 1H), 4.42-4.49 (m, 2H), 3.58 (br. s., 1H), 3.45 (br. s., 1H), 3.18 (dd, J=12.28, 7.45 Hz, 2H), 3.02 (br. s., 1H), 2.88 (br. s., 1H), 2.60-2.70 (m, 2H), 1.72 (d, J=11.84 Hz, 2H), 1.61 (d, J=14.91 Hz, 2 H).

Example 54
Synthesis of N,N'-(piperidine-1,4-diyl)bis(2-(4-(trifluoromethyl)phenoxy)acetamide
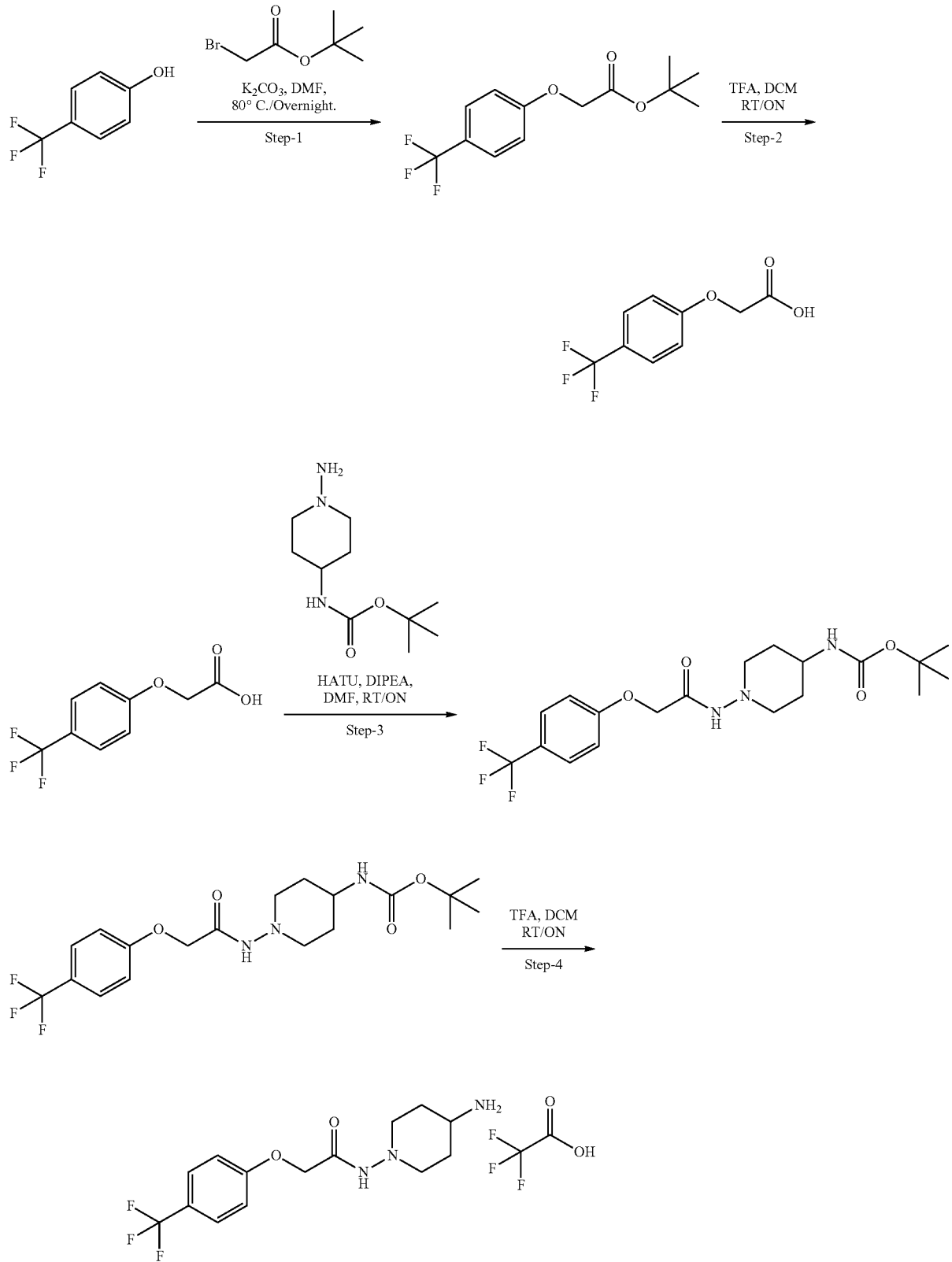

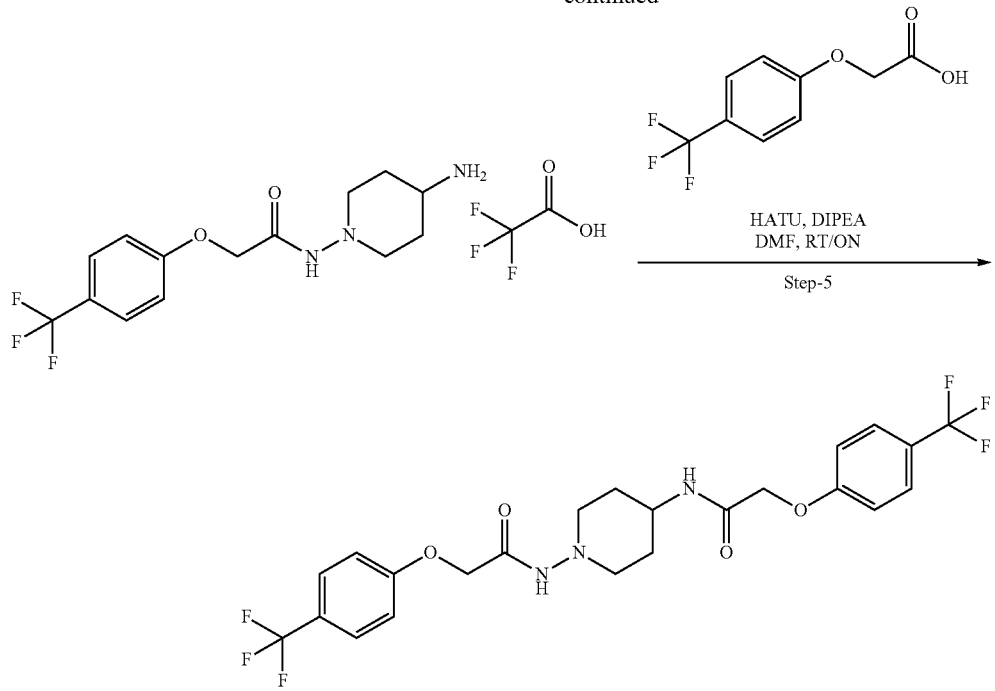

Step 1—Synthesis of tert-butyl 2-(4-(trfluoromethyl)phenoxy)acetate

To a solution of 4-(trifluoromethyl)phenol (1.0 g, 6.1 mmol, 1.0 equiv) in DMF (10 mL) was added tert-butyl 2-bromoacetate (1.44 g, 7.4 mmol, 1.2 equiv), $K_2CO_3$ (1.68 g, 12.2 mmol, 2.0 equiv). The resulting reaction mixture was heated at 80° C. for overnight. Product formation was confirmed by $^1$H NMR. After completion of reaction, the mixture was diluted with water (50 mL) and extracted with ethyl acetate (100 mL×2). Combined organic extracts were washed with water (50 mL×4), dried over anhydrous Na2SO4 and concentrated to obtain tert-butyl 2-(4-(trifluoromethyl)phenoxy)acetate (1.0 g, 60%) as colorless oil. $^1$H NMR (400 MHz, DMSO-$d_6$) δ 7.66 (m, J=8.77 Hz, 2H), 7.09 (m, J=8.33 Hz, 2H), 4.78 (s, 2H), 1.42 (s, 9 H).

Step 2—Synthesis of 2-(4-(trifluoromethyl)phenoxy)acetic acid

To a stirred solution of tert-butyl 2-(4-(trifluoromethyl) phenoxy)acetate (1.0 g, 3.6 mmol, 1.0 equiv) in DCM (10 mL), was added trifluoroacetic acid (05 mL) and the resultant reaction mixture was stirred at RT for 1 h under nitrogen atmosphere. Reaction was monitored by TLC and LCMS. After completion of reaction, the reaction mixture was concentrated under reduced pressure to obtain sticky crude compound which was triturated with hexane (10 mL) and diethyl ether and dried under vacuum to obtain 2-(4-(trifluoromethyl)phenoxy)acetic acid (0.700 g, 88%) as an off white solid. $^1$H NMR (400 MHz, DMSO-$d_6$) δ 13.11 (br. s., 1H), 7.64 (s, 2 H), 7.10 (d, J=8.77 Hz, 2H), 4.80 (s, 2H).

Step 3—Synthesis of tert-butyl (1-(2-(4-(trifluoromethyl)phenoxy)acetamido)piperidin-4-yl)carbamate To a stirred solution of tert-butyl (1-aminopiperidin-4-yl) carbamate (0.200 g, 0.93 mmol, 1.0 equiv) in DMF (05 mL) was added HATU (0.706 g, 1.86 mmol, 2.0 equiv) at RT and stirred for 10 minutes. 2-(4-(trifluoromethyl)phenoxy)acetic acid (0.204 g, 0.93 mmol, 1.0 equiv) was added followed by the addition of DIPEA (0.5 mL, 2.79 mmol, 3.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to obtain tert-butyl (1-(2-(4-(trifluoromethyl)phenoxy)acetamido)piperidin-4-yl)carbamate (0.300 g, 77% Yield) as an off white solid. LCMS 418.3 [M+H]$^+$; $^1$H NMR (400 MHz, DMSO-$d_6$) δ 9.13 (s, 1H), 8.78 (br. s., 1H), 7.62-7.70 (m, 2H), 7.12 (s, 1H), 7.03 (d, J=8.33 Hz, 1H), 4.52 (s, 2H), 3.02 (br. s., 1 H), 2.89 (s, 2H), 2.73 (s, 1H), 2.67 (br. s., 1H), 1.72 (br. s., 2H), 1.49 (br. s., 2H), 1.33-1.44 (m, 9H).

Step 4—Synthesis of N-(4-aminopiperidin-1-yl)-2-(4-(trifluoromethyl)phenoxy)acetamide 2,2,2-trifluoroacetate To a stirred solution of tert-butyl (1-(2-(4-(trifluoromethyl)phenoxy)acetamido)piperidin-4-yl)carbamate (0.300 g, 0.77 mmol, 1.0 equiv) in DCM (10 mL), was added trifluoroacetic acid (03 mL) and the resultant reaction mixture was stirred at RT for 1 h under nitrogen atmosphere. Reaction was monitored by TLC and LCMS. After completion of reaction, the reaction mixture was concentrated under reduced pressure to obtain sticky crude compound which was triturated with hexane (10 mL) and diethyl ether and dried under vacuum to obtain N-(4-aminopiperidin-1-yl)-2-(4-(trifluoromethyl)phenoxy)acetamide 2,2,2-trifluoroacetate (0.200 g, Quantitative yield) as a semi solid. LCMS 318.1 [M+H]$^+$; $^1$H NMR (400 MHz, DMSO-$d_6$) δ 9.13 (s, 1H), 8.78 (br. s., 1 H), 7.62-7.70 (m, 2H), 7.12 (s, 1H), 7.03 (d, J=8.33 Hz, 1H), 4.52 (s, 2H), 3.02 (br. s., 1H), 2.89 (s, 2H), 2.73 (s, 1H), 2.67 (br. s., 1H), 1.72 (br. s., 2H), 1.49 (br. s., 2H).

Step 5—Synthesis of N,N'-(piperidine-1,4-diyl)bis(2-(4-(trifluoromethyl)phenoxy)acetamide)

To a stirred solution of N-(4-aminopiperidin-1-yl)-2-(4-(trifluoromethyl)phenoxy)acetamide 2,2,2-trifluoroacetate (0.200 g, 0.46 mmol, 1.0 equiv) in DMF (05 mL) was added HATU (0.350 g, 0.92 mmol, 2.0 equiv) at RT and stirred for 10 minutes. 2-(4-(trifluoromethyl)phenoxy)acetic acid (0.102 g, 0.46 mmol, 1.0 equiv) was added followed by the addition of DIPEA (0.3 mL, 1.38 mmol, 3.0 equiv). The resulting reaction mixture was allowed to stir at RT for overnight. Product formation was confirmed by LCMS. The reaction mixture was diluted with water (50 mL). The resulting solid was filtered off, washed with water (20 mL×4) and dried under vacuum to obtain N,N'-(piperidine-1,4-diyl)bis(2-(4-(trifluoromethyl)phenoxy)acetamide) (Compound 35-0.150 g, 40% Yield) as an off white solid.

LCMS 520.4 [M+H]$^+$; $^1$H NMR (400 MHz, DMSO-$d_6$) δ 9.19 (s, 1H), 8.83 (br. s., 1H), 7.64-7.71 (m, 4H), 7.07-7.17 (m, 4H), 4.50-4.60 (m, 4H), 3.62 (br. s., 1H), 3.07 (br. s., 1H), 2.92 (br. s., 1H), 2.66 (d, J=8.33 Hz, 2H), 1.73 (d, J=11.84 Hz, 2H), 1.57-1.68 (m, 2H).

Example 55

Synthesis of 5-chloro-N-(1-((2-(4-chloro-3-fluorophenoxy)ethyl)amino)piperidin-4-yl)-2,3-dihydrobenzofuran-2-carboxamide

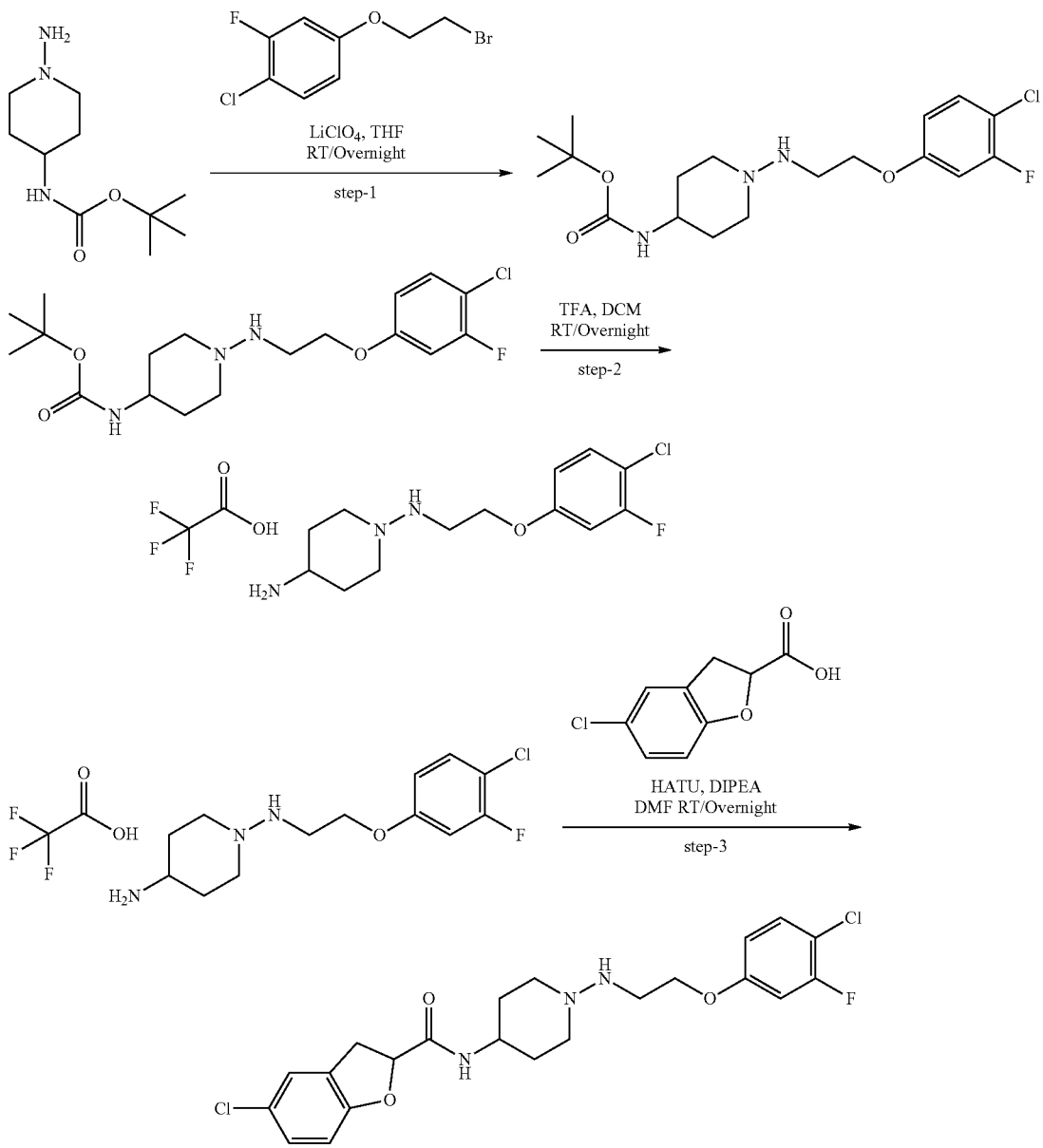

Step 1—Synthesis of tert-butyl (1-((2-(4-chloro-3-fluorophenoxy)ethyl)amino)piperidin-4-yl)carbamate To a stirred solution of tert-butyl (1-aminopiperidin-4-yl) carbamate (1.00 g, 4.6 mmol, 1.0 equiv) in THF (15 mL) was added LiClO$_4$ (0.975 g, 9.2 mmol, 2.0 equiv) at RT and stirred for 10 minutes. 4-(2-bromoethoxy)-1-chloro-2-fluorobenzene (1.10 g, 4.6 mmol, 1.0 equiv). The resulting reaction mixture was allowed to stir at RT for overnight. Product formation was confirmed by LCMS. The reaction mixture was diluted with water (50 mL) and extracted with EtOAc (100 mL×2). The combined organic layer was washed with water (50 mL), brine solution (50 mL×2), dried over anhydrous sodium sulfate and concentrated under reduced pressure to obtain tert-butyl (1-((2-(4-chloro-3-fluorophenoxy)ethyl)amino)piperidin-4-yl)carbamate (1.00 g, 55% Yield) as a yellow semi solid. LCMS 388.2 [M+H]$^+$; $^1$H NMR (400 MHz, DMSO-d$_6$) δ 7.40-7.51 (m, 1H), 7.12 (dd, J=11.62, 2.85 Hz, 1H), 6.86 (d, J=9.21 Hz, 1 H), 4.28-4.40 (m, 2H), 3.73-3.83 (m, 2H), 3.52-3.61 (m, 1H), 2.83 (br. s., 2H), 2.14 (br. s., 2H), 2.04 (d, J=10.52 Hz, 2H), 1.65 (br. s., 2H), 1.45 (s, 9H).

Step 2—Synthesis of NJ-(2-(4-chloro-3-fluorophenoxy)ethyl)piperidine-1,4-diamine 2,2,2-trifluoroacetate To a stirred solution of tert-butyl (1-((2-(4-chloro-3-fluorophenoxy)ethyl)amino)piperidin-4-yl)carbamate (1.00 g, 2.57 mmol, 1.0 equiv) in DCM (10 mL), was added trifluoroacetic acid (5 mL) and the resultant reaction mixture was stirred at RT for 1 h under nitrogen atmosphere. Reaction was monitored by TLC and LCMS. After completion of reaction, the reaction mixture was concentrated under reduced pressure to obtain sticky crude compound which was triturated with hexane (10 mL) and diethyl ether and dried under vacuum to obtain N1-(2-(4-chloro-3-fluorophenoxy)ethyl)piperidine-1,4-diamine 2,2,2-trifluoroacetate (0.700 g, 70% Yield) as a yellow semi solid. LCMS 288.2 [M+H]$^+$;

Step 3—Synthesis of 5-chloro-N-(1-((2-(4-chloro-3-fluorophenoxy)ethyl)amino)piperidin-4-yl)-2,3-dihydrobenzofuran-2-carboxamide To a stirred solution of N1-(2-(4-chloro-3-fluorophenoxy) ethyl)piperidine-1,4-diamine 2,2,2-trifluoroacetate (0.200 g, 0.49 mmol, 1.0 equiv) in DMF (05 mL) was added HATU (0.343 g, 0.98 mmol, 2.0 equiv) at RT and stirred for 10 minutes. 5-chloro-2,3-dihydrobenzofuran-2-carboxylic acid (0.097 g, 0.49 mmol, 1.0 equiv) was added followed by the addition of DIPEA (0.3 mL, 1.47 mmol, 3.0 equiv). Product formation was confirmed by LCMS. The reaction mixture was diluted with water (50 mL) and extracted with EtOAc (50 mL×2). The combined organic layer was washed with water (50 mL), brine solution (50 mL×2), dried over anhydrous sodium sulfate and concentrated under reduced pressure to obtain crude which was purified by reverse phase of HPLC to obtain 5-chloro-N-(1-((2-(4-chloro-3-fluorophenoxy)ethyl)amino)piperidin-4-yl)-2,3-dihydrobenzofuran-2-carboxamide (Compound 73-0.010 g, 4% Yield) as an off white solid. LCMS 469.3 [M+H]$^+$; $^1$H NMR (400 MHz, DMSO-d$_6$) δ 8.31 (d, J=7.89 Hz, 1H), 7.48 (t, J=8.99 Hz, 1H), 7.21-7.29 (m, 1H), 7.08-7.19 (m, 1H), 6.73-6.92 (m, 2H), 5.13 (dd, J=10.30, 6.80 Hz, 2H), 4.50-4.62 (m, 2H), 3.65-3.81 (m, 2H), 3.44-3.61 (m, 5H), 3.13-3.24 (m, 3H), 3.10 (br. s., 2H), 2.15-2.29 (m, 2H), 1.51-1.68 (m, 2H).

Example 56

Synthesis of N-(4-((3-(4-chloro-3-fluorophenoxy)-2-hydroxypropyl)amino)piperidin-1-yl)-2-(4-chlorophenoxy)acetamide

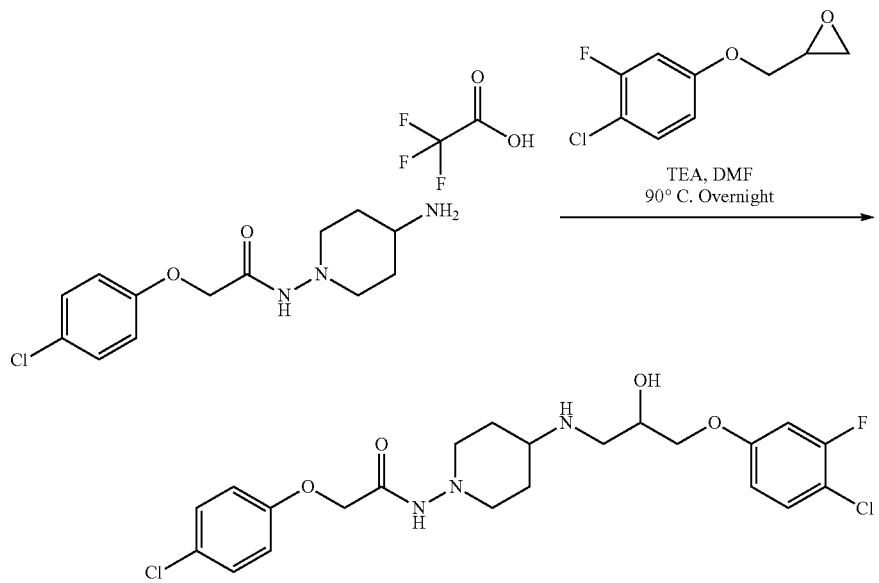

To a stirred solution of N-(4-aminopiperidin-1-yl)-2-(4-chlorophenoxy)acetamide 2,2,2-trifluoroacetate (0.100 g, 0.25 mmol, 1.0 equiv) 2-((4-chloro-3-fluorophenoxy) methyl)oxirane (0.051 g, 0.25 mmol, 1.0 equiv) in DMF (5 mL), was added TEA (0.14 mL, 1.00 mmol, 4.0 equiv) and the resultant reaction mixture was heated at 90° C. for overnight. Progress of the reaction was monitored by LCMS. After completion of reaction, the reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure to obtain crude which was purified by flash chromatography (0-5% MeOH in DCM as an eluent) to obtain N-(4-((3-(4-chloro-3-fluorophenoxy)-2-hydroxypropyl)

amino)piperidin-1-yl)-2-(4-chlorophenoxy)acetamide (Compound 74-0.060 g, 50% Yield) as an off white solid. LCMS 486.1 [M+H]+; $^1$H NMR (400 MHz, DMSO-d$_6$) δ 8.75 (br. s., 1H), 7.46 (t, J=8.99 Hz, 1H), 7.30 (d, J=9.21 Hz, 1H), 7.34 (d, J=9.21 Hz, 1H), 7.07 (dd, J=11.40, 2.63 Hz, 1H), 6.95 (d, J=9.21 Hz, 1H), 6.83 (d, J=9.21 Hz, 1H), 6.87 (d, J=8.77 Hz, 1H), 5.04 (br. s., 1H), 4.82 (s, 1H), 4.41 (s, 1H), 3.99 (dd, J=9.65, 3.95 Hz, 1H), 3.76-3.96 (m, 2H), 3.00 (br. s., 1H), 2.87 (d, J=10.52 Hz, 1H), 2.67 (br. s., 1H), 2.56-2.64 (m, 2H), 2.33 (br. s., 2H), 1.90 (s, 1H), 1.81 (br. s., 2H), 1.33 (d, J=9.21 Hz, 2H)

Example 57

Synthesis of 2-(4-chloro-3-fluorophenoxy)-N-(4-(2-(4-ethynylphenoxy)acetamido)piperidin-1-yl)acetamide

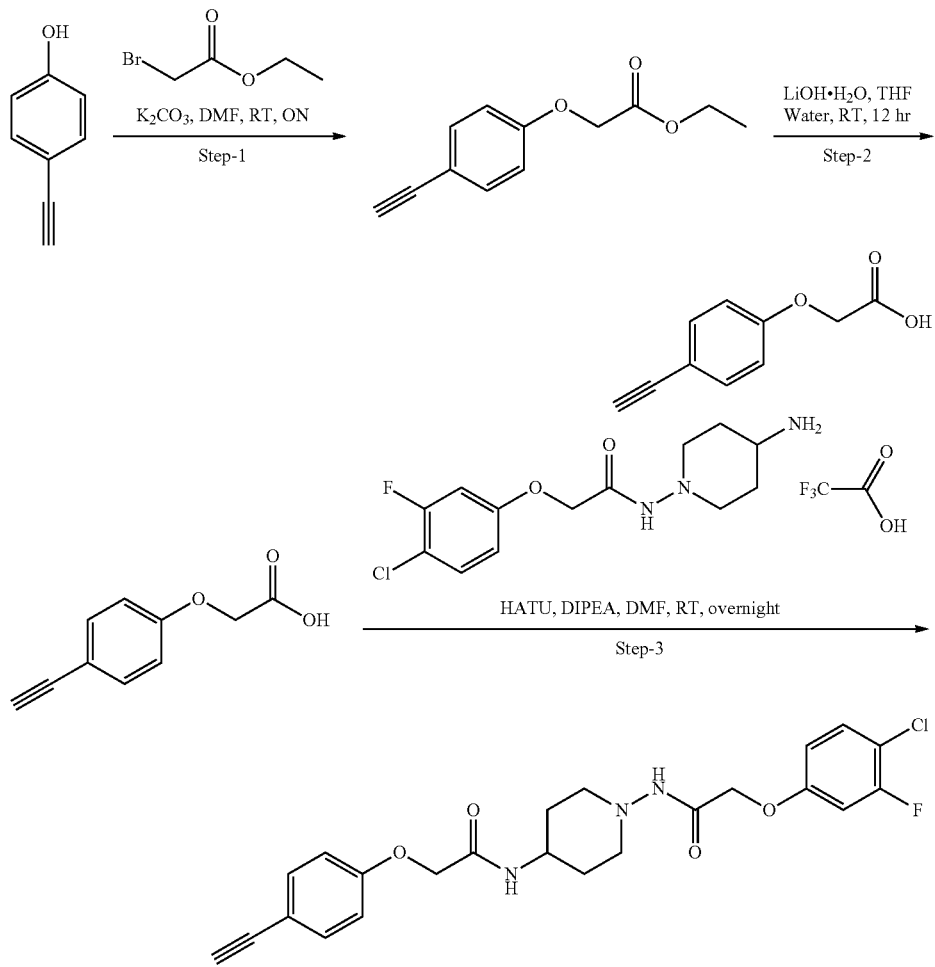

Step 1—Synthesis of ethyl 2-(4-ethynylphenoxy)acetate

To a stirred solution of 4-ethynylphenol (0.100 g, 0.847 mmol, 1.0 equiv) in DMF (2 mL) was added K$_2$CO$_3$ (0.233 g, 1.694 mmol, 2.0 equiv) and Ethyl 2-Bromoacetate (0.212 g, 1.271 mmol, 1.5 equiv), resultant reaction mixture was stirred at RT for overnight. Progress of the reaction was monitored by TLC and LCMS. After completion of reaction, the reaction mixture was diluted with water (30 mL) and extracted with EtOAc (50 mL×2). The combined organic layer was washed with water (30 mL), brine solution (30 mL×2), dried over anhydrous sodium sulfate and concentrated under reduced pressure to obtain crude which was purified by combi-flash chromatography (Silica gel 100-200 mesh: Elution 0-10% EA in Hexane) to afford titled compound ethyl 2-(4-ethynylphenoxy)acetate (0.090 g, 52.32%) as a white solid. LCMS 204.9 [M+H]+; $^1$H NMR (400 MHz, Chloroform-d) δ 7.43 (d, J=8.77 Hz, 2H), 6.85 (d, J=8.77 Hz, 2H), 4.62 (s, 2H), 4.27 (d, J=7.02 Hz, 2H), 3.00 (s, 1H), 1.29 (t, J=7.24 Hz, 3H).

Step 2—Synthesis of 2-(4-ethynylphenoxy) acetic acid

To a stirred solution of ethyl 2-(4-ethynylphenoxy) acetate (0.090 g, 0.441 mmol, 1.0 equiv) in THF (3 ml) was added a solution of LiOH.H$_2$O (0.027 g, 0.661 mmol, 1.5 equiv) in water (2 ml). The reaction mixture was stirred at RT for 12 hr. Product formation was confirmed by TLC. Reaction mixture was diluted with water (20 ml) and washed with ethyl acetate (25 mL×3). Aqueous layer was acidified with 1N HCl and extracted with ethyl acetate (25 mL×3). Combined organic extracts were washed with water (30 mL×2) & brine (30 mL), dried over anhydrous Na$_2$SO$_4$ and concentrated to obtained 2-(4-ethynylphenoxy)acetic acid (0.075 g, 97.40% Yield) as a white solid. LCMS 176.9

[M+H]+; 1H NMR (400 MHz, DMSO-d6) δ13.06 (br. s., 1H), 7.40 (m, J=8.77 Hz, 2H), 6.91 (m, J=8.77 Hz, 2H), 4.64-4.77 (m, 2H), 4.02 (s, 1 H).

Step 3—Synthesis of 2-(4-chloro-3-fluorophenoxy)-N-(4-(2-(4-ethynylphenoxy)acetamido)piperidin-1-yl)acetamide To a stirred solution of N-(4-aminopiperidin-1-yl)-2-(4-chloro-3-fluorophenoxy) acetamide 2,2,2-trifluoroacetate (0.100 g, 0.240 mmol, 1.0 equiv) in DMF (2 mL) was added HATU (0.137 g, 0.361 mmol, 1.5 equiv) at RT and stirred for 5 minutes. 2-(4-ethynylphenoxy)acetic acid (0.063 g, 0.361 mmol, 1.5 equiv) was added followed by the addition of DIPEA (0.08 mL, 0.481 mmol, 2.0 equiv). The resulting reaction mixture was allowed to stir at RT for overnight. Product formation was confirmed by LCMS. The reaction mixture was diluted with water (30 mL) and extracted with EtOAc (30 mL×2). The combined organic layer was washed with water (30 mL), brine solution (30 mL×2), dried over anhydrous sodium sulfate and concentrated under reduced pressure. The crude product was purified by reversed phase HPLC to 2-(4-chloro-3-fluorophenoxy)-N-(4-(2-(4-ethynylphenoxy)acetamido)piperidin-1-yl)acetamide (Compound 37). LCMS 460.2 [M+H]+

BIOLOGICAL EXAMPLES

Example B1—ATF4 Expression Inhibition Assay

The ATF4 reporter was prepared by fusing the human full length 5'UTR of ATF4 (NCBI Accession No. BC022088.2) upstream of the firefly luciferase coding sequence lacking the initiator methionine. The fused sequence was cloned into pLenti-EF1a-C-Myc-DDK-IRES-Puro cloning vector (Origen #PS100085) using standard methods. Virus production was carried out by using Lenti-X™ Packaging Single Shots Protocol (Clonetech #631276). Viral particles were used to transduce HEK293T cells (ATCC #CRL-3216, ATCC Manassas, Va.), which were subsequently selected with puromycin to generate stable cell line. Cells were maintained at 37° C. and 5% CO2 in DMEM-F12 (Hyclone #SH30023.02) supplemented with 10% heat-inactivated fetal bovine serum (Gibco #16000-044), 2 mM L-glutamine (Gibco #25030-081), 100 U/ml penicillin, and 100 µg/ml streptomycin (Gibco #15140-122).

HEK293T cells carrying the ATF4 luciferase reporter were plated on 96-well plates (Nunc) at 10,000 cells per well. Cells were treated two days after seeding with 100 nM thapsigargin (Tg) (Sigma-Aldrich #T9033) in the presence of 100 nM or 1 µM. For the assessment of the half-maximal inhibitory concentration (IC$_{50}$) for selected compounds, dose-response assays were performed. Compounds were serially diluted using DMSO ranging from 0.1 nM to 1 µM. Cells without treatment or cells treated with Tg alone were used as controls. Assay plates containing cells were incubated for 3 hours at 37° C.

Luciferase reactions were performed using Luciferase Assay System (Promega #E1501) as specified by the manufacturer. Luminescence was read with an integration time of 1 s and a gain of 110 using a Cytation-5 multi-mode microplate reader (BioTek). Relative luminescence units were normalized to Tg treatment (0% inhibition) and untreated cells (100% inhibition) and the percentage of ATF4 inhibition was calculated.

Percentages of ATF4 inhibition after induction with Tg in the presence of 100 nM or 1 µM of certain test compounds are shown in Table 2. Also shown in Table 2 is the calculated IC$_{50}$ for certain test compounds. Under ISR stressed conditions (resulting from treatment with Tg), ATF4 expression is generally upregulated. Accordingly, inhibition of ATF4 expression as a result of the test compound indicates suppression of the ISR pathway.

Figure 2:
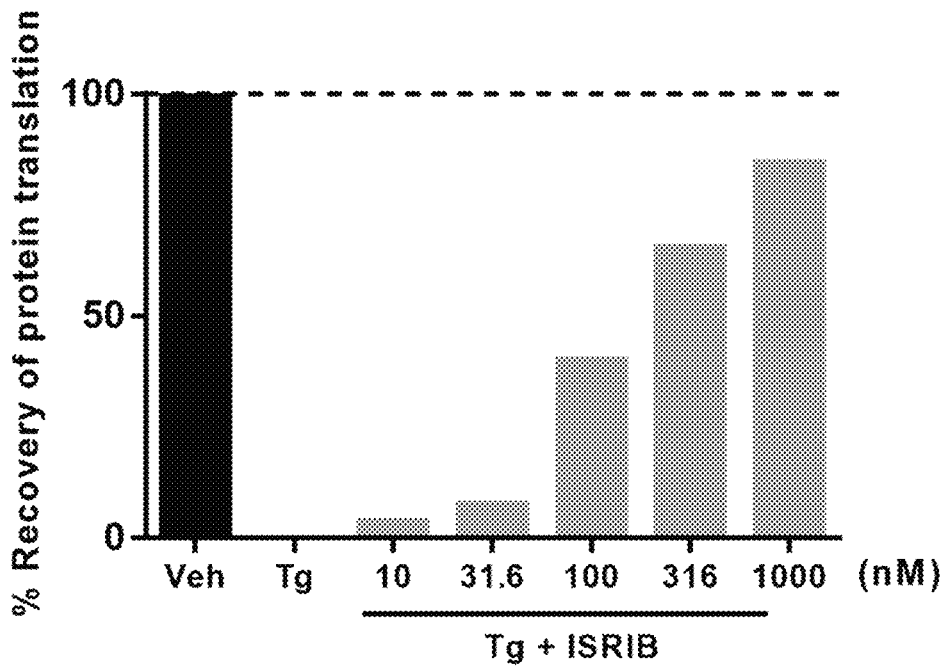
FIG. 2 shows the percent recovery of protein translation in stressed HEK293T cells after exposure to 10 nM, 31.6 nM, 100 nM, 316 nM, or 1000 nM of ISRIB.
Figure 3:
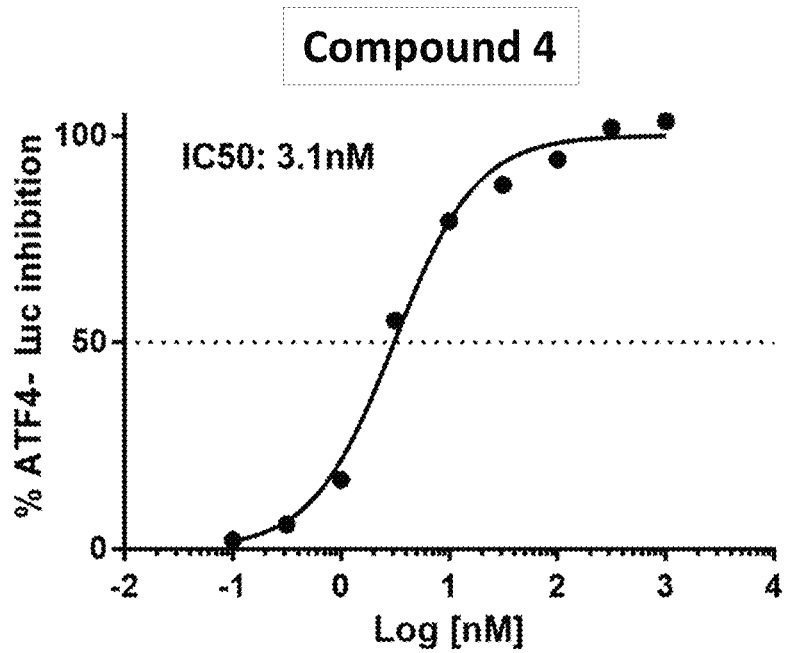
FIG. 3 shows an $IC_{50}$ titration for inhibition of ATF4 in stressed HEK293T cells using a luciferase assay for compound 4. Compound 4 was found to have an $IC_{50}$ of 3.1 nM.
Figure 4:
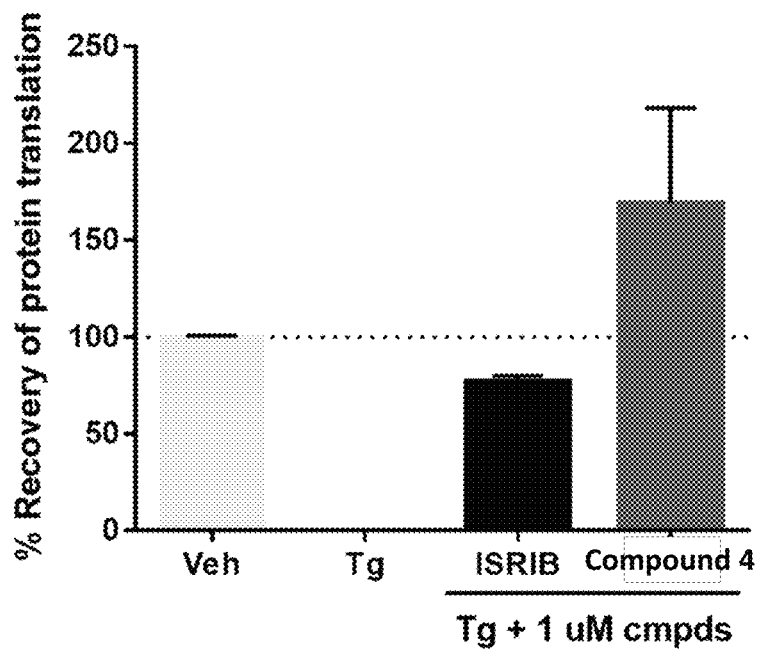
FIG. 4 shows the percent recovery of protein translation in stressed HEK293T cells after exposure to 1 µM of ISRIB or compound 4.

ISRIB (trans-N,N'-1,4-cyclohexanediylbis[2-(4-chlorophenoxy)-acetamide) was found to inhibit ATF4 expression with an IC$_{50}$ of 5 nM (FIG. 1). Despite the great potency on the inhibition of ATF4 expression, ISRIB is not able to completely restore protein synthesis when the global protein translation is decreased under these stress conditions. Even at higher concentration—up to 200-fold its IC$_{50}$ value—ISRIB only partially restores protein translation (FIG. 2). Compound 4 has a great potency for the inhibition of ATF4 expression under stress condition (FIG. 3) and is much better at restoring global protein translation under ER stress-mediated repression and going beyond a 100% recovery (FIG. 4).

TABLE 2

| Compound No. | % ATF4 inhibition at 100 nM | % ATF4 inhibition at 1 µM | ATF4 inhbition IC$_{50}$ (nM) |
|---|---|---|---|
| 1 | 93.7 | 97.9 | 3.6 |
| 2 | 87.1 | 97.6 | 18.4 |
| 3 | 88.1 | 92.2 | 10.6 |
| 4 | 93.2 | 94.7 | 3.1 |
| 5 | 85.7 | 93.7 | 18.8 |
| 6 | 75.9 | 83.8 | 30.8 |
| 7 | 16.1 | 13.9 | >1,000 |
| 8 | 44.2 | 70.9 | 152.6 |
| 9 | 77.1 | 86.8 | <100 |
| 10 | 68.2 | 87.2 | <100 |
| 11 | 67.8 | 90.5 | <100 |
| 12 | 69.4 | 88.5 | <100 |
| 13 | 60.7 | 86.7 | <100 |
| 14 | 89.3 | 98.9 | 10.2 |
| 15 | 87.8 | 100 | 12.4 |
| 16 | 46.3 | 91.6 | 124.7 |
| 17 | 58.6 | 92.7 | 79.1 |
| 18 | 59.1 | 94.6 | 76.3 |
| 19 | 87.3 | 95.8 | 11.5 |
| 20 | 24.7 | 33.7 | >10,000 |
| 21 | 68.6 | 86.9 | 61.9 |
| 22 | 87.5 | 92.8 | 10.3 |
| 23 | 67.2 | 89.3 | 55.6 |
| 24 | 88.0 | 99.5 | 32.2 |
| 25 | 8.1 | 8.5 | >1,000 |
| 26 | 37.5 | 49.4 | n/a |
| 30 | 29.5 | 97.1 | 187.3 |
| 31 | 94.8 | 92.7 | 4.16 |
| 32 | 85.7 | 92.4 | 12.0 |
| 35 | 92.1 | 91.6 | <100 |
| 39 | 91.0 | 91.5 | <100 |
| 44 | 51.5 | 82.0 | 150.9 |
| 45 | 92.7 | 92.4 | 2.6 |
| 46 | 100 | 99.3 | 3.6 |
| 47 | 98.2 | 99.0 | 1.98 |
| 48 | 96.5 | 97.4 | 3.36 |
| 49 | 55.4 | 100 | 69.7 |
| 50 | 97.2 | 100 | 1.93 |
| 51 | 79.3 | 100 | 19.8 |
| 52 | 75.3 | 81.2 | 26.9 |
| 53 | 36.1 | 69.8 | 268 |
| 54 | 87.2 | 97.2 | 1.6 |
| 55 | 58.1 | 80.5 | 101.7 |
| 56 | 63.4 | 75.6 | 71.7 |
| 57 | 25.9 | 39.8 | >10,000 |
| 58 | 86.5 | 97.6 | 5.7 |
| 59 | 38.8 | 66.0 | 569.6 |
| 60 | 92.6 | 94.6 | 1.5 |
| 61 | 72.4 | 86.6 | 29.4 |
| 62 | 85.9 | 88.8 | <100 |
| 63 | 14.8 | 84.6 | <1,000 |

TABLE 2-continued

| Compound No. | % ATF4 inhibition at 100 nM | % ATF4 inhibition at 1 μM | ATF4 inhbition IC$_{50}$ (nM) |
|---|---|---|---|
| 64 | 20.0 | 56.6 | n/a |
| 65 | 22.6 | 80.5 | <1,000 |
| 66 | 0 | 0 | >1,000 |
| 67 | 3.6 | 27.8 | >1,000 |
| 68 | 9.0 | 50.9 | n/a |
| 69 | 37.0 | 78.1 | <1,000 |
| 70 | 0.4 | 21.4 | >1,000 |
| 71 | 83.4 | 89.9 | <100 |

Example B2—ATF4 Expression Inhibition Assay

HEK293T cells were maintained at 37° C. and 5% CO2 in Dulbecco's Modified Eagle's Media (DMEM) supplemented with 10% fetal bovine serum (FBS), 2 mM L-glutamine, 100 U/ml penicillin, and 100 μg/ml streptomycin. After reaching 80% of confluence, cells were detached and seeded on 6 well plates in complete media, allowed to recover overnight and treated for 3 hours with 100 nM thapsigargin (Tg) in the presence of various concentrations ranging from 0.1 nM to 10 μM. Cells without treatment (Veh) or cells treated with Tg alone were used as controls.

After 3 hours of treatment with Tg and the test compound, cells were lysed with SDS-PAGE lysis buffer. Lysates were transferred to 1.5 ml tubes and sonicated for 3 min, and total protein amounts were quantified using BCA Protein Assay Kit (Pierce). Equal amount of proteins was loaded on SDS-PAGE gels. Proteins were transferred onto 0.2 m PVDF membranes (BioRad) and probed with primary antibodies diluted in Tris-buffered saline supplemented with 0.1% Tween 20 and 3% bovine serum albumin.

ATF4 (11815) antibody (Cell Signaling Technologies) and β-actin (Sigma-Aldrich) antibodies were used as primary antibodies. A horseradish peroxidase (HRP)-conjugated secondary antibody (Rockland) was employed to detect immune-reactive bands using enhanced chemiluminescence (ECL Western Blotting Substrate, Pierce) and photographed by a gel imaging equipment (Chemidoc).

Under ISR stressed conditions (resulting from treatment with Tg), ATF4 expression is generally upregulated. Accordingly, inhibition of ATF4 expression as a result of the test compound indicates suppression of the ISR pathway.

Figure 6:
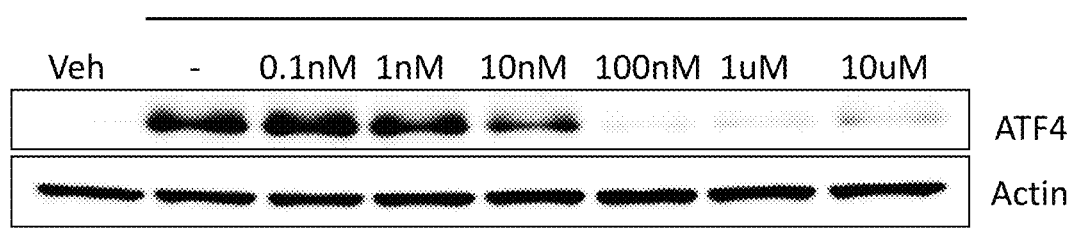
FIG. 6 shows ATF4 expression in unstressed condition (Veh) or under Tg stress alone or in the presence of compound 58 at the indicated concentration.

ATF4 expression in unstressed condition (Veh) or under Tg stress alone or in the presence of compound 58 at the indicated concentration is shown in FIG. 6. Actin expression was used as a loading control. Compound 58 inhibits the expression of ATF4 under Tg treatment in a dose dependent manner.

Example B3—Protein Translation Assay

Chinese hamster ovary (CHO) cells were maintained at 37° C. and 5% CO$_2$ in Dulbecco's Modified Eagle's Media (DMEM) supplemented with 10% fetal bovine serum, 2 mM L-glutamine, 100 U/ml penicillin, and 100 μg/ml streptomycin. After reaching 80% of confluence, cells were detached and seeded on 6 well plates in complete media, allowed to recover overnight and treated for 2 hours with 1 μM of the test compound (to assess protein synthesis levels in unstressed condition), or for 1 hour with 100 nM or 1 μM of the test compound and then co-treated with 300 nM Tg and 100 nM or 1 μM of the test compound (to assess the recovery of protein synthesis in a stressed condition). Cells treated with Tg alone were used as controls.

After the 2 hours treatments, media were replaced by adding 10 μg/ml puromycin (Sigma Aldrich #P8833) in complete media for 30 min. Media were removed and cells were lysed with SDS-PAGE lysis buffer. Lysates were transferred to 1.5 ml tubes and sonicated for 3 min and total protein amount were quantified using BCA Protein Assay Kit (Pierce). Equal amount of protein (30 μg) was loaded on SDS-PAGE gels. Proteins were transferred onto 0.2 μm PVDF membranes (BioRad) and probed with primary antibodies diluted in Tris-buffered saline supplemented with 0.1% Tween 20 (Merck #S6996184 505) and 3% bovine serum albumin (Rockland #BSA-50).

Puromycin (12D10) (Merck #MABE343) and β-actin (Sigma Aldrich #A5441) antibodies were used as primary antibody. A HRP-conjugated secondary antibody (Rockland) was employed to detect immune-reactive bands using enhanced chemiluminescence (ECL Western Blotting Substrate, Pierce). Quantification of protein bands was done by densitometry using ImageJ software.

Percent increase of protein synthesis in unstressed cells (without Tg treatment) in the presence of media alone or certain test compounds is shown in Table 3 The percentage levels were normalized to the media alone condition, which correspond to 100% protein synthesis. Certain compounds stimulated protein synthesis above baseline, indicating that these test compounds result in increased protein synthesis in unstressed cells.

Percent recovery of protein synthesis in stressed cells (with Tg treatment) due to the test compounds at 100 nM or 1 μM is also shown in Table 3. The levels were normalized to the media alone and to Tg alone conditions, which correspond to 100% and 0% respectively.

TABLE 3

| Compound No. | % Protein synthesis in unstressed cells (1 μM test compound) | % Recovery of protein expression (100 nM test compound) | % Recovery of protein expression (1 μM test compound) |
|---|---|---|---|
| 1 | 111.9 | 88.6 | 218.3 |
| 2 | 87.5 | 40.2 | 123.2 |
| 3 | 152.3 | 81.6 | 190.0 |
| 4 | 105.4 | 83.5 | 169.2 |
| 5 | 134.6 | -7.1 | 109.5 |
| 6 | 97.9 | 16.7 | 105.1 |
| 8 | 121.4 | n/a | 52.1 |
| 14 | 138.9 | n/a | 174.7 |
| 15 | 119.2 | n/a | 247.9 |
| 16 | 66.1 | n/a | -5.5 |
| 17 | 117.3 | n/a | 188.2 |
| 18 | 89.3 | n/a | 142.7 |
| 19 | 115.4 | n/a | 174.7 |
| 20 | 154.7 | n/a | 358.4 |
| 21 | 129.3 | n/a | 236.3 |
| 22 | 94.8 | n/a | 105.4 |
| 23 | 177.9 | n/a | 249.0 |
| 24 | 143.6 | n/a | 183.0 |
| 30 | 49.3 | n/a | 31.7 |
| 31 | 155.4 | n/a | 146.2 |
| 32 | 115.7 | n/a | 74.8 |
| 44 | 146.3 | n/a | 120.0 |
| 45 | 114.1 | n/a | 82.3 |
| 46 | 114.4 | n/a | 63.3 |
| 47 | 89.4 | n/a | 46.7 |
| 48 | 85.3 | n/a | 76.2 |
| 49 | 82.3 | n/a | 70.7 |
| 50 | 96.8 | n/a | 7.4 |
| 51 | 110.4 | n/a | 22.1 |
| 52 | 113.1 | n/a | 75.8 |

TABLE 3-continued

| Compound No. | % Protein synthesis in unstressed cells (1 μM test compound) | % Recovery of protein expression (100 nM test compound) | % Recovery of protein expression (1 μM test compound) |
|---|---|---|---|
| 53 | 83.7 | n/a | 46.2 |
| 54 | 99.7 | n/a | 69.9 |
| 55 | 109.9 | n/a | 49.6 |
| 56 | 154.7 | n/a | 46.1 |
| 57 | 138.6 | n/a | 69.6 |
| 58 | 164.4 | n/a | 118.4 |
| 59 | 179.7 | n/a | 98.7 |
| 60 | 140.4 | n/a | 126 |
| 61 | 195.2 | n/a | 171 |
| 62 | 99.5 | n/a | 40.2 |
| 63 | 107.4 | n/a | 16.4 |
| 64 | 109.2 | n/a | 34.7 |
| 65 | 99.0 | n/a | 51.1 |
| 66 | 84.9 | n/a | 17.6 |
| 67 | 80.0 | n/a | 27.6 |
| 68 | 81.8 | n/a | 49.3 |
| 69 | 128.8 | n/a | 43.1 |

Example B4—ATF4 Inhibition Assay Under Aβ Stimulation

Chinese hamster ovary (CHO) cells that stably express human APP751 incorporating the familial Alzheimer's disease mutation V717F were used as a source of Aβ monomer and low-n oligomers. These cells, referred to as 7PA2 CHO cells, were cultured in 100 mm dishes with Dulbecco's modified Eagle's medium (DMEM) containing 10% fetal bovine serum, 2 mM L-glutamine, 100 U/ml penicillin, and 100 μg/ml penicillin, streptomycin and 200 ρg/ml G418. Upon reaching 90-100% confluency, cells were washed with 5 mL of glutamine- and serum-free DMEM and incubated for approximately 16 h in 5 mL of the same DMEM. Conditioned media (CM) was collected.

SH-SY5Y cells were maintained at 37° C. and 5% CO2 in RPMI 1640 media supplemented with 10% fetal bovine serum (FBS), penicillin and streptomycin. After reaching 80% of confluence, cells were detached and seeded on 6 well plates in complete media, allowed to recover 48 h and treated for 16 hours with CM from WT CHO cells (wtCM) or 7PA2 CHO cells (7PA2CM) in the presences of various concentrations ranging from 1 nM to 10 μM of compound 58.

After 16 hours treatment, culture media were removed and cells were lysed with SDS-PAGE lysis buffer. Lysates were transferred to 1.5 ml tubes and sonicated for 3 min. Total protein amount was quantified using BCA Protein Assay Kit (Pierce). Equal amount of proteins (30 μg) were loaded on SDS-PAGE gels. Proteins were transferred onto 0.2 μm PVDF membranes (BioRad) and probed with primary antibodies diluted in Tris-buffered saline supplemented with 0.1% Tween 20 and 3% bovine serum albumin. ATF4 (11815) antibody (Cell Signaling Technologies) and β-actin (Sigma-Aldrich) antibodies were used as primary antibodies. A HRP-conjugated secondary antibody (Rockland) was employed to detect immune-reactive bands using enhanced chemiluminescence (ECL Western Blotting Substrate, Pierce) and photographed by a gel imaging equipment (Chemidoc).

Figure 7:
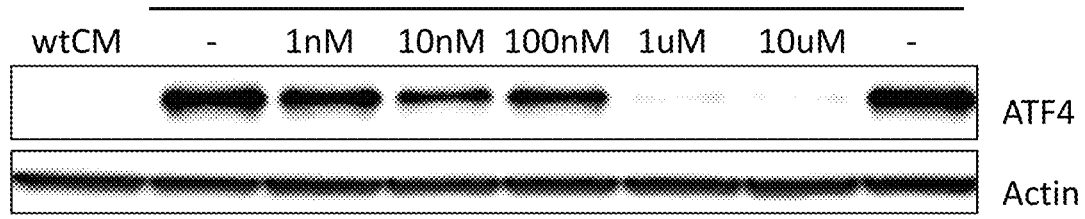
FIG. 7 shows ATF4 expression in SH-SY5Y cells after incubation with CM from the 7PA2 CHO cells alone or in the presence of compound 58 at the indicated concentrations.

ATF4 expression in SH-SY5Y cells after incubation with CM from the 7PA2 CHO cells alone or in the presence of compound 58 at the indicated concentrations is shown in FIG. 7. Actin expression was used as a loading control. Compound 58 inhibits the expression of ATF4 in the presence of Aβ oligomers treatment in a dose dependent manner.

Example B5—Electrophysiology and Long-Term Potentiation

Hippocampal slices were prepared as described in Ardiles et al., Pannexin 1 regulates bidirectional hippocampal synaptic plasticity in adult mice. Front Cell Neurosci, vol. 8, art. 326 (2014). Six to nine-month-old WT C57BL/6 or transgenic APP/PS1 mice (Jackson Lab 34829-JAX) were deeply anesthetized with isoflurane and their brains were quickly removed. 5-10 slices (350 μm) from each animal were dissected in ice-cold dissection buffer using a vibratome (Leica VT1200S, Leica Microsystems, Nussloch, Germany). Slices were incubated with 5 μM ISRIB (trans-N, N'-1,4-cyclohexanediylbis[2-(4-chlorophenoxy)-acetamide) or a vehicle (complete medium containing 0.1% DMSO) 20 min before conditioning stimulation. Synaptic responses were evoked by stimulating the Schaffer collaterals with 0.2 ms pulses delivered through concentric bipolar stimulating electrodes, and recorded extracellularly in the stratum radiatum of the CA1 subfield. Long-term potentiation (LTP) was induced by four-theta burst stimulation (TBS) (10 trains of four pulses at 100 Hz; 5 Hz inter-burst interval) delivered at 0.1 Hz. LTP magnitude based on field excitatory postsynaptic potential (fEPSP) was calculated as the average (normalized to baseline) of the responses recorded 60 min after conditioning stimulation. Similar experiments can be performed using a test compound in place of ISRIB.

Figure 5A:
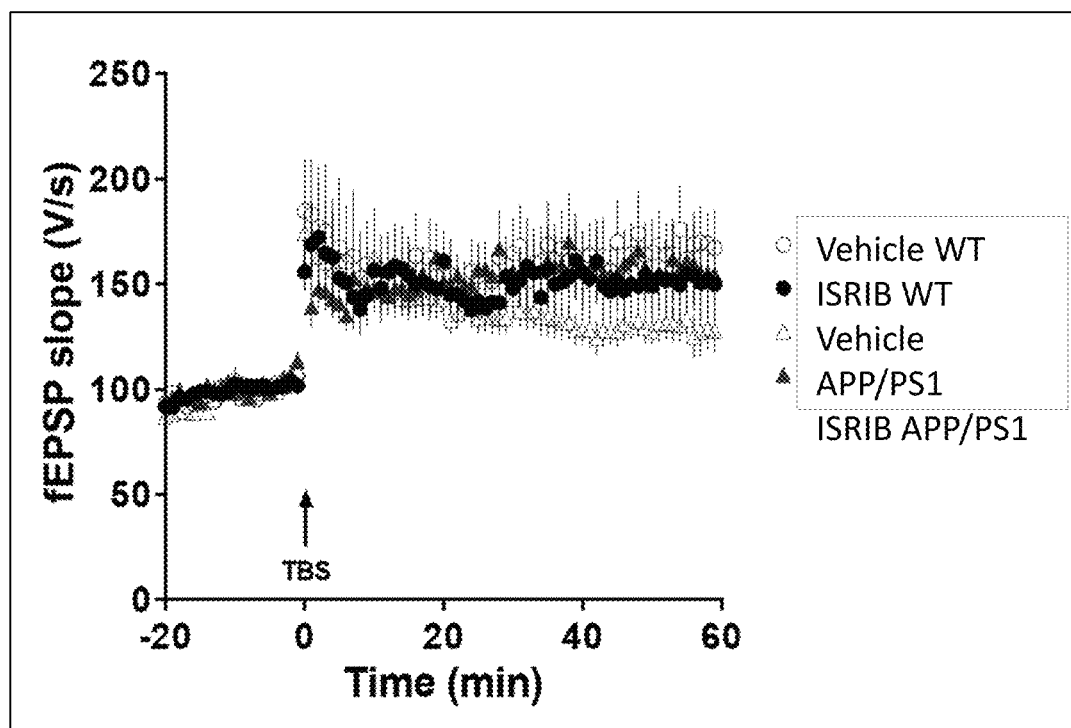
FIG. 5A shows long-term potentiation (LTP) of a stimulated hippocampal slice from a WT C57BL/6 mouse or a transgenic APP/PS1 mouse with or without incubation with ISRIB. LTP was based on field excitatory postsynaptic potential (fEPSP) slope, measured from 20 minutes prior to theta burst stimulation (TBS) to 60 minutes after TBS.
Figure 5B:
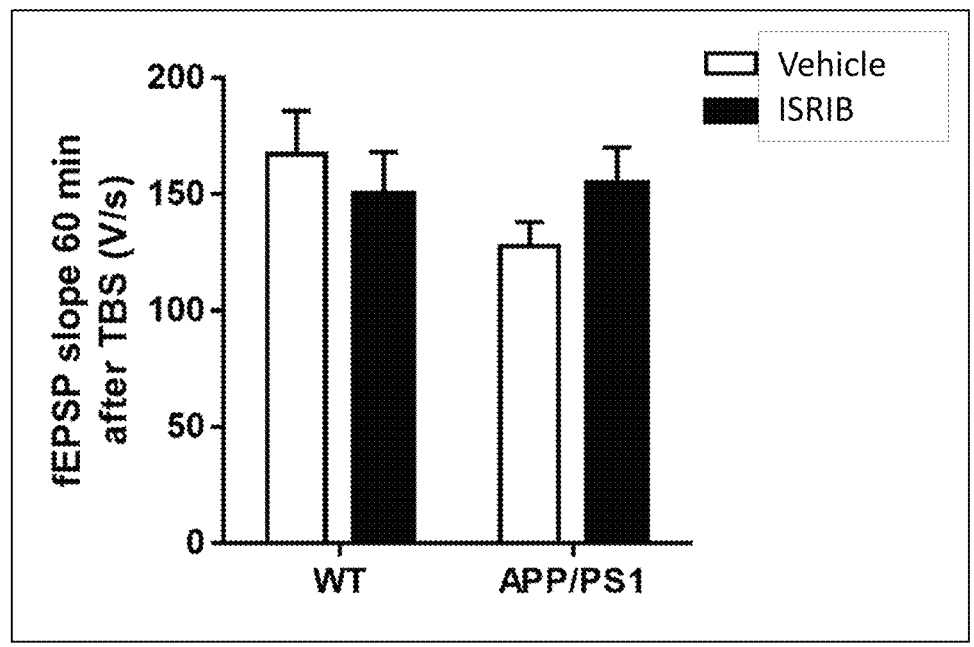
FIG. 5B shows the LTP (based on fEPSP) for the stimulated hippocampal slices after 60 minutes.

Results for ISRIB are shown in FIGS. 5A and 5B. Treatment of the slices from both the WT C57BL/6 and APP/PS1 mice treated with the vehicle resulted in LTP 60 minutes after stimulation, with the APP/PS1 sample showing significantly reduced LTP. Treatment of the slices from the APP/PS1 mouse with ISRIB, however, resulted in partial LTP recovery.

Example B6—Learning Memory in Aged Mice

Wild type 19-month old male C57BU/6J mice are used in an 8-arm radial water maze (RAWM) to measure the hippocampal-mediated learning memory. The maze involves a pool 118.5 cm in diameter and 25 cm high with 8 arms, each 41 cm in length, and an escape platform that can be moved. The pool is filled with water that is rendered opaque by adding white paint (Crayola, 54-2128-053). The escape platform remains hidden during the experiment. Visual cues are placed around the room such that they are visible to animals exploring the maze.

Nine mice are intraperitoneally injected with 5 mg/kg of a test compound formulated in 50% Polyethylene glycol (PEG-400) in distilled water and other 9 animals are intraperitoneally injected with the vehicle 50% PEG-400 in distilled water as a control group. Animals run 6 trials a day for two days. Animals are allowed 1 min to locate the escape platform. On successfully finding the platform, animals will remain for 10 seconds before being returned to their holding cage. On a failed trial, animals are guided to the escape platform and then will be returned to their holding cage 10 seconds later.

Behavioral tests are recorded and scored using a video tracking and analysis setup (Ethovision XT 8.5, Noldus Information Technology). The program automatically analyzes the number of incorrect arm entries (termed number of errors) made per trial. The last three trials are averaged to determine learning memory after training.

At the end of the behavioral test, animals are sacrificed and the hippocampi are extracted and immediately frozen in liquid nitrogen and are stored at −80° C. The frozen samples are then homogenized with a T 10 basic ULTRA-TURRAX (IKa) in ice-cold buffer lysis (Cell Signaling 9803) and protease and phosphatase inhibitors (Roche). Lysates are sonicated for 3 min and centrifuged at 13,000 rpm for 20 minutes at 4° C. Protein concentration in supernatants is determined using BCA Protein Assay Kit (Pierce). Equal amount of protein is loaded on SDS-PAGE gels. Proteins are transferred onto 0.2 μm PVDF membranes (BioRad) and probed with primary antibodies diluted in Tris-buffered saline supplemented with 0.1% Tween 20 and 3% bovine serum albumin.

ATF4 (11815) antibody (Cell Signaling Technologies) and β-actin (Sigma-Aldrich) antibodies are used as primary antibodies. A HRP-conjugated secondary antibody (Rockland) is employed to detect immune-reactive bands using enhanced chemiluminescence (ECL Western Blotting Substrate, Pierce). Quantification of protein bands is done by densitometry using ImageJ software.

Results of RAWM task and levels of ATF4 expression normalized to β-actin expression in hippocampi can be reported.

Example B7—Learning Memory, Long-Term Memory and Social Behavior after Traumatic Brain Injury (TBI)

Wild type three-month-old male C57B1/6J mice are randomly assigned to TBI or sham surgeries. Animals are anesthetized and maintained at 2% isoflurane and secured to a stereotaxic frame with nontraumatic ear bars. The hair on their scalp is removed, and eye ointment and betadine are applied to their eyes and scalp, respectively. A midline incision is made to expose the skull. A unilateral TBI is induced in the right parietal lobe using the controlled cortical impact model (Nat Neurosci. 2014 August; 17(8): 1073-82). Mice receive a 3.5-mm diameter craniectomy, a removal of part of the skull, using an electric microdrill. The coordinates of the craniectomy are: anteroposterior, −2.00 mm and mediolateral, +2.00 mm with respect to bregma. After the craniectomy, the contusion is induced using a 3-mm convex tip attached to an electromagnetic impactor (Leica). The contusion depth is set to 0.95 mm from dura with a velocity of 4.0 m/s sustained for 300 ms. These injury parameters are chosen to target, but not penetrate, the hippocampus. Sham animals received craniectomy surgeries but without the focal injury. After focal TBI surgery, the scalp was sutured and the animal is allowed to recover in an incubation chamber set to 37° C. Animals are returned to their home cage after showing normal walking and grooming behavior. Recovery from the surgical procedures as exhibited by normal behavior and weight maintenance is monitored throughout the duration of the experiments.

After 28 days post injury (dpi), animals are tested on the RAWM assay (see Example B6, above). Animals run 12 trials during learning test and 4 trials during memory test. Last three trials from learning test and all four trials from memory test are averaged to determine learning memory (learning test) and long-term memory (memory test).

Animals are intraperitoneally injected with 5 mg/kg of a test compound formulated in 50% PEG-400 in distilled water (n=10) or vehicle (50% PEG-400 in distilled water; n=10 for TBI group and n=8 for sham group) starting the day prior to behavior tests (27 dpi), after each of the final trials of the learning-test days (28 and 29 dpi) and before the social behavior test (42 dpi, see below) for a total of four injections. No injections is given when long-term memory was tested on day 35 dpi.

To quantitate social tendencies of the treated mice, the time spent with a novel conspecific mouse was measured in a Crawley's three-chamber box (J Vis Exp. 2011; (48): 2473). Treated animals are left to explore all three empty chambers freely for 10 min for habituation. A social pair mouse is placed in the housing cage at one side of the apparatus and treated animals in opposite chamber so that the mouse can freely explore the entire apparatus for 10 min. The time spent with the never-before-met animal is recorded. Direct contact between the treated mouse and the housing cage or stretching of the body of the subject mouse in an area 3-5 cm around the housing cage is counted as an active contact.

Learning memory, long-term memory, and social behavior after TBI in mice can be reported.

Example B8—Fasting-Induced Muscle Atrophy

Wild type eight-weeks-old male Balb/c mice obtained from the vivarium Fundación Ciencia & Vida Chile (Santiago, Chile) were used. Mice were housed in independent plastic cages in a room maintained at 25° C. with a 12-h: 12-h light:dark cycle.

Twenty-four hours before and during the 2 days of fasted procedures, animals were weighed and receive oral administration via feeding tubes (15 gauge) of vehicle (50% Polyethylene glycol 400 (Sigma-Aldrich P3265) in distilled water or 10 mg/kg of test compound formulated in vehicle solution.

After 2 days of fasting the animals were weighed and sacrificed. Quadriceps were removed from both hindlimbs and weighed. Mice with feed and water ad libitum were used as control.

For in vivo measurements of protein synthesis, puromycin (Sigma-Aldrich, P8833) was prepared at 0.04 μmol/g body weight in a volume of 200 μL of PBS, and subsequently administered into the animals via IP injection, 30 min prior to muscle collection.

Upon collection, muscles were immediately frozen in liquid nitrogen and then stored at −80° C. The frozen muscles were then homogenized with a T 10 basic ULTRA-TURRAX (IKa) in ice-cold buffer lysis (Cell Signaling 9803) and protease and phosphatase inhibitors (Roche). Lysates were sonicated for 3 min and centrifuged at 13,000 rpm for 20 minutes at 4° C. Protein concentration in supernatants was determined using BCA Protein Assay Kit (Pierce). Equal amount of proteins was loaded on SDS-PAGE gels. Proteins were transferred onto 0.2 um PVDF membranes (BioRad) and probed with primary antibodies diluted in Tris-buffered saline supplemented with 0.1% Tween 20 and 3% bovine serum albumin.

Puromycin (12D10) (Merck Millipore) ATF4 (Abcam), Atrogin-1 (ECM Biosciences), MuRF-1 (Santa Cruz Biotechnology) and β-actin (Sigma-Aldrich) antibodies were used as primary antibodies. A HRP-conjugated secondary antibody (Rockland) was employed to detect immune-reactive bands using enhanced chemiluminescence (ECL Western Blotting Substrate, Pierce). Quantification of protein bands was done by densitometry using ImageJ software.

Figure 8A:
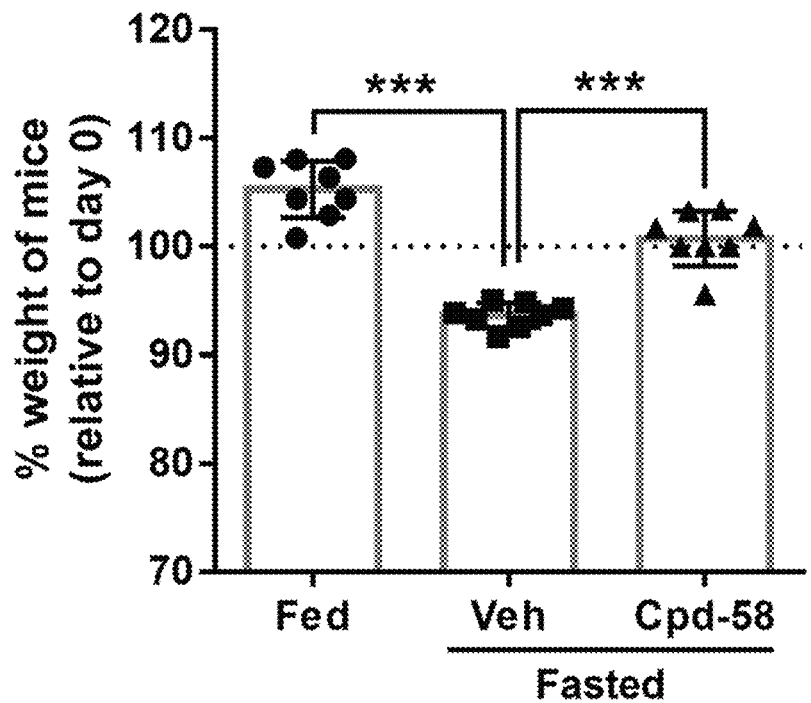
FIG. 8A shows weight of fed mice and fasted mice treated either with vehicle or compound 58.

Weight of fed mice and fasted mice treated either with vehicle or compound 58 is shown in FIG. 8A. Percentage of mice weight was calculated as the percentage of weight at the end of the study relative to the weight at the beginning of the study (day 0), where the weight of fed mice at day 0 corresponds to 100%.

Figure 8B:
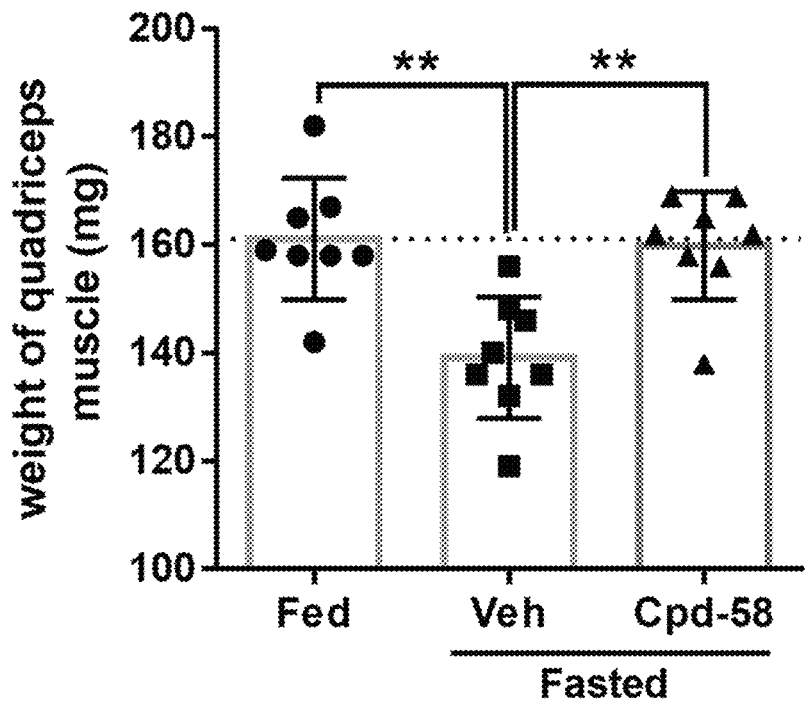
FIG. 8B shows weight of quadriceps muscle in fed mice and in fasted mice treated either with vehicle or compound 58.

Weight of quadriceps from different groups is shown in FIG. 8B.

Figure 8C:
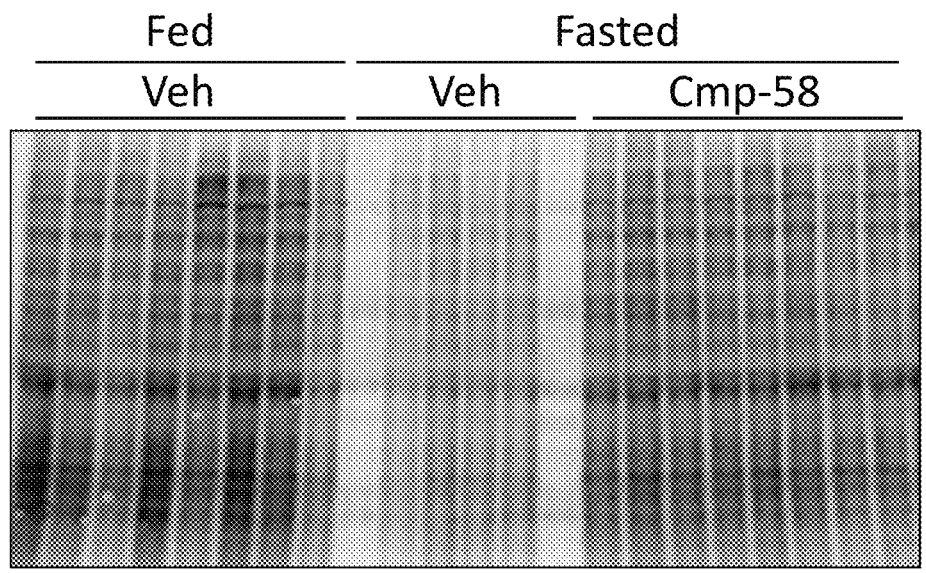
FIG. 8C presents an immunoblot of puromycin labelling in quadriceps samples of each mouse from fed or fasted animals treated with vehicle or compound 58. Each lane corresponds to a sample derived from each mouse.
Figure 8D:
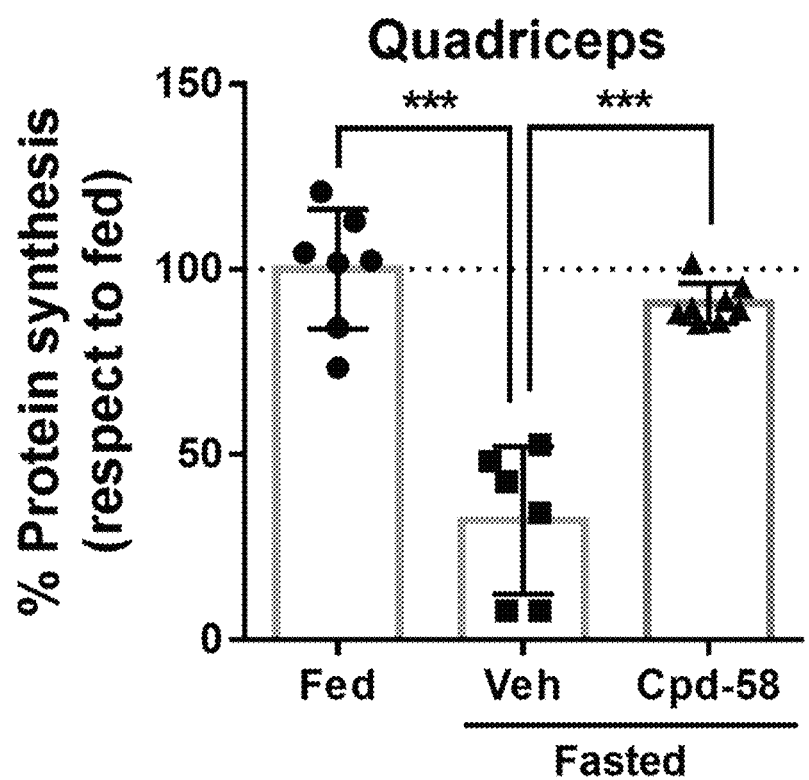
FIG. 8D shows percent of protein synthesis in muscles from fed or fasted animals treated with vehicle or compound 58.

Immunoblot of puromycin labelling in quadriceps samples of each mouse from fed or fasted animals treated with vehicle or compound 58 is shown in FIG. 8C. Each lane corresponds to a sample derived from each mouse. Percent of protein synthesis in muscles from each group is shown in FIG. 8D. Percentage was calculated from FIG. 8C as the percent relative to protein synthesis levels from control mice (Fed) which correspond to 100%.

Figure 8E:
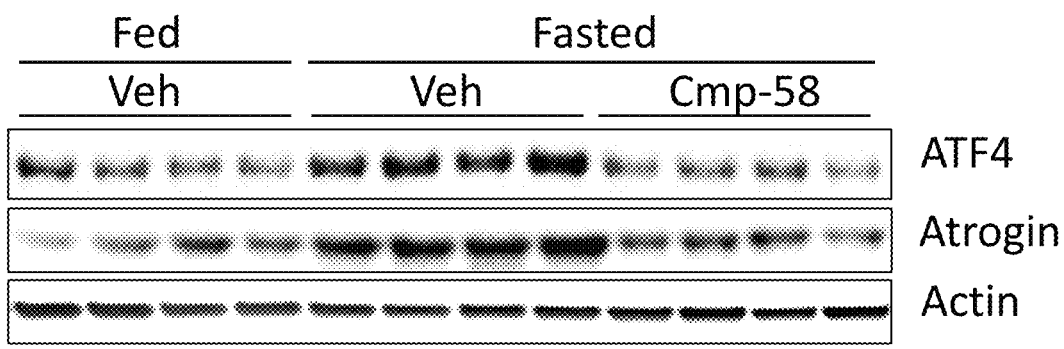
FIG. 8E shows the expression of ATF4 and the muscle atrophy marker, Atrogin-1, of quadriceps derived from fed mice or fasted mice treated with vehicle or compound 58.
Figure 8F:
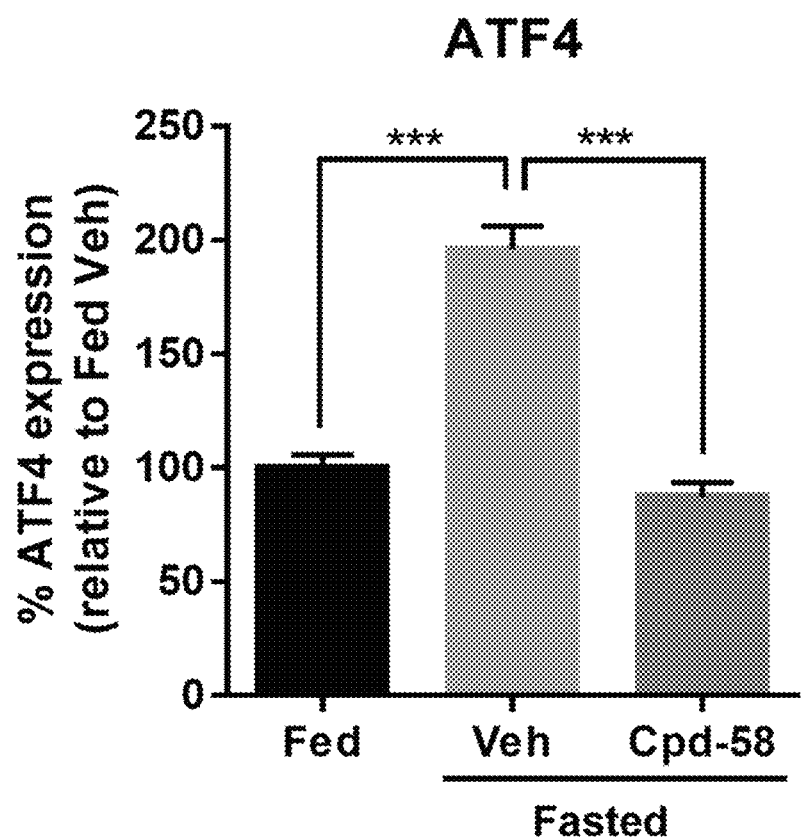
FIG. 8F shows percent of ATF4 expression of quadriceps derived from fed mice or fasted mice treated with vehicle or compound 58.
Figure 8G:
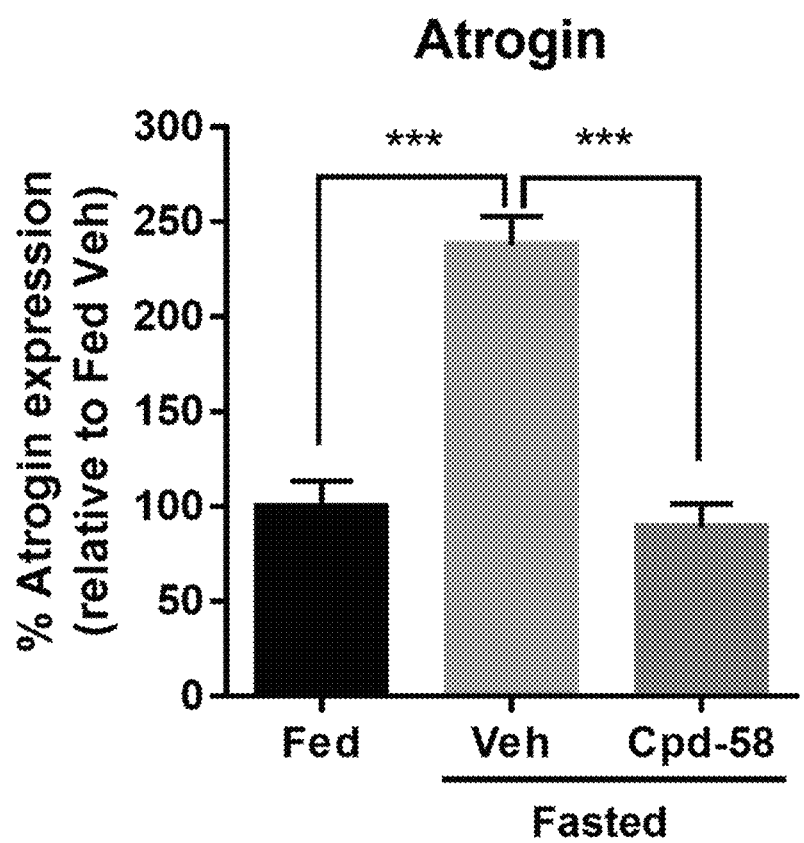
FIG. 8G shows percent of Atrogin expression of quadriceps derived from fed mice or fasted mice treated with vehicle or compound 58.

Expression of ATF4 and the muscle atrophy marker, Atrogin-1, of quadriceps derived from fed mice or fasted mice treated with vehicle or compound 58 are shown in FIG. 8E. Percent of ATF4 and Atrogin expression from FIG. 8E are shown in FIGS. 8F and 8G respectively. The levels were normalized to β-actin expression and percentage was calculated as the percent relative to the expression from control mice (Fed) which corresponds to 100%. Treatment of fasted mice with compound 58 results in a reduction of both ATF4 and Atrogin-1 expression compared to vehicle-treated fasted mice and it was comparable to levels observed in control mice (Fed).

Example B9—Immobilization-Induced Muscle Atrophy

Wild type eight-weeks-old male Balb/c mice obtained from the vivarium Fundación Ciencia & Vida Chile (Santiago, Chile) were used. Mice were housed in independent plastic cages, fed ad libitum in a room maintained at 25° C. with a 12-h:12-h light:dark cycle.

Twenty-four hours before and during the 3 days of immobilization procedures, animals receive oral administration via feeding tubes (15 gauge) of vehicle (50% Polyethylene glycol 400 (Sigma-Aldrich P3265) in distilled water or 10 mg/kg of test compound formulated in vehicle.

One hindlimb is immobilized with a plastic stick placed over and under the limb and fixed with a medical adhesive bandage. Animals were daily monitored. The immobilization procedure prevents movement of the immobilized leg alone. After 3 days, the animals were sacrificed and gastrocnemius muscle is removed from both hindlimbs, the contralateral, non-immobilized leg being used as an internal control.

For in vivo measurements of protein synthesis, puromycin (Sigma-Aldrich, P8833) is prepared at 0.04 μmol/g body weight in a volume of 200 μl of PBS, and subsequently administered into the animals via intraperitoneal injection, 30 min prior to muscle collection.

Upon collection, muscles were immediately frozen in liquid nitrogen and stored at −80° C. The frozen muscles were then homogenized with a T 10 basic ULTRA-TURRAX (IKa) in ice-cold buffer lysis (Cell Signaling 9803) and protease and phosphatase inhibitors (Roche). Lysates were sonicated for 3 min and centrifuged at 13,000 rpm for 20 minutes at 4° C. Protein concentration in supernatants is determined using BCA Protein Assay Kit (Pierce). Equal amount of protein is loaded on SDS-PAGE gels. Proteins were transferred onto 0.2 um PVDF membranes (BioRad) and probed with primary antibodies diluted in Tris-buffered saline supplemented with 0.1% Tween 20 and 3% bovine serum albumin.

Puromycin (12D10) (Merck Millipore), ATF4 (Abcam), Atrogin-1 (ECM Biosciences), MuRF-1 (Santa Cruz Biotechnology) and β-actin (Sigma-Aldrich) antibodies were used as primary antibodies. A HRP-conjugated secondary antibody (Rockland) is employed to detect immune-reactive bands using enhanced chemiluminescence (ECL Western Blotting Substrate, Pierce). Quantification of protein bands is done by densitometry using ImageJ software.

Figure 9A:
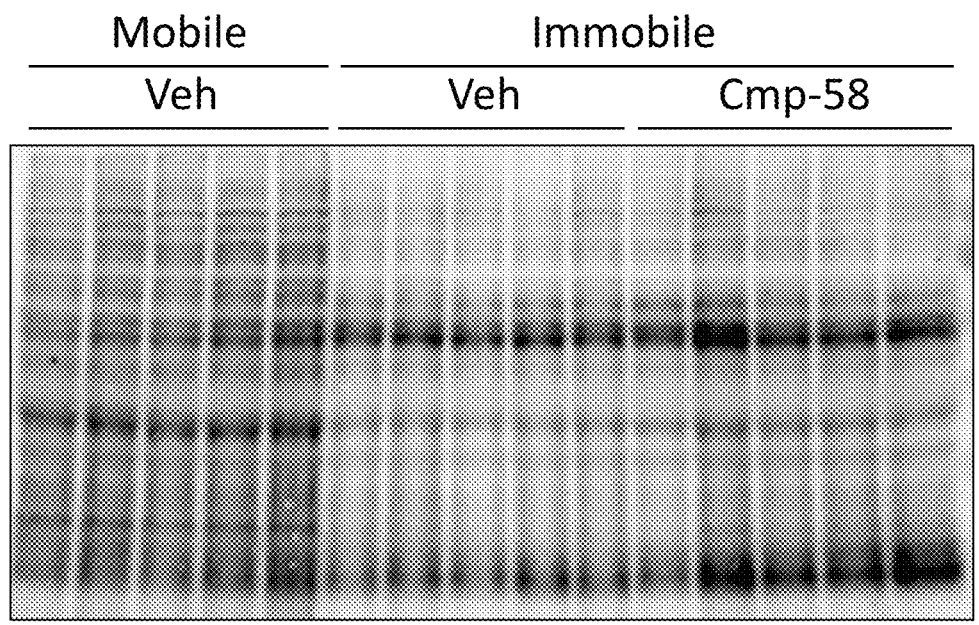
FIG. 9A presents an immunoblot of puromycin labelling in gastrocnemius samples of mobile and immobile hind limb from mouse treated with vehicle or compound 58. Each lane corresponds to a sample derived from the indicated hind limb.

Immunoblot of puromycin labelling in gastrocnemius samples of mobile and immobile hind limb from mouse treated with vehicle or compound 58 is shown in FIG. 9A. Each lane corresponds to a sample derived from the indicated hind limb.

Figure 9B:
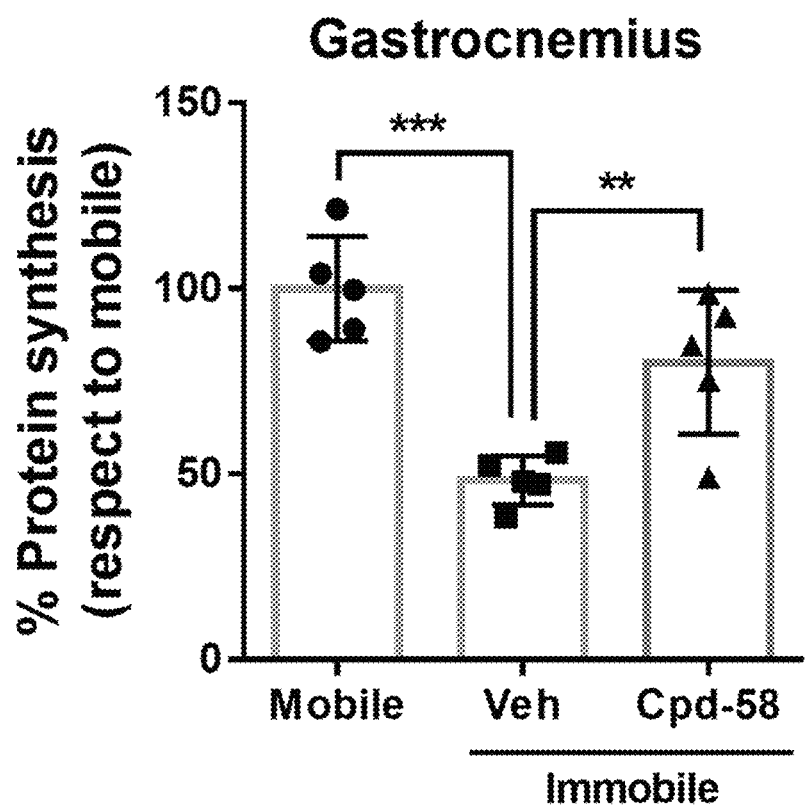
FIG. 9B shows percent of protein synthesis in mobile and immobile hind limbs sections from gastrocnemius derived from mice treated with vehicle or compound 58.

Percent of protein synthesis in mobile and immobile hind limbs sections from gastrocnemius derived from mice treated with vehicle or compound 58 is shown in FIG. 9B. The levels were normalized to β-actin expression and percentage was calculated as the percent relative to protein synthesis levels from mobile limb of control mice (vehicle-treated) which correspond to 100%.

Figure 9C:
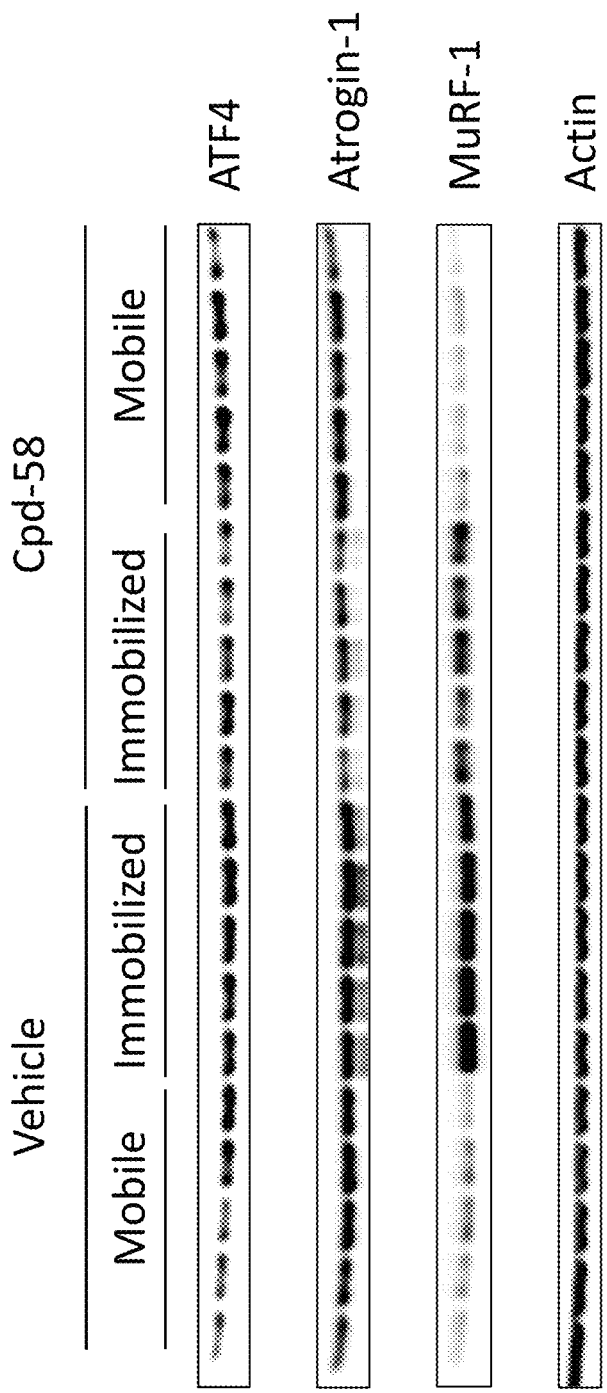
FIG. 9C shows the expression of ATF4 and the muscle atrophy markers, Atrogin-1 and MuRF-1, of gastrocnemius derived from mobilized and immobilized hind limbs of mice treated with vehicle or compound 58.
Figure 9D:
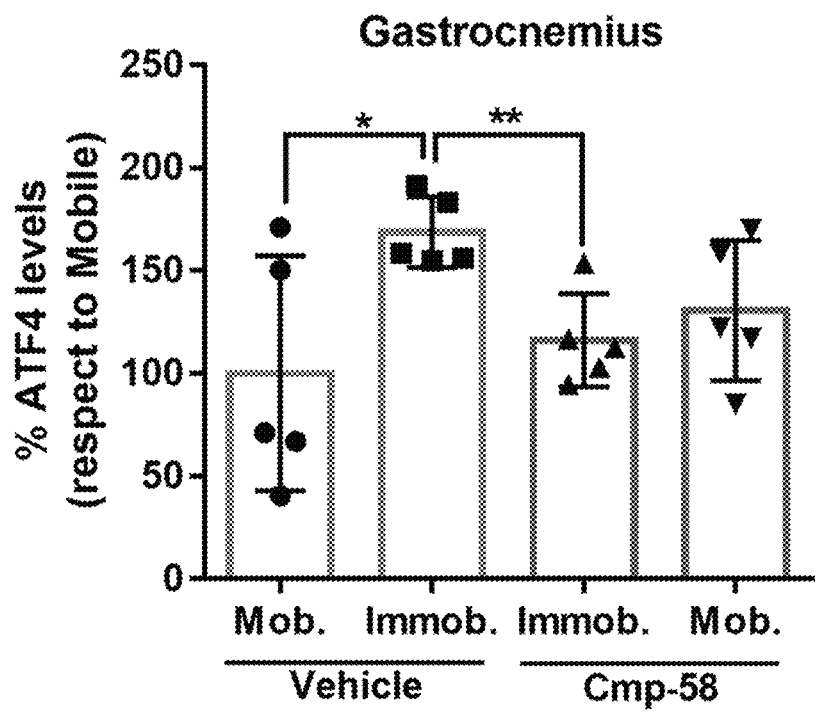
FIG. 9D shows percent of ATF4 expression of gastrocnemius derived from mobilized and immobilized hind limbs of mice treated with vehicle or compound 58.
Figure 9E:
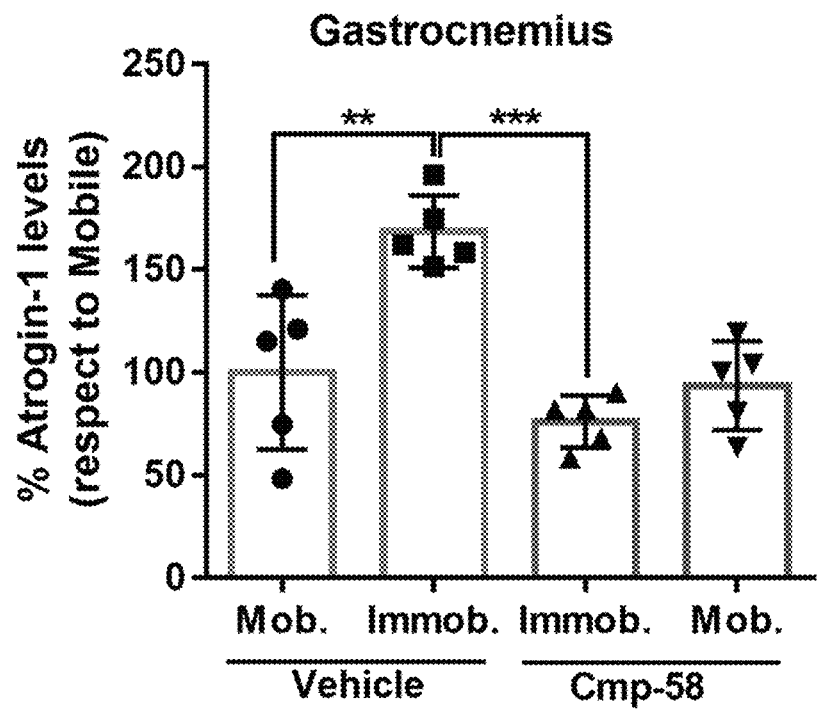
FIG. 9E shows percent of Atrogin-1 expression of gastrocnemius derived from mobilized and immobilized hind limbs of mice treated with vehicle or compound 58.
Figure 9F:
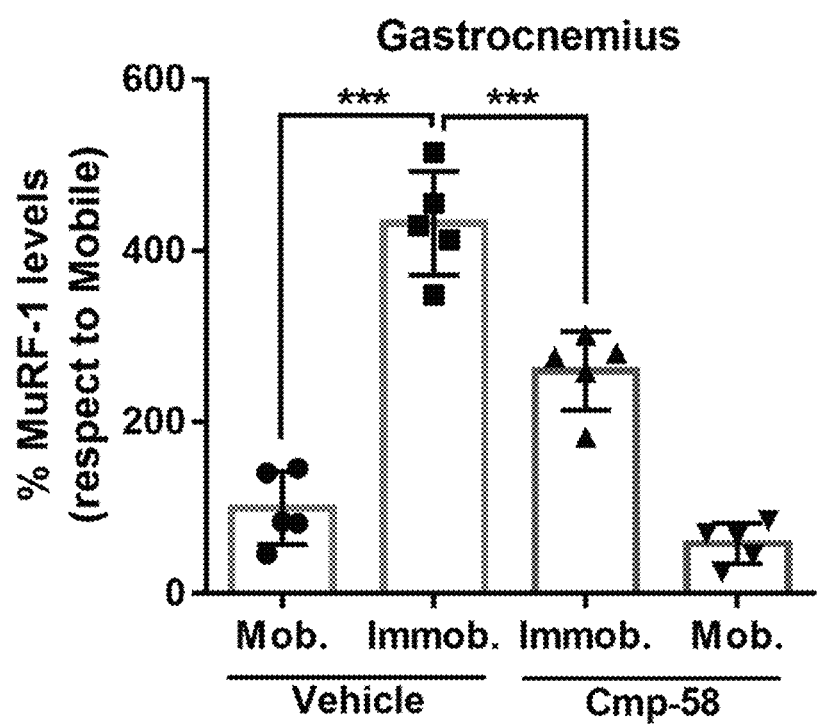
FIG. 9F shows percent of MuRF-1 expression of gastrocnemius derived from mobilized and immobilized hind limbs of mice treated with vehicle or compound 58.

Expression of ATF4 and the muscle atrophy markers, Atrogin-1 and MuRF-1, of gastrocnemius derived from mobilized and immobilized hind limbs of mice treated with vehicle or compound 58 are shown in FIG. 9C. Percent of ATF4, Atrogin-1 and MuRF-1 expression from FIG. 9C are shown in FIGS. 9D, 9E and 9F respectively. The levels were normalized to β-actin expression and percentage is calculated as the percent relative to the expression of mobile hind limb from control mice (Vehicle) which corresponds to 100%. Treatment of immobilized animals with compound 58 promotes a reduction of ATF4, Atrogin-1 and MuRF-1 expression compared to immobilized animals treated with vehicle.

Example B10—Cachexia-Induced Muscle Atrophy

Wild type six-weeks-old male Balb/c mice obtained from the vivarium Fundación Ciencia & Vida Chile (Santiago, Chile) were used. Mice were housed in independent plastic cages in a room maintained at 25° C. with a 12-h:12-h light:dark cycle.

$1 \times 10^6$ CT26 colon carcinoma cell line (ATCC #CRL-2638, ATCC Manassas, Va.) were injected subcutaneously in the right lower flank of each animal for induction of cachexia-induced muscle atrophy as described (Nat Commun. 2012 Jun. 12; 3:896). Non-injected animals were used as controls. At day 7 post tumor-cell injection, animals were randomized into two groups and treated with 10 mg/kg of test compound formulated in 50% Polyethylene glycol (PEG-400) in distilled water, or with vehicle (50% PEG-400 in distilled water) by daily oral gavage for 12 days.

After 12 treatments, animals were sacrificed and gastrocnemius were removed from both hindlimbs. Muscles derived from non-tumor-bearing mice were used as control.

Upon collection, muscles were immediately frozen in liquid nitrogen and then stored at −80° C. The frozen muscles were then homogenized with a T 10 basic ULTRA-TURRAX (IKa) in ice-cold buffer lysis (Cell Signaling 9803) and protease and phosphatase inhibitors (Roche). Lysates were sonicated for 3 min and centrifuged at 13,000 rpm for 20 minutes at 4° C. Protein concentration in supernatants was determined using BCA Protein Assay Kit (Pierce). Equal amount of protein was loaded on SDS-PAGE gels. Proteins were transferred onto 0.2 um PVDF membranes (BioRad) and probed with primary antibodies diluted in Tris-buffered saline supplemented with 0.1% Tween 20 and 3% bovine serum albumin.

ATF4 (Abcam), Atrogin-1 (ECM Biosciences), MuRF-1 (Santa Cruz Biotechnology) and β-actin (Sigma-Aldrich)

antibodies were used as primary antibodies. A HRP-conjugated secondary antibody (Rockland) was employed to detect immune-reactive bands using enhanced chemiluminescence (ECL Western Blotting Substrate, Pierce). Quantification of protein bands was done by densitometry using ImageJ software.

Figure 10A:
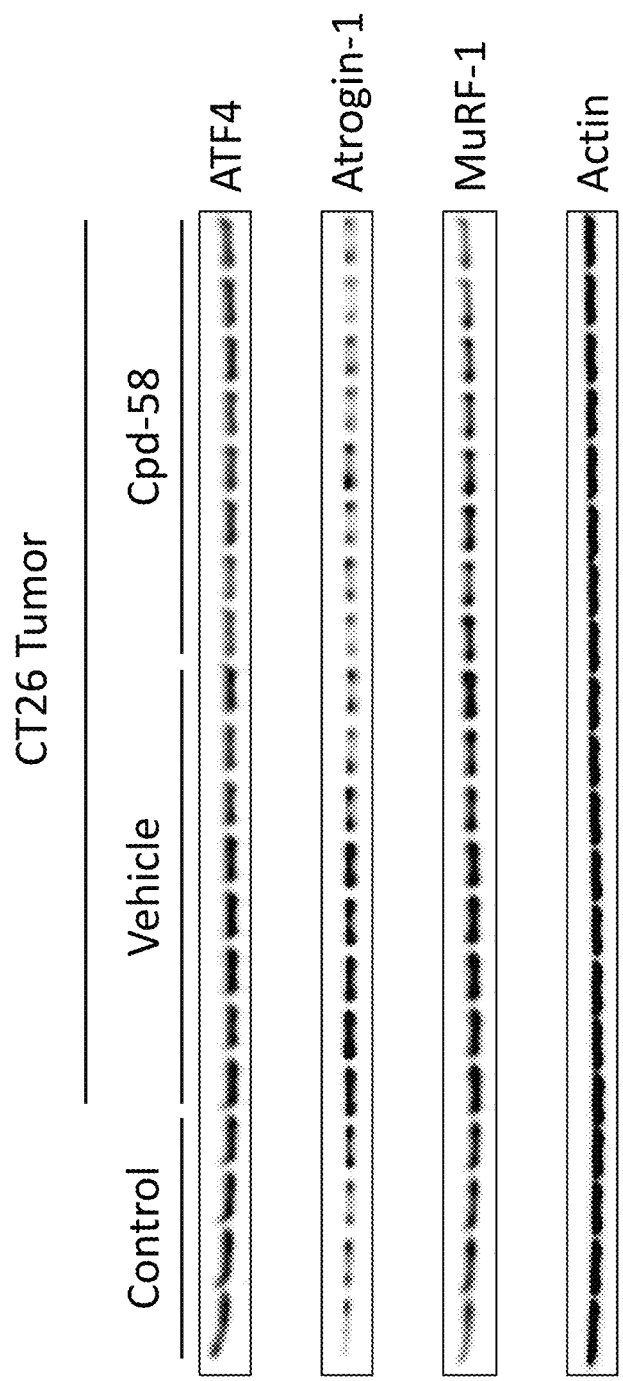
FIG. 10A shows the expression of ATF4 and the muscle atrophy markers, Atrogin-1 and MuRF-1, of gastrocnemius derived from control and CT26 tumor-bearing mice treated with vehicle or compound 58.
Figure 10B:
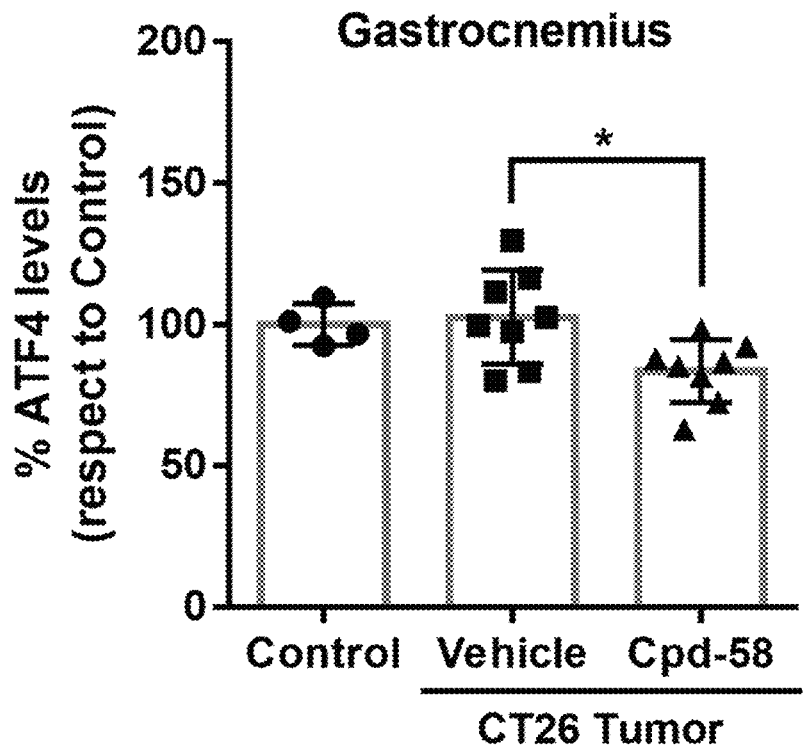
FIG. 10B shows percent of ATF4 expression of gastrocnemius derived from control and CT26 tumor-bearing mice treated with vehicle or compound 58.
Figure 10C:
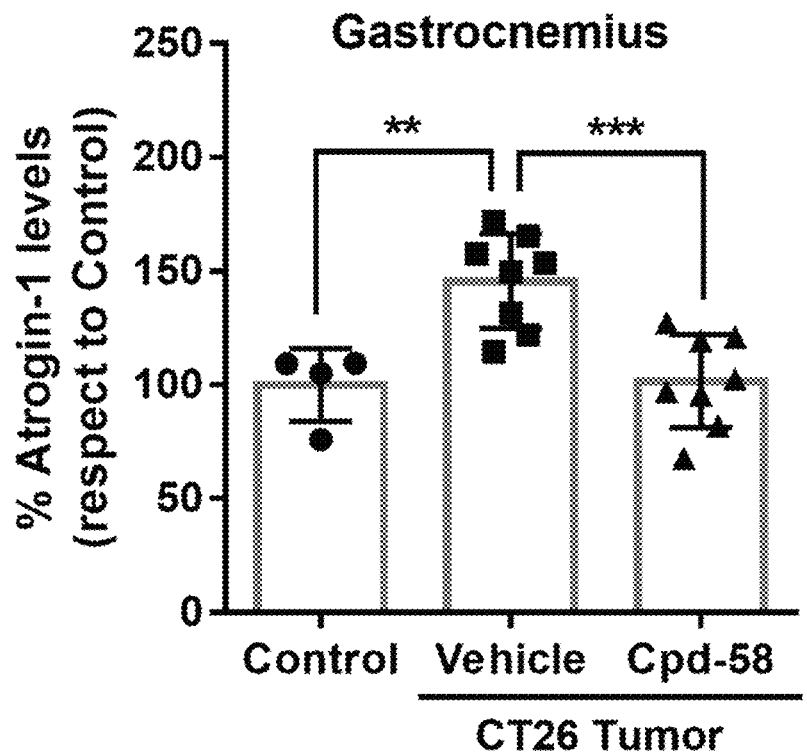
FIG. 10C shows percent of Atrogin-1 expression of gastrocnemius derived from control and CT26 tumor-bearing mice treated with vehicle or compound 58.
Figure 10D:
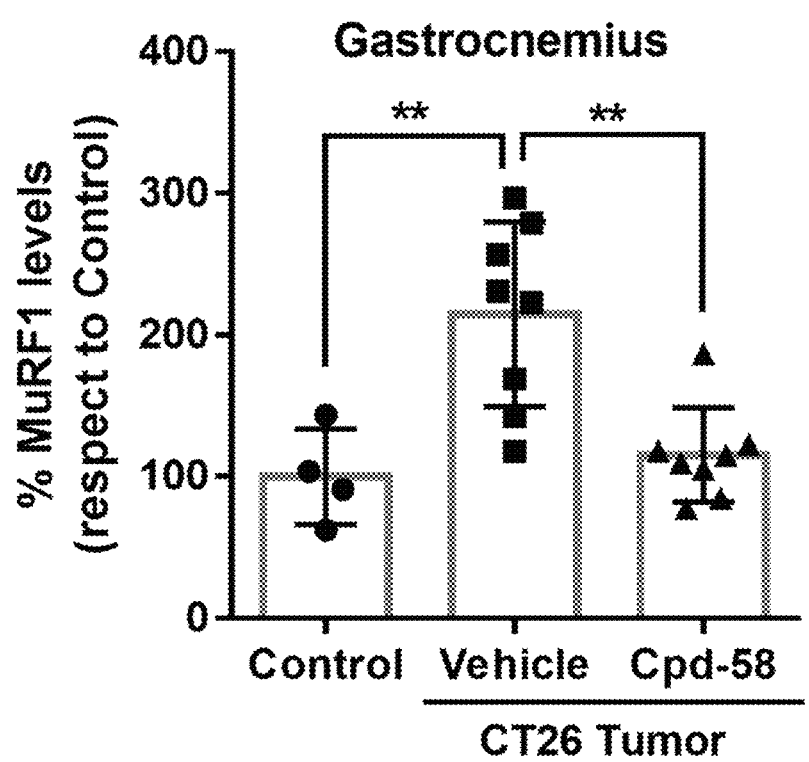
FIG. 10D shows percent of MuRF-1 expression of gastrocnemius derived from control and CT26 tumor-bearing mice treated with vehicle or compound 58.

Expression of ATF4 and the muscle atrophy markers, Atrogin-1 and MuRF-1, of gastrocnemius derived from control and CT26 tumor-bearing mice treated with vehicle or compound 58 are shown in FIG. 10A. Percent of ATF4, Atrogin-1 and MuRF-1 expression from FIG. 10A are shown in FIG. 10B, 10C and 10D respectively. The levels were normalized to β-actin expression and percentage was calculated as the percent relative to the expression of non-tumor-bearing mice (Control) which corresponds to 100%. Treatment of tumor-bearing animals with compound 58 results in a reduction of ATF4, Atrogin-1 and MuRF-1 expression in muscles compared to those of tumor-bearing animals treated with vehicle.

Example B11—Denervation-Induced Muscle Atrophy

Wild type eight-weeks-old male Balb/c mice obtained from the vivarium Fundación Ciencia & Vida Chile (Santiago, Chile) were used. Mice were housed in independent plastic cages in a room maintained at 25° C. with a 12-h:12-h light:dark cycle.

After a deeply anesthetized (isoflurane inhaled in medical oxygen), mice were denervated by surgical removal of ~2 mm of sciatic nerve from one hindlimb. The incisions were closed using sutures. All procedures were performed under sterile conditions and the mice were daily monitored.

After seven days of denervation, animals receive oral administration every day via feeding tubes (15 gauge) of vehicle (50% Polyethylene glycol 400 (Sigma-Aldrich P3265) in distilled water) or 10 mg/kg of compound 58 formulated in vehicle solution.

After 14 days of denervation, animals were sacrificed and tibialis anterior were removed from both hindlimbs. Muscles derived from non-denervated hind limb were used as control.

Upon collection, muscles were immediately frozen in liquid nitrogen and stored at −80° C. The frozen muscles were then homogenized with a T 10 basic ULTRA-TURRAX (IKa) in ice-cold buffer lysis (Cell Signaling 9803) and protease and phosphatase inhibitors (Roche). Lysates were sonicated for 3 min and centrifuged at 13,000 rpm for 20 minutes at 4° C. Protein concentration in supernatants was determined using BCA Protein Assay Kit (Pierce). Equal amount of protein was loaded on SDS-PAGE gels. Proteins were transferred onto 0.2 um PVDF membranes (BioRad) and probed with primary antibodies diluted in Tris-buffered saline supplemented with 0.1% Tween 20 and 3% bovine serum albumin.

ATF4 (Abcam), Atrogin-1 (ECM Biosciences), MuRF-1 (Santa Cruz Biotechnology) and R-actin (Sigma-Aldrich) antibodies were used as primary antibodies. A HRP-conjugated secondary antibody (Rockland) was employed to detect immune-reactive bands using enhanced chemiluminescence (ECL Western Blotting Substrate, Pierce). Quantification of protein bands was done by densitometry using ImageJ software.

Figure 11A:
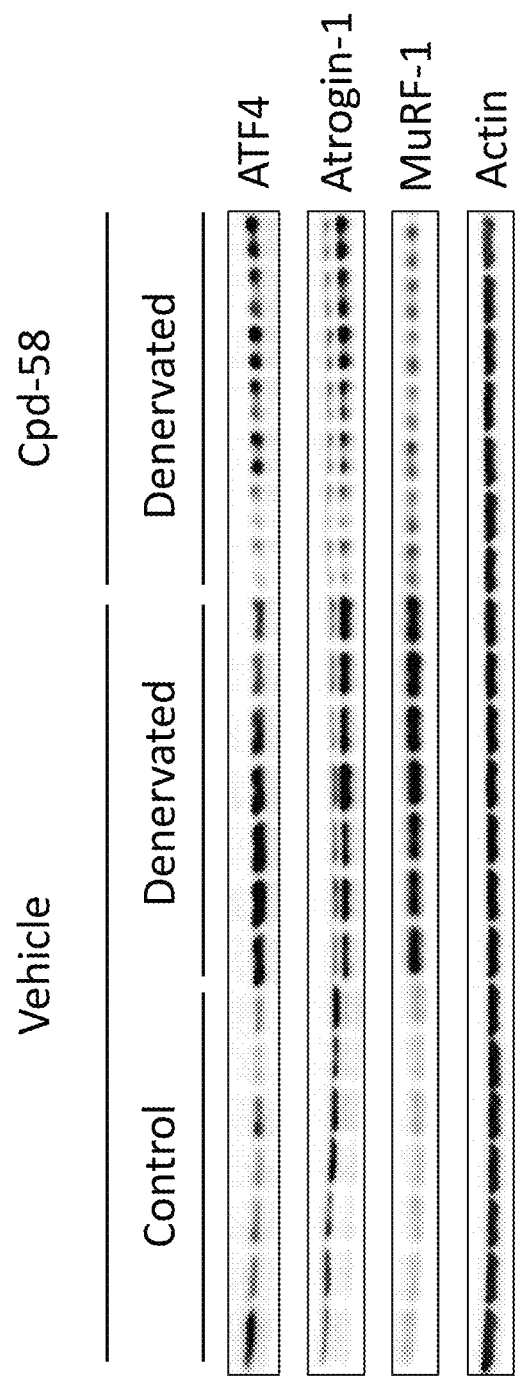
FIG. 11A shows the expression of ATF4 and the muscle atrophy markers, Atrogin-1 and MuRF-1, of tibialis anterior derived from control and denervated hind limbs of mice treated with vehicle or compound 58.
Figure 11B:
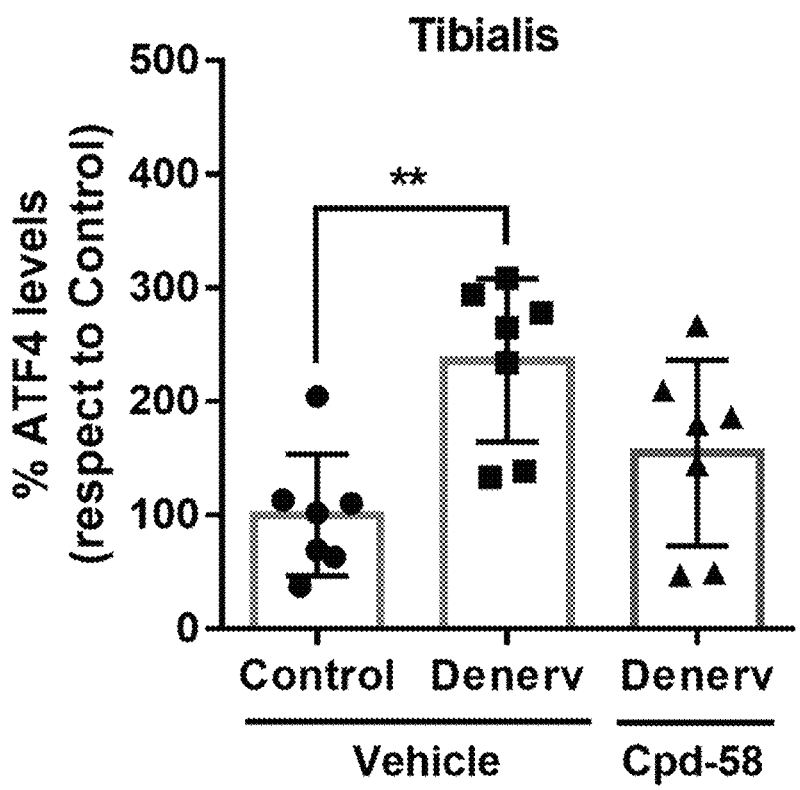
FIG. 11B shows percent of ATF4 expression of tibialis anterior derived from control and denervated hind limbs of mice treated with vehicle or compound 58.
Figure 11C:
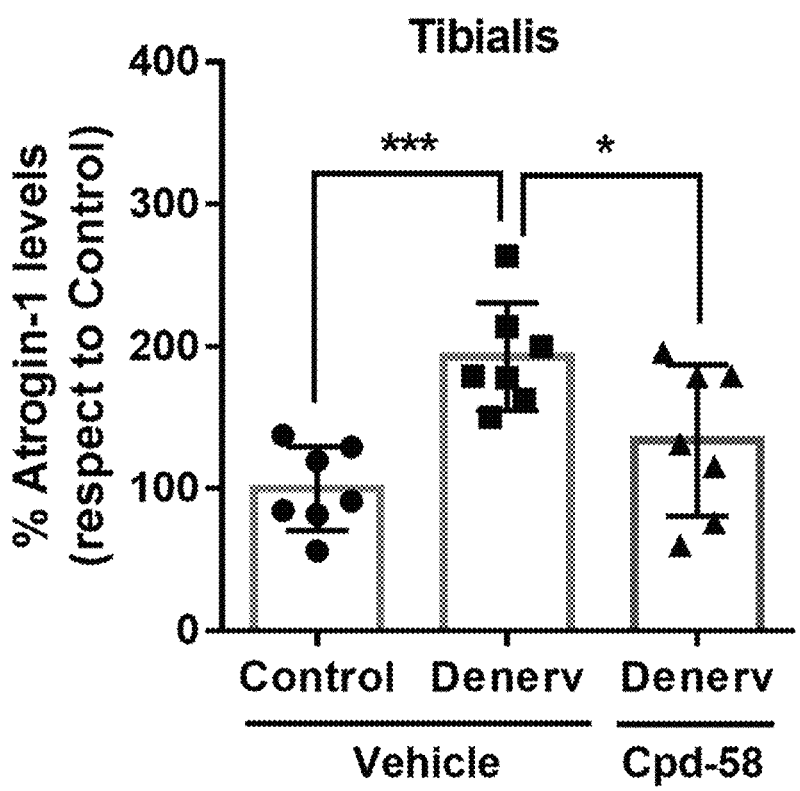
FIG. 11C shows percent of Atrogin-1 expression of tibialis anterior derived from control and denervated hind limbs of mice treated with vehicle or compound 58.
Figure 11D:
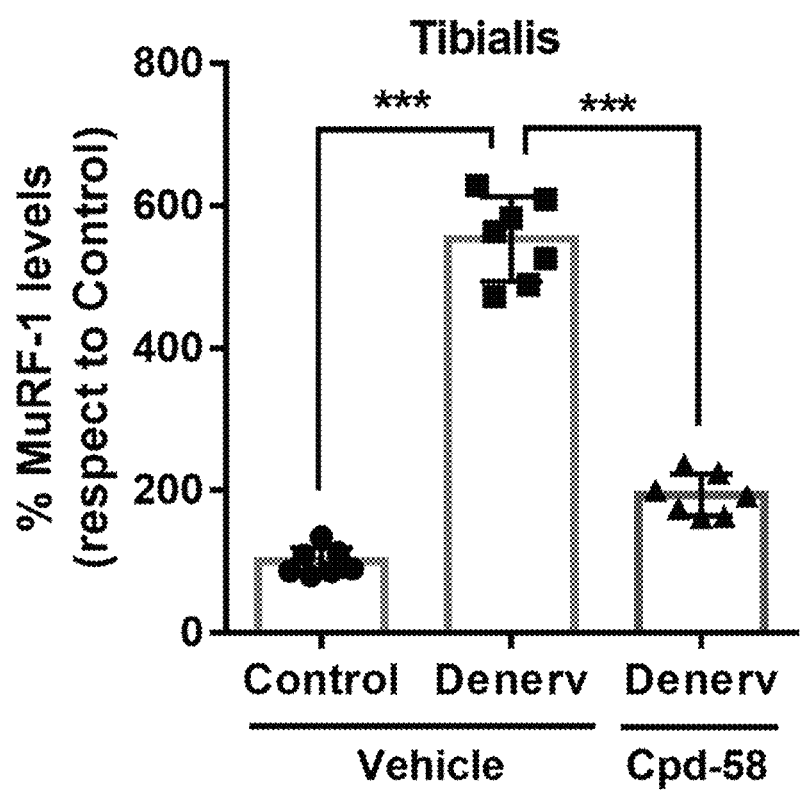
FIG. 11D shows percent of MuRF-1 expression of tibialis anterior derived from control and denervated hind limbs of mice treated with vehicle or compound 58.

Expression of ATF4 and the muscle atrophy markers, Atrogin-1 and MuRF-1, of tibialis anterior derived from control and denervated hind limbs of mice treated with vehicle or compound 58 are shown in FIG. 11A. Percent of ATF4, Atrogin-1 and MuRF-1 expression from FIG. 11A are shown in FIGS. 11B, 11C and 11D respectively. The levels were normalized to pi-actin expression and percentage was calculated as the percent relative to the expression of non-denervated hind limbs from control mice (Vehicle) which corresponds to 100%. Treatment of denervated animals with compound 58 results in a reduction of ATF4, Atrogin-1 and MuRF-1 expression in muscles compared to those of denervated animals treated with vehicle.

Example B12—Protein Production by Transient Gene Expression

CHO cells were maintained at 37° C. and 5% CO2 in DMEM supplemented with 10% fetal bovine serum (FBS), 2 mM L-glutamine, 100 U/ml penicillin, and 100 μg/ml streptomycin. After reaching 80% of confluence, cells were detached and seeded on 6-well plates in complete media and allowed to recover for 48 h. Cells were then washed three times with PBS and transfected with 1 μg of plasmid pIRES2-AcGFP1 (Clonetech 632435) using Lipofectamine LTX (Thermofisher Scientific) according to manufacturer instructions. Transfection media was supplemented with culture medium alone (vehicle) or 1 μM or 5 μM compound 58 in culture medium.

After 24 hours treatment, culture media were removed and cells were lysed with SDS-PAGE lysis buffer. Lysates were transferred to 1.5 ml tubes and sonicated for 3 min. Total protein amount was quantified using BCA Protein Assay Kit (Pierce). Equal amount of proteins (30 μg) was loaded on SDS-PAGE gels. Proteins were transferred onto 0.2 μm PVDF membranes (BioRad) and probed with primary antibodies diluted in Tris-buffered saline supplemented with 0.1% Tween 20 and 3% bovine serum albumin.

GFP (cell Signaling) and β-actin (Sigma-Aldrich) antibodies were used as primary antibodies. A HRP-conjugated secondary antibody (Rockland) was employed to detect immune-reactive bands using enhanced chemiluminescence (ECL Western Blotting Substrate, Pierce). Quantification of protein bands was done by densitometry using ImageJ software.

Figure 12A:
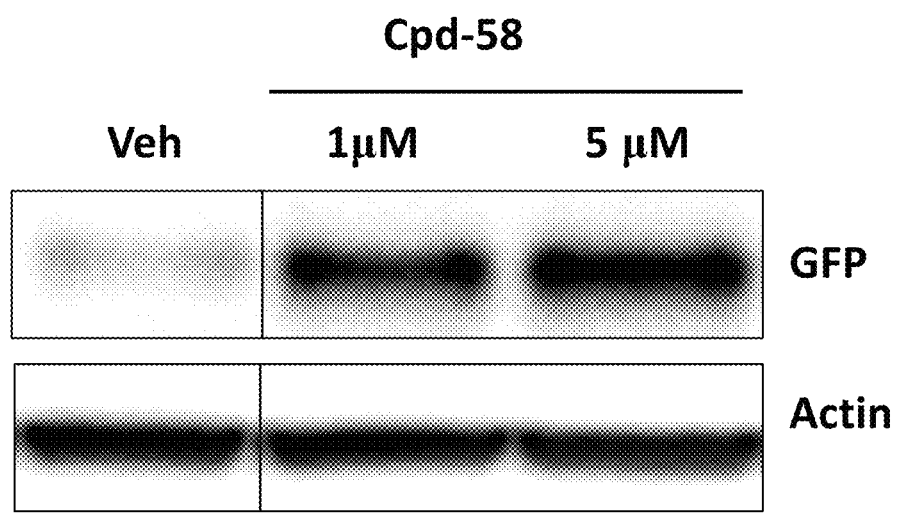
FIG. 12A shows the expression of GFP after 24 hours in untreated (Veh) or treated CHO cells with 1 μM or 5 μM compound 58.
Figure 12B:
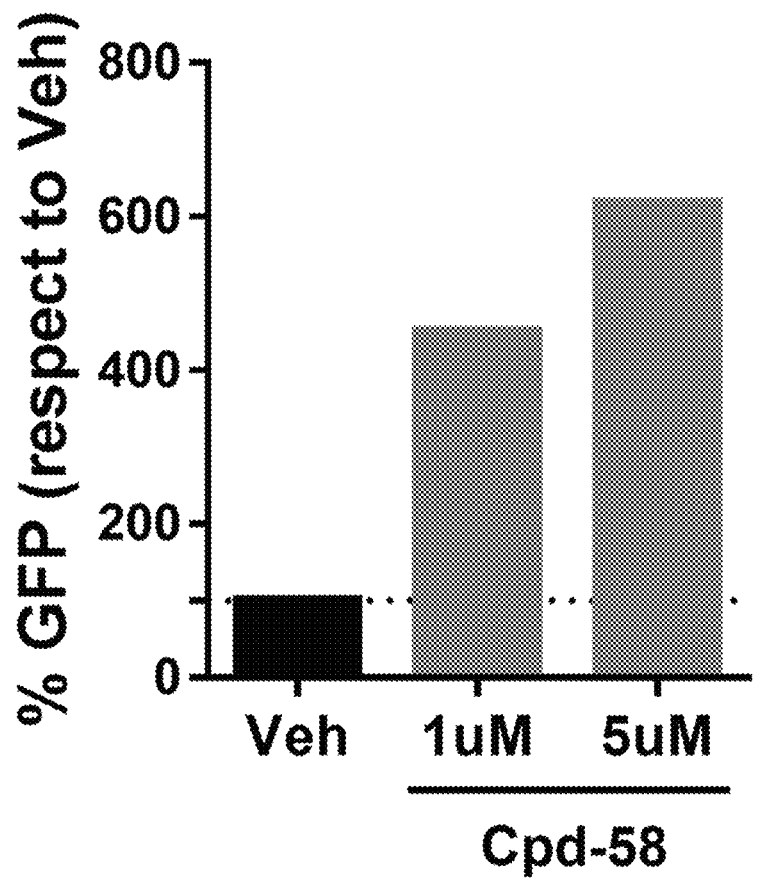
FIG. 12B shows percent expression of GFP after 24 hours in untreated (Veh) or treated CHO cells with 1 μM or 5 μM compound 58.

Expression of GFP after 24 hours in untreated (Veh) or treated CHO cells with 1 μM or 5 μM compound 58 is shown in FIG. 12A. Figure shows 2 sections of the same gel prepared at same conditions for each antibody. Percent expression of GFP from FIG. 12A is shown in FIG. 12B. The levels were normalized to β-actin expression and percentage was calculated as the percent relative to the expression of GFP in untreated condition (Veh) which corresponds to 100%. Treatment with compound 58 results in an increased expression of GFP after transient transfection of the pIRES-AcGFP which encodes GFP protein.

Example B13—Frontotemporal Dementia Cellular Model

MEF cells were maintained at 37° C. and 5% CO2 in DMEM supplemented with 10% fetal bovine serum (FBS), 2 mM L-glutamine, 100 U/ml penicillin, and 100 μg/ml streptomycin. After reaching 80% of confluence, cells were detached and seeded on 6-well plates in complete media at a density of $3 \times 10^5$ cells/well and allowed to recover for 48 h. To perform a knockdown expression of the progranulin protein, cells were then washed three times with PBS and treated with small interference RNA (siRNA) mix, that target progranulin (PGRN) gene (Qiagen FlexiTube siRNA mix, Cat No 1027416), according to manufacturer instructions.

Transfection media with siRNA mix was supplemented with OPTIMEM medium alone (GRN7) or 1 μM or 5 μM compound 58 in OPTIMEM medium. Transfection media without siRNA mix (Veh) and cells cultured in OPTIMEM medium alone (Unt) were used as controls.

After 48 hours treatment, culture media were removed and cells were lysed with SDS-PAGE lysis buffer. Lysates were transferred to 1.5 ml tubes and sonicated for 3 min. Total protein amount was quantified using BCA Protein Assay Kit (Pierce). Equal amount of proteins (30 μg) was loaded on SDS-PAGE gels. Proteins were transferred onto 0.2 μm PVDF membranes (BioRad) and probed with primary antibodies diluted in Tris-buffered saline supplemented with 0.1% Tween 20 and 3% bovine serum albumin.

PGRN (R&D Systems) and β-actin (Sigma-Aldrich) antibodies were used as primary antibodies. A HRP-conjugated secondary antibody (Rockland) was employed to detect immune-reactive bands using enhanced chemiluminescence (ECL Western Blotting Substrate, Pierce). Quantification of protein bands was done by densitometry using ImageJ software.

Figure 13:
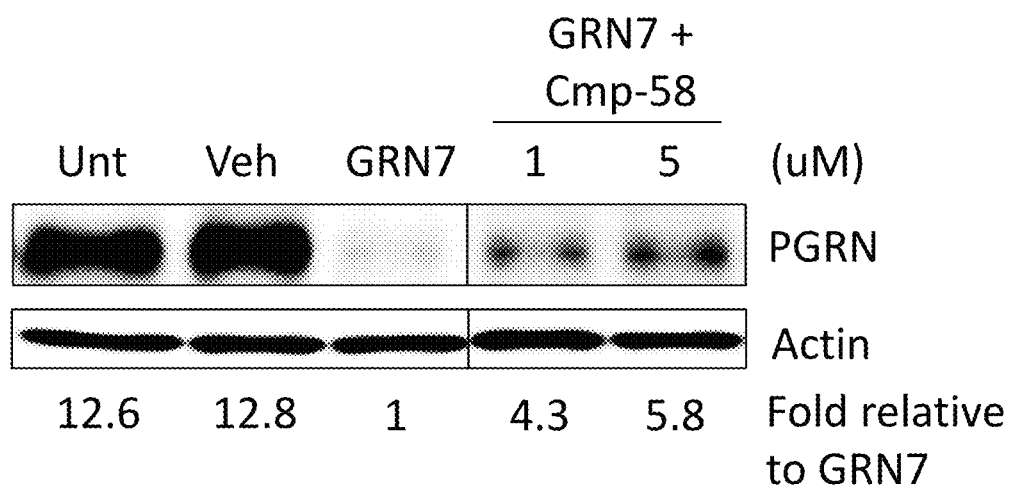
FIG. 13 shows the expression of PGRN after 48 hours in untreated MEF cells (Unt), or MEF treated with transfection media without siRNA mix (Veh) or treated with transfection media with siRNA mix alone (GRN7) or in the presence of 1 μM or 5 μM compound 58.

Expression of PGRN after 48 hours in untreated MEF cells (Unt), or MEF treated with transfection media without siRNA mix (Veh) or treated with transfection media with siRNA mix alone (GRN7) or in the presence of 1 μM or 5 μM compound 58 is shown in FIG. 13. Figure shows 2 sections of the same gel prepared at same conditions for each antibody. The levels were normalized to β-actin expression and the fold change was calculated as the expression relative to the expression of PGRN in the presence of siRNA alone condition (GRN7) which corresponds to 1. Treatment with compound 58 results in an increased expression of progranulin in a knockdown condition.

All references throughout, such as publications, patents, patent applications and published patent applications, are incorporated herein by reference in their entireties.

The invention claimed is:
1. A compound of formula (I):

$$A^1 \text{—}[O]_{q1} \text{—} \left[ \begin{array}{c} R^{8a} \\ R^{8b} \end{array} \right]_{p1} \text{—} \left[ \begin{array}{c} O \\ \| \\ S \\ \| \\ O \end{array} \right] \text{—} \left[ \begin{array}{c} R^{7a} \\ R^{7b} \end{array} \right]_{n1} \text{—} \left[ \begin{array}{c} R^{6a} \ R^{5a} \\ R^{6b} \ R^{5b} \end{array} \right]_{m1} \text{—} \left[ \begin{array}{c} R^{N\text{-}k} \\ N \end{array} \right]_k$$

$$\left[ \begin{array}{c} R^{j\text{-}a} \\ R^{j\text{-}b} \end{array} \right]_j \text{—} \left[ \begin{array}{c} R^{1a} \ R^{1b} \ R^{4a} \\ R^{2a} \ R^{2b} \ R^{3a} \ R^{3b} \end{array} \right]_r \text{—} \left[ \begin{array}{c} R^N \\ N \end{array} \right]_s \text{—} \left[ \begin{array}{c} R^{9a} \ R^{10a} \\ R^{9b} \ R^{10b} \end{array} \right]_{m2}$$

$$\text{—} \left[ \begin{array}{c} R^{11a} \\ R^{11b} \end{array} \right]_{n2} \text{—} \left[ \begin{array}{c} O \\ \| \\ S \\ \| \\ O \end{array} \right] \text{—} \left[ \begin{array}{c} R^{12a} \\ R^{12b} \end{array} \right]_{p2} \text{—}[O]_{q2} \text{—} A^2$$

or a pharmaceutically acceptable salt thereof, wherein:
$m^2$ is 1, $n^2$ is 0, $p^2$ is 0, and $q^2$ is 1;
and either:
(a) $m^1$ is 0, $n^1$ is 0, $p^1$ is 1, and $q^1$ is 0; or
(b) $m^1$ is 1, $n^1$ is 0, $p^1$ is 0, and $q^1$ is 1;
r is 1 and s is 1;
X is $CR^X$;
$R^X$ is selected from the group consisting of hydrogen, $C_1$-$C_6$ alkyl, $C_2$-$C_6$ alkenyl, and $C_2$-$C_6$ alkynyl;
j is 0;
k is 1;
$R^{N\text{-}k}$ is H or $C_1$-$C_6$ alkyl;
$R^N$ is H or $C_1$-$C_6$ alkyl;
$A^1$ is selected from the group consisting of:
a substituent of formula ($A^1$-a)

$$(R^{14})_{x1} \underset{Z^3}{\overset{Z^1}{\diagdown}} \overset{R^{13}}{\underset{Z^2}{\diagup}} *$$ (A$^1$-a)

wherein
* represents the attachment point to the remainder of the molecule;
$Z^1$ is selected from the group consisting of $CR^{Z1\text{-}1}R^{Z1\text{-}2}$, $NR^{Z1\text{-}2}$, $C(R^{Z1\text{-}1}R^{Z1\text{-}2})N(R^{Z1\text{-}2})$, O, $C(R^{Z1\text{-}1}R^{Z1\text{-}2})O$, S, $C(R^{Z1\text{-}1}R^{Z1\text{-}2})S$, and —$CR^{Z1\text{-}1}$=$CR^{Z\text{-}1\text{-}1}$—;
wherein $R^{Z1\text{-}1}$ is H or $R^{14}$; and $R^{Z1\text{-}2}$ is H or $R^{14}$;
$Z^2$ is selected from the group consisting of $CR^{Z2\text{-}1}R^{Z2\text{-}2}$, $NR^{Z2\text{-}2}$, $C(R^{Z2\text{-}1}R^{Z2\text{-}2})N(R^{Z2\text{-}2})$, O, $C(R^{Z2\text{-}1}R^{Z2\text{-}2})O$, S, $C(R^{Z2\text{-}1}R^{Z2\text{-}2})S$, and —$CR^{Z2\text{-}1}$=$CR^{Z\text{-}1}$—;
wherein $R^{Z2\text{-}1}$ is H or $R^{14}$; and $R^{Z2\text{-}2}$ is H or $R^{14}$;
$Z^3$, independently at each occurrence, is CH, $CR^{14}$, or N;
$R^{13}$ is hydrogen or $R^{14}$, or $R^{13}$ and $R^{Z1\text{-}2}$ are taken together to form a double bond between the carbon atom bearing $R^{13}$ and $Z^1$, or $R^{13}$ and $R^{Z2\text{-}2}$ are taken together to form a double bond between the carbon atom bearing $R^{13}$ and $Z^2$; and
x1 is 0, 1, 2, 3, or 4;
$C_6$-$C_{14}$ aryl optionally substituted with one or more $R^{14}$ substituents; and
5-14 membered heteroaryl optionally substituted with one or more $R^{14}$ substituents;
$R^{14}$ is selected, independently at each occurrence, from the group consisting of halogen, $NO_2$, $C_1$-$C_6$ alkyl, $C_2$-$C_6$ alkenyl, $C_2$-$C_6$ alkynyl, $C_1$-$C_6$ haloalkyl, —$O(C_1$-$C_6$ alkyl), —$O(C_1$-$C_6$ haloalkyl), —$S(C_1$-$C_6$ alkyl), —$S(C_1$-$C_6$ haloalkyl), —$N(C_1$-$C_6$ alkyl)$_2$, —$N(C_1$-$C_6$ haloalkyl)$_2$, —$NR^{14\text{-}a}R^{14\text{-}b}$, and —CN;
wherein $R^{14\text{-}a}$ and $R^{14\text{-}b}$ are taken together with the nitrogen atom to which they are attached to form a 3-10 membered heterocycle;
$A^2$ is selected from the group consisting of:
$C_6$-$C_{14}$ aryl optionally substituted with one or more $R^{16}$ substituents; and
5-14 membered heteroaryl optionally substituted with one or more $R^{16}$ substituents;
$R^{16}$ is selected, independently at each occurrence, from the group consisting of halogen, $NO_2$, $C_1$-$C_6$ alkyl, $C_2$-$C_6$ alkenyl, $C_2$-$C_6$ alkynyl, $C_1$-$C_6$ haloalkyl, —$O(C_1$-$C_6$ alkyl), —$O(C_1$-$C_6$ haloalkyl), —$S(C_1$-$C_6$ alkyl), —$S(C_1$-$C_6$ haloalkyl), —$N(C_1$-$C_6$ alkyl)$_2$, —$N(C_1$-$C_6$ haloalkyl)$_2$, —$NR^{16\text{-}a}R^{16\text{-}b}$, and —CN wherein $R^{16-a}$ and $R^{16-b}$ are taken together with the nitrogen atom to which they are attached to form a 3-10 membered heterocycle;

$R^{1a}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen, or $R^{1a}$ is taken together with $R^{2a}$ to form a $C_1$-$C_6$ alkylene moiety, or $R^{1a}$ is taken together with an $R^{3a}$ moiety to form a $C_1$-$C_6$ alkylene moiety;

$R^{1b}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{2a}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{2b}$ is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{3a}$ independently at each occurrence is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen, or $R^{3a}$ is taken together with $R^{4a}$ to form a $C_1$-$C_6$ alkylene moiety;

$R^{3b}$ independently at each occurrence is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{4a}$ independently at each occurrence is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{4b}$ independently at each occurrence is selected from the group consisting of hydrogen, $C_1$-$C_6$ alkyl, —C(O)OH, —C(O)O($C_1$-$C_6$ alkyl), —C(O)O($C_1$-$C_6$ haloalkyl), and halogen;

$R^{5a}$ and $R^{5b}$ are taken together to form an oxo (=O) substituent or an imido (=NH) substituent, or $R^{5a}$ and $R^{5b}$ are both hydrogen;

$R^{6a}$ is hydrogen;

$R^{6b}$ is hydrogen;

$R^{8a}$ and $R^{8b}$ are taken together to form an oxo (=O) substituent;

$R^{9a}$ and $R^{9b}$ are taken together to form an oxo (=O) substituent or an imido (=NH) substituent, or $R^{9a}$ and $R^{9b}$ are both hydrogen; and $R^{10a}$ is hydrogen and $R^{10b}$ is hydrogen;

provided that when $m^1$ is 0, $n^1$ is 0, $q^1$ is 0, and $p^1$ is 1, then $R^{8a}$ and $R^{8b}$ are taken together to form an oxo (=O) substituent, and $A^1$ is a substituent of formula ($A^1$-a)

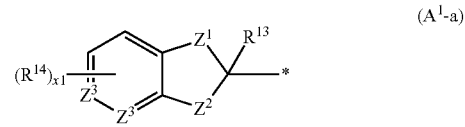

wherein

* represents the attachment point to the remainder of the molecule;

$Z^1$ is selected from the group consisting of $CR^{Z1-1}R^{Z1-2}$, $NR^{Z1-2}$, $C(R^{Z1-1}R^{Z1-2})N(R^{Z1-2})$, O, $C(R^{Z1-1}R^{Z1-2})O$, S, $C(R^{Z1-1}R^{Z1-2})S$, and —$CR^{Z1-1}$=$CR^{Z1-1}$—;

wherein $R^{Z1-1}$ is H or $R^{14}$; and $R^{Z1-2}$ is H or $R^{14}$;

$Z^2$ is selected from the group consisting of $CR^{Z2-1}R^{Z2-2}$, $NR^{Z2-2}$, $C(R^{Z2-1}R^{Z2-2})N(R^{Z2-2})$, O, $C(R^{Z1-1}R^{Z2-2})O$, S, $C(R^{Z1-1}R^{Z2-2})S$, and —$CR^{Z1-1}$=$CR^{Z2-1}$—;

wherein $R^{Z2-1}$ is H or $R^{14}$; and $R^{Z2-2}$ is H or $R^{14}$;

$Z^3$, independently at each occurrence, is CH, $CR^{14}$, or N;

$R^{13}$ is hydrogen or $R^{14}$, or $R^{13}$ and $R^{Z1-2}$ are taken together to form a double bond between the carbon atom bearing $R^{13}$ and $Z^1$, or $R^{13}$ and $R^{Z2-2}$ are taken together to form a double bond between the carbon atom bearing $R^{13}$ and $Z^2$; and x1 is 0, 1, 2, 3, or 4.

2. The compound of claim 1, or a pharmaceutically acceptable salt thereof, wherein the compound of formula (I), or the pharmaceutically acceptable salt thereof, is a compound of formula (II-2-1):

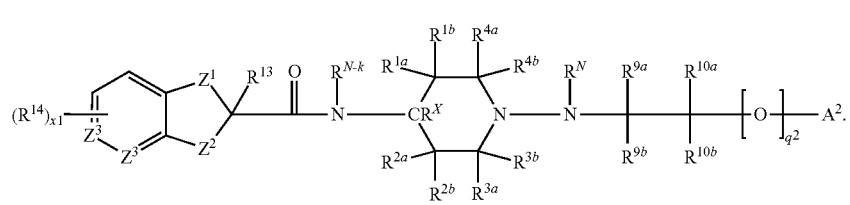

or a pharmaceutically acceptable salt thereof.

3. The compound of claim 1, or a pharmaceutically acceptable salt thereof, wherein the compound of formula (I), or the pharmaceutically acceptable salt thereof, is a compound of formula (II-2-2):

(II-2-2)

$A^1$—[O]$_{q1}$—... —N—$CR^X$—N—N—...—[O]$_{q2}$—$A^2$.

(with substituents $R^{6a}$, $R^{5a}$, $R^{N-k}$, $R^{1a}$, $R^{1b}$, $R^{4a}$, $R^{4b}$, $R^N$, $R^{9a}$, $R^{10a}$, $R^{6b}$, $R^{5b}$, $R^{2a}$, $R^{2b}$, $R^{3a}$, $R^{3b}$, $R^{9b}$, $R^{10b}$)

or a pharmaceutically acceptable salt thereof.

4. The compound of claim 1, or a pharmaceutically acceptable salt thereof, wherein $R^{N-k}$ is H.

5. The compound of claim 1, or a pharmaceutically acceptable salt thereof, wherein $R^N$ is H.

6. The compound of claim 1, or a pharmaceutically acceptable salt thereof, wherein $R^{1a}$, $R^{1b}$, $R^{2a}$, $R^{2b}$, $R^{3a}$, $R^{3b}$, $R^{4a}$, $R^{4b}$ are all hydrogen.

7. The compound of claim 1, or a pharmaceutically acceptable salt thereof, wherein $m^1$ is 0, $n^1$ is 0, $p^1$ is 1, $q^1$ is 0, $R^{8a}$ and $R^{8b}$ are taken together to form an oxo (=O) substituent, and $R^{9a}$ and $R^{9b}$ are taken together to form an oxo (=O) substituent.

8. The compound of claim 1, or a pharmaceutically acceptable salt thereof, wherein $m^1$ is 1, $n^1$ is 0, $p^1$ is 0, $q^1$ is 1, $R^{5a}$ and $R^{5b}$ are taken together to form an oxo (=O) substituent, and $R^{9a}$ and $R^{9b}$ are taken together to form an oxo (=O) substituent.

9. The compound of claim 1, or a pharmaceutically acceptable salt thereof, wherein $A^1$ is selected from the group consisting of

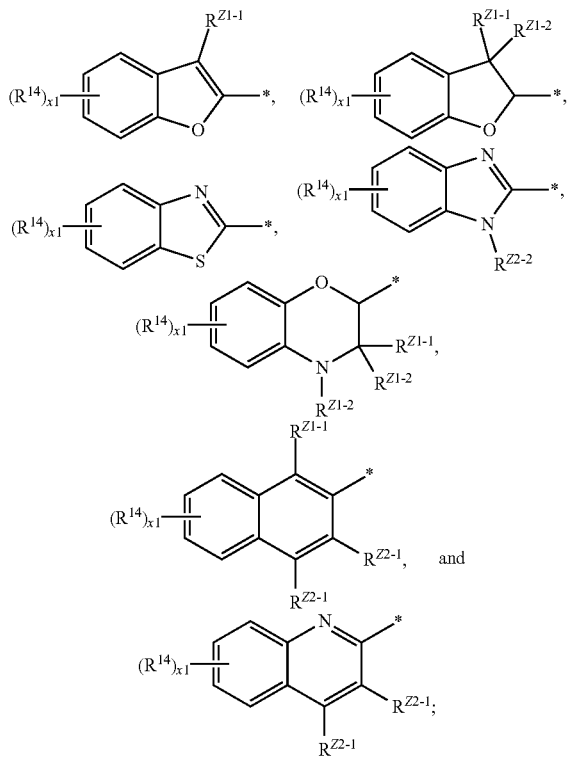

wherein the * represents the attachment point to the remainder of the molecule.

10. The compound of claim 1, or a pharmaceutically acceptable salt thereof, wherein $A^1$ is selected from the group consisting of

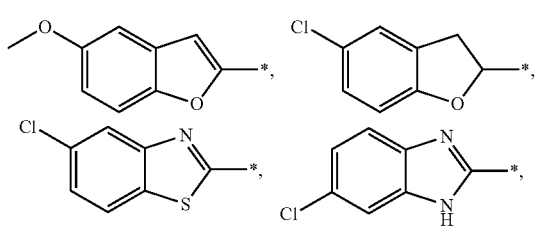

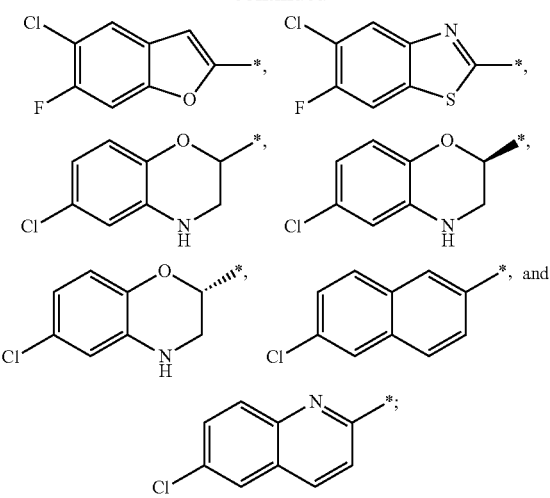

wherein the * represents the attachment point to the remainder of the molecule.

11. The compound of claim 1, or a pharmaceutically acceptable salt thereof, wherein $A^1$ is selected from the group consisting of wherein the * represents the attachment point to the remainder of the molecule.

12. The compound of claim 1, or a pharmaceutically acceptable salt thereof, wherein $A^1$ is $C_6$-$C_{14}$ aryl optionally substituted with one or more $R^{14}$ substituents.

13. The compound of claim 1, or a pharmaceutically acceptable salt thereof, wherein $A^1$ is 5-14 membered heteroaryl optionally substituted with one or more $R^{14}$ substituents.

14. The compound of claim 1, or a pharmaceutically acceptable salt thereof, wherein $A^1$ is selected from the group consisting of

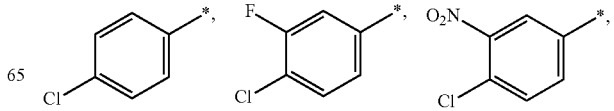

-continued

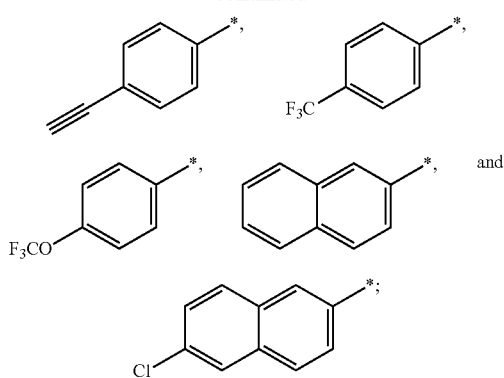

wherein the * represents the attachment point to the remainder of the molecule.

15. The compound of claim 1, or a pharmaceutically acceptable salt thereof, wherein $A^1$ is

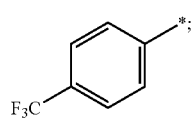

wherein the * represents the attachment point to the remainder of the molecule.

16. The compound of claim 1, or a pharmaceutically acceptable salt thereof, wherein $A^2$ is $C_6$-$C_{14}$ aryl optionally substituted with one or more $R^{16}$ substituents.

17. The compound of claim 1, or a pharmaceutically acceptable salt thereof, wherein $A^2$ is 5-14 membered heteroaryl optionally substituted with one or more $R^{16}$ substituents.

18. The compound of claim 1, or a pharmaceutically acceptable salt thereof, wherein $A^2$ is selected from the group consisting of

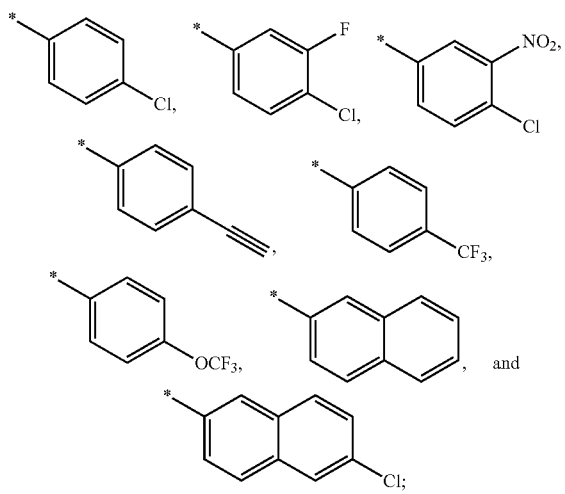

wherein the * represents the attachment point to the remainder of the molecule.

19. The compound of claim 1, or a pharmaceutically acceptable salt thereof, wherein $A^2$ is

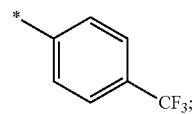 [SMILES: *c1ccc(C(F)(F)F)cc1]

wherein the * represents the attachment point to the remainder of the molecule.

20. The compound of claim 1, or a pharmaceutically acceptable salt thereof, wherein the compound is selected from the group consisting of

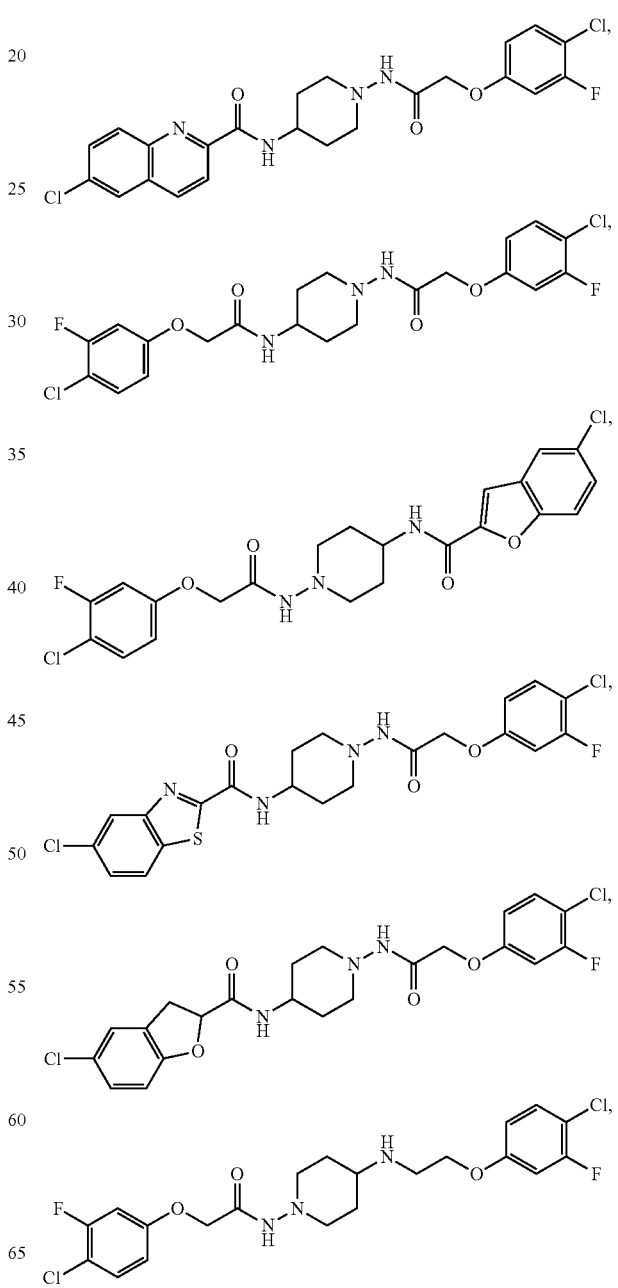

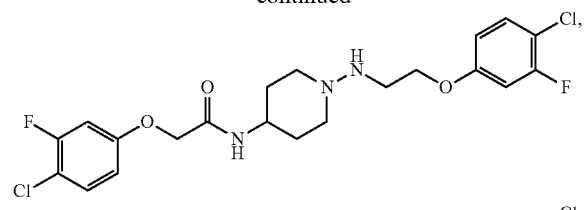
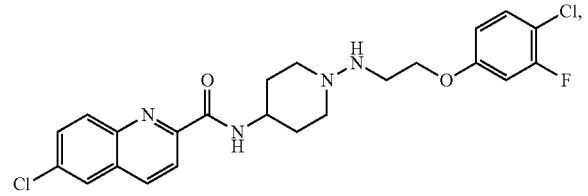
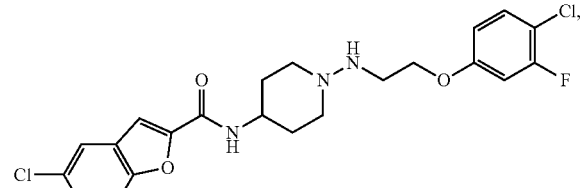
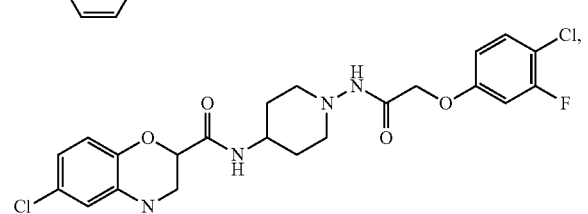
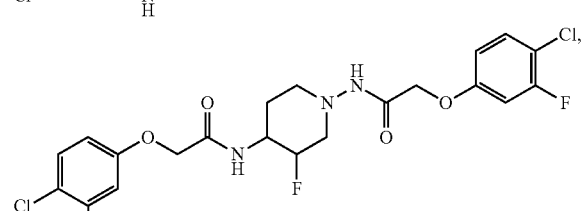
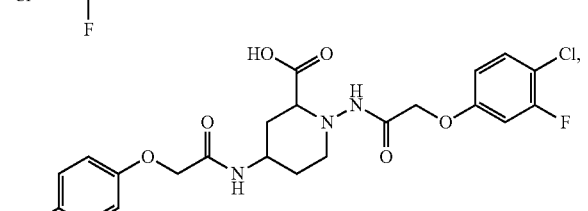
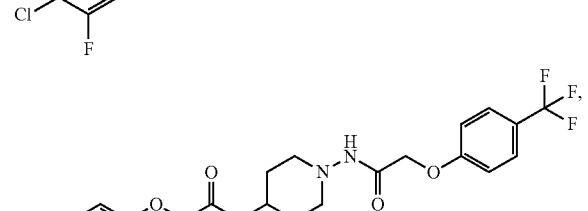
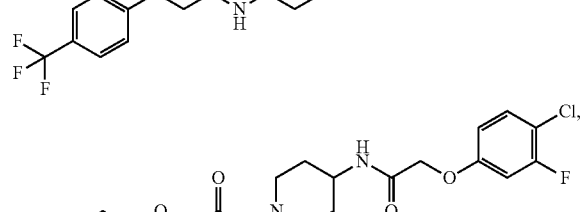
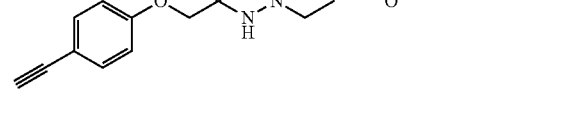
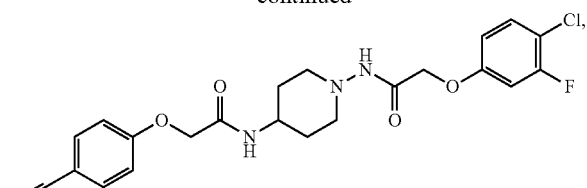
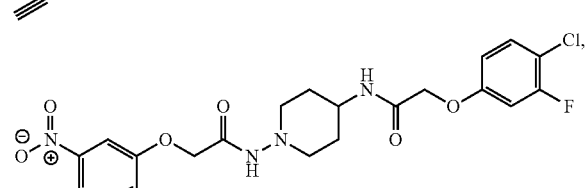
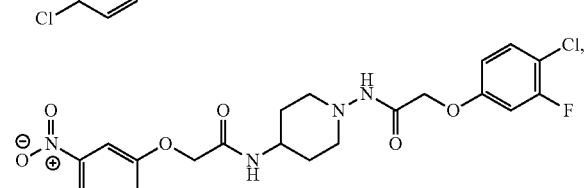
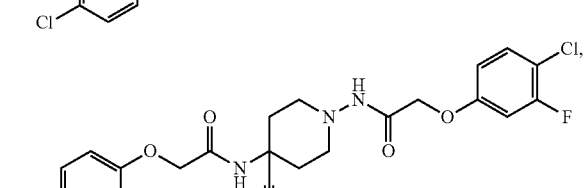
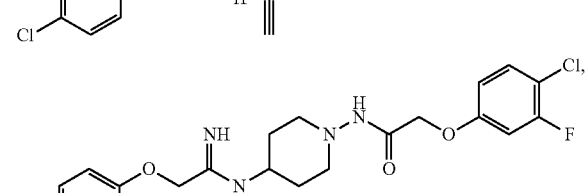
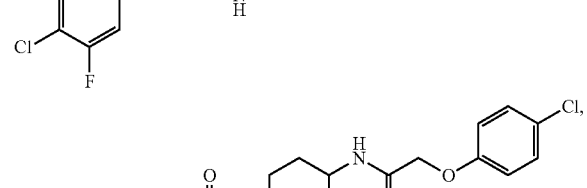
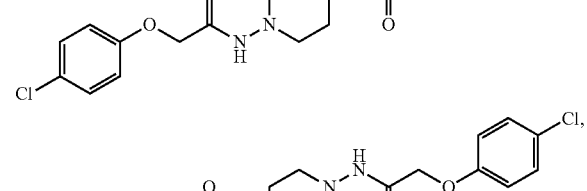
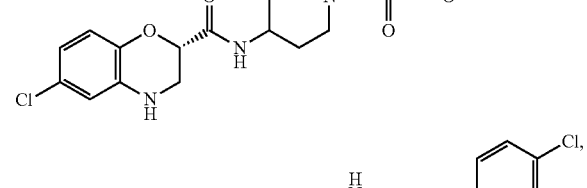
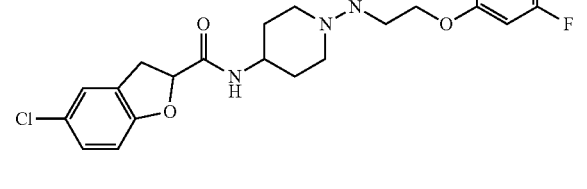
and pharmaceutically acceptable salts of any of the foregoing.

21. The compound of claim 1, or a pharmaceutically acceptable salt thereof, wherein the compound is selected from the group consisting of

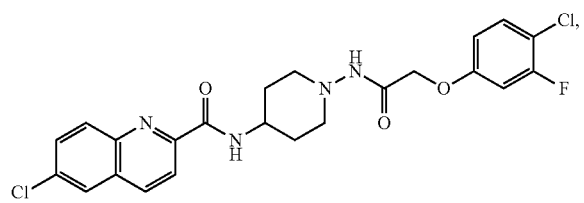

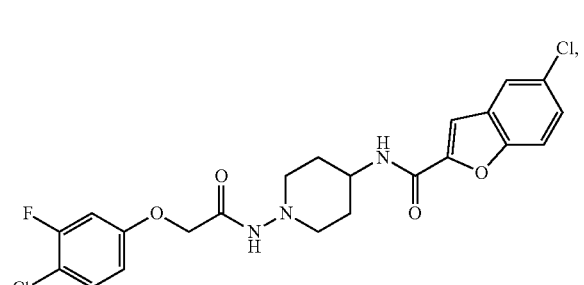

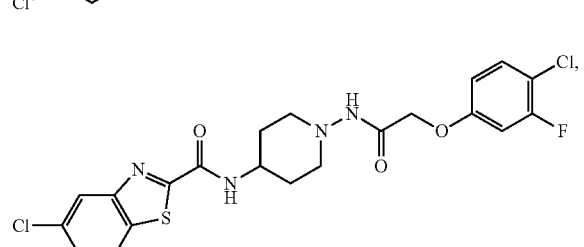

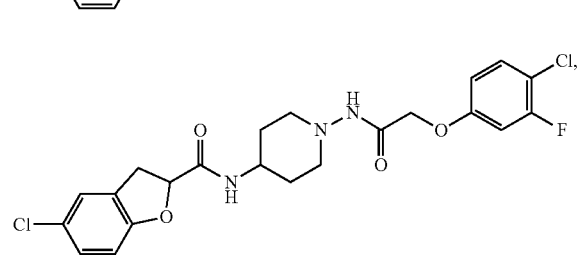

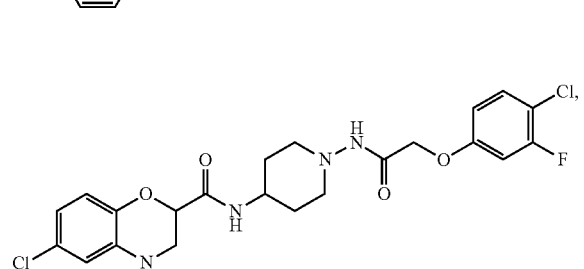

and pharmaceutically acceptable salts of any of the foregoing.

22. The compound of claim 1, or a pharmaceutically acceptable salt thereof, wherein the compound is selected from the group consisting of

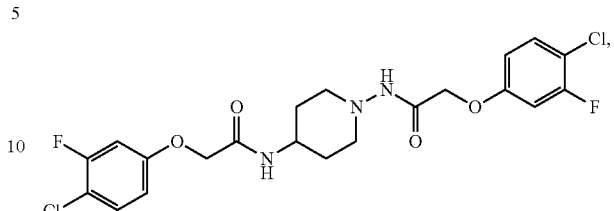

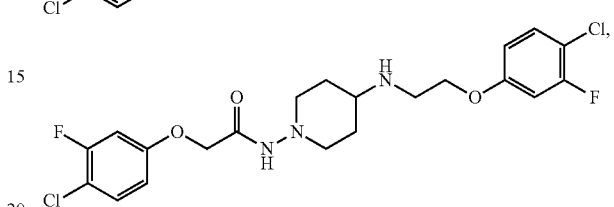

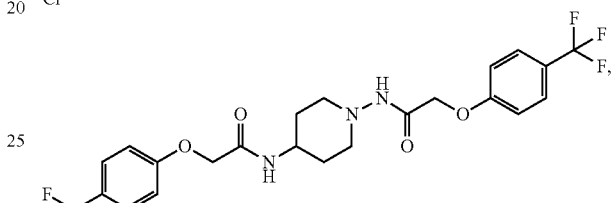

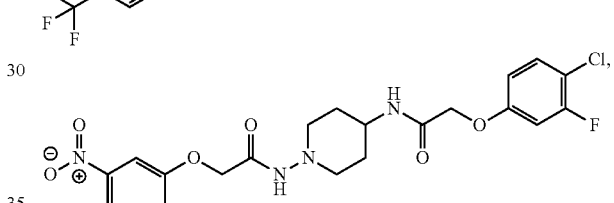

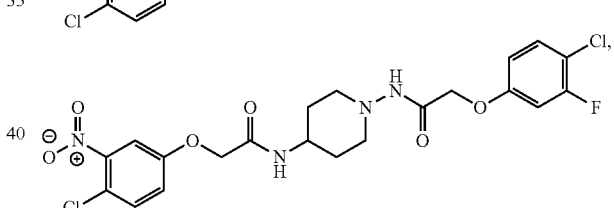

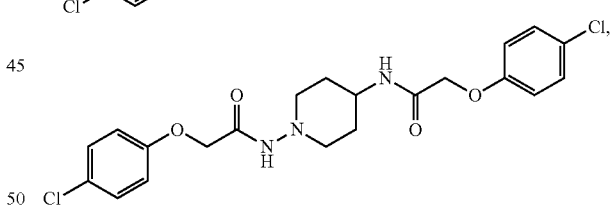

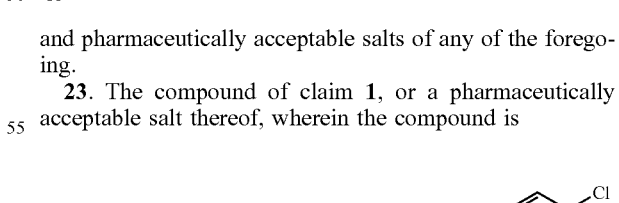

and pharmaceutically acceptable salts of any of the foregoing.

23. The compound of claim 1, or a pharmaceutically acceptable salt thereof, wherein the compound is

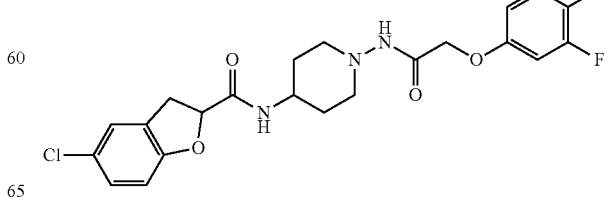

or a pharmaceutically acceptable salt thereof.

24. The compound of claim 1, or a pharmaceutically acceptable salt thereof, wherein the compound is

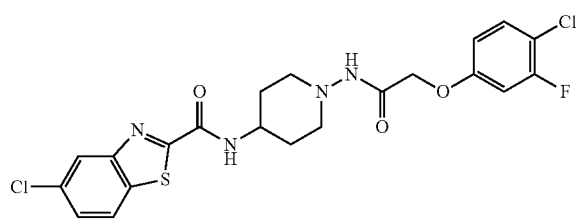 [SMILES: O=C(COc1ccc(Cl)c(F)c1)NN1CCC(NC(=O)c2nc3cc(Cl)ccc3s2)CC1]

or a pharmaceutically acceptable salt thereof.

25. The compound of claim 1, or a pharmaceutically acceptable salt thereof, wherein the compound is

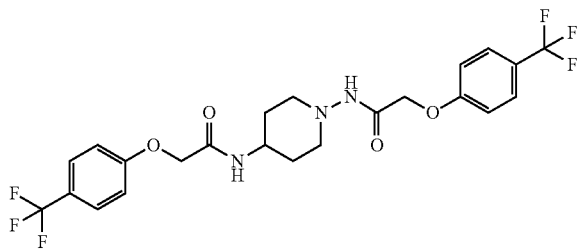 [SMILES: O=C(COc1ccc(C(F)(F)F)cc1)NC1CCN(NC(=O)COc2ccc(C(F)(F)F)cc2)CC1]

or a pharmaceutically acceptable salt thereof.

26. The compound of claim 1, or a pharmaceutically acceptable salt thereof, wherein the compound is

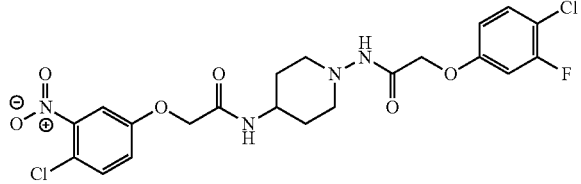 [SMILES: O=C(COc1ccc(Cl)c([N+](=O)[O-])c1)NC1CCN(NC(=O)COc2ccc(Cl)c(F)c2)CC1]

or a pharmaceutically acceptable salt thereof.

27. The compound of claim 1, or a pharmaceutically acceptable salt thereof,
wherein the compound is

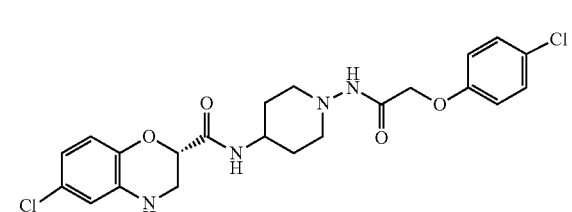

or a pharaceutically acceptable salt thereof.

28. The compound of claim 1, or a pharmaceutically acceptable salt thereof,
wherein the compound is

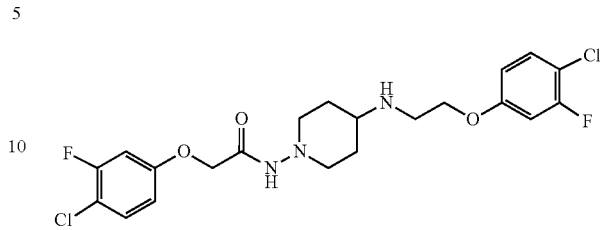

or a pharmaceutically acceptable salt thereof.

29. The compound of claim 1, or a pharaceutically acceptable salt thereof,
wherein the compound is

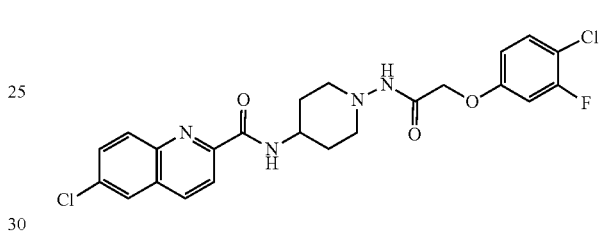

or a pharmaceutically acceptable salt thereof.

30. The compound of claim 1, or a pharmaceutically acceptable salt thereof,
wherein the compound is

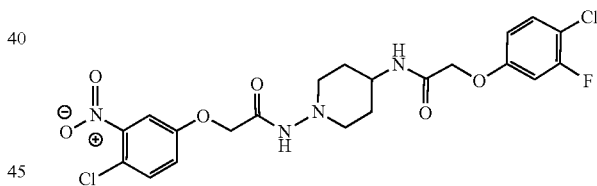

or a pharmaceutically acceptable salt thereof.

31. The compound of claim 1, or a pharmaceutically acceptable salt thereof,
wherein the compound is

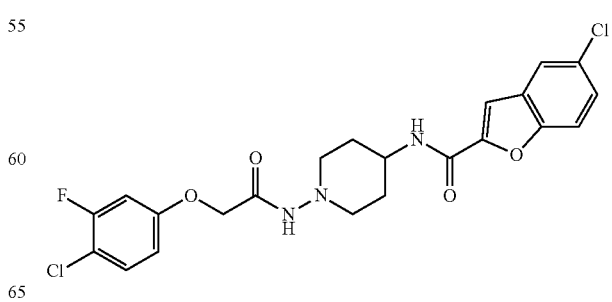

or a pharmaceutically acceptable salt thereof.

32. The compound of claim 1, or a pharmaceutically acceptable salt thereof,
wherein the compound is

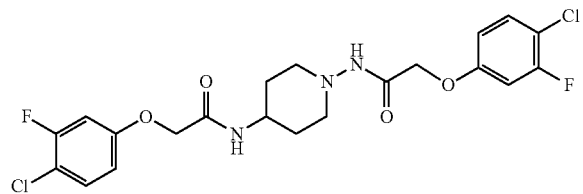 [SMILES: O=C(COc1ccc(Cl)c(F)c1)NC1CCN(NC(=O)COc2ccc(Cl)c(F)c2)CC1]

or a pharmaceutically acceptable salt thereof.

33. The compound of claim 1, or a pharmaceutically acceptable salt thereof,
wherein the compound is

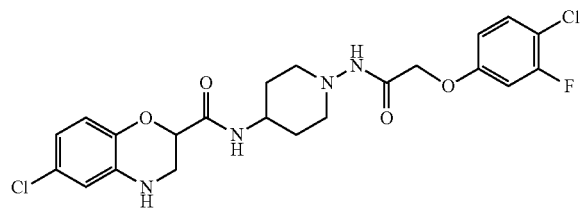 [SMILES: O=C(COc1ccc(Cl)c(F)c1)NN1CCC(NC(=O)C2CNc3cc(Cl)ccc3O2)CC1]

or a pharmaceutically acceptable salt thereof.

34. The compound of claim 1, or a pharmaceutically acceptable salt thereof,
wherein the compound is

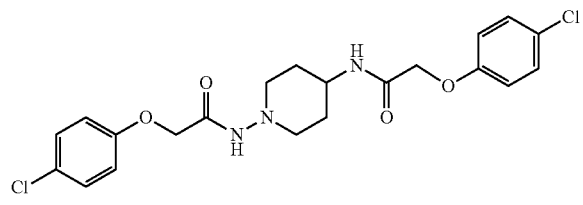 [SMILES: O=C(COc1ccc(Cl)cc1)NC1CCN(NC(=O)COc2ccc(Cl)cc2)CC1]

or a pharmaceutically acceptable salt thereof.

35. A pharmaceutical composition comprising a compound of claim 1, or a pharmaceutically acceptable salt thereof, and a pharmaceutically acceptable carrier.

36. A method of treating a disease or disorder mediated by an integrated stress response (ISR) pathway in an individual in need thereof comprising administering to the individual a therapeutically effective amount of a compound of claim 1, or a pharmaceutically acceptable salt thereof.

37. The method of claim 36, wherein the compound, or the pharmaceutically acceptable salt thereof, is administered in combination with a therapeutically effective amount of one or more additional anti-cancer agents.

38. The method of claim 37, wherein the disease or disorder is mediated by phosphorylation of eIF2α and/or the guanine nucleotide exchange factor (GEF) activity of eIF2B.

39. The method of claim 36, wherein the disease or disorder is mediated by a decrease in protein synthesis.

40. The method of claim 36, wherein the disease or disorder is mediated by the expression of ATF4, CHOP or BACE-1.

41. The method of claim 36, wherein the disease or disorder is a neurodegenerative disease, an inflammatory disease, an autoimmune disease, a metabolic syndrome, a cancer, a vascular disease, an ocular disease, a musculoskeletal disease, or a genetic disorder.

42. The method of claim 41, wherein the disease is vanishing white matter disease, childhood ataxia with CNS hypomyelination, intellectual disability syndrome, Alzheimer's disease, prion disease, Creutzfeldt-Jakob disease, Parkinson's disease, amyotrophic lateral sclerosis (ALS) disease, cognitive impairment, frontotemporal dementia (FTD), traumatic brain injury, postoperative cognitive dysfunction (PCD), neuro-otological syndromes, hearing loss, Huntington's disease, stroke, chronic traumatic encephalopathy, spinal cord injury, dementias or cognitive impairment, arthritis, psoriatic arthritis, psoriasis, juvenile idiopathic arthritis, asthma, allergic asthma, bronchial asthma, tuberculosis, chronic airway disorder, cystic fibrosis, glomerulonephritis, membranous nephropathy, sarcoidosis, vasculitis, ichthyosis, transplant rejection, interstitial cystitis, atopic dermatitis or inflammatory bowel disease, Crohn's disease, ulcerative colitis, celiac disease, systemic lupus erythematosus, type 1 diabetes, multiple sclerosis, rheumatoid arthritis, alcoholic liver steatosis, obesity, glucose intolerance, insulin resistance, hyperglycemia, fatty liver, dyslipidemia, hyperlipidemia, type 2 diabetes, pancreatic cancer, breast cancer, kidney cancer, bladder cancer, prostate cancer, testicular cancer, urothelial cancer, endometrial cancer, ovarian cancer, cervical cancer, renal cancer, esophageal cancer, gastrointestinal stromal tumor (GIST), multiple myeloma, cancer of secretory cells, thyroid cancer, gastrointestinal carcinoma, chronic myeloid leukemia, hepatocellular carcinoma, colon cancer, melanoma, malignant glioma, glioblastoma, glioblastoma multiforme, astrocytoma, dysplastic gangliocytoma of the cerebellum, Ewing's sarcoma, rhabdomyosarcoma, ependymoma, medulloblastoma, ductal adenocarcinoma, adenosquamous carcinoma, nephroblastoma, acinar cell carcinoma, lung cancer, non-Hodgkin's lymphoma, Burkitt's lymphoma, chronic lymphocytic leukemia, monoclonal gammopathy of undetermined significance (MGUS), plasmocytoma, lymphoplasmacytic lymphoma, acute lymphoblastic leukemia, Pelizaeus-Merzbacher disease, atherosclerosis, abdominal aortic aneurism, carotid artery disease, deep vein thrombosis, Buerger's disease, chronic venous hypertension, vascular calcification, telangiectasia or lymphoedema, glaucoma, age-related macular degeneration, inflammatory retinal disease, retinal vascular disease, diabetic retinopathy, uveitis, rosacea, Sjogren's syndrome or neovascularization in proliferative retinopathy, hyperhomocysteinemia, skeletal muscle atrophy, myopathy, muscular dystrophy, muscular wasting, sarcopenia, Duchenne muscular dystrophy (DMD), Becker's disease, myotonic dystrophy, X-linked dilated cardiomyopathy, spinal muscular atrophy (SMA), Down syndrome, MEHMO syndrome, metaphyseal chondrodysplasia, Schmid type (MCDS), depression, or social behavior impairment.

* * * * *